US012747239B2

(12) United States Patent
Aoki et al.

(10) Patent No.: US 12,747,239 B2
(45) Date of Patent: Sep. 29, 2026

(54) NITROGEN-CONTAINING HETEROCYCLIC COMPOUND HAVING MYT1 INHIBITORY ACTIVITY

(71) Applicant: CHUGAI SEIYAKU KABUSHIKI KAISHA, Tokyo (JP)

(72) Inventors: Toshihiro Aoki, Tokyo (JP); Takashi Chiba, Yokohama City (JP); Masami Kochi, Yokohama City (JP); Masaki Tomizawa, Yokohama City (JP); Yoshihisa Murata, Yokohama City (JP); Eigo Suyama, Yokohama City (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 19/308,769

(22) Filed: Aug. 25, 2025

(65) Prior Publication Data

US 2026/0062412 A1 Mar. 5, 2026

Related U.S. Application Data

(63) Continuation of application No. PCT/JP2024/007072, filed on Feb. 27, 2024.

(30) Foreign Application Priority Data

Feb. 28, 2023 (JP) ................................ 2023-029673

(51) Int. Cl.

| | |
|---|---|
| ***C07D 471/02*** | (2006.01) |
| ***A61K 31/4745*** | (2006.01) |
| ***A61P 35/00*** | (2006.01) |
| ***C07D 471/04*** | (2006.01) |

(52) U.S. Cl.

CPC ........ *C07D 471/04* (2013.01); *A61K 31/4745* (2013.01); *A61P 35/00* (2018.01)

(58) Field of Classification Search

CPC .... C07D 471/02; A61K 31/4745; A61P 35/00
USPC ............................................ 546/81; 514/292
See application file for complete search history.

(56) References Cited

U.S. PATENT DOCUMENTS

| | | | |
|---|---|---|---|
| 3,202,661 | A | 8/1965 | Brust et al. |
| 4,014,883 | A | 3/1977 | Fryer et al. |
| 2024/0293379 | A1 | 9/2024 | Ohte et al. |

FOREIGN PATENT DOCUMENTS

| | | | |
|---|---|---|---|
| CL | 2011002433 | A1 | 2/2012 |
| CL | 2022001938 | A1 | 4/2023 |
| CL | 2025002551 | A1 | 11/2025 |
| CL | 2025002628 | A1 | 11/2025 |
| CL | 2025002367 | A1 | 12/2025 |
| CN | 109111426 | A | 1/2019 |
| CN | 109824674 | A | 5/2019 |
| CN | 114369061 | A | 4/2022 |
| EP | 2441753 | A1 | 4/2012 |
| EP | 4094804 | A1 | 11/2022 |
| EP | 4582102 | A1 | 7/2025 |
| GB | 2503789 | A | 1/2014 |
| JP | 2001513560 | A | 9/2001 |
| JP | 2007506739 | A | 3/2007 |
| JP | 2019526606 | A | 9/2019 |
| KR | 20140141071 | A | 12/2014 |
| WO | WO9909983 | A1 | 3/1999 |

(Continued)

OTHER PUBLICATIONS

Healy, A.M. et al,: Pharmaceutical solvates, hydrates and amorphous forms: A special emphasis on cocrystals. Adv. Drug Deliv. Rev., vol. 117, pp. 25-46, 2017.*

(Continued)

*Primary Examiner* — Charanjit Aulakh

(74) *Attorney, Agent, or Firm* — Nixon & Vanderhye P.C.

(57) ABSTRACT

Provided is a compound having new MYT1 inhibitory activity or a salt thereof, or a solvate thereof.

A compound represented by the formula (1):

[Formula 1]

(1)

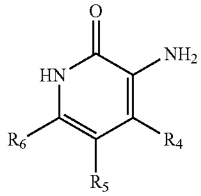

wherein $R_4$ is selected from the group consisting of optionally substituted $C_6$-$C_{10}$ aryl ($R_{4A}$), optionally substituted 4- to 10-membered heterocyclyl, and optionally substituted 5- to 10-membered heteroaryl ($R_{4HA}$); $R_5$ and $R_6$, together with the atoms to which they are attached, form an optionally substituted Ring D; Ring D is selected from the group consisting of a 3- to 10-membered monocyclic cycloaliphatic ring, a benzene ring, a 3- to 12-membered monocyclic heterocyclic ring, and a 5- to 6-membered monocyclic aromatic heterocyclic ring ($D_{HA}$); and any two adjacent substituents on Ring D, together with the atoms to which they are attached, may form optionally substituted Ring E, or a salt thereof, or a solvate thereof.

25 Claims, 19 Drawing Sheets

Specification includes a Sequence Listing.

(56) References Cited

FOREIGN PATENT DOCUMENTS

| | | | |
|---|---|---|---|
| WO | WO0244183 | A2 | 6/2002 |
| WO | WO02076396 | A2 | 10/2002 |
| WO | WO2005018551 | A2 | 3/2005 |
| WO | WO2005018556 | A2 | 3/2005 |
| WO | WO2005030792 | A2 | 4/2005 |
| WO | WO2005047258 | A2 | 5/2005 |
| WO | WO2005051324 | A2 | 6/2005 |
| WO | WO2006029115 | A2 | 3/2006 |
| WO | WO2006032470 | A1 | 3/2006 |
| WO | WO2006121767 | A2 | 11/2006 |
| WO | WO2007051119 | A1 | 5/2007 |
| WO | WO2007075468 | A1 | 7/2007 |
| WO | WO2007090461 | A1 | 8/2007 |
| WO | WO2015088564 | A1 | 6/2015 |
| WO | WO2018049296 | A1 | 3/2018 |
| WO | WO2018183586 | A1 | 10/2018 |
| WO | WO2023022659 | A1 | 2/2023 |
| WO | WO2024048687 | A1 | 3/2024 |
| WO | WO2024179948 | A1 | 9/2024 |
| WO | WO2024180018 | A1 | 9/2024 |
| WO | WO2024182404 | A1 | 9/2024 |
| WO | WO2024182466 | A1 | 9/2024 |

OTHER PUBLICATIONS

Alhmoud, J. F., et al., "DNA Damage/Repair Management in Cancers," Cancers, 12(4):1050 (2020).
Belikov, V. G., et al., "Study of Decomposition Kinetics of Phenazepam in Tablets," Farmatsiya, 34(5):34-38 (1985).
Croix, C., et al., "Synthesis of naphthryidin-2(1H)-one derivatives via ring expansion of 3-substituted-1H-pyrrolo[2,3-b]pyridine-2(3H)-one derivatives," Chem Commun., 54:5538-5541 (2018).
Gallo, D., et al., "CCNE1 amplification is synthetic lethal with PKMYT1 kinase inhibition," Nature, 604(7907):749-756 (2022).
Groelly, F. J., et al., "Targeting DNA damage response pathways in cancer," Nat Rev Cancer, 23(2):78-94 (2023).
Hewawasam, P., et al., "The Synthesis and Structure-Activity Relationships of 4-Aryl-3-aminoquinolin-2-ones: A New Class of Calcium-Dependent, Large Conductance, Potassium (Maxi-K) Channel Openers Targeting for Post-Stroke Neuroprotection," Bioorg Med Chem Lett., 12(13):1779-1783 (2002).
Jaszkowska, A. and Serafin, B., "Cyclization of Some o-Substituted Benzophenone Derivatives," Roczniki Chemii, 48(6):1029-1040 (1974).
Kovac, T., et al., "New Synthesis of 7-Bromo-1,3-dihydro-3-hydroxy-5-(2'-pyridyl)-2H-1,4-benzodiazepin-2-one," J Heterocyclic Chem., 18:59-62 (1981).
Li, L., et al., "DNA Repair Pathways in Cancer Therapy and Resistance," Front Immunol., 11:629266 (2021).
Moore, K., et al., "Maintenance Olaparib in Patients with Newly Diagnosed Advanced Ovarian Cancer," N Engl J Med., 379(26):2495-2505 (2018).
Queiroz, M. J. R. P., et al., "New strategies for the synthesis of heteroannulated 2-pyridinones, substituted 2-quinolinones and coumarins from dehydroamino acid derivatives," Tetrahedron, 64(22):5139-5146 (2008).
Shatsauskas, A. L., et al., "Synthesis and Photophysical Properties of 3-Amino-4-arylpyridin-2(1H)-ones," Synthesis, 52(2):227-238 (2020).
Taylor, J. B. and Tully, W. R., "Synthesis of Some 1H-1,3-Benzodiazepines," Journal of Chemical Society, Perkin Transactions I, Organic and Bio-organic Chemistry, 12:1331-1338 (1976).
Zhang, W., et al., "Synthesis of Benzo-Fused Bensodiazepines Employed as Probes of the Agonist Pharmacophore of Benzodiazepine Receptors," J Med Chem., 37(6):745-757 (1994).

* cited by examiner

SEQUENCE LISTING

```
Sequence total quantity: 2
SEQ ID NO: 1            moltype = DNA  length = 2787
FEATURE                 Location/Qualifiers
source                  1..2787
                        mol_type = other DNA
                        organism = Homo sapiens
SEQUENCE: 1
atgccgccca aaaccccccg aaaaacggcc gccaccgccg ccgctgccgc cgcggaaccc  60
ccggcaccgc cgccgccgcc ccctcctgag gaggacccag agcaggacag cggcccggag  120
gacctgcctc tcgtcaggct tgagtttgaa gaaacagaag aacctgattt tactgcatta  180
tgtcagaaat taaagatacc agatcatgtc agagagagag cttggttaac ttgggagaaa  240
gtttcatctg tggatggagt attgggaggt tatattcaaa agaaaaagga actgtgggga  300
atctgtatct ttattgcagc agttgaccta gatgagatgt cgttcacttt tactgagcta  360
cagaaaaaca tagaaatcag tgtccataaa ttctttaact tactaaaaga aattgatacc  420
agtaccaaag ttgataatgc tatgtcaaga ctgttgaaga agtatgatgt attgtttgca  480
ctcttcagca aattggaaag gacatgtgaa cttatatatt tgacacaacc cagcagttcg  540
atatctactg aaataaattc tgcattggtg ctaaaagttt cttggatcac atttttatta  600
gctaaagggg aagtattaca aatggaagat gatctggtga tttcatttca gttaatgcta  660
tgtgtccttg actattttat taaactctca cctcccatgt tgctcaaaga accatataaa  720
acagctgtta tacccattaa tggttcacct cgaacaccca ggcgaggtca gaacaggagt  780
gcacggatag caaaacaact agaaaatgat acaagaatta ttgaagttct ctgtaaagaa  840
catgaatgta atatagatga ggtgaaaaat gtttatttca aaaattttat accttttatg  900
aattctcttg gacttgtaac atctaatgga cttccagagg ttgaaaatct ttctaaacga  960
tacgaagaaa tttatcttaa aaataaagat ctagatgcaa gattattttt ggatcatgat  1020
aaaactcttc agactgattc tatagacagt tttgaaacac agagaacacc acgaaaaagt  1080
aaccttgatg aagaggtgaa tgtaattcct ccacacactc cagttaggac tgttatgaac  1140
actatccaac aattaatgat gattttaaat tcagcaagtg atcaaccttc agaaaatctg  1200
atttcctatt ttaacaactg cacagtgaat ccaaaagaaa gtatactgaa aagagtgaag  1260
gatataggat acatctttaa agagaaattt gctaaagctg tgggacaggg ttgtgtcgaa  1320
attggatcac agcgatacaa acttggagtt cgcttgtatt accgagtaat ggaatccatg  1380
cttaaatcag aagaagaacg attatccatt caaaatttta gcaaacttct gaatgacaac  1440
```

-continued

```
atttttcata tgtctttatt ggcgtgcgct cttgaggttg taatggccac atatagcaga  1500
agtacatctc agaatcttga ttctggaaca gatttgtctt tcccatggat tctgaatgtg  1560
cttaatttaa aagcctttga tttttacaaa gtgatcgaaa gttttatcaa agcagaaggc  1620
aacttgacaa gagaaatgat aaaacattta gaacgatgtg aacatcgaat catggaatcc  1680
cttgcatggc tctcagattc acctttattt gatcttatta aacaatcaaa ggaccgagaa  1740
ggaccaactg atcaccttga atctgcttgt cctcttaatc ttcctctcca gaataatcac  1800
actgcagcag atatgtatct ttctcctgta agatctccaa agaaaaaagg ttcaactacg  1860
cgtgtaaatt ctactgcaaa tgcagagaca caagcaacct cagccttcca gacccagaag  1920
ccattgaaat ctacctctct ttcactgttt tataaaaaag tgtatcggct agcctatctc  1980
cggctaaata cactttgtga acgccttctg tctgagcacc cagaattaga acatatcatc  2040
tggacccttt tccagcacac cctgcagaat gagtatgaac tcatgagaga caggcatttg  2100
gaccaaatta tgatgtgttc catgtatggc atatgcaaag tgaagaatat agaccttaaa  2160
ttcaaaatca ttgtaacagc atacaaggat cttcctcatg ctgttcagga gacattcaaa  2220
cgtgttttga tcaaagaaga ggagtatgat tctattatag tattctataa ctcggtcttc  2280
atgcagagac tgaaaacaaa tattttgcag tatgcttcca ccaggccccc taccttgtca  2340
ccaatacctc acattcctcg aagcccttac aagtttccta gttcaccctt acggattcct  2400
ggagggaaca tctatatttc acccctgaag agtccatata aaatttcaga aggtctgcca  2460
acaccaacaa aaatgactcc aagatcaaga atcttagtat caattggtga atcattcggg  2520
acttctgaga agttccagaa aataaatcag atggtatgta acagcgaccg tgtgctcaaa  2580
agaagtgctg aaggaagcaa ccctcctaaa ccactgaaaa aactacgctt tgatattgaa  2640
ggatcagatg aagcagatgg aagtaaacat ctcccaggag agtccaaatt tcagcagaaa  2700
ctggcagaaa tgacttctac tcgaacacga atgcaaaagc agaaaatgaa tgatagcatg  2760
gatacctcaa acaaggaaga gaaatga                                    2787

SEQ ID NO: 2            moltype = AA  length = 928
FEATURE                 Location/Qualifiers
source                  1..928
                        mol_type = protein
                        organism = Homo sapiens
SEQUENCE: 2
MPPKTPRKTA ATAAAAAAEP PAPPPPPPPE EDPEQDSGPE DLPLVRLEFE ETEEPDFTAL  60
CQKLKIPDHV RERAWLTWEK VSSVDGVLGG YIQKKKELWG ICIFIAAVDL DEMSFTFTEL  120
QKNIEISVHK FFNLLKEIDT STKVDNAMSR LLKKYDVLFA LFSKLERTCE LIYLTQPSSS  180
ISTEINSALV LKVSWITFLL AKGEVLQMED DLVISFQLML CVLDYFIKLS PPMLLKEPYK  240
TAVIPINGSP RTPRRGQNRS ARIAKQLEND TRIIEVLCKE HECNIDEVKN VYFKNFIPFM  300
NSLGLVTSNG LPEVENLSKR YEEIYLKNKD LDARLFLDHD KTLQTDSIDS FETQRTPRKS  360
NLDEEVNVIP PHTPVRTVMN TIQQLMMILN SASDQPSENL ISYFNNCTVN PKESILKRVK  420
DIGYIFKEKF AKAVGQGCVE IGSQRYKLGV RLYYRVMESM LKSEEERLSI QNFSKLLNDN  480
IFHMSLLACA LEVVMATYSR STSQNLDSGT DLSFPWILNV LNLKAFDFYK VIESFIKAEG  540
NLTREMIKHL ERCEHRIMES LAWLSDSPLF DLIKQSKDRE GPTDHLESAC PLNLPLQNNH  600
TAADMYLSPV RSPKKKGSTT RVNSTANAET QATSAFQTQK PLKSTSLSLF YKKVYRLAYL  660
RLNTLCERLL SEHPELEHII WTLFQHTLQN EYELMRDRHL DQIMMCSMYG ICKVKNIDLK  720
FKIIVTAYKD LPHAVQETFK RVLIKEEEYD SIIVFYNSVF MQRLKTNILQ YASTRPPTLS  780
PIPHIPRSPY KFPSSPLRIP GGNIYISPLK SPYKISEGLP TPTKMTPRSR ILVSIGESFG  840
TSEKFQKINQ MVCNSDRVLK RSAEGSNPPK PLKKLRFDIE GSDEADGSKH LPGESKFQQK  900
LAEMTSTRTR MQKQKMNDSM DTSNKEEK                                   928
```

NITROGEN-CONTAINING HETEROCYCLIC COMPOUND HAVING MYT1 INHIBITORY ACTIVITY

CROSS-REFERENCE TO RELATED APPLICATIONS

This application is a continuation of PCT Application No. PCT/JP2024/007072, filed Feb. 27, 2024, which claims the benefit of Japanese Patent Application No. 2023-029673, filed Feb. 28, 2023, each of which is incorporated herein by reference in its entirety.

REFERENCE TO SEQUENCE LISTING SUBMITTED ELECTRONICALLY

The content of the electronically submitted sequence listing (Name: 6663_0365_Sequence_Listing.xml; Size: 6,485 bytes; and Date of Creation: Aug. 22, 2025) filed with the application is incorporated herein by reference in its entirety.

TECHNICAL FIELD

The present invention relates to a nitrogen-containing heterocyclic compound having MYT1 inhibitory activity or a salt thereof, or a solvate thereof. The present invention also relates to a medicament useful for treatment and prevention of cancer containing any of them as the active ingredient.

BACKGROUND ART

Cells are daily exposed to exogenous or endogenous stress factors, and DNA thereof is damaged. Usually, cells whose DNA is damaged repair DNA damage by activating the DDR (DNA damage response) pathway. Many types of cancers are known to have an abnormality in gene and protein involved in the DDR pathway, and treatment methods are examined (Non Patent Literatures 1 to 2). One of the treatment methods for cancer having an abnormality in the gene and the protein involved in the DDR pathway is use of a PARP inhibitor, which is used for the treatment of cancer having a BRCA1 mutation or a BRCA2 mutation (Non Patent Literature 3). Moreover, the gene and the protein involved in the DDR pathway, ATM, ATR, CHK1, DNA-PK, WEE1, and the like are mentioned as the target candidates to date, and intensively researched (Non Patent Literature 4).

MYT1 is an enzyme of the WEE1 family and is known as a negative adjustment factor of CDK1. MYT1 inactivates CDK1 by phosphorylation and plays an important role in cell cycle regulation. In recent years, a new MYT1 inhibitor is reported to cause synthetic lethality in specific cancers (Non Patent Literature 5). However, there is no approved pharmaceuticals yet, and thus a new therapeutic agent is desired.

CITATION LIST

Non Patent Literature

[Non Patent Literature 1] Cancers (Basel), 2020 Apr. 23; 12 (4): 1050.

[Non Patent Literature 2] Front Pharmacol., 2021 Feb. 8; 11:629266.

[Non Patent Literature 3] N. Engl. J. Med., 2018 Dec. 27; 379 (26): 2495-2505.

[Non Patent Literature 4] Nat. Rev. Cancer, 2023 23, 78-94.

[Non Patent Literature 5] Nature, 2022 April; 604 (7907): 749-756.

[Non Patent Literature 6] T. W. Greene, P. G. M. Wuts, Protective Groups in Organic Synthesis (5th edition, John Wiley & Sons 2014)

[Non Patent Literature 7] Tetrahedron Lett., 2019 vol. 60, 151147

[Non Patent Literature 8] Chem. Rev., 1995, vol. 95, no. 7, p. 2457-2483.

[Non Patent Literature 9] Acc. Chem. Res., 2008, vol. 41, No. 11, p. 1461-1473.

[Non Patent Literature 10] Synthesis, 1992, vol. 9, p. 803-815.

[Non Patent Literature 11] Org. Process Res. Dev., 2018, vol. 22, no. 4, p. 430-445.

[Non Patent Literature 12] Tetrahedron, 1992, vol. 48, no. 44, p. 9577-9648.

[Non Patent Literature 13] Aldrichimica Acta, 2005, vol. 38, no. 4, p. 71-88.

[Non Patent Literature 14] Chem. Soc. Rev., 2011, vol. 40, p. 5084-5121.

[Non Patent Literature 15] Chem. Rev., 2016, vol. 116, p. 12564-12649.

[Non Patent Literature 16] Org. Process Res. Dev., 2022, vol. 26, no. 6, p. 1690-1750.

[Non Patent Literature 17] J. Am. Chem. Soc., 2016, vol. 138, no. 26, p. 8084-8087.

[Non Patent Literature 18] ACS Med. Chem. Lett., 2020, vol. 11, no. 4, p. 597-604.

[Non Patent Literature 19] Nature, 2021, 598, p. 451-456.

[Non Patent Literature 20] ACS Cent. Sci. 2017, vol. 3, issue 6, p. 647-653.

[Non Patent Literature 21] Tetrahedron 2008, vol. 64, p. 5139-5146.

[Non Patent Literature 22] Nature. 2019 May; 569 (7757): 503-508.

[Non Patent Literature 23] PLOS Comput Biol. 2019 May 20; 15 (5): e1006752.

SUMMARY OF INVENTION

Problems to be Solved by the Invention

An object of the present invention is to provide a compound having new MYT1 inhibitory activity or a salt thereof, or a solvate thereof. Another object is to provide a medicament useful for treatment and prevention of cancer containing any of them as the active ingredient.

Means for Solving the Problems

That is, in one aspect of the present invention, the following inventions are provided.

[A1]

A compound represented by the formula (1):

[Formula 1]

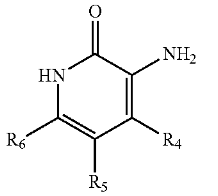

(1)

wherein $R_4$ is selected from the group consisting of optionally substituted $C_6$-$C_{10}$ aryl ($R_{4A}$), optionally substituted 4- to 10-membered heterocyclyl, and optionally substituted 5- to 10-membered heteroaryl ($R_{4HA}$);

$R_5$ and $R_6$, together with the atoms to which they are attached, form optionally substituted Ring D;

Ring D is selected from the group consisting of a 3- to 10-membered monocyclic cycloaliphatic ring, a benzene ring, a 3- to 12-membered monocyclic heterocyclic ring, and a 5- to 6-membered monocyclic aromatic heterocyclic ring ($D_{HA}$); and any two adjacent substituents on Ring D, together with the atoms to which they are attached, may form optionally substituted Ring E;

or a salt thereof, or a solvate thereof.

[A2]

The compound or a salt thereof, or a solvate thereof according to [A1], wherein Ring D is a benzene ring or a 5- to 6-membered monocyclic aromatic heterocyclic ring ($D_{HA}$).

[A3]

The compound or a salt thereof, or a solvate thereof according to [A1], wherein Ring D is a benzene ring.

[A4]

The compound according to [A1], wherein Ring D is a 5- to 6-membered monocyclic aromatic heterocyclic ring ($D_{HA}$), or a salt thereof, or a solvate thereof.

[A5]

The compound or a salt thereof, or a solvate thereof according to [A4], wherein the 5- to 6-membered monocyclic aromatic heterocyclic ring ($D_{HA}$) is selected from the group consisting of a furan ring, a thiophene ring, a pyrrole ring, an imidazole ring, a pyrazole ring, a thiazole ring, an isothiazole ring, an oxazole ring, an isoxazole ring, an oxadiazole ring, a thiadiazole ring, a triazole ring, a tetrazole ring, a pyridine ring, a pyrimidine ring, a pyridazine ring, a pyrazine ring, and a triazine ring.

[A6]

The compound or a salt thereof, or a solvate thereof according to [A4], wherein the 5- to 6-membered monocyclic aromatic heterocyclic ring ($D_{HA}$) is selected from the group consisting of a pyridine ring, a pyrimidine ring, a pyridazine ring, and a pyrazine ring.

[A7]

The compound or a salt thereof, or a solvate thereof according to [A4], wherein the 5- to 6-membered monocyclic aromatic heterocyclic ring ($D_{HA}$) is a pyridine ring.

[A8]

The compound or a salt thereof, or a solvate thereof according to any of [A1] to [A7], wherein Ring D is unsubstituted or substituted with one or more $R_D$;

each of one or more $R_D$ is independently selected from the group consisting of deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, oxo, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted.

[A9]

The compound or a salt thereof, or a solvate thereof according to any of [A1] to [A7], wherein Ring D is unsubstituted or substituted with one or more $R_D$;

each of one or more $R_D$ is independently selected from the group consisting of halogen, cyano, hydroxy, $C_1$-$C_6$ alkylthio, $C_1$-$C_6$ acylamino, mono $C_1$-$C_6$ alkylamino, $C_1$-$C_6$ alkylsulfonylamino, $C_3$-$C_8$ cycloalkylsulfonylamino, $C_1$-$C_6$ alkoxy, halo $C_1$-$C_6$ alkoxy, hydroxy $C_1$-$C_6$ alkoxy, $C_1$-$C_6$ alkoxy $C_1$-$C_6$ alkoxy, $C_3$-$C_8$ cycloalkyl $C_1$-$C_6$ alkoxy, 4- to 10-membered heterocyclyl $C_1$-$C_6$ alkoxy, $C_3$-$C_8$ cycloalkoxy, 4- to 10-membered heterocyclyloxy, $C_1$-$C_6$ acyl, mono $C_3$-$C_8$ cycloalkylaminocarbonyl, 4- to 8-membered cyclic aminocarbonyl, di $C_1$-$C_6$ alkylphosphoryl, $C_1$-$C_6$ alkyl, halo $C_1$-$C_6$ alkyl, hydroxy $C_1$-$C_6$ alkyl, di $C_1$-$C_6$ alkylaminocarbonyl $C_1$-$C_6$ alkyl, $C_3$-$C_8$ cycloalkyl $C_1$-$C_6$ alkyl, $C_2$-$C_6$ alkenyl, hydroxy $C_2$-$C_6$ alkenyl, $C_2$-$C_6$ alkynyl, hydroxy $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the $C_1$-$C_6$ alkylthio, $C_1$-$C_6$ alkoxy, $C_1$-$C_6$ alkoxy $C_1$-$C_6$ alkoxy, $C_3$-$C_8$ cycloalkyl $C_1$-$C_6$ alkoxy, 4- to 10-membered heterocyclyl $C_1$-$C_6$ alkoxy, $C_3$-$C_8$ cycloalkoxy, 4- to 10-membered heterocyclyloxy, $C_1$-$C_6$ alkyl, $C_3$-$C_8$ cycloalkyl $C_1$-$C_6$ alkyl, $C_3$-$C_8$ cycloalkyl, 4- to 10-membered heterocyclyl, $C_6$-$C_{10}$ aryl, and 5- to 10-membered heteroaryl are independently optionally substituted with one or more substituents selected from the group consisting of halogen, cyano, hydroxy, $C_1$-$C_6$ alkyl, $C_1$-$C_6$ alkoxy, oxo, halo $C_1$-$C_6$ alkyl, and $C_3$-$C_8$ cycloalkyl.

[A10]

The compound or a salt thereof, or a solvate thereof according to any of [A1] to [A7], wherein Ring D is unsubstituted or substituted with one or more $R_D$; and each of one or more $R_D$ is independently selected from the group consisting of halogen, $C_1$-$C_6$ alkoxy, halo $C_1$-$C_6$ alkoxy, $C_3$-$C_8$ cycloalkyl $C_1$-$C_6$ alkoxy, $C_3$-$C_8$ cycloalkoxy, $C_1$-$C_6$ alkyl, halo $C_1$-$C_6$ alkyl, $C_3$-$C_8$ cycloalkyl $C_1$-$C_6$ alkyl, and $C_3$-$C_8$ cycloalkyl.

[A11]

The compound or a salt thereof, or a solvate thereof according to any of [A1] to [A7], wherein Ring D is unsubstituted or substituted with one or more $R_D$; and each of one or more $R_D$ is independently selected from the group consisting of $C_1$-$C_6$ alkoxy, $C_1$-$C_6$ alkyl, and $C_3$-$C_8$ cycloalkyl.

[A12]

The compound or a salt thereof, or a solvate thereof according to any of [A1] to [A7], wherein Ring D is unsubstituted or substituted with one or more $R_D$; and each of one or more $R_D$ is independently selected from the group consisting of methoxy, ethoxy, propoxy, propan-2-yloxy, 3-methylbutoxy, [(2S)-butan-2-yl]oxy, [(2R)-butan-2-yl]oxy, methyl, ethyl, propyl, propan-2-yl, 2-methylpropyl, butan-2-yl, 3-methylbutyl, pentan-3-yl, cyclopropyl, cyclobutyl, cyclopentyl, 1-methylcyclopropyl, 3,3-dimethylcyclobutyl, and spiro[2.3]hexan-5-yl.

[A13]

The compound or a salt thereof, or a solvate thereof according to any of [A1] to [A12], wherein any two adjacent substituents on Ring D, together with the atoms to which they are attached, form optionally substituted Ring E.

[A14]

The compound or a salt thereof, or a solvate thereof according to any of [A1] to [A13], wherein Ring E is selected from the group consisting of a 3- to 10-membered monocyclic cycloaliphatic ring, a benzene ring, a 3- to 12-membered monocyclic heterocyclic ring, and a 5- to 6-membered monocyclic aromatic heterocyclic ring (EHA).

[A15]

The compound or a salt thereof, or a solvate thereof according to any of [A1] to [A13], wherein Ring E is a benzene ring or a 5- to 6-membered monocyclic aromatic heterocyclic ring (EHA).

[A16]

The compound or a salt thereof, or a solvate thereof according to any of [A1] to [A13], wherein Ring E is a benzene ring.

[A17]

The compound or a salt thereof, or a solvate thereof according to any of [A1] to [A13], wherein Ring E is a 5- to 6-membered monocyclic aromatic heterocyclic ring (EHA).

[A18]

The compound or a salt thereof, or a solvate thereof according to [A17], wherein the 5- to 6-membered monocyclic aromatic heterocyclic ring (EHA) is selected from the group consisting of a furan ring, a thiophene ring, a pyrrole ring, an imidazole ring, a pyrazole ring, a thiazole ring, an isothiazole ring, an oxazole ring, an isoxazole ring, an oxadiazole ring, a thiadiazole ring, a triazole ring, a tetrazole ring, a pyridine ring, a pyrimidine ring, a pyridazine ring, a pyrazine ring, and a triazine ring.

[A19]

The compound or a salt thereof, or a solvate thereof according to [A17], wherein the 5- to 6-membered monocyclic aromatic heterocyclic ring (EHA) is selected from the group consisting of a thiophene ring, an imidazole ring, a pyrazole ring, a thiazole ring, an isothiazole ring, a pyridine ring, a pyrimidine ring, a pyridazine ring, and a pyrazine ring.

[A20]

The compound or a salt thereof, or a solvate thereof according to [A17], wherein the 5- to 6-membered monocyclic aromatic heterocyclic ring (EHA) is selected from the group consisting of a pyridine ring, a pyrimidine ring, a pyridazine ring, and a pyrazine ring.

[A20.5]

The compound or a salt thereof, or a solvate thereof according to [A17], wherein the 5- to 6-membered monocyclic aromatic heterocyclic ring (EHA) is a pyridine ring or a pyrazine ring.

[A21]

The compound or a salt thereof, or a solvate thereof according to [A17], wherein the 5- to 6-membered monocyclic aromatic heterocyclic ring (EHA) is a pyridine ring.

[A22]

The compound or a salt thereof, or a solvate thereof according to [A17], wherein Ring D and Ring E form a bicycle represented by the following formula:

[Formula 2]

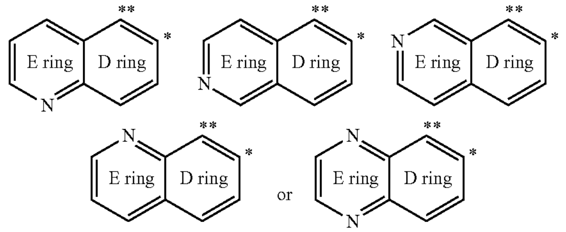

or wherein * represents a carbon to which $R_5$ is attached in the formula (1), and ** represents a carbon to which $R_6$ is attached in the formula (1); the Ring D is referred to as "D ring" and the Ring E is referred to as "E ring" in the formula.

[A23]

The compound or a salt thereof, or a solvate thereof according to [A17], wherein Ring D and Ring E form a bicycle represented by the following formula:

[Formula 3]

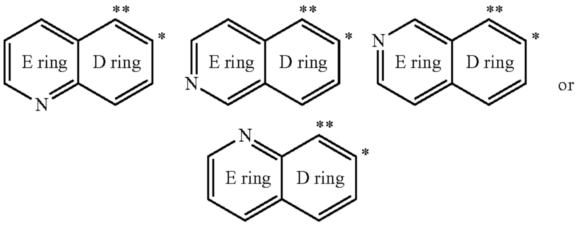

or wherein * represents a carbon to which $R_5$ is attached in the formula (1), and ** represents a carbon to which $R_6$ is attached in the formula (1); the Ring D is referred to as "D ring" and the Ring E is referred to as "E ring" in the formula.

[A24]

The compound or a salt thereof, or a solvate thereof according to any of [A14] to [A23], wherein Ring E is unsubstituted or substituted with one or more $R_E$;

each of one or more $R_E$ is independently selected from the group consisting of deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, oxo, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted.

[A25]

The compound or a salt thereof, or a solvate thereof according to any of [A14] to [A23], wherein Ring E is unsubstituted or substituted with one or more $R_E$; and each of one or more $R_E$ is independently selected from the group consisting of halogen, $C_1$-$C_6$ alkyl, $C_1$-$C_6$ alkoxy, and boryl.

[A25.5]

The compound or a salt thereof, or a solvate thereof according to any of [A14] to [A23], wherein Ring E is unsubstituted or substituted with one or more $R_E$; and each of one or more $R_E$ is independently selected from the group consisting of fluorine, chlorine, methoxy, dihydroxyboryl, methyl, and t-butyl.

[A26]

The compound or a salt thereof, or a solvate thereof according to any of [A1] to [A25.5], wherein $R_4$ is optionally substituted $C_6$-$C_{10}$ aryl ($R_{4A}$) or optionally substituted 5- to 10-membered heteroaryl ($R_{4HA}$).

[A27]

The compound or a salt thereof, or a solvate thereof according to any of [A1] to [A26], wherein $R_4$ is optionally substituted $C_6$-$C_{10}$ aryl ($R_{4A}$).

[A28]

The compound or a salt thereof, or a solvate thereof according to [A26] or [A27], wherein the $C_6$-$C_{10}$ aryl ($R_{4A}$) is phenyl.

[A29]

The compound or a salt thereof, or a solvate thereof according to any of [A26] to [A28], wherein the $C_6$-$C_{10}$ aryl ($R_{4A}$) is unsubstituted or substituted with one or more $R_a$;

each of one or more $R_a$ is independently selected from the group consisting of deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, oxo, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted.

[A30]

The compound or a salt thereof, or a solvate thereof according to any of [A26] to [A28], wherein the $C_6$-$C_{10}$ aryl ($R_{4A}$) is unsubstituted or substituted with one or more $R_a$; and each of one or more $R_a$ is independently selected from the group consisting of halogen, cyano, hydroxy, amino, $C_1$-$C_6$ alkyl, halo $C_1$-$C_6$ alkyl, hydroxy $C_1$-$C_6$ alkyl, $C_1$-$C_6$ alkoxy, halo $C_1$-$C_6$ alkoxy, and $C_1$-$C_6$ alkylsulfonylamino.

[A31]

The compound or a salt thereof, or a solvate thereof according to any of [A26] to [A28], wherein the $C_6$-$C_{10}$ aryl ($R_{4A}$) is unsubstituted or substituted with one or more $R_a$; and each of one or more $R_a$ is independently selected from the group consisting of halogen, hydroxy, halo $C_1$-$C_6$ alkyl, $C_1$-$C_6$ alkoxy, halo $C_1$-$C_6$ alkoxy, and $C_1$-$C_6$ alkylsulfonylamino.

[A32]

The compound or a salt thereof, or a solvate thereof according to any of [A1] to [A26], wherein $R_4$ is optionally substituted 5- to 10-membered heteroaryl ($R_{4HA}$).

[A33]

The compound or a salt thereof, or a solvate thereof according to [A26] or [A32], wherein the 5- to 10-membered heteroaryl ($R_{4HA}$) is selected from the group consisting of furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, benzotriazolyl, indolyl, isoindolyl, indazolyl, azaindolyl, quinolyl, isoquinolyl, cinnolinyl, quinazolinyl, quinoxalinyl, indolizinyl, imidazopyridyl, pyrazolopyridyl, triazolopyridyl, pyrrolopyrazinyl, and flopyridyl.

[A34]

The compound or a salt thereof, or a solvate thereof according to [A26] or [A32], wherein the 5- to 10-membered heteroaryl ($R_{4HA}$) is selected from the group consisting of furyl, thienyl, pyrrolyl, pyrazolyl, thiazolyl, isothiazolyl, oxazolyl, isoxazolyl, oxadiazolyl, thiadiazolyl, triazolyl, tetrazolyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, benzotriazolyl, indolyl, isoindolyl, indazolyl, azaindolyl, quinolyl, isoquinolyl, cinnolinyl, quinazolinyl, quinoxalinyl, indolizinyl, imidazopyridyl, pyrazolopyridyl, triazolopyridyl, pyrrolopyrazinyl, and flopyridyl.

[A35]

The compound or a salt thereof, or a solvate thereof according to [A26] or [A32], wherein the 5- to 10-membered heteroaryl ($R_{4HA}$) is selected from the group consisting of pyridyl, pyrimidyl, benzimidazolyl, indolyl, indazolyl, and pyrazolopyridyl.

[A36]

The compound or a salt thereof, or a solvate thereof according to [A26] or [A32], wherein the 5- to 10-membered heteroaryl ($R_{4HA}$) is selected from the group consisting of pyrimidyl, benzimidazolyl, indolyl, indazolyl, and pyrazolopyridyl.

[A37]

The compound or a salt thereof, or a solvate thereof according to [A26] or [A32], wherein the 5- to 10-membered heteroaryl ($R_{4HA}$) is 1H-indazol-6-yl or 1H-indazol-4-yl.

[A38]

The compound or a salt thereof, or a solvate thereof according to [A26] or [A32], wherein the 5- to 10-membered heteroaryl ($R_{4HA}$) is 1H-indazol-4-yl.

[A39]

The compound or a salt thereof, or a solvate thereof according to any of [A32] to [A38], wherein the 5- to 10-membered heteroaryl ($R_{4HA}$) is unsubstituted or substituted with one or more $R_a$;

each of one or more $R_a$ is independently selected from the group consisting of deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, oxo, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted.

[A40]

The compound or a salt thereof, or a solvate thereof according to any of [A32] to [A38], wherein the 5- to 10-membered heteroaryl ($R_{4HA}$) is unsubstituted or substituted with one or more $R_a$; and each of one or more $R_a$ is independently selected from the group consisting of halogen, cyano, hydroxy, amino, $C_1$-$C_6$ alkyl, halo $C_1$-$C_6$ alkyl, hydroxy $C_1$-$C_6$ alkyl, $C_1$-$C_6$ alkoxy, halo $C_1$-$C_6$ alkoxy, and $C_1$-$C_6$ alkylsulfonylamino.

[A41]

The compound or a salt thereof, or a solvate thereof according to any of [A32] to [A38], wherein the 5- to 10-membered heteroaryl ($R_{4HA}$) is unsubstituted or substituted with one or more $R_a$; and each of one or more $R_a$ is independently selected from the group consisting of halogen, cyano, amino, $C_1$-$C_6$ alkyl, and halo $C_1$-$C_6$ alkyl.

[A42]

The compound or a salt thereof, or a solvate thereof according to any of [A32] to [A38], wherein the 5- to 10-membered heteroaryl ($R_{4HA}$) is 1H-indazol-4-yl, or 1H-indazol-4-yl substituted with one or more halogens.

[A43]

The compound or a salt thereof, or a solvate thereof according to any of [A32] to [A38], wherein the 5- to 10-membered heteroaryl ($R_{4HA}$) is 1H-indazol-4-yl substituted with one or more halogens.

[A44]

The compound or a salt thereof, or a solvate thereof according to any of [A32] to [A38], wherein the 5- to 10-membered heteroaryl ($R_{4HA}$) is 1H-indazol-4-yl in which at least one of position 5, position 6, and position 7 is substituted with a halogen.

[A44.5]

The compound or a salt thereof, or a solvate thereof according to any of [A32] to [A38], wherein the 5- to 10-membered heteroaryl ($R_{4HA}$) is represented by the following formula:

[Formula 4]

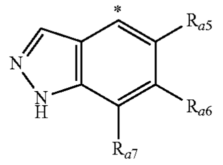

wherein * represents carbon to which $R_4$ is bonded in the formula (1), $R_{a5}$, $R_{a6}$, and $R_{a7}$ are each independently hydrogen or halogen, and at least one of $R_{a5}$, $R_{a6}$, and $R_{a7}$ is not hydrogen.

[A45]

The compound or a salt thereof, or a solvate thereof according to any of [A32] to [A38], wherein the 5- to 10-membered heteroaryl ($R_{4HA}$) is 1H-indazol-4-yl in which at least one of position 5, position 6, and position 7 is substituted with a halogen; and the halogen is fluorine or chlorine.

[A46]

The compound or a salt thereof, or a solvate thereof according to any of [A32] to [A38], wherein the 5- to 10-membered heteroaryl ($R_{4HA}$) is 1H-indazol-4-yl in which any one or two of position 5, position 6, and position 7 are substituted with a halogen; and the halogen is selected from the group consisting of fluorine, chlorine, a combination of fluorine and fluorine, and a combination of fluorine and chlorine.

[A46.5]

The compound or a salt thereof, or a solvate thereof according to any of [A32] to [A38], wherein the 5- to 10-membered heteroaryl ($R_{4HA}$) is 1H-indazol-4-yl substituted at any one or two of positions 5, 6, and 7 by halogen, and the halogen is independently fluorine or chlorine.

[B1]

A compound or a salt thereof, or a solvate thereof represented by the formula (2):

[Formula 5]

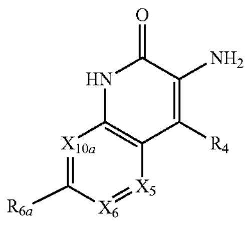

(2)

wherein $R_4$ is selected from the group consisting of optionally substituted $C_6$-$C_{10}$ aryl ($R_{4A}$), optionally substituted 4- to 10-membered heterocyclyl, and optionally substituted 5- to 10-membered heteroaryl ($R_{4HA}$);

$X_5$ is $CR_{x5}$ or N;

$X_6$ is $CR_{x6}$ or N;

$X_{10a}$ is $CR_{x10a}$ or N;

each of $R_{x5}$, $R_{x6}$, $R_{6a}$, and $R_{x10a}$ is independently selected from the group consisting of hydrogen, deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl;

the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted; and $R_{x5}$ and $R_{x6}$, $R_{x6}$ and $R_{6a}$, or $R_{6a}$ and $R_{x10a}$, together with the atoms to which they are attached, may form optionally substituted Ring E.

[B2]

The compound or a salt thereof, or a solvate thereof according to [B1], wherein $X_5$ is $CR_{x5}$ or N;

$X_6$ is $CR_{x6}$; and $X_{10a}$ is $CR_{x10a}$ or N.

[B3]

The compound or a salt thereof, or a solvate thereof according to [B1] or [B2], wherein $X_5$ is CH;

$X_6$ is $CR_{x6}$; and $X_{10a}$ is $CR_{x10a}$.

[B4]

The compound or a salt thereof, or a solvate thereof according to any of [B1] to [B3], wherein $R_{x6}$ is selected from the group consisting of hydrogen, halogen, hydroxy, $C_1$-$C_6$ alkylthio, $C_1$-$C_6$ acylamino, mono $C_1$-$C_6$ alkylamino, $C_1$-$C_6$ alkylsulfonylamino, $C_3$-$C_8$ cycloalkylsulfonylamino, $C_1$-$C_6$ alkoxy, halo $C_1$-$C_6$ alkoxy, hydroxy $C_1$-$C_6$ alkoxy, $C_1$-$C_6$ alkoxy $C_1$-$C_6$ alkoxy, $C_3$-$C_8$ cycloalkyl $C_1$-$C_6$ alkoxy, 4- to 10-membered heterocyclyl $C_1$-$C_6$ alkoxy, $C_3$-$C_8$ cycloalkoxy, 4- to 10-membered heterocyclyloxy, $C_1$-$C_6$ acyl, mono $C_3$-$C_8$ cycloalkylaminocarbonyl, 4- to 8-membered cyclic aminocarbonyl, di $C_1$-$C_6$ alkylphosphoryl, $C_1$-$C_6$ alkyl, halo $C_1$-$C_6$ alkyl, hydroxy $C_1$-$C_6$ alkyl, di $C_1$-$C_6$ alkylaminocarbonyl $C_1$-$C_6$ alkyl, $C_3$-$C_8$ cycloalkyl $C_1$-$C_6$ alkyl, $C_2$-$C_6$ alkenyl, hydroxy $C_2$-$C_6$ alkenyl, $C_2$-$C_6$ alkynyl, hydroxy $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the $C_1$-$C_6$ alkylthio, $C_1$-$C_6$ alkoxy, $C_1$-$C_6$ alkoxy $C_1$-$C_6$ alkoxy, $C_3$-$C_8$ cycloalkyl $C_1$-$C_6$ alkoxy, 4- to 10-membered heterocyclyl $C_1$-$C_6$ alkoxy, $C_3$-$C_8$ cycloalkoxy, 4- to 10-membered heterocyclyloxy, $C_1$-$C_6$ alkyl, $C_3$-$C_8$ cycloalkyl $C_1$-$C_6$ alkyl, $C_3$-$C_8$ cycloalkyl, 4- to 10-membered heterocyclyl, $C_6$-$C_{10}$ aryl, and 5- to 10-membered heteroaryl are independently optionally substituted with one or more substituents selected from the group consisting of halogen, cyano, hydroxy, $C_1$-$C_6$ alkyl, $C_1$-$C_6$ alkoxy, oxo, halo $C_1$-$C_6$ alkyl, and $C_3$-$C_8$ cycloalkyl.

[B5]

The compound or a salt thereof, or a solvate thereof according to any of [B1] to [B3], wherein $R_{x6}$ is selected from the group consisting of hydrogen, halogen, $C_1$-$C_6$ alkoxy, halo $C_1$-$C_6$ alkoxy, $C_3$-$C_8$ cycloalkyl $C_1$-$C_6$ alkoxy, $C_3$-$C_8$ cycloalkoxy, $C_1$-$C_6$ alkyl, halo $C_1$-$C_6$ alkyl, $C_3$-$C_8$ cycloalkyl $C_1$-$C_6$ alkyl, and $C_3$-$C_8$ cycloalkyl.

[B6]

The compound or a salt thereof, or a solvate thereof according to any of [B1] to [B3], wherein $R_{x6}$ is selected from the group consisting of hydrogen, $C_1$-$C_6$ alkoxy, $C_1$-$C_6$ alkyl, and $C_3$-$C_8$ cycloalkyl.

[B7]

The compound or a salt thereof, or a solvate thereof according to any of [B1] to [B3], wherein $R_{x6}$ is selected from the group consisting of hydrogen, methoxy, ethoxy, propoxy, propan-2-yloxy, 3-methylbutoxy, [(2S)-butan-2-yl]oxy, [(2R)-butan-2-yl]oxy, methyl, ethyl, propyl, propan-2-yl, 2-methylpropyl, butan-2-yl, 3-methylbutyl, pentan-3-yl, cyclopropyl, cyclobutyl, cyclopentyl, 1-methylcyclopropyl, 3,3-dimethylcyclobutyl, and spiro[2.3]hexan-5-yl.

[B8]

The compound or a salt thereof, or a solvate thereof according to any of [B1] to [B7], wherein $R_{x10a}$ is selected from the group consisting of hydrogen, halogen, cyano, $C_1$-$C_6$ alkyl, $C_2$-$C_6$ alkenyl, $C_2$-$C_6$ alkynyl, and $C_3$-$C_8$ cycloalkyl.

[B9]

The compound or a salt thereof, or a solvate thereof according to any of [B1] to [B7], wherein $R_{x10a}$ is selected from the group consisting of hydrogen, chlorine, bromine, cyano, methyl, ethyl, propyl, propan-2-yl, vinyl, ethynyl, and cyclopropyl.

[B10]

The compound or a salt thereof, or a solvate thereof according to any of [B1] to [B9], wherein $R_{6a}$ is selected from the group consisting of hydrogen, halogen, cyano, halo $C_1$-$C_6$ alkoxy, and $C_1$-$C_6$ alkyl.

[B11]

The compound or a salt thereof, or a solvate thereof according to any of [B1] to [B9], wherein $R_{6a}$ is selected from the group consisting of hydrogen, fluorine, chlorine, bromine, cyano, difluoromethoxy, methyl, and ethyl.

[B12]

The compound or a salt thereof, or a solvate thereof according to any of [B1] to [B7], wherein $R_{6a}$ and $R_{x10a}$, together with the atoms to which they are attached, form optionally substituted Ring E.

[B13]

The compound or a salt thereof, or a solvate thereof according to [B12], wherein Ring E is selected from the group consisting of a 3- to 10-membered monocyclic cycloaliphatic ring, a benzene ring, a 3- to 12-membered monocyclic heterocyclic ring, and a 5- to 6-membered monocyclic aromatic heterocyclic ring (EHA).

[B14]

The compound or a salt thereof, or a solvate thereof according to [B12], wherein Ring E is a benzene ring or a 5- to 6-membered monocyclic aromatic heterocyclic ring (EHA).

[B15]

The compound or a salt thereof, or a solvate thereof according to [B13] or [B14], wherein the 5- to 6-membered monocyclic aromatic heterocyclic ring (EHA) is selected from the group consisting of a thiophene ring, an imidazole ring, a pyrazole ring, a thiazole ring, an isothiazole ring, a pyridine ring, a pyrimidine ring, a pyridazine ring, and a pyrazine ring.

[B16]

The compound or a salt thereof, or a solvate thereof according to [B13] or [B14], wherein the 5- to 6-membered monocyclic aromatic heterocyclic ring (EHA) is selected from the group consisting of a pyridine ring, a pyrimidine ring, a pyridazine ring, and a pyrazine ring.

[B17]

The compound or a salt thereof, or a solvate thereof according to [B13] or [B14], wherein the 5- to 6-membered monocyclic aromatic heterocyclic ring (EHA) is a pyridine ring or a pyrazine ring.

[B18]

The compound or a salt thereof, or a solvate thereof according to [B13] or [B14], wherein the 5- to 6-membered monocyclic aromatic heterocyclic ring (EHA) is a pyridine ring.

[B19]

The compound or a salt thereof, or a solvate thereof according to [B12], wherein Ring E is represented by the following formula:

[Formula 6]

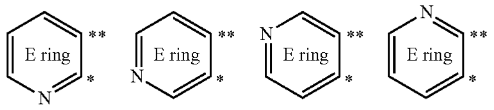

or

-continued

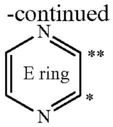

wherein * represents a carbon to which $R_{6a}$ is attached in the formula (2), and ** represents a carbon to which $R_{x10a}$ is attached in the formula (2); the Ring E is referred to as “E ring” in the formula.

[B20]

The compound or a salt thereof, or a solvate thereof according to [B12], wherein Ring E is represented by the following formula:

[Formula 7]

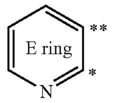 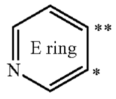 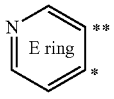 or 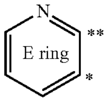

wherein * represents a carbon to which $R_{6a}$ is attached in the formula (2), and ** represents a carbon to which $R_{x10a}$ is attached in the formula (2); the Ring E is referred to as “E ring” in the formula.

[B21]

The compound or a salt thereof, or a solvate thereof according to any of [B12] to [B20], wherein Ring E is unsubstituted or substituted with one or more $R_E$;

each of one or more $R_E$ is independently selected from the group consisting of deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, oxo, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted.

[B22]

The compound or a salt thereof, or a solvate thereof according to any of [B12] to [B20], wherein Ring E is unsubstituted or substituted with one or more $R_E$; and each of one or more $R_E$ is independently selected from the group consisting of halogen, $C_1$-$C_6$ alkoxy, boryl, and $C_1$-$C_6$ alkyl.

[B23]

The compound or a salt thereof, or a solvate thereof according to any of [B12] to [B20], wherein Ring E is unsubstituted or substituted with one or more $R_E$; and each of one or more $R_E$ is independently selected from the group consisting of fluorine, chlorine, methoxy, dihydroxyboryl, methyl, and t-butyl.

[B24]

The compound or a salt thereof, or a solvate thereof according to any of [B1] to [B23], wherein $R_4$ is optionally substituted $C_6$-$C_{10}$ aryl ($R_{4A}$) or optionally substituted 5- to 10-membered heteroaryl ($R_{4HA}$).

[B25]

The compound or a salt thereof, or a solvate thereof according to any of [B1] to [B23], wherein $R_4$ is optionally substituted $C_6$-$C_{10}$ aryl ($R_{4A}$).

[B26]

The compound or a salt thereof, or a solvate thereof according to [B24] or [B25], wherein the $C_6$-$C_{10}$ aryl ($R_{4A}$) is phenyl.

[B27]

The compound or a salt thereof, or a solvate thereof according to any of [B24] to [B26], wherein the $C_6$-$C_{10}$ aryl ($R_{4A}$) is unsubstituted or substituted with one or more $R_a$;

each of one or more $R_a$ is independently selected from the group consisting of deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, oxo, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted.

[B28]

The compound or a salt thereof, or a solvate thereof according to any of [B24] to [B26], wherein the $C_6$-$C_{10}$ aryl ($R_{4A}$) is unsubstituted or substituted with one or more $R_a$; and each of one or more $R_a$ is independently selected from the group consisting of halogen, cyano, hydroxy, amino, $C_1$-$C_6$ alkyl, halo $C_1$-$C_6$ alkyl, hydroxy $C_1$-$C_6$ alkyl, $C_1$-$C_6$ alkoxy, halo $C_1$-$C_6$ alkoxy, and $C_1$-$C_6$ alkylsulfonylamino.

[B29]

The compound or a salt thereof, or a solvate thereof according to any of [B24] to [B26], wherein the $C_6$-$C_{10}$ aryl ($R_{4A}$) is unsubstituted or substituted with one or more $R_a$;

each of one or more $R_a$ is independently selected from the group consisting of halogen, hydroxy, halo $C_1$-$C_6$ alkyl, $C_1$-$C_6$ alkoxy, halo $C_1$-$C_6$ alkoxy, and $C_1$-$C_6$ alkylsulfonylamino.

[B30]

The compound or a salt thereof, or a solvate thereof according to any of [B1] to [B23], wherein $R_4$ is optionally substituted 5- to 10-membered heteroaryl ($R_{4HA}$).

[B31]

The compound or a salt thereof, or a solvate thereof according to [B24] or [B30], wherein the 5- to 10-membered heteroaryl ($R_{4HA}$) is selected from the group consisting of furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, benzotriazolyl, indolyl, isoindolyl, indazolyl, azaindolyl, quinolyl, isoquinolyl, cinnolinyl, quinazolinyl, quinoxalinyl, indolizinyl, imidazopyridyl, pyrazolopyridyl, triazolopyridyl, pyrrolopyrazinyl, and flopyridyl.

[B32]

The compound or a salt thereof, or a solvate thereof according to [B24] or [B30], wherein the 5- to 10-membered heteroaryl ($R_{4HA}$) is selected from the group consisting of furyl, thienyl, pyrrolyl, pyrazolyl, thiazolyl, isothiazolyl, oxazolyl, isoxazolyl, oxadiazolyl, thiadiazolyl, triazolyl, tetrazolyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, benzotriazolyl, indolyl, isoindolyl, indazolyl, azaindolyl, quinolyl, isoquinolyl, cinnolinyl, quinazolinyl, quinoxalinyl, indolizinyl, imidazopyridyl, pyrazolopyridyl, triazolopyridyl, pyrrolopyrazinyl and flopyridyl.

[B33]

The compound or a salt thereof, or a solvate thereof according to [B24] or [B30], wherein the 5- to 10-membered heteroaryl ($R_{4HA}$) is selected from the group consisting of pyridyl, pyrimidyl, benzimidazolyl, indolyl, indazolyl, and pyrazolopyridyl.

[B34]

The compound or a salt thereof, or a solvate thereof according to [B24] or [B30], wherein the 5- to 10-membered heteroaryl ($R_{4HA}$) is selected from the group consisting of pyrimidyl, benzimidazolyl, indolyl, indazolyl, and pyrazolopyridyl.

[B35]

The compound or a salt thereof, or a solvate thereof according to [B24] or [B30], wherein the 5- to 10-membered heteroaryl ($R_{4HA}$) is 1H-indazol-6-yl or 1H-indazol-4-yl.

[B36]

The compound or a salt thereof, or a solvate thereof according to [B24] or [B30], wherein the 5- to 10-membered heteroaryl ($R_{4HA}$) is 1H-indazol-4-yl.

[B37]

The compound or a salt thereof, or a solvate thereof according to any one of [B31] to [B36], wherein the 5- to 10-membered heteroaryl ($R_{4HA}$) is unsubstituted or substituted with one or more $R_a$;

each of one or more $R_a$ is independently selected from the group consisting of halogen, cyano, nitro, hydroxy, thio, amino, $C_1$-$C_6$ alkoxy, $C_1$-$C_6$ alkylthio, carbonyl, carboxy, sulfonyl, phosphoryl, boryl, oxo, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted.

[B38]

The compound or a salt thereof, or a solvate thereof according to any one of [B31] to [B36], wherein the 5- to 10-membered heteroaryl ($R_{4HA}$) is unsubstituted or substituted with one or more $R_a$; and each of one or more $R_a$ is independently selected from the group consisting of halogen, cyano, hydroxy, amino, $C_1$-$C_6$ alkyl, halo $C_1$-$C_6$ alkyl, hydroxy $C_1$-$C_6$ alkyl, $C_1$-$C_6$ alkoxy, halo $C_1$-$C_6$ alkoxy, and $C_1$-$C_6$ alkylsulfonylamino.

[B39]

The compound or a salt thereof, or a solvate thereof according to any one of [B31] to [B36], wherein the 5- to 10-membered heteroaryl ($R_{4HA}$) is unsubstituted or substituted with one or more $R_a$; and each of one or more $R_a$ is independently selected from the group consisting of halogen, cyano, amino, $C_1$-$C_6$ alkyl, and halo $C_1$-$C_6$ alkyl.

[B40]

The compound or a salt thereof, or a solvate thereof according to any of [B31] to [B36], wherein the 5- to 10-membered heteroaryl ($R_{4HA}$) is 1H-indazol-4-yl, or 1H-indazol-4-yl substituted with one or more halogens.

[B41]

The compound or a salt thereof, or a solvate thereof according to any of [B31] to [B36], wherein the 5- to 10-membered heteroaryl ($R_{4HA}$) is 1H-indazol-4-yl substituted with one or more halogens.

[B42]

The compound or a salt thereof, or a solvate thereof according to any of [B31] to [B36], wherein the 5- to 10-membered heteroaryl ($R_{4HA}$) is 1H-indazol-4-yl in which at least one of position 5, position 6, and position 7 is substituted with a halogen.

[B43]

The compound or a salt thereof, or a solvate thereof according to any of [B31] to [B36], wherein the 5- to 10-membered heteroaryl ($R_{4HA}$) is 1H-indazol-4-yl in which at least one of position 5, position 6, and position 7 is substituted with a halogen; and the halogen is fluorine or chlorine.

[B44]

The compound or a salt thereof, or a solvate thereof according to any of [B31] to [B36], wherein the 5- to 10-membered heteroaryl ($R_{4HA}$) is 1H-indazol-4-yl in which any one or two of position 5, position 6, and position 7 are substituted with a halogen; and the halogen is selected from the group consisting of fluorine, chlorine, a combination of fluorine and fluorine, and a combination of fluorine and chlorine.

[B44.5]

The compound or a salt thereof, or a solvate thereof according to any of [B31] to [B36], wherein the 5- to 10-membered heteroaryl ($R_{4HA}$) is 1H-indazol-4-yl substituted at any one or two of positions 5, 6, and 7 by halogen, and the halogen is independently fluorine or chlorine.

[C1]

A compound represented by the formula (3):

[Formula 8]

(3)

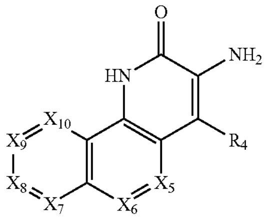

wherein $R_4$ is selected from the group consisting of optionally substituted $C_6$-$C_{10}$ aryl ($R_{4A}$), optionally substituted 4- to 10-membered heterocyclyl, and optionally substituted 5- to 10-membered heteroaryl ($R_{4HA}$);

$X_5$ is $CR_{x5}$ or N;

$X_6$ is $CR_{x6}$ or N;

$X_7$ is $CR_{x7}$ or N;

$X_8$ is $CR_{x8}$ or N;

$X_9$ is $CR_{x9}$ or N;

$X_{10}$ is $CR_{x10}$ or N;

each of $R_{x5}$, $R_{x6}$, $R_{x7}$, $R_{x8}$, $R_{x9}$, and $R_{x10}$ is independently selected from the group consisting of hydrogen, deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted, or a salt thereof, or a solvate thereof.

[C2]

The compound or a salt thereof, or a solvate thereof according to [C1], wherein $X_5$ is $CR_{x5}$ or N;
$X_6$ is $CR_{x6}$;
$X_7$ is $CR_{x7}$ or N;
$X_8$ is $CR_{x8}$ or N;
$X_9$ is $CR_{x9}$ or N; and
$X_{10}$ is $CR_{x10}$ or N.

[C3]

The compound or a salt thereof, or a solvate thereof according to [C1] or [C2], wherein $X_5$ is CH;
$X_6$ is $CR_{x6}$;
$X_7$ is $CR_{x7}$ or N;
$X_8$ is $CR_{x8}$ or N;
$X_9$ is $CR_{x9}$ or N; and
$X_{10}$ is $CR_{x10}$ or N.

[C4]

The compound or a salt thereof, or a solvate thereof according to any of [C1] to [C3], wherein $X_7$ is N, $X_8$ is $CR_{x8}$, $X_9$ is $CR_{x9}$, and $X_{10}$ is $CR_{x10}$;
$X_7$ is $CR_{x7}$, $X_8$ is N, $X_9$ is $CR_{x9}$, and $X_{10}$ is $CR_{x10}$;
$X_7$ is $CR_{x7}$, $X_8$ is $CR_{x8}$, $X_9$ is N, and $X_{10}$ is $CR_{x10}$;
$X_7$ is $CR_{x7}$, $X_8$ is $CR_{x8}$, $X_9$ is $CR_{x9}$, and $X_{10}$ is N;
$X_7$ is N, $X_8$ is $CR_{x8}$, $X_9$ is $CR_{x9}$, and $X_{10}$ is N;
$X_7$ is $CR_{x7}$, $X_8$ is N, $X_9$ is $CR_{x9}$, and $X_{10}$ is N; or
$X_7$ is N, $X_8$ is N, $X_9$ is $CR_{x9}$, and $X_{10}$ is $CR_{x10}$.

[C4.5]

The compound or a salt thereof, or a solvate thereof according to any of [C1] to [C3], wherein $X_7$ is N, $X_8$ is $CR_{x8}$, $X_9$ is $CR_{x9}$, and $X_{10}$ is $CR_{x10}$, or
$X_7$ is $CR_{x7}$, $X_8$ is N, $X_9$ is $CR_{x9}$, and $X_{10}$ is $CR_{x10}$, or
$X_7$ is $CR_{x7}$, $X_8$ is $CR_{x8}$, $X_9$ is N, and $X_{10}$ is $CR_{x10}$, or
$X_7$ is $CR_{x7}$, $X_8$ is $CR_{x8}$, $X_9$ is $CR_{x9}$, and $X_{10}$ is N.

[C5]

The compound or a salt thereof, or a solvate thereof according to any of [C1] to [C4], wherein $R_{x6}$ is selected from the group consisting of hydrogen, halogen, hydroxy, $C_1$-$C_6$ alkylthio, $C_1$-$C_6$ acylamino, mono $C_1$-$C_6$ alkylamino, $C_1$-$C_6$ alkylsulfonylamino, $C_3$-$C_8$ cycloalkylsulfonylamino, $C_1$-$C_6$ alkoxy, halo $C_1$-$C_6$ alkoxy, hydroxy $C_1$-$C_6$ alkoxy, $C_1$-$C_6$ alkoxy $C_1$-$C_6$ alkoxy, $C_3$-$C_8$ cycloalkyl $C_1$-$C_6$ alkoxy, 4- to 10-membered heterocyclyl $C_1$-$C_6$ alkoxy, $C_3$-$C_8$ cycloalkoxy, 4- to 10-membered heterocyclyloxy, $C_1$-$C_6$ acyl, mono $C_3$-$C_8$ cycloalkylaminocarbonyl, 4- to 8-membered cyclic aminocarbonyl, di $C_1$-$C_6$ alkylphosphoryl, $C_1$-$C_6$ alkyl, halo $C_1$-$C_6$ alkyl, hydroxy $C_1$-$C_6$ alkyl, di $C_1$-$C_6$ alkylaminocarbonyl $C_1$-$C_6$ alkyl, $C_3$-$C_8$ cycloalkyl $C_1$-$C_6$ alkyl, $C_2$-$C_6$ alkenyl, hydroxy $C_2$-$C_6$ alkenyl, $C_2$-$C_6$ alkynyl, hydroxy $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the $C_1$-$C_6$ alkylthio, $C_1$-$C_6$ alkoxy, $C_1$-$C_6$ alkoxy $C_1$-$C_6$ alkoxy, $C_3$-$C_8$ cycloalkyl $C_1$-$C_6$ alkoxy, 4- to 10-membered heterocyclyl $C_1$-$C_6$ alkoxy, $C_3$-$C_8$ cycloalkoxy, 4- to 10-membered heterocyclyloxy, $C_1$-$C_6$ alkyl, $C_3$-$C_8$ cycloalkyl $C_1$-$C_6$ alkyl, $C_3$-$C_8$ cycloalkyl, 4- to 10-membered heterocyclyl, $C_6$-$C_{10}$ aryl, and 5- to 10-membered heteroaryl are independently optionally substituted with one or more substituents selected from the group consisting of halogen, cyano, hydroxy, $C_1$-$C_6$ alkyl, $C_1$-$C_6$ alkoxy, oxo, halo $C_1$-$C_6$ alkyl, and $C_3$-$C_8$ cycloalkyl.

[C5.1]

The compound or a salt thereof, or a solvate thereof according to any of [C1] to [C3], wherein $R_{x6}$ is selected from the group consisting of hydrogen, halogen, $C_1$-$C_6$ alkoxy, halo $C_1$-$C_6$ alkoxy, $C_3$-$C_8$ cycloalkyl $C_1$-$C_6$ alkoxy, $C_3$-$C_8$ cycloalkoxy, $C_1$-$C_6$ alkyl, halo $C_1$-$C_6$ alkyl, $C_3$-$C_8$ cycloalkyl $C_1$-$C_6$ alkyl, and $C_3$-$C_8$ cycloalkyl.

[C5.2]

The compound or a salt thereof, or a solvate thereof according to any of [C1] to [C4], wherein $R_{x6}$ is selected from the group consisting of hydrogen, $C_1$-$C_6$ alkoxy, $C_1$-$C_6$ alkyl, and $C_3$-$C_8$ cycloalkyl.

[C6]

The compound or a salt thereof, or a solvate thereof according to any of [C1] to [C4], wherein $R_{x6}$ is selected from the group consisting of hydrogen, methoxy, ethoxy, propoxy, propan-2-yloxy, 3-methylbutoxy, [(2S)-butan-2-yl]oxy, [(2R)-butan-2-yl]oxy, methyl, ethyl, propyl, propan-2-yl, 2-methylpropyl, butan-2-yl, 3-methylbutyl, pentan-3-yl, cyclopropyl, cyclobutyl, cyclopentyl, 1-methylcyclopropyl, 3,3-dimethylcyclobutyl, and spiro[2.3]hexan-5-yl.

[C6.5]

A compound represented by the formula (3):

[Formula 9]

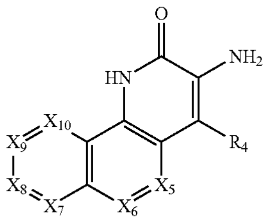
(3)

wherein $R_4$ is optionally substituted 5- to 10-membered heteroaryl ($R_{4HA}$);
the 5- to 10-membered heteroaryl ($R_{4HA}$) is 1H-indazol-4-yl, or 1H-indazol-4-yl substituted with one or more halogens;
$X_5$ is $CR_{x5}$ or N;
$X_6$ is $CR_{x6}$;
$R_{x6}$ is selected from the group consisting of hydrogen, methoxy, ethoxy, propoxy, propan-2-yloxy, 3-methylbutoxy, [(2S)-butan-2-yl]oxy, [(2R)-butan-2-yl]oxy, methyl, ethyl, propyl, propan-2-yl, 2-methylpropyl, butan-2-yl, 3-methylbutyl, pentan-3-yl, cyclopropyl, cyclobutyl, cyclopentyl, 1-methylcyclopropyl, 3,3-dimethylcyclobutyl, and spiro[2.3]hexan-5-yl;
$X_7$ is $CR_{x7}$ or N;
$X_8$ is $CR_{x8}$ or N;
$X_9$ is $CR_{x9}$ or N;
$X_{10}$ is $CR_{x10}$ or N;
each of $R_{x5}$, $R_{x7}$, $R_{x8}$, $R_{x9}$, and $R_{x10}$ is independently selected from the group consisting of hydrogen, deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted;

or a salt thereof, or a solvate thereof.

[C6.6]

A compound represented by the formula (3):

[Formula 10]

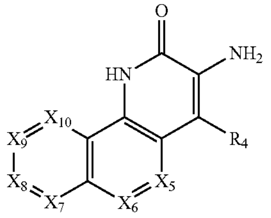

(3)

wherein $R_4$ is 1H-indazol-4-yl, or 1H-indazol-4-yl substituted by one or more halogen atoms, $X_5$ is $CR_{x5}$ or N, $X_6$ is $CR_{x6}$, $R_{x6}$ is selected from the group consisting of hydrogen, methoxy, ethoxy, propoxy, propan-2-yloxy, 3-methylbutoxy, [(2S)-butan-2-yl]oxy, [(2R)-butan-2-yl]oxy, methyl, ethyl, propyl, propan-2-yl, 2-methylpropyl, butan-2-yl, 3-methylbutyl, pentan-3-yl, cyclopropyl, cyclobutyl, cyclopentyl, 1-methylcyclopropyl, 3,3-dimethylcyclobutyl, and spiro[2.3]hexan-5-yl, $X_7$ is $CR_{x7}$ or N, $X_8$ is $CR_{x8}$ or N, $X_9$ is $CR_{x9}$ or N, $X_{10}$ is $CR_{x10}$ or N, $R_{x5}$, $R_{x7}$, $R_{x8}$, $R_{x9}$, and $R_{x10}$ are each independently selected from the group consisting of hydrogen, deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl, and each of the hydroxy, the thio, the amino, the $C_1$-$C_6$ alkoxy, the $C_1$-$C_6$ alkylthio, the carbonyl, the carboxy, the sulfonyl, the phosphoryl, the boryl, the $C_1$-$C_6$ alkyl, the $C_2$-$C_6$ alkenyl, the $C_2$-$C_6$ alkynyl, the $C_3$-$C_8$ cycloalkyl, the 4- to 10-membered heterocyclyl, the $C_6$-$C_{10}$ aryl, and the 5- to 10-membered heteroaryl is optionally further substituted, or a salt thereof, or a solvate thereof.

[C7]

The compound or a salt thereof, or a solvate thereof according to any of [C1] to [C6.5], wherein $X_7$ is $CR_{x7}$.

[C8]

The compound or a salt thereof, or a solvate thereof according to [C7], wherein $R_{x7}$ is hydrogen, halogen, $C_1$-$C_6$ alkoxy, or $C_1$-$C_6$ alkyl.

[C9]

The compound or a salt thereof, or a solvate thereof according to any of [C1] to [C6.5], wherein $X_7$ is N.

[C10]

The compound or a salt thereof, or a solvate thereof according to any of [C1] to [C9], wherein $X_8$ is $CR_{x8}$.

[C11]

The compound or a salt thereof, or a solvate thereof according to [C10], wherein $R_{x8}$ is hydrogen, halogen, $C_1$-$C_6$ alkoxy, or $C_1$-$C_6$ alkyl.

[C12]

The compound or a salt thereof, or a solvate thereof according to any of [C1] to [C9], wherein $X_8$ is N.

[C13]

The compound or a salt thereof, or a solvate thereof according to any of [C1] to [C12], wherein $X_9$ is $CR_{x9}$.

[C14]

The compound or a salt thereof, or a solvate thereof according to [C13], wherein $R_{x9}$ is selected from the group consisting of hydrogen, halogen, $C_1$-$C_6$ alkoxy, $C_1$-$C_6$ alkyl, and boryl.

[C15]

The compound or a salt thereof, or a solvate thereof according to any of [C1] to [C12], wherein $X_9$ is N.

[C16]

The compound or a salt thereof, or a solvate thereof according to any of [C1] to [C15], wherein $X_{10}$ is $CR_{x10}$.

[C17]

The compound or a salt thereof, or a solvate thereof according to [C16], wherein $R_{x10}$ is hydrogen, halogen, $C_1$-$C_6$ alkoxy, or $C_1$-$C_6$ alkyl.

[C18]

The compound or a salt thereof, or a solvate thereof according to any of [C1] to [C12], wherein $X_{10}$ is N.

[C20]

The compound or a salt thereof, or a solvate thereof according to any of [C1] to [C18](except for [C6.5] and [C6.6]), wherein $R_4$ is optionally substituted $C_6$-$C_{10}$ aryl ($R_{4A}$) or optionally substituted 5- to 10-membered heteroaryl ($R_{4HA}$).

[C21]

The compound or a salt thereof, or a solvate thereof according to any of [C1] to [C18](except for [C6.5] and [C6.6]), wherein $R_4$ is optionally substituted $C_6$-$C_{10}$ aryl ($R_{4A}$).

[C22]

The compound or a salt thereof, or a solvate thereof according to [C20] or [C21], wherein the $C_6$-$C_{10}$ aryl ($R_{4A}$) is phenyl.

[C23]

The compound or a salt thereof, or a solvate thereof according to any of [C20] to [C22], wherein the $C_6$-$C_{10}$ aryl ($R_{4A}$) is unsubstituted or substituted with one or more $R_a$;

each of one or more $R_a$ is independently selected from the group consisting of deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, oxo, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted.

[C24]

The compound or a salt thereof, or a solvate thereof according to any of [C20] to [C22], wherein the $C_6$-$C_{10}$ aryl ($R_{4A}$) is unsubstituted or substituted with one or more $R_a$; and each of one or more $R_a$ is independently selected from the group consisting of halogen, cyano, hydroxy, amino, $C_1$-$C_6$ alkyl, halo $C_1$-$C_6$ alkyl, hydroxy $C_1$-$C_6$ alkyl, $C_1$-$C_6$ alkoxy, halo $C_1$-$C_6$ alkoxy, and $C_1$-$C_6$ alkylsulfonylamino.

[C25]

The compound or a salt thereof, or a solvate thereof according to any of [C20] to [C22], wherein the $C_6$-$C_{10}$ aryl ($R_{4A}$) is unsubstituted or substituted with one or more $R_a$; and each of one or more $R_a$ is independently selected from the group consisting of halogen, hydroxy, halo $C_1$-$C_6$ alkyl, $C_1$-$C_6$ alkoxy, halo $C_1$-$C_6$ alkoxy, and alkylsulfonylamino.

[C26]

The compound or a salt thereof, or a solvate thereof according to any of [C1] to [C18] (except for [C6.5] and [C6.6]), wherein $R_4$ is optionally substituted 5- to 10-membered heteroaryl ($R_{4HA}$).

[C27]

The compound or a salt thereof, or a solvate thereof according to [C20] or [C26], wherein the 5- to 10-membered heteroaryl ($R_{4HA}$) is selected from the group consisting of furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, benzotriazolyl, indolyl, isoindolyl, indazolyl, azaindolyl, quinolyl, isoquinolyl, cinnolinyl, quinazolinyl, quinoxalinyl, indolizinyl, imidazopyridyl, pyrazolopyridyl, triazolopyridyl, pyrrolopyrazinyl, and flopyridyl.

[C28]

The compound or a salt thereof, or a solvate thereof according to [C20] or [C26], wherein the 5- to 10-membered heteroaryl ($R_{4HA}$) is selected from the group consisting of furyl, thienyl, pyrrolyl, pyrazolyl, thiazolyl, isothiazolyl, oxazolyl, isoxazolyl, oxadiazolyl, thiadiazolyl, triazolyl, tetrazolyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, benzotriazolyl, indolyl, isoindolyl, indazolyl, azaindolyl, quinolyl, isoquinolyl, cinnolinyl, quinazolinyl, quinoxalinyl, indolizinyl, imidazopyridyl, pyrazolopyridyl, triazolopyridyl, pyrrolopyrazinyl, and flopyridyl.

[C29]

The compound or a salt thereof, or a solvate thereof according to [C20] or [C26], wherein the 5- to 10-membered heteroaryl ($R_{4HA}$) is selected from the group consisting of pyridyl, pyrimidyl, benzimidazolyl, indolyl, indazolyl, and pyrazolopyridyl.

[C30]

The compound or a salt thereof, or a solvate thereof according to [C20] or [C26], wherein the 5- to 10-membered heteroaryl ($R_{4HA}$) is selected from the group consisting of pyrimidyl, benzimidazolyl, indolyl, indazolyl, and pyrazolopyridyl.

[C31]

The compound or a salt thereof, or a solvate thereof according to [C20] or [C26], wherein the 5- to 10-membered heteroaryl ($R_{4HA}$) is 1H-indazol-6-yl or 1H-indazol-4-yl.

[C32]

The compound or a salt thereof, or a solvate thereof according to [C20] or [C26], wherein the 5- to 10-membered heteroaryl ($R_{4HA}$) is 1H-indazol-4-yl.

[C33]

The compound or a salt thereof, or a solvate thereof according to any of [C27] to [C32], wherein the 5- to 10-membered heteroaryl ($R_{4HA}$) is unsubstituted or substituted with one or more $R_a$;

each of one or more $R_a$ is independently selected from the group consisting of deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, oxo, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted.

[C34]

The compound or a salt thereof, or a solvate thereof according to any of [C27] to [C32], wherein the 5- to 10-membered heteroaryl ($R_{4HA}$) is unsubstituted or substituted with one or more $R_a$; and each of one or more $R_a$ is independently selected from the group consisting of halogen, cyano, hydroxy, amino, $C_1$-$C_6$ alkyl, halo $C_1$-$C_6$ alkyl, hydroxy $C_1$-$C_6$ alkyl, $C_1$-$C_6$ alkoxy, halo $C_1$-$C_6$ alkoxy, and alkylsulfonylamino.

[C35]

The compound or a salt thereof, or a solvate thereof according to any of [C27] to [C32], wherein the 5- to 10-membered heteroaryl ($R_{4HA}$) is unsubstituted or substituted with one or more $R_a$; and each of one or more $R_a$ is independently selected from the group consisting of halogen, cyano, amino, $C_1$-$C_6$ alkyl, and halo $C_1$-$C_6$ alkyl.

[C36]

The compound or a salt thereof, or a solvate thereof according to any of [C27] to [C32], wherein the 5- to 10-membered heteroaryl ($R_{4HA}$) is 1H-indazol-4-yl, or 1H-indazol-4-yl substituted with one or more halogens.

[C37]

The compound or a salt thereof, or a solvate thereof according to any of [C27] to [C32], wherein the 5- to 10-membered heteroaryl ($R_{4HA}$) is 1H-indazol-4-yl substituted with one or more halogens.

[C38]

The compound or a salt thereof, or a solvate thereof according to any of [C27] to [C32], wherein the 5- to 10-membered heteroaryl ($R_{4HA}$) is 1H-indazol-4-yl in which at least one of position 5, position 6, and position 7 is substituted with a halogen.

[C39]

The compound or a salt thereof, or a solvate thereof according to any of [C27] to [C32], wherein the 5- to 10-membered heteroaryl ($R_{4HA}$) is 1H-indazol-4-yl in which at least one of position 5, position 6, and position 7 is substituted with a halogen; and the halogen is fluorine or chlorine.

[C40]

The compound or a salt thereof, or a solvate thereof according to any of [C27] to [C32], wherein the 5- to 10-membered heteroaryl ($R_{4HA}$) is 1H-indazol-4-yl in which any one or two of position 5, position 6, and position 7 are substituted with a halogen; and the halogen is selected from the group consisting of fluorine, chlorine, a combination of fluorine and fluorine, and a combination of fluorine and chlorine.

[C40.5]

The compound or a salt thereof, or a solvate thereof according to any of [C27] to [C32], wherein the 5- to 10-membered heteroaryl ($R_{4HA}$) is 1H-indazol-4-yl substituted at any one or two of positions 5, 6, and 7 by halogen, and the halogen is independently fluorine or chlorine.

[D1]

A compound selected from the following compounds:

3-amino-7-chloro-6-cyclopropyl-4-(7-fluoro-1H-indazol-4-yl)-1H-benzo[h]quinolin-2-one,
3-amino-6-cyclopropyl-4-(7-fluoro-1H-indazol-4-yl)-1H-benzo[h]quinolin-2-one,
3-amino-4-(7-fluoro-1H-indazol-4-yl)-6-methyl-1H-benzo[h]quinolin-2-one,
3-amino-4-(7-chloro-1H-indazol-4-yl)-6-cyclopropyl-1H-benzo[h]quinolin-2-one,
3-amino-4-(7-chloro-1H-indazol-4-yl)-6-methyl-1H-benzo[h]quinolin-2-one,
3-amino-4-(7-fluoro-1H-indazol-4-yl)-6-propan-2-yl-1H-1,7-phenanthrolin-2-one,
3-amino-4-(7-fluoro-1H-indazol-4-yl)-6-propan-2-yloxy-1H-1,7-phenanthrolin-2-one,
3-amino-4-(7-chloro-1H-indazol-4-yl)-6-cyclopropyl-1H-1,7-phenanthrolin-2-one,
3-amino-4-(7-chloro-1H-indazol-4-yl)-6-cyclobutyl-1H-1,7-phenanthrolin-2-one,
3-amino-4-(7-chloro-1H-indazol-4-yl)-6-ethyl-1H-1,7-phenanthrolin-2-one,
3-amino-4-(7-chloro-1H-indazol-4-yl)-6-methyl-1H-1,7-phenanthrolin-2-one,
3-amino-4-(5-fluoro-1H-indazol-4-yl)-6-methyl-1H-1,7-phenanthrolin-2-one,
3-amino-6-cyclopropyl-4-(5-fluoro-1H-indazol-4-yl)-1H-1,7-phenanthrolin-2-one,
(S)-3-amino-6-cyclopropyl-4-(5-fluoro-1H-indazol-4-yl)-1H-1,7-phenanthrolin-2-one,
3-amino-4-(6,7-difluoro-1H-indazol-4-yl)-6-methyl-1H-1,7-phenanthrolin-2-one,
3-amino-6-cyclopropyl-4-(6,7-difluoro-1H-indazol-4-yl)-1H-1,7-phenanthrolin-2-one,
3-amino-4-(6,7-difluoro-1H-indazol-4-yl)-6-ethyl-1H-1,7-phenanthrolin-2-one,
3-amino-4-(7-chloro-6-fluoro-1H-indazol-4-yl)-6-ethoxy-1H-1,7-phenanthrolin-2-one,
3-amino-4-(7-chloro-6-fluoro-1H-indazol-4-yl)-6-propan-2-yloxy-1H-1,7-phenanthrolin-2-one,
3-amino-4-(7-chloro-6-fluoro-1H-indazol-4-yl)-6-cyclopropyl-1H-1,7-phenanthrolin-2-one,
3-amino-4-(7-chloro-6-fluoro-1H-indazol-4-yl)-6-methyl-1H-1,7-phenanthrolin-2-one,
3-amino-4-(7-fluoro-1H-indazol-4-yl)-6-methoxy-1H-1,7-phenanthrolin-2-one,
3-amino-4-(7-fluoro-1H-indazol-4-yl)-6-propoxy-1H-1,7-phenanthrolin-2-one,
3-amino-4-(6,7-difluoro-1H-indazol-4-yl)-6-methoxy-1H-1,7-phenanthrolin-2-one,
3-amino-4-(6,7-difluoro-1H-indazol-4-yl)-6-ethoxy-1H-1,7-phenanthrolin-2-one,
3-amino-4-(6,7-difluoro-1H-indazol-4-yl)-6-propan-2-yloxy-1H-1,7-phenanthrolin-2-one,
3-amino-4-(7-chloro-1H-indazol-4-yl)-6-methoxy-1H-1,7-phenanthrolin-2-one,
3-amino-4-(7-chloro-6-fluoro-1H-indazol-4-yl)-6-methoxy-1H-1,7-phenanthrolin-2-one,
3-amino-6-ethoxy-4-(7-fluoro-1H-indazol-4-yl)-1H-1,7-phenanthrolin-2-one,
3-amino-6-cyclopropyl-4-(7-fluoro-1H-indazol-4-yl)-1H-1,7-phenanthrolin-2-one,
3-amino-4-(7-fluoro-1H-indazol-4-yl)-6-methyl-1H-1,7-phenanthrolin-2-one,
3-amino-6-ethyl-4-(7-fluoro-1H-indazol-4-yl)-1H-1,7-phenanthrolin-2-one,
3-amino-6-cyclobutyl-4-(7-fluoro-1H-indazol-4-yl)-1H-1,7-phenanthrolin-2-one,
3-amino-4-(7-fluoro-1H-indazol-4-yl)-6-methoxy-1H-1,10-phenanthrolin-2-one,
3-amino-6-cyclopropyl-4-(7-fluoro-1H-indazol-4-yl)-1H-1,10-phenanthrolin-2-one,
3-amino-4-(7-fluoro-1H-indazol-4-yl)-6-methyl-1H-1,10-phenanthrolin-2-one,
3-amino-6-ethyl-4-(7-fluoro-1H-indazol-4-yl)-1H-1,10-phenanthrolin-2-one,
3-amino-9-fluoro-4-(7-fluoro-1H-indazol-4-yl)-6-methoxy-1H-1,7-phenanthrolin-2-one,
3-amino-9-fluoro-4-(7-fluoro-1H-indazol-4-yl)-6-methyl-1H-1,7-phenanthrolin-2-one,
3-amino-4-(6,7-difluoro-1H-indazol-4-yl)-9-fluoro-6-methoxy-1H-1,7-phenanthrolin-2-one,
3-amino-4-(6,7-difluoro-1H-indazol-4-yl)-9-fluoro-6-methyl-1H-1,7-phenanthrolin-2-one,
8-amino-7-(7-fluoro-1H-indazol-4-yl)-5-methoxy-10H-pyrido[2,3-f]quinoxalin-9-one,
8-amino-7-(7-fluoro-1H-indazol-4-yl)-5-propan-2-yloxy-10H-pyrido[2,3-f]quinoxalin-9-one,
8-amino-7-(7-fluoro-1H-indazol-4-yl)-5-methyl-10H-pyrido[2,3-f]quinoxalin-9-one,
8-amino-5-cyclopropyl-7-(7-fluoro-1H-indazol-4-yl)-10H-pyrido[2,3-f]quinoxalin-9-one,
8-amino-7-(7-fluoro-1H-indazol-4-yl)-5-methyl-10H-pyrido[3,2-h]quinazolin-9-one,
8-amino-5-cyclopropyl-7-(7-fluoro-1H-indazol-4-yl)-10H-pyrido[3,2-h]quinazolin-9-one,
3-amino-6-cyclopropyl-4-(7-fluoro-1H-indazol-4-yl)-1H-1,8-phenanthrolin-2-one,
3-amino-4-(6,7-difluoro-1H-indazol-4-yl)-5,6-dimethyl-1H-1,7-phenanthrolin-2-one,
3-amino-6-cyclopropyl-4-(6,7-difluoro-1H-indazol-4-yl)-5-methyl-1H-1,7-phenanthrolin-2-one,
3-amino-4-(6,7-difluoro-1H-indazol-4-yl)-5-methyl-1H-1,7-phenanthrolin-2-one,
3-amino-4-(6,7-difluoro-1H-indazol-4-yl)-5-fluoro-6-methyl-1H-1,7-phenanthrolin-2-one,
3-amino-6-cyclopropyl-4-(6,7-difluoro-1H-indazol-4-yl)-5-fluoro-1H-1,7-phenanthrolin-2-one,
3-amino-4-(6,7-difluoro-1H-indazol-4-yl)-5-fluoro-1H-1,7-phenanthrolin-2-one,
3-amino-4-(5,7-difluoro-1H-indazol-4-yl)-6-methyl-1H-1,7-phenanthrolin-2-one,
3-amino-6-methyl-4-(1H-pyrazolo[4,3-c]pyridin-4-yl)-1H-1,7-phenanthrolin-2-one,
3-amino-4-(1H-benzotriazol-4-yl)-6-methyl-1H-1,7-phenanthrolin-2-one, or
3-amino-6-(tert-butyl)-4-(7-fluoro-1H-indazol-4-yl)-1H-1,7-phenanthrolin-2-one, or a salt thereof, or a solvate thereof.

[D2]

3-Amino-7-chloro-6-cyclopropyl-4-(7-fluoro-1H-indazol-4-yl)-1H-benzo[h]quinolin-2-one or a salt thereof, or a solvate thereof.

[D3]

3-Amino-6-cyclopropyl-4-(7-fluoro-1H-indazol-4-yl)-1H-benzo[h]quinolin-2-one or a salt thereof, or a solvate thereof.

[D4]

3-Amino-4-(7-fluoro-1H-indazol-4-yl)-6-methyl-1H-benzo[h]quinolin-2-one or a salt thereof, or a solvate thereof.

[D5]

3-Amino-4-(7-chloro-1H-indazol-4-yl)-6-cyclopropyl-1H-benzo[h]quinolin-2-one or a salt thereof, or a solvate thereof.

[D6]

3-Amino-4-(7-chloro-1H-indazol-4-yl)-6-methyl-1H-benzo[h]quinolin-2-one or a salt thereof, or a solvate thereof.

[D7]

3-Amino-4-(7-fluoro-1H-indazol-4-yl)-6-propan-2-yl-1H-1,7-phenanthrolin-2-one or a salt thereof, or a solvate thereof.

[D8]

3-Amino-4-(7-fluoro-1H-indazol-4-yl)-6-propan-2-yloxy-1H-1,7-phenanthrolin-2-one or a salt thereof, or a solvate thereof.

[D9]

3-Amino-4-(7-chloro-1H-indazol-4-yl)-6-cyclopropyl-1H-1,7-phenanthrolin-2-one or a salt thereof, or a solvate thereof.

[D10]

3-Amino-4-(7-chloro-1H-indazol-4-yl)-6-cyclobutyl-1H-1,7-phenanthrolin-2-one or a salt thereof, or a solvate thereof.

[D11]

3-Amino-4-(7-chloro-1H-indazol-4-yl)-6-ethyl-1H-1,7-phenanthrolin-2-one or a salt thereof, or a solvate thereof.

[D12]

3-Amino-4-(7-chloro-1H-indazol-4-yl)-6-methyl-1H-1,7-phenanthrolin-2-one or a salt thereof, or a solvate thereof.

[D13]

3-Amino-4-(5-fluoro-1H-indazol-4-yl)-6-methyl-1H-1,7-phenanthrolin-2-one or a salt thereof, or a solvate thereof.

[D14]

3-Amino-6-cyclopropyl-4-(5-fluoro-1H-indazol-4-yl)-1H-1,7-phenanthrolin-2-one or a salt thereof, or a solvate thereof.

[D15]

(S)-3-Amino-6-cyclopropyl-4-(5-fluoro-1H-indazol-4-yl)-1H-1,7-phenanthrolin-2-one or a salt thereof, or a solvate thereof.

[D16]

3-Amino-4-(6,7-difluoro-1H-indazol-4-yl)-6-methyl-1H-1,7-phenanthrolin-2-one or a salt thereof, or a solvate thereof.

[D16.5]

3-Amino-4-(6,7-difluoro-1H-indazol-4-yl)-6-methyl-1H-1,7-phenanthrolin-2-one hydrochloride monohydrate.

[D17]

3-Amino-6-cyclopropyl-4-(6,7-difluoro-1H-indazol-4-yl)-1H-1,7-phenanthrolin-2-one or a salt thereof, or a solvate thereof.

[D18]

3-Amino-4-(6,7-difluoro-1H-indazol-4-yl)-6-ethyl-1H-1,7-phenanthrolin-2-one or a salt thereof, or a solvate thereof.

[D19]

3-Amino-4-(7-chloro-6-fluoro-1H-indazol-4-yl)-6-ethoxy-1H-1,7-phenanthrolin-2-one or a salt thereof, or a solvate thereof.

[D20]

3-Amino-4-(7-chloro-6-fluoro-1H-indazol-4-yl)-6-propan-2-yloxy-1H-1,7-phenanthrolin-2-one or a salt thereof, or a solvate thereof.

[D21]

3-Amino-4-(7-chloro-6-fluoro-1H-indazol-4-yl)-6-cyclopropyl-1H-1,7-phenanthrolin-2-one or a salt thereof, or a solvate thereof.

[D22]

3-Amino-4-(7-chloro-6-fluoro-1H-indazol-4-yl)-6-methyl-1H-1,7-phenanthrolin-2-one or a salt thereof, or a solvate thereof.

[D23]

3-Amino-4-(7-fluoro-1H-indazol-4-yl)-6-methoxy-1H-1,7-phenanthrolin-2-one or a salt thereof, or a solvate thereof.

[D23.5]

3-Amino-4-(7-fluoro-1H-indazol-4-yl)-6-methoxy-1H-1,7-phenanthrolin-2-one hydrochloride.

[D24]

3-Amino-4-(7-fluoro-1H-indazol-4-yl)-6-propoxy-1H-1,7-phenanthrolin-2-one or a salt thereof, or a solvate thereof.

[D25]

3-Amino-4-(6,7-difluoro-1H-indazol-4-yl)-6-methoxy-1H-1,7-phenanthrolin-2-one or a salt thereof, or a solvate thereof.

[D26]

3-Amino-4-(6,7-difluoro-1H-indazol-4-yl)-6-ethoxy-1H-1,7-phenanthrolin-2-one or a salt thereof, or a solvate thereof.

[D27]

3-Amino-4-(6,7-difluoro-1H-indazol-4-yl)-6-propan-2-yloxy-1H-1,7-phenanthrolin-2-one or a salt thereof, or a solvate thereof.

[D28]

3-Amino-4-(7-chloro-1H-indazol-4-yl)-6-methoxy-1H-1,7-phenanthrolin-2-one or a salt thereof, or a solvate thereof.

[D29]

3-Amino-4-(7-chloro-6-fluoro-1H-indazol-4-yl)-6-methoxy-1H-1,7-phenanthrolin-2-one or a salt thereof, or a solvate thereof.

[D30]

3-Amino-6-ethoxy-4-(7-fluoro-1H-indazol-4-yl)-1H-1,7-phenanthrolin-2-one or a salt thereof, or a solvate thereof.

[D31]

3-Amino-6-cyclopropyl-4-(7-fluoro-1H-indazol-4-yl)-1H-1,7-phenanthrolin-2-one or a salt thereof, or a solvate thereof.

[D31.5]

A solvate of 3-amino-6-cyclopropyl-4-(7-fluoro-1H-indazol-4-yl)-1H-1,7-phenanthrolin-2-one.

[D32]

3-Amino-4-(7-fluoro-1H-indazol-4-yl)-6-methyl-1H-1,7-phenanthrolin-2-one or a salt thereof, or a solvate thereof.

[D32.5]

3-Amino-4-(7-fluoro-1H-indazol-4-yl)-6-methyl-1H-1,7-phenanthrolin-2-one hydrochloride monohydrate.

[D33]

3-Amino-6-ethyl-4-(7-fluoro-1H-indazol-4-yl)-1H-1,7-phenanthrolin-2-one or a salt thereof, or a solvate thereof.

[D34]

3-Amino-6-cyclobutyl-4-(7-fluoro-1H-indazol-4-yl)-1H-1,7-phenanthrolin-2-one or a salt thereof, or a solvate thereof.

[D35]

3-Amino-4-(7-fluoro-1H-indazol-4-yl)-6-methoxy-1H-1,10-phenanthrolin-2-one or a salt thereof, or a solvate thereof.

[D36]

3-Amino-6-cyclopropyl-4-(7-fluoro-1H-indazol-4-yl)-1H-1,10-phenanthrolin-2-one or a salt thereof, or a solvate thereof.

[D37]

3-Amino-4-(7-fluoro-1H-indazol-4-yl)-6-methyl-1H-1,10-phenanthrolin-2-one or a salt thereof, or a solvate thereof.

[D38]

3-Amino-6-ethyl-4-(7-fluoro-1H-indazol-4-yl)-1H-1,10-phenanthrolin-2-one or a salt thereof, or a solvate thereof.

[D39]

3-Amino-9-fluoro-4-(7-fluoro-1H-indazol-4-yl)-6-methoxy-1H-1,7-phenanthrolin-2-one or a salt thereof, or a solvate thereof.

[D40]

3-Amino-9-fluoro-4-(7-fluoro-1H-indazol-4-yl)-6-methyl-1H-1,7-phenanthrolin-2-one or a salt thereof, or a solvate thereof.

[D41]

3-Amino-4-(6,7-difluoro-1H-indazol-4-yl)-9-fluoro-6-methoxy-1H-1,7-phenanthrolin-2-one or a salt thereof, or a solvate thereof.

[D42]

3-Amino-4-(6,7-difluoro-1H-indazol-4-yl)-9-fluoro-6-methyl-1H-1,7-phenanthrolin-2-one or a salt thereof, or a solvate thereof.

[D43]

8-Amino-7-(7-fluoro-1H-indazol-4-yl)-5-methoxy-10H-pyrido[2,3-f]quinoxalin-9-one or a salt thereof, or a solvate thereof.

[D44]

8-Amino-7-(7-fluoro-1H-indazol-4-yl)-5-propan-2-yloxy-10H-pyrido[2,3-f]quinoxalin-9-one or a salt thereof, or a solvate thereof.

[D45]

8-Amino-7-(7-fluoro-1H-indazol-4-yl)-5-methyl-10H-pyrido[2,3-f]quinoxalin-9-one or a salt thereof, or a solvate thereof.

[D46]

8-Amino-5-cyclopropyl-7-(7-fluoro-1H-indazol-4-yl)-10H-pyrido[2,3-f]quinoxalin-9-one or a salt thereof, or a solvate thereof.

[D47]

8-Amino-7-(7-fluoro-1H-indazol-4-yl)-5-methyl-10H-pyrido[3,2-h]quinazolin-9-one or a salt thereof, or a solvate thereof.

[D48]

8-Amino-5-cyclopropyl-7-(7-fluoro-1H-indazol-4-yl)-10H-pyrido[3,2-h]quinazolin-9-one or a salt thereof, or a solvate thereof.

[D49]

3-Amino-6-cyclopropyl-4-(7-fluoro-1H-indazol-4-yl)-1H-1,8-phenanthrolin-2-one 2,2,2-trifluoroacetate or a salt thereof, or a solvate thereof.

[D49.1]

3-Amino-4-(6,7-difluoro-1H-indazol-4-yl)-5,6-dimethyl-1H-1,7-phenanthrolin-2-one or a salt thereof, or a solvate thereof.

[D49.2]

3-Amino-6-cyclopropyl-4-(6,7-difluoro-1H-indazol-4-yl)-5-methyl-1H-1,7-phenanthrolin-2-one or a salt thereof, or a solvate thereof.

[D49.3]

3-Amino-4-(6,7-difluoro-1H-indazol-4-yl)-5-methyl-1H-1,7-phenanthrolin-2-one or a salt thereof, or a solvate thereof.

[D49.4]

3-Amino-4-(6,7-difluoro-1H-indazol-4-yl)-5-fluoro-6-methyl-1H-1,7-phenanthrolin-2-one or a salt thereof, or a solvate thereof.

[D49.5]

3-Amino-6-cyclopropyl-4-(6,7-difluoro-1H-indazol-4-yl)-5-fluoro-1H-1,7-phenanthrolin-2-one or a salt thereof, or a solvate thereof.

[D49.6]

3-Amino-4-(6,7-difluoro-1H-indazol-4-yl)-5-fluoro-1H-1,7-phenanthrolin-2-one or a salt thereof, or a solvate thereof.

[D49.7]

3-Amino-4-(5,7-difluoro-1H-indazol-4-yl)-6-methyl-1H-1,7-phenanthrolin-2-one or a salt thereof, or a solvate thereof.

[D49.8]

3-Amino-6-methyl-4-(1H-pyrazolo[4,3-c]pyridin-4-yl)-1H-1,7-phenanthrolin-2-one or a salt thereof, or a solvate thereof.

[D49.9]

3-Amino-4-(1H-benzotriazol-4-yl)-6-methyl-1H-1,7-phenanthrolin-2-one or a salt thereof, or a solvate thereof.

[D49.10]

3-Amino-6-(tert-butyl)-4-(7-fluoro-1H-indazol-4-yl)-1H-1,7-phenanthrolin-2-one or a salt thereof, or a solvate thereof.

[D50]

The compound or a salt thereof, or a solvate thereof according to any of [A1] to [A46], [B1] to [B44], and [C1] to [C40], wherein the compounds represented by the formula (1), the formula (2), and the formula (3) or salts thereof, or solvates thereof are the compounds represented by the formula (1), the formula (2), and the formula (3) or salts thereof.

[D51]

The compound or a salt thereof, or a solvate thereof according to any of [A1] to [A46], [B1] to [B44], and [C1] to [C40], wherein the compounds represented by the formula (1), the formula (2), and the formula (3) or salts thereof, or solvates thereof are the compounds represented by the formula (1), the formula (2), and the formula (3).

[D52]

The compound or a salt thereof, or a solvate thereof according to any of [A1] to [A46], [B1] to [B44], and [C1] to [C40], wherein the compounds represented by the formula (1), the formula (2), and the formula (3) or salts thereof, or solvates thereof are the salts of the compounds represented by the formula (1), the formula (2), and the formula (3).

[D53]

The compound or a salt thereof, or a solvate thereof according to any of [A1] to [A46], [B1] to [B44], and [C1] to [C40], wherein the compounds represented by the formula (1), the formula (2), and the formula (3) or salts thereof, or solvates thereof are the solvates of the compounds represented by the formula (1), the formula (2), and the formula (3) or salts thereof.

[D54]

The compound or a salt thereof, or a solvate thereof according to any of [A1] to [A46], [B1] to [B44], and [C1] to [C40], wherein the compounds represented by the formula (1), the formula (2), and the formula (3) or salts thereof, or solvates thereof are the compounds represented by the formula (1), the formula (2), and the formula (3) or salts thereof, or hydrates thereof.

[D55]

The compound or a salt thereof, or a solvate thereof according to any of [A1] to [A46], [B1] to [B44], and [C1] to [C40], wherein the compounds represented by the formula (1), the formula (2), and the formula (3) or salts thereof, or solvates thereof are the hydrates of the compounds represented by the formula (1), the formula (2), and the formula (3) or salts thereof.

[D56]

The compound or a salt thereof, or a solvate thereof according to any of [D1] to [D49], wherein the compounds or salts thereof, or solvates thereof according to any of [D1] to [D49] are the compounds or salts thereof according to any of [D1] to [D49].

[D57]

The compound or a salt thereof, or a solvate thereof according to any of [D1] to [D49], wherein the compounds or salts thereof, or solvates thereof according to any of [D1] to [D49] are the compounds according to any of [D1] to [D49].

[D58]

The compound or a salt thereof, or a solvate thereof according to any of [D1] to [D49], wherein the compounds or salts thereof, or solvates thereof according to any of [D1] to [D49] are the salts of the compounds according to any of [D1] to [D49].

[D59]

The compound or a salt thereof, or a solvate thereof according to any of [D1] to [D49], wherein the compounds or salts thereof, or solvates thereof according to any of [D1] to [D49] are the solvates of the compounds or salts thereof according to any of [D1] to [D49].

[D60]

The compound or a salt thereof, or a solvate thereof according to any of [D1] to [D49], wherein the compounds or salts thereof, or solvates thereof according to any of [D1] to [D49] are the compounds or salts thereof, or a hydrates thereof according to any of [D1] to [D49].

[D61]

The compound or a salt thereof, or a solvate thereof according to any of [D1] to [D49], wherein the compounds or salts thereof, or solvates thereof according to any of [D1] to [D49] are the hydrates of the compounds or salts according to any of [D1] to [D49].

[E1]

A pharmaceutical composition comprising the compound or a salt thereof, or a solvate thereof according to any of [A1] to [A46], [B1] to [B44], [C1] to [C40], and [D1] to [D61] as an active ingredient.

[E2]

A prophylactic agent and/or a therapeutic agent for cancer comprising the compound or a salt thereof, or a solvate thereof according to any of [A1] to [A46], [B1] to [B44], [C1] to [C40], and [D1] to [D61] as an active ingredient.

[E3]

An MYT1 inhibitor comprising the compound or a salt thereof, or a solvate thereof according to any of [A1] to [A46], [B1] to [B44], [C1] to [C40], and [D1] to [D61].

[E4]

A method for preventing and/or treating cancer comprising administering an effective amount of the compound or a salt thereof, or a solvate thereof according to any of [A1] to [A46], [B1] to [B44], [C1] to [C40], and [D1] to [D61] to a subject.

[E5]

The compound or a salt thereof, or a solvate thereof according to any of [A1] to [A46], [B1] to [B44], [C1] to [C40], and [D1] to [D61] for use in prevention and/or treatment of cancer.

[E6]

Use of the compound or a salt thereof, or a solvate thereof according to any of [A1] to [A46], [B1] to [B44], [C1] to [C40], and [D1] to [D61] for producing a pharmaceutical composition for prevention and/or treatment of cancer.

[E6.2]

The pharmaceutical composition, the prophylactic agent and/or a therapeutic agent for cancer, the MYT1 inhibitor, the method, the compound or a salt thereof, or a solvate thereof according to any of [A1] to [A46], [B1] to [B44], [C1] to [C40], and [D1] to [D61] for use, or the use according to any of [E1] to [E6], being used in combination with a chemotherapeutic agent.

[E7]

A pharmaceutical composition for treating or preventing a cancer in a cancer patient in which positivity of RB1 gene mutation, or decreased expression of RB1 gene or protein has been detected, in combination with a chemotherapeutic agent, the pharmaceutical composition comprising a MYT1 inhibitor as an active ingredient,

- wherein the MYT1 inhibitor is the compound or a salt thereof, or a solvate thereof according to any of [A1] to [A46], [B1] to [B44], [C1] to [C40], and [D1] to [D61].

[E7.2]

A pharmaceutical composition for treating or preventing a cancer in a cancer patient in which positivity of RB1 gene mutation, or decreased expression of RB1 gene or protein has occurred, in combination with a chemotherapeutic agent, the pharmaceutical composition comprising an MYT1 inhibitor as an active ingredient,

- wherein the MYT1 inhibitor is a compound or a salt thereof, or a solvate thereof according to any of [A1] to [A46], [B1] to [B44], [C1] to [C40], and [D1] to [D61].

[E7.5]

A pharmaceutical composition for treating or preventing a cancer in a cancer patient in which positivity of RB1 gene mutation, or decreased expression of RB1 gene or protein has been detected, in combination with an MYT1 inhibitor, the pharmaceutical composition comprising a chemotherapeutic agent as an active ingredient,

- wherein the MYT1 inhibitor is a compound or a salt thereof, or a solvate thereof according to any of [A1] to [A46], [B1] to [B44], [C1] to [C40], and [D1] to [D61].

[E7.7]

A pharmaceutical composition for treating or preventing a cancer in a cancer patient in which positivity of RB1 gene mutation, or decreased expression of RB1 gene or protein has occurred, in combination with an MYT1 inhibitor, the pharmaceutical composition comprising a chemotherapeutic agent as an active ingredient,

- wherein the MYT1 inhibitor is a compound or a salt thereof, or a solvate thereof according to any of [A1] to [A46], [B1] to [B44], [C1] to [C40], and [D1] to [D61].

[E8]

A method for treating or preventing cancer in a cancer patient in which positivity of RB1 gene mutation, or decreased expression of RB1 gene or protein has been detected, the method comprising:

- administering a chemotherapeutic agent and an MYT1 inhibitor in combination to the cancer patient,
- wherein the MYT1 inhibitor is the compound or a salt thereof, or a solvate thereof according to any of [A1] to [A46], [B1] to [B44], [C1] to [C40], and [D1] to [D61].

[E8.1]

A method for treating or preventing cancer, the method comprising:

detecting positivity of RB1 gene mutation, or decreased expression of RB1 gene or protein in a biological sample derived from a cancer patient, or allowing a third party to detect it; and administering a chemotherapeutic agent and an MYT1 inhibitor in combination to the cancer patient, wherein the MYT1 inhibitor is the compound or a salt thereof, or a solvate thereof according to any of [A1] to [A46], [B1] to [B44], [C1] to [C40], and [D1] to [D61].

[E8.2]

A method for treating or preventing a cancer in a cancer patient in which positivity of RB1 gene mutation, or decreased expression of RB1 gene or protein has occurred, the method comprising:

administering a chemotherapeutic agent and an MYT1 inhibitor in combination to the cancer patient, wherein the MYT1 inhibitor is a compound or a salt thereof, or a solvate thereof according to any of [A1] to [A46], [B1] to [B44], [C1] to [C40], and [D1] to [D61].

[E9]

A method for suppressing growth of cancer cells in a cancer patient in which positivity of RB1 gene mutation, or decreased expression of RB1 gene or protein has been detected, the method comprising:

contacting an MYT1 inhibitor and a chemotherapeutic agent with the cancer cells, wherein the MYT1 inhibitor is the compound or a salt thereof, or a solvate thereof according to any of [A1] to [A46], [B1] to [B44], [C1] to [C40], and [D1] to [D61].

[E9.1]

A method for suppressing growth of cancer cells, the method comprising:

detecting positivity of RB1 gene mutation, or decreased expression of RB1 gene or protein in a biological sample derived from a cancer patient, or allowing a third party to detect it; and contacting an MYT1 inhibitor and a chemotherapeutic agent with the cancer cells, wherein the MYT1 inhibitor is the compound or a salt thereof, or a solvate thereof according to any of [A1] to [A46], [B1] to [B44], [C1] to [C40], and [D1] to [D61].

[E9.2]

A method for suppressing growth of cancer cells in a cancer patient in which positivity of RB1 gene mutation, or decreased expression of RB1 gene or protein has occurred, the method comprising:

contacting an MYT1 inhibitor and a chemotherapeutic agent with the cancer cells, wherein the MYT1 inhibitor is a compound or a salt thereof, or a solvate thereof according to any of [A1] to [A46], [B1] to [B44], [C1] to [C40], and [D1] to [D61].

[E10]

A method for improving responsiveness to cancer treatment with a chemotherapeutic agent, the cancer being a cancer in a cancer patient in which positivity of RB1 gene mutation, decreased expression of RB1 gene or protein, or positivity of expression of hyperphosphorylated RB1 protein has been detected, the method comprising administering an MYT1 inhibitor together with the chemotherapeutic agent to the cancer patient, wherein the MYT1 inhibitor is the compound or a salt thereof, or a solvate thereof according to any of [A1] to [A46], [B1] to [B44], [C1] to [C40], and [D1] to [D61].

[E10.1]

A method for improving responsiveness to cancer treatment with a chemotherapeutic agent, the method comprising:

detecting positivity of RB1 gene mutation, or decreased expression of RB1 gene or protein in a biological sample derived from a cancer patient, or allowing a third party to detect it; and administering an MYT1 inhibitor together with the chemotherapeutic agent to the cancer patient, wherein the MYT1 inhibitor is the compound or a salt thereof, or a solvate thereof according to any of [A1] to [A46], [B1] to [B44], [C1] to [C40], and [D1] to [D61].

[E10.2]

A method for improving responsiveness to cancer treatment with a chemotherapeutic agent, the cancer being a cancer in a cancer patient characterized by positivity of RB1 gene mutation or decreased expression of RB1 gene or protein, the method comprising administering an MYT1 inhibitor together with the chemotherapeutic agent to the cancer patient, wherein the MYT1 inhibitor is a compound or a salt thereof, or a solvate thereof according to any of [A1] to [A46], [B1] to [B44], [C1] to [C40], and [D1] to [D61].

[E11]

A method for predicting responsiveness to cancer treatment with a combination of an MYT1 inhibitor and a chemotherapeutic agent, the method comprising:

detecting the presence or absence of RB1 gene mutation, or the presence or absence of decreased expression of RB1 gene or protein in a biological sample derived from a cancer patient, or allowing a third party to detect it; and determining the patient as having responsiveness to cancer treatment with a combination of an MYT1 inhibitor and a chemotherapeutic when the RB1 gene mutation is positive, or when the expression of RB1 gene or protein is decreased, or when the expression of hyperphosphorylated RB1 protein is positive, wherein the MYT1 inhibitor is the compound or a salt thereof, or a solvate thereof according to any of [A1] to [A46], [B1] to [B44], [C1] to [C40], and [D1] to [D61].

[E12]

A method for selecting a cancer patient for which administration of an MYT1 inhibitor and a chemotherapeutic agent in combination is more effective than single-agent administration of the MYT1 inhibitor or/and the chemotherapeutic agent, the method comprising:

detecting the presence or absence of RB1 gene mutation or the presence, or absence of decreased expression of RB1 gene or protein in a biological sample derived from a cancer patient, or allowing a third party to detect it; and determining the cancer patient as a cancer patient for which administration of an MYT1 inhibitor and a chemotherapeutic agent in combination is more effective than single-agent administration of the MYT1 inhibitor or/and the chemotherapeutic agent, on the basis of the presence of the mutation or the decreased expression, wherein the MYT1 inhibitor is a compound or a salt thereof, or a solvate thereof according to any of [A1] to [A46], [B1] to [B44], [C1] to [C40], and [D1] to [D61].

[E13]

A method for screening for a compound effective for treatment or prevention of cancer in a cancer patient in which positivity of RB1 gene mutation, or decreased expression of RB1 gene or protein has been detected, the method comprising:

measuring MYT1 inhibitory activity of a candidate compound; and selecting a candidate compound having MYT1 inhibitory activity as a compound effective for treatment of the cancer.

[E13.2]

A method for screening for a compound effective for treatment or prevention of cancer in a cancer patient in which positivity of RB1 gene mutation, or decreased expression of RB1 gene or protein has occurred, the method comprising:

measuring MYT1 inhibitory activity of a candidate compound; and selecting a candidate compound having MYT1 inhibitory activity as a compound effective for treatment of the cancer.

[E14]

An MYT1 inhibitor for use in combination with a chemotherapeutic agent in treatment or prevention of cancer in a cancer patient in which positivity of RB1 gene mutation, decreased expression of RB1 gene or protein, or positivity of expression of hyperphosphorylated RB1 protein has been detected, wherein the MYT1 inhibitor is the compound or a salt thereof, or a solvate thereof according to any of [A1] to [A46], [B1] to [B44], [C1] to [C40], and [D1] to [D61].

[E14.2]

An MYT1 inhibitor for use in combination with a chemotherapeutic agent in treatment or prevention of cancer in a cancer patient in which positivity of RB1 gene mutation, or decreased expression of RB1 gene or protein has occurred, wherein the MYT1 inhibitor is a compound or a salt thereof, or a solvate thereof according to any of [A1] to [A46], [B1] to [B44], [C1] to [C40], and [D1] to [D61].

[E15]

A chemotherapeutic agent for use in combination with an MYT1 inhibitor in treatment or prevention of cancer in a cancer patient in which positivity of RB1 gene mutation, or decreased expression of RB1 gene or protein has been detected, wherein the MYT1 inhibitor is the compound or a salt thereof, or a solvate thereof according to any of [A1] to [A46], [B1] to [B44], [C1] to [C40], and [D1] to [D61].

[E15.2]

A chemotherapeutic agent for use in combination with a MYT1 inhibitor in treatment or prevention of cancer in a cancer patient in which positivity of RB1 gene mutation or decreased expression of RB1 gene or protein has occurred, wherein the MYT1 inhibitor is a compound or a salt thereof, or a solvate thereof according to any of [A1] to [A46], [B1] to [B44], [C1] to [C40], and [D1] to [D61].

[E16]

Use of an MYT1 inhibitor for producing a pharmaceutical composition for treatment or prevention of cancer in a cancer patient in which positivity of RB1 gene mutation, decreased expression of RB1 gene or protein has been detected, the MYT1 inhibitor being administered in combination with a chemotherapeutic agent, wherein the MYT1 inhibitor is the compound or a salt thereof, or a solvate thereof according to any of [A1] to [A46], [B1] to [B44], [C1] to [C40], and [D1] to [D61].

[E16.2]

Use of an MYT1 inhibitor for producing a pharmaceutical composition for treatment or prevention of cancer in a cancer patient in which positivity of RB1 gene mutation or decreased expression of RB1 gene or protein has occurred, the pharmaceutical composition being administered in combination with a chemotherapeutic agent, wherein the MYT1 inhibitor is a compound or a salt thereof, or a solvate thereof according to any of [A1] to [A46], [B1] to [B44], [C1] to [C40], and [D1] to [D61].

[E17]

Use of a chemotherapeutic agent for producing a pharmaceutical composition for treatment or prevention of cancer in a cancer patient in which positivity of RB1 gene mutation, or decreased expression of RB1 gene or protein has been detected, the pharmaceutical composition being administered in combination with an MYT1 inhibitor, wherein the MYT1 inhibitor is the compound or a salt thereof, or a solvate thereof according to any of [A1] to [A46], [B1] to [B44], [C1] to [C40], and [D1] to [D61].

[E17.2]

Use of a chemotherapeutic agent for producing a pharmaceutical composition for treatment or prevention of cancer in a cancer patient in which positivity of RB1 gene mutation or decreased expression of RB1 gene or protein has occurred, the pharmaceutical composition being administered in combination with an MYT1 inhibitor, wherein the MYT1 inhibitor is a compound or a salt thereof, or a solvate thereof according to any of [A1] to [A46], [B1] to [B44], [C1] to [C40], and [D1] to [D61].

[E18]

The pharmaceutical composition, method, MYT1 inhibitor for use, chemotherapeutic agent for use, or use according to any one of [E7] to [E17], wherein the chemotherapeutic agent is an antimetabolite.

[E19]

The pharmaceutical composition, method, MYT1 inhibitor for use, chemotherapeutic agent for use, or use according to [E18], wherein the antimetabolite is an antifolate.

[E20]

The pharmaceutical composition, method, MYT1 inhibitor for use, chemotherapeutic agent for use, or use according to [E19], wherein the antifolate is pemetrexed.

[E21]

The pharmaceutical composition, method, MYT1 inhibitor for use, chemotherapeutic agent for use, or use according to any one of [E7] to [E20], wherein the cancer is lung cancer. In the above numbering, the number cited in the dependent item also includes the same number but with a different number after a decimal point, unless otherwise specified. For example, [C6] cited in the dependent item shows that not only [C6] but also [C6.5] are included. The same applies to other numberings.

Advantageous Effect of Invention

The present invention can provide a compound having new MYT1 inhibitory activity or a salt thereof, or a solvate thereof. The present invention can also provide a medicament useful for treatment and prevention of cancer containing any of them as the active ingredient.

MODE FOR CARRYING OUT THE INVENTION

Figure 1:
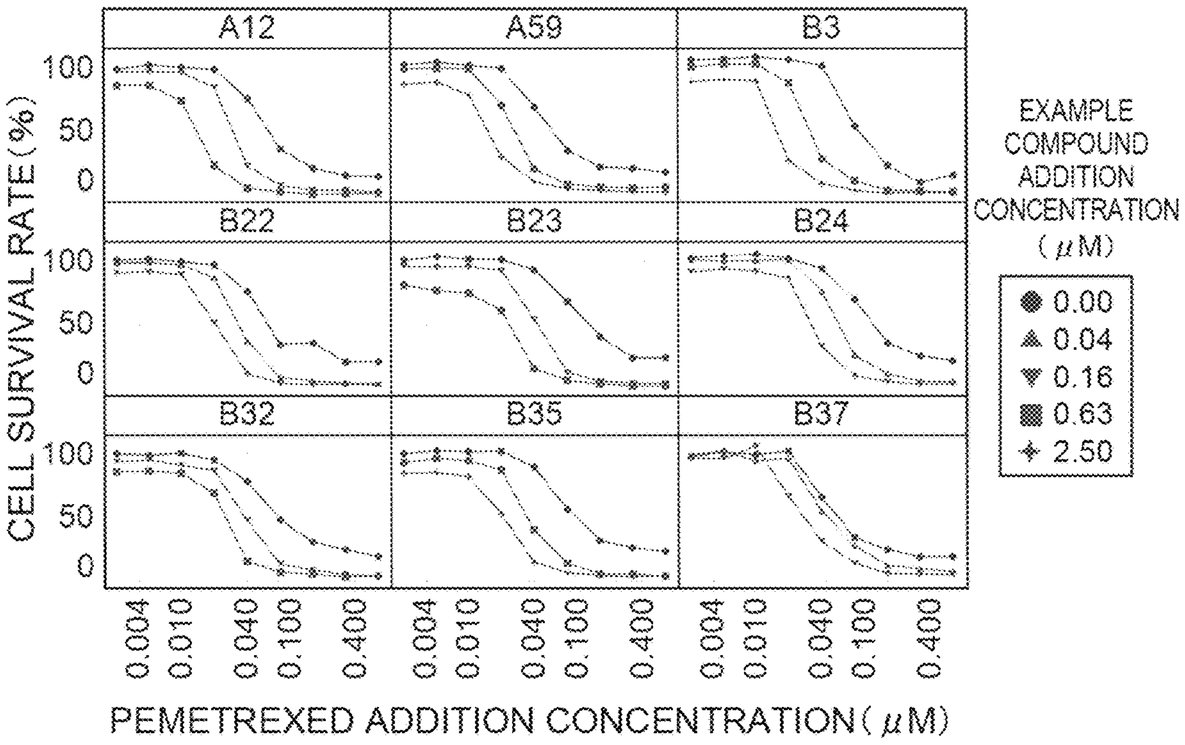
FIG. 1 is a graph showing cell survival rates calculated in a cytotoxicity test with pemetrexed when example compounds (A12, A59, B3, B22, B23, B24, B32, B35, and B37) are added.
Figure 2:
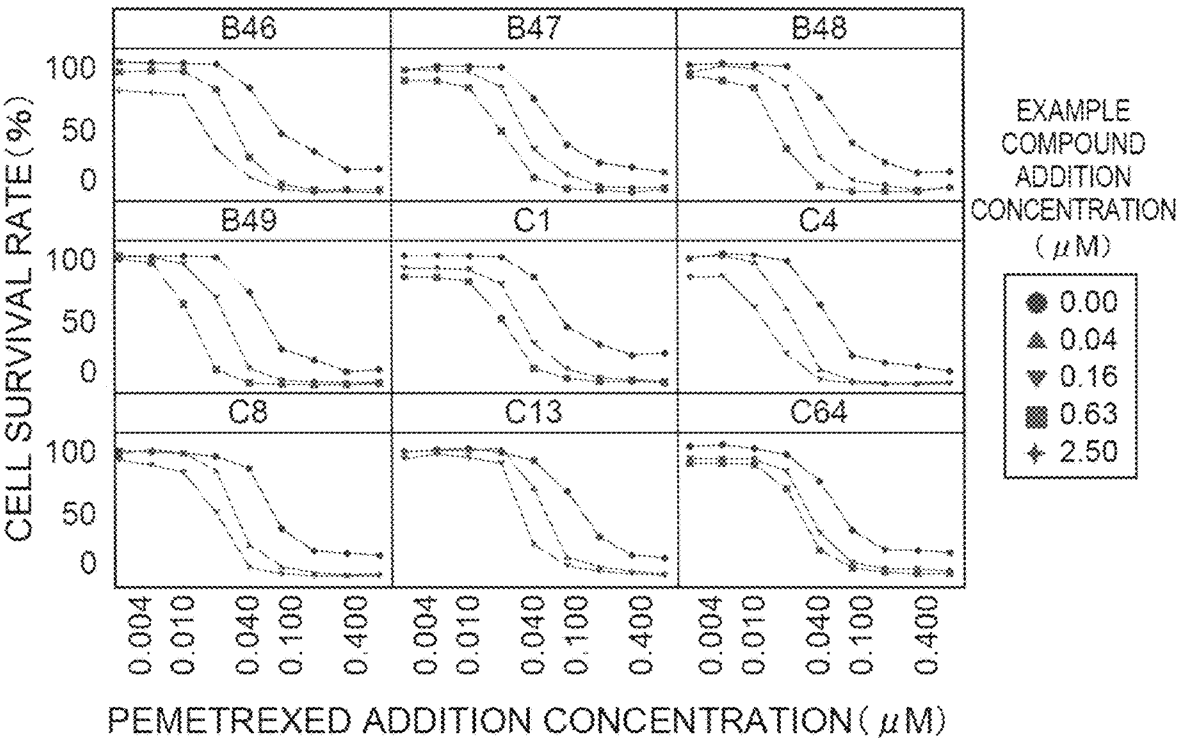
FIG. 2 is a graph showing cell survival rates calculated in a cytotoxicity test with pemetrexed when example compounds (B46, B47, B48, B49, C1, C4, C8, C13, and C64) are added.
Figure 3:
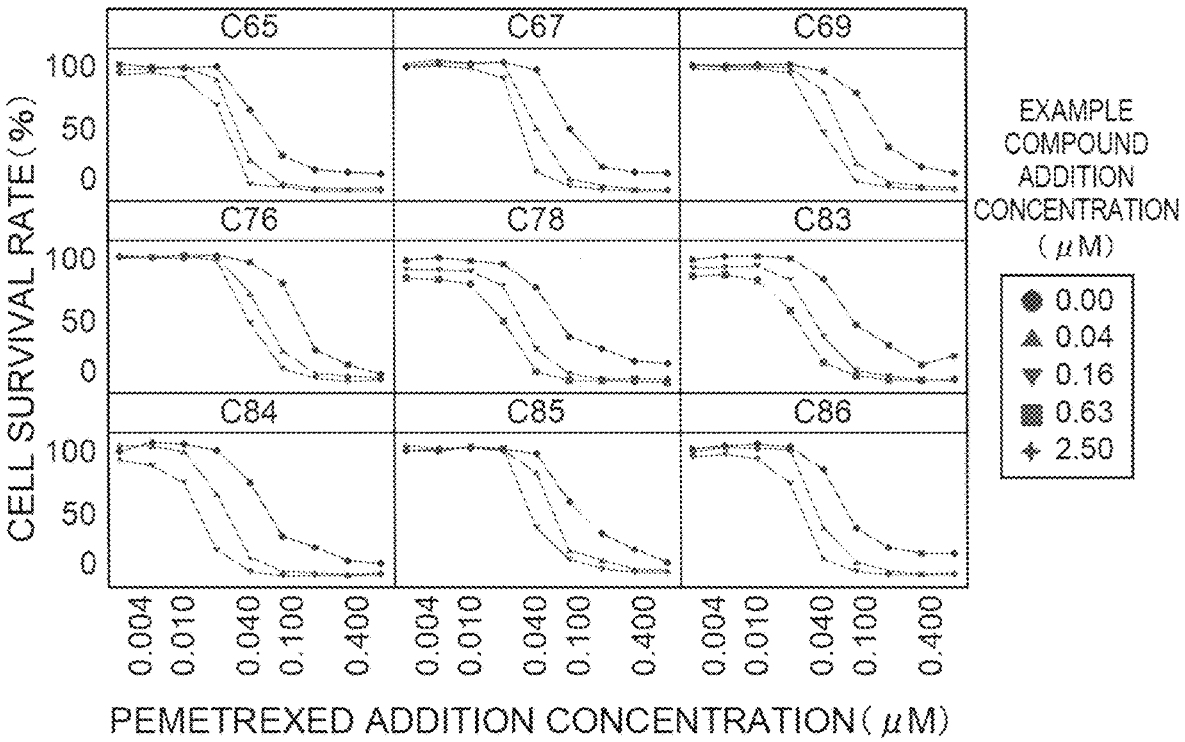
FIG. 3 is a graph showing cell survival rates calculated in a cytotoxicity test with pemetrexed when example compounds (C65, C67, C69, C76, C78, C83, C84, C85, and C86) are added.
Figure 4:
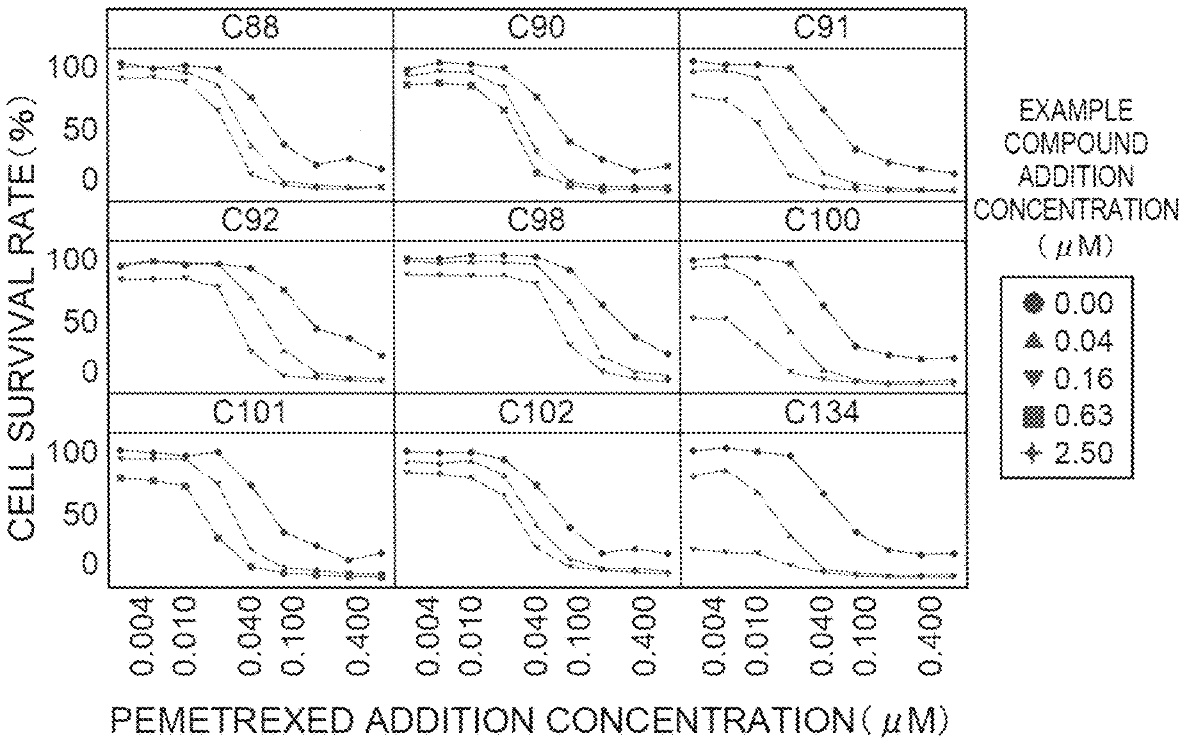
FIG. 4 is a graph showing cell survival rates calculated in a cytotoxicity test with pemetrexed when example compounds (C88, C90, C91, C92, C98, C100, C101, C102, and C134) are added.
Figure 5:
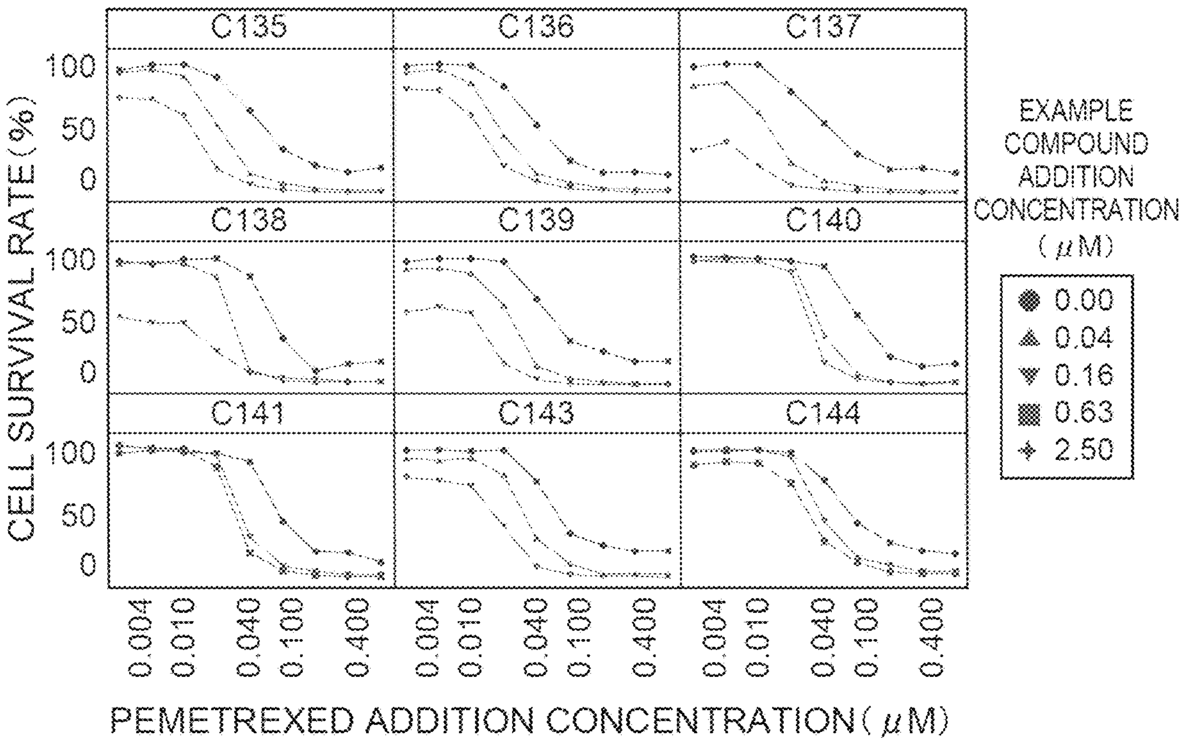
FIG. 5 is a graph showing cell survival rates calculated in a cytotoxicity test with pemetrexed when example compounds (C135, C136, C137, C138, C139, C140, C141, C143, and C144) are added.
Figure 6:
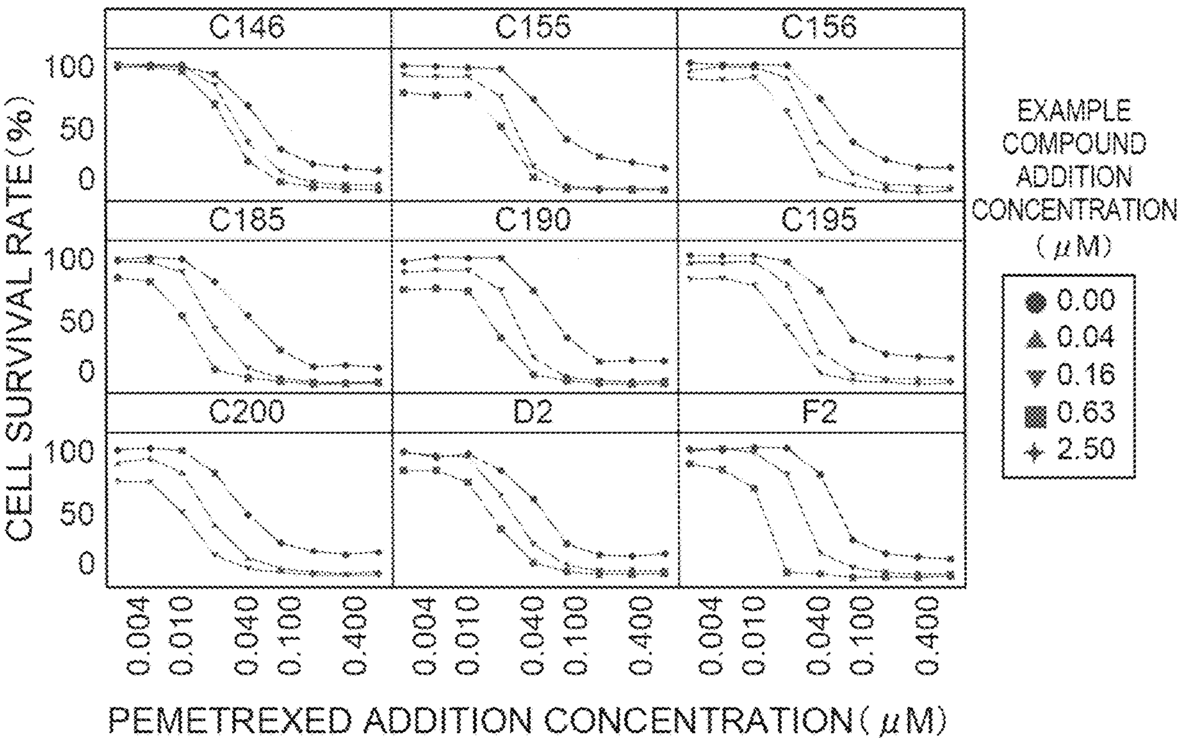
FIG. 6 is a graph showing cell survival rates calculated in a cytotoxicity test with pemetrexed when example compounds (C146, C155, C156, C185, C190, C195, C200, D2, and F2) are added.
Figure 7:
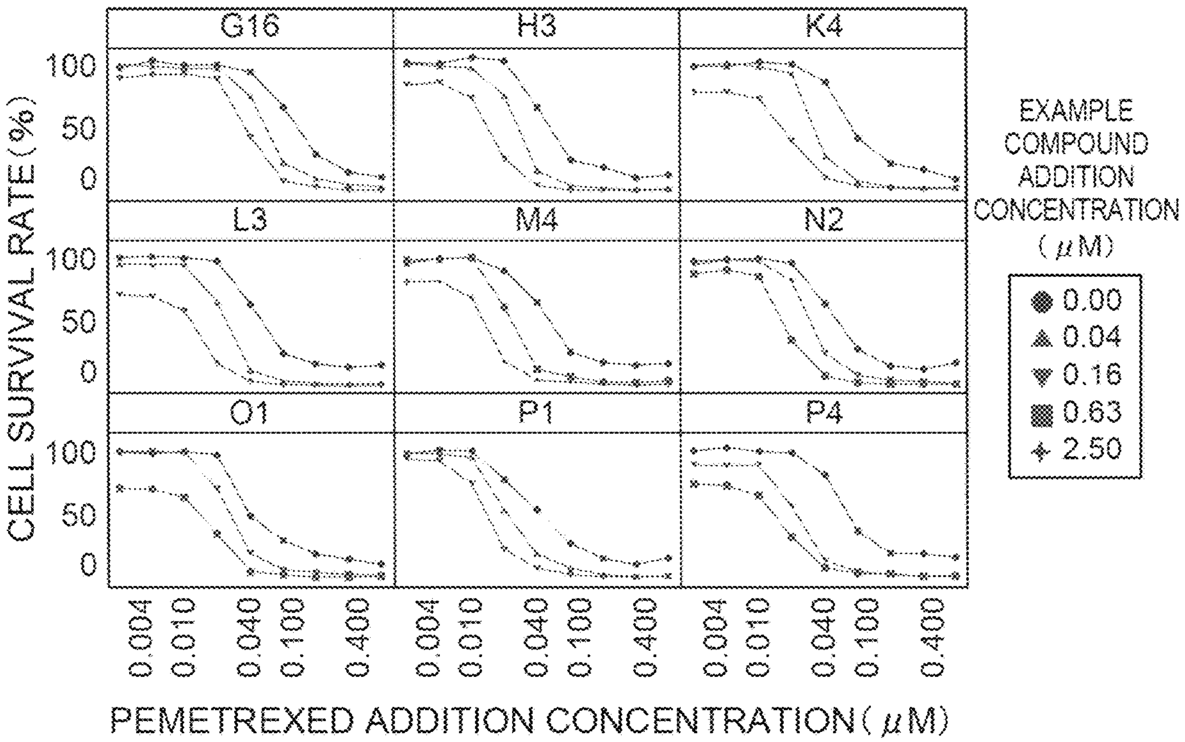
FIG. 7 is a graph showing cell survival rates calculated in a cytotoxicity test with pemetrexed when example compounds (G16, H3, K4, L3, M4, N2, O1, P1, and P4) are added.
Figure 8:
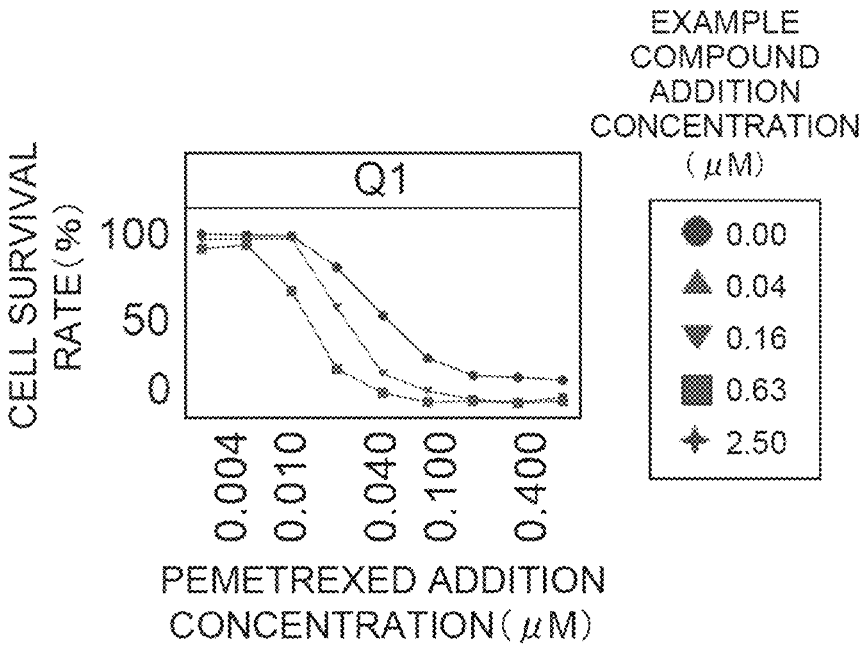
FIG. 8 is a graph showing cell survival rates calculated in a cytotoxicity test with pemetrexed when an example compound (Q1) is added.

Hereinafter, the definitions of the symbols, terms, and the like as used herein, the embodiments of the present invention, and the like will be described, and the present invention will be described in detail.

The term “halogen” as used herein means fluorine, chlorine, bromine, or iodine.

The term “thio (thiol)” as used herein means —SH.

The term “amino” as used herein means —NRR'. In this context, each of R and R' is independently selected from the group consisting of hydrogen, alkyl, alkenyl, alkynyl, cycloalkyl, heterocyclyl, aryl, and heteroaryl, or R and R', together with the nitrogen atom to which they are attached, form a group forming a ring. The amino is preferably —$NH_2$, mono $C_1$-$C_6$ alkylamino (hereinafter, “$C_p$-$C_q$” means that the number of carbon atoms is p to q), and di $C_1$-$C_6$ alkylamino, or 4- to 8-membered cyclic amino.

The term “alkoxy” as used herein means an oxy group to which the “alkyl” as defined herein is attached. The alkoxy is preferably $C_1$-$C_6$ alkoxy, and more preferably $C_1$-$C_4$ alkoxy. Specific examples of the alkoxy include methoxy, ethoxy, 1-propoxy, 2-propoxy, n-butoxy, i-butoxy, s-butoxy, t-butoxy, pentyloxy, and 3-methylbutoxy.

The term "alkylthio" as used herein means a "thio" group to which the "alkyl" as defined herein is attached. The alkylthio is preferably $C_1$-$C_6$ alkylthio, and more preferably $C_1$-$C_4$ alkylthio. Specific examples of the alkylthio include methylthio, ethylthio, 1-propylthio, 2-propylthio, n-butylthio, i-butylthio, s-butylthio, and t-butylthio.

The term "sulfonyl" as used herein means —S(=O)$_2$—R. In this context, R is selected from the group consisting of hydroxy, alkyl, alkenyl, alkynyl, cycloalkyl, heterocyclyl, aryl, and heteroaryl. The sulfonyl is preferably $C_1$-$C_6$ alkylsulfonyl.

The term "phosphoryl" as used herein means —P(=O)RR'. In this context, each of R and R' is independently selected from the group consisting of alkyl, alkenyl, alkynyl, cycloalkyl, heterocyclyl, aryl, and heteroaryl. The phosphoryl is preferably mono $C_1$-$C_6$ alkylphosphoryl or di $C_1$-$C_6$ alkylphosphoryl.

The term "boryl" as used herein means-BRR'. In this context, each of R and R' is independently selected from the group consisting of hydrogen, hydroxy, alkyl, alkenyl, alkynyl, cycloalkyl, heterocyclyl, aryl, and heteroaryl, or R and R', together with the boron atom to which they are attached, form a ring. The boryl is preferably dihydroxyboryl, mono $C_1$-$C_6$ alkylboryl, di $C_1$-$C_6$ alkylboryl, or 4- to 8-membered cyclic boryl. Specific examples of the boryl include a dihydroxyboryl group, a pinacolatoboryl group, a neopentanediolatoboryl group, a catecholatoboryl group, and a 9-borabicyclo[3.3.1]nonan-9-yl group.

The term "alkyl" as used herein is a monovalent group derived from an aliphatic hydrocarbon by removing any one hydrogen atom, and has a subset of hydrocarbyl or hydrocarbon group structures that do not contain a heteroatom (which is an atom other than carbon and hydrogen atoms) or an unsaturated carbon-carbon bond, and contain hydrogen and carbon atoms in the backbone. The alkyl includes not only a linear form but a branched form. The alkyl is preferably $C_1$-$C_6$ alkyl, and more preferably $C_1$-$C_4$ alkyl. Specific examples of the alkyl include methyl, ethyl, n-propyl, i-propyl, n-butyl, s-butyl, t-butyl, isobutyl (2-methylpropyl), n-pentyl, s-pentyl (1-methylbutyl), t-pentyl (1,1-dimethylpropyl), neopentyl (2,2-dimethylpropyl), isopentyl (3-methylbutyl), 3-pentyl (1-ethylpropyl), 1,2-dimethylpropyl, 2-methylbutyl, n-hexyl, 1,1,2-trimethylpropyl, 1,2,2-trimethylpropyl, 1,1,2,2-tetramethylpropyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, and 2-ethylbutyl.

The term "alkenyl" as used herein is a monovalent group having at least one double bond (two adjacent $sp^2$ carbon atoms). Depending on the conformation of the double bond and a substituent (if present), the geometric morphology of the double bond can assume entgegen (E) or zusammen (Z) and cis or trans conformations. The alkenyl includes not only a linear form but a branched form. The alkenyl is preferably $C_2$-$C_6$ alkenyl, and more preferably $C_2$-$C_4$ alkenyl. Specific examples of the alkenyl include vinyl, allyl, 1-propenyl, 2-propenyl, 1-butenyl, 2-butenyl (which includes cis and trans), 3-butenyl, pentenyl, 3-methyl-2-butenyl, and hexenyl.

The term "alkynyl" as used herein is a monovalent group having at least one triple bond (two adjacent SP carbon atoms). The alkynyl includes not only a linear form but a branched form. The alkynyl is preferably $C_2$-$C_6$ alkynyl, and more preferably $C_2$-$C_4$ alkynyl. Specific examples of the alkynyl include ethynyl, 1-propynyl, propargyl, 3-butynyl, pentynyl, hexynyl, 3-phenyl-2-propynyl, 3-(2'-fluorophenyl)-2-propynyl, 2-hydroxy-2-propynyl, 3-(3-fluorophenyl)-2-propynyl, and 3-methyl-(5-phenyl)-4-pentynyl.

The term "cycloalkyl" as used herein means a saturated or partially saturated cyclic monovalent aliphatic hydrocarbon group and includes a monocyclic ring, a bicyclo ring, and a spiro ring. The cycloalkyl is preferably $C_3$-$C_8$ cycloalkyl, and more preferably $C_3$-$C_6$ cycloalkyl. Specific examples of the cycloalkyl include cyclopropyl, cyclobutyl, cyclopentyl, cyclohexyl, cycloheptyl, cyclooctyl, bicyclo[2.2.1]heptyl, spiro[3,3]heptyl, spiro[2.3]hexyl, and spiro[4.5]decyl.

The term "aryl" as used herein means a monovalent aromatic hydrocarbon ring, that is, an aromatic hydrocarbon ring group. The aryl is preferably $C_6$-$C_{10}$ aryl. Specific examples of the aryl include phenyl and naphthyl (e.g., 1-naphthyl and 2-naphthyl).

The term "heterocyclyl" as used herein means a nonaromatic cyclic monovalent group containing a carbon atom as well as 1 to 5 heteroatoms. The heterocyclyl may have a double and/or triple bond in the ring. A carbon atom in the ring may form carbonyl through oxidation, and the ring may be a monocyclic ring, a condensed ring, or a spiro ring. In the case of the condensed ring, an aromatic ring such as a benzene ring, a pyridine ring, or a pyrimidine ring may form the condensed ring with a saturated cycloaliphatic ring such as a cyclopentane ring or a cyclohexane ring, or a saturated heterocyclic ring such as a tetrahydropyran ring, a dioxane ring, or a pyrrolidine ring. The number of atoms constituting the ring of heterocyclyl is preferably 4 to 10 (4- to 10-membered heterocyclyl), and more preferably 4 to 7 (4- to 7-membered heterocyclyl). Specific examples of the heterocyclyl include azetidinyl, oxoazetidinyl, oxiranyl, oxetanyl, azetidinyl, dihydrofuryl, tetrahydrofuryl (oxolan-2-yl, oxolan-3-yl), dihydropyranyl, tetrahydropyranyl (oxan-4-yl), tetrahydropyridyl, tetrahydropyrimidyl, morpholinyl, thiomorpholinyl, pyrrolidinyl, oxopyrrolidinyl, piperidinyl, piperazinyl, pyrazolidinyl, imidazolinyl, imidazolidinyl, oxazolidinyl, isooxazolidinyl, thiazolidinyl, isothiazolidinyl, 1,2-thiazinane, thiadiazolidinyl, oxazolidonyl, benzodioxanyl, benzoxazolyl, dioxolanyl, dioxanyl, tetrahydropyrrolo[1,2-c]imidazole, thietanyl, 3,6-diazabicyclo[3.1.1]heptanyl, 2,5-diazabicyclo[2.2.1]heptanyl, 3-oxa-8-azabicyclo[3.2.1]octanyl, 2,4,5-trimethylpiperazin-1-yl, sultam, 2-oxaspiro[3,3]heptyl, 6,7-dihydro-pyrrolo[1,2-a]imidazolyl, 4,5,6,7-tetrahydropyrazolo[1,5-a]pyrazinyl, azepanyl, dioxepanyl, 5,9-dioxaspiro[3.5]nonanyl, 1,1-dioxo-1,4-thiazinan-4-yl, carbonylazetidinyl, acetylpiperidinyl, 2-oxa-6-azaspiro[3,3]heptan-6-yl, 2-oxa-7-azaspiro[3.4]octan-7-yl, 3-oxa-6-azabicyclo[3.1.1]heptan-6-yl, 6-oxa-3-azabicyclo[3.1.1]heptan-3-yl, (9aR)-3,4,6,7,9,9a-hexahydro-1H-pyrazino[2,1-c][1,4]oxazin-8-yl, 3-(azetidin-1-yl) azetidin-1-yl, 1-(oxetane-3-yl) piperidin-4-yl, 1-(oxan-4-yl) piperidin-4-yl, 4-pyrrolidin-1-ylpiperidin-1-yl, and 4-morpholin-4-ylpiperidin-1-yl.

The term "heteroaryl" as used herein means an aromatic cyclic monovalent group containing a carbon atom as well as 1 to 5 heteroatoms, that is, an aromatic heterocyclic group. The ring may be a monocyclic ring or a condensed ring with another ring. The number of atoms constituting the ring of heteroaryl is preferably 5 to 10 (5- to 10-membered heteroaryl), and more preferably 5 to 7 (5- to 7-membered heteroaryl). Specific examples of the heteroaryl include furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, benzotriazolyl, indolyl, isoindolyl, indazolyl, azaindolyl, quinolyl, isoquinolyl, cinnolinyl, quinazolinyl, quinoxalinyl, indolizinyl, and imidazopyridyl, pyrazolopyridyl, triazolopyridyl, pyrrolopyrazinyl, and flopyridyl.

The term "alkylsulfonyl" as used herein means a "sulfonyl" group to which the "alkyl" or "cycloalkyl" as defined herein is attached. The alkylsulfonyl is preferably $C_1$-$C_6$ alkylsulfonyl or $C_3$-$C_8$ cycloalkylsulfonyl, and more preferably $C_1$-$C_4$ alkylsulfonyl or $C_3$-$C_6$ cycloalkylsulfonyl. Specific examples of the alkylsulfonyl include methylsulfonyl, ethylsulfonyl, 1-propylsulfonyl, 2-propylsulfonyl, n-butylsulfonyl, i-butylsulfonyl, s-butylsulfonyl, and t-butylsulfonyl.

The term "acylamino" as used herein means a group in which R is hydrogen and R' is the "acyl" as defined herein, in the "amino" as defined herein. The acylamino is preferably $C_1$-$C_6$ acylamino, and more preferably $C_1$-$C_4$ acylamino. Specific examples of the acylamino include acetylamino.

The term "monoalkylamino" as used herein means a group in which R is hydrogen and R' is the "alkyl" as defined herein, in the "amino" as defined herein. The monoalkylamino is preferably mono $C_1$-$C_6$ alkylamino, and more preferably mono $C_1$-$C_4$ alkylamino. Specific examples of the monoalkylamino include methylamino, ethylamino, n-propylamino, i-propylamino, n-butylamino, s-butylamino, and t-butylamino.

The term "alkylsulfonylamino" as used herein means a group in which R is hydrogen and R' is the "alkylsulfonyl" as defined herein, in the "amino" as defined herein. The alkylsulfonylamino is preferably $C_1$-$C_6$ alkylsulfonylamino or $C_3$-$C_8$ cycloalkylsulfonylamino, and more preferably $C_1$-$C_4$ alkylsulfonylamino or $C_3$-$C_6$ cycloalkylsulfonylamino. Specific examples of the alkylsulfonylamino include methylsulfonylamino, ethylsulfonylamino, and cyclopropylsulfonylamino.

The term "haloalkoxy" as used herein means a group in which one or more hydrogen of the "alkoxy" as defined herein are replaced with "halogen". The haloalkoxy is preferably halo $C_1$-$C_6$ alkoxy, and more preferably halo $C_1$-$C_4$ alkoxy. Specific examples of the haloalkoxy include difluoromethoxy, trifluoromethoxy, 2,2-difluoroethoxy, 2,2,2-trifluoroethoxy, 3-fluoropropoxy, 2,2-difluoropropoxy, 3,3-difluoropropoxy, (2R)-2-fluoropropoxy, [(2S)-1,1,1-trifluoropropan-2-yl]oxy, [(2R)-1,1,1-trifluoropropan-2-yl]oxy, and 3,3,3-trifluoro-2,2-dimethylpropoxy.

The term "hydroxyalkoxy" as used herein means a group in which one or more hydrogen of the "alkoxy" as defined herein are replaced with a hydroxy group. The hydroxyalkoxy is preferably hydroxy $C_1$-$C_6$ alkoxy, and more preferably hydroxy $C_1$-$C_4$ alkoxy. Specific examples of the hydroxyalkoxy include 2-hydroxy-2-methylpropoxy, 3-hydroxy-3-methylbutoxy, and 4-hydroxybutoxy.

The term "alkoxyalkoxy" as used herein means a group in which the "alkoxy" is attached to "alkoxy" as defined herein. The alkoxyalkoxy is preferably $C_1$-$C_6$ alkoxy $C_1$-$C_6$ alkoxy, and more preferably $C_1$-$C_4$ alkoxy $C_1$-$C_4$ alkoxy. Specific examples of the alkoxyalkoxy include 2-methoxyethoxy, (2S)-2-methoxypropoxy, and (2R)-2-methoxypropoxy.

The term "cycloalkylalkoxy" as used herein means an oxy group to which the "cycloalkylalkyl" as defined herein is attached. The cycloalkylalkoxy is preferably $C_3$-$C_8$ cycloalkyl $C_1$-$C_6$ alkoxy, and more preferably $C_3$-$C_6$ cycloalkyl $C_1$-$C_4$ alkoxy. Specific examples of the cycloalkylalkoxy include cyclopropylmethoxy, cyclobutanylmethoxy, cyclopentylmethoxy, cyclohexylmethoxy, and 1-bicyclo[1.1.1]pentanylmethoxy.

The term "heterocyclylalkoxy" as used herein means an oxy group to which the "heterocyclyl" as defined herein is attached through the "alkyl". The heterocyclylalkoxy is preferably 4- to 10-membered heterocyclyl $C_1$-$C_6$ alkoxy, and more preferably 4- to 7-membered heterocyclyl $C_1$-$C_4$ alkoxy. Specific examples of the heterocyclylalkoxy include (1,1-dioxothian-4-yl)oxy, oxolan-2-ylmethoxy, oxolan-3-ylmethoxy, oxan-4-ylmethoxy, 1,4-dioxan-2-ylmethoxy, (1-methylpiperidin-4-yl)methoxy, 3-morpholin-4-ylpropoxy, and (oxetan-3-yl)methoxy.

The term "cycloalkoxy" as used herein means an oxy group to which the "cycloalkyl" as defined herein is attached. The cycloalkoxy is preferably $C_3$-$C_8$ cycloalkoxy, and more preferably $C_3$-$C_6$ cycloalkoxy. Specific examples of the cycloalkoxy include cyclopropoxy, cyclobutyloxy, cyclopentyloxy, and cyclohexyloxy.

The term "heterocyclyloxy" as used herein means an oxy group to which the "heterocyclyl" as defined herein is attached. The number of atoms constituting the ring of heterocyclyl is preferably 4 to 10 (4- to 10-membered heterocyclyloxy), and more preferably 4 to 7 (4- to 7-membered heterocyclyloxy). Specific examples of the heterocyclyloxy include azetidinyloxy, oxiranyloxy, oxetanyloxy, azetidinyloxy, dihydrofuryloxy, tetrahydrofuryloxy([(3R)-oxolan-3-yl]oxy, [(3S)-oxolan-3-yl]oxy), dihydropyranyloxy, tetrahydropyranyloxy(oxan-4-yloxy), [(3S)-oxan-3-yl]oxy, [(3R)-oxan-3-yl]oxy), tetrahydropyridyloxy, tetrahydropyrimidyloxy, morpholinyloxy, thiomorpholinyloxy, pyrrolidinyloxy, piperidinyloxy, piperazinyloxy, pyrazolidinyloxy, imidazolinyloxy, imidazolidinyloxy, oxazolidinyloxy, isooxazolidinyloxy, thiazolidinyloxy, isothiazolidinyloxy, 1,2-thiazinanoxy, thiadiazolidinyloxy, oxazolidonyloxy, benzodioxanyloxy, benzoxazolyloxy, dioxolanyloxy, dioxanyloxy, tetrahydropyrrolo[1,2-c]imidazoloxy, thietanyloxy, 3,6-diazabicyclo[3.1.1]heptanyloxy, 2,5-diazabicyclo[2.2.1]heptanyloxy, 3-oxa-8-azabicyclo[3.2.1]octanyloxy, sultamoxy, 2-oxaspiro[3,3]heptyloxy, and tetrahydrothiopyranyloxy.

The term "acyl (alkanoyl)" as used herein means a group in which a carbonyl group is attached to hydrogen or the "alkyl" as defined herein. The acyl is preferably $C_1$-$C_6$ acyl, and more preferably $C_2$-$C_4$ acyl. Specific examples of the acyl include formyl, acetyl, propionyl, and butanoyl.

The term "aminocarbonyl" as used herein means a carbonyl group to which the "amino" as defined herein is attached. Preferred examples of the aminocarbonyl include —$CONH_2$, mono $C_1$-$C_6$ alkylaminocarbonyl, mono $C_3$-$C_8$ cycloalkylaminocarbonyl, di $C_1$-$C_6$ alkylaminocarbonyl, and 4- to 8-membered cyclic aminocarbonyl. Specific examples of the aminocarbonyl include —$CONH_2$, dimethylaminocarbonyl, 1-azetidinylcarbonyl, 1-pyrrolidinylcarbonyl, 1-piperidinylcarbonyl, 1-piperazinylcarbonyl, 4-morpholinylcarbonyl, 3-oxazolidinylcarbonyl, 1,1-dioxydothiomorpholinyl-4-ylcarbonyl, 3-oxa-8-azabicyclo[3.2.1]octan-8-ylcarbonyl, and N-cyclopropylaminocarbonyl.

The term "alkylphosphoryl" as used herein means "phosphoryl" to which the "alkyl" as defined herein is attached. The alkylphosphoryl is preferably, mono $C_1$-$C_6$ alkylphosphoryl, di $C_1$-$C_6$ alkylphosphoryl, and more preferably mono $C_1$-$C_4$ alkylphosphoryl or di $C_1$-$C_4$ alkylphosphoryl. Specific examples of the alkylphosphoryl include methylphosphoryl, ethylphosphoryl, dimethylphosphoryl, and diethylphosphoryl.

The term "haloalkyl" as used herein means a group in which one or more hydrogen of the "alkyl" as defined herein are replaced with "halogen". The haloalkyl is preferably halo $C_1$-$C_6$ alkyl, and more preferably halo $C_1$-$C_4$ alkyl. Specific examples of the haloalkyl include difluoromethyl, trifluoromethyl, 2,2-difluoroethyl, 2,2,2-trifluoroethyl, 3-fluoropropyl, 3,3-difluoropropyl, 3,3,3-trifluoropropyl, 1,1,1-trifluoro-2-propyl, 4,4-difluorobutyl, and 5,5-difluoropentyl.

The term "hydroxyalkyl" as used herein means a group in which one or more hydrogen of the "alkyl" as defined herein are replaced with a hydroxy group. The hydroxyalkyl is preferably hydroxy $C_1$-$C_6$ alkyl, and more preferably hydroxy $C_1$-$C_4$ alkyl. Specific examples of the hydroxyalkyl include hydroxymethyl, 1-hydroxyethyl, 2-hydroxyethyl, 2-hydroxy-2-methylpropyl, and 5-hydroxypentyl.

The term "aminocarbonylalkyl" as used herein means a group in which one or more hydrogen of the "alkyl" as defined herein are replaced with the "aminocarbonyl" as defined herein. The aminocarbonylalkyl is preferably aminocarbonyl $C_1$-$C_6$ alkyl, mono $C_1$-$C_6$ alkylaminocarbonyl $C_1$-$C_6$ alkyl, or di $C_1$-$C_6$ alkylaminocarbonyl $C_1$-$C_6$ alkyl, and more preferably aminocarbonyl $C_1$-$C_4$ alkyl, mono $C_1$-$C_4$ alkylaminocarbonyl $C_1$-$C_4$ alkyl, or di $C_1$-$C_4$ alkylaminocarbonyl $C_1$-$C_4$ alkyl. Specific examples of the aminocarbonylalkyl include methylaminocarbonylmethyl, dimethylaminocarbonylmethyl, t-butylaminocarbonylmethyl, 1-azetidinylcarbonylmethyl, 1-pyrrolidinylcarbonylmethyl, 1-piperidinylcarbonylmethyl, 4-morpholinylcarbonylmethyl, 2-(methylaminocarbonyl)ethyl, 2-(dimethylaminocarbonyl)ethyl, 2-(1-azetidinylcarbonyl)ethyl, 2-(1-pyrrolidinylcarbonyl)ethyl, 2-(4-morpholinylcarbonyl)ethyl, 3-(dimethylaminocarbonyl) propyl, and 4-(dimethylaminocarbonyl)butyl.

The term "cycloalkylalkyl" as used herein means a group in which one or more hydrogen of the "alkyl" defined above are replaced with the "cycloalkyl" as defined above. The cycloalkylalkyl is preferably $C_3$-$C_8$ cycloalkyl $C_1$-$C_6$ alkyl, and more preferably $C_3$-$C_6$ cycloalkyl $C_1$-$C_4$ alkyl. Specific examples of the cycloalkylalkyl include cyclopropylmethyl, cyclobutylmethyl, cyclopentylmethyl, and cyclohexylmethyl.

The term "hydroxyalkenyl" as used herein means a group in which one or more hydrogen of the "alkenyl" as defined herein are replaced with a hydroxy group. The hydroxyalkenyl is preferably hydroxy $C_2$-$C_6$ alkenyl, and more preferably hydroxy $C_2$-$C_4$ alkenyl. Specific examples of the hydroxyalkenyl include (E)-4-hydroxybuta-1-enyl.

The term "hydroxyalkynyl" as used herein means a group in which one or more hydrogen of the "alkynyl" as defined herein are replaced with a hydroxy group. The hydroxyalkynyl is preferably hydroxy $C_2$-$C_6$ alkynyl, and more preferably hydroxy $C_2$-$C_4$ alkynyl. Specific examples of the hydroxyalkynyl include 3-hydroxy-3-methylbut-1-ynyl.

The term "cycloaliphatic ring" as used herein means a nonaromatic hydrocarbon ring. The cycloaliphatic ring may have an unsaturated bond in the ring. A carbon atom constituting the ring may form carbonyl through oxidation. The cycloaliphatic ring may be a monocycle (referred to as the monocyclic cycloaliphatic ring herein), or may form the condensed ring with a saturated cycloaliphatic ring such as a cyclopentane ring and a cyclohexane ring or an aromatic hydrocarbon ring such as a benzene ring and a naphthalene ring. The cycloaliphatic ring is preferably a 3- to 10-membered cycloaliphatic ring. Specific examples of the cycloaliphatic ring include a cyclopropane ring, a cyclobutane ring, a cyclopentane ring, a cyclohexane ring, a cycloheptane ring, a cyclooctane ring, and a bicyclo[2.2.1]heptane ring.

The term "aromatic hydrocarbon ring" as used herein means a hydrocarbon ring constituted by a monocyclic or condensed ring exhibiting aromaticity. The aromatic hydrocarbon ring is preferably a 6- to 10-membered aromatic hydrocarbon ring. Specific examples of the aromatic hydrocarbon ring include a benzene ring and a naphthalene ring.

The term "heterocyclic ring" as used herein means a nonaromatic heterocyclic ring containing preferably 1 to 5, more preferably 1 to 3 heteroatoms among the atoms constituting the ring. The heterocyclic ring may have a double and/or triple bond in the ring, and a carbon atom in the ring may form carbonyl through oxidation. The heterocyclic ring may be a monocycle (referred to as the monocyclic heterocyclic ring herein), or may form the condensed ring or spiro ring with a saturated cycloaliphatic ring such as a cyclopentane ring or a cyclohexane ring, or a saturated heterocyclic ring such as a tetrahydropyran ring, a dioxane ring, or a pyrrolidine ring. The number of atoms constituting the ring of the heterocyclic ring is preferably 3 to 12 (3- to 12-membered heterocyclic ring), and more preferably 4 to 10 (4- to 10-membered heterocyclic ring). Specific examples of the heterocyclic ring include an azetidine ring, an oxetane ring, a tetrahydrofuran ring, a tetrahydropyran ring, a morpholine ring, a thiomorpholine ring, a pyrrolidine ring, a 4-oxopyrrolidine ring, a piperidine ring, a 4-oxopiperidine ring, a piperazine ring, a pyrazolidine ring, an imidazolidine ring, an oxazolidine ring, an isoxazolidine ring, a thiazolidine ring, an isothiazolidine ring, a thiadiazolysine ring, an oxazolidone ring, a dioxolane ring, a dioxane ring, a thiethane ring, an octahydroindole ring, a 6,7-dihydro-pyrrolo[1,2-a]imidazole ring, an azocane ring, a 4,5,6,7-tetrahydro-pyrazolo[1,5-a]pyrazine ring, an azepane ring, a dioxepane ring, a 5,9-dioxaspiro[3.5]nonane ring, or rings in which one or more single bonds in any of these saturated heterocyclic rings are replaced with a double bond or a triple bond.

The term "aromatic heterocyclic ring" as used herein means a cyclic compound constituted by a monocyclic or condensed ring containing one or more heteroatoms and exhibiting aromaticity. The cyclic compound constituted by a monocycle exhibiting aromaticity as used herein is referred to as the monocyclic aromatic heterocyclic ring. The aromatic heterocyclic ring is preferably a 5- to 10-membered aromatic heterocyclic ring. Specific examples of the aromatic heterocyclic ring include a furan ring, a thiophene ring, a pyrrole ring, an imidazole ring, a pyrazole ring, a thiazole ring, an isothiazole ring, an oxazole ring, an isoxazole ring, an oxadiazole ring, a thiadiazole ring, a triazole ring, a tetrazole ring, a pyridine ring, a pyrimidine ring, a pyridazine ring, a pyrazine ring, a triazine ring, a benzofuran ring, a benzothiophene ring, a benzothiadiazoline ring, a benzothiazoline ring, a benzoxazoline ring, a benzoxadiazoline ring, a benzimidazole ring, a benzotriazole ring, an indole ring, an isoindole ring, an indazole ring, an azaindole ring, a quinoline ring, an isoquinoline ring, a cinnoline ring, a quinazoline ring, a quinoxaline ring, a benzodioxole ring, an indolysine ring, an imidazopyridine ring, a pyrazolopyridine ring, an imidazopyridine ring, a triazolopyridine ring, a pyrrolopyrazine ring, and a furopyridine ring.

The term "optionally substituted" means that a group is unsubstituted or substituted with one or more substituents, and when the group is substituted with a plurality of substituents, these substituents may be the same or different from each other. Furthermore, a substituent may be added to each of the substituents. Such a substituent is not limited and can be one or two or more substituents each independently freely selected from any substituents including a halogen atom, an oxygen atom, a sulfur atom, a nitrogen atom, a boron atom, a silicon atom, or a phosphorus atom. Examples of the substituent include deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, oxo, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl.

The term "one or more" as used herein means a number of 1 or 2 or larger. When the term "one or more" is used in a context related to a substituent for a certain group, this term means a number from 1 to the maximum number of substituents accepted by the group.

As used herein, the term "to" that indicates a numerical range includes values of both ends thereof. For example, "A to B" means the numerical range of A or more and B or less.

The term "about" as used herein means the value range of +10% and −10% of the numeric value, when used in combination with a numeric value.

The meaning of the term "and/or" as used herein includes any combination in which "and" and "or" are appropriately combined. Specifically, for example, the term "A, B and/or C" includes the following seven variations; (i) A, (ii) B, (iii) C, (iv) A and B, (v) A and C, (vi) B and C, and (vii) A, B and C.

One embodiment of the present invention is a compound represented by the formula (1) (hereinafter, also referred to as the "compound (1)" or a salt, or a solvate thereof.

In the compound (1), $R_4$ is selected from the group consisting of optionally substituted $C_6$-$C_{10}$ aryl ($R_{4A}$), optionally substituted 4- to 10-membered heterocyclyl, and optionally substituted 5- to 10-membered heteroaryl ($R_{4HA}$).

$R_4$ is preferably optionally substituted $C_6$-$C_{10}$ aryl ($R_{4A}$) or optionally substituted 5- to 10-membered heteroaryl ($R_{4HA}$).

When $R_4$ is optionally substituted $C_6$-$C_{10}$ aryl ($R_{4A}$), $R_{4A}$ is preferably phenyl.

As one preferred aspect (i) of $C_6$-$C_{10}$ aryl ($R_{4A}$), $R_{4A}$ is unsubstituted or substituted with one or more $R_a$; each of one or more $R_a$ is independently selected from the group consisting of deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, oxo, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted.

As one preferred aspect (ii) of $C_6$-$C_{10}$ aryl ($R_{4A}$), $R_{4A}$ is unsubstituted or substituted with one or more $R_a$, and each of one or more $R_a$ is independently selected from the group consisting of halogen, cyano, hydroxy, amino, $C_1$-$C_6$ alkyl, halo $C_1$-$C_6$ alkyl, hydroxy $C_1$-$C_6$ alkyl, $C_1$-$C_6$ alkoxy, halo $C_1$-$C_6$ alkoxy, and $C_1$-$C_6$ alkylsulfonylamino.

As one preferred aspect (iii) of $C_6$-$C_{10}$ aryl ($R_{4A}$), $R_{4A}$ is unsubstituted or substituted with one or more $R_a$, and each of one or more $R_a$ is independently selected from the group consisting of halogen, hydroxy, halo $C_1$-$C_6$ alkyl, $C_1$-$C_6$ alkoxy, halo $C_1$-$C_6$ alkoxy, and $C_1$-$C_6$ alkylsulfonylamino.

When $R_4$ is optionally substituted 5- to 10-membered heteroaryl ($R_{4HA}$), $R_{4HA}$ is preferably selected from the group consisting of furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, benzotriazolyl, indolyl, isoindolyl, indazolyl, azaindolyl, quinolyl, isoquinolyl, cinnolinyl, quinazolinyl, quinoxalinyl, indolizinyl, imidazopyridyl, pyrazolopyridyl, triazolopyridyl, pyrrolopyrazinyl, and flopyridyl; more preferably selected from the group consisting of furyl, thienyl, pyrrolyl, pyrazolyl, thiazolyl, isothiazolyl, oxazolyl, isoxazolyl, oxadiazolyl, thiadiazolyl, triazolyl, tetrazolyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzimidazolyl, benzotriazolyl, indolyl, isoindolyl, indazolyl, azaindolyl, quinolyl, isoquinolyl, cinnolinyl, quinazolinyl, quinoxalinyl, indolizinyl, imidazopyridyl, pyrazolopyridyl, triazolopyridyl, pyrrolopyrazinyl and flopyridyl; further preferably selected from the group consisting of pyridyl, pyrimidyl, benzimidazolyl, indolyl, indazolyl, and pyrazolopyridyl; further more preferably selected from the group consisting of pyrimidyl, benzimidazolyl, indolyl, indazolyl, and pyrazolopyridyl; particularly preferably 1H-indazol-6-yl or 1H-indazol-4-yl; and most preferably 1H-indazol-4-yl.

As one preferred aspect (i) of 5- to 10-membered heteroaryl ($R_{4HA}$), $R_{4HA}$ is unsubstituted or substituted with one or more $R_a$; each of one or more $R_a$ is independently selected from the group consisting of deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, oxo, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted.

As one preferred aspect (ii) of 5- to 10-membered heteroaryl ($R_{4HA}$), $R_{4HA}$ is unsubstituted or substituted with one or more $R_a$, and each of one or more $R_a$ is independently selected from the group consisting of halogen, cyano, hydroxy, amino, $C_1$-$C_6$ alkyl, halo $C_1$-$C_6$ alkyl, hydroxy $C_1$-$C_6$ alkyl, $C_1$-$C_6$ alkoxy, halo $C_1$-$C_6$ alkoxy, and $C_1$-$C_6$ alkylsulfonylamino.

As one preferred aspect (iii) of 5- to 10-membered heteroaryl ($R_{4HA}$), $R_{4HA}$ is unsubstituted or substituted with one or more $R_a$, and each of one or more $R_a$ is independently selected from the group consisting of halogen, cyano, amino, $C_1$-$C_6$ alkyl, and halo $C_1$-$C_6$ alkyl.

As one preferred aspect (iv) of 5- to 10-membered heteroaryl ($R_{4HA}$), $R_{4HA}$ is 1H-indazol-4-yl, or 1H-indazol-4-yl substituted with one or more halogens.

As one preferred aspect (v) of 5- to 10-membered heteroaryl ($R_{4HA}$), $R_{4HA}$ is 1H-indazol-4-yl substituted with one or more halogens.

As one preferred aspect (vi) of 5- to 10-membered heteroaryl ($R_{4HA}$), $R_{4HA}$ is 1H-indazol-4-yl in which at least one of position 5, position 6, and position 7 is substituted with a halogen.

As one preferred aspect (vii) of 5- to 10-membered heteroaryl ($R_{4HA}$), $R_{4HA}$ is 1H-indazol-4-yl in which at least one of position 5, position 6, and position 7 is substituted with a halogen, and the halogen is fluorine or chlorine.

As one preferred aspect (viii) of 5- to 10-membered heteroaryl ($R_{4HA}$), $R_{4HA}$ is 1H-indazol-4-yl in which at least one or two of position 5, position 6, and position 7 are substituted with a halogen, and the halogen is selected from the group consisting of fluorine, chlorine, a combination of fluorine and fluorine, and a combination of fluorine and chlorine.

In the compound (1), $R_5$ and $R_6$, together with the atoms to which they are attached, form optionally substituted Ring D; Ring D is selected from the group consisting of a 3- to 10-membered monocyclic cycloaliphatic ring, a benzene ring, a 3- to 12-membered monocyclic heterocyclic ring, and a 5- to 6-membered monocyclic aromatic heterocyclic ring ($D_{HA}$); and any two adjacent substituents on Ring D, together with the atoms to which they are attached, may form optionally substituted Ring E.

Ring D is preferably a benzene ring or a 5- to 6-membered monocyclic aromatic heterocyclic ring ($D_{HA}$).

When Ring D is the 5- to 6-membered monocyclic aromatic heterocyclic ring ($D_{HA}$), $D_{HA}$ is preferably selected from the group consisting of a furan ring, a thiophene ring, a pyrrole ring, an imidazole ring, a pyrazole ring, a thiazole ring, an isothiazole ring, an oxazole ring, an isoxazole ring, an oxadiazole ring, a thiadiazole ring, a triazole ring, a tetrazole ring, a pyridine ring, a pyrimidine ring, a pyridazine ring, a pyrazine ring, and a triazine ring, more preferably selected from the group consisting of a pyridine ring, a pyrimidine ring, a pyridazine ring, and a pyrazine ring, and further preferably a pyridine ring.

As one preferred aspect (i) of Ring D, Ring D is unsubstituted or substituted with one or more $R_D$; each of one or more $R_D$ is independently selected from the group consisting of deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, oxo, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted.

As one preferred aspect (ii) of Ring D, Ring D is unsubstituted or substituted with one or more $R_D$, each of one or more $R_D$ is independently selected from the group consisting of halogen, cyano, hydroxy, $C_1$-$C_6$ alkylthio, $C_1$-$C_6$ acylamino, mono $C_1$-$C_6$ alkylamino, $C_1$-$C_6$ alkylsulfonylamino, $C_3$-$C_8$ cycloalkylsulfonylamino, $C_1$-$C_6$ alkoxy, halo $C_1$-$C_6$ alkoxy, hydroxy $C_1$-$C_6$ alkoxy, $C_1$-$C_6$ alkoxy $C_1$-$C_6$ alkoxy, $C_3$-$C_8$ cycloalkyl $C_1$-$C_6$ alkoxy, 4- to 10-membered heterocyclyl $C_1$-$C_6$ alkoxy, $C_3$-$C_8$ cycloalkoxy, 4- to 10-membered heterocyclyloxy, $C_1$-$C_6$ acyl, mono $C_3$-$C_8$ cycloalkylaminocarbonyl, 4- to 8-membered cyclic aminocarbonyl, di $C_1$-$C_6$ alkylphosphoryl, $C_1$-$C_6$ alkyl, halo $C_1$-$C_6$ alkyl, hydroxy $C_1$-$C_6$ alkyl, di $C_1$-$C_6$ alkylaminocarbonyl $C_1$-$C_6$ alkyl, $C_3$-$C_8$ cycloalkyl $C_1$-$C_6$ alkyl, $C_2$-$C_6$ alkenyl, hydroxy $C_2$-$C_6$ alkenyl, $C_2$-$C_6$ alkynyl, hydroxy $C_2$-$C_6$ alkynyl, $C_3$-$C_8$ cycloalkyl, 4- to 10-membered heterocyclyl, $C_6$-$C_{10}$ aryl, and 5- to 10-membered heteroaryl, and the $C_1$-$C_6$ alkylthio, $C_1$-$C_6$ alkoxy, $C_1$-$C_6$ alkoxy $C_1$-$C_6$ alkoxy, $C_3$-$C_8$ cycloalkyl $C_1$-$C_6$ alkoxy, 4- to 10-membered heterocyclyl $C_1$-$C_6$ alkoxy, $C_3$-$C_8$ cycloalkoxy, 4- to 10-membered heterocyclyloxy, $C_1$-$C_6$ alkyl, $C_3$-$C_8$ cycloalkyl $C_1$-$C_6$ alkyl, $C_3$-$C_8$ cycloalkyl, 4- to 10-membered heterocyclyl, $C_6$-$C_{10}$ aryl, and 5- to 10-membered heteroaryl are independently optionally substituted with one or more substituents selected from the group consisting of halogen, cyano, hydroxy, $C_1$-$C_6$ alkoxy, oxo, halo $C_1$-$C_6$ alkyl, and $C_3$-$C_8$ cycloalkyl.

As the preferred aspect (iii) of Ring D, Ring D is unsubstituted or substituted with one or more $R_D$, and each of one or more $R_D$ is independently selected from the group consisting of halogen, $C_1$-$C_6$ alkoxy, halo $C_1$-$C_6$ alkoxy, $C_3$-$C_8$ cycloalkyl $C_1$-$C_6$ alkoxy, $C_3$-$C_8$ cycloalkoxy, $C_1$-$C_6$ alkyl, halo $C_1$-$C_6$ alkyl, $C_3$-$C_8$ cycloalkyl $C_1$-$C_6$ alkyl, and $C_3$-$C_8$ cycloalkyl.

As the preferred aspect (iv) of Ring D, Ring D is unsubstituted or substituted with one or more $R_D$, and each of one or more $R_D$ is independently selected from the group consisting of $C_1$-$C_6$ alkoxy, $C_1$-$C_6$ alkyl, and $C_3$-$C_8$ cycloalkyl.

As the preferred aspect (v) of Ring D, Ring D is unsubstituted or substituted with one or more $R_D$, each of one or more $R_D$ is independently selected from the group consisting of methoxy, ethoxy, propoxy, propan-2-yloxy, 3-methylbutoxy, [(2S)-butan-2-yl]oxy, [(2R)-butan-2-yl]oxy, methyl, ethyl, propyl, propan-2-yl, 2-methylpropyl, butan-2-yl, 3-methylbutyl, pentan-3-yl, cyclopropyl, cyclobutyl, cyclopentyl, 1-methylcyclopropyl, 3,3-dimethylcyclobutyl, and spiro[2.3]hexan-5-yl.

As one aspect of the compound (1), any two adjacent substituents on Ring D, together with the atoms to which they are attached, form optionally substituted Ring E. In this case, Ring E is preferably selected from the group consisting of a 3- to 10-membered monocyclic cycloaliphatic ring, a benzene ring, a 3- to 12-membered monocyclic heterocyclic ring, and a 5- to 6-membered monocyclic aromatic heterocyclic ring (EHA), and more preferably a benzene ring or a 5- to 6-membered monocyclic aromatic heterocyclic ring (EHA).

When Ring E is the 5- to 6-membered monocyclic aromatic heterocyclic ring (EHA) in the compound (1), EHA is preferably selected from the group consisting of a furan ring, a thiophene ring, a pyrrole ring, an imidazole ring, a pyrazole ring, a thiazole ring, an isothiazole ring, an oxazole ring, an isoxazole ring, an oxadiazole ring, a thiadiazole ring, a triazole ring, a tetrazole ring, a pyridine ring, a pyrimidine ring, a pyridazine ring, a pyrazine ring, and a triazine ring, more preferably selected from the group consisting of a thiophene ring, an imidazole ring, a pyrazole ring, a thiazole ring, an isothiazole ring, a pyridine ring, a pyrimidine ring, a pyridazine ring, and a pyrazine ring, further preferably selected from the group consisting of a pyridine ring, a pyrimidine ring, a pyridazine ring, and a pyrazine ring, particularly preferably a pyridine ring or a pyrazine ring, and most preferably a pyridine ring.

As one aspect of the present invention, in the compound (1), Ring D and Ring E form a bicycle represented by the following formula:

[Formula 11]

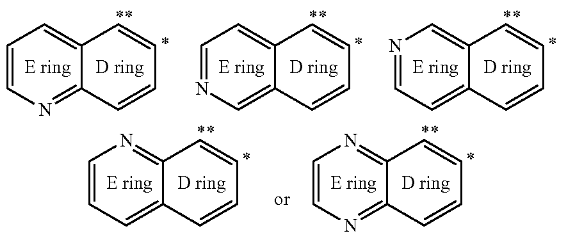

or wherein * represents a carbon to which $R_5$ is attached in the formula (1), and ** represents a carbon to which $R_6$ is attached in the formula (1); the Ring D is referred to as "D ring" and the Ring E is referred to as "E ring" in the formula.

As one preferred aspect of the present invention, in the compound (1), Ring D and Ring E form a bicycle represented by the following formula:

[Formula 12]

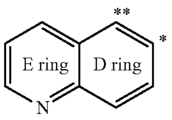 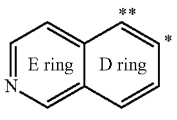 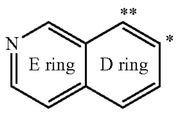 or 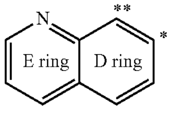

wherein * represents a carbon to which $R_5$ is attached in the formula (1), and ** represents a carbon to which $R_6$ is attached in the formula (1); the Ring D is referred to as "D ring" and the Ring E is referred to as "E ring" in the formula.

As one preferred aspect (i) of Ring E in the compound (1), Ring E is unsubstituted or substituted with one or more $R_E$; each of one or more $R_E$ is independently selected from the group consisting of deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, oxo, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted.

As one preferred aspect (ii) of Ring E in the compound (1), Ring E is unsubstituted or substituted with one or more $R_E$, and each of one or more $R_E$ is independently selected from the group consisting of halogen, $C_1$-$C_6$ alkyl, $C_1$-$C_6$ alkoxy, and boryl.

As one preferred aspect (iii) of Ring E in the compound (1), Ring E is unsubstituted or substituted with one or more $R_E$, and each of one or more $R_E$ is independently selected from the group consisting of fluorine, chlorine, methoxy, dihydroxyboryl, methyl, and t-butyl.

Another embodiment of the present invention is a compound represented by the general formula (2) (hereinafter, also referred to as the "compound (2)") or a salt, or a solvate thereof.

$R_4$ in the compound (2) has the same meaning as $R_4$ in the above-described compound (1).

In the compound (2), $X_5$ is $CR_{x5}$ or N. $X_5$ is preferably $CR_{x5}$, and more preferably CH.

In the compound (2), $X_6$ is $CR_{x6}$ or N. $X_6$ is preferably $CR_{x6}$.

In the compound (2), $X_{10a}$ is $CR_{x10a}$ or N. $X_{10a}$ is preferably $CR_{x10a}$.

In the compound (2), each of $R_{x5}$, $R_{x6}$, $R_{6a}$, and $R_{x10a}$ is independently selected from the group consisting of hydrogen, deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted; and $R_{x5}$ and $R_{x6}$, $R_{x6}$ and $R_{6a}$, or $R_{6a}$ and $R_{x10a}$, together with the atoms to which they are attached, may form optionally substituted Ring E.

As one preferred aspect (i) of $R_{x6}$, $R_{x6}$ is selected from the group consisting of hydrogen, halogen, hydroxy, $C_1$-$C_6$ alkylthio, $C_1$-$C_6$ acylamino, mono $C_1$-$C_6$ alkylamino, $C_1$-$C_6$ alkylsulfonylamino, $C_3$-$C_8$ cycloalkylsulfonylamino, $C_1$-$C_6$ alkoxy, halo $C_1$-$C_6$ alkoxy, hydroxy $C_1$-$C_6$ alkoxy, $C_1$-$C_6$ alkoxy $C_1$-$C_6$ alkoxy, $C_3$-$C_8$ cycloalkyl $C_1$-$C_6$ alkoxy, 4- to 10-membered heterocyclyl $C_1$-$C_6$ alkoxy, $C_3$-$C_8$ cycloalkoxy, 4- to 10-membered heterocyclyloxy, $C_1$-$C_6$ acyl, mono $C_3$-$C_8$ cycloalkylaminocarbonyl, 4- to 8-membered cyclic aminocarbonyl, di $C_1$-$C_6$ alkylphosphoryl, $C_1$-$C_6$ alkyl, halo $C_1$-$C_6$ alkyl, hydroxy $C_1$-$C_6$ alkyl, di $C_1$-$C_6$ alkylaminocarbonyl $C_1$-$C_6$ alkyl, $C_3$-$C_8$ cycloalkyl $C_1$-$C_6$ alkyl, $C_2$-$C_6$ alkenyl, hydroxy $C_2$-$C_6$ alkenyl, $C_2$-$C_6$ alkynyl, hydroxy $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; the $C_1$-$C_6$ alkylthio, $C_1$-$C_6$ alkoxy, $C_1$-$C_6$ alkoxy $C_1$-$C_6$ alkoxy, $C_3$-$C_8$ cycloalkyl $C_1$-$C_6$ alkoxy, 4- to 10-membered heterocyclyl $C_1$-$C_6$ alkoxy, $C_3$-$C_8$ cycloalkoxy, 4- to 10-membered heterocyclyloxy, $C_1$-$C_6$ alkyl, $C_3$-$C_8$ cycloalkyl $C_1$-$C_6$ alkyl, $C_3$-$C_8$ cycloalkyl, 4- to 10-membered heterocyclyl, $C_6$-$C_{10}$ aryl, and 5- to 10-membered heteroaryl are further independently optionally substituted with one or more substituents selected from the group consisting of halogen, cyano, hydroxy, $C_1$-$C_6$ alkoxy, oxo, halo $C_1$-$C_6$ alkyl, and $C_3$-$C_8$ cycloalkyl.

As one preferred aspect (ii) of $R_{x6}$, $R_{x6}$ is selected from the group consisting of hydrogen, halogen, $C_1$-$C_6$ alkoxy, halo $C_1$-$C_6$ alkoxy, $C_3$-$C_8$ cycloalkyl $C_1$-$C_6$ alkoxy $C_3$-$C_8$ cycloalkyl, $C_3$-$C_8$ cycloalkoxy, $C_1$-$C_6$ alkyl, halo $C_1$-$C_6$ alkyl, $C_3$-$C_8$ cycloalkyl $C_1$-$C_6$ alkyl, and $C_3$-$C_8$ cycloalkyl.

As one preferred aspect (iii) of $R_{x6}$, $R_{x6}$ is selected from the group consisting of hydrogen, $C_1$-$C_6$ alkoxy, $C_1$-$C_6$ alkyl, and $C_3$-$C_8$ cycloalkyl.

As one preferred aspect (iv) of $R_{x6}$, $R_{x6}$ is selected from the group consisting of hydrogen, methoxy, ethoxy, propoxy, propan-2-yloxy, 3-methylbutoxy, [(2S)-butan-2-yl]oxy, [(2R)-butan-2-yl]oxy, methyl, ethyl, propyl, propan-2-yl, 2-methylpropyl, butan-2-yl, 3-methylbutyl, pentan-3-yl, cyclopropyl, cyclobutyl, cyclopentyl, 1-methylcyclopropyl, 3,3-dimethylcyclobutyl, and spiro[2.3]hexan-5-yl.

As one preferred aspect (i) of $R_{x10a}$, $R_{x10a}$ is selected from the group consisting of hydrogen, halogen, cyano, $C_1$-$C_6$ alkyl, $C_2$-$C_6$ alkenyl, $C_2$-$C_6$ alkynyl, and $C_3$-$C_8$ cycloalkyl.

As one preferred aspect (ii) of $R_{x10a}$, $R_{x10a}$ is selected from the group consisting of hydrogen, chlorine, bromine, cyano, methyl, ethyl, propyl, propan-2-yl, vinyl, ethynyl, and cyclopropyl.

As one preferred aspect (i) of $R_{6a}$, $R_{6a}$ is selected from the group consisting of hydrogen, halogen, cyano, halo $C_1$-$C_6$ alkoxy, and $C_1$-$C_6$ alkyl.

As one preferred aspect (ii) of $R_{6a}$, $R_{6a}$ is selected from the group consisting of hydrogen, fluorine, chlorine, bromine, cyano, difluoromethoxy, methyl, and ethyl.

As one aspect of the compound (2), $R_{6a}$ and $R_{x10a}$, together with the atoms to which they are attached, form optionally substituted Ring E. In this case, Ring E is preferably selected from the group consisting of a 3- to 10-membered monocyclic cycloaliphatic ring, a benzene ring, a 3- to 12-membered monocyclic heterocyclic ring, and a 5- to 6-membered monocyclic aromatic heterocyclic ring (EHA), and more preferably a benzene ring or a 5- to 6-membered monocyclic aromatic heterocyclic ring (EHA).

When Ring E is the 5- to 6-membered monocyclic aromatic heterocyclic ring (EHA), EHA is preferably selected from the group consisting of a thiophene ring, an imidazole ring, a pyrazole ring, a thiazole ring, an isothiazole ring, a pyridine ring, a pyrimidine ring, a pyridazine ring, and a pyrazine ring, more preferably selected from the group consisting of a pyridine ring, a pyrimidine ring, a pyridazine ring, and a pyrazine ring, further preferably a pyridine ring or a pyrazine ring, and most preferably a pyridine ring.

As one preferred aspect of the present invention, in the compound (2), Ring E is represented by the following formula:

[Formula 13]

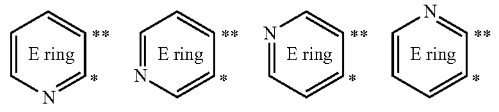

or

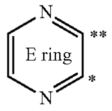

wherein * represents a carbon to which $R_{6a}$ is attached in the formula (2), and ** represents a carbon to which $R_{x10a}$ is attached in the formula (2); the Ring E is referred to as "E ring" in the formula.

As one preferred aspect of the present invention, in the compound (2), Ring E is represented by the following formula:

[Formula 14]

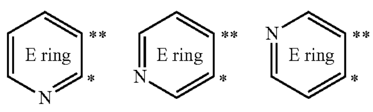

or

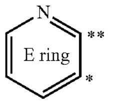

wherein * represents a carbon to which $R_{6a}$ is attached in the formula (2), and ** represents a carbon to which $R_{x10a}$ is attached in the formula (2); the Ring E is referred to as "E ring" in the formula.

As one preferred aspect (i) of the E ring in the compound (2), the E ring is unsubstituted or substituted with one or more $R_E$; each of one or more $R_E$ is independently selected from the group consisting of deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, oxo, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl; and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted.

As one preferred aspect (ii) of Ring E in the compound (2), Ring E is unsubstituted or substituted with one or more $R_E$, and each of one or more $R_E$ is independently selected from the group consisting of halogen, $C_1$-$C_6$ alkoxy, boryl, and $C_1$-$C_6$ alkyl.

As one preferred aspect (iii) of Ring E in the compound (2), Ring E is unsubstituted or substituted with one or more $R_E$, and each of one or more $R_E$ is independently selected from the group consisting of fluorine, chlorine, methoxy, dihydroxyboryl, methyl, and t-butyl.

Another embodiment of the present invention is a compound represented by the general formula (3) (hereinafter, also referred to as the "compound (3)") or a salt, or a solvate thereof.

$R_4$ in the compound (3) has the same meaning as $R_4$ in the above-described compound (1), and $X_5$ and $X_6$ in the compound (3) have the same meaning as $X_5$ and $X_6$ in the above-described compound (2).

In the compound (3), $X_7$ is $CR_{x7}$ or N.

In the compound (3), $X_8$ is $CR_{x8}$ or N.

In the compound (3), $X_9$ is $CR_{x9}$ or N.

In the compound (3), $X_{10}$ is $CR_{x10}$ or N.

In the compound (3), the combination of $X_7$, $X_8$, $X_9$, and $X_{10}$ is preferably a combination in which $X_7$ is N, $X_8$ is $CR_{x8}$, $X_9$ is $CR_{x9}$, and $X_{10}$ is $CR_{x10}$, a combination in which $X_7$ is $CR_{x7}$, $X_8$ is N, $X_9$ is $CR_{x9}$, and $X_{10}$ is $CR_{x10}$, a combination in which $X_7$ is $CR_{x7}$, $X_8$ is $CR_{x8}$, $X_9$ is N, and $X_{10}$ is $CR_{x10}$, a combination in which $X_7$ is $CR_{x7}$, $X_8$ is $CR_{x8}$, $X_9$ is $CR_{x9}$, and $X_{10}$ is N, a combination in which $X_7$ is N, $X_8$ is $CR_{x8}$, $X_9$ is $CR_{x9}$, and $X_{10}$ is N, a combination in which $X_7$ is $CR_{x7}$, $X_8$ is N, $X_9$ is $CR_{x9}$, and $X_{10}$ is N; or a combination in which $X_7$ is N, $X_8$ is N, $X_9$ is $CR_{x9}$, and $X_{10}$ is $CR_{x10}$.

In the compound (3), the combination of $X_7$, $X_8$, $X_9$, and $X_{10}$ is more preferably a combination in which $X_7$ is N, $X_8$ is $CR_{x8}$, $X_9$ is $CR_{x9}$, and $X_{10}$ is $CR_{x10}$, a combination in which $X_7$ is $CR_{x7}$, $X_8$ is N, $X_9$ is $CR_{x9}$, and $X_{10}$ is $CR_{x10}$, a combination in which $X_7$ is $CR_{x7}$, $X_8$ is $CR_{x8}$, $X_9$ is N, and $X_{10}$ is $CR_{x10}$, or a combination in which $X_7$ is $CR_{x7}$, $X_8$ is $CR_{x8}$, $X_9$ is $CR_{x9}$, and $X_{10}$ is N.

In the compound (3), each of $R_{x7}$, $R_{x8}$, $R_{x9}$, and $R_{x10}$ is independently selected from the group consisting of hydrogen, deuterium, halogen, cyano, nitro, hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl, and the hydroxy, thio, amino, $C_1$-$C_6$ alkoxy, $C_1$-$C_6$ alkylthio, carbonyl, carboxy, sulfonyl, phosphoryl, boryl, $C_1$-$C_6$ alkyl, $C_2$-$C_6$ alkenyl, $C_2$-$C_6$ alkynyl, $C_3$-$C_8$ cycloalkyl, 4- to 10-membered heterocyclyl, $C_6$-$C_{10}$ aryl, and 5- to 10-membered heteroaryl are optionally substituted.

$R_{x7}$ is preferably selected from the group consisting of hydrogen, halogen, $C_1$-$C_6$ alkoxy, and $C_1$-$C_6$ alkyl.

$R_{x8}$ is preferably selected from the group consisting of hydrogen, halogen, $C_1$-$C_6$ alkoxy, and $C_1$-$C_6$ alkyl.

$R_{x9}$ is preferably selected from the group consisting of hydrogen, halogen, $C_1$-$C_6$ alkoxy, $C_1$-$C_6$ alkyl, and boryl.

$R_{x10}$ is preferably selected from the group consisting of hydrogen, halogen, $C_1$-$C_6$ alkoxy, and $C_1$-$C_6$ alkyl.

Another embodiment of the invention is a compound or salt or a solvate thereof as described in Table 1-1 below.

TABLE 1-1
| Structure of compound | Name of compound |
| --- | --- |
| 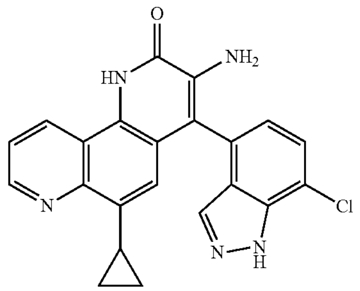 [SMILES: Nc1c(-c2ccc(Cl)c3[nH]ncc23)c2cc(C3CC3)c3ncccc3c2[nH]c1=O] | 3-amino-4-(7-chloro-1H-indazol-4-yl)-6-cyclopropyl-1H-1,7-phenanthrolin-2-one |
| 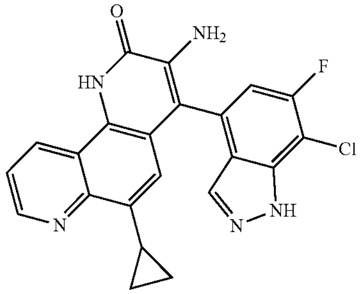 [SMILES: Nc1c(-c2cc(F)c(Cl)c3[nH]ncc23)c2cc(C3CC3)c3ncccc3c2[nH]c1=O] | 3-amino-4-(7-chloro-6-fluoro-1H-indazol-4-yl)-6-cyclopropyl-1H-1,7-phenanthrolin-2-one |
| 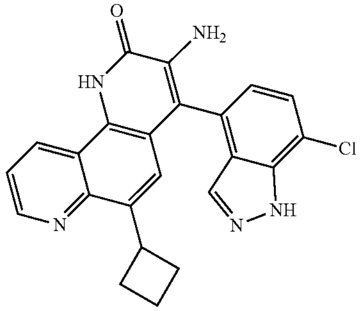 [SMILES: Nc1c(-c2ccc(Cl)c3[nH]ncc23)c2cc(C3CCC3)c3ncccc3c2[nH]c1=O] | 3-amino-4-(7-chloro-1H-indazol-4-yl)-6-cyclobutyl-1H-1,7-phenanthrolin-2-one |
| 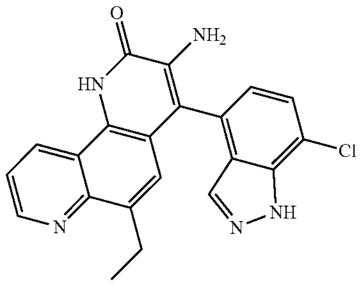 [SMILES: CCc1cc2c(-c3ccc(Cl)c4[nH]ncc34)c(N)c(=O)[nH]c2c2cccnc12] | 3-amino-4-(7-chloro-1H-indazol-4-yl)-6-ethyl-1H-1,7-phenanthrolin-2-one |
| 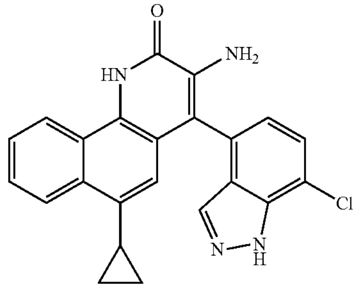 [SMILES: Nc1c(-c2ccc(Cl)c3[nH]ncc23)c2cc(C3CC3)c3ccccc3c2[nH]c1=O] | 3-amino-4-(7-chloro-1H-indazol-4-yl)-6-cyclopropyl-1H-benzo[h]quinolin-2-one |

TABLE 1-1-continued
| Structure of compound | Name of compound |
| --- | --- |
| 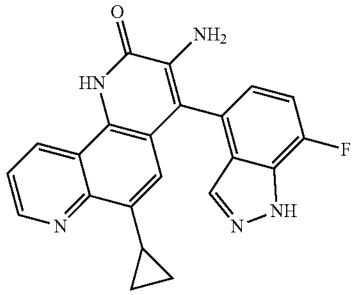 [SMILES: Nc1c(-c2ccc(F)c3[nH]ncc23)c2cc(C3CC3)c3ncccc3c2[nH]c1=O] | 3-amino-6-cyclopropyl-4-(7-fluoro-1H-indazol-4-yl)-1H-1,7-phenanthrolin-2-one |
| 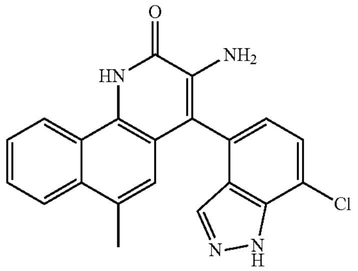 [SMILES: Cc1cc2c(-c3ccc(Cl)c4[nH]ncc34)c(N)c(=O)[nH]c2c2ccccc12] | 3-amino-4-(7-chloro-1H-indazol-4-yl)-6-methyl-1H-benzo[h]quinolin-2-one |
| 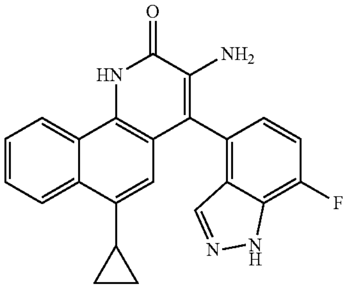 [SMILES: Nc1c(-c2ccc(F)c3[nH]ncc23)c2cc(C3CC3)c3ccccc3c2[nH]c1=O] | 3-amino-6-cyclopropyl-4-(7-fluoro-1H-indazol-4-yl)-1H-benzo[h]quinolin-2-one |
| 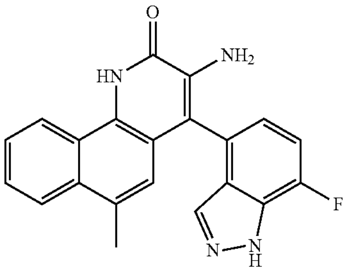 [SMILES: Cc1cc2c(-c3ccc(F)c4[nH]ncc34)c(N)c(=O)[nH]c2c2ccccc12] | 3-amino-4-(7-fluoro-1H-indazol-4-yl)-6-methyl-1H-benzo[h]quinolin-2-one |
| 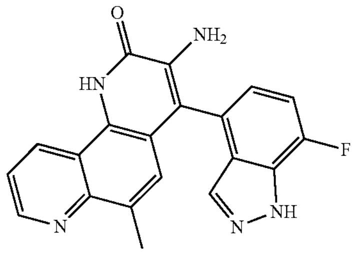 [SMILES: Cc1cc2c(-c3ccc(F)c4[nH]ncc34)c(N)c(=O)[nH]c2c2cccnc12] | 3-amino-4-(7-fluoro-1H-indazol-4-yl)-6-methyl-1H-1,7-phenanthrolin-2-one |

TABLE 1-1-continued
| Structure of compound | Name of compound |
| --- | --- |
| 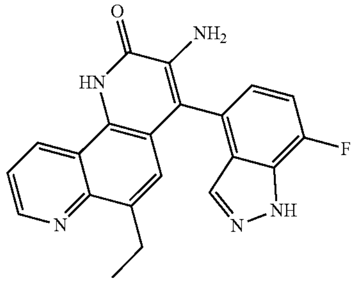 [SMILES: CCc1cc2c(-c3ccc(F)c4[nH]ncc34)c(N)c(=O)[nH]c2c2cccnc12] | 3-amino-6-ethyl-4-(7-fluoro-1H-indazol-4-yl)-1H-1,7-phenanthrolin-2-one |
| 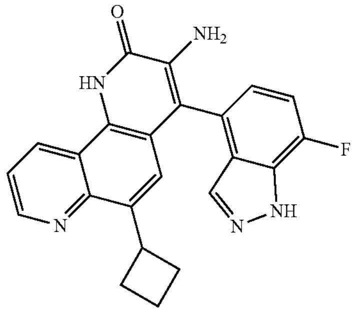 [SMILES: Nc1c(-c2ccc(F)c3[nH]ncc23)c2cc(C3CCC3)c3ncccc3c2[nH]c1=O] | 3-amino-6-cyclobutyl-4-(7-fluoro-1H-indazol-4-yl)-1H-1,7-phenanthrolin-2-one |
| 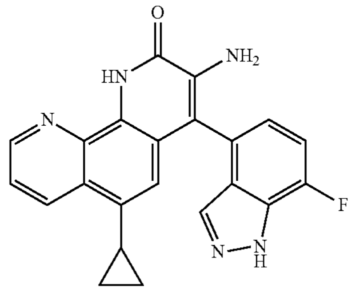 [SMILES: Nc1c(-c2ccc(F)c3[nH]ncc23)c2cc(C3CC3)c3cccnc3c2[nH]c1=O] | 3-amino-6-cyclopropyl-4-(7-fluoro-1H-indazol-4-yl)-1H-1,10-phenanthrolin-2-one |
| 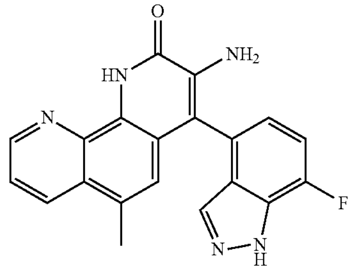 [SMILES: Cc1cc2c(-c3ccc(F)c4[nH]ncc34)c(N)c(=O)[nH]c2c2ncccc12] | 3-amino-4-(7-fluoro-1H-indazol-4-yl)-6-methyl-1H-1,10-phenanthrolin-2-one |
| 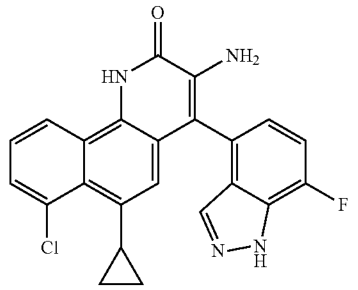 [SMILES: Nc1c(-c2ccc(F)c3[nH]ncc23)c2cc(C3CC3)c3c(Cl)cccc3c2[nH]c1=O] | 3-amino-7-chloro-6-cyclopropyl-4-(7-fluoro-1H-indazol-4-yl)-1H-benzo[h]quinolin-2-one |

TABLE 1-1-continued
| Structure of compound | Name of compound |
|---|---|
| 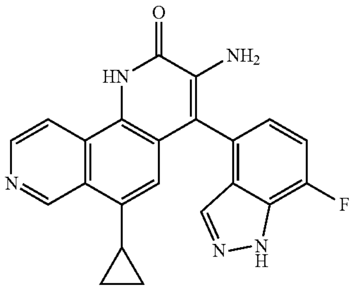 [SMILES: Nc1c(-c2ccc(F)c3[nH]ncc23)c2cc(C3CC3)c3cnccc3c2[nH]c1=O] | 3-amino-6-cyclopropyl-4-(7-fluoro-1H-indazol-4-yl)-1H-1,8-phenanthrolin-2-one |
| 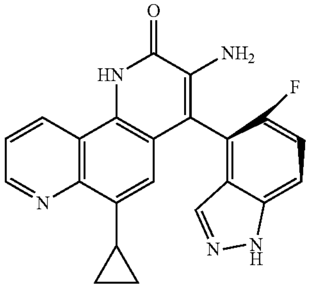 | (S)-3-amino-6-cyclopropyl-4-(5-fluoro-1H-indazol-4-yl)-1H-1,7-phenanthrolin-2-one |
| 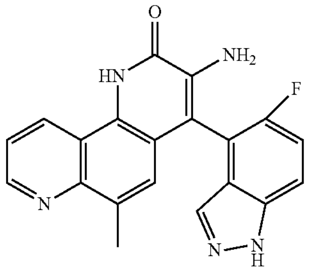 [SMILES: Cc1cc2c(-c3c(F)ccc4[nH]ncc34)c(N)c(=O)[nH]c2c2cccnc12] | 3-amino-4-(5-fluoro-1H-indazol-4-yl)-6-methyl-1H-1,7-phenanthrolin-2-one |
| 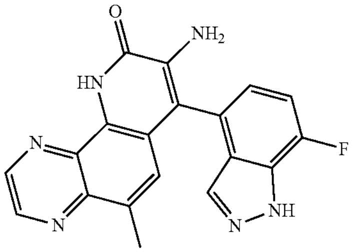 [SMILES: Cc1cc2c(-c3ccc(F)c4[nH]ncc34)c(N)c(=O)[nH]c2c2nccnc12] | 8-amino-7-(7-fluoro-1H-indazol-4-yl)-5-methyl-10H-pyrido[2,3-f]quinoxalin-9-one |
| 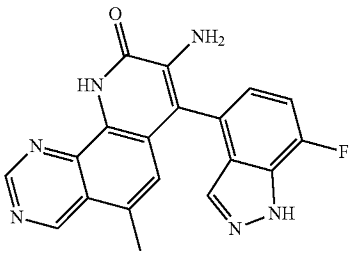 [SMILES: Cc1cc2c(-c3ccc(F)c4[nH]ncc34)c(N)c(=O)[nH]c2c2ncncc12] | 8-amino-7-(7-fluoro-1H-indazol-4-yl)-5-methyl-10H-pyrido[3,2-h]quinazolin-9-one |

TABLE 1-1-continued
| Structure of compound | Name of compound |
|---|---|
| 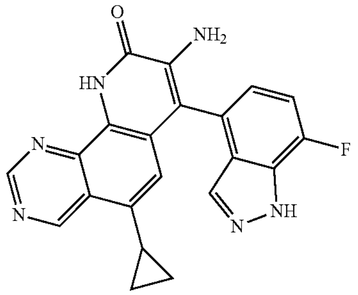 [SMILES: Nc1c(-c2ccc(F)c3[nH]ncc23)c2cc(C3CC3)c3cncnc3c2[nH]c1=O] | 8-amino-5-cyclopropyl-7-(7-fluoro-1H-indazol-4-yl)-10H-pyrido[3,2-h]quinazolin-9-one |
| 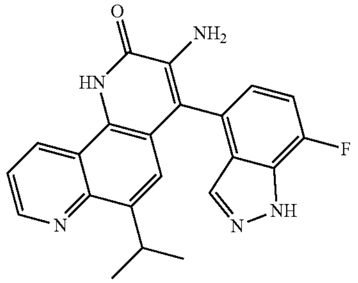 [SMILES: CC(C)c1cc2c(-c3ccc(F)c4[nH]ncc34)c(N)c(=O)[nH]c2c2cccnc12] | 3-amino-4-(7-fluoro-1H-indazol-4-yl)-6-propan-2-yl-1H-1,7-phenanthrolin-2-one |
| 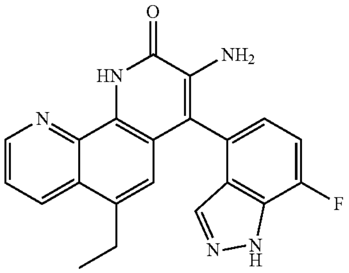 [SMILES: CCc1cc2c(-c3ccc(F)c4[nH]ncc34)c(N)c(=O)[nH]c2c2ncccc12] | 3-amino-6-ethyl-4-(7-fluoro-1H-indazol-4-yl)-1H-1,10-phenanthrolin-2-one |
| 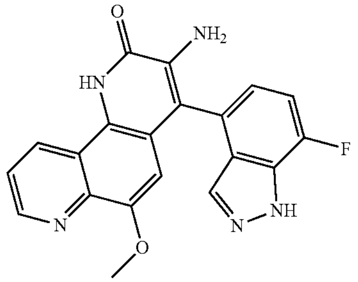 [SMILES: COc1cc2c(-c3ccc(F)c4[nH]ncc34)c(N)c(=O)[nH]c2c2cccnc12] | 3-amino-4-(7-fluoro-1H-indazol-4-yl)-6-methoxy-1H-1,7-phenanthrolin-2-one |
| 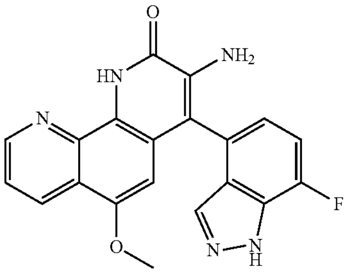 [SMILES: COc1cc2c(-c3ccc(F)c4[nH]ncc34)c(N)c(=O)[nH]c2c2ncccc12] | 3-amino-4-(7-fluoro-1H-indazol-4-yl)-6-methoxy-1H-1,10-phenanthrolin-2-one |

TABLE 1-1-continued
| Structure of compound | Name of compound |
| --- | --- |
| 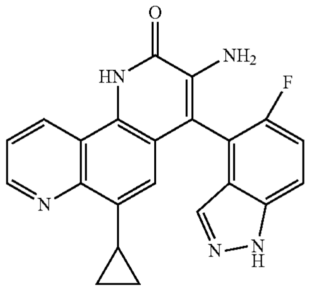 [SMILES: Nc1c(-c2c(F)ccc3[nH]ncc23)c2cc(C3CC3)c3ncccc3c2[nH]c1=O] | 3-amino-6-cyclopropyl-4-(5-fluoro-1H-indazol-4-yl)-1H-1,7-phenanthrolin-2-one |
| 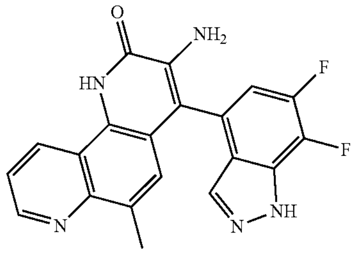 [SMILES: Cc1cc2c(-c3cc(F)c(F)c4[nH]ncc34)c(N)c(=O)[nH]c2c2cccnc12] | 3-amino-4-(6,7-difluoro-1H-indazol-4-yl)-6-methyl-1H-1,7-phenanthrolin-2-one |
| 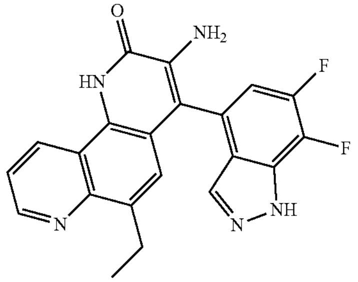 [SMILES: CCc1cc2c(-c3cc(F)c(F)c4[nH]ncc34)c(N)c(=O)[nH]c2c2cccnc12] | 3-amino-4-(6,7-difluoro-1H-indazol-4-yl)-6-ethyl-1H-1,7-phenanthrolin-2-one |
| 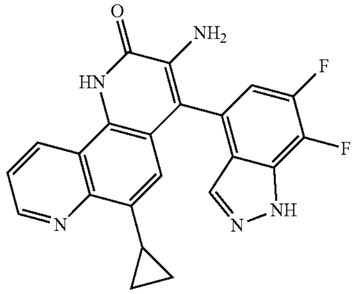 [SMILES: Nc1c(-c2cc(F)c(F)c3[nH]ncc23)c2cc(C3CC3)c3ncccc3c2[nH]c1=O] | 3-amino-6-cyclopropyl-4-(6,7-difluoro-1H-indazol-4-yl)-1H-1,7-phenanthrolin-2-one |
| 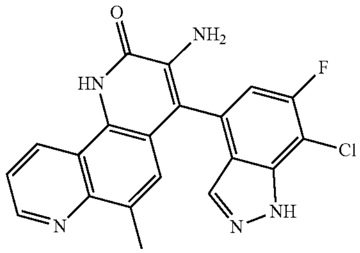 [SMILES: Cc1cc2c(-c3cc(F)c(Cl)c4[nH]ncc34)c(N)c(=O)[nH]c2c2cccnc12] | 3-amino-4-(7-chloro-6-fluoro-1H-indazol-4-yl)-6-methyl-1H-1,7-phenanthrolin-2-one |

TABLE 1-1-continued
| Structure of compound | Name of compound |
| --- | --- |
| 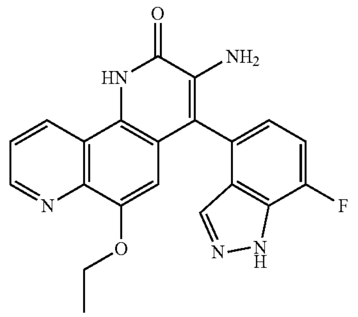 [SMILES: CCOc1cc2c(-c3ccc(F)c4[nH]ncc34)c(N)c(=O)[nH]c2c2cccnc12] | 3-amino-6-ethoxy-4-(7-fluoro-1H-indazol-4-yl)-1H-1,7-phenanthrolin-2-one |
| 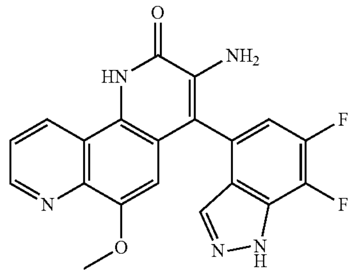 [SMILES: COc1cc2c(-c3cc(F)c(F)c4[nH]ncc34)c(N)c(=O)[nH]c2c2cccnc12] | 3-amino-4-(6,7-difluoro-1H-indazol-4-yl)-6-methoxy-1H-1,7-phenanthrolin-2-one |
| 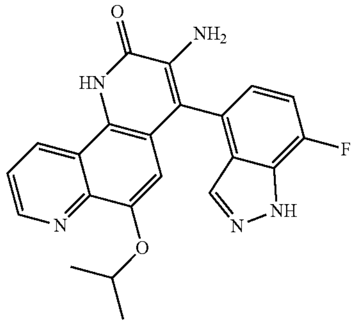 [SMILES: CC(C)Oc1cc2c(-c3ccc(F)c4[nH]ncc34)c(N)c(=O)[nH]c2c2cccnc12] | 3-amino-4-(7-fluoro-1H-indazol-4-yl)-6-propan-2-yloxy-1H-1,7-phenanthrolin-2-one |
| 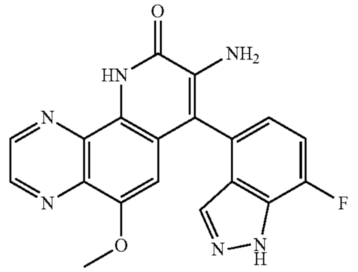 [SMILES: COc1cc2c(-c3ccc(F)c4[nH]ncc34)c(N)c(=O)[nH]c2c2nccnc12] | 8-amino-7-(7-fluoro-1H-indazol-4-yl)-5-methoxy-10H-pyrido[2,3-f]quinoxalin-9-one |
| 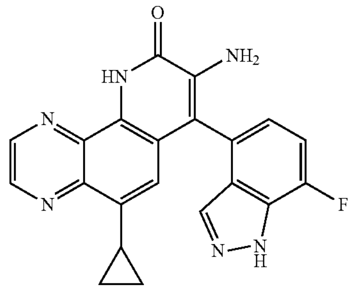 [SMILES: Nc1c(-c2ccc(F)c3[nH]ncc23)c2cc(C3CC3)c3nccnc3c2[nH]c1=O] | 8-amino-5-cyclopropyl-7-(7-fluoro-1H-indazol-4-yl)-10H-pyrido[2,3-f]quinoxalin-9-one |

TABLE 1-1-continued
| Structure of compound | Name of compound |
| --- | --- |
| 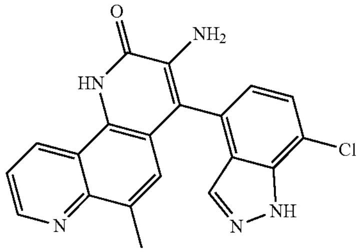 [SMILES: Cc1cc2c(-c3ccc(Cl)c4[nH]ncc34)c(N)c(=O)[nH]c2c2cccnc12] | 3-amino-4-(7-chloro-1H-indazol-4-yl)-6-methyl-1H-1,7-phenanthrolin-2-one |
| 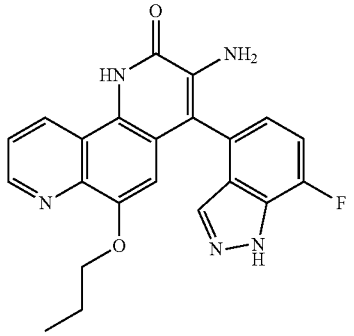 [SMILES: CCCOc1cc2c(-c3ccc(F)c4[nH]ncc34)c(N)c(=O)[nH]c2c2cccnc12] | 3-amino-4-(7-fluoro-1H-indazol-4-yl)-6-propoxy-1H-1,7-phenanthrolin-2-one |
| 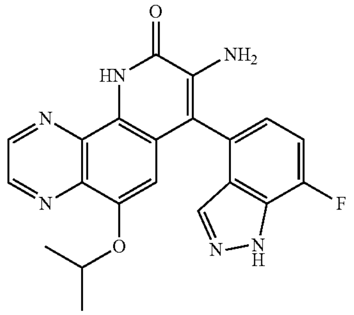 [SMILES: CC(C)Oc1cc2c(-c3ccc(F)c4[nH]ncc34)c(N)c(=O)[nH]c2c2nccnc12] | 8-amino-7-(7-fluoro-1H-indazol-4-yl)-5-propan-2-yloxy-10H-pyrido[2,3-f]quinoxalin-9-one |
| 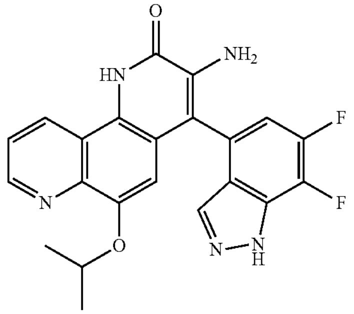 [SMILES: CC(C)Oc1cc2c(-c3cc(F)c(F)c4[nH]ncc34)c(N)c(=O)[nH]c2c2cccnc12] | 3-amino-4-(6,7-difluoro-1H-indazol-4-yl)-6-propan-2-yloxy-1H-1,7-phenanthrolin-2-one |
| 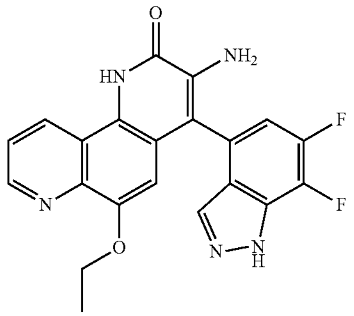 [SMILES: CCOc1cc2c(-c3cc(F)c(F)c4[nH]ncc34)c(N)c(=O)[nH]c2c2cccnc12] | 3-amino-4-(6,7-difluoro-1H-indazol-4-yl)-6-ethoxy-1H-1,7-phenanthrolin-2-one |

TABLE 1-1-continued

| Structure of compound | Name of compound |
| --- | --- |
| 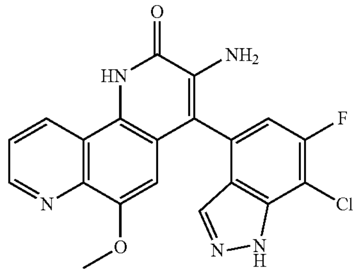 [SMILES: COc1cc2c(-c3cc(F)c(Cl)c4[nH]ncc34)c(N)c(=O)[nH]c2c2cccnc12] | 3-amino-4-(7-chloro-6-fluoro-1H-indazol-4-yl)-6-methoxy-1H-1,7-phenanthrolin-2-one |
| 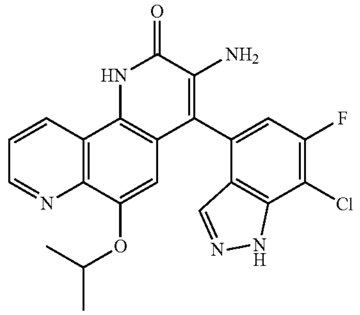 [SMILES: CC(C)Oc1cc2c(-c3cc(F)c(Cl)c4[nH]ncc34)c(N)c(=O)[nH]c2c2cccnc12] | 3-amino-4-(7-chloro-6-fluoro-1H-indazol-4-yl)-6-propan-2-yloxy-1H-1,7-phenanthrolin-2-one |
| 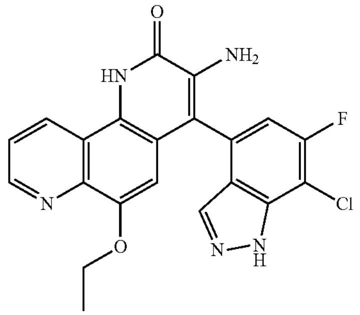 [SMILES: CCOc1cc2c(-c3cc(F)c(Cl)c4[nH]ncc34)c(N)c(=O)[nH]c2c2cccnc12] | 3-amino-4-(7-chloro-6-fluoro-1H-indazol-4-yl)-6-ethoxy-1H-1,7-phenanthrolin-2-one |
| 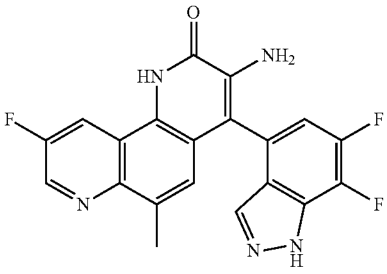 [SMILES: Cc1cc2c(-c3cc(F)c(F)c4[nH]ncc34)c(N)c(=O)[nH]c2c2cc(F)cnc12] | 3-amino-4-(6,7-difluoro-1H-indazol-4-yl)-9-fluoro-6-methyl-1H-1,7-phenanthrolin-2-one |
| 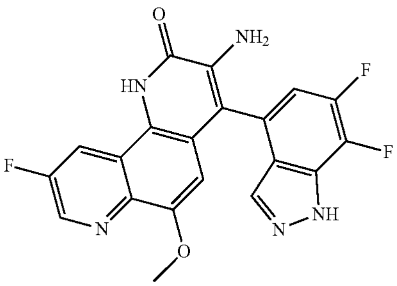 [SMILES: COc1cc2c(-c3cc(F)c(F)c4[nH]ncc34)c(N)c(=O)[nH]c2c2cc(F)cnc12] | 3-amino-4-(6,7-difluoro-1H-indazol-4-yl)-9-fluoro-6-methoxy-1H-1,7-phenanthrolin-2-one |

TABLE 1-1-continued
| Structure of compound | Name of compound |
|---|---|
| 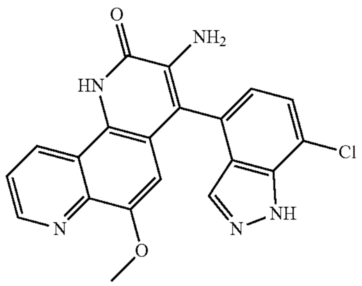 [SMILES: COc1cc2c(-c3ccc(Cl)c4[nH]ncc34)c(N)c(=O)[nH]c2c2cccnc12] | 3-amino-4-(7-chloro-1H-indazol-4-yl)-6-methoxy-1H-1,7-phenanthrolin-2-one |
| 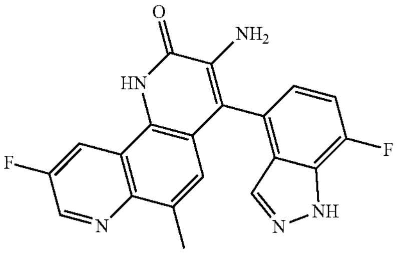 [SMILES: Cc1cc2c(-c3ccc(F)c4[nH]ncc34)c(N)c(=O)[nH]c2c2cc(F)cnc12] | 3-amino-9-fluoro-4-(7-fluoro-1H-indazol-4-yl)-6-methyl-1H-1,7-phenanthrolin-2-one |
| 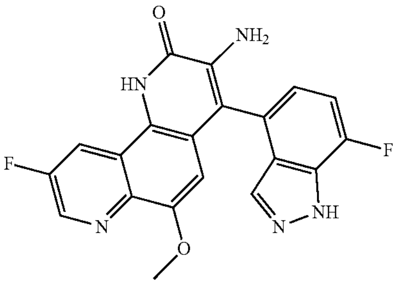 [SMILES: COc1cc2c(-c3ccc(F)c4[nH]ncc34)c(N)c(=O)[nH]c2c2cc(F)cnc12] | 3-amino-9-fluoro-4-(7-fluoro-1H-indazol-4-yl)-6-methoxy-1H-1,7-phenanthrolin-2-one |
| 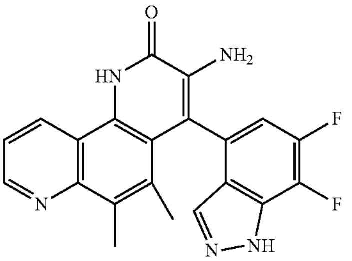 [SMILES: Cc1c(C)c2c(-c3cc(F)c(F)c4[nH]ncc34)c(N)c(=O)[nH]c2c2cccnc12] | 3-amino-4-(6,7-difluoro-1H-indazol-4-yl)-5,6-dimethyl-1H-1,7-phenanthrolin-2-one |
| 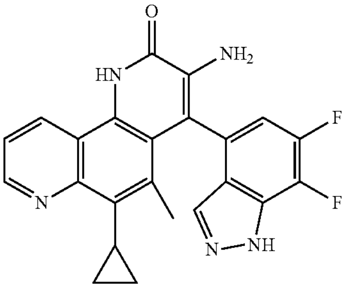 [SMILES: Cc1c(C2CC2)c2ncccc2c2[nH]c(=O)c(N)c(-c3cc(F)c(F)c4[nH]ncc34)c12] | 3-amino-6-cyclopropyl-4-(6,7-difluoro-1H-indazol-4-yl)-5-methyl-1H-1,7-phenanthrolin-2-one |

TABLE 1-1-continued
| Structure of compound | Name of compound |
|---|---|
| 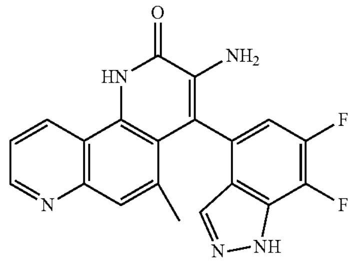 [SMILES: Cc1cc2ncccc2c2[nH]c(=O)c(N)c(-c3cc(F)c(F)c4[nH]ncc34)c12] | 3-amino-4-(6,7-difluoro-1H-indazol-4-yl)-5-methyl-1H-1,7-phenanthrolin-2-one |
| 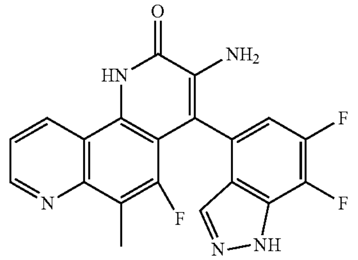 [SMILES: Cc1c(F)c2c(-c3cc(F)c(F)c4[nH]ncc34)c(N)c(=O)[nH]c2c2cccnc12] | 3-amino-4-(6,7-difluoro-1H-indazol-4-yl)-5-fluoro-6-methyl-1H-1,7-phenanthrolin-2-one |
| 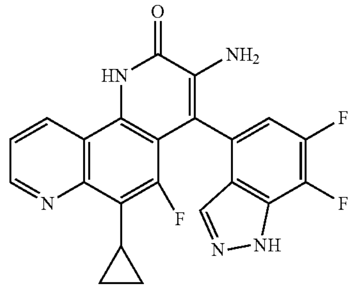 | 3-amino-6-cyclopropyl-4-(6,7-difluoro-1H-indazol-4-yl)-5-fluoro-1H-1,7-phenanthrolin-2-one |
| 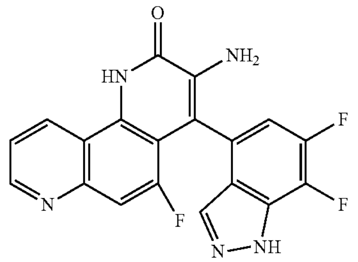 [SMILES: Nc1c(-c2cc(F)c(F)c3[nH]ncc23)c2c(F)cc3ncccc3c2[nH]c1=O] | 3-amino-4-(6,7-difluoro-1H-indazol-4-yl)-5-fluoro-1H-1,7-phenanthrolin-2-one |
| 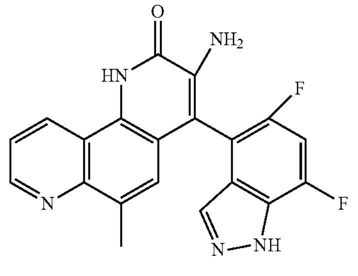 [SMILES: Cc1cc2c(-c3c(F)cc(F)c4[nH]ncc34)c(N)c(=O)[nH]c2c2cccnc12] | 3-amino-4-(5,7-difluoro-1H-indazol-4-yl)-6-methyl-1H-1,7-phenanthrolin-2-one |

TABLE 1-1-continued

| Structure of compound | Name of compound |
| --- | --- |
| 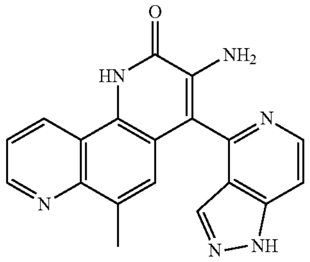 [SMILES: Cc1cc2c(-c3nccc4[nH]ncc34)c(N)c(=O)[nH]c2c2cccnc12] | 3-amino-6-methyl-4-(1H-pyrazolo[4,3-c]pyridin-4-yl)-1H-1,7-phenanthrolin-2-one |
| 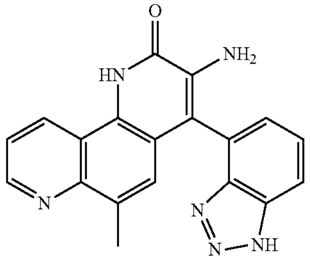 [SMILES: Cc1cc2c(-c3cccc4[nH]nnc34)c(N)c(=O)[nH]c2c2cccnc12] | 3-amino-4-(1H-benzotriazol-4-yl)-6-methyl-1H-1,7-phenanthrolin-2-one |
| 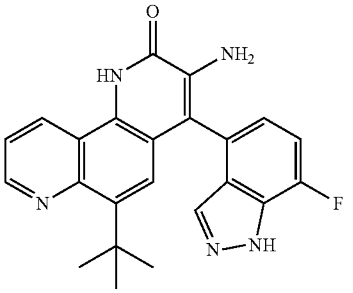 [SMILES: CC(C)(C)c1cc2c(-c3ccc(F)c4[nH]ncc34)c(N)c(=O)[nH]c2c2cccnc12] | 3-amino-6-(tert-butyl)-4-(7-fluoro-1H-indazol-4-yl)-1H-1,7-phenanthrolin-2-one |

The term "compound or a salt thereof, or a solvate thereof" as used herein includes the compound, a salt of the compound, a solvate of the compound, and a solvate of a salt of the compound.

The compound described herein may be a salt thereof, preferably a pharmaceutically acceptable salt thereof. The compound described herein or a salt thereof may be a solvate thereof, preferably a pharmaceutically acceptable solvate thereof. Examples of the salt of the compound include hydrochloride; hydrobromide; hydroiodide; phosphate; phosphonate; sulfate; sulfonate such as methanesulfonate and p-toluenesulfonate; carboxylate such as acetate, citrate, malate, tartrate, succinate, and salicylate; alkali metal salts such as sodium salts and potassium salts; alkaline earth metal salts such as magnesium salt and calcium salt; and ammonium salts such as ammonium salt, alkylammonium salt, dialkylammonium salt, trialkylammonium salt, and tetraalkylammonium salt. These salts are produced by, for example, bringing the compound into contact with an acid or a base. The solvate as used herein is one in which a compound and a solvent together form a molecular aggregate, and is not particularly limited as long as it is a solvate formed by a solvent acceptable for ingestion along with administration of a medicament. Examples of the solvate include hydrates, alcohol solvates (such as ethanol solvates, methanol solvates, 1-propanol solvates, and 2-propanol solvates), and not only solvates formed with a single solvent such as dimethyl sulfoxide, but also solvates formed with a plurality of solvents per one molecule of compound, or solvates formed with a plurality of types of solvents per one molecule of compound. When the solvent is water, the solvates are called hydrates. The solvate of the compound of the present invention is preferably a hydrate. Specific examples of such a hydrate include a mono- to deca-hydrate, preferably a mono- to penta-hydrate, further preferably a mono- to tri-hydrate.

When the compound according to the present invention is obtained as a free form, the compound can be conventionally transformed into a state of a salt, a hydrate thereof or a solvate thereof which may be formed by the compound. Examples thereof include hydrates and ethanolates of the compound represented by the formula (1) or a salt thereof. Specific examples thereof include, but are not limited to, hemihydrates, monohydrates, dihydrates, trihydrates, tetrahydrates, pentahydrates, hexahydrates, heptahydrates, octahydrates, nonahydrates, decahydrates, or monoethanolates of the compound represented by the formula (1); hemihydrates, monohydrates, dihydrates, trihydrates, tetrahydrates, pentahydrates, hexahydrates, heptahydrates, octahydrates, nonahydrates, decahydrates, or monoethanolates of sodium salts of the compound represented by the formula (1); or hydrates or ethanolates of hydrochlorides of the compound represented by the formula (1). The hydrate or solvate may be produced in a crystalline form or non-crystalline form. In the case of the crystalline form, the hydrate or solvate may have crystalline polymorphs. As for the method for producing the hydrate or solvate, the hydrate or solvate can be obtained by a conventional method, for example, by adding a solvent such as ethanol and/or water to the compound represented by the formula (1), followed by stirring, cooling, concentrating, and/or drying.

When the compound according to the present invention is obtained as a salt, a hydrate, or a solvate of the compound, the compound can be conventionally transformed into a free form thereof.

The compound described herein may contain an isotopic atom at a non-natural ratio in one or more atoms that constitute the compounds. The compound in which any atom in the compound is replaced with another isotopic atom having the same atomic number (number of protons) and a different mass number (sum of the numbers of protons and neutrons), thereby the abundance ratio of the isotope is different from the abundance ratio in nature, that is, a compound labeled with an isotopic atom, is also included in the present invention. Examples of the isotopic element contained in the compounds herein include a hydrogen atom, a carbon atom, a nitrogen atom, an oxygen atom, a phosphorus atom, a sulfur atom, a fluorine atom, and a chlorine atom, and they include $^{2}H$, $^{3}H$; $^{13}C$, $^{14}C$; $^{15}N$; $^{17}O$, $^{18}O$; $^{32}P$; $^{35}S$; $^{18}F$; $^{36}Cl$; and the like, respectively. The compound labeled with an isotopic atom is useful as a therapeutic or prophylactic agent, a research reagent (e.g., assay reagent), and a diagnostic agent (e.g., in vivo imaging diagnostic agent). For the compounds as used herein, all the compounds containing any proportions of radioactive or non-radioactive isotopic element are encompassed within the scope of the present invention. The compound labeled with an isotopic atom can be produced in a manner similar to methods for producing unlabeled compounds by using a reagent or a solvent containing a corresponding isotopic atom.

The compound described herein, a salt thereof, or a solvate thereof includes all stereoisomers (e.g. enantiomers and diastereomers (including cis- and trans-geometric isomers)), racemates of the isomers, and other mixtures. For example, the compound of the present invention may have one or more asymmetric points, and the present invention includes racemic mixtures, diastereomer mixtures, and enantiomers of such compounds. Also, for example, the compounds of the present invention may have axial asymmetry, and the present invention includes each stereoisomer of such compounds and mixtures thereof.

<General Production Method>

Examples of the production methods of the compounds represented by the formula (1) to the formula (3) or salts thereof, or solvates thereof will be described by the following scheme groups. The compound of the present invention can be synthesized by various methods. The following production methods are illustrative only, and the present invention is not limited to the indicated chemical reactions and conditions. In the following scheme of the production method, some substituents are eliminated for clarity, but this is not intended to limit the scheme disclosure. The typical compound of the present invention can be synthesized by using an appropriate intermediate, a known compound, and a reagent. Unless otherwise specified, variable groups represented by $R_1$, $R_2$, and the like and variables represented by n and the like in the formulas in the following general synthesis method have the same meanings as variable groups represented by $R_1$, $R_2$, and the like and variables represented by n and the like in the compound represented by the general formula as defined herein. When a starting material or intended product in a step is undesirably, chemically transformed under the reaction conditions of the step, the intended product of the step can be obtained, for example, by protecting and deprotecting a functional group. Here, for the selection of a protective group and the selection of the methods for protection and deprotection, for example, T. W. Greene, P. G. M. Wuts, Protective Groups in Organic Synthesis (5th edition, John Wiley & Sons 2014) (Non Patent Literature 6) can be referenced. Some of the protection and deprotection of functional groups are also described in the following scheme.

The compounds obtained in each step may be isolated by a general technique, and, if necessary, may be purified by crystallization or chromatography.

Examples and meanings of the abbreviations as used herein are listed below.

Boc: tert-butoxycarbonyl
DCM: dichloromethane
DMA: N,N-dimethylacetamide
DMF: N,N-dimethylformamide
DMSO: dimethyl sulfoxide
EtOH: ethanol
MeOH: methanol
NMP: N-methyl-2-pyrrolidone
TFA: trifluoroacetylacetic acid
THF: tetrahydrofuran
TBME: tert-butyl methyl ether
TFE: 2,2,2-trifluoroethanol
HATU: O-(7-azabenzotriazol-1-yl)-N,N,N',N'-tetramethyluronium hexafluorophosphate
DIPEA: N,N-diisopropylethylamine
XPhos Pd G3: (2-dicyclohexylphosphino-2',4',6'-triisopropyl-1,1'-biphenyl) (2-(2'-amino-1,1'-biphenyl))palladium(II) methanesulfonate (CAS number: 1445085-55-1)
XPhos Pd G4: (2-dicyclohexylphosphino-2',4',6'-triisopropyl-1, 1'-biphenyl) (2-(2'-(N-methyl)amino-1,1'-biphenyl))palladium(II) methanesulfonate (CAS number: 1599466-81-5)
DPPF Pd G4: (1,1'-bis(diphenylphosphino)ferrocene) (2-(2'-(N-methyl)amino-1,1'-biphenyl))palladium(II) methanesulfonate (CAS number: 1621274-17-6)
CPhos Pd G3: (2-dicyclohexylphosphino-2',6'-bis(N,N-dimethylamino) biphenyl) (2-(2'-amino-1,1-biphenyl)) palladium(II) methanesulfonate (CAS number: 1447963-73-6)
CPhos Pd G2: chloro [(2-dicyclohexylphosphino-2',6'-bis (N,N-dimethylamino)-1,1'-biphenyl)-2-(2'-amino-1,1'-biphenyl)]palladium(II) (CAS number: 2230788-62-0)
tBuBrettPhos Pd G3: [(2-di-tert-butylphosphino-3,6-dimethoxy-2',4',6'-triisopropyl-1,1'-biphenyl)-2-(2'-amino-1,1'-biphenyl)]palladium(II) methanesulfonate (CAS number: 1536473-72-9)
BINAP Pd G4: [(+)-2,2'-bis(diphenylphosphino)-1,1'-binaphthalene](2'-methylamino-1,1'-biphenyl-2-yl)palladium(II) methanesulfonate (CAS number: 1599466-90-6)
Xantphos Pd G3: [9,9-dimethyl-4,5-bis(diphenylphosphino)xanthene](2'-amino-1,1'-biphenyl-2-yl)palladium(II) methanesulfonate (CAS number: 1445085-97-1)
Xantphos Pd G4: [9,9-dimethyl-4,5-bis(diphenylphosphino)xanthene](2'-methylamino-1,1'-biphenyl-2-yl) palladium(II) methanesulfonate (CAS number: 1621274-19-8)
tBuXPhos Pd G3: [(2-di-tert-butylphosphino-2',4',6'-triisopropyl-1,1'-biphenyl)-2-(2'-amino-1,1'-biphenyl)] palladium(II) methanesulfonate (CAS number: 1447963-75-8)
DCC: N,N'-dicyclohexylcarbodiimide EDC: N-ethyl-N'-(3-dimethylaminopropyl) carbodiimide COMU: (1-cyano-2-ethoxy-2-oxoethylideneaminooxy) dimethylamino-morpholino-carbenium hexafluorophosphate LiHMDS: lithium hexamethyldisilazide NaHMDS: sodium hexamethyldisilazide KHMDS: potassium hexamethyldisilazide LDA: lithium diisopropylamide DIAD: diisopropyl azodicarboxylate CMMP: (cyanomethylene)trimethylphosphorane CMBP: (cyanomethylene)tributylphosphorane DCE: 1,2-dichloroethane FA: formic acid The compound of the present invention can be synthesized, for example, by the production method described below.

(General Production Method 1-1)

The general production method 1-1 is a preferred production method of a compound in which $R_4$ is optionally substituted $C_6$-$C_{10}$ aryl or optionally substituted 5- to 10-membered heteroaryl, among the compounds represented by the general formulas (1) to (3).

[Formula 15]

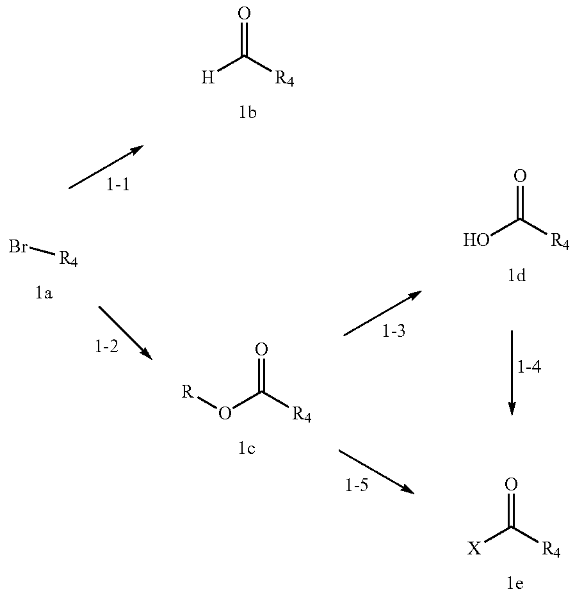

Step 1-1

The present step is the formylation step of the aromatic bromide 1a. The compound 1b can be produced by reacting the aromatic bromide 1a with a metal species, followed by reacting with a formylating reagent. Examples of the metal species include metals such as magnesium and lithium, and organic metal reagents. Examples of the organic metal reagent include isopropylmagnesium bromide, an isopropylmagnesium chloride-lithium chloride complex, n-butyllithium, and sec-butyllithium. The isopropylmagnesium chloride-lithium chloride complex is preferable. The formylating reagent is selected from N-formamide and an orthoformic acid ester. N-formamide is preferably DMF, and the orthoformic acid ester is preferably trimethyl orthoformate. Examples of the solvent used in the present step include aprotic solvents such as n-hexane, cyclohexane, ethers (dialkyl ethers such as diethyl ether, and cyclic ethers such as 1,2-dimethoxyethane, THF, and 2-methyltetrahydrofuran are exemplified), and toluene, as well as mixed solvents thereof. THF, 1,2-dimethoxyethane, toluene, and mixed solvents thereof are preferable.

Step 1-2

The present step is a step of producing an aromatic ester from the aromatic bromide 1a. The aromatic ester 1c (wherein R represents $C_1$-$C_6$ alkyl, 2,4,6-trichlorophenyl, or 2,5-dioxopyrrolidin-1-yl) can be produced by reacting the aromatic bromide 1a with a carbonylating reagent in the presence of a Pd catalyst and a base. The present step can be conducted, for example, with reference to the method described in Tetrahedron Lett., 2019 vol. 60, 151147 (Non Patent Literature 7) and the like. Examples of the carbonylating reagent include formic acid esters, oxalic acid esters, and salts thereof. 2,4,6-Trichlorophenyl formate is preferable. Examples of the base include tertiary amine. Triethylamine and DIPEA are preferable. Examples of the solvent used in the present step include aprotic solvents such as toluene, acetonitrile, THF, and DMF, and mixed solvents thereof. Toluene is preferable. The Pd catalyst is preferably a combination of palladium acetate and 4,5-bis(diphenylphosphino)-9,9-dimethylxanthene, Xantphos Pd G4, and Xantphos Pd G3. The present step can be carried out at −20° C. to a reaction temperature near the boiling point of the solvent, and is preferably carried out at 60° C. to a temperature near the boiling point of the solvent.

Step 1-3

The present step is a hydrolysis step of the aromatic ester 1c. The aromatic carboxylic acid 1d can be produced by reacting the aromatic ester 1c with a hydroxide. The hydroxide can be, for example, selected from the group consisting of sodium hydroxide, lithium hydroxide, potassium hydrate, and barium hydroxide. Examples of the solvent used in the present step include polar solvents such as water, ethers, alcohols, and DMSO, and mixed solvents thereof. A mixed solvent of THF and water and a mixed solvent of methanol and water are preferable.

Step 1-4

The present step is an amidation step of the aromatic carboxylic acid 1d. The aromatic amide 1e (wherein X represents methyl(methoxy)amino or morpholinyl) can be produced by reacting the aromatic carboxylic acid 1d with an amine or amine salt in the presence of a condensing agent. The condensing agent can be, for example, selected from the group consisting of DCC, EDC, EDC hydrochloride, HATU, COMU, and propylphosphonic acid anhydride (cyclic trimer), and is preferably HATU. A base may be used as the additive in the present step. Examples of the base include DIPEA, triethylamine, and diazabicycloundecene, and DIPEA is preferable. Examples of the solvent used in the present step include DMF, DMA, NMP, DCM, THF, 1,4-dioxane, 1,2-dimethoxyethane, ethyl acetate, acetonitrile, and mixed solvents thereof. Examples of the amine or amine salt include N,O-dimethylhydroxylamine hydrochloride and morpholine, and N,O-dimethylhydroxylamine hydrochloride is preferable.

Step 1-5

The present step is an alternative method for synthesizing the aromatic amide 1e, and is a step of carrying out the ester-amide exchange reaction of the aromatic ester 1c. The present step can be conducted when R in the aromatic ester 1c is 2,4,6-trichlorophenyl, 2,5-dioxopyrrolidin-1-yl, and the like. The aromatic amide 1e (wherein X represents methyl(methoxy)amino or morpholinyl) can be produced by reacting the aromatic ester 1c with amine. The amine is preferably morpholine. Examples of the solvent used in the present step include toluene, DMF, DMA, THF, 1,4-dioxane, 1,2-dimethoxyethane, acetonitrile, and mixed solvents thereof, and toluene is preferable. The present step can be carried out at −20° C. to a reaction temperature near the boiling point of the solvent, and is preferably carried out at 60° C. or more to a temperature near the boiling point of the solvent.

(General Production Method 1-2)

The general production method 1-2 is a preferred production method of a compound in which $R_4$ is optionally substituted $C_6$-$C_{10}$ aryl or optionally substituted 5- to 10-membered heteroaryl, among the compounds represented by the general formulas (1) to (3).

[Formula 16]

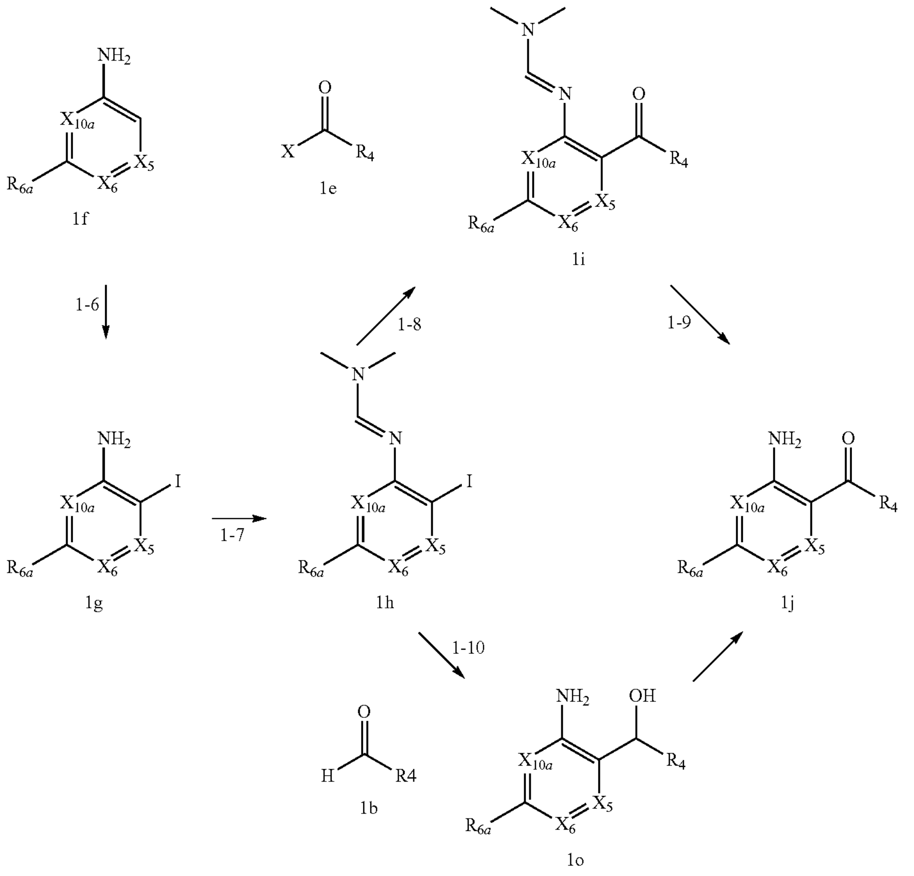

[Formula 17]

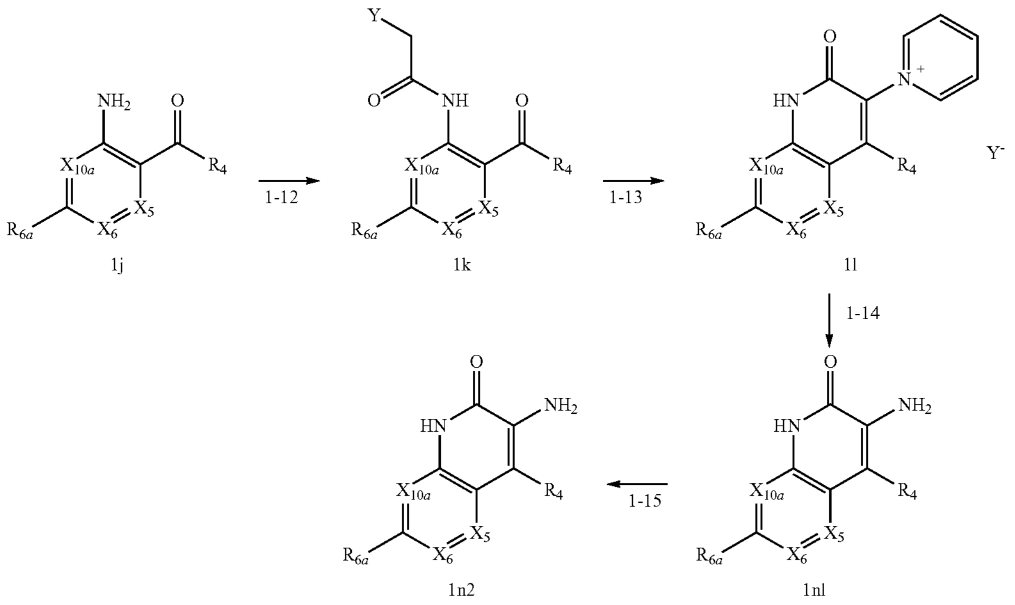

Step 1-6

The present step is a step of iodinating the aromatic amine 1f. The aromatic amine 1g can be produced by reacting the aromatic amine 1f with an iodinating reagent. Examples of the iodinating reagent include iodine, N-iodosuccinimide, 1,3-diiodo-5,5-dimethylhydantoin, N-iodosaccharin, and iodine chloride, and N-iodosuccinimide is preferable. Examples of the solvent used in the present step include DCM, acetonitrile, ethyl acetate, DMSO, and acetic acid, and DCM and DMSO are preferable. As the additive in the present step, an acid exemplified by TFA, acetic acid, sulfuric acid, methanesulfonic acid, trifluoromethanesulfonic acid, and the like may be appropriately used.

Step 1-7

The present step is a step of transforming the amino group in the aromatic amine 1g by using an N,N-dimethylformamidinating reagent. The aromatic iodine compound 1h can be produced by transforming the amino group in the aromatic amine 1g into an N,N-dimethylformamidino group. Examples of the N,N-dimethylformamidinating reagent include N,N-dimethylformamide dimethyl acetal, N,N-dimethylformamide di-tert-butyl acetal, and a combination of DMF and phosphorus (V) oxychloride. N,N-dimethylformamide dimethyl acetal is preferable. Examples of the solvent used in the present step include alcohols, DMSO, THF, DMF, DMA, NMP, toluene, 1,4-dioxane, 1,2-dimethoxyethane, ethyl acetate, acetonitrile, and mixed solvents thereof. Ethanol and DMSO are preferable. The present step can be carried out at −20° C. to a reaction temperature near the boiling point of the solvent, and is preferably carried out at 40° C. to a temperature near the boiling point of the solvent.

Step 1-8

The present step is a step of synthesizing the ketone 1i by reacting the aromatic iodine compound 1h with a metal species, and then reacting the aromatic amide 1e (wherein X represents methyl(methoxy)amino or morpholinyl). Examples of the metal species include metals such as magnesium and lithium, and organic metal reagents. Examples of the organic metal reagent include isopropylmagnesium bromide, an isopropylmagnesium chloride-lithium chloride complex, n-butyllithium, and sec-butyllithium. The isopropylmagnesium chloride-lithium chloride complex is preferable. Examples of the solvent used in the present step include aprotic solvents such as n-hexane, cyclohexane, ethers, and toluene, and mixed solvents thereof. THF, 1,2-dimethoxyethane, toluene, and mixed solvents thereof are preferable. The additive such as hexamethylphosphoric triamide, N,N'-dimethylpropylene urea, or a crown ether may be optionally added. The additive is preferably N,N'-dimethylpropylene urea.

Step 1-9

The present step is a step of transforming the dimethylformamidine 1i into the aniline 1j by a hydrolysis reaction. The aniline 1j can be produced by reacting the dimethylformamidine compound 1i with a hydroxide. Examples of the hydroxide include sodium hydroxide, lithium hydroxide, potassium hydrate, and barium hydroxide. Sodium hydroxide is preferable. Examples of the solvent used in the present step include polar solvents such as THF, alcohols, and DMSO. DMSO is preferable.

Step 1-10

The present step is a step of producing an alcohol by reacting the aromatic iodine compound 1h with a metal species, followed by reacting with the aromatic aldehyde 1b. Examples of the metal species include metals such as magnesium and lithium, and organic metal reagents. Examples of the organic metal reagent include isopropylmagnesium bromide, an isopropylmagnesium chloride-lithium chloride complex, n-butyllithium, and sec-butyllithium. The isopropylmagnesium chloride-lithium chloride complex is preferable. Examples of the solvent used in the present step include aprotic solvents such as n-hexane, cyclohexane, ethers, and toluene, and mixed solvents thereof. THF, 1,2-dimethoxyethane, toluene, and mixed solvents thereof are preferable. As the additive, hexamethylphosphoric triamide, N,N'-dimethylpropylene urea, a crown ether, or the like may be added. The additive is preferably N,N'-dimethylpropylene urea. By sequentially adding an acid and a base to the reaction mixture, the N,N-dimethylformamidino group can be transformed into an amino group. The acid is preferably formic acid. The base is preferably ethylenediamine.

Step 1-11

The present step is a step of transforming the benzyl alcohol 1o into a ketone by an oxidation reaction. The aromatic amine 1j can be produced by reacting the benzyl alcohol 1o with an oxidizing agent. Examples of the oxidizing agent include manganese dioxide, Dess-Martin periodinane, chromium (IV) oxide, and pyridinium dichromate. Manganese dioxide is preferable. Examples of the solvent used in the present step include aprotic solvents such as DCM, chloroform, acetonitrile, and ethyl acetate, and mixed solvents thereof. DCM is preferable.

Step 1-12

The present step is a step of haloacetylating the aromatic amine 1j. The present step can be carried out in accordance with the following method-1 or method-2.

Method-1: The haloacetamide 1k (wherein Y represents a halogen) can be produced by reacting the aromatic amine 1j with a haloacetylating agent. As the haloacetylating agent, for example, chloroacetyl chloride, bromoacetyl chloride, or the like can be used. In the present step, a base may be appropriately used. As the base, for example, an organic base such as DIPEA, triethylamine, or pyridine can be used. Examples of the solvent used in the present step include DCM, acetonitrile, THF, DMF, DMA, and NMP. DCM and DMA are preferable.

Method-2: The haloacetamide 1k (wherein Y represents a halogen) can be produced by reacting the aromatic amine 1j with a haloacetic acid in the presence of a condensing agent. As the haloacetic acid, chloroacetic acid and bromoacetic acid can be used. Examples of the condensing agent include DCC, EDC, EDC hydrochloride, HATU, COMU, and propylphosphonic acid anhydride (cyclic trimer). HATU and propylphosphonic acid anhydride (cyclic trimer) are preferable. Examples of the base include DIPEA and triethylamine. DIPEA is preferable. Examples of the solvent used in the present step include DMF, DMA, NMP, DCM, acetone, THF, 1,4-dioxane, 1,2-dimethoxyethane, ethyl acetate, acetonitrile, and mixed solvents thereof. DMF is preferable.

Step 1-13

The present step is a step of constructing a pyridone skeleton from the haloacetamide 1k (wherein Y represents a halogen) by a cyclization reaction. The pyridinium ylide 1l (wherein Y represents a halogen) can be produced by reacting the haloacetamide 1k with pyridine. Pyridine may be used as the solvent of the present step. In addition, the reaction mixture of step 1-12 may be reacted with pyridine. The present step can be carried out at −20° C. to a reaction temperature near the boiling point of the solvent, and is preferably carried out at 40° C. to a temperature near the boiling point of the solvent.

Step 1-14

The present step is a deprotection step of the pyridinium ylide 11. The 3-aminopyridone compound 1n1 can be produced by reacting the pyridinium ylide 11 with a nucleophilic agent. Examples of the nucleophilic agent include hydrazine, hydrazine hydrochloride, hydrazine monohydrate, and hydroxylamine. Hydrazine monohydrate and hydrazine hydrochloride are preferable. The reaction mixture of step 1-13 may be used as it is. The present step can be carried out at −20° C. to a reaction temperature near the boiling point of the solvent, and is preferably carried out at 40° C. to a temperature near the boiling point of the solvent.

Step 1-15

The present step is a step of adding an acid to the 3-aminopyridone compound 1n1 and eliminating a protective group removable with an acid exemplified by 2-tetrahydropyranyl, when $R_4$ in the 3-aminopyridone compound 1n1 has a protective group removable with an acid exemplified by 2-tetrahydropyranyl. Examples of the acid include sulfuric acid, hydrochloric acid, sulfonic acid, and carboxylic acid. TFA is preferable. Examples of the solvent used in the present step include alcohols (e.g., alkyl alcohols and fluoroalkyl alcohols), water, and DCM. In addition, for example, an acid may be produced using trimethylsilyl chloride (TMSCl) in the alcohol used as the solvent to eliminate the protective group removable with an acid exemplified by a 2-tetrahydropyranyl group. As the combination of an acid and a solvent, for example, a combination of TMSCl and TFE, a combination of TFA and DCM, and a combination of TFA and water are preferable.

(General Production Method 2)

The general production method 2 is another preferred method for synthesizing the 3-aminopyridone compound 1n2. The general production method 2 is a preferred production method of a compound in which $R_4$ is optionally substituted $C_6$-$C_{10}$ aryl or optionally substituted 5- to 10-membered heteroaryl, among the compounds represented by the general formulas (1) to (3).

[Formula 18]

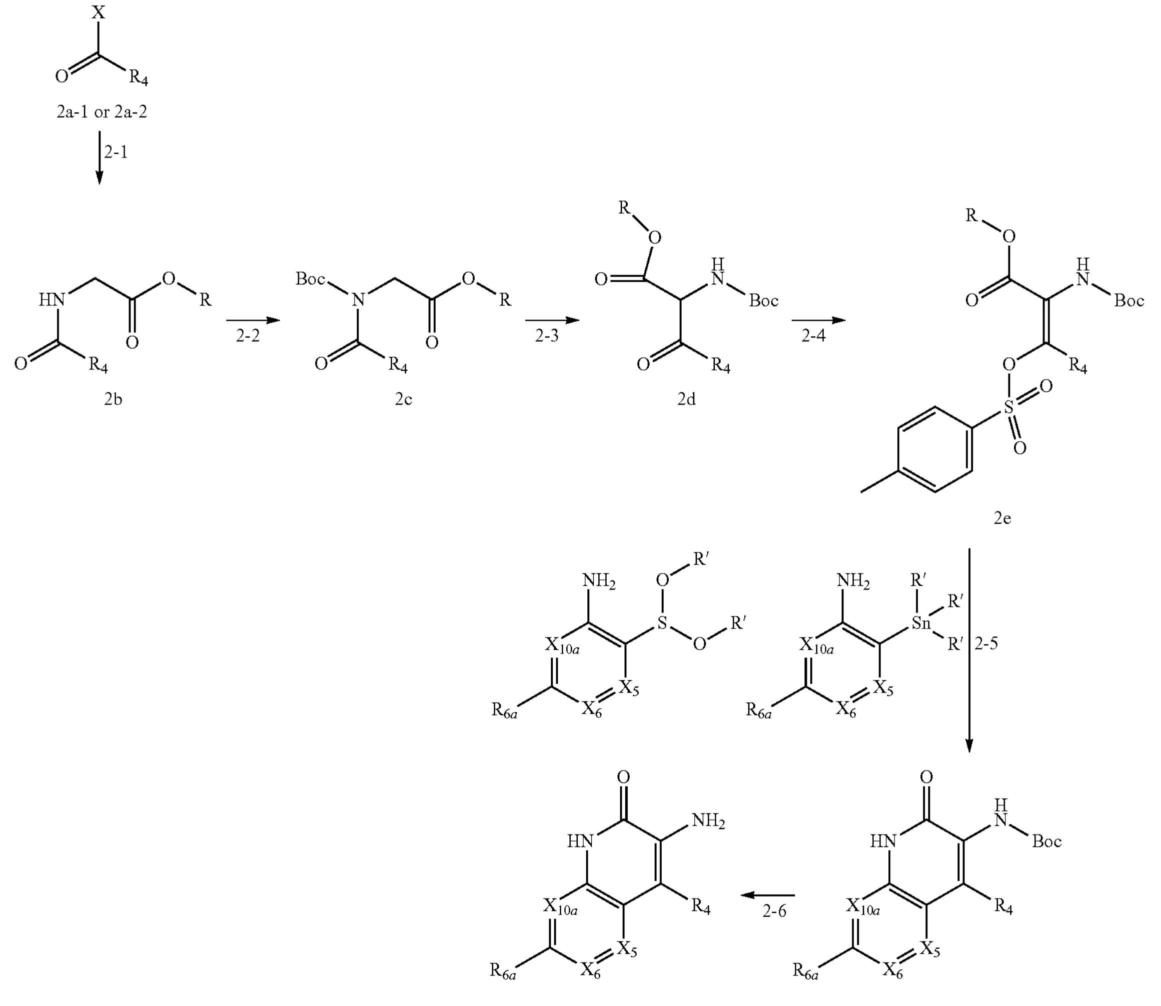

2b 2c 2d 2e 1n2 2f

-continued

[Formula 19]

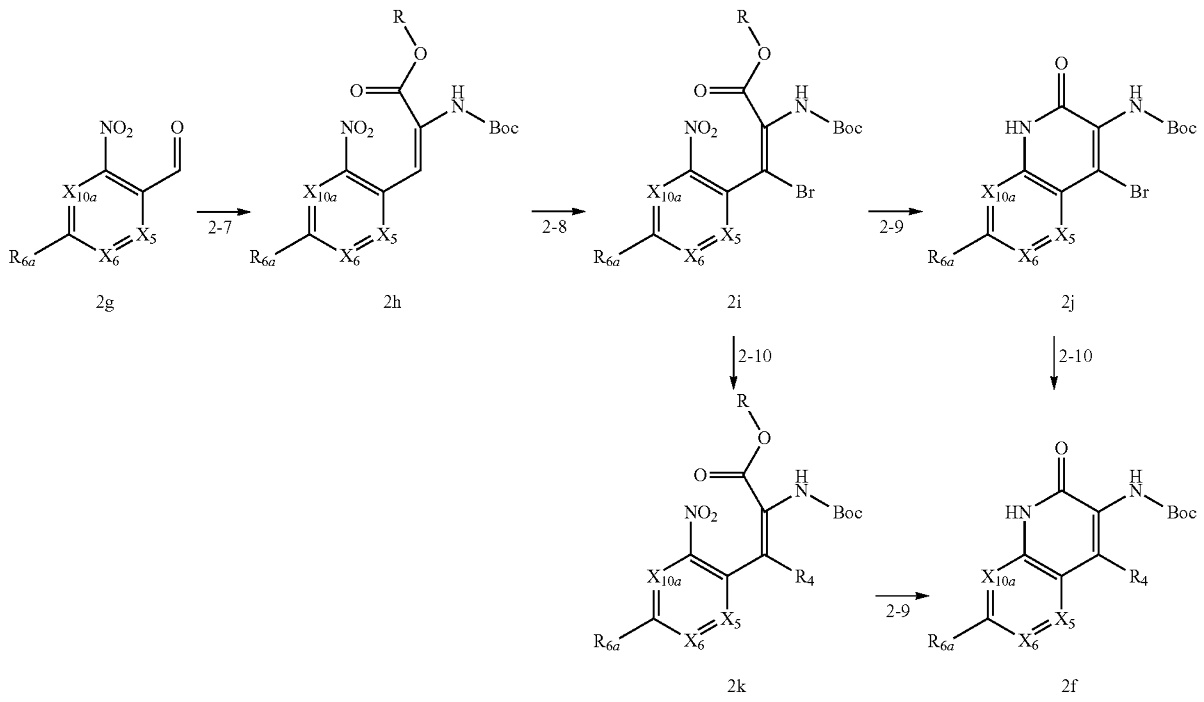

Step 2-1

Step 2-1 is a step of condensing the acid chloride 2a-1 (wherein X represents chlorine) or the carboxylic acid 2a-2 (wherein X represents hydroxy) with glycine alkyl ester or a salt of glycine alkyl ester. The present step can be carried out in accordance with the following method-1 or method-2.

Method-1: The amide 2b can be produced by reacting the acid chloride 2a-1 with glycine alkyl ester or a salt of glycine alkyl ester (wherein R is $C_1$-$C_6$ alkyl) in the presence of a base. As the salt of glycine alkyl ester, glycine alkyl ester hydrochloride is preferable. Examples of the base include organic bases such as DIPEA, triethylamine, and pyridine, and inorganic bases such as carbonates and sodium hydroxide. Triethylamine or DIPEA are preferable. Examples of the solvent used in the present step include DCM, acetonitrile, THF, DMF, DMA, NMP, and water. DCM and THE are preferable.

Method-2: The amide 2b can be produced by reacting the carboxylic acid 2a-2 with glycine alkyl ester or a salt of glycine alkyl ester in the presence of a condensing agent. As the salt of glycine alkyl ester, glycine alkyl ester hydrochloride is preferable. Examples of the condensing agent include DCC, EDC, EDC hydrochloride, HATU, COMU, and propylphosphonic acid anhydride (cyclic trimer). HATU and propylphosphonic acid anhydride (cyclic trimer) are preferable. A base may be used as the additive in the present step. Examples of the base include DIPEA and triethylamine, and DIPEA is preferable. The solvent used in the present step is a solvent selected from the group consisting of DMF, DMA, NMP, DCM, acetone, THF, 1,4-dioxane, 1,2-dimethoxyethane, ethyl acetate, and acetonitrile, or a mixed solvent thereof. DMF is preferable.

Step 2-2

The present step is a step of protecting the amide 2b with Boc. The Boc protecting compound 2c can be produced by reacting the amide 2b with a tert-butoxycarbonylating reagent. In the present step, a base and a catalyst may be appropriately used. Examples of the base include DIPEA, triethylamine, and diazabicycloundecene. Examples of the catalyst include DMAP. The solvent used in the present step is a solvent selected from the group consisting of DMF, DMA, DCM, acetone, THF, 1,4-dioxane, 1,2-dimethoxyethane, ethyl acetate, and acetonitrile, or a mixed solvent thereof. DMF is preferable.

Step 2-3

The present step is a step of carrying out the rearrangement of the acyl group of the Boc protecting compound 2c in the presence of a base. As the base, for example, a base selected from the group consisting of sodium tert-butoxide, potassium tert-butoxide, LiHMDS, NaHMDS, KHMDS, and LDA may be used alone or in combination thereof. Potassium tert-butoxide, LiHMDS, and a mixture thereof are preferable. The solvent used in the present step is a solvent selected from the group consisting of toluene, xylene, n-hexane, cyclohexane, THF, 1,2-dimethoxyethane, N,N'-dimethylpropylene urea, and hexamethylphosphoric triamide, or a mixed solvent thereof. THF is preferable.

Step 2-4

The present step is a step of tosylating the ketone compound 2d using a base. As the base, for example, a base selected from the group consisting of sodium tert-butoxide, potassium tert-butoxide, LiHMDS, NaHMDS, KHMDS, LDA, DIPEA, triethylamine, and diazabicycloundecene, or a combination of these bases may be used. LDA, LiHMDS, DIPEA, and triethylamine are preferable. The solvent used in the present step is a solvent selected from the group consisting of toluene, xylene, n-hexane, cyclohexane, THF, 1,2-dimethoxyethane, acetonitrile, and DCM, or a mixed solvent thereof. THF is preferable. The reaction may be carried out by using the reaction mixture of step 2-3 as it is.

Step 2-5

The present step is a cross coupling step and a cyclocondensation step with a Pd catalyst. The compound 2e is reacted with a corresponding organic boron compound (wherein R' is exemplified by hydrogen, alkyl, or alkylene) or organic tin compound (wherein R' is exemplified by hydrogen, alkyl, or alkylene) in the presence of a Pd catalyst. Since the organic boron compound or organic tin compound to be used has an amino group at the ortho position of boron or tin, the cross coupling step occurs and subsequently the cyclocondensation step occurs. The present step can be carried out in accordance with the following method-1 or method-2.

Method-1 (Suzuki-Miyaura cross coupling): The method-1 can be conducted by the method described in, for example, Chem. Rev. 1995, vol. 95, no. 7, p. 2457-2483. (Non Patent Literature 8), or Acc. Chem. Res. 2008, vol. 41, No. 11, p. 1461-1473. (Non Patent Literature 9). Examples of the base used in the present method include inorganic salts such as carbonates, phosphates, and hydroxides, and amines such as triethylamine and DIPEA. Cesium carbonate, potassium carbonate, and triethylamine are preferable. Examples of the solvent used in the present method include polar solvents such as toluene, xylene, THF, 2-methyltetrahydrofuran, 4-methyltetrahydropyran, 1,4-dioxane, DMF, DMA, NMP, and water, and mixed solvents thereof. 2-Methyltetrahydrofuran, and a mixed solvent of 4-methyltetrahydropyran and water are preferable. Examples of the Pd catalyst include $PdCl_2(PPh_3)_2$, $Pd(PPh_3)_4$, and [1,1'-bis(diphenylphosphino)ferrocene]palladium(II) dichloride, 1,4-bis(diphenylphosphino)butane]palladium(II) dichloride, XPhos Pd G3, and XPhos Pd G4. [1,1'-Bis(diphenylphosphino)ferrocene]palladium(II) dichloride, 1,4-bis(diphenylphosphino)butane]palladium(II) dichloride, XPhos Pd G3, and XPhos Pd G4 are preferable. The present step can be carried out at −20° C. to a reaction temperature near the boiling point of the solvent, and is preferably carried out at 80° C. or more to a temperature near the boiling point of the solvent.

Method-2 (Stille cross coupling): The method-2 can be conducted by the method described in, for example, Synthesis 1992, vol. 9, p. 803-815. (Non Patent Literature 10). Examples of the Pd catalyst include $PdCl_2(PPh_3)_2$, $Pd(PPh_3)_4$, and [1,1'-bis(diphenylphosphino)ferrocene]palladium(II) dichloride and 1,4-bis(diphenylphosphino)butane]palladium(II) dichloride. $Pd(PPh_3)$ 4 is preferable. Examples of the solvent used in the present method include toluene, xylene, THF, 2-methyltetrahydrofuran, 4-methyltetrahydropyran, 1,4-dioxane, DMF, DMA, and NMP. Toluene is preferable. The present step can be carried out at −20° C. to a reaction temperature near the boiling point of the solvent, and is preferably carried out at 80° C. to a temperature near the boiling point of the solvent.

Step 2-6

The present step is a step of deprotecting Boc of the Boc protecting compound 2f. The step can be carried out under the same conditions as those in step 1-15.

Step 2-7

The present step is a step of carrying out a Wittig reaction on the formyl compound 2g. The α,β-unsaturated ester compound 2h can be produced by reacting the formyl compound 2g with a phosphorus reagent in the presence of a base. Examples of the phosphorus reagent include 2-(BOC-amino)-2-(dimethoxyphosphoryl)acetate and an equivalent thereof (wherein R is $C_1$-$C_6$ alkyl). Methyl 2-(BOC-amino)-2-(dimethoxyphosphoryl)acetate is preferable. The base is a base selected from the group consisting of sodium tert-butoxide, potassium tert-butoxide, LiHMDS, NaHMDS, KHMDS, LDA, and 1,4-diazabicyclo[2.2.2]octane, or a mixture thereof. Examples of the solvent used in the present method include toluene, THF, 1,2-dimethoxyethane, acetonitrile, and DCM.

Step 2-8

The present step is a bromination step of the α,β-unsaturated ester compound 2h. The aromatic nitro product 2i can be produced by reacting the «,β-unsaturated ester 2h with a bromination reagent, and further isomerizing the reaction product in the presence of a base. Examples of the bromination reagent include NBS, 1,3-dibromo-5,5'-dimethylhydantoin, and N-bromosaccharin. NBS is preferable. Examples of the base include 1,4-diazabicyclo[2.2.2]octane, diazabicycloundecene, sodium tert-butoxide, potassium tert-butoxide, LiHMDS, NaHMDS, and KHMDS. 1,4-Diazabicyclo[2.2.2]octane and diazabicycloundecene are preferable. Examples of the solvent used in the present method include acetonitrile and DCM.

Step 2-9

The present step is a reduction step and a continuous cyclization step of the aromatic nitro compound 2i. The reduction step can be conducted by the method described in, for example, Org. Process Res. Dev. 2018, vol. 22, no. 4, p. 430-445. (Non Patent Literature 11), and in particular, the reaction is preferably carried out with a combination of Pd(OH) 2/H2 in a solvent such as methanol and ethyl acetate, or with a combination of $Fe/NH_4Cl$ in ethanol. By carrying out the reaction at room temperature to a temperature near the boiling point of the solvent, the cyclization step can be continuously carried out.

Step 2-10

The present step is a cross coupling step with a Pd catalyst. The compound 2i or 2j is reacted with a corresponding organic boron compound ($R_4$—$B(OR)_2$, $R_4$—$BF_3K$) or organic tin compound ($R_4$—$SnR_3$) (wherein R is exemplified by hydrogen or alkyl). The step can be carried out under the same conditions as those in step 2-5.

(General Production Method 3)

The general production method 3 is a method that can be conducted when, in the formula, $X_6$ is $CR_{x6}$ and $R_{x6}$ is a halogen in the 3-aminopyridone compound 1n1 or 1n2.

[Formula 20]

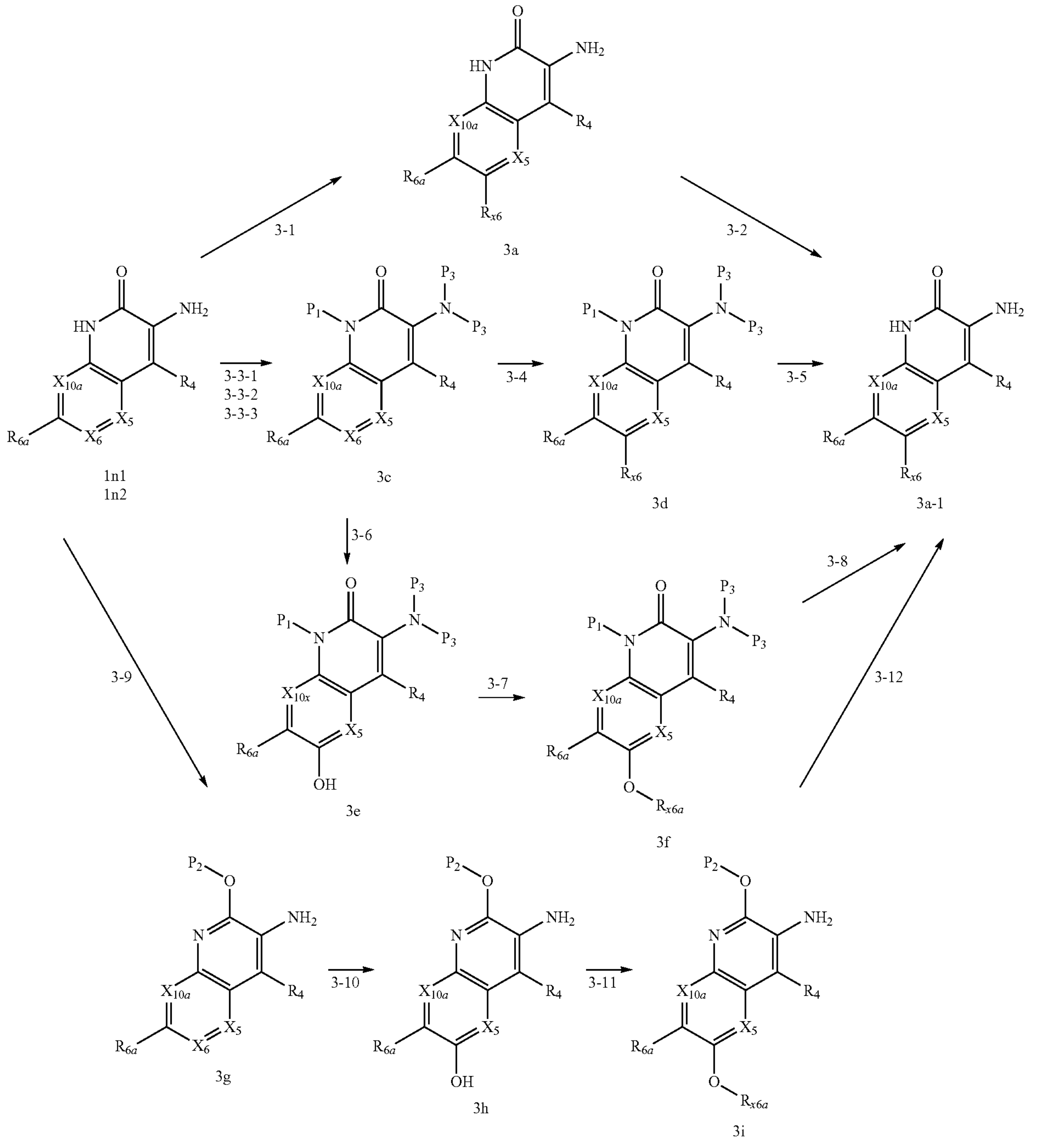

Step 3-1

The present step is a step of introducing a substituent $R_{x6}$ into the 3-aminopyridone compound 1n1 or 1n2 in the presence of a metal catalyst. The present step can be carried out in accordance with any of the following method-1 to method-6.

Method-1 (Suzuki-Miyaura cross coupling): The 3-aminopyridone compound 1n1 or 1n2 is reacted with a corresponding organic boron compound (Rx6-B (OR) 2, Rx6-BF3K) or organic tin compound (Rx6-SnR3) (wherein R is exemplified by hydrogen or alkyl). The step can be carried out under the same conditions as those in the method-1 of step 2-5.

Method-2 (alkylation or alkenylation by Negishi cross coupling): The 3-aminopyridone compound 3a can be produced by reacting the 3-aminopyridone compound 1n1 or 1n2 with an organic zinc reagent ($R_{x6}$—ZnX) (wherein X is a halogen) in the presence of Pd or Ni. The method-2 can be conducted by the method described in, for example, Tetrahedron. 1992, vol. 48, no. 44, p. 9577-9648. (Non Patent Literature 12) or Aldrichimica Acta. 2005, vol. 38, p. 71-88. (Non Patent Literature 13). Examples of the solvent used in the present step include polar solvents such as THF, 1,4-dioxane, DMF, DMA, and NMP, or mixed solvents thereof. THF is preferable. Examples of Pd or Ni include those described in Tetrahedron. 1992, vol. 48, no. 44, p. 9577-9648. (Non Patent Literature 12) or Aldrichimica Acta. 2005, vol. 38, p. 71-88. (Non Patent Literature 13); $PdCl_2(PPh_3)_2$, $Pd(PPh_3)_4$, and [1,1'-bis(diphenylphosphino)ferrocene]palladium(II) dichloride. $PdCl_2(PPh_3)_2$, $Pd(PPh_3)_4$, and [1,1'-bis(diphenylphosphino)ferrocene]palladium(II) dichloride are preferable.

Method-3 (Sonogashira cross coupling): The 3-aminopyridone compound 3a can be produced by reacting the 3-aminopyridone compound In1 or In2 with a corresponding alkyne (R—C≡C—H, wherein R—C≡C— represents $R_{x6}$—) in the presence of Pd, Cu, and a base. The method-3 can be conducted by the method described in, for example, Chem. Soc. Rev. 2011, vol. 40, p. 5084-5121. (Non Patent Literature 14). The corresponding alkyne may have a silyl group, and examples thereof include trimethylsilyl acetylene. Examples of the base include amines such as triethylamine, DIPEA, and diazabicycloundecene, and inorganic bases such as sodium acetate. Triethylamine and DIPEA are preferable. Examples of Pd include $PdCl_2(PPh_3)_2$, $Pd(PPh_3)_4$, [1,1'-bis(diphenylphosphino)ferrocene]palladium(II) dichloride, $Pd(OAc)_2$, and $Pd_2(dba)_3$. $PdCl_2(PPh_3)_2$, $Pd(PPh_3)_4$, and [1,1'-bis(diphenylphosphino)ferrocene]palladium(II) dichloride are preferable. Examples of Cu include copper iodide, copper bromide, and copper chloride. Copper iodide is preferable. Examples of the solvent used in the present step include polar solvents such as THF, 1,4-dioxane, DMF, DMA, NMP, DMSO, methanol, ethanol, and 2-propanol, and mixed solvents thereof. DMSO, DMF, DMA, and NMP are preferable.

Method-4 (thioetherification): The 3-aminopyridone compound 3a can be produced by reacting the 3-aminopyridone compound In1 or In2 with a corresponding mercaptan or mercaptan salt in the presence of Pd and a base. Examples of mercaptan include 2-ethylhexyl and 3-mercaptopropionic acid. Examples of the base include amines such as triethylamine, DIPEA, diazabicycloundecene, and piperidine. Triethylamine and DIPEA are preferable. Examples of Pd include zero-valent Pd complexes such as $Pd(PPh_3)_4$. Xantphos Pd G3 is preferable. Examples of the solvent used in the present step include polar solvents such as THF, 1,4-dioxane, DMF, DMA, NMP, DMSO, methanol, ethanol, and 2-propanol, and mixed solvents thereof. 1,4-Dioxane is preferable.

Method-5 (etherification or hydroxylation): The 3-aminopyridone compound 3a can be produced by reacting the 3-aminopyridone compound In1 or In2 with a corresponding alcohol or water in the presence of Pd. In the case of etherification, for example, a sodium salt and a potassium salt of the corresponding alcohol may be used as the base. In the case of hydroxylation, for example, a sodium hydroxide and a potassium hydrate may be used. Examples of Pd include zero-valent Pd complexes such as $Pd(PPh_3)_4$. tBuBrettPhos Pd G3 is preferable. Examples of the solvent used in the present step include polar solvents such as THF, 1,4-dioxane, DMF, DMA, and NMP. 1,4-Dioxane is preferable.

Method-6 (amination): The 3-aminopyridone compound 3a can be produced by reacting the 3-aminopyridone compound In1 or In2 with a corresponding amine in the presence of Pd or Cu, and a base. In the case of using Pd, the method-6 can be conducted by the method described in, for example, Chem. Rev. 2016, vol. 116, p. 12564-12649. (Non Patent Literature 15). Examples of Pd include zero-valent Pd complexes such as $Pd(PPh_3)_4$. Xantphos Pd G3, Xantphos Pd G4, and tBuXPhos Pd G3 are preferable. Examples of the base include carbonates, phosphates, sodium tert-butoxide, potassium, and tert-butoxide. Sodium tert-butoxide is preferable. Examples of the solvent used in the present step include polar solvents such as THF, 1,4-dioxane, DMF, DMA, NMP, and DMSO, and mixed solvents thereof. 1,4-Dioxane is preferable. In the case of using Cu, the method-6 can be conducted by the method described in Org. Process Res. Dev. 2022, vol. 26, no. 6, p. 1690-1750. (Non Patent Literature 16). Examples of Cu include copper iodide, copper bromide, and copper chloride. Copper iodide is preferable. Examples of the ligand of Cu include 1,10-phenanthroline, L-proline, and 2-((2,6-dimethylphenyl)amino)-2-oxoacetic acid (DMPAO). 2-((2,6-Dimethylphenyl)amino)-2-oxoacetic acid (DMPAO) is preferable. Examples of the base include carbonates, phosphate, sodium tert-butoxide, and potassium tert-butoxide. Cesium carbonate, potassium carbonate, and tripotassium phosphate are preferable. Examples of the solvent used in the present step include polar solvents such as THF, 1,4-dioxane, DMF, DMA, NMP, and DMSO, and mixed solvents thereof. DMSO is preferable.

Step 3-2

When the 3-aminopyridone compound 3a has a Boc group, a 2-tetrahydropyranyl group, or both of them, the present step is a step of deprotecting the Boc group, the 2-tetrahydropyranyl group, or both of them. The step can be carried out under the same conditions as those in step 1-15.

Each of step 3-3-1, step 3-3-2, and step 3-3-3 is a step of protecting the 3-aminopyridone compound In1 or In2 with a protective group.

Step 3-3-1: Protection by Tert-Butoxycarbonylation

The present step is a step of protecting the 3-aminopyridone compound In1 or In2 with a Boc group. The 3-aminopyridone protecting compound 3c can be produced by reacting the 3-aminopyridone compound In1 or In2 with a tert-butoxycarbonylating reagent. In the present step, a base and a catalyst may be appropriately used. In the present step, in the formula, P1 is a Boc group and P3 is a Boc group or H. The present step can be conducted under the same conditions as those in step 2-2.

Step 3-3-2: Protection by Paramethoxybenzylation

The present step is a step of reacting the 3-aminopyridone compound In1 or In2 with a p-methoxybenzylating reagent in the presence of a base for paramethoxybenzylation. In the present step, in the formula, P1 is a p-methoxybenzyl group and P3 is H. Examples of the p-methoxybenzylating reagent include p-methoxybenzylchloride or p-methoxybenzylbromide. Examples of the base include inorganic bases such as potassium carbonate, silver carbonate, cesium carbonate, and sodium hydride. Potassium carbonate and silver carbonate are preferable. Examples of the solvent used in the present step include aprotic solvents such as DMF, DMA, NMP, THF, DCM, and DCE. DMF, DMA, or DCE is preferable.

Step 3-3-3: Protection by 2-(Trimethylsilyl)Ethoxymethylation

The present step is a step of reacting the 3-aminopyridone compound 1n1 or In2 with a 2-(trimethylsilyl)ethoxymethylating reagent in the presence of a base for 2-(trimethylsilyl)ethoxymethylation. In the present step, in the formula, P1 is a 2-(trimethylsilyl)ethoxymethyl group and P3 is H. Examples of the 2-(trimethylsilyl)ethoxymethylating reagent include 2-(trimethylsilyl)ethoxymethyl chloride. Examples of the base include inorganic bases such as potassium carbonate, silver carbonate, cesium carbonate, and sodium hydride. Potassium carbonate or cesium carbonate is preferable. Examples of the solvent used in the present step include aprotic solvents such as DMF, DMA, NMP, THF, DCM, and 1,2-dichloroethane. DMF and DMA are preferable.

Step 3-4

The present step is an alkylation step of the protected 3-aminopyridone 3c. The protected 3-aminopyridone 3c can be alkylated by being reacted with an alcohol ($R_{x6}$—OH) or haloalkyl ($R_{x6}$—X, wherein X is a halogen) in the presence of a photoredox catalyst. The step can be carried out with reference to the methods described in JACS. 2016, vol. 138, no. 26, p. 8084-8087. (Non Patent Literature 17), ACS Med. Chem. Lett. 2020, 11, 597-604. (Non Patent Literature 18), Nature 2021, vol. 598, p. 451-456. (Non Patent Literature 19), and the like.

Step 3-5

When the 3-aminopyridone product 3d has a Boc group or a 2-tetrahydropyranyl group, the present step is a step of deprotecting the Boc group or the 2-tetrahydropyranyl group. The step can be carried out under the same conditions as those in step 1-15.

Step 3-6

The present step is a hydroxylation step of the protected 3-aminopyridone 3c. The step can be carried out under the same conditions as those in the hydroxylation of the method 5 of step 3-1.

Step 3-7

The present step is an alkylation step of the hydroxyl compound 3e. The present step can be carried out in accordance with the following method-1 or method-2.

Method-1 (nucleophilic substitution reaction): The alkylation compound 3f (wherein $R_{x6a}O$ represents $R_{x6}$) can be produced by reacting the hydroxyl compound 3e with a corresponding haloalkyl, alkyl triflate, or alkyl nonaflate in the presence of a base. Examples of the base include inorganic bases such as carbonates, and phosphates. Cesium carbonate and potassium carbonate are preferable. Examples of the solvent used in the present step include THF, 1,4-dioxane, DMF, DMA, and NMP.

Method-2 (Mitsunobu reaction): The alkylated product 3f (wherein $R_{x62}O$ represents $R_{x6}$) can be produced by reacting the hydroxyl compound 3e with a corresponding alcohol in the presence of a Mitsunobu reagent. Examples of the Mitsunobu reagent include a combination of triphenylphosphine and DIAD; CMMP, and CMBP. Examples of the solvent used in the present step include aprotic solvents such as toluene, DCM, THF, n-hexane, cyclohexane, ethyl acetate, DMA, DMF, NMP, and 1,4-dioxane. DCM and THF are preferable.

Step 3-8

When the alkylated compound 3f has a 2-(trimethylsilyl)ethoxymethyl group, a p-methoxybenzyl group, or a 2-tetrahydropyranyl group, the present step is a step of deprotecting the 2-(trimethylsilyl)ethoxymethyl group, the p-methoxybenzyl group, or the 2-tetrahydropyranyl group. The step can be carried out under the same conditions as those in step 1-15.

Step 3-9

The present step is a p-methoxybenzylation step of the 3-aminopyridone compound 1n1 or 1n2. Step 3-9 can be conducted under the same conditions as those in step 3-3-2. In the formula, P2 represents a p-methoxybenzyl group.

Step 3-10

The present step is a hydroxylation step of the p-methoxybenzyl protecting compound 3g. The step can be carried out under the same conditions as those in the hydroxylation of the method 5 of step 3-1.

Step 3-11

The present step is an alkylation step of the hydroxyl compound 3 h. The step can be conducted under the same conditions as those in step 3-7 (In the formula of the compound 3i, $R_{x6a}O$ represents $R_{x6}$).

Step 3-12

When the compound 3i has a p-methoxybenzyl group or a 2-tetrahydropyranyl group, the present step is a step of deprotecting the p-methoxybenzyl group or the 2-tetrahydropyranyl group. The step can be carried out under the same conditions as those in step 1-15.

(General Production Method 4)

The general production method 4 is a preferred production method of a compound in which $R_4$ is optionally substituted 4- to 10-membered heterocyclyl, among the compounds represented by the general formulas (1) to (3).

[Formula 21]

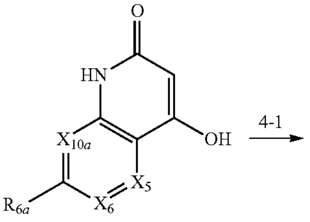

4a

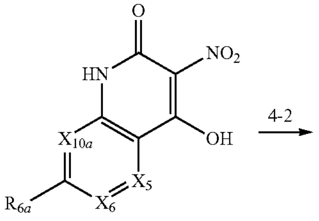

4b

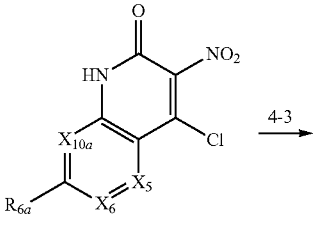

4c

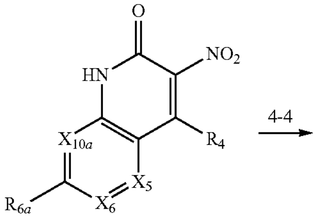

4d

-continued

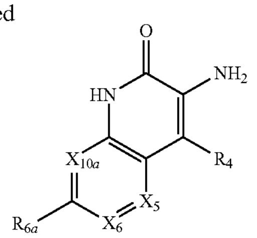

4e

Step 4-1

The present step is a nitration step of the 4-hydroxylpyridone compound 4a. The 3-nitropyridone compound 4b can be produced by reacting the 4-hydroxylpyridone compound 4a with a nitration reagent under the acidic conditions. Examples of the nitration reagent include nitric acid and nitrate salts. Examples of the solvent used in the present step include acetic acid, sulfuric acid, and nitric acid.

Step 4-2

The present step is a chlorination step of the 3-nitropyridone compound 4b. The 4-chloropyridone compound 4c can be produced by reacting the 3-nitropyridone compound 4b with a chlorination reagent. Examples of the chlorination reagent include phosphorus oxychloride, thionyl chloride, and oxalyl chloride, and these chlorination reagents may be used in a solvent amount. DMF may be used as the catalyst in the present step.

Step 4-3

The present step is a step of carrying out the aromatic nucleophilic substitution reaction of the 4-chloropyridone compound 4c. The 3-nitropyridone compound 4d can be produced by reacting the 4-chloropyridone compound 4c with a corresponding amine (e.g., piperidine).

Examples of the solvent used in the present step include aprotic solvents such as toluene, THF, n-hexane, cyclohexane, ethyl acetate, DMA, DMF, NMP, 1,4-dioxane, and DMSO. DMF is preferable.

Step 4-4

The present step is a reduction step of the 3-nitropyridone compound 4d. The 3-aminopyridone compound 4e can be produced by reacting the 3-nitropyridone compound 4d with a reduction reagent. The present step can be conducted by the method described in, for example, Org. Process Res. Dev. 2018, vol. 22, no. 4, p. 430-445. (Non Patent Literature 11), and a combination of Pd(OH) 2/H2 in a solvent such as methanol and ethyl acetate or a combination of Fe/$NH_4Cl$ in ethanol is preferable.

<Pharmaceutical Composition>

The present invention provides a pharmaceutical composition containing the compound represented by the formula (1) or a salt thereof, or a solvate thereof of the present invention (the first ingredient) (hereinafter, also referred to as the "pharmaceutical composition of the present invention").

The pharmaceutical composition of the present invention can be formulated by known methods by introducing a pharmaceutically acceptable carrier in addition to the compound represented by the formula (1) or a salt thereof, or a solvate thereof of the present invention. The pharmaceutical composition of the present invention can be formulated with conventional excipients, binders, lubricants, colorants, or flavor modifiers, and if necessary, stabilizers, emulsifiers, absorption enhancers, surfactants, pH adjusters, preservatives, antioxidants, or the like, and are formulated by a conventional method by mixing ingredients generally used as raw materials for pharmaceutical formulations.

In the formulation, the active ingredient used in the pharmaceutical can be processed into an optimal form or shape, that is, dosage form according to the use method or use purpose by known methods. Examples of the conventional dosage form include, but are not limited to, liquid pharmaceutical formulations (liquids) such as injections, suspensions, emulsions, and ophthalmic solutions; and solid pharmaceutical formulations (solid formulations) such as tablets, powders, fine granules, granules, coated tablets, capsules, dry syrups, troches, and suppositories.

For the production of a liquid, the pharmaceutical composition can be formulated, for example, by appropriately combining pharmacologically acceptable carriers or media, specifically, pharmaceutically acceptable additives usually used in the field of pharmaceutical formulations, such as sterile water or physiological saline, a plant oil, an emulsifier, a suspending agent, a surfactant, a stabilizer, a flavoring agent, an excipient, a vehicle, an antiseptic, and a binder, adding them to the compound represented by the formula (1) or a salt thereof, or a solvate thereof of the present invention, and then mixing the mixture into a unit dosage form required for generally accepted pharmaceutical practice. In addition, it is also possible to dissolve a solid formulation prepared for liquids at time of use by adding an appropriate solvent such as sterile water or physiological saline before administration, and then use the liquid for administration.

For example, such a liquid can be parenterally used in an injection form of a sterile solution or suspension with water or any of other pharmaceutically acceptable liquids. Such a liquid can be formulated, for example, by being mixed in an appropriate combination with a pharmacologically acceptable carrier or medium, specifically, sterile water or physiological saline, a plant oil, an emulsifier, a suspending agent, a surfactant, a stabilizer, a flavoring agent, an excipient, a vehicle, an antiseptic, a binder, etc. into a unit dosage form required for generally accepted pharmaceutical practice. Specific examples of the carrier include light anhydrous silicic acid, lactose, crystalline cellulose, mannitol, starch, carmellose calcium, carmellose sodium, hydroxypropylcellulose, hydroxypropylmethylcellulose, polyvinylacetal diethylaminoacetate, polyvinylpyrrolidone, gelatin, medium chain fatty acid triglyceride, polyoxyethylene hardened castor oil 60, saccharose, carboxymethylcellulose, corn starch, and inorganic salts. The amount of the active ingredient in these formulations is determined so as to give an appropriate volume in a prescribed range.

A sterile composition for injection can be formulated according to usual pharmaceutical practice using a vehicle such as distilled water for injection.

Examples of the aqueous solution for injection include an isotonic solution containing saline or other adjuncts, for example, D-sorbitol, D-mannose, D-mannitol, and sodium chloride, which may be appropriately used in combination with an appropriate solubilizing agent, for example, an alcohol, specifically ethanol, a polyalcohol, for example, propylene glycol and polyethylene glycol, and a nonionic surfactant, for example, polysorbate 80 (registered trademark) and HCO-50.

Examples of the oily liquid include sesame oil and soybean oil, which may be used in combination with benzyl benzoate and benzyl alcohol as a solubilizing agent. In addition, it may also be blended with a buffering agent, for example, a phosphate buffer solution and a sodium acetate buffer solution, a soothing agent, for example, procaine hydrochloride, a stabilizer, for example, benzyl alcohol and phenol, and an antioxidant. The prepared injection solution is usually filled into an appropriate ampule.

For the production of a solid formulation, for example, an excipient, and furthermore, if necessary, pharmaceutically acceptable additives usually used in the field of pharmaceutical formulations, such as a binder, a disintegrant, a lubricant, a colorant, and a flavor modifier are added to the compound represented by the formula (1) or a salt thereof, or a solvate thereof of the present invention in an appropriate combination, and thereafter, the mixture is formed into tablets, powders, fine granules, granules, coated tablets, capsules, dry syrups, troches, suppositories, or the like, by a conventional method.

Examples of the pharmaceutically acceptable additive used in such a solid formulation include animal and plant oils such as soybean oil, beef tallow, and synthetic glyceride; hydrocarbons such as liquid paraffin, squalane, and solid paraffin; ester oils such as octyldodecyl myristate and isopropyl myristate; higher alcohols such as cetostearyl alcohol and behenyl alcohol; silicon resins; silicon oils; surfactants such as polyoxyethylene fatty acid ester, sorbitan fatty acid ester, glycerin fatty acid ester, polyoxyethylene sorbitan fatty acid ester, polyoxyethylene hydrogenated castor oil, and polyoxyethylene polyoxypropylene block copolymer; water-soluble polymers such as hydroxyethyl cellulose, polyacrylic acid, carboxyvinyl polymer, polyethylene glycol, polyvinylpyrrolidone, and methylcellulose; lower alcohols such as ethanol and isopropanol; polyhydric alcohols such as glycerin, propylene glycol, dipropylene glycol, and sorbitol; saccharides such as lactose, lactose monohydrate, fructose, and sucrose; inorganic powders such as silicic anhydride, magnesium aluminum silicate, and aluminum silicate; and purified water.

Examples of the excipient include sugars (e.g., lactose, lactose monohydrate, fructose, and sucrose), sugar alcohols (e.g., mannitol), starches (corn starch, potato starch, wheat starch, rice starch, partially pregelatinized starch, and pregelatinized starch), celluloses (e.g., crystalline cellulose), and inorganic salts (e.g., calcium silicate, anhydrous dibasic calcium phosphate, and precipitated calcium carbonate).

Examples of the binder include polyvinyl alcohol, polyvinyl ether, methylcellulose, ethylcellulose, gum arabic, tragacanth, gelatin, shellac, hydroxypropyl methylcellulose, hydroxypropylcellulose, polyvinylpyrrolidone, and polypropylene glycol-polyoxyethylene block polymer.

Examples of the disintegrant include croscarmellose sodium, carmellose sodium, hydroxypropyl cellulose, carmellose, carmellose calcium, methylcellulose, crystalline cellulose, sodium lauryl sulfate, povidone, and polysorbate.

Examples of the lubricant include magnesium stearate, calcium stearate, talc, sucrose fatty acid esters, sodium stearyl fumarate, and hardened oil.

Examples of the colorant include those that are permitted to be added to pharmaceuticals. Examples of the flavor modifier include cocoa powder, menthol, aromatic powder, mint oil, borneol, and cinnamon powder.

These tablets and granules may of course be sugar-coated, and, if necessary, coated with other appropriate coating. In addition, the liquid formulation such as a syrup or injectable formulation can be produced by adding a pH adjusting agent, a solubilizer, an isotonic agent, or the like, and further, if necessary, a solubilizing agent, a stabilizer, or the like, to the compound according to the present invention or a pharmacologically acceptable salt thereof, and formulating the mixture by a conventional method.

<Treatment or Prevention of Cancer in Cancer Patient in which Positivity of RB1 Gene Mutation or Decreased Expression of RB1 Gene or Protein has been Detected, or Cancer Patient in which Positivity of RB1 Gene Mutation or Decreased Expression of RB1 Gene or Protein has Occurred>

The MYT1 inhibitor can be used alone or in combination with a chemotherapeutic agent for the purpose of treating or preventing a cancer in a cancer patient in which positivity of RB1 gene mutation or decreased expression of RB1 gene or protein has been detected, or a cancer patient in which positivity of RB1 gene mutation or decreased expression of RB1 gene or protein.

The term "in combination" means two or more ingredients are used in combination. For example, use of the MYT1 inhibitor (hereinafter, also referred to as the "first ingredient") and the chemotherapeutic agent (hereinafter, also referred to as the "second ingredient") in combination includes an "aspect in which a single formulation containing the first ingredient and second ingredient is administered" (that is, an aspect in which the first ingredient and the second ingredient are used in combination as a compounding agent), and "an aspect in which each of the first ingredient and the second ingredient is simultaneously or separately administered as separate formulations". In the latter aspect, a formulation containing the first ingredient may be administered first, or a formulation containing the second ingredient may be administered first. The latter aspect may be any of an "aspect in which the first ingredient and the second ingredient are separately formulated and simultaneously administered by the same route of administration", an "aspect in which the first ingredient and second ingredient are separately formulated and separately administered by the same route of administration with a time difference", an "aspect in which the first ingredient and the second ingredient are separately formulated and simultaneously administered by different routes of administration (administered at different sites of the same patient)", and an "aspect in which the first ingredient and the second ingredient are separately formulated and separately administered by different routes of administration with a time difference". In the case of the "aspect in which the first ingredient and the second ingredient are separately formulated and simultaneously administered by the same route of administration", both formulations may be mixed immediately before administration. The term "separately" means that a certain formulation is administered before or after administration of another formulation.

In other words, the term "in combination" is said to be a use method for allowing another ingredient to be present in the body of a patient, in a state where one ingredient is present in the body of the patient. That is, an aspect in which the first ingredient and the second ingredient are administered so as to be simultaneously present in the body of a patient, for example, in the blood is preferable, and an aspect in which certain formulations are simultaneously administered to a patient, or, after a certain formulation is administered, another formulation is administered within 48 hours is preferable.

The "treatment of cancer" in the present invention means a decrease in the number of cancer cells in an individual, suppression of the growth of cancer cells, a decrease in tumor volume, a decrease in tumor weight, suppression of the metastasis of cancer cells, or amelioration of various symptoms caused by cancer, and combinations thereof. The "prevention of cancer" in the present invention means prevention of new cancer cells from occurring, prevention of an increase in the number of cancer cells due to regrowth of the decreased cancer cells, prevention of the regrowth of the cancer cells whose growth is suppressed, prevention of a re-increase of the decreased tumor volume or weight, and combinations thereof.

First Embodiment Relating to Treatment or Prevention of Cancer

One embodiment of the present invention is a pharmaceutical composition for treating or preventing a cancer in a cancer patient in which positivity of RB1 gene mutation, or decreased expression of RB1 gene or protein has been detected, in combination with a chemotherapeutic agent, the pharmaceutical composition comprising a MYT1 inhibitor as an active ingredient.

One embodiment of the present invention is a pharmaceutical composition for treating or preventing a cancer in a cancer patient in which positivity of RB1 gene mutation, or decreased expression of RB1 gene or protein has occurred, in combination with a chemotherapeutic agent, the pharmaceutical composition comprising an MYT1 inhibitor as an active ingredient.

RB1 (retinoblastoma gene, also called Rb or RB) is a gene encoding RB1 protein which is a typical cell cycle-regulating factor, and is involved in the G1/S checkpoint. RB1 protein (also called RB1 or pRb) suppresses the action of E2F by forming a complex with a transcription factor E2F which induces expression of a gene involved in the transition of cell cycle from the G1 phase to the S phase. When the action of E2F is suppressed, the transition from the G1 phase to the S phase is inhibited.

In cell cycle, typically, cyclin D is synthesized by the cell growth stimulation and bonds to CDK4 to form a complex. The complex is phosphorylated (activated) by CAK to phosphorylate RB protein. When RB protein is phosphorylated, the transcription factor E2F bound to RB protein is liberated, which induces the expression of the gene group necessary for the progress of the S phase or DNA replication. Among the genes that are induced are cyclin E, which complexes with CDK2 and further phosphorylates RB1, leading to further deactivation of RB1 protein. When the RB1 gene has a mutation (in particular, a mutation that decreases the function of the RB1 protein), or the expression level of the RB1 gene or protein is decreased, the cell cycle progresses.

As used herein, "RB1 gene mutation positivity" means that, when a nucleotide sequence corresponding to the RB1 gene of a subject is analyzed, any of the mutations (e.g., a mutation that causes insertion, substitution, deletion, and/or addition of at least one amino acid residue to the wild-type RB1 protein) is found in the nucleotide sequence to the nucleotide sequence of a wild-type RB1 gene, or when the mutation to the nucleotide sequence of the RB1 gene is reflected in the change of a base in a transcription product or the change of an amino acid in a translation product, the change is detected in the transcription product or the translation product. In a specific embodiment, the RB1 gene mutation positivity is detected in a cancer patient-derived biological sample (e.g., cancer cell). The term "detecting a mutation" as used herein means that a mutation on genome DNA is detected in principle. When the mutation on genome DNA is reflected in a change of a base in a transcription product or a change of an amino acid in a translation product, the meaning also includes detection of the change of the transcription product or the translation product (i.e. indirect detection). The preferred aspect of the method of the present specification is a method for detecting a mutation by directly determining a nucleotide sequence of the region of a gene for RB1 in a cancer cell. The method for detecting the RB1 gene mutation positivity is not particularly limited, but for example, the RB1 gene mutation positivity can be confirmed and determined by next generation sequencer (NGS).

In the present invention, the term "region of a gene for RB1" means a certain region on genome DNA including a gene for RB1. The regions also each independently include, in addition to translated regions, untranslated regions such as an expression control region for the relevant gene (e.g. promotor region or enhancer region), a 3'-end untranslated region for the relevant gene, and the like. In this method, first, a DNA sample is prepared from a biological sample. Examples of the DNA sample include genome DNA samples, and cDNA samples prepared by reverse transcription from RNA.

The method for extracting genome DNA or RNA from a biological sample is not particularly limited, and a known method can be appropriately selected and used. Examples of the method for extracting genome DNA include a SDS phenol method (a method in which protein of a tissue stored in a urea-containing solution or ethanol is denatured with a proteinase (proteinase K), a surfactant (SDS) and phenol, and DNA is precipitated and extracted from the tissue with ethanol), and DNA extraction methods using Clean Columns (registered trademark, manufactured by NexTec Co., Ltd.), AquaPure (registered trademark, manufactured by Bio-Rad Laboratories, Inc.), ZR Plant/Seed DNA Kit (manufactured by Zymo Research), AquaGenomicSolution (registered trademark, manufactured by Mo Bi Tec GmbH), prepGEM (registered trademark, manufactured by ZyGEM LLC) and BuccalQuick (registered trademark, manufactured by TrimGen Corporation).

The method for extracting RNA from a biological sample and the method for preparing cDNA from extracted RNA is not particularly limited, and a known method can be appropriately selected and used. Examples thereof include extraction methods using phenol and a chaotropic salt (more specifically, extraction methods using a commercially available kit such as TRIzol (manufactured by Invitrogen Corporation) or ISOGEN (manufactured by Wako Pure Chemical Industries, Ltd.)), and methods using another commercially available kit (e.g. RNAPrep Total RNA Extraction Kit (manufactured by Beckman Coulter Inc.), RNeasy Mini (manufactured by QIAGEN N.V.) or RNA Extraction Kit (manufactured by Pharmacia Biotech, Inc.)). Further, the reverse transcriptase used for preparation of cDNA from extracted RNA is not particularly limited, and examples thereof include reverse transcriptases derived from retroviruses such as RAV (Rous associated virus) and AMV (Avian myeloblastosis virus), and reverse transcriptases derived from mouse retroviruses such as MMLV (Moloney murine leukemia virus).

In this aspect, subsequently, DNA containing the region of a gene for RB1 is isolated, and the nucleotide sequence of the isolated DNA is determined. The isolation of DNA can be performed by PCR with genome DNA or RNA as a template, or the like using a pair of oligonucleotide primers designed to sandwich all or part of the region of a gene for RB1. The determination of the nucleotide sequence of the isolated DNA can be performed by a method known to those skilled in the art, such as a Maxam-Gilbert method or a Sanger method. It is also possible to use a next-generation sequencer which enables analysis such that nucleotide sequences of genes can be read rapidly and exhaustively, etc.

By comparing the determined nucleotide sequence of DNA or cDNA (for example, when the biological sample is a cancer patient-derived sample, the nucleotide sequence of DNA or cDNA derived from a non-cancer tissue of the same patient, or a known database), the presence or absence of a mutation in the region of a gene for RB1 in a cancer cell of the biological sample can be determined.

As the method for detecting a mutation in the region of a gene for RB1, various methods capable of detecting a mutation can be used in addition to methods for directly determining the nucleotide sequence of DNA or cDNA.

For example, the detection of a mutation in the present invention can also be performed by the following method. First, a DNA or cDNA sample is prepared from a biological sample. Subsequently, an oligonucleotide probe is prepared which has a nucleotide sequence complementary to a nucleotide sequence containing a mutation site of the region of a gene for RB1 and is labeled with a reporter fluorescent dye and a quencher fluorescent dye. The oligonucleotide probe is hybridized to the DNA or cDNA sample, and the nucleotide sequence containing the mutation site of the region of a gene for RB1 is amplified using, as a template, the DNA or cDNA sample to which the oligonucleotide probe is hybridized. Fluorescence generated by the reporter fluorescent dye due to degradation of the oligonucleotide probe which is caused by the amplification is detected, and the detected fluorescence is then compared to a control. Examples of such a method include a double-dye probe method, so called a TaqMan (registered trademark) probe method.

In still another method, a DNA or cDNA sample is prepared from a biological sample. Subsequently, in a reaction system containing an intercalator which generated fluorescence when inserted between DNA double strands, a nucleotide sequence containing a mutation site of the region of a gene for RB1 is amplified using the DNA or cDNA sample as a template. The temperature of the reaction system is changed, a variation in intensity of fluorescence generated by the intercalator is detected, and the variation in intensity of the fluorescence with the detected change in temperature is compared to a control. Examples of such a method include a HRM (high resolution melting) analysis method.

In still another method, first, a DNA or cDNA sample is prepared from a biological sample. Subsequently, DNA containing all or part of the region of a gene for RB1 is amplified. Further, the amplified DNA is cleaved by a restriction enzyme. Subsequently, DNA fragments are separated according to the sizes thereof. Subsequently, the size of the detected DNA fragment is compared to a control. Examples of such a method include methods utilizing restriction fragment length polymorphism (RFLP), and a PCR-RFLP method.

In still another method, first, a DNA or cDNA sample is prepared from a biological sample. Subsequently, DNA containing all or part of the region of a gene for RB1 is amplified. Further, the amplified DNA is dissociated into single-stranded DNA. Subsequently, the dissociated single-stranded DNA is separated on a non-denaturing gel. The mobility of the separated single-stranded DNA on the gel is compared to a control. Examples of such a method include a PCR-SSCP (single-strand conformation polymorphism) method.

In still another method, first, a DNA or cDNA sample is prepared from a biological sample. Subsequently, DNA containing all or part of the region of a gene for RB1 is amplified. Further, the amplified DNA is separated on a gel in which the concentration of a DNA denaturant increases in steps. Subsequently, the mobility of the separated DNA on the gel is compared to a control. Examples of such a method include a denaturant gradient gel electrophoresis (DGGE) method.

As still another method, there is a method using DNA prepared from a biological sample and containing a mutation site of the region of a gene for RB1, and a substrate on which an oligonucleotide probe hybridized to the DNA is fixed. Examples of such a method include a DNA array method.

In still another method, first, a DNA or cDNA sample is prepared from a biological sample. An "oligonucleotide primer having a nucleotide sequence complementary to bases on the 3' side of the bases of all or part of the region of a gene for RB1 by one base and a nucleotide sequence on the 3' side thereof" is prepared. Subsequently, with the DNA as a template, a ddNTP primer elongation reaction is carried out using the primer. Subsequently, the primer elongation reaction product is applied to a mass analyzer to perform mass measurement. Subsequently, the gene type is determined from the result of the mass measurement. Subsequently, the determined gene type is compared to a control. Examples of such a method include a MALDI-TOF/MS method.

In still another method, first, a DNA or cDNA sample is prepared from a biological sample. Subsequently, an oligonucleotide probe consisting of 5'-"nucleotide sequence complementary to the bases of all or part of the region of a gene for RB1 and a nucleotide sequence on the 5' side thereof"-"nucleotide sequence which is not hybridized to bases on the 3' side of all or part of the region of a gene for RB1 by one base and a nucleotide sequence on the 3' side thereof"-3' (flap) is prepared. An "oligonucleotide probe having a nucleotide sequence complementary to the bases of all or part of the region of a gene for RB1 and a nucleotide sequence on the 3' side thereof" is prepared. Subsequently, the two oligonucleotide probes are hybridized to the prepared DNA or cDNA sample. Subsequently, the hybridized DNA is cleaved by a single-stranded DNA cleavage enzyme to liberate the flap. The single-stranded DNA cleavage enzyme is not particularly limited, and examples thereof include cleavases. In this method, subsequently, an oligonucleotide probe which has a sequence complementary to the flap and is labeled with reporter fluorescence and quencher fluorescence is hybridized to the flap. Subsequently, the intensity of generated fluorescence is measured. Subsequently, the measured fluorescence intensity is compared to a control. Examples of such a method include an Invader method.

In still another method, first, a DNA or cDNA sample is prepared from a biological sample. Subsequently, DNA containing all or part of the region of a gene for RB1 is amplified. The amplified DNA is dissociated into single-stranded DNA, and only one strand is separated from the dissociated single-stranded DNA. Subsequently, an elongation reaction is carried out base by base from near the bases of all or part of the region of a gene for RB1, pyrophosphoric acid generated at this time is enzymatically caused to emit light, and the intensity of emission is measured. The measured fluorescence intensity is compared to a control. Examples of such a method include a Pyrosequencing method.

In still another method, first, a DNA or cDNA sample is prepared from a biological sample. Subsequently, DNA containing all or part of the region of a gene for RB1 is amplified. Subsequently, an "oligonucleotide primer having a nucleotide sequence complementary to bases on the 3' side of the bases of all or part of the region of a gene for RB1 by one base and a nucleotide sequence on the 3' side thereof"

is prepared. Subsequently, with the amplified DNA as a template, a single-base elongation reaction is carried out using the prepared primer in the presence of a fluorescently labeled nucleotide. The polarization degree of fluorescence is measured. Subsequently, the measured polarization degree of fluorescence is compared to a control. Examples of such a method include an AcycloPrime method.

In still another method, first, a DNA or cDNA sample is prepared from a biological sample. Subsequently, DNA containing all or part of the region of a gene for RB1 is amplified. Subsequently, an "oligonucleotide primer having a nucleotide sequence complementary to bases on the 3' side of the bases of all or part of the region of a gene for RB1 by one base and a nucleotide sequence on the 3' side thereof" is prepared. Subsequently, with the amplified DNA as a template, a single-base elongation reaction is carried out using the prepared primer in the presence of a fluorescently labeled nucleotide. Subsequently, the type of base used for the single-base elongation reaction is determined. Subsequently, the determined type of base is compared to a control. Examples of such a method include a SNuPE method.

When the mutation is associated with a change of an amino acid in RB1 protein, the sample prepared from the biological sample may be protein. Here, for detecting a mutation, a method using a molecule binding specifically to a site at which a change of amino acids occurs due to the mutation, peptide mass fingerprinting method (PMF), a protein sequencer (Edman degradation method), or the like can be used.

As used herein, "a decrease in the expression of an RB1 gene or protein" means that, when an RB1 gene or protein of a subject is analyzed, the expression level of the RB1 gene or protein thereof is lower compared to that of the control (e.g., the expression level in a healthy individual or in a non-cancer tissue of the same patient). In a specific embodiment, the decrease in the expression level of the RB1 gene or protein is detected in a cancer patient-derived biological sample (e.g., cancer cell).

Examples of the method for detecting a decrease in the expression of an RB1 gene include, but are not particularly limited to, a method in which the expression level of RB1 is detected at a transcriptional level or a translational level, and compared to the control. In the method for detecting the expression level of an RB1 gene at a transcriptional level, first, RNA or cDNA is prepared from a biological sample. The method for extracting RNA from a biological sample and the method for preparing cDNA from extracted RNA is not particularly limited, and a known method can be appropriately selected and used. Examples thereof include extraction methods using phenol and a chaotropic salt (more specifically, extraction methods using a commercially available kit such as TRIzol (manufactured by Invitrogen Corporation) or ISOGEN (manufactured by Wako Pure Chemical Industries, Ltd.)), and methods using another commercially available kit (e.g. RNAPrep Total RNA Extraction Kit (manufactured by Beckman Coulter Inc.), RNeasy Mini (manufactured by QIAGEN N.V.) or RNA Extraction Kit (manufactured by Pharmacia Biotech, Inc.)). Further, the reverse transcriptase used for preparation of cDNA from extracted RNA is not particularly limited, and examples thereof include reverse transcriptases derived from retroviruses such as RAV (Rous associated virus) and AMV (Avian myeloblastosis virus), and reverse transcriptases derived from mouse retroviruses such as MMLV (Moloney murine leukemia virus).

Subsequently, an oligonucleotide primer or an oligonucleotide probe is used for an amplification reaction or a hybridization reaction, and an amplified product or a hybrid product thereof is detected. As such a method, for example, a RT-PCR method, a Northern blot method, a dot blot method, a DNA array method, an in situ hybridization method, a RNase protection assay method, mRNA-seq, or the like can be used. Those skilled in the art can design an oligonucleotide primer or an oligonucleotide probe suitable for each method in a conventional manner on the basis of a nucleotide sequence of cDNA for RB1.

It is known in the art that one of causes of a decrease in expression of a gene is excessive methylation of a promotor. Therefore, the presence or absence of a suppressed function of RB1 may be detected using methylation of a gene promotor for RB1 as an indicator. For detection of methylation of a promotor, it is possible to use, for example, a known method such as a method in which a change of a nucleotide sequence after treatment with bisulfite having an activity that converts methylated cytosine into uracil is directly detected by determination of the nucleotide sequence, or indirectly detected using a restriction endonuclease which can recognize (cleave) a nucleotide sequence before the bisulfite treatment and cannot recognize (cleave) a nucleotide sequence after the bisulfite treatment.

The method for detecting the decrease in expression of RB1 protein is not particularly limited, but for example, the decrease can be confirmed and determined by IHC (immunohistochemistry) using an antibody specific to RB1 protein. In a method for detecting protein using an antibody, first, a protein sample is prepared from a biological sample. Subsequently, using an antibody specific to RB1 protein, an antigen-antibody reaction is used, and RB1 protein is detected. When the sample is labeled with antibody specific to RB1 protein, RB1 protein can be directly detected, and when the sample is not labeled, a labeled molecule which recognizes the antibody (e.g. secondary antibody or protein A) can be further applied to indirectly detect RB1 protein using the label of the molecule. As such a method, for example, an immunohistochemistry (immunostaining) method, a Western blotting method, an ELISA method, flow cytometry, imaging cytometry, radioimmunoassay, an immunoprecipitation method, or an analysis method using an antibody array can be used. This method also has an advantage that additional information such as a form or a distribution state of cancer cells in a tissue can also be obtained immunohistochemically.

The type, the origin, and the like of an antibody used are not particularly limited, and a monoclonal antibody is preferable. An oligoclonal antibody (mixture of several antibodies or dozens of antibodies) or a polyclonal antibody can also be used as long as it is possible to detect RB 1 protein with sufficient specificity. Functional fractions of antibodies such as Fab, Fab', $F(ab')_2$, Fv, scFv, $sc(Fv)_2$, dsFv and diabodies, and multimers (e.g. dimers, trimers, tetramers and polymers) thereof can also be used. Such an anti-RB1 protein antibody may be a marketed product.

The RB1 protein can also be detected by mass spectrometry (MS). In particular, analysis by a mass spectrometer coupled with liquid chromatography (LC/MS) is sensitive, and therefore advantageous. Detection by mass spectrometry can be performed by, for example, labeling the protein sample with the protein, fractionating the labeled protein, subjecting the fractionated protein to mass analysis, and identifying RB1 protein from the mass analysis value. As the label, an isotopic labeling reagent known in the art can be used, and an appropriate labeling reagent can be obtained as a marketed product. The fractionation can be performed by a method known in the art, and for example, a commercially available ion-exchange column or the like can be used.

As used herein, the amplification of the copy number of the CCNE1 gene can be determined in the diagnosis or prognostic assay by an evaluation of the copy number of the CCNE1 gene using a cancer patient-derived biological sample (e.g., next generation sequencer, digital PCR, array CGH method, or FISH method).

As used herein, the "patient" may be mice, rats, guinea pigs, monkeys, dogs, sheep, horses, or humans. In the present invention, the "cancer patient" may be not only those affected with a cancer, but those possibly affected with a cancer. In a specific embodiment, a subject to be treated or prevented is a cancer patient in which an increase in the CCNE1 gene is not detected as compared to a control. In addition, in a specific embodiment, the subject to be treated or prevented is not a mouse implanted with OVCAR3. The pharmaceutical composition is suitably applicable to humans.

The "cancer patient-derived biological sample" as used herein is not particularly limited as long as it is a biological sample allowing the presence or absence of the RB1 gene mutation or the presence or absence of the decrease in expression of an RB1 gene or protein to be detected, and a specimen material such as a cancer biopsy specimen material, blood, urine, body cavity fluid or tumor cell-derived circulating DNA (circulating tumor DNA: ctDNA). The cancer patient-derived biological sample may be a protein extract or a nucleic acid extract obtained from the specimen material (e.g. an mRNA extract, or a cDNA preparation or a cRNA preparation prepared from an mRNA extract). The "biological sample" as used herein includes cancer patient-derived samples and cancer cell culture-derived samples.

The RB1 gene mutation may include mutations that cause insertion, deletion, or addition of at least one amino acid residue, or substitution of an existing amino acid residue to the wild-type RB1 protein. The RB1 gene mutation may be a nonsense mutation, a frameshift mutation, a splice site mutation, heterozygous deletion, or a homozygous deletion. The RB1 gene mutation is preferably a mutation that decreases the function of RB1. The "mutation that decreases the function of RB1" can be confirmed, for example, by Internet <URL: https://www.oncokb.org/gene/RB1> [searched on Feb. 20, 2023].

A nucleotide sequence of typical DNA (cDNA) of a wild-type human RB1 gene is set forth as SEQ ID NO: 1 (NCBI reference number: NM_000321.3), and a typical amino acid sequence of a wild-type human RB1 gene is set forth as SEQ ID NO: 2 (NCBI reference number: NP_000312.2). In the case of human RB1 gene, the RB1 gene mutation means that the nucleotide sequence is a nucleotide sequence different from the genomic sequence of human RB1 described from positions 48,303,751 to 48,481,890 in NCBI reference No. NC_13.11, means that the nucleotide sequence is a nucleotide sequence different from the nucleotide sequence of human RB1 described from positions 4921 to 5161 in NCBI reference No. NG_9009.1, or includes a mutation that brings about an amino acid sequence different from the amino acid sequence of human RB1 protein as set forth in SEQ ID NO: 2. The mutation is capable of bringing about at least one of the following (1) to (5). Note that, sequences may have individual differences depending on the polymorphism and the like, even in RB1 having no mutation.

(1) The codon corresponding to the serine residue(S) at position 82 of the amino acid sequence of SEQ ID No: 2 is replaced with a stop codon,
(2) the codon corresponding to the arginine residue (R) at position 467 of the amino acid sequence of SEQ ID No: 2 is replaced with a stop codon,
(3) in the codon corresponding to the amino acid residue at position 182 of the amino acid sequence of SEQ ID No: 2, at least one base is inserted or deleted, a new reading frame starting from an isoleucine residue (I) is formed, and the third reading frame therefrom is a stop codon,
(4) the glutamic acid residue (E) at position 837 of the amino acid sequence of SEQ ID No: 2 is replaced with a lysine residue (K), and a part of the RB1 gene is homozygously deleted, and
(5) the glycine residue (G) at position 449 of the amino acid sequence of SEQ ID No: 2 is replaced with a glutamic acid residue (E), and a part of the RB1 gene is homozygously deleted.

As used herein, the decrease in expression of an RB1 gene or protein includes a decrease in gene expression through methylation of the RB1 gene or micro RNA.

The pharmaceutical composition of the present invention can be used for treatment or prevention of cancer, and is particularly suitable for treatment or prevention of cancer in a patient in which positivity of RB1 gene mutation, or decreased expression of RB1 gene or protein has been detected, or cancer in a patient in which positivity of RB1 gene mutation, or decreased expression of RB1 gene or protein has occurred. The pharmaceutical composition of the present invention can be used alone or in combination with a chemotherapeutic agent.

In a specific embodiment, cancer is lung cancer. The pharmaceutical composition of the present invention is suitable for treatment or prevention of cancer, and especially more suitable for treatment or prevention of lung cancer.

In an aspect, the compounds represented by the formulas (1) to (3) of the present invention or salts thereof, or solvates thereof can be used as the MYT1 inhibitor.

The pharmaceutical composition containing the compounds represented by the formulas (1) to (3) of the present invention or salts thereof, or solvates thereof (the first ingredient) as the active ingredient (hereinafter, also referred to as the "pharmaceutical composition of the present invention") may be used in combination with a chemotherapeutic agent (the second ingredient). In an embodiment, the pharmaceutical composition of the present invention is simultaneously or separately administered with the chemotherapeutic agent. In another embodiment, the pharmaceutical composition of the present invention is administered as a compounding agent with the chemotherapeutic agent.

The chemotherapeutic agent is a substance having anticancer activity (also referred to as antitumor activity). The chemotherapeutic agent may be, for example, an antimetabolite.

An antimetabolite is a substance having a chemical structure similar to a metabolite (e.g., folic acid) that competes with or inhibits the metabolic mechanism of an organism. Examples of the antimetabolite include antifolates.

An antifolate is a substance that inhibits DNA synthesis by suppressing or inhibiting the action of the enzyme that reduces folic acid to active folic acid essential for nucleic acid biosynthesis. Examples of the antifolate include methotrexate and pemetrexed. The antifolate is more preferably pemetrexed.

In the present embodiment, the preferred combination of the MYT1 inhibitor and the chemotherapeutic agent is such that the MYT1 inhibitor is the compounds represented by the formulas (1) to (3) of the present invention or salts thereof, or solvates thereof, and the chemotherapeutic agent is pemetrexed.

The dose of the compounds represented by the formulas (1) to (3) of the present invention or salts thereof, or solvates thereof is preferably 0.001 to 50 mg per day per kg body weight of the subject to be administered (0.001 to 50 mg/kg/day), more preferably 0.001 to 20 mg/kg/day, and further preferably 0.002 to 10 mg/kg/day. When the dose of the compounds represented by the formulas (1) to (3) of the present invention or salts thereof, or solvates thereof falls within the range, the effect of treating or preventing cancer is further enhanced. The dosing frequency of the compounds represented by the formulas (1) to (3) of the present invention or salts thereof, or solvates thereof may be, for example, once a week or more, twice a week, once a day, or twice a day.

The dose of the chemotherapeutic agent is preferably 0.005 to 300 mg per day per kg body weight of the subject to be administered (0.005 to 300 mg/kg/day), more preferably 0.01 to 250 mg/kg/day, and further preferably 0.02 to 200 mg/kg/day. When the dose of the chemotherapeutic agent falls within the range, the effect of treating or preventing cancer is further enhanced. The dosing frequency of the chemotherapeutic agent may be, for example, once a week or more, twice a week, once a day, or twice a day.

The doses of the compounds represented by the formulas (1) to (3) of the present invention or salts thereof, or solvates thereof (the first ingredient) and the chemotherapeutic agent (the second ingredient) are preferably such that the first ingredient is 0.0001 to 50 mg/kg/day and the second ingredient is 0.005 to 300 mg/kg/day, more preferably such that the first ingredient is 0.001 to 20 mg/kg/day and the second ingredient is 0.01 to 250 mg/kg/day, and further preferably such that the first ingredient is 0.002 to 10 mg/kg/day and the second ingredient is 0.02 to 200 mg/kg/day per kg body weight of the subject to be administered. When the doses of the first ingredient and second ingredient fall within the range, the effect of treating or preventing cancer is further enhanced.

In the present invention, examples of administration methods include oral, rectal, parenteral (intravenous, intramuscular, subcutaneous, percutaneous absorption), intracisternal, intravaginal, intraperitoneal, intravesical, or local (injections, drops, powders, ointments, gels, or cream) administration, and by inhalation (a buccal or nasal spray). Examples of dosage forms include tablets, capsules, granules, powders, pills, aqueous and non-aqueous oral solutions and suspensions, and parenteral solutions packaged in containers adapted for subdivision into individual doses. The dosage forms can be adapted for various administration methods including controlled release formulations, such as subcutaneous implants.

The first ingredient may be administered by, for example, any of the above administration methods, and the second ingredient may be administered by, for example, the same administration method as the first ingredient or an administration method different from the first ingredient. The dosing interval between the first ingredient and the second ingredient may be, for example, an interval of 0 days to 14 days, an interval of 0 days to 10 days, or an interval of 0 days to 7 days. The dosing interval can be determined using, for example, AUC, Cmax, Tmax, the elimination half-life, and the state of health of the subject, as the criteria. For example, the first ingredient may be orally administered (tablets, capsules, or the like) and the second ingredient may be administered by drops. For example, both the first ingredient and the second ingredient may be orally administered (tablets, capsules, or the like). For example, the first ingredient may be administered by drops and the second ingredient may be orally administered (tablets, capsules, or the like). For example, both the first ingredient and the second ingredient may be administered by drops. In such a case, the first ingredient and second ingredient may be administered at any interval, such as three times daily, twice daily, once daily, once a week, and once every two weeks. More specifically, both the first ingredient and the second ingredient may be administered once daily, and in this case, they may be administered before, between, or after meals. Before, between, or after meals may be before, between, or after any of breakfast, lunch, dinner, supper, or snack. When the dosing interval between the first ingredient and the second ingredient falls within 24 hours, it means that both ingredients are administered once daily. If necessary, the first ingredient and the second ingredient are respectively administered twice daily and once daily, once daily and once daily, once daily and twice daily, once daily and once every two days, once daily and once every three days, once daily and once every seven days, three times daily and once every seven days, or twice daily and once every seven days, in some cases. If necessary, only the dosing interval of the second ingredient may be increased or reduced, and/or only the dosing interval of the first ingredient may be increased or reduced. Administration of the second ingredient may be started on the start day of administration of the first ingredient, and the start day of administration of the first ingredient and the start day of administration of the second ingredient may be different from each other. For the duration of administration, the total number of courses may be one course or more, or two courses or more, with 7 days as one course. Each course may be continuously carried out, or a rest period may be provided. A rest period may be provided in a course. If necessary, it is also possible to continuously administer only the first ingredient and stop administration of the second ingredient in a course, or stop administration of only the first ingredient and continuously administer the second ingredient. The first ingredient and the second ingredient may be included in the same tablet, capsule, or the like.

The pharmaceutical composition according to the present embodiment can be administered, for example, in combination with a pharmaceutical composition containing an MYT1 inhibitor described as the "second embodiment relating to treatment or prevention of cancer" below (combined administration).

One aspect of the present embodiment is an MYT1 inhibitor for use in combination with a chemotherapeutic agent in treatment or prevention of cancer in a cancer patient in which positivity of RB1 gene mutation, decreased expression of RB1 gene or protein, or positivity of expression of hyperphosphorylated RB 1 protein has been detected.

One aspect of the present embodiment is an MYT1 inhibitor for use in combination with a chemotherapeutic agent in treatment or prevention of cancer in a cancer patient in which positivity of RB1 gene mutation, or decreased expression of RB1 gene or protein has occurred.

Another aspect of the present embodiment is use of an MYT1 inhibitor for producing a pharmaceutical composition for treatment or prevention of cancer in a cancer patient in which positivity of RB1 gene mutation, decreased expression of RB1 gene or protein has been detected, the MYT1 inhibitor being administered in combination with a chemotherapeutic agent.

Another aspect of the present embodiment is use of an MYT1 inhibitor for producing a pharmaceutical composition for treatment or prevention of cancer in a cancer patient in which positivity of RB1 gene mutation or decreased expression of RB1 gene or protein has occurred, the pharmaceutical composition being administered in combination with a chemotherapeutic agent.

Second Embodiment Relating to Treatment or Prevention of Cancer

The second embodiment relating to treatment or prevention of cancer of the present invention is a pharmaceutical composition for treating or preventing a cancer in a cancer patient in which positivity of RB1 gene mutation, or decreased expression of RB1 gene or protein has been detected, in combination with an MYT1 inhibitor, the pharmaceutical composition comprising a chemotherapeutic agent as an active ingredient.

Each term in the present specification (e.g., MYT1 inhibitor, chemotherapeutic agent, RB1 gene mutation, administration method, type of cancer) can be referred to the definitions in the "first embodiment relating to treatment or prevention of cancer". In the present specification, a cancer in a cancer patient in which positivity of RB1 gene mutation, decreased expression of RB1 gene or protein has been detected may be a cancer in a patient in which positivity of RB1 gene mutation or decreased expression of RB1 gene or protein has occurred. The pharmaceutical composition according to the present embodiment can be administered, for example, in combination with the pharmaceutical composition containing the MYT1 inhibitor described as the "first embodiment relating to treatment or prevention of cancer" (combined administration).

In a specific embodiment, the pharmaceutical composition contains the chemotherapeutic agent (the second ingredient) as an active ingredient. The pharmaceutical composition containing the chemotherapeutic agent as an active ingredient is used in combination with the MYT1 inhibitor (the first ingredient). In an embodiment, the pharmaceutical composition containing the chemotherapeutic agent is simultaneously or separately administered with the MYT1 inhibitor. In another embodiment, the pharmaceutical composition containing the chemotherapeutic agent is administered as a compounding agent with the MYT1 inhibitor.

In the present embodiment, the preferred combination of the MYT1 inhibitor and the chemotherapeutic agent is such that the MYT1 inhibitor is the compounds represented by the formulas (1) to (3) of the present invention or salts thereof, or solvates thereof, and the chemotherapeutic agent is pemetrexed.

The doses of the MYT1 inhibitor (the first ingredient) and the chemotherapeutic agent (the second ingredient) are preferably such that the first ingredient is 0.0001 to 50 mg/kg/day and the second ingredient is 0.005 to 300 mg/kg/day, more preferably such that the first ingredient is 0.001 to 20 mg/kg/day and the second ingredient is 0.01 to 250 mg/kg/day, and further preferably such that the first ingredient is 0.002 to 10 mg/kg/day and the second ingredient is 0.02 to 200 mg/kg/day per kg body weight of the subject to be administered. When the doses of the first ingredient and second ingredient fall within the range, the effect of treating or preventing cancer is further enhanced.

One aspect of the present embodiment is also a chemotherapeutic agent for use in combination with an MYT1 inhibitor in treatment or prevention of cancer in a cancer patient in which positivity of RB1 gene mutation, or decreased expression of RB1 gene or protein has been detected.

Another aspect of the present embodiment is use of a chemotherapeutic agent for producing a pharmaceutical composition for treatment or prevention of cancer in a cancer patient in which positivity of RB1 gene mutation, or decreased expression of RB1 gene or protein has been detected, the pharmaceutical composition being administered in combination with an MYT1 inhibitor.

Third Embodiment Relating to Treatment or Prevention of Cancer

The third embodiment relating to treatment or prevention of cancer of the present invention is a method for treating or preventing cancer in a cancer patient in which positivity of RB1 gene mutation, or decreased expression of RB1 gene or protein has been detected, the method comprising administering a chemotherapeutic agent and an MYT1 inhibitor in combination to the cancer patient. One aspect of the present embodiment is a method for treating or preventing cancer, the method comprising detecting positivity of RB1 gene mutation, or decreased expression of RB1 gene or protein in a biological sample derived from a cancer patient, or allowing a third party to detect it and administering a chemotherapeutic agent and an MYT1 inhibitor in combination to the cancer patient.

The doses of the MYT1 inhibitor (the first ingredient) and the chemotherapeutic agent (the second ingredient) are preferably such that the first ingredient is 0.0001 to 50 mg/kg/day and the second ingredient is 0.005 to 300 mg/kg/day, more preferably such that the first ingredient is 0.001 to 20 mg/kg/day and the second ingredient is 0.01 to 250 mg/kg/day, and further preferably such that the first ingredient is 0.002 to 10 mg/kg/day and the second ingredient is 0.02 to 200 mg/kg/day per kg body weight of the subject to be administered. When the doses of the first ingredient and second ingredient fall within the range, the effect of treating or preventing cancer is further enhanced.

When the combination of the chemotherapeutic agent and the MYT1 inhibitor is administered, both the MYT1 inhibitor and the chemotherapeutic agent may be simultaneously administered, or may be separately administered with a certain dosing interval. Routes of administration of each of the MYT1 inhibitor and the chemotherapeutic agent may be the same or different from each other. The MYT1 inhibitor and the chemotherapeutic agent may be administered in a form of a compounding agent containing the MYT1 inhibitor and the chemotherapeutic agent. That is, the pharmaceutical composition may contain both the MYT1 inhibitor and the chemotherapeutic agent.

Fourth Embodiment Relating to Treatment or Prevention of Cancer

The fourth embodiment relating to treatment or prevention of cancer of the present invention is a method for suppressing growth of cancer cells in a cancer patient in which positivity of RB1 gene mutation, or decreased expression of RB1 gene or protein has been detected, the method comprising contacting an MYT1 inhibitor and a chemotherapeutic agent with the cancer cells. One aspect of the present embodiment is a method for suppressing growth of cancer cells, the method comprising detecting positivity of RB1 gene mutation, or decreased expression of RB1 gene or protein in a biological sample derived from a cancer patient, or allowing a third party to detect it; and contacting an MYT1 inhibitor and a chemotherapeutic agent with the cancer cells.

The method according to the present embodiment comprises any form of in vivo, in vitro, and ex vivo. For example, the subject in which RB1 gene mutation positivity or a decrease in expression of an RB1 gene or protein is detected may be an animal in which RB1 gene mutation positivity or a decrease in expression of an RB1 gene or protein is detected. Examples of animal species include mice, rats, guinea pigs, monkeys, dogs, sheep, horses, or humans. In the case of in vivo, the growth of cancer cells can be suppressed by administering the MYT1 inhibitor and the chemotherapeutic agent to the above subject. In the case of in vitro, the growth of cancer cells can be suppressed by adding the MYT1 inhibitor and the chemotherapeutic agent to the system containing cancer cells collected from the above subject. In the case of ex vivo, the growth of cancer cells can be suppressed by collecting an organ containing cancer cells (e.g., lung in the case of lung cancer) from the subject, and administering the MYT1 inhibitor and the chemotherapeutic agent to the organ. The doses of the first ingredient (MYT1 inhibitor) and the second ingredient (chemotherapeutic agent) can be appropriately set depending on the amount of cancer cells and the types of the MYT1 inhibitor and the chemotherapeutic agent to be used.

Fifth Embodiment Relating to Treatment or Prevention of Cancer

The fifth embodiment relating to treatment or prevention of cancer of the present invention is a method for improving responsiveness to cancer treatment with a chemotherapeutic agent, the cancer being a cancer in a cancer patient in which positivity of RB1 gene mutation, decreased expression of RB1 gene or protein, or positivity of expression of hyperphosphorylated RB1 protein has been detected, the method comprising administering an MYT1 inhibitor together with the chemotherapeutic agent to the cancer patient. One aspect of the present embodiment is a method for improving responsiveness to cancer treatment with a chemotherapeutic agent, the method comprising detecting positivity of RB1 gene mutation, or decreased expression of RB1 gene or protein in a biological sample derived from a cancer patient, or allowing a third party to detect it; and administering an MYT1 inhibitor together with the chemotherapeutic agent to the cancer patient.

In the treatment of cancer of a patient in which RB1 gene mutation positivity or a decrease in expression of an RB1 gene or protein is detected, the method according to the present embodiment comprises administering the chemotherapeutic agent in combination with the MYT1 inhibitor to the patient. The efficacy of cancer treatment by the chemotherapeutic agent can be improved by administering the chemotherapeutic agent in combination with the MYT1 inhibitor.

When the MYT1 inhibitor is administered to the cancer patient together with the chemotherapeutic agent, both the MYT1 inhibitor and the chemotherapeutic agent may be simultaneously administered, or may be separately administered with a certain dosing interval. Routes of administration of each of the MYT1 inhibitor and the chemotherapeutic agent may be the same or different from each other. The MYT1 inhibitor and the chemotherapeutic agent may be administered in a form of a compounding agent containing the MYT1 inhibitor and the chemotherapeutic agent. Even in a patient to which the therapeutic effect of an existing chemotherapeutic agent is insufficient, the chemotherapeutic agent may exhibit sufficient therapeutic efficacy by being combined with the MYT1 inhibitor.

The doses of the MYT1 inhibitor (the first ingredient) and the chemotherapeutic agent (the second ingredient) are preferably such that the first ingredient is 0.0001 to 50 mg/kg/day and the second ingredient is 0.005 to 300 mg/kg/day, more preferably such that the first ingredient is 0.001 to 20 mg/kg/day and the second ingredient is 0.01 to 250 mg/kg/day, and further preferably such that the first ingredient is 0.002 to 10 mg/kg/day and the second ingredient is 0.02 to 200 mg/kg/day per kg body weight of the subject to be administered. When the doses of the first ingredient and second ingredient fall within the range, the effect of treating or preventing cancer is further enhanced.

Sixth Embodiment Relating to Treatment or Prevention of Cancer

The sixth embodiment relating to treatment or prevention of cancer of the present invention is a method for predicting responsiveness to cancer treatment with a combination of an MYT1 inhibitor and a chemotherapeutic agent, the method comprising detecting the presence or absence of RB1 gene mutation, or the presence or absence of decreased expression of RB1 gene or protein in a biological sample derived from a cancer patient, or allowing a third party to detect it; and determining the patient as having responsiveness to cancer treatment with a combination of an MYT1 inhibitor and a chemotherapeutic when the RB1 gene mutation is positive, or when the expression of RB1 gene or protein is decreased, or when the expression of hyperphosphorylated RB1 protein is positive.

In the method according to the present embodiment, when the presence or absence of an RB1 gene mutation or the presence or absence of a decrease in expression of an RB1 gene or protein is detected or detected by a third person, and the RB1 gene mutation is positive or the expression of the RB1 gene or protein is decreased in cancer cells collected from a cancer patient which is a subject to be treated, the cancer patient is determined to have responsiveness (efficacy) to the treatment in which the combination of the MYT1 inhibitor and the chemotherapeutic agent is administered.

According to the method according to the present embodiment, even in a patient to which the therapeutic efficacy of existing chemotherapeutic agents is insufficient, as long as the cancer patient is a patient in which RB1 gene mutation is positive or the expression of the RB1 gene or protein is decreased, the chemotherapeutic agent can be determined as having therapeutic efficacy by administering the chemotherapeutic agent in combination with the MYT1 inhibitor. As a result, it is possible to present effective chemotherapy in advance to a cancer patient that could not obtain a sufficient therapeutic effect only from existing chemotherapeutic agents.

The detection of the RB1 gene mutation, or the decrease in expression of an RB1 gene or protein in cancer cells can be conducted by a method well known to the skilled in the art. Examples thereof include a direct sequencing method, a PCR method, a TaqMan Genotyping method, and a next generation sequencing method.

One aspect of the present embodiment is also a method for selecting a cancer patient for which the administration of a combination of an MYT1 inhibitor and a chemotherapeutic agent is more effective. The method comprises detecting or allowing a third person to detect the presence or absence of an RB1 gene mutation or the presence or absence of a decrease in expression of an RB1 gene or protein, in cancer patient-derived cancer cells, and determining the cancer patient as a cancer patient for which the administration of the combination of an MYT1 inhibitor and a chemotherapeutic agent is more effective, based on the presence of the mutation.

Another aspect of the present embodiment is also a method for diagnosing a specific cancer patient that the administration of a combination of an MYT1 inhibitor and a chemotherapeutic agent is more effective for cancer treatment as compared to administration of the chemotherapeutic agent alone. The method comprises detecting or allowing a third person to detect the presence or absence of an RB1 gene mutation or the presence or absence of a decrease in expression of an RB1 gene or protein, in cancer patient-derived cancer cells, and determining the cancer patient as a cancer patient for which the administration of the combination of an MYT1 inhibitor and a chemotherapeutic agent is more effective, based on the presence of the mutation.

Seventh Embodiment Relating to Treatment or Prevention of Cancer

The seventh embodiment relating to treatment or prevention of cancer of the present invention is a method for screening for a compound effective for treatment or prevention of cancer in a cancer patient in which positivity of RB1 gene mutation, or decreased expression of RB1 gene or protein has been detected, the method comprising measuring MYT1 inhibitory activity of a candidate compound; and selecting a candidate compound having MYT1 inhibitory activity as a compound effective for treatment of the cancer.

The method according to the present embodiment comprises measuring the MYT1 inhibitory activity of a candidate compound, and selecting the candidate compound as the compound effective for treatment of cancer when the candidate compound has the MYT1 inhibitory activity.

In the present invention, the MYT1 inhibitor means a substance capable of directly or indirectly neutralizing, blocking, inhibiting, reducing, or preventing the MYT1 activity. Examples of the activity of MYT1 protein include threonine kinase activity or tyrosine kinase activity.

Inhibition of the threonine kinase activity or tyrosine kinase activity of MYT1 by the compound can be confirmed by, for example, treating a purified MYT1 protein standard sample with the test compound, adding ATP, and using the degree of hydrolysis of ATP as the criterion. The degree of ATP hydrolysis can be evaluated by using Kinase-Glo (manufactured by Promega) or ADP-Glo (manufactured by Promega) (Non Patent Literature 8). When the threonine kinase activity or tyrosine kinase activity of MYT1 is inhibited by the test compound, a decrease in the ATP hydrolysis is confirmed, in comparison to the control (e.g., the degree of ATP hydrolysis by MYT1 which is not treated with the test compound).

Inhibition of the threonine kinase activity of MYT1 protein by the compound can be confirmed by, for example, treating a purified MYT1 protein standard sample with the test compound, adding CDK1 which is a substrate of MYT1, and using the degree of phosphorylation of Thr at position 14 of CDK1 as the criterion. The degree of phosphorylation at the position can be evaluated by a Western blotting method using an antibody that specifically recognizes phosphorylation of Thr at position 14 of CDK1 (manufactured by Abcam plc), an ELISA method using an antibody that specifically recognizes CDK1 and the antibody that specifically recognizes phosphorylation of Thr at position 14 of CDK1, or an AlphaLISA method using the antibody that specifically recognizes CDK1 and the antibody that specifically recognizes phosphorylation of Thr at position 14 of CDK1 (manufactured by PerkinElmer, Inc.). When the threonine kinase activity of MYT1 is inhibited by the test compound, a decrease in phosphorylation is confirmed, in comparison to the control (e.g., the degree of phosphorylation of Thr at position 14 of CDK1 by MYT1 which is not treated with the test compound).

Inhibition of the threonine kinase activity of MYT1 by the compound can be confirmed by, for example, using the degree of phosphorylation of Thr at position 14 of CDK1 which is the substrate protein of the threonine kinase activity of MYT1 as the criterion, to a lysate of a cell treated with the test compound. The degree of phosphorylation at the position can be evaluated by a Western blotting method using an antibody that specifically recognizes phosphorylation of Thr at position 14 of CDK1 (manufactured by Abcam plc), an ELISA method using an antibody that specifically recognizes CDK1 and the antibody that specifically recognizes phosphorylation of Thr at position 14 of CDK1, or an AlphaLISA method using the antibody that specifically recognizes CDK1 and the antibody that specifically recognizes phosphorylation of Thr at position 14 of CDK1 (manufactured by PerkinElmer, Inc.) (Non Patent Literature 8). When the threonine kinase activity of MYT1 is inhibited by the test compound, a decrease in phosphorylation is confirmed, in comparison to the control (e.g., the degree of phosphorylation of Thr at position 14 of CDK1 in a lysate of a cell which is not treated with the test compound).

Inhibition of the expression of MYT1 by the compound can be confirmed by, for example, detecting a decrease in expression of MYT1 in a cell treated with the test compound. Examples of the method for detecting a decrease in expression of MYT1 include a method in which normally, the expression level of MYT1 is detected at a transcriptional level or a translational level, and compared to a control (e.g. expression level in a cell which is not treated with the test compound) to confirm that the expression level is lower than the control.

In the method for detecting the expression level of MYT1 at a transcriptional level, first, RNA or cDNA is prepared from a cell treated with the test compound. The method for extracting RNA from the cell is not particularly limited, and a known method can be appropriately selected and used. Examples thereof include extraction methods using phenol and a chaotropic salt (more specifically, extraction methods using a commercially available kit such as TRIzol (manufactured by Invitrogen Corporation) or ISOGEN (manufactured by Wako Pure Chemical Industries, Ltd.)), and methods using another commercially available kit (e.g. RNAPrep Total RNA Extraction Kit (manufactured by Beckman Coulter Inc.), RNeasy Mini (manufactured by QIAGEN N.V.) or RNA Extraction Kit (manufactured by Pharmacia Biotech, Inc.)). Further, the reverse transcriptase used for preparation of cDNA from extracted RNA is not particularly limited, and examples thereof include reverse transcriptases derived from retroviruses such as RAV (Rous associated virus) and AMV (Avian myeloblastosis virus), and reverse transcriptases derived from mouse retroviruses such as MMLV (Moloney murine leukemia virus).

Subsequently, an oligonucleotide primer or an oligonucleotide probe is used for an amplification reaction or a hybridization reaction, and an amplified product or a hybrid product thereof is detected. As such a method, for example, an RT-PCR method, a Northern blot method, a dot blot method, a DNA array method, an in situ hybridization method, an RNase protection assay method, mRNA-seq, or the like can be used. Those skilled in the art can design an oligonucleotide primer or an oligonucleotide probe suitable for each method in a conventional manner on the basis of a nucleotide sequence of cDNA for MYT1.

In the method for detecting the expression level of MYT1 at a translational level, first, a protein sample is prepared from a cell treated with the test compound. Subsequently, using an antibody specific to MYT1 protein, an antigen-antibody reaction is carried out, and MYT1 protein is detected. In such a method for detecting protein using an antibody, for example, an antibody specific to MYT1 protein is added to the protein sample to carry out an antigen-antibody reaction, and binding of the antibody to MYT1 protein is detected. When the sample is labeled with antibody specific to MYT1 protein, MYT1 protein can be directly detected, and when the sample is not labeled, a labeled molecule that recognizes the antibody (e.g. secondary antibody or protein A) can be further applied to indirectly detect MYT1 protein using the label of the molecule. As such a method, for example, an immunohistochemistry (immunostaining) method, a Western blotting method, an ELISA method, flow cytometry, imaging cytometry, radioimmunoassay, an immunoprecipitation method, or an analysis method using an antibody array can be used.

The type, the origin, and the like of an antibody used are not particularly limited, and a monoclonal antibody is preferable. An oligoclonal antibody (mixture of several antibodies or dozens of antibodies) or a polyclonal antibody can also be used as long as it is possible to detect MYT1 protein with sufficient specificity. Functional fractions of antibodies such as Fab, Fab', F(ab')2, Fv, scFv, sc(Fv)2, dsFv and diabodies, and multimers (e.g. dimers, trimers, tetramers, and polymers) thereof can also be used. Such an anti-MYT1 protein antibody may be a marketed product.

The MYT1 protein can also be detected by mass spectrometry (MS). In particular, analysis by a mass spectrometer coupled with liquid chromatography (LC/MS) is sensitive, and therefore advantageous. Detection by mass spectrometry can be performed by, for example, labeling the protein sample with the protein, fractionating the labeled protein, subjecting the fractionated protein to mass analysis, and identifying MYT1 protein from the mass analysis value. As the label, an isotopic labeling reagent known in the art can be used, and an appropriate labeling reagent can be obtained as a marketed product. The fractionation can be performed by a method known in the art, and for example, a commercially available ion-exchange column or the like can be used.

As used herein, the term "having MYT1 inhibitory activity" means that the MYT1 activity is reduced in vitro, in a cell culture system, or in animals, and for example, the inhibitory activity $IC_{50}$ of MYT1 measured is preferably 10 μM or less, 5 μM or less, or 1 μM or less. A compound having an MYT1 inhibitory activity ($IC_{50}$) of 100 nM or less, 10 nM or less, 3 nM or less, 100 pM or less, or 10 pM or less is more preferable. A compound having an MYT1 inhibitory activity ($IC_{50}$) of 1 nM to 1 μM, 1 nM to 750 nM, 1 nM to 500 nM, or 1 nM to 250 nM is further preferable. A compound having an MYT1 inhibitory activity ($IC_{50}$) of less than 20 nM, or 1 nM to 20 nM is particularly preferable. A compound having higher MYT1 inhibitory activity (having lower $IC_{50}$) can be selected as the compound more effective for treatment or prevention of cancer in a patient in which RB1 gene mutation positivity or a decrease in expression of an RB1 gene or protein is detected.

The therapeutic efficacy of the compound selected by the method according to the present embodiment is further enhanced by using the compound in combination with a chemotherapeutic agent in treatment of cancer in a patient in which RB1 gene mutation positivity or a decrease in expression of an RB1 gene or protein is detected.

EXAMPLES

Hereinafter, the present disclosure will be described in more detail based on Examples, but the present disclosure is not limited to the following Examples.

NMR analysis was carried out using AVANCE III HD400 (400 MHz) manufactured by BRUKER. NMR data were shown in ppm (parts per million) (δ), and referred to deuterium lock signals from sample solvents.

Mass spectrum data were obtained using a single quadrupole mass detector (LCMS-2020) equipped with an ultra-high performance liquid chromatography (Nexera UC) manufactured by SHIMADZU CORPORATION, and a single quadrupole mass detector (SQD or SQD2) equipped with an Acquity ultra-high performance liquid chromatography (UPLC or UPLC I-Class) manufactured by Waters Corporation.

The analysis by high-performance liquid chromatography was carried out using any of the analysis conditions A to W described in the following Table 1 and Table 2. In the following Table 1 and Table 2, "TFA" means trifluoroacetic acid, "FA" means formic acid, "AA" means ammonium acetate, and "AC" means ammonium hydrogencarbonate.

TABLE 1

| Analysis conditions | Apparatus | Column | Column temperature | Detected wavelength (PDA) |
|---|---|---|---|---|
| A | Acquity SQD/SQD2 | Ascentis Express C18 2.1 mm I.D. × 50 mm L, 2.7 μm | 35° C. | 210-400 nm |
| B | Acquity SQD/SQD2 | Ascentis Express C18 2.1 mm I.D. × 50 mm L, 2.7 μm | 35° C. | 210-400 nm |
| C | Acquity SQD/SQD2 | ACQUITY UPLC BEH Phenyl 2.1 mm I.D. × 50 mm L, 1.7 μm | 35° C. | 210-400 nm |
| D | Acquity SQD/SQD2 | Ascentis Express C18 2.1 mm I.D. × 50 mm L, 2.7 μm | 35° C. | 210-400 nm |
| E | Acquity SQD/SQD2 | ACQUITY UPLC BEH Phenyl 2.1 mm I.D. × 50 mm L, 1.7 μm | 35° C. | 210-400 nm |

TABLE 1-continued

| Analysis conditions | Apparatus | Column | Column temperature | Detected wavelength (PDA) |
|---|---|---|---|---|
| F | Nexera UC LCMS-2020 | Ascentis Express C18 2.1 mm I.D. × 50 mm L, 2.7 μm | 35° C. | 210-400 nm |
| G | Acquity SQD/SQD2 | Xselect CSH C18 2.1 mm I.D. × 50 mm L, 2.5 μm | 35° C. | 210-400 nm |
| H | Acquity SQD/SQD2 | Ascentis Express C18 2.1 mm I.D. × 50 mm L, 5 μm | 35° C. | 210-400 nm |
| I | Nexera UC LCMS-2020 | Kinetex EVO C18 2.1 mm I.D. × 50 mm, 2.6 μm | 35° C. | 210-400 nm |
| J | Acquity SQD/SQD2 | YMC Triart C18 3 mm I.D. × 50 mm L, 5 μm | 30° C. | 190-400 nm |
| K | Acquity SQD/SQD2 | YMC Triart C18 3 mm I.D. × 50 mm L, 5 μm | 30° C. | 190-400 nm |
| L | Acquity SQD/SQD2 | YMC Triart C18 3 mm I.D. × 50 mm L, 5 μm | 30° C. | 190-400 nm |
| M | Acquity SQD/SQD2 | YMC Triart C18 3 mm I.D. × 50 mm L, 5 μm | 30° C. | 190-400 nm |
| N | Acquity SQD/SQD2 | Waters X-Bridge C18 3 mm I.D. × 50 mm L, 5 μm | 30° C. | 190-400 nm |
| O | Acquity SQD/SQD2 | Waters X-Bridge C18 3 mm I.D. × 50 mm L, 5 μm | 30° C. | 210-400 nm |
| P | Acquity SQD/SQD2 | CHIRALCEL OZ-H 4.6 mm I.D. × 250 mm, 5 μm | 25° C. | 300 nm |
| Q | Acquity SQD/SQD2 | Ascentis Express C18 2.1 mm I.D. × 50 mm L, 2.7 μm | 35° C. | 210-400 nm |
| R | Nexera UC LCMS-2020 | YMC Triart C18 3 mm I.D. × 50 mm L, 2.5 μm | 40° C. | 190-400 nm |
| S | Nexera UC LCMS-2020 | HALO 90A C18 3 mm I.D. × 30 mm L, 2.0 μm | 40° C. | 190-400 nm |
| T | Nexera UC LCMS-2020 | Shim-pack XR ODS-C18 3.0 mm I.D. × 50 mm L, 2.2 μm | 40° C. | 190-400 nm |
| U | Acquity SQD/SQD2 | Ascentis Express C18 2.1 mm I.D. × 50 mm L, 2.7 μm | 35° C. | 210-400 nm |
| V | Acquity SQD/SQD2 | Ascentis Express C18 2.1 mm I.D. × 50 mm L, 2.7 μm | 35° C. | 210-400 nm |
| W | Acquity SQD/SQD2 | Ascentis Express C18 2.1 mm I.D. × 50 mm L, 2.7 μm | 35° C. | 210-400 nm |
| X | Acquity QDa | Acquity UPLC HSS T3 2.1 mm I.D. × 50 mm L, 1.8 μm | 40° C. | 210-400 nm |
| Y | Acquity SQD/SQD2 | Ascentis Express RP amide 2.1 mm I.D. × 50 mm L, 2.7 μm | 35° C. | 210-400 nm |
| Z | Acquity SQD/SQD2 | YMC Triart C18 3 mm I.D. × 50 mm L, 5 μm | 30° C. | 190-400 nm |

TABLE 2

| Analysis conditions | Mobile phase | Time after injection (min) | Mobile phase A)/B) | Flow velocity (mL/min) |
|---|---|---|---|---|
| A | A) 0.1% FA/$CH_3CN$ | 0-1.0 | 5/95 → 100/0 | 1.00 |
| | B) 0.1% FA/$H_2O$ | 1.0-1.4 | 100/0 | |
| B | A) 0.05% TFA/$CH_3CN$ | 0-1.0 | 5/95 → 100/0 | 1.00 |
| | B) 0.05% TFA/$H_2O$ | 1.0-1.4 | 100/0 | |
| C | A) 0.05% TFA/$CH_3CN$ | 0-3.0 | 20/80 → 100/0 | 1.00 |
| | B) 0.05% TFA/$H_2O$ | 3.0-3.6 | 100/0 | |
| D | A) 0.1% FA/$CH_3CN$ | 0-4.5 | 5/95 → 100/0 | 1.00 |
| | B) 0.1% FA/$H_2O$ | 4.5-5.0 | 100/0 | |
| E | A) 0.05% TFA/$CH_3CN$ | 0-3.0 | 5/95 → 67/33 | 1.00 |
| | B) 0.05% TFA/$H_2O$ | 3.0-3.2 | 67/33 → 100/0 | |
| | | 3.2-3.6 | 100/0 → 100/0 | |
| | | 3.6-5.0 | 99/1 → 95/5 | |
| F | A) 0.1% FA/$CH_3CN$ | 0-1.5 | 5/95 → 100/0 | 1.00 |
| | B) 0.1% FA/$H_2O$ | 1.5-2.0 | 100/0 → 100/0 | |
| G | A) MeOH | 0-0.5 | 5/95 → 100/0 | 1.00 |
| | B) 10 mM AC/$H_2O$ | 0.5-2.5 | 100/0 → 100/0 | |
| | | 2.5-3.0 | 100/0 → 5/95 | |
| H | A) MeOH | 0-1.0 | 5/95 → 100 | 1.00 |
| | B) 10 mM AA/$H_2O$ | 1.0-1.4 | 100/0 | |
| I | A) $CH_3CN$ | 0-1.5 | 5/95 → 95/5 | 1.00 |
| | B) 10 mM AC/$H_2O$ | 1.5-2.0 | 95/5 | |

TABLE 2-continued

| Analysis conditions | Mobile phase | Time after injection (min) | Mobile phase A)/B) | Flow velocity (mL/min) |
|---|---|---|---|---|
| J | A) 0.05% TFA/$CH_3CN$ | 0-1.0 | 10/90 → 10/90 | 1.27 |
| | B) 0.05% TFA/$H_2O$ | 1.0-1.5 | 10/90 → 30/70 | |
| | | 1.5-4.5 | 30/70 → 70/30 | |
| | | 4.5-5.0 | 70/30 → 90/10 | |
| | | 5.0-6.0 | 90/10 → 90/10 | |
| K | A) 0.05% TFA/$CH_3CN$ | 0-1.0 | 10/90 → 10/90 | 1.27 |
| | B) 0.05% TFA/$H_2O$ | 1.0-4.0 | 10/90 → 60/40 | |
| | | 4.0-5.0 | 60/40 → 99/1 | |
| | | 5.0-6.0 | 99/1 → 99/1 | |
| L | A) 0.1% FA/$CH_3CN$ | 0-1.0 | 10/90 → 10/90 | 1.27 |
| | B) 0.1% FA/$H_2O$ | 1.0-1.5 | 10/90 → 30/70 | |
| | | 1.5-4.5 | 30/70 → 70/30 | |
| | | 4.5-5.0 | 70/30 → 90/10 | |
| | | 5.0-6.0 | 90/10 → 90/10 | |
| M | A) MeOH | 0-1.0 | 10/90 → 10/90 | 1.27 |
| | B) 10 mM AC/$H_2O$ | 1.0-1.5 | 10/90 → 30/70 | |
| | | 1.5-4.5 | 30/70 → 70/30 | |
| | | 4.5-5.0 | 70/30 → 90/10 | |
| | | 5.0-6.0 | 90/10 → 90/10 | |
| N | A) 0.05% TFA/$CH_3CN$ | 0-1.0 | 10/90 → 10/90 | 1.27 |
| | B) 0.05% TFA/$H_2O$ | 1.0-1.5 | 10/90 → 30/70 | |
| | | 1.5-4.5 | 30/70 → 70/30 | |
| | | 4.5-5.0 | 70/30 → 90/10 | |
| | | 5.0-6.0 | 90/10 → 90/10 | |
| O | A) 0.05% TFA/$CH_3CN$ | 0-1.0 | 10/90 → 10/90 | 1.27 |
| | B) 0.05% TFA/$H_2O$ | 1.0-4.0 | 10/90 → 60/40 | |
| | | 4.0-5.0 | 60/40 → 99/1 | |
| | | 5.0-6.0 | 99/1 → 99/1 | |
| P | A) Hexane | 0-10 | 50/50 | 1.00 |
| | B) EtOH | | | |
| Q | A) 0.05% FA/$CH_3CN$ | 0-1.0 | 5/95 → 100/0 | 1.00 |
| | B) 0.05% FA/$H_2O$ | 1.0-1.4 | 100/0 | |
| R | A) 0.1% FA/$CH_3CN$ | 0-0.01 | 5/95 → 5/95 | 1.20 |
| | B) 0.1% FA/$H_2O$ | 0.01-1.10 | 5/95 → 95/5 | |
| | | 1.10-1.70 | 95/5 → 95/5 | |
| | | 1.70-1.75 | 95/5 → 5/95 | |
| | | 1.75-2.00 | 5/95 → 5/95 | |
| S | A) 0.1% FA/$CH_3CN$ | 0-0.01 | 5/95 → 5/95 | 1.50 |
| | B) 0.1% FA/$H_2O$ | 0.01-0.70 | 5/95 → 100/0 | |
| | | 0.70-1.10 | 100/0 → 100/0 | |
| | | 1.10-1.12 | 100/0 → 5/95 | |
| | | 1.12-1.20 | 5/95 → 5/95 | |
| T | A) 0.05% TFA/$CH_3CN$ | 0-0.01 | 5/95 → 5/95 | 1.20 |
| | B) 0.05% TFA/$H_2O$ | 0.01-1.00 | 5/95 → 95/5 | |
| | | 1.00-1.55 | 95/5 → 95/5 | |
| | | 1.55-1.65 | 95/5 → 5/9 | |
| | | 1.65-1.80 | 5/95 → 5/95 | |
| U | A) 0.1% FA/$CH_3CN$ | 0-1.0 | 50/50 → 100/0 | 1.00 |
| | B) 0.1% FA/$H_2O$ | 1.0-1.4 | 100/0 | |
| V | A) 0.1% FA/$CH_3CN$ | 0-1.0 | 40/60 → 100/0 | 1.00 |
| | B) 0.1% FA/$H_2O$ | 1.0-1.4 | 100/0 | |
| W | A) 0.1% FA/$CH_3CN$ | 0-1.0 | 20/80 → 100/0 | 1.00 |
| | B) 0.1% FA/$H_2O$ | 1.0-1.4 | 100/0 | |
| X | A) 0.1% FA/$CH_3CN$ | 0-5.0 | 100/0 → 0/100 | 0.50 |
| | B) 0.1% FA/$H_2O$ | 5.0-7.0 | 0/100 → 0/100 | |
| | | 7.0-7.1 | 0/100 → 100/0 | |
| | | 7.1-9.1 | 100/0 → 100/0 | |
| Y | A) 0.1% FA/$CH_3CN$ | 0-4.5 | 95/5 → 0/100 | 0.50 |
| | B) 0.1% FA/$H_2O$ | 4.50-5.00 | 0/100 → 0/100 | |
| | | 5.00-5.01 | 0/100 → 95/5 | |
| | | 5.01-7.0 | 95/5 → 95/5 | |
| Z | A) 0.05% TFA/$CH_3CN$ | 0-1.0 | 1/99 → 1/99 | 1.27 |
| | B) 0.05% TFA/$H_2O$ | 1.0-4.0 | 1/99 → 40/60 | |
| | | 4.0-5.0 | 40/60 → 90/10 | |
| | | 5.0-6.0 | 90/10 → 90/10 | |
| | | 6.0-6.2 | 90/10 → 1/99 | |
| | | 6.2-7.0 | 1/99 → 1/99 | |

The microwave reaction was conducted using Initiator manufactured by Biotage. A snap cap reaction vial was used for the microwave reaction. The operation of equipment was carried out in accordance with the manual attached to the equipment.

The photoredox catalysis was carried out using Penn PhD M2 Integrated Photoreactor (ACS Cent. Sci. 2017, vol. 3, issue 6, p. 647-653 (Non Patent Literature 20)). The operation of equipment was carried out in accordance with the manual attached to the equipment.

The commercially available reagent was used without further purification. All the non-aqueous reactions were conducted by using commercially available dehydrated solvents. Concentration under reduced pressure and solvent distillation were carried out using a rotary evaporator.

As used herein, the term "room temperature" means a temperature from about 20° C. to about 25° C.

Compound a-1

4-Bromo-7-chloro-2-(oxan-2-yl)indazole

[Formula 22]

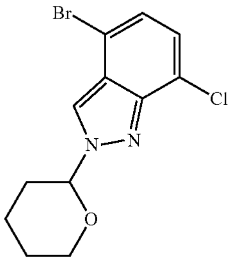

To a solution of 4-bromo-7-chloro-1H-indazole (44.97 g, 194 mmol) in DCM (900 mL) in a reaction vessel, 3,4-dihydro-2H-pyran (32.68 g, 388 mmol) and pyridinium p-toluenesulfonate (9.77 g, 38.9 mmol) were added, and the mixture was stirred at room temperature for 6 hours. To the reaction mixture, a saturated aqueous sodium bicarbonate solution was added, and the mixture was extracted twice with DCM. The organic layer was dried over anhydrous sodium sulfate, the drying agent was filtered off, and then the filtrate was concentrated under reduced pressure. The obtained residue was suspended in a mixed solution of hexane/ethyl acetate (3/1), and the solid was collected by filtration. The filtrate was concentrated under reduced pressure, the obtained residue was purified by silica gel column chromatography, and the purified product was combined with the previously obtained solid to obtain the title compound (55.17 g, yield 90%) as a yellow solid.

LCMS: m/z 315 $[M+H]^+$

HPLC retention time: 4.97 min (analysis condition J)

Compound a-2

(2,4,6-Trichlorophenyl) 7-chloro-2-(oxan-2-yl)indazole-4-carboxylate

[Formula 23]

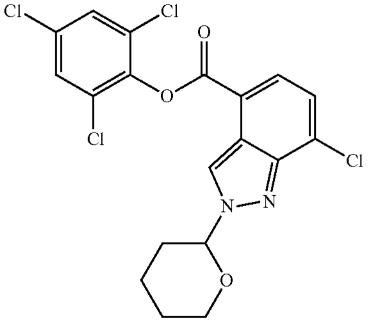

To a solution of 4-bromo-7-chloro-2-(oxan-2-yl)indazole (compound a-1, 24.16 g, 76.55 mmol) in toluene (340 mL) in a reaction vessel, triethylamine (15.5 g, 153.18 mmol) was added, the reaction vessel was degassed under reduced pressure and subjected to nitrogen replacement. Xantphos Pd G4 (3.69 g, 3.83 mmol) was added to the mixture, and the reaction vessel was further degassed under reduced pressure and subjected to nitrogen replacement. After the reaction mixture was heated to 65° C., a solution of 2,4,6-trichlorophenyl formate (19.85 g, 88 mmol) in toluene (54 mL) which was degassed under reduced pressure and subjected to nitrogen replacement was added dropwise thereto over 3 hours. The reaction mixture was stirred at 65° C. under nitrogen atmosphere for further 20 min, then cooled to room temperature, and filtered. The filtrate was concentrated under reduced pressure to obtain the crude product of the title compound (46.69 g).

LCMS: m/z 459 $[M+H]^+$

HPLC retention time: 4.86 min (analysis condition K)

Compound a-3

7-Chloro-2-(oxan-2-yl)indazole-4-carboxylic acid

[Formula 24]

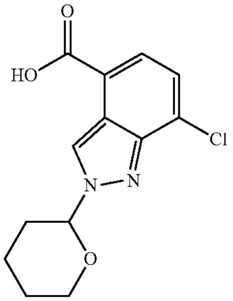

To a suspension of the crude product (46.69 g) of (2,4,6-trichlorophenyl) 7-chloro-2-(oxan-2-yl)indazole-4-carboxylate (compound a-2) in THF (470 mL) in a reaction vessel, a 2M aqueous sodium hydroxide solution (230 mL, 460 mmol) was added, and the mixture was stirred at 60° C. for 16 hours. The reaction mixture was cooled to room temperature, ethyl acetate, water, and an aqueous phosphoric acid solution were added thereto, and the mixture was adjusted to pH 4 and then extracted twice with ethyl acetate. The organic layer was washed with water (500 mL) and then extracted four times with a saturated aqueous sodium bicarbonate solution (400 mL) and a 5% aqueous sodium bicarbonate solution (400 mL). The obtained aqueous layers were combined and then cooled to 5° C., an aqueous phosphoric acid solution was added, and the mixture was adjusted to pH 4. The mixture was extracted four times with ethyl acetate. The organic layer was dried over anhydrous sodium sulfate, the drying agent was filtered off, then the filtrate was combined with the organic layer of another rot which was synthesized by carrying out the same operation, and the mixture was concentrated under reduced pressure to obtain the title compound (38.76 g) as a pale yellow solid.

LCMS: m/z 281 $[M+H]^+$

HPLC retention time: 2.79 min (analysis condition K)

Compound a-4

7-Chloro-N-methoxy-N-methyl-2-(oxan-2-yl)indazole-4-carboxamide

[Formula 25]

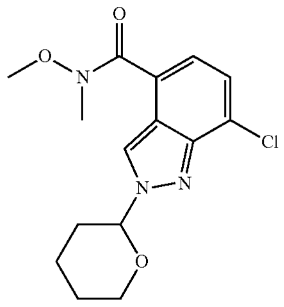

To a solution of 7-chloro-2-(oxan-2-yl)indazole-4-carboxylic acid (compound a-3, 38.76 g, 138 mmol) in THF (388 mL) in a reaction vessel, triethylamine (55.89 g, 552 mmol), N,O-dimethylhydroxylamine hydrochloride (26.94 g, 276 mmol), and HATU (68.25 g, 180 mmol) were added, and the mixture was stirred at room temperature for 15 hours. Water was added to the reaction mixture, and the mixture was extracted with ethyl acetate. The organic layer was washed with a saturated aqueous sodium bicarbonate solution and dried over anhydrous sodium sulfate, the drying agent was filtered off, and then the filtrate was concentrated under reduced pressure. The obtained residue was purified by silica gel column chromatography (hexane/ethyl acetate) to obtain the title compound (31.74 g, yield 71%) as a colorless solid.

LCMS: m/z 324 $[M+H]^+$

HPLC retention time: 0.66 min (analysis condition A)

Compound a-5

4-Bromo-5-fluoro-2-iodoaniline

[Formula 26]

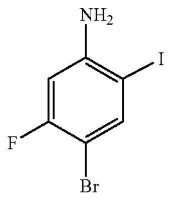

To a solution of 4-bromo-3-fluoroaniline (15.43 g, 81.2 mmol) in acetic acid (200 mL) in a reaction vessel, N-iodosuccinimide (19.18 g, 85.248 mmol) was added, and the mixture was stirred at room temperature under nitrogen atmosphere for 1 hour. The reaction mixture was cooled to 0° C., and the solid was collected by filtration and washed with water. The obtained solid was dissolved in DCM, and the mixture was washed with a saturated aqueous sodium carbonate solution. The organic layer was dried over anhydrous sodium sulfate, the drying agent was filtered off, and then the filtrate was concentrated under reduced pressure. The obtained residue was purified by silica gel column chromatography (hexane/ethyl acetate) to obtain the title compound (22.01 g, yield 86%) as a brown solid.

LCMS: m/z 316 $[M+H]^+$

HPLC retention time: 4.55 min (analysis condition J)

Compound a-6

(E)-N'-(4-Bromo-5-fluoro-2-iodophenyl)-N,N-dimethylmethanimidamide

[Formula 27]

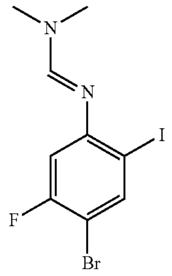

4-Bromo-5-fluoro-2-iodoaniline (compound a-5, 28.58 g, 190.47 mmol) in a reaction vessel was dissolved in EtOH (180 mL), N,N-dimethylformamidedimethylacetal (43.12 g, 361.9 mmol) was added thereto, and the mixture was stirred at 80° C. for 1.5 hours. The reaction mixture was cooled to room temperature, and then concentrated under reduced pressure. The obtained residue was purified by silica gel column chromatography (hexane/DCM) to obtain the title compound (31.7 g, yield 95%) as a pale red solid.

LCMS: m/z 371 $[M+H]^+$

HPLC retention time: 2.59 min (analysis condition J)

Compound a-7

(E)-N'-[4-Bromo-2-[7-chloro-2-(oxan-2-yl)indazole-4-carbonyl]-5-fluorophenyl]-N,N-dimethylmethanimidamide

[Formula 28]

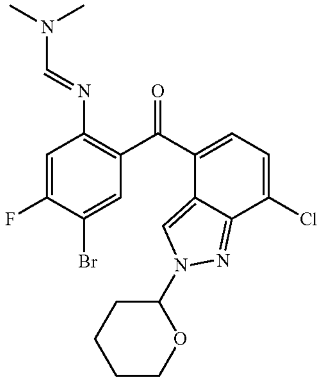

A solution of (E)-N'-(4-bromo-5-fluoro-2-iodophenyl)-N,N-dimethylmethanimidamide (compound a-6, 16.39 g, 44.18 mmol) in toluene (164 mL) in a reaction vessel was cooled to −40° C., a 1.3 M solution of isopropylmagnesium chloride-lithium chloride complex in THF (34 mL, 44.2 mmol) was added dropwise thereto, and then the mixture was stirred for 1 hour. A solution of 7-chloro-N-methoxy-N-methyl-2-(oxan-2-yl)indazole-4-carboxamide (compound a-4, 11.14 g, 34 mmol) in toluene (110 mL) was added dropwise to the reaction mixture over 30 min, and then the mixture was stirred at 0° C. for 1 hour. To the reaction mixture, a saturated aqueous sodium bicarbonate solution was added, and the mixture was extracted three times with ethyl acetate. The organic layer was dried over anhydrous sodium sulfate, the drying agent was filtered off, and then the filtrate was concentrated under reduced pressure to obtain the crude product of the title compound (22.38 g).

LCMS: m/z 507 $[M+H]^+$

HPLC retention time: 3.65 min (analysis condition J)

Compound a-8

(2-Amino-5-bromo-4-fluorophenyl)-[7-chloro-2-(oxan-2-yl)indazol-4-yl]methanone

[Formula 29]

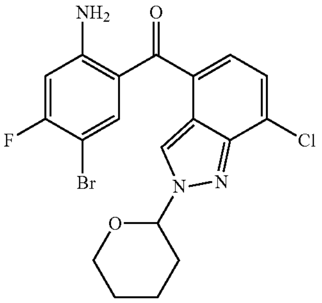

The crude product of (E)-N'-[4-bromo-2-[7-chloro-2-(oxan-2-yl)indazole-4-carbonyl]-5-fluorophenyl]-N,N-dimethylmethanimidamide (compound a-7, 22.38 g) in a reaction vessel was dissolved in DMSO (220 mL), a 5 M aqueous sodium hydroxide solution (20.4 mL) was added thereto, and the mixture was stirred at room temperature for 30 min. To the reaction mixture, a saturated aqueous ammonium chloride solution (300 mL) and water (1 L) were added. The solid was collected by filtration and washed with water. The obtained solid was purified three times by silica gel column chromatography to obtain the title compound (7.41 g, yield 48%) as a yellow solid.

LCMS: m/z 452 $[M+H]^+$

HPLC retention time: 5.42 min (analysis condition J)

Compound a-9

N-[4-Bromo-2-[7-chloro-2-(oxan-2-yl)indazole-4-carbonyl]-5-fluorophenyl]-2-chloroacetamide

[Formula 30]

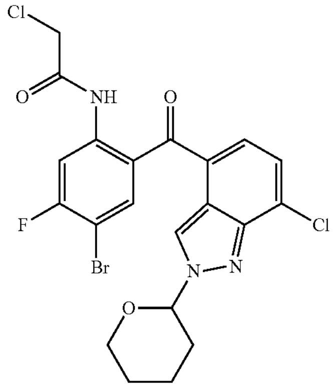

A solution of (2-amino-5-bromo-4-fluorophenyl)-[7-chloro-2-(oxan-2-yl)indazol-4-yl]methanone (compound a-8, 7.41 g, 16.37 mmol) in DMA (120 mL) in a reaction vessel was cooled to 0° C., chloroacetyl chloride (1.96 mL, 24.64 mmol) was added thereto, and the mixture was stirred at room temperature for 1 hour to obtain a solution of the title compound in DMA.

LCMS: m/z 528 $[M+H]^+$

HPLC retention time: 5.57 min (analysis condition J)

Compound a-10

6-Bromo-4-[7-chloro-2-(oxan-2-yl)indazol-4-yl]-7-fluoro-3-pyridin-1-ium-1-yl-1H-quinolin-2-one; chloride

[Formula 31]

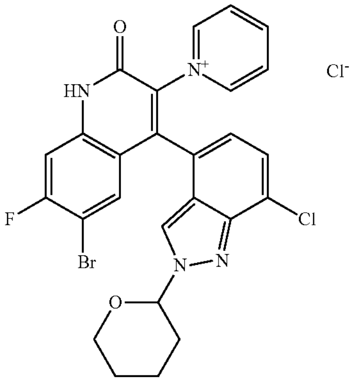

To the solution of N-[4-bromo-2-[7-chloro-2-(oxan-2-yl)indazole-4-carbonyl]-5-fluorophenyl]-2-chloroacetamide (compound a-9) in DMA in a reaction vessel, pyridine (74 mL) was added, and the mixture was stirred at 60° C. for 4 hours. The reaction mixture was cooled to room temperature to obtain a solution of the title compound in DMA/pyridine.

LCMS: m/z 553 $[M]^+$

HPLC retention time: 3.44 min (analysis condition J)

Compound a-11

3-Amino-6-bromo-4-[7-chloro-2-(oxan-2-yl)indazol-4-yl]-7-fluoro-1H-quinolin-2-one

[Formula 32]

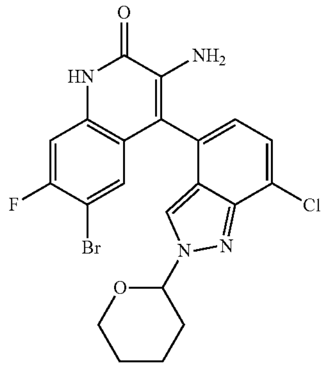

To the solution of 6-bromo-4-[7-chloro-2-(oxan-2-yl)indazol-4-yl]-7-fluoro-3-pyridin-1-ium-1-yl-1H-quinolin-2-one; chloride (compound a-10) in DMA/pyridine, hydrazine monohydrate (8.2 g, 163.8 mmol) was added, the mixture was stirred at 60° C. for 4 hours, and further stirred at room temperature for 13 hours. Water was added to the reaction mixture, and then the produced solid was collected by filtration and washed with water. The obtained solid was purified by silica gel column chromatography (hexane/ethyl acetate) to obtain the title compound (7.3 g, yield 91%) as a colorless solid.

LCMS: m/z 491 $[M+H]^+$

HPLC retention time: 4.65 min (analysis condition J)

Compound a-12

3-Amino-6-bromo-4-[7-chloro-2-(oxan-2-yl)indazol-4-yl]-7-fluoro-1-[(4-methoxyphenyl)methyl]quinolin-2-one

[Formula 33]

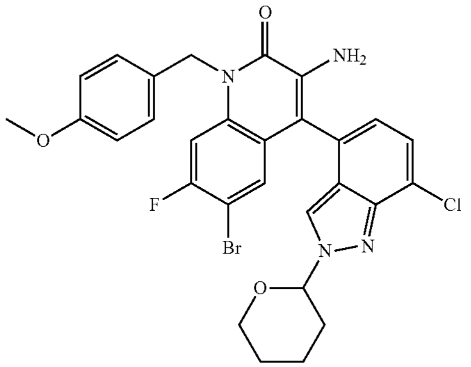

3-Amino-6-bromo-4-[7-chloro-2-(oxan-2-yl)indazol-4-yl]-7-fluoro-1H-quinolin-2-one (compound a-11, 7.3 g, 14.84 mmol) in a reaction vessel and potassium carbonate (5.13 g, 37.12 mmol) were suspended in NMP (73 mL), p-methoxybenzylchloride (2.83 mL, 20.78 mmol) was added thereto, and the mixture was stirred at 70° C. for 2 hours. The reaction mixture was cooled to room temperature, and water was added thereto. The solid was collected by filtration and washed with water and hexane. The obtained solid was purified by silica gel column chromatography to obtain the title compound (4.79 g, yield 53%) as a pale yellow solid.

LCMS: m/z 611 $[M+H]^+$

HPLC retention time: 5.76 min (analysis condition J)

Compound a-13

3-Amino-4-[7-chloro-2-(oxan-2-yl)indazol-4-yl]-7-fluoro-6-hydroxy-1-[(4-methoxyphenyl methyl]quinolin-2-one

[Formula 34]

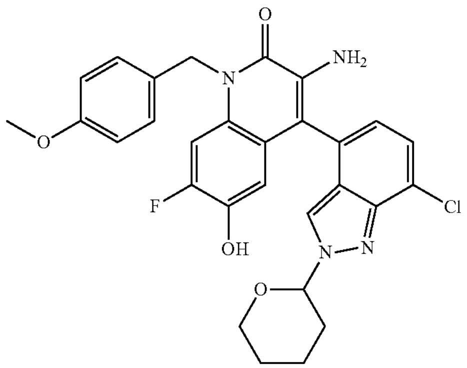

To a reaction vessel, 3-amino-6-bromo-4-[7-chloro-2-(oxan-2-yl)indazol-4-yl]-7-fluoro-1-[(4-methoxyphenyl) methyl]quinolin-2-one (compound a-12, 500 mg, 0.817 mmol) and tBuBrettPhos Pd G3 (69.8 mg, 0.0817 mmol) were added, and the reaction vessel was degassed under reduced pressure and subjected to argon replacement. DMA (8 mL) and 8 M potassium hydrate (245.1 μL, 1.961 mmol) were added, the reaction vessel was degassed under reduced pressure and subjected to argon replacement, and then the mixture was stirred at room temperature for 21 hours. Potassium dihydrogen phosphate (445 mg) and water were added thereto, and the produced solid was collected by filtration. The filtrate was extracted with ethyl acetate, the organic layer was dried over anhydrous sodium sulfate, the drying agent was filtered off, and then the filtrate was concentrated under reduced pressure. The residue was combined with the previously obtained solid, and the mixture was purified by silica gel column chromatography to obtain the title compound (308 mg, yield 68.7%) as a light brown solid.

LCMS: m/z 549 $[M+H]^+$

HPLC retention time: 4.49 min (analysis condition J)

Compound a-14

3-Amino-4-[7-chloro-2-(oxan-2-yl)indazol-4-yl]-7-fluoro-1-[(4-methoxyphenyl)methyl]-6-propan-2-yloxyquinolin-2-one

[Formula 35]

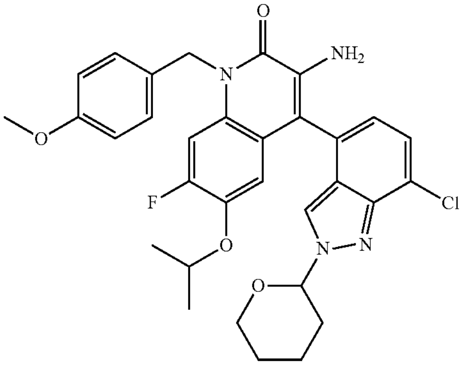

3-Amino-4-[7-chloro-2-(oxan-2-yl)indazol-4-yl]-7-fluoro-6-hydroxy-1-[(4-methoxyphenyl)methyl]quinolin-2-one (compound a-13, 210 mg, 0.383 mmol) in a reaction vessel and potassium carbonate (265 mg, 1.917 mmol) were suspended in DMF (4.4 mL), 2-iodopropane (190.2 μL, 1.913 mmol) was added thereto, and the mixture was stirred at room temperature for 18 hours. Water was added to the reaction mixture, and the mixture was extracted with ethyl acetate. The organic layer was washed with water and a saturated aqueous sodium bicarbonate solution and then dried over anhydrous sodium sulfate, the drying agent was filtered off, and then the filtrate was concentrated under reduced pressure. The obtained residue was purified by silica gel column chromatography (hexane/ethyl acetate) to obtain the title compound (201 mg, yield 89%) as a yellow solid.

LCMS: m/z 591 $[M+H]^+$

HPLC retention time: 5.60 min (analysis condition J)

Compound A1

3-Amino-4-(7-chloro-1H-indazol-4-yl)-7-fluoro-6-propan-2-yloxy-1H-quinolin-2-one

[Formula 36]

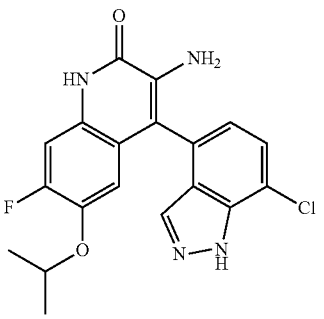

To 3-amino-4-[7-chloro-2-(oxan-2-yl)indazol-4-yl]-7-fluoro-1-[(4-methoxyphenyl)methyl]-6-propan-2-yloxyquinolin-2-one (compound a-14, 201 mg, 0.34 mmol) in a reaction vessel, TFA/water (3/1, 3 mL) was added, and the mixture was stirred at 100° C. for 4 hours. The reaction mixture was cooled to room temperature and concentrated under reduced pressure. MeOH was added to the residue, and the mixture was further concentrated. MeOH (4 mL) and 12 M hydrochloric acid (100 μL) were added to the residue, and the mixture was stirred at room temperature for 20 hours. The reaction mixture was concentrated, then the obtained residue was dissolved in MeOH, and triethylamine was added thereto. The reaction mixture was concentrated under reduced pressure, and the obtained residue was purified by silica gel column chromatography (hexane/ethyl acetate) to obtain the title compound (48.3 mg, yield 37%) as a pale yellow solid.

LCMS: m/z 387 $[M+H]^+$

HPLC retention time: 0.67 min (analysis condition A)

Compound a-15

3-Amino-4-[7-chloro-2-(oxan-2-yl)indazol-4-yl]-6-(3,3-difluoropropoxy)-7-fluoro-1-[(4-methoxyphenyl)methyl]quinolin-2-one

[Formula 37]

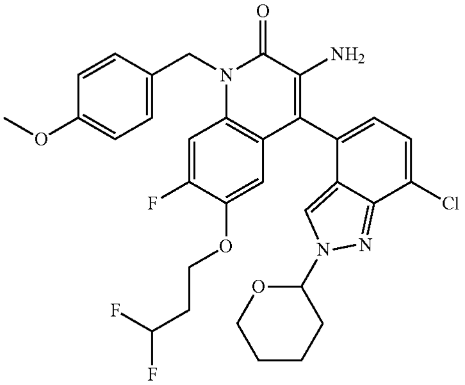

To 3-amino-4-[7-chloro-2-(oxan-2-yl)indazol-4-yl]-7-fluoro-6-hydroxy-1-[(4-methoxyphenyl)methyl]quinolin-2-one (compound a-13, 231 mg, 0.421 mmol) and 3,3-difluoropropan-1-ol (123 mg, 1.28 mmol) in a reaction vessel, a 0.5 M solution of cyanomethylenetrimethylphosphorane in THF (2.53 mL, 1.265 mmol) was added, the reaction vessel was degassed under reduced pressure and subjected to argon replacement, and then the mixture was stirred at 80° C. for 2.5 hours. The reaction mixture was cooled to room temperature, water (231 μL) was added thereto, and the mixture was stirred at 80° C. for 15 hours. The reaction mixture was cooled to room temperature and concentrated under reduced pressure. THF was added to the obtained residue, and the mixture was further concentrated under reduced pressure. The obtained residue was purified by silica gel column chromatography to obtain the title compound (233 mg, yield 88%) as a pale yellow solid.

LCMS: m/z 627 $[M+H]^+$

HPLC retention time: 5.40 min (analysis condition J)

Compound A2

3-Amino-4-(7-chloro-1H-indazol-4-yl)-6-(3,3-difluoropropoxy)-7-fluoro-1H-quinolin-2-one

[Formula 38]

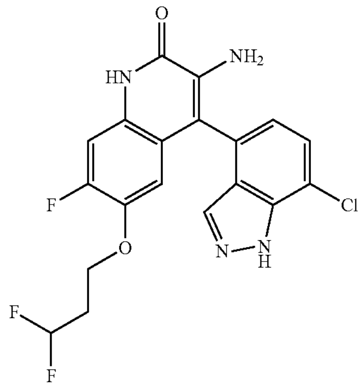

The title compound was synthesized from 3-amino-4-[7-chloro-2-(oxan-2-yl)indazol-4-yl]-6-(3,3-difluoropropoxy)-7-fluoro-1-[(4-methoxyphenyl)methyl]quinolin-2-one (compound a-15) under the same conditions as the production example of the compound A1.

LCMS: m/z 423 $[M+H]^+$

HPLC retention time: 0.65 min (analysis condition A)

Compound a-22

3-Amino-6-bromo-4-[7-chloro-2-(oxan-2-yl)indazol-4-yl]-7-fluoro-1-(2-trimethylsilylethoxymethyl)quinolin-2-one

[Formula 39]

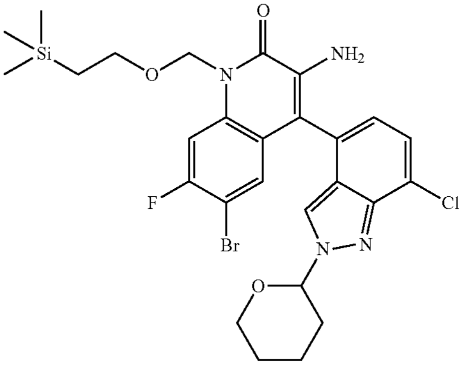

A solution of 3-amino-6-bromo-4-[7-chloro-2-(oxan-2-yl)indazol-4-yl]-7-fluoro-1H-quinolin-2-one (compound a-11, 1.732 g, 3.522 mmol) in THF (25 mL) in a reaction vessel was cooled to 0° C., 60% sodium hydride/mineral oil (564 mg, 14.08 mmol) was added, and the mixture was stirred for 30 min. To the reaction mixture, 2-(chloromethoxy)ethyltrimethylsilane (1.86 mL, 10.6 mmol) was added, and the mixture was further stirred for 30 min. To the reaction mixture, a saturated aqueous sodium bicarbonate solution was added, and the mixture was extracted twice with ethyl acetate. The organic layer was dried over anhydrous sodium sulfate, the drying agent was filtered off, and then the filtrate was concentrated under reduced (hexane/ethyl acetate) to obtain the title compound (1.87 g, yield 85%) as a pale yellow solid.

LCMS: m/z 621 $[M+H]^+$

HPLC retention time: 6.33 min (analysis condition J)

Compound a-23

3-Amino-4-[7-chloro-2-(oxan-2-yl)indazol-4-yl]-7-fluoro-6-hydroxy-1-(2-trimethylsilylethoxymethyl)quinolin-2-one

[Formula 40]

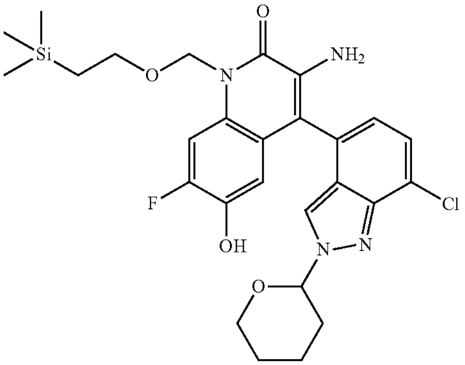

The title compound was synthesized from 3-amino-6-bromo-4-[7-chloro-2-(oxan-2-yl)indazol-4-yl]-7-fluoro-1-(2-trimethylsilylethoxymethyl)quinolin-2-one (compound a-22) under the same conditions as the production example of the compound a-13.

LCMS: m/z 559 $[M+H]^+$

HPLC retention time: 5.35 min (analysis condition J)

Compound a-24

3-Amino-4-[7-chloro-2-(oxan-2-yl)indazol-4-yl]-6-cyclobutyloxy-7-fluoro-1-(2-trimethylsilylethoxymethyl)quinolin-2-one

[Formula 41]

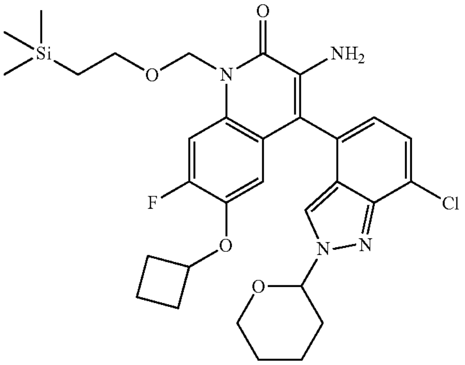

The title compound was synthesized from 3-amino-4-[7-chloro-2-(oxan-2-yl)indazol-4-yl]-7-fluoro-6-hydroxy-1-(2-trimethylsilylethoxymethyl)quinolin-2-one (compound a-23) under the same conditions as the production example of compound a-14, except that bromocyclobutane was used instead of 2-iodopropane used in the production example of the compound a-14. In addition, the reaction was carried out by heating the reaction mixture to 70° C.

LCMS: m/z 613 $[M+H]^+$

HPLC retention time: 5.00 min (analysis condition K)

Compound A7

3-Amino-4-(7-chloro-1H-indazol-4-yl)-6-cyclobutyloxy-7-fluoro-1H-quinolin-2-one

[Formula 42]

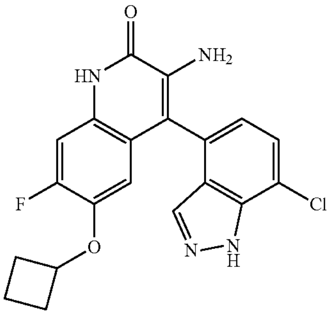

To a solution of 3-amino-4-[7-chloro-2-(oxan-2-yl)indazol-4-yl]-6-cyclobutyloxy-7-fluoro-1-(2-trimethylsilylethoxymethyl)quinolin-2-one (compound a-24, 70.8 mg, 0.115 mmol) in DCM (0.8 mL) in a reaction vessel, anisole (125 mg, 1.15 mmol) and TFA (0.8 mL) were added, and the mixture was stirred at room temperature for 3.5 hours. The reaction mixture was concentrated under reduced pressure, MeOH was added thereto, and the mixture was further concentrated under reduced pressure. The obtained residue was purified by reversed phase column chromatography (0.1% aqueous TFA solution/0.1% TFA acetonitrile solution). The fractions containing the title compound were combined, and saturated sodium bicarbonate was added for neutralization. The mixed solution was concentrated under reduced pressure, the produced solid was collected by filtration and washed with water to obtain the title compound (10.7 mg, yield 23%) as a yellow solid.

LCMS: m/z 399 $[M+H]^+$

HPLC retention time: 0.69 min (analysis condition A)

Compound A72

3-Amino-4-(7-chloro-1H-indazol-4-yl)-7-fluoro-6-[(1-fluorocyclopropyl)methoxy]-1H-quinolin-2-one

[Formula 43]

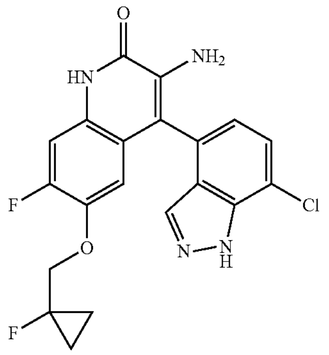

The title compound was synthesized from 3-amino-4-[7-chloro-2-(oxan-2-yl)indazol-4-yl]-7-fluoro-6-hydroxy-1-(2-trimethylsilylethoxymethyl)quinolin-2-one (compound a-23) under the same conditions as the production examples of compound a-15 and compound A7, except that (1-fluorocyclopropyl) methanol was used instead of 3,3-difluoropropan-1-ol used in the production example of the compound a-15.

LCMS: m/z 417 $[M+H]^+$

HPLC retention time: 0.65 min (analysis condition A)

Compound a-16

6-Bromo-4-[7-chloro-2-(oxan-2-yl)indazol-4-yl]-7-fluoro-2-[(4-methoxyphenyl)methoxy]quinoline-3-amine

[Formula 44]

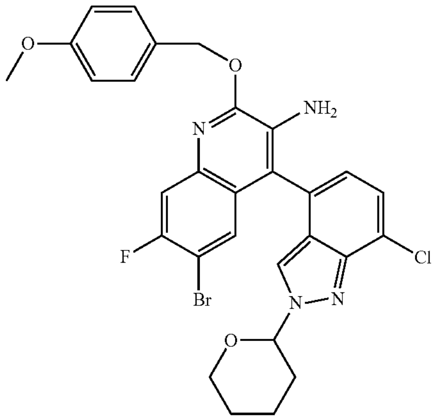

3-Amino-6-bromo-4-[7-chloro-2-(oxan-2-yl)indazol-4-yl]-7-fluoro-1H-quinolin-2-one (compound a-11, 1.496 g, 3.042 mmol) and silver carbonate (1.26 g, 4.57 mmol) were suspended in 1,2-dichloroethane (37 mL), then p-methoxybenzylchloride (705 μL, 5.18 mmol) was added, and the mixture was stirred at 95° C. for 16 hours. The reaction mixture was cooled to room temperature, filtered using Celite, and washed with ethyl acetate. The obtained filtrate was concentrated under reduced pressure. The obtained residue was purified by silica gel column chromatography (hexane/ethyl acetate) to obtain the title compound (765 mg, yield 41%).

Compound a-17

3-Amino-4-[7-chloro-2-(oxan-2-yl)indazol-4-yl]-7-fluoro-2-[(4-methoxyphenyl)methoxy]quinolin-6-ol

[Formula 45]

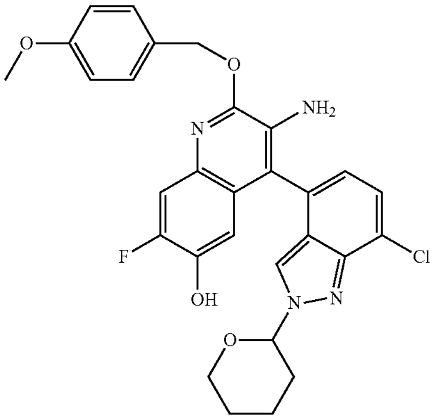

The title compound was synthesized from 6-bromo-4-[7-chloro-2-(oxan-2-yl)indazol-4-yl]-7-fluoro-2-[(4-methoxyphenyl)methoxy]quinoline-3-amine (compound a-16) under the same conditions as the production example of the compound a-13.

LCMS: m/z 549 $[M+H]^+$

HPLC retention time: 4.39 min (analysis condition L)

Compound A3

3-Amino-4-(7-chloro-1H-indazol-4-yl)-6-(cyclopropylmethoxy)-7-fluoro-1H-quinolin-2-one

[Formula 46]

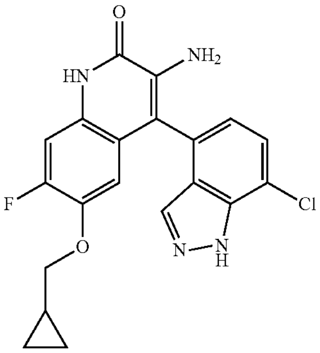

The title compound was synthesized from 3-amino-4-[7-chloro-2-(oxan-2-yl)indazol-4-yl]-7-fluoro-2-[(4-methoxyphenyl)methoxy]quinolin-6-ol (compound a-17) under the same conditions as the production examples of the compounds a-14 and A7, except that (iodomethyl)cyclopropane was used instead of 2-iodopropane used in the production example of the compound a-14.

LCMS: m/z 399 $[M+H]^+$

HPLC retention time: 0.67 min (analysis condition A)

Compound a-102

(1s,3s)-3-Fluorocyclobutyl trifluoromethanesulfonate

[Formula 47]

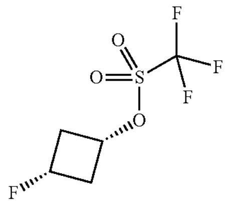

A solution of (1s,3s)-3-fluorocyclobutan-1-ol (200 mg, 2.22 mmol) in DCM (2 mL) in a reaction vessel was cooled to 0° C., pyridine (197 μL, 2.44 mmol) and trifluoromethane sulfonic acid anhydride (413 μL, 2.44 mmol) were added thereto, and the mixture was stirred at room temperature for 1 hour. The reaction mixture was purified by silica gel column chromatography (DCM) to obtain the title compound (540 mg).

$^1$H-NMR ($d_6$-DMSO) δ: 5.41-5.16 (1H, m), 5.28-5.16 (1H, m), 2.69-2.57 (4H, m)

Compound a-103

(1s,3s)-3-Cyanocyclobutyl trifluoromethanesulfonate

[Formula 48]

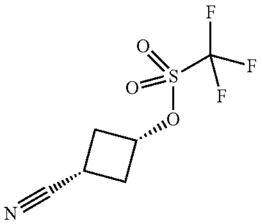

The title compound was synthesized using a corresponding alcohol under the same conditions as the production example of the compound a-102.

$^1$H-NMR ($d_6$-DMSO) δ: 5.22-5.12 (1H, m), 3.61-3.39 (1H, m), 2.79-2.55 (4H, m).

Compound A4

3-Amino-4-(7-chloro-1H-indazol-4-yl)-7-fluoro-6-((1r,3r)-3-fluorocyclobutyl)oxy-1H-quinolin-2-one

[Formula 49]

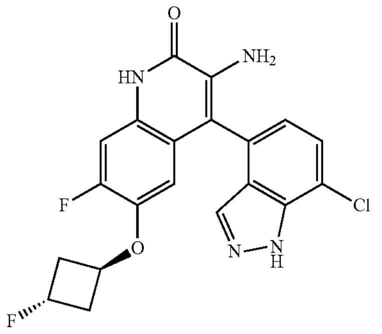

The title compound was synthesized from 3-amino-4-[7-chloro-2-(oxan-2-yl)indazol-4-yl]-7-fluoro-2-[(4-methoxyphenyl)methoxy]quinolin-6-ol (compound a-17) under the same conditions as the production examples of the compounds a-14 and A7, except that the (1s,3s)-3-fluorocyclobutyl trifluoromethanesulfonate compound (a-102) was used instead of 2-iodopropane used in the production example of the compound a-14.

LCMS: m/z 417 $[M+H]^+$

HPLC retention time: 0.65 min (analysis condition A)

Compound A5

(1r,3r)-3-[[3-Amino-4-(7-chloro-1H-indazol-4-yl)-7-fluoro-2-oxo-1H-quinolin-6-yl]oxy]cyclobutane-1-carbonitrile

[Formula 50]

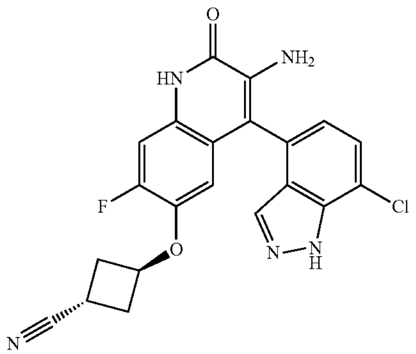

The title compound was synthesized from 3-amino-4-[7-chloro-2-(oxan-2-yl)indazol-4-yl]-7-fluoro-2-[(4-methoxyphenyl)methoxy]quinolin-6-ol (compound a-17) under the same conditions as the production examples of the compounds a-14 and A7, except that (1s,3s)-3-cyanocyclobutyl trifluoromethanesulfonate (compound a-103) was used instead of 2-iodopropane used in the production example of the compound a-14.

LCMS: m/z 424 $[M+H]^+$

HPLC retention time: 0.60 min (analysis condition A)

Compound A6

3-Amino-4-(7-chloro-1H-indazol-4-yl)-7-fluoro-6-(3-fluoropropoxy)-1H-quinolin-2-one

[Formula 51]

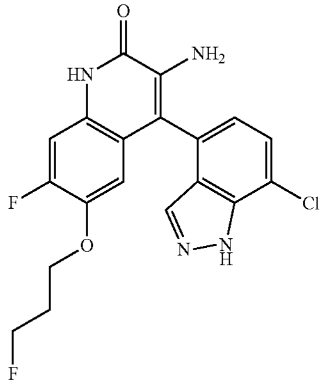

The title compound was synthesized from 3-amino-4-[7-chloro-2-(oxan-2-yl)indazol-4-yl]-7-fluoro-2-[(4-methoxyphenyl)methoxy]quinolin-6-ol (compound a-17) under the same conditions as the production examples of the compounds a-14 and A7, except that 1-fluoro-3-iodopropane was used instead of 2-iodopropane used in the production example of the compound a-14.

LCMS: m/z 405 $[M+H]^+$

HPLC retention time: 0.64 min (analysis condition A)

Compound a-25

4-Bromo-5-chloro-2-iodoaniline

[Formula 52]

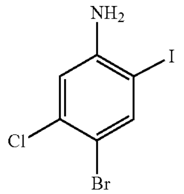

The title compound was synthesized from 4-bromo-3-chloroaniline under the same conditions as the production example of the compound a-5.

LCMS: m/z 332 $[M+H]^+$

HPLC retention time: 4.42 min (analysis condition N)

Compound a-26

(E)-N'-(4-Bromo-5-chloro-2-iodophenyl)-N,N-dimethylmethanimidamide

[Formula 53]

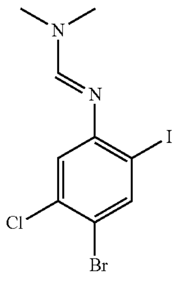

The title compound was synthesized from 4-bromo-5-chloro-2-iodoaniline (compound a-25) under the same conditions as the production example of the compound a-6.

LCMS: m/z 387 $[M+H]^+$

HPLC retention time: 2.60 min (analysis condition N)

Compound a-27

(E)-N'-[4-Bromo-5-chloro-2-[7-chloro-2-(oxan-2-yl)indazole-4-carbonyl]phenyl]-N,N-dimethylmethanimidamide

[Formula 54]

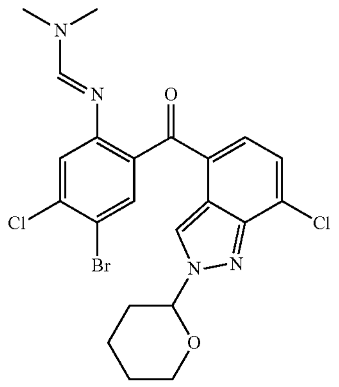

The title compound was synthesized from (E)-N'-(4-bromo-5-chloro-2-iodophenyl)-N,N-dimethylmethanimidamide (compound a-26) under the same conditions as the production example of the compound a-7.

LCMS: m/z 523 $[M+H]^+$

HPLC retention time: 3.88 min (analysis condition J)

Compound a-28

(2-Amino-5-bromo-4-chlorophenyl)-[7-chloro-2-(oxan-2-yl)indazol-4-yl]methanone

[Formula 55]

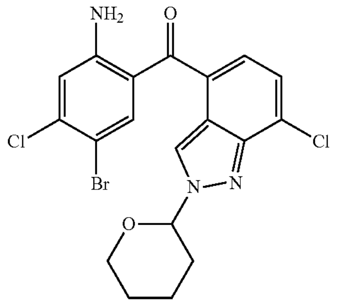

The title compound was synthesized from (E)-N'-[4-bromo-5-chloro-2-[7-chloro-2-(oxan-2-yl)indazole-4-carbonyl]phenyl]-N,N-dimethylmethanimidamide (compound a-27) under the same conditions as the production example of the compound a-8.

LCMS: m/z 468 $[M+H]^+$

HPLC retention time: 5.66 min (analysis condition J)

Compound a-31

3-Amino-6-bromo-7-chloro-4-[7-chloro-2-(oxan-2-yl)indazol-4-yl]-1H-quinolin-2-one

[Formula 56]

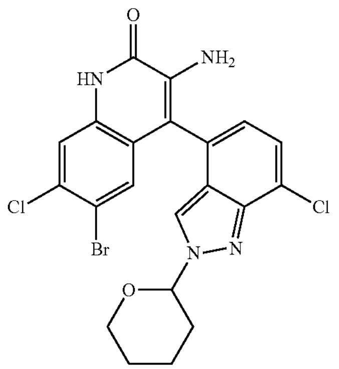

The title compound was synthesized from (2-amino-5-bromo-4-chlorophenyl)-[7-chloro-2-(oxan-2-yl)indazol-4-yl]methanone (compound a-28) under the same conditions as the production examples of the compounds a-9, a-10, and a-11.

LCMS: m/z 507 $[M+H]^+$

HPLC retention time: 4.96 min (analysis condition J)

Compound a-32

3-Amino-6-bromo-7-chloro-4-[7-chloro-2-(oxan-2-yl)indazol-4-yl]-1-[(4-methoxyphenyl)methyl]quinolin-2-one

[Formula 57]

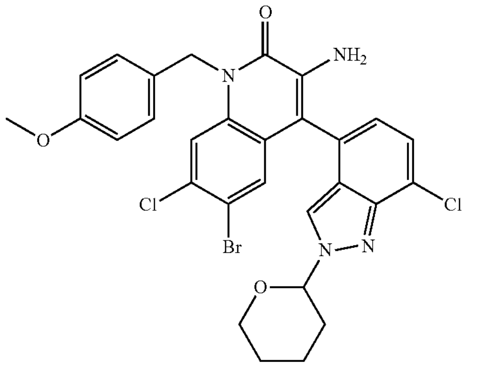

The title compound was synthesized from 3-amino-6-bromo-7-chloro-4-[7-chloro-2-(oxan-2-yl)indazol-4-yl]-1H-quinolin-2-one (compound a-31) under the same conditions as the production example of the compound a-12.

LCMS: m/z 627 $[M+H]^+$

HPLC retention time: 4.14 min (analysis condition O)

Compound a-33

3-Amino-7-chloro-4-[7-chloro-2-(oxan-2-yl)indazol-4-yl]-6-hydroxy-1-[(4-methoxyphenyl)methyl]quinolin-2-one

[Formula 58]

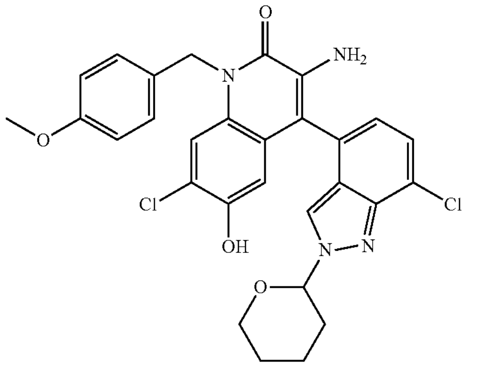

The title compound was synthesized from 3-amino-6-bromo-7-chloro-4-[7-chloro-2-(oxan-2-yl)indazol-4-yl]-1-[(4-methoxyphenyl)methyl]quinolin-2-one (compound a-32) under the same conditions as the production example of the compound a-13.

LCMS: m/z 565 $[M+H]^+$

HPLC retention time: 3.09 min (analysis condition O)

Compound a-34

3-Amino-7-chloro-4-[7-chloro-2-(oxan-2-yl)indazol-4-yl]-1-[(4-methoxyphenyl)methyl]-6-propan-2-yloxyquinolin-2-one

[Formula 59]

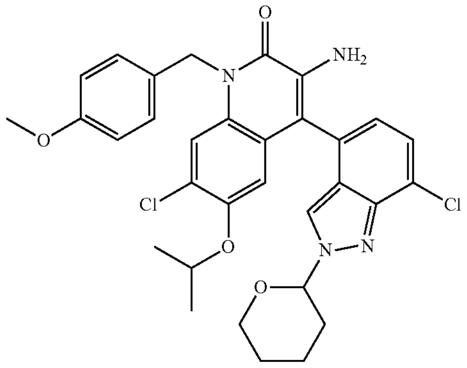

The title compound was synthesized from 3-amino-7-chloro-4-[7-chloro-2-(oxan-2-yl)indazol-4-yl]-6-hydroxy-1-[(4-methoxyphenyl)methyl]quinolin-2-one (compound a-33) under the same conditions as the production example of the compound a-14.

LCMS: m/z 607 $[M+H]^+$

HPLC retention time: 3.98 min (analysis condition O)

Compound A8

3-Amino-7-chloro-4-(7-chloro-1H-indazol-4-yl)-6-propan-2-yloxy-1H-quinolin-2-one

[Formula ]

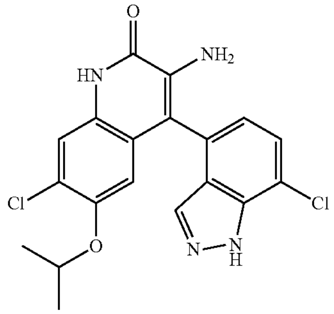

The title compound was synthesized from 3-amino-7-chloro-4-[7-chloro-2-(oxan-2-yl)indazol-4-yl]-1-[(4-methoxyphenyl)methyl]-6-propan-2-yloxyquinolin-2-one (compound a-34) under the same conditions as the production example of the compound A1.

LCMS: m/z 403 $[M+H]^+$

HPLC retention time: 0.72 min (analysis condition A)

Compound a-35

3-Amino-7-chloro-4-[7-chloro-2-(oxan-2-yl)indazol-4-yl]-6-(3,3-difluoropropoxy)-1-[(4-methoxyphenyl)methyl]quinolin-2-one

[Formula 61]

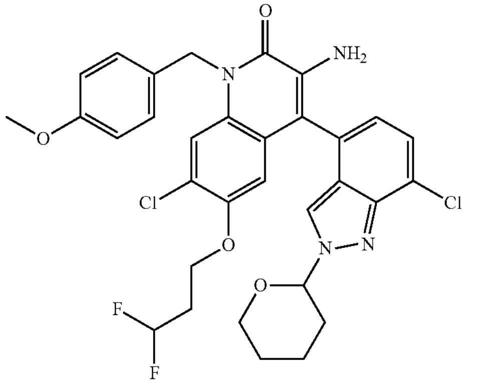

The title compound was synthesized from 3-amino-7-chloro-4-[7-chloro-2-(oxan-2-yl)indazol-4-yl]-6-hydroxy-1-[(4-methoxyphenyl)methyl]quinolin-2-one (compound a-33) under the same conditions as the production example of the compound a-15, except that cyanomethylenetributylphosphorane and THF were used instead of the 0.5 M solution of cyanomethylenetrimethylphosphorane in THF used in the production example of the compound a-15.

LCMS: m/z 643 $[M+H]^+$

HPLC retention time: 3.68 min (analysis condition O)

Compound A9

3-Amino-7-chloro-4-(7-chloro-1H-indazol-4-yl)-6-(3,3-difluoropropoxy)-1H-quinolin-2-one

[Formula 62]

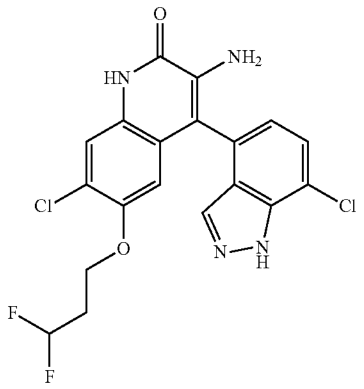

The title compound was synthesized from 3-amino-7-chloro-4-[7-chloro-2-(oxan-2-yl)indazol-4-yl]-6-(3,3-difluoropropoxy)-1-[(4-methoxyphenyl)methyl]quinolin-2-one (compound a-35) under the same conditions as the production example of the compound A1.

LCMS: m/z 439 $[M+H]^+$

HPLC retention time: 0.69 min (analysis condition A)

Compound a-36

6-Bromo-7-chloro-4-[7-chloro-2-(oxan-2-yl)indazol-4-yl]-2-[(4-methoxyphenyl)methoxy]quinolin-3-amine

[Formula 63]

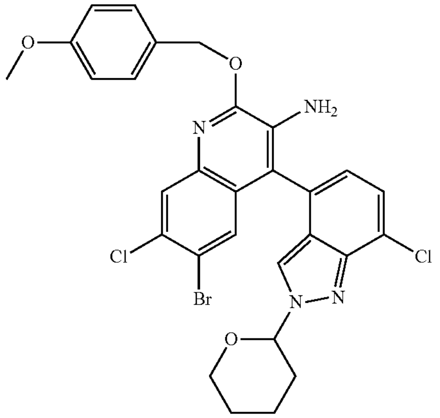

The title compound was synthesized from 3-amino-6-bromo-7-chloro-4-[7-chloro-2-(oxan-2-yl)indazol-4-yl]-1H-quinolin-2-one (compound a-31) under the same conditions as the production example of the compound a-16.

LCMS: m/z 627 $[M+H]^+$

HPLC retention time: 5.04 min (analysis condition O)

Compound a-37

3-Amino-7-chloro-4-[7-chloro-2-(oxan-2-yl)indazol-4-yl]-2-[(4-methoxyphenyl)methoxy]quinolin-6-ol

[Formula 64]

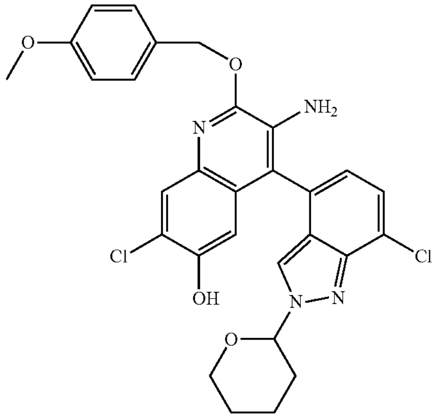

The title compound was synthesized from 6-bromo-7-chloro-4-[7-chloro-2-(oxan-2-yl)indazol-4-yl]-2-[(4-methoxyphenyl)methoxy]quinoline-3-amine (compound a-36) under the same conditions as the production example of the compound a-13.

LCMS: m/z 565 $[M+H]^+$

HPLC retention time: 2.98 min (analysis condition O)

Compound A10

3-Amino-7-chloro-4-(7-chloro-1H-indazol-4-yl)-6-cyclobutyloxy-1H-quinolin-2-one

[Formula 65]

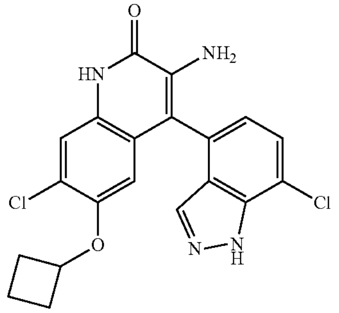

The title compound was synthesized from 3-amino-7-chloro-4-[7-chloro-2-(oxan-2-yl)indazol-4-yl]-2-[(4-methoxyphenyl)methoxy]quinolin-6-ol (compound a-37) under the same conditions as the production examples of the compounds a-15 and A7, except that cyanomethylenetributylphosphorane, THF, and cyclobutanol were used instead of the 0.5 M solution of cyanomethylenetrimethylphosphorane in THF and 3,3-difluoropropan-1-ol used in the production example of the compound a-15.

LCMS: m/z 415 $[M+H]^+$

HPLC retention time: 0.74 min (analysis condition A)

Compound A11

3-Amino-7-chloro-4-(7-chloro-1H-indazol-4-yl)-6-((1r,3r)-3-fluorocyclobutyl)oxy-1H-quinolin-2-one

[Formula 66]

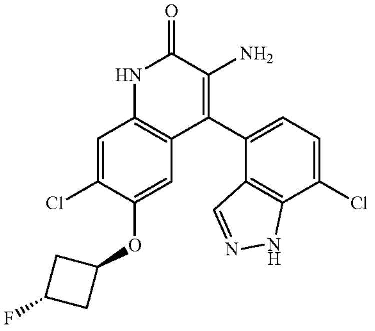

The title compound was synthesized from 3-amino-7-chloro-4-[7-chloro-2-(oxan-2-yl)indazol-4-yl]-2-[(4-methoxyphenyl)methoxy]quinolin-6-ol (compound a-37) under the same conditions as the production examples of the compounds a-14 and A7, except that the (1s,3s)-3-fluorocyclobutyl trifluoromethanesulfonate compound (a-102) was used instead of 2-iodopropane used in the production example of the compound a-14.

LCMS: m/z 433 $[M+H]^+$

HPLC retention time: 0.70 min (analysis condition A)

Compound A12

(1r,3r)-3-[[3-Amino-7-chloro-4-(7-chloro-1H-indazol-4-yl)-2-oxo-1H-quinolin-6-yl]oxy]cyclobutane-1-carbonitrile

[Formula 67]

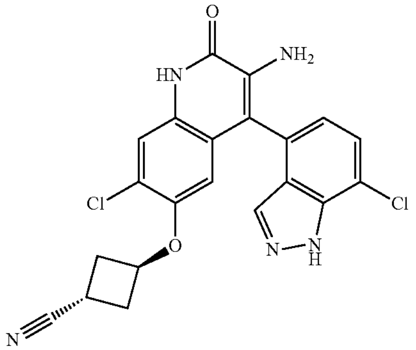

The title compound was synthesized from 3-amino-7-chloro-4-[7-chloro-2-(oxan-2-yl)indazol-4-yl]-2-[(4-methoxyphenyl)methoxy]quinolin-6-ol (compound a-37) under the same conditions as the production examples of the compounds a-14 and A7, except that (1s,3s)-3-cyanocyclobutyl trifluoromethanesulfonate (compound a-103) was used instead of 2-iodopropane used in the production example of the compound a-14.

LCMS: m/z 440 $[M+H]^+$

HPLC retention time: 0.64 min (analysis condition A)

Compound A13

3-Amino-7-chloro-4-(7-chloro-1H-indazol-4-yl)-6-(cyclopropylmethoxy)-1H-quinolin-2-one

[Formula 68]

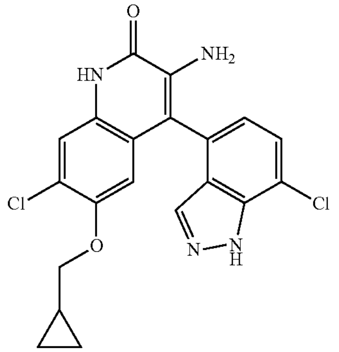

The title compound was synthesized from 3-amino-7-chloro-4-[7-chloro-2-(oxan-2-yl)indazol-4-yl]-2-[(4-methoxyphenyl)methoxy]quinolin-6-ol (compound a-37) under the same conditions as the production examples of the compounds a-14 and A7, except that (iodomethyl)cyclopropane was used instead of 2-iodopropane used in the production example of the compound a-14.

LCMS: m/z 415 [M+H]$^+$

HPLC retention time: 0.72 min (analysis condition A)

Compound A14

3-Amino-7-chloro-4-(7-chloro-1H-indazol-4-yl)-6-(3-fluoropropoxy)-1H-quinolin-2-one

[Formula 69]

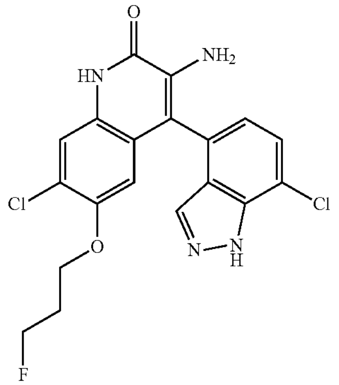

The title compound was synthesized from 3-amino-7-chloro-4-[7-chloro-2-(oxan-2-yl)indazol-4-yl]-2-[(4-methoxyphenyl)methoxy]quinolin-6-ol (compound a-37) under the same conditions as the production examples of the compounds a-14 and A7, except that 1-fluoro-3-iodopropane was used instead of 2-iodopropane used in the production example of the compound a-14.

LCMS: m/z 421 [M+H]$^+$

HPLC retention time: 0.68 min (analysis condition A)

Compound a-43

5-Bromo-3-iodo-6-methylpyridine-2-amine

[Formula 70]

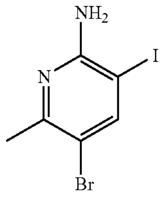

The title compound was synthesized from 6-amino-3-bromo-2-methylpyridine under the same conditions as the production example of the compound a-5.

LCMS: m/z 313 [M+H]$^+$

HPLC retention time: 2.55 min (analysis condition N)

Compound a-44

(E)-N'-(5-Bromo-3-iodo-6-methylpyridin-2-yl)-N,N-dimethylmethanimidamide

[Formula 71]

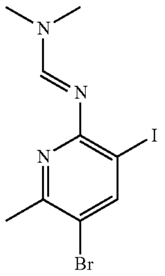

The title compound was synthesized from 5-bromo-3-iodo-6-methylpyridine-2-amine (compound a-43) under the same conditions as the production example of the compound a-6.

LCMS: m/z 368 [M+H]$^+$

HPLC retention time: 2.37 min (analysis condition N)

Compound a-45

(E)-N'-[5-bromo-3-[7-chloro-2-(oxan-2-yl)indazole-4-carbonyl]-6-methylpyridin-2-yl]-N,N-dimethyl-methanimidamide

[Formula 72]

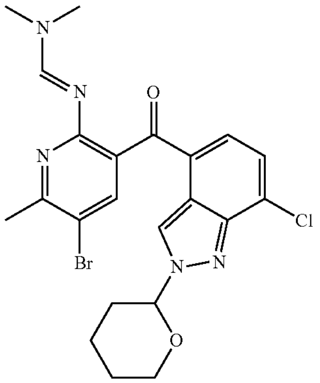

The title compound was synthesized from (E)-N'-(5-bromo-3-iodo-6-methylpyridine-2-yl)-N,N-dimethylmethanimidamide (compound a-44) under the same conditions as the production example of the compound a-7.

LCMS: m/z 504 [M+H]$^+$

HPLC retention time: 3.69 min (analysis condition J)

Compound a-46

(2-Amino-5-bromo-6-methylpyridin-3-yl)-[7-chloro-2-(oxan-2-yl)indazol-4-yl]methanone

[Formula 73]

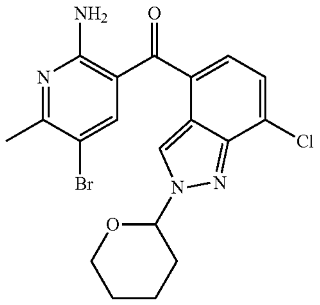

The title compound was synthesized from (E)-N'-[5-bromo-3-[7-chloro-2-(oxan-2-yl)indazole-4-carbonyl]-6-methylpyridin-2-yl]-N,N-dimethylmethanimidamide (compound a-45) under the same conditions as the production example of the compound a-8.

LCMS: m/z 449 [M+H]$^+$

HPLC retention time: 4.53 min (analysis condition J)

Compound a-49

3-Amino-6-bromo-4-[7-chloro-2-(oxan-2-yl)indazol-4-yl]-7-methyl-1H-1,8-naphthyridin-2-one

[Formula 74]

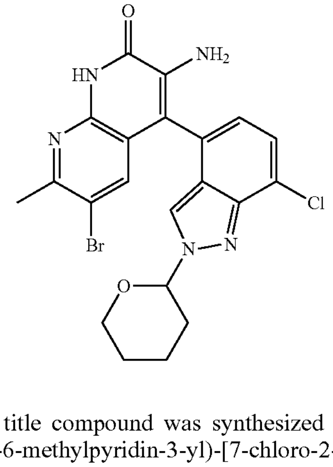

The title compound was synthesized from (2-amino-5-bromo-6-methylpyridin-3-yl)-[7-chloro-2-(oxan-2-yl)indazol-4-yl]methanone (compound a-46) under the same conditions as the production examples of the compounds a-9, a-10, and a-11.

LCMS: m/z 488 [M+H]$^+$

HPLC retention time: 4.61 min (analysis condition J)

Compound a-50

3-Amino-6-bromo-4-[7-chloro-2-(oxan-2-yl)indazol-4-yl]-7-methyl-1-(2-trimethylsilylethoxymethyl)-1,8-naphthyridin-2-one

[Formula 75]

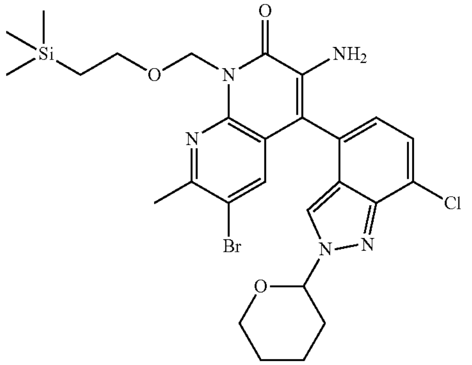

The title compound was synthesized from 3-amino-6-bromo-4-[7-chloro-2-(oxan-2-yl)indazol-4-yl]-7-methyl-1H-1,8-naphthyridin-2-one (compound a-49) under the same conditions as the production example of the compound a-22, except that potassium carbonate and DMA were used instead of 60% sodium hydride/mineral oil and THE used in the production example of the compound a-22. In addition, the reaction was carried out by heating the reaction mixture to 70° C.

LCMS: m/z 618 [M+H]$^+$

HPLC retention time: 6.51 min (analysis condition J)

Compound a-51

3-Amino-4-[7-chloro-2-(oxan-2-yl)indazol-4-yl]-6-hydroxy-7-methyl-1-(2-trimethylsilylethoxymethyl)-1,8-naphthyridin-2-one

[Formula 76]

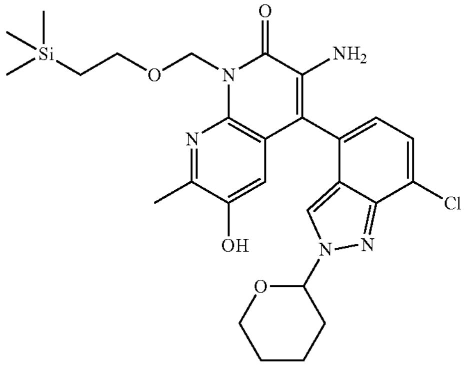

The title compound was synthesized from 3-amino-6-bromo-4-[7-chloro-2-(oxan-2-yl)indazol-4-yl]-7-methyl-1-(2-trimethylsilylethoxymethyl)-1,8-naphthyridin-2-one (compound a-50) under the same conditions as the production example of the compound a-13.

LCMS: m/z 556 $[M+H]^+$

HPLC retention time: 5.44 min (analysis condition J)

Compound A15

3-Amino-4-(7-chloro-1H-indazol-4-yl)-6-((1r,3r)-3-fluorocyclobutyl)oxy-7-methyl-1H-1,8-naphthyridin-2-one

[Formula 77]

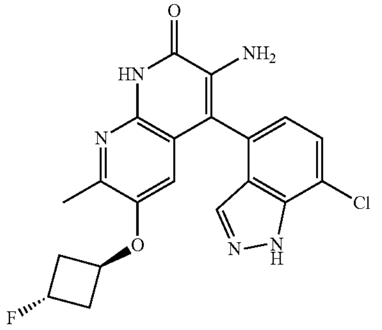

The title compound was synthesized from 3-amino-4-[7-chloro-2-(oxan-2-yl)indazol-4-yl]-6-hydroxy-7-methyl-1-(2-trimethylsilylethoxymethyl)-1,8-naphthyridin-2-one (compound a-51) under the same conditions as the production examples of the compounds a-14 and A7, except that (1s,3s)-3-fluorocyclobutyl trifluoromethanesulfonate (compound a-102) was used instead of 2-iodopropane used in the production example of the compound a-14.

LCMS: m/z 414 $[M+H]^+$

HPLC retention time: 0.65 min (analysis condition A)

Compound A16

(1r,3r)-3-[[6-Amino-5-(7-chloro-1H-indazol-4-yl)-2-methyl-7-oxo-8H-1,8-naphthyridine-3-yl]oxy]cyclobutane-1-carbonitrile

[Formula 78]

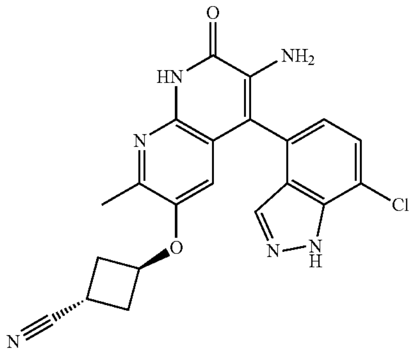

The title compound was synthesized from 3-amino-4-[7-chloro-2-(oxan-2-yl)indazol-4-yl]-6-hydroxy-7-methyl-1-(2-trimethylsilylethoxymethyl)-1,8-naphthyridin-2-one (compound a-51) under the same conditions as the production examples of the compounds a-14 and A7, except that, (1s,3s)-3-cyanocyclobutyl trifluoromethanesulfonate (compound a-103) was used instead of 2-iodopropane used in the production example of the compound a-14.

LCMS: m/z 421 $[M+H]^+$

HPLC retention time: 0.59 min (analysis condition A)

Compound a-54

[7-Chloro-2-(oxan-2-yl)indazol-4-yl]-morpholin-4-ylmethanone

[Formula 79]

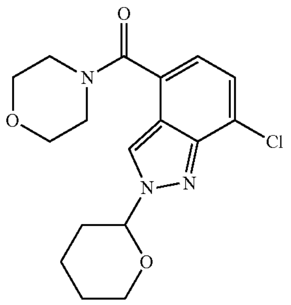

To a solution of (2,4,6-trichlorophenyl) 7-chloro-2-(oxan-2-yl)indazole-4-carboxylate (compound a-2, 7.35 g, 15.97 mmol) in THF (64.1 mL) in a reaction vessel, morpholine (4.17 g, 47.9 mmol) was added, and the mixture was stirred at 80° C. under nitrogen atmosphere for 5 hours. The reaction mixture was cooled to room temperature and concentrated under reduced pressure. The obtained residue was purified by silica gel column chromatography (DCM/MeOH) to obtain the title compound (2.93 g, yield 53%) as a light brown solid.

LCMS: m/z 350 $[M+H]^+$

HPLC retention time: 0.60 min (analysis condition A)

Compound a-55

(E)-N'-(2-bromo-4-chloro-6-iodophenyl)-N,N-dimethylmethanimidamide

[Formula 80]

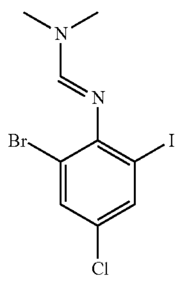

The title compound was synthesized from 2-bromo-4-chloro-6-iodo-aniline under the same conditions as the production example of the compound a-6.

LCMS: m/z 387 $[M+H]^+$

HPLC retention time: 0.55 min (analysis condition Q)

Compound a-56

(E)-N'-[2-bromo-4-chloro-6-[7-chloro-2-(oxan-2-yl) indazole-4-carbonyl]phenyl]-N,N-dimethylmethanimidamide

[Formula 81]

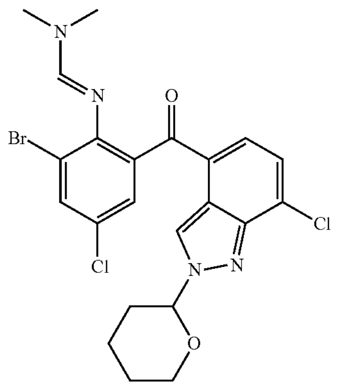

The title compound was synthesized from (E)-N'-(2-bromo-4-chloro-6-iodophenyl)-N,N-dimethylmethanimidamide (compound a-55) and [7-chloro-2-(oxan-2-yl)indazol-4-yl]-morpholin-4-ylmethanone (compound a-54) under the same conditions as the production example of the compound a-7, except that, a 1 M solution of isopropylmagnesium bromide in THF was used instead of the 1.3 M solution of isopropylmagnesium chloride-lithium chloride complex in THE used in the production example of the compound a-7.

LCMS: m/z 523 $[M+H]^+$

HPLC retention time: 0.89 min (analysis condition Q)

Compound a-57

(2-Amino-3-bromo-5-chlorophenyl)-[7-chloro-2-(oxan-2-yl)indazol-4-yl]methanone

[Formula 82]

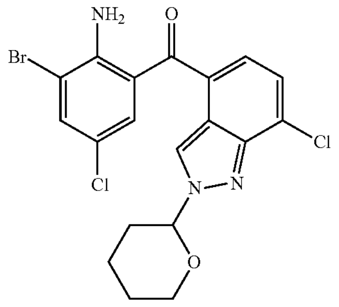

The title compound was synthesized from (E)-N'-[2-bromo-4-chloro-6-[7-chloro-2-(oxan-2-yl)indazole-4-carbonyl]phenyl]-N,N-dimethylmethanimidamide (compound a-56) under the same conditions as the production example of the compound a-8.

LCMS: m/z 468 $[M+H]^+$

HPLC retention time: 1.14 min (analysis condition Q)

Compound A17

3-Amino-8-bromo-6-chloro-4-(7-chloro-1H-indazol-4-yl)-1H-quinolin-2-one

[Formula 83]

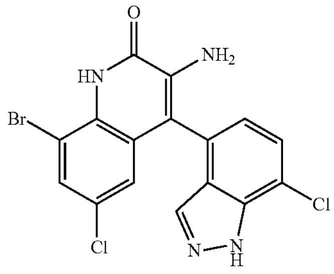

LCMS: m/z 423 $[M+H]^+$

HPLC retention time: 0.79 min (analysis condition A)

Compound a-60

3-Amino-8-bromo-6-chloro-4-[7-chloro-2-(oxan-2-yl)indazol-4-yl]-1H-quinolin-2-one

[Formula 84]

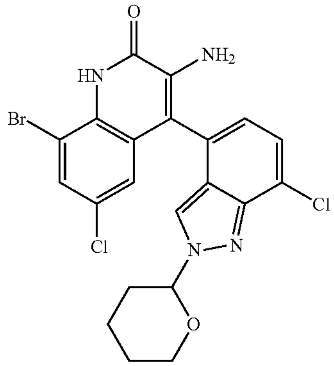

The compound A17 and the compound a-60 were synthesized from (2-amino-3-bromo-5-chlorophenyl)-[7-chloro-2-(oxan-2-yl)indazol-4-yl]methanone (compound a-57) under the same conditions as the production examples of the compounds a-9, a-10, and a-11, except that, pyridine and THF were used instead of DMA used in the production example of the compound a-9.

LCMS: m/z 507 $[M+H]^+$

HPLC retention time: 0.96 min (analysis condition Q)

Compound a-61

3-Amino-6-chloro-4-[7-chloro-2-(oxan-2-yl)indazol-4-yl]-8-(2-trimethylsilylethynyl)-1H-quinolin-2-one

[Formula 85]

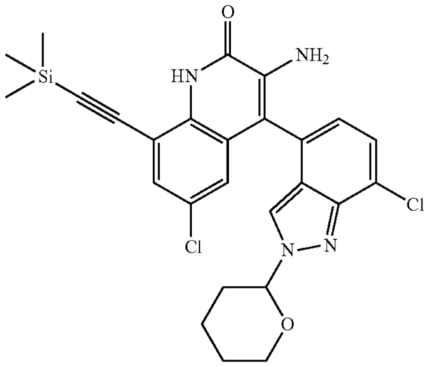

3-Amino-8-bromo-6-chloro-4-[7-chloro-2-(oxan-2-yl)indazol-4-yl]-1H-quinolin-2-one (compound a-60, 100 mg, 0.197 mmol) in a reaction vessel, ethynyltrimethylsilane (166 μL, 1.181 mmol), bis(triphenylphosphine)palladium (II) dichloride (27.6 mg, 0.039 mmol), triethylamine (137 μL, 0.984 mmol), and copper (I) iodide (11.2 mg, 0.059 mmol) were suspended in DMF (984 μL), the reaction vessel was degassed under reduced pressure and subjected to nitrogen replacement, and then the mixture was stirred at 130° C. for 1 hour. The reaction mixture was cooled to room temperature and purified by silica gel column chromatography (hexane/ethyl acetate) to obtain the title compound (60 mg, yield 58%) as a grayish solid.

LCMS: m/z 525 $[M+H]^+$

HPLC retention time: 1.17 min (analysis condition B)

Compound A18

3-Amino-6-chloro-4-(7-chloro-1H-indazol-4-yl)-8-ethynyl-1H-quinolin-2-one

[Formula 86]

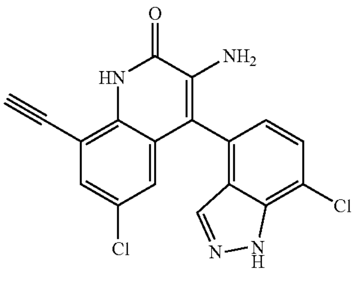

To a solution of 3-amino-6-chloro-4-[7-chloro-2-(oxan-2-yl)indazol-4-yl]-8-(2-trimethylsilylethynyl)-1H-quinolin-2-one (compound a-61, 60 mg, 0.114 mmol) in MeOH (1.14 mL), potassium carbonate (15.78 mg, 0.114 mmol) was added, and the mixture was stirred at room temperature for 2 hours. Water was added to the reaction mixture, and the mixture was extracted with DCM. The organic layer was dried over anhydrous sodium sulfate, the drying agent was filtered off, and then the filtrate was concentrated under reduced pressure. A 0.5 M solution of hydrogen chloride in MeOH (4.41 mL) was added to the residue, and the mixture was stirred at room temperature for 1 hour. The reaction mixture was concentrated under reduced pressure, and the obtained residue was purified by reversed phase column chromatography (0.1% aqueous formic acid solution/0.1% formic acid in acetonitrile solution) to obtain the title compound (28.3 mg, yield 70%) as a colorless solid.

LCMS: m/z 369 $[M+H]^+$

HPLC retention time: 0.75 min (analysis condition A)

Compound a-62

3-Amino-6-chloro-4-[7-chloro-2-(oxan-2-yl)indazol-4-yl]-8-propyl-1H-quinolin-2-one

[Formula 87]

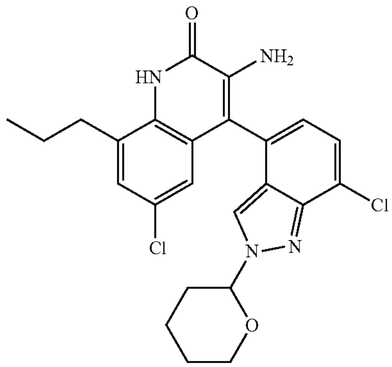

To 3-amino-8-bromo-6-chloro-4-[7-chloro-2-(oxan-2-yl)indazol-4-yl]-1H-quinolin-2-one (compound a-60), tetrakis(triphenylphosphine)palladium (0) (45.5 mg, 0.039 mmol), cesium carbonate (385 mg, 1.181 mmol), and potassium propyltrifluoroborate (148 mg, 0.984 mmol) in a reaction vessel, dioxane (1574 μL) and water (394 μL) were added, the reaction vessel was degassed under reduced pressure and subjected to nitrogen replacement, and then the mixture was stirred at 120° C. for 5 hours. The reaction mixture was cooled to room temperature, purified by reversed phase column chromatography (0.1% aqueous formic acid solution/0.1% formic acid in acetonitrile solution), and concentrated. The residue was purified by silica gel column chromatography (hexane/ethyl acetate) to obtain the title compound (32 mg, yield 34%) as a colorless solid.

LCMS: m/z 471 $[M+H]^+$

HPLC retention time: 1.00 min (analysis condition Q)

Compound A22

3-Amino-6-chloro-4-(7-chloro-1H-indazol-4-yl)-8-propyl-1H-quinolin-2-one

[Formula 88]

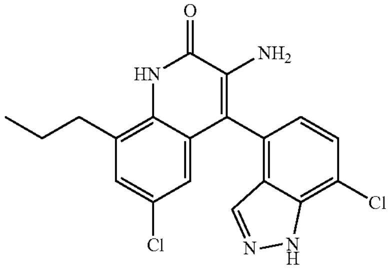

To 3-amino-6-chloro-4-[7-chloro-2-(oxan-2-yl)indazol-4-yl]-8-propyl-1H-quinolin-2-one (compound a-62, 30 mg, 0.064 mmol) in a reaction vessel, a 0.5 M solution of hydrogen chloride in MeOH (2.55 mL) was added, and the mixture was stirred at room temperature for 10 min. To the reaction mixture, acetonitrile was added, and the produced solid was collected by filtration to obtain the title compound (12.7 mg, yield 52%) as a colorless solid.

LCMS: m/z 387 $[M+H]^+$

HPLC retention time: 0.88 min (analysis condition A)

Compound A23

3-Amino-6-chloro-4-(7-chloro-1H-indazol-4-yl)-8-ethenyl-1H-quinolin-2-one

[Formula 89]

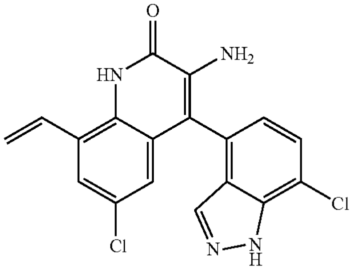

The title compound was synthesized from 3-amino-8-bromo-6-chloro-4-[7-chloro-2-(oxan-2-yl)indazol-4-yl]-1H-quinolin-2-one (compound a-60) under the same conditions as the production examples of the compounds a-62 and A22, except that potassium vinyltrifluoroborate was used instead of potassium propyltrifluoroborate used in the production example of the compound a-62.

LCMS: m/z 371 $[M+H]^+$

HPLC retention time: 0.79 min (analysis condition A)

Compound A24

3-Amino-6-chloro-4-(7-chloro-1H-indazol-4-yl)-8-cyclopropyl-1H-quinolin-2-one

[Formula 90]

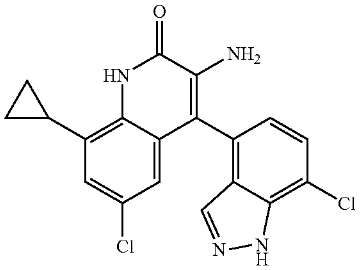

The title compound was synthesized from 3-amino-8-bromo-6-chloro-4-[7-chloro-2-(oxan-2-yl)indazol-4-yl]-1H-quinolin-2-one (compound a-60) under the same conditions as the production examples of the compounds a-62 and A22, except that potassium cyclopropyltrifluoroborate was used instead of potassium propyltrifluoroborate used in the production example of the compound a-62.

LCMS: m/z 385 $[M+H]^+$

HPLC retention time: 0.83 min (analysis condition A)

Compound A25

3-Amino-6-chloro-4-(7-chloro-1H-indazol-4-yl)-8-ethyl-1H-quinolin-2-one

[Formula 91]

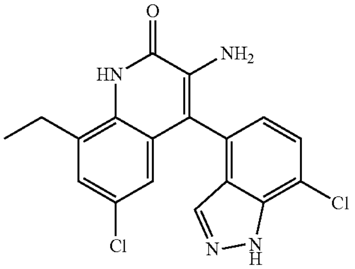

The title compound was synthesized from 3-amino-8-bromo-6-chloro-4-[7-chloro-2-(oxan-2-yl)indazol-4-yl]-1H-quinolin-2-one (compound a-60) under the same conditions as the production examples of the compounds a-62 and A22, except that potassium ethyltrifluoroborate was used instead of potassium cyclopropyltrifluoroborate used in the production example of the compound a-62.

LCMS: m/z 373 $[M+H]^+$

HPLC retention time: 0.80 min (analysis condition A)

Compound A26

3-Amino-6-chloro-4-(7-chloro-1H-indazol-4-yl)-8-methyl-1H-quinolin-2-one

[Formula 92]

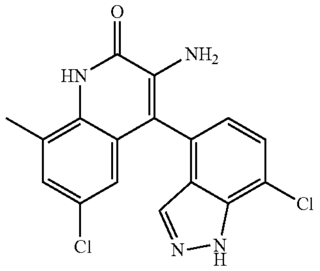

The title compound was synthesized from 3-amino-8-bromo-6-chloro-4-[7-chloro-2-(oxan-2-yl)indazol-4-yl]-1H-quinolin-2-one (compound a-60) under the same conditions as the production examples of the compounds a-62 and A22, except that potassium methyltrifluoroborate was used instead of potassium propyltrifluoroborate used in the production example of the compound a-62.

LCMS: m/z 359 $[M+H]^+$

HPLC retention time: 0.75 min (analysis condition A)

Compound A19

3-Amino-6-chloro-4-(7-chloro-1H-indazol-4-yl)-8-propan-2-yl-1H-quinolin-2-one

[Formula 93]

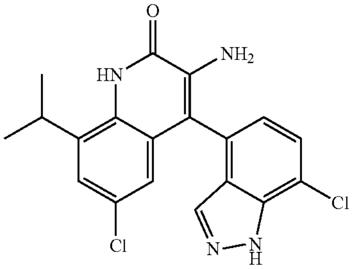

3-Amino-8-bromo-6-chloro-4-(7-chloro-1H-indazol-4-yl)-1H-quinolin-2-one (compound A17, 100 mg, 0.236 mmol) in a reaction vessel, palladium(II) acetate (5.29 mg, 0.024 mmol), and 2-(dicyclohexylphosphino)-2'-(dimethylamino) biphenyl (18.56 mg, 0.047 mmol) were suspended in THF (472 μL), the reaction vessel was degassed under reduced pressure and subjected to argon replacement. A 0.5 M solution of 2-propylzincbromide in THF (2.83 mL, 1.415 mmol) was added thereto, and the mixture was stirred at room temperature for 4 hours. The reaction mixture was concentrated under reduced pressure, and the obtained residue was purified by reversed phase column chromatography (0.1% aqueous formic acid solution/0.1% formic acid in acetonitrile solution) to obtain the title compound (9.3 mg, yield 10%) as a colorless solid.

LCMS: m/z 387 $[M+H]^+$

HPLC retention time: 0.80 min (analysis condition A)

Compound A20

3-Amino-6,8-dichloro-4-(7-chloro-1H-indazol-4-yl)-1H-quinolin-2-one

[Formula 94]

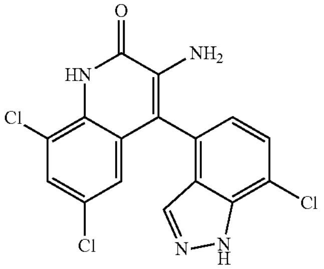

3-Amino-8-bromo-6-chloro-4-(7-chloro-1H-indazol-4-yl)-1H-quinolin-2-one (compound A17, 80 mg, 0.189 mmol) in a reaction vessel and copper (I) chloride (93 mg, 0.943 mmol) were suspended in NMP (943 μL), and the mixture was stirred at 150° C. for 15 hours. The reaction mixture was purified by reversed phase column chromatography (0.1% aqueous formic acid solution/0.1% formic acid in acetonitrile solution) to obtain the title compound (43 mg, yield 60%) as a light brown solid.

LCMS: m/z 379 $[M+H]^+$

HPLC retention time: 0.81 min (analysis condition A)

Compound A21

3-Amino-6-chloro-4-(7-chloro-1H-indazol-4-yl)-2-oxo-1H-quinoline-8-carbonitrile

[Formula 95]

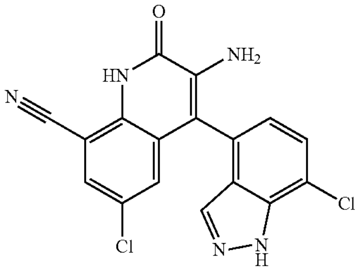

The title compound was synthesized from 3-amino-8-bromo-6-chloro-4-(7-chloro-1H-indazol-4-yl)-1H-quinolin-2-one (compound A17) under the same conditions as the production example of the compound A20, except that copper (I) cyanide was used instead of copper (I) chloride used in the production example of the compound A20.

LCMS: m/z 370 $[M+H]^+$

HPLC retention time: 0.73 min (analysis condition A)

Compound a-68

(E)-N'-(5-bromo-4-chloro-2-iodophenyl)-N,N-dimethylmethanimidamide

[Formula 96]

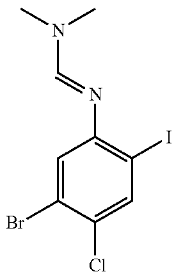

The title compound was synthesized from 3-bromo-4-chloroaniline under the same conditions as the production examples of the compounds a-5 and a-6, except that DMSO was used instead of acetic acid used in the production example of the compound a-5.

LCMS: m/z 387 $[M+H]^+$

HPLC retention time: 0.53 min (analysis condition B)

Compound a-69

(E)-N'-[5-bromo-4-chloro-2-[7-chloro-2-(oxan-2-yl)indazole-4-carbonyl]phenyl]-N,N-dimethylmethanimidamide

[Formula 97]

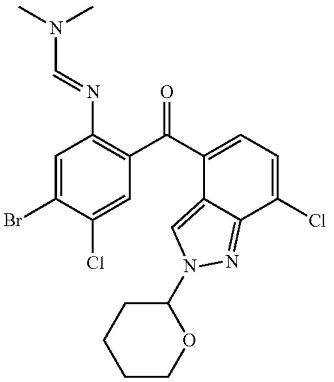

The title compound was synthesized from (E)-N'-(5-bromo-4-chloro-2-iodophenyl)-N,N-dimethylmethanimidamide (compound a-68) and [7-chloro-2-(oxan-2-yl)indazol-4-yl]-morpholin-4-ylmethanone (compound a-54) under the same conditions as the production example of the compound a-7, except that THF was used instead of toluene used in the production example of the compound a-7.

LCMS: m/z 523 $[M+H]^+$

HPLC retention time: 0.71 min (analysis condition B)

Compound a-70

(2-Amino-4-bromo-5-chlorophenyl)-[7-chloro-2-(oxan-2-yl)indazol-4-yl]methanone

[Formula 98]

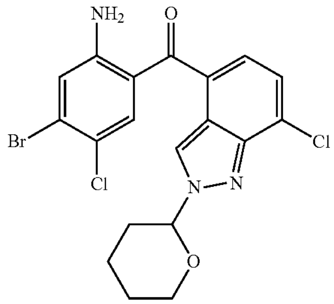

The title compound was synthesized from (E)-N'-[5-bromo-4-chloro-2-[7-chloro-2-(oxan-2-yl)indazole-4-carbonyl]phenyl]-N,N-dimethylmethanimidamide (compound a-69) under the same conditions as the production example of the compound a-8.

LCMS: m/z 468 $[M+H]^+$

HPLC retention time: 1.05 min (analysis condition B)

Compound a-71

N-[5-bromo-4-chloro-2-[7-chloro-2-(oxan-2-yl)indazole-4-carbonyl]phenyl]-2-chloroacetamide

[Formula 99]

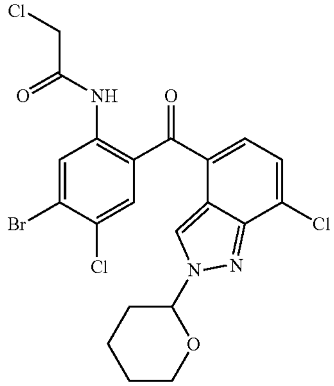

A solution of (2-amino-4-bromo-5-chlorophenyl)-[7-chloro-2-(oxan-2-yl)indazol-4-yl]methanone (compound a-70, 120 mg, 0.256 mmol) in DCM (1.2 mL) in a reaction vessel was cooled to 0° C., pyridine (33.1 μL) and chloroacetyl chloride (30.7 μL, 0.384 mmol) were added thereto, and the mixture was stirred for 30 min. The reaction mixture was concentrated under reduced pressure to obtain the crude product of the title compound.

LCMS: m/z 544 $[M+H]^+$

HPLC retention time: 1.07 min (analysis condition B)

Compound a-72

7-Bromo-6-chloro-4-[7-chloro-2-(oxan-2-yl)indazol-4-yl]-3-pyridin-1-ium-1-yl-1H-quinolin-2-one; chloride

[Formula 100]

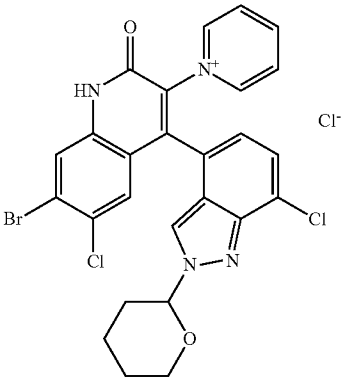

Pyridine (3.6 mL) was added to the crude product of N-[5-bromo-4-chloro-2-[7-chloro-2-(oxan-2-yl)indazole-4-carbonyl]phenyl]-2-chloroacetamide (compound a-71) in a reaction vessel, and the mixture was heated at 80° C. for 1 hour to obtain a pyridine solution of the title compound.

LCMS: m/z 569 $[M]^+$

HPLC retention time: 0.67 min (analysis condition B)

Compound a-73

3-Amino-7-bromo-6-chloro-4-[7-chloro-2-(oxan-2-yl)indazol-4-yl]-1H-quinolin-2-one

[Formula 101]

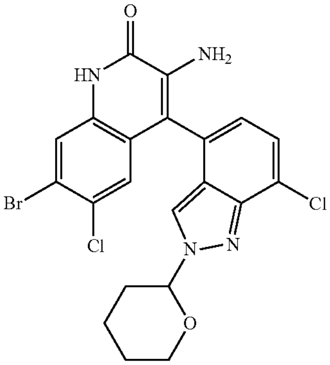

To the pyridine solution of 7-bromo-6-chloro-4-[7-chloro-2-(oxan-2-yl)indazol-4-yl]-3-pyridin-1-ium-1-yl-1H-quinolin-2-one; chloride (compound a-72) in a reaction vessel, hydrazine monohydrate (253 μL, 5.12 mmol) was added, and the mixture was further stirred at 80° C. for 1 hour. The reaction mixture was concentrated to obtain a pyridine solution of the title compound.

LCMS: m/z 507 $[M+H]^+$

HPLC retention time: 0.92 min (analysis condition B)

Compound A27

3-Amino-7-bromo-6-chloro-4-(7-chloro-1H-indazol-4-yl)-1H-quinolin-2-one

[Formula 102]

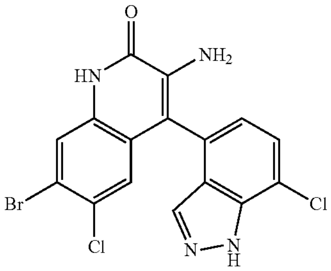

To the pyridine solution of 3-amino-7-bromo-6-chloro-4-[7-chloro-2-(oxan-2-yl)indazol-4-yl]-1H-quinolin-2-one (compound a-73) in a reaction vessel, a 10% solution of hydrogen chloride in MeOH (2.36 mL) was added, and the mixture was stirred at room temperature for 1 hour. The reaction mixture was concentrated. To the obtained residue, a saturated aqueous sodium bicarbonate solution and water were added, and the mixture was extracted with ethyl acetate. The organic layer was sequentially washed with water and brine, and concentrated. The obtained residue was suspended in acetonitrile, and the solid was collected by filtration to obtain the title compound (91 mg, yield 84%) as a light brown solid.

LCMS: m/z 423 $[M+H]^+$

HPLC retention time: 0.75 min (analysis condition A)

Compound A28

3-Amino-6-chloro-4-(7-chloro-1H-indazol-4-yl)-7-ethyl-1H-quinolin-2-one

[Formula 103]

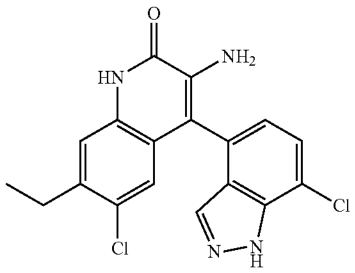

To a solution of 3-amino-7-bromo-6-chloro-4-(7-chloro-1H-indazol-4-yl)-1H-quinolin-2-one (compound A27, 10 mg, 0.024 mmol) in DMA (100 μL) in a reaction vessel, a 1 M solution of diethylzinc in hexane (94 μL) was added, the reaction vessel was degassed under reduced pressure and subjected to nitrogen replacement, then CPhos Pd G3 (1.9 mg, 2.36 μmol) was added thereto, and the mixture was stirred at room temperature for 1 hour. To the reaction mixture, a 10% aqueous formic acid solution was added, and the mixture was extracted with ethyl acetate. The organic layer was dried over anhydrous sodium sulfate, the drying agent was filtered off, and then the filtrate was concentrated under reduced pressure. The obtained residue was purified by reversed phase column chromatography (0.1% aqueous formic acid solution/0.1% formic acid in acetonitrile solution) to obtain the title compound (2.1 mg, yield 24%) as a colorless solid.

LCMS: m/z 373 [M+H]$^+$

HPLC retention time: 2.17 min (analysis condition D)

Compound A29

3-Amino-6-chloro-4-(7-chloro-1H-indazol-4-yl)-2-oxo-1H-quinoline-7-carbonitrile

[Formula 104]

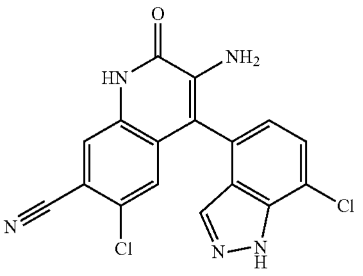

To a solution of 3-amino-7-bromo-6-chloro-4-(7-chloro-1H-indazol-4-yl)-1H-quinolin-2-one (compound A27, 15 mg, 0.035 mmol) in DMA (300 μL) in a reaction vessel, zinc cyanide (12.46 mg, 0.106 mmol) and XPhos Pd G4 (1.5 mg, 1.769 μmol) were added, the reaction vessel was degassed under reduced pressure and subjected to nitrogen replacement, and then the mixture was heated at 100° C. for 4 hours. XPhos Pd G4 (3.04 mg, 3.54 μmol) was added thereto, and the mixture was further heated at 100° C. for 6 hours. The reaction mixture was cooled to room temperature, a 10% aqueous formic acid solution was added, and the produced solid was collected by filtration and washed with ethyl acetate. The solid was purified by reversed phase column chromatography to obtain the title compound (2 mg, yield 15%) as a grayish solid.

LCMS: m/z 370 [M+H]$^+$

HPLC retention time: 0.67 min (analysis condition B)

Compound a-75

(E)-N'-[4-chloro-5-(difluoromethoxy)-2-iodophenyl]-N,N-dimethylmethanimidamide

[Formula 105]

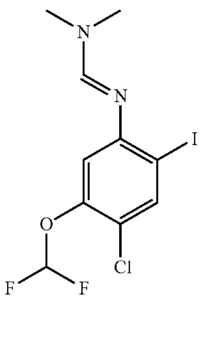

The title compound was synthesized from 4-chloro-3-(difluoromethoxy) aniline under the same conditions as the production examples of the compounds a-5 and a-6, except that DMSO was used instead of acetic acid used in the production example of the compound a-5.

LCMS: m/z 375 [M+H]$^+$

HPLC retention time: 0.54 min (analysis condition B)

Compound a-76

(E)-N'-[4-chloro-2-[7-chloro-2-(oxan-2-yl)indazole-4-carbonyl]-5-(difluoromethoxy)phenyl]-N,N-dimethylmethanimidamide

[Formula 106]

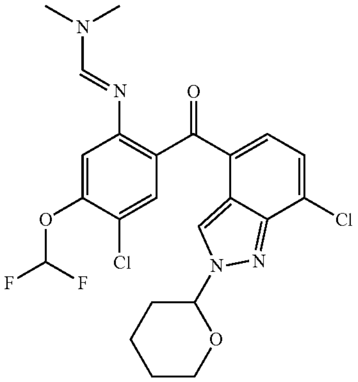

The title compound was synthesized from (E)-N'-[4-chloro-5-(difluoromethoxy)-2-iodophenyl]-N,N-dimethylmethanimidamide (compound a-75) and [7-chloro-2-(oxan-2-yl)indazol-4-yl]-morpholin-4-ylmethanone (compound a-54) under the same conditions as the production example of the compound a-7, except that THF was used instead of toluene used in the production example of the compound a-7.

LCMS: m/z 511 [M+H]$^+$

HPLC retention time: 0.71 min (analysis condition B)

Compound a-77

[2-Amino-5-chloro-4-(difluoromethoxy)phenyl]-[7-chloro-2-(oxan-2-yl)indazol-4-yl]methanone

[Formula 107]

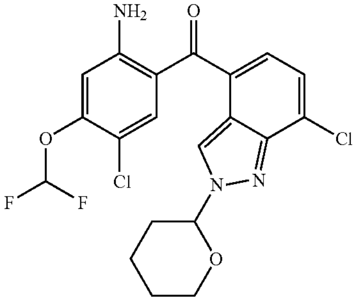

The title compound was synthesized from (E)-N'-[4-chloro-2-[7-chloro-2-(oxan-2-yl)indazole-4-carbonyl]-5-(difluoromethoxy)phenyl]-N,N-dimethylmethanimidamide (compound a-76) under the same conditions as the production example of the compound a-8.

LCMS: m/z 456 $[M+H]^+$

HPLC retention time: 0.98 min (analysis condition B)

Compound A30

3-Amino-6-chloro-4-(7-chloro-1H-indazol-4-yl)-7-(difluoromethoxy)-1H-quinolin-2-one

[Formula 108]

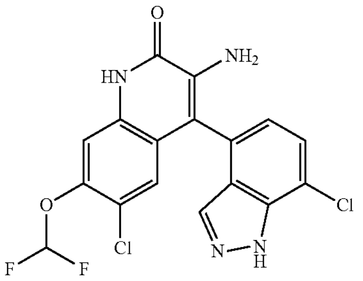

The title compound was synthesized from [2-amino-5-chloro-4-(difluoromethoxy)phenyl]-[7-chloro-2-(oxan-2-yl)indazol-4-yl]methanone (compound a-77) under the same conditions as the production examples of the compounds a-71, a-72, a-73, and A27.

LCMS: m/z 411 $[M+H]^+$

HPLC retention time: 0.72 min (analysis condition B)

Compound a-79

(E)-N'-(4-bromo-2-iodophenyl)-N,N-dimethylmethanimidamide

[Formula 109]

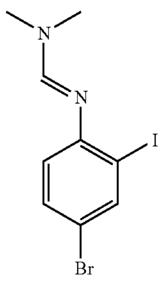

The title compound was synthesized from 4-bromoaniline under the same conditions as the production examples of the compounds a-5 and a-6, except that DMSO was used instead of acetic acid used in the production example of the compound a-5.

LCMS: m/z 353 $[M+H]^+$

HPLC retention time: 0.39 min (analysis condition A)

Compound a-80

(E)-N'-[4-bromo-2-[7-chloro-2-(oxan-2-yl)indazole-4-carbonyl]phenyl]-N,N-dimethylmethanimidamide

[Formula 110]

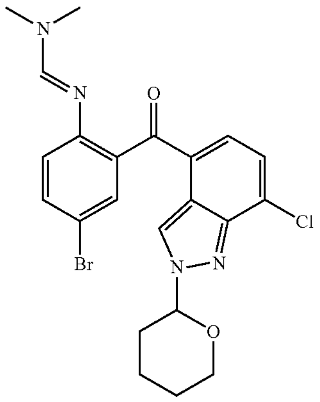

The title compound was synthesized from (E)-N'-(4-bromo-2-iodophenyl)-N,N-dimethylmethanimidamide (compound a-79) and [7-chloro-2-(oxan-2-yl)indazol-4-yl]-morpholin-4-ylmethanone (compound a-54) under the same conditions as the production example of the compound a-7, except that THF was used instead of toluene used in the production example of the compound a-7.

LCMS: m/z 489 $[M+H]^+$

HPLC retention time: 0.56 min (analysis condition A)

Compound a-81

(2-Amino-5-bromophenyl)-[7-chloro-2-(oxan-2-yl)indazol-4-yl]methanone

[Formula 111]

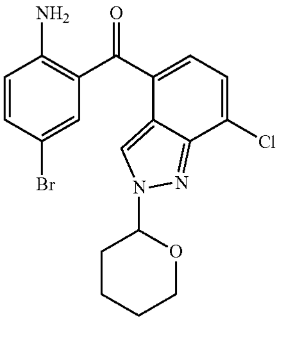

The title compound was synthesized from (E)-N'-[4-bromo-2-[7-chloro-2-(oxan-2-yl)indazole-4-carbonyl]phenyl]-N,N-dimethylmethanimidamide (compound a-80) under the same conditions as the production example of the compound a-8.

LCMS: m/z 434 $[M+H]^+$

HPLC retention time: 0.96 min (analysis condition A)

Compound a-82 tert-Butyl N-[6-bromo-4-[7-chloro-2-(oxan-2-yl) indazol-4-yl]-2-oxo-1H-quinolin-3-yl]carbamate

[Formula 112]

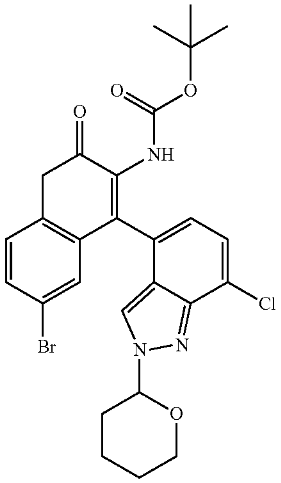

To a solution of (2-amino-5-bromophenyl)-[7-chloro-2-(oxan-2-yl)indazol-4-yl]methanone (compound a-81, 1 g, 2.3 mmol) in THF (10 mL) in a reaction vessel, a 1 M solution of LiHMDS in THF (13.8 mL, 13.8 mmol) was added, and the mixture was stirred at room temperature for 30 min. To the reaction mixture, N-(tert-butoxycarbonyl) glycine methyl (1.306 g, 6.9 mmol) was added, and the mixture was further stirred at room temperature for 30 min. To the reaction mixture, water (4 mL) was added, and the mixture was stirred for 30 min. To the reaction mixture, formic acid (0.62 mL, 16.1 mmol) and water were added, and the mixture was extracted three times with ethyl acetate. The organic layer was concentrated under reduced pressure, and the obtained residue was purified by silica gel column chromatography to obtain the title compound (1.2 g, yield 91%) as a solid.

LCMS: m/z 573 $[M+H]^+$

HPLC retention time: 0.87 min (analysis condition A)

Compound a-83 tert-Butyl N-[6-acetyl-4-(7-chloro-1H-indazol-4-yl)-2-oxo-1H-quinolin-3-yl]carbamate

[Formula 113]

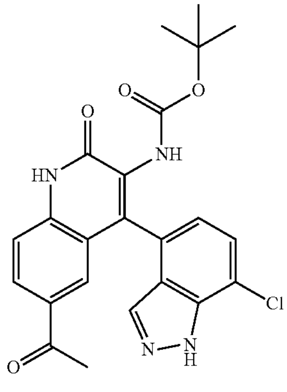

To a solution of tert-butyl N-[6-bromo-4-[7-chloro-2-(oxan-2-yl)indazol-4-yl]-2-oxo-1H-quinolin-3-yl]carbamate (compound a-82, 100 mg, 0.174 mmol) in 1,4-dioxane (1 mL) in a reaction vessel, tetrakis (triphenylphosphine)palladium (0) (20.1 mg, 0.017 mmol) and tributyl(1-ethoxyvinyl) stannane (69.2 mg, 0.192 mmol) were added, the mixture was degassed under reduced pressure and subjected to nitrogen replacement, and then the mixture was stirred at 80° C. for 3 hours. The reaction mixture was cooled to room temperature, then a 1 M hydrochloric acid was added thereto, and the mixture was stirred at room temperature for 3 hours. The reaction mixture was extracted with ethyl acetate, and the organic layer was concentrated under reduced pressure to obtain the crude product of the title compound.

LCMS: m/z 453 $[M+H]^+$

HPLC retention time: 0.60 min (analysis condition A)

Compound A31

6-Acetyl-3-amino-4-(7-chloro-1H-indazol-4-yl)-1H-quinolin-2-one

[Formula 114]

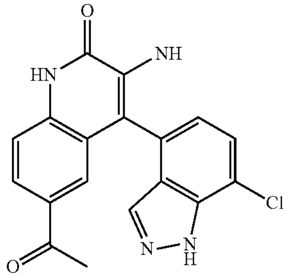

The title compound was synthesized from the crude product of tert-butyl N-[6-acetyl-4-(7-chloro-1H-indazol-4-yl)-2-oxo-1H-quinolin-3-yl]carbamate (compound a-83) under the same conditions as the production example of the compound A22.

LCMS: m/z 353 $[M+H]^+$

HPLC retention time: 0.55 min (analysis condition B)

Compound A32

3-Amino-4-(7-chloro-1H-indazol-4-yl)-6-(1-hydroxyethyl)-1H-quinolin-2-one

[Formula 115]

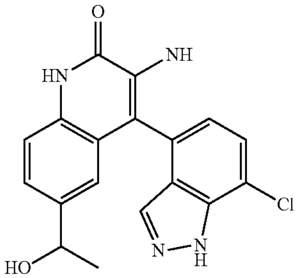

To a solution of 6-acetyl-3-amino-4-(7-chloro-1H-indazol-4-yl)-1H-quinolin-2-one (compound A31, 5 mg, 0.014 mmol) in MeOH (200 μL), sodium borohydride (1.61 mg, 0.043 mmol) was added, and the mixture was stirred at room temperature for 1 hour. The reaction mixture was purified by reversed phase column chromatography to obtain the title compound (3.03 mg, yield 60%) as a grayish solid.

LCMS: m/z 355 $[M+H]^+$

HPLC retention time: 0.49 min (analysis condition B)

Compound a-84 tert-Butyl 4-[4-[7-chloro-2-(oxan-2-yl)indazol-4-yl]-3-[(2-methylpropan-2-yl)oxycarbonylamino]-2-oxo-1H-quinolin-6-yl]piperidine-1-carboxylate

[Formula 116]

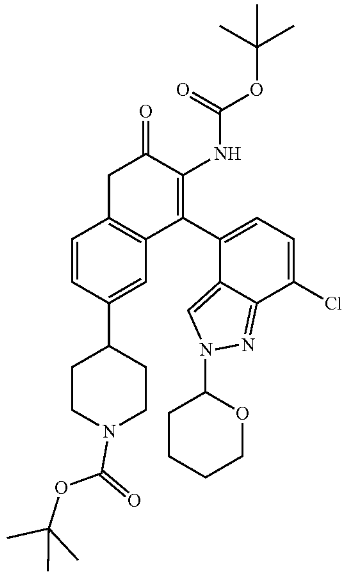

The title compound was synthesized from tert-butyl N-[6-bromo-4-[7-chloro-2-(oxan-2-yl)indazol-4-yl]-2-oxo-1H-quinolin-3-yl]carbamate (compound a-82) under the same conditions as the production example of the compound A28, except that a solution of 1 M 1-(tert-butoxycarbonyl) piperidin-4-yl]zinc iodide in DMA, and THF were used instead of the 1 M solution of diethylzinc in hexane, and DMA used in the production example of the compound A28.

LCMS: m/z 678.6 $[M+H]^+$

HPLC retention time: 2.30 min (analysis condition G)

Compound A33

3-Amino-4-(7-chloro-1H-indazol-4-yl)-6-piperidin-4-yl-1H-quinolin-2-one; 2,2,2-trifluoroacetate

[Formula 117]

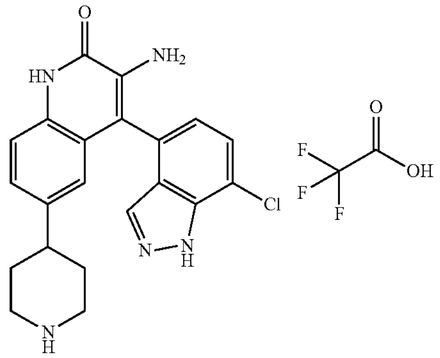

To a solution of tert-butyl 4-[4-[7-chloro-2-(oxan-2-yl)indazol-4-yl]-3-[(2-methylpropan-2-yl)oxycarbonylamino]-2-oxo-1H-quinolin-6-yl]piperidine-1-carboxylate (compound a-84, 237 mg, 0.35 mmol) in TFE (4.74 mL), trimethylsilyl chloride (671 μL, 5.25 mmol) was added, and the mixture was stirred at room temperature for 30 min. The reaction mixture was concentrated under reduced pressure, the obtained residue was purified by reversed phase column chromatography (0.05% aqueous TFA solution/0.05% TFA acetonitrile solution) to obtain the title compound (101 mg, yield 57%) as a light brown solid.

LCMS: m/z 394 $[M+H]^+$

HPLC retention time: 1.10 min (analysis condition G)

Compound A34

3-Amino-4-(7-chloro-1H-indazol-4-yl)-6-(1-propan-2-ylpiperidin-4-yl)-1H-quinolin-2-one

[Formula 118]

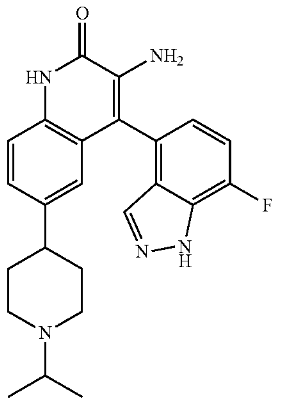

To a solution of 3-amino-4-(7-chloro-1H-indazol-4-yl)-6-piperidin-4-yl-1H-quinolin-2-one 2,2,2-trifluoroacetate (compound A33, 15 mg, 0.03 mmol) in DMA (300 μL), acetone (22 μL) and triacetoxysodium borohydride (18.78 mg, 0.089 mmol) were added, and the mixture was stirred at 60° C. for 1 hour. The reaction mixture was purified by reversed phase column chromatography to obtain the title compound (3 mg, yield 23%) as a colorless solid.

LCMS: m/z 436 $[M+H]^+$

HPLC retention time: 1.44 min (analysis condition G)

Compound A35

3-Amino-4-(7-chloro-1H-indazol-4-yl)-6-(1-cyclobutylpiperidin-4-yl)-1H-quinolin-2-one

[Formula 119]

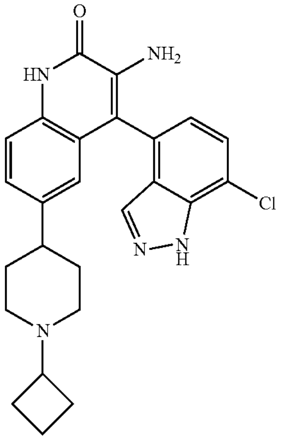

The title compound was synthesized from 3-amino-4-(7-chloro-1H-indazol-4-yl)-6-piperidin-4-yl-1H-quinolin-2-one 2,2,2-trifluoroacetate (compound A33) under the same conditions as the production example of the compound A34, except that cyclobutanone was used instead of acetone used in the production example of the compound A34.

LCMS: m/z 448 $[M+H]^+$

HPLC retention time: 1.65 min (analysis condition G)

Compound A36

3-Amino-4-(7-chloro-1H-indazol-4-yl)-6-[1-(oxetane-3-yl) piperidin-4-yl]-1H-quinolin-2-one

[Formula 120]

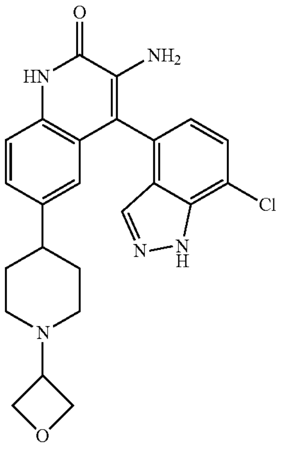

The title compound was synthesized from 3-amino-4-(7-chloro-1H-indazol-4-yl)-6-piperidin-4-yl-1H-quinolin-2-one 2,2,2-trifluoroacetate (compound A33) under the same conditions as the production example of the compound A34, except that 3-oxetanone was used instead of acetone used in the production example of the compound A34.

LCMS: m/z 450 $[M+H]^+$

HPLC retention time: 1.40 min (analysis condition G)

Compound a-87

3-Amino-6-(azetidin-3-yl)-4-(7-chloro-1H-indazol-4-yl)-1H-quinolin-2-one; dihydrochloride

[Formula 121]

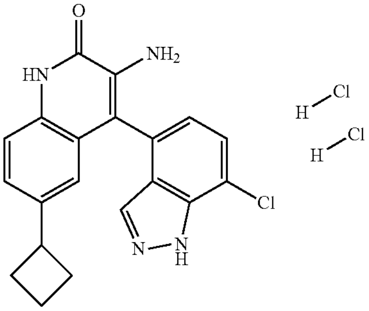

The title compound was synthesized from tert-butyl N-[6-bromo-4-[7-chloro-2-(oxan-2-yl)indazol-4-yl]-2-oxo-1H-quinolin-3-yl]carbamate (compound a-82) under the same conditions as the production examples of the compound A28 and A33, except that a 1 M solution of 1-tert-butoxycarbonylazetidine-3-yl zinc iodide in DMA, 2-dicyclohexylphosphino-2',4',6'-triisopropylbiphenyl, tris(dibenzylideneacetone) dipalladium (0), and THF were used instead of the 1 M solution of diethylzinc in hexane, CPhos Pd G3, and DMA used in the production example of the compound A28.

LCMS: m/z 366 $[M+H]^+$

HPLC retention time: 1.01 min (analysis condition G)

Compound A39

3-Amino-4-(7-chloro-1H-indazol-4-yl)-6-(1-methylazetidin-3-yl)-1H-quinolin-2-one

[Formula 122]

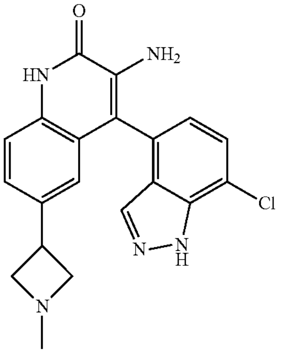

The title compound was synthesized from 3-amino-6-(azetidin-3-yl)-4-(7-chloro-1H-indazol-4-yl)-1H-quinolin-2-one; dihydrochloride (compound a-87) under the same conditions as the production example of the compound A34, except that a 37% formaldehyde solution was used instead of acetone used in the production example of the compound A34. In addition, the reaction was carried out by adding 5 equivalent of triethylamine and 30 equivalent of acetic acid based on the raw material.

LCMS: m/z 380 $[M+H]^+$

HPLC retention time: 1.19 min (analysis condition G)

Compound a-85

(2,4,6-Trichlorophenyl) 4-(7-chloro-2-(oxan-2-yl)indazol-4-yl)-3-[(2-methylpropan-2-yl)oxycarbonylamino]-2-oxo-1H-quinoline-6-carboxylate

[Formula 123]

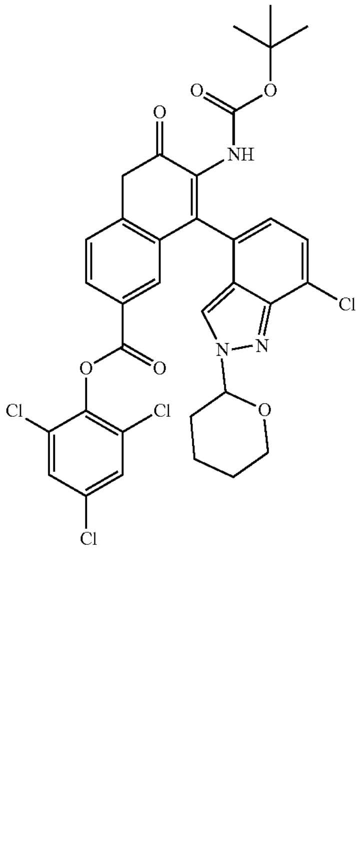

The title compound was synthesized from tert-butyl N-[6-bromo-4-[7-chloro-2-(oxan-2-yl)indazol-4-yl]-2-oxo-1H-quinolin-3-yl]carbamate (compound a-82) under the same conditions as the production example of the compound a-2.

LCMS: m/z 717 $[M+H]^+$

HPLC retention time: 2.61 min (analysis condition G)

Compound a-88 tert-Butyl N-[4-(7-chloro-2-(oxan-2-yl)indazol-4-yl)-6-(cyclopropylcarbamoyl)-2-oxo-1H-quinolin-3-yl]carbamate

[Formula 124]

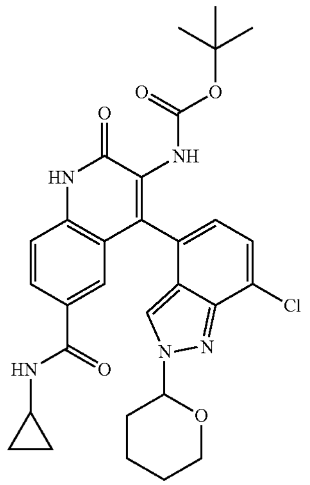

The title compound was synthesized from (2,4,6-trichlorophenyl) 4-(7-chloro-1H-indazol-4-yl)-3-[(2-methylpropan-2-yl)oxycarbonylamino]-2-oxo-1H-quinoline-6-carboxylate (compound a-85) under the same conditions as the production example of the compound a-54, except that cyclopropylamine was used instead of morpholine used in the production example of the compound a-54.

LCMS: m/z 578.5 $[M+H]^+$

HPLC retention time: 1.71 min (analysis condition G)

Compound A37

3-Amino-4-(7-chloro-1H-indazol-4-yl)-N-cyclopropyl-2-oxo-1H-quinoline-6-carboxamide

[Formula 125]

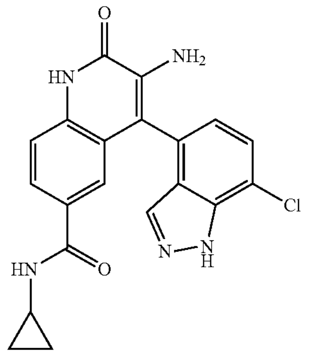

The title compound was synthesized from tert-butyl N-[4-(7-chloro-1H-indazol-4-yl)-6-(cyclopropylcarbamoyl)-2-oxo-1H-quinolin-3-yl]carbamate (compound a-88) under the same conditions as the production example of the compound A33.

LCMS: m/z 394 $[M+H]^+$

HPLC retention time: 1.26 min (analysis condition G)

Compound a-89 tert-Butyl N-[4-(7-chloro-2-(oxan-2-yl)indazol-4-yl)-6-(morpholine-4-carbonyl)-2-oxo-1H-quinolin-3-yl]carbamate

[Formula 126]

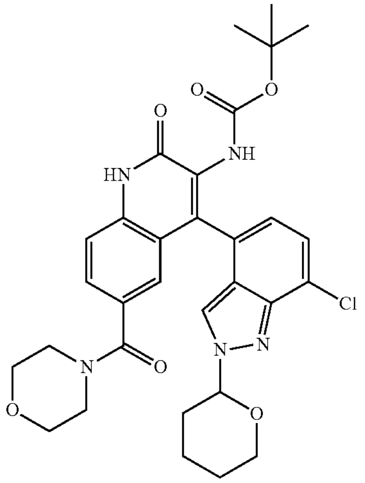

The title compound was synthesized from (2,4,6-trichlorophenyl) 4-(7-chloro-1H-indazol-4-yl)-3-[(2-methylpropan-2-yl)oxycarbonylamino]-2-oxo-1H-quinoline-6-carboxylate (compound a-85) under the same conditions as the production example of the compound a-54.

LCMS: m/z 608.5 $[M+H]^+$

HPLC retention time: 1.64 min (analysis condition G)

Compound A38

3-Amino-4-(7-chloro-1H-indazol-4-yl)-6-(morpholine-4-carbonyl)-1H-quinolin-2-one

[Formula 127]

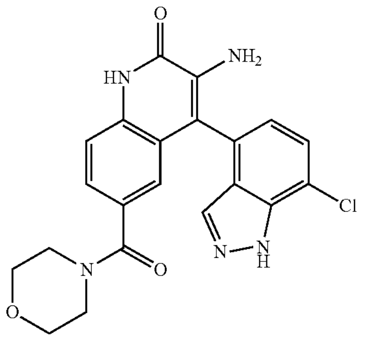

The title compound was synthesized from tert-butyl N-[4-(7-chloro-1H-indazol-4-yl)-6-(morpholine-4-carbonyl)-2-oxo-1H-quinolin-3-yl]carbamate (compound a-89) under the same conditions as the production example of the compound A33.

LCMS: m/z 424 $[M+H]^+$

HPLC retention time: 1.18 min (analysis condition G)

Compound a-94

Methyl (E)-3-(5-chloro-2-nitrophenyl)-2-[(2-methylpropan-2-yl)oxycarbonylamino]prop-2-enoate

[Formula 128]

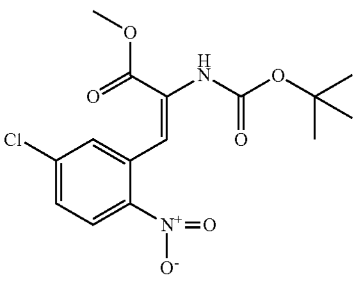

To a solution of methyl 2-((tert-butoxycarbonyl)amino)-2-(dimethoxyphosphoryl)acetate (20 g, 67.285 mmol) in DCM (330 mL) in a reaction vessel, 1,8-diazabicyclo[5.4.0]undec-7-ene (10.45 g, 68.63 mmol) was added, and the mixture was stirred at room temperature for 30 min. The mixture was cooled to 0° C., 5-chloro-2-nitrobenzaldehyde (12.74 g, 68.63 mmol) was added, and the mixture was stirred at room temperature for 30 min. To the reaction mixture, DCM was added, and the mixture was sequentially washed twice with a saturated aqueous ammonium chloride solution and once with an aqueous saturated sodium chloride solution. The organic layer was dried over anhydrous sodium sulfate, the drying agent was filtered off, and then the filtrate was concentrated under reduced pressure to obtain the crude product of the title compound (23.9 g).

LCMS: m/z 257 $[M+2H-BOC]^+$

HPLC retention time: 1.50 min (analysis condition R)

Compound a-95

Methyl (Z)-3-bromo-3-(5-chloro-2-nitrophenyl)-2-[(2-methylpropan-2-yl)oxycarbonylamino]prop-2-enoate

[Formula 129]

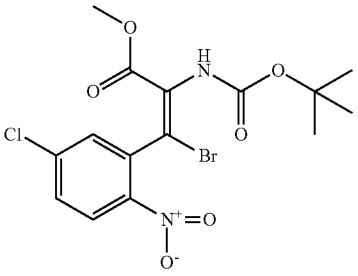

Methyl (E)-3-(5-chloro-2-nitrophenyl)-2-[(2-methylpropan-2-yl)oxycarbonylamino]prop-2-enoate (compound a-94) in a reaction vessel was dissolved in DCM (140 mL), N-bromosuccinimide (4.79 g, 26.9 mmol) was added, and the mixture was stirred at room temperature for 15 hours. To the reaction mixture, 1,4-diazabicyclo[2.2.2]octane (3.77 g, 33.6 mmol) was added, and the mixture was further stirred at room temperature for 15 hours. To the reaction mixture, a saturated aqueous ammonium chloride solution was added, and the mixture was extracted three times with ethyl acetate. The organic layer was sequentially washed with a saturated aqueous ammonium chloride solution, a saturated aqueous sodium bicarbonate solution, and an aqueous saturated sodium chloride solution. The organic layer was dried over anhydrous sodium sulfate, the drying agent was filtered off, and then the filtrate was concentrated under reduced pressure. The obtained residue was suspended in ethyl acetate/petroleum ether (1/5), and the solid was collected by filtration to obtain the title compound (6.0 g, yield 61%) as a yellow solid.

LCMS: m/z 334.9 $[M+2H-BOC]^+$

HPLC retention time: 0.86 min (analysis condition A)

Compound a-96 tert-Butyl N-(4-bromo-6-chloro-2-oxo-1H-quinolin-3-yl) carbamate

[Formula 130]

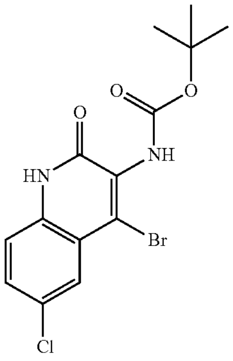

To a solution of methyl (Z)-3-bromo-3-(5-chloro-2-nitrophenyl)-2-[(2-methylpropan-2-yl)oxycarbonylamino]prop-2-enoate (compound a-95, 3.0 g, 6.886 mmol) and iron powder (3.85 g, 68.86 mmol) in EtOH (24 mL) in a reaction vessel, a saturated aqueous ammonium chloride solution (6 mL) was added, and the mixture was stirred at 70° C. for 30 min. The reaction mixture was filtered, and insoluble matter was washed with MeOH at 50° C. The filtrate was concentrated under reduced pressure, and the obtained residue was suspended in ethyl acetate/petroleum ether (1/4). The solid was collected by filtration to obtain the title compound (1.1 g, yield 42.3%).

LCMS: m/z 316.9 $[M+2H-tBu]^+$

HPLC retention time: 0.76 min (analysis condition A)

Compound a-100 tert-Butyl N-[6-chloro-4-(2-methoxypyridin-4-yl)-2-oxo-1H-quinolin-3-yl]carbamate

[Formula 131]

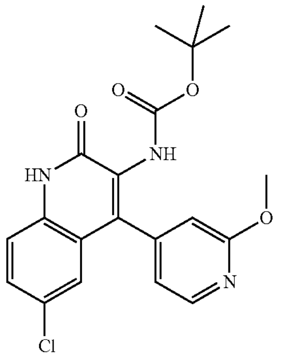

tert-Butyl N-(4-bromo-6-chloro-2-oxo-1H-quinolin-3-yl) carbamate (compound a-96, 300 mg, 0.803 mmol) in a reaction vessel, (2-methoxypyridin-4-yl) boronic acid (368.4 mg, 2.409 mmol), [1,1'-bis(diphenylphosphino)ferrocene]dichloropalladium(II) (58.75 mg, 0.08 mmol), and cesium carbonate (918.47 mg, 2.81 mmol) were suspended in THF/water (4/1, 6 mL), and the mixture was stirred at 70° C. under nitrogen atmosphere for 1 hour. The reaction mixture was cooled to room temperature, and diluted with ethyl acetate. The mixture was washed with water, then the organic layer was dried over anhydrous sodium sulfate, and the drying agent was filtered off, and then the filtrate was concentrated under reduced pressure. The obtained residue was purified by reversed phase column chromatography to obtain the title compound (256.2 mg, yield 81%) as a grayish solid.

HPLC retention time: 1.33 min (analysis condition T)

Compound A68

3-Amino-6-chloro-4-(2-oxo-1H-pyridin-4-yl)-1H-quinolin-2-one

[Formula 132]

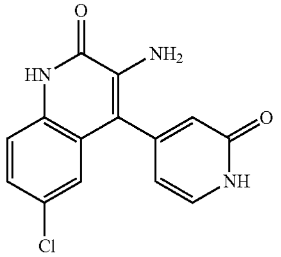

To a solution of tert-butyl N-[6-chloro-4-(2-methoxypyridin-4-yl)-2-oxo-1H-quinolin-3-yl]carbamate (compound a-100, 256 mg, 0.634 mmol) in DMF (5 mL) in a reaction vessel, lithium chloride (268.9 mg, 6.34 mmol) and p-toluenesulfonic acid (1.2 g, 6.34 mmol) were added, and the mixture was stirred at 120° C. for 30 min. The reaction mixture was cooled to room temperature, and the mixture was purified by reversed phase column chromatography to obtain the title compound (43.9 mg, yield 96%) as a pale yellow solid.

LCMS: m/z 288 $[M+H]^+$

HPLC retention time: 0.44 min (analysis condition A)

Compound a-90

Methyl 3-(4-chloro-2-nitrophenyl)-2-[(2-methylpropan-2-yl)oxycarbonylamino]prop-2-enoate

[Formula 133]

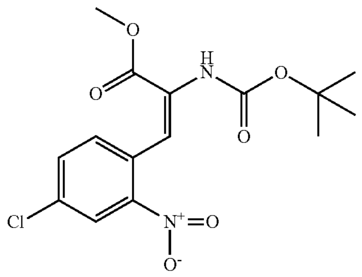

The title compound was synthesized from 4-chloro-2-nitrobenzaldehyde under the same conditions as the production example of the compound a-94.

LCMS: m/z 301 $[M+2H-BOC]^+$

HPLC retention time: 0.85 min (analysis condition A)

Compound a-91

Methyl (Z)-3-bromo-3-(4-chloro-2-nitrophenyl)-2-[(2-methylpropan-2-yl)oxycarbonylamino]prop-2-enoate

[Formula 134]

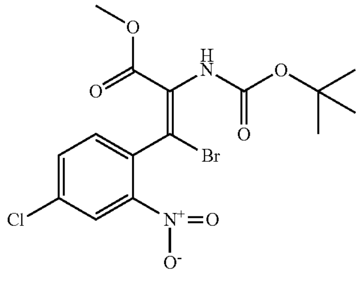

The title compound was synthesized from methyl 3-(4-chloro-2-nitrophenyl)-2-[(2-methylpropan-2-yl)oxycarbonylamino]prop-2-enoate (compound a-90) under the same conditions as the production example of the compound a-95, except that 1,8-diazabicyclo[5.4.0]undec-7-ene was used instead of 1,4-diazabicyclo[2.2.2]octane used in the production example of the compound a-95.

LCMS: m/z 379 $[M+2H-BOC]^+$

HPLC retention time: 0.89 min (analysis condition A)

Compound a-92 tert-Butyl N-(4-bromo-7-chloro-2-oxo-1H-quinolin-3-yl) carbamate

[Formula 135]

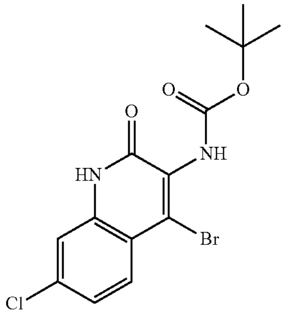

The title compound was synthesized from methyl (Z)-3-bromo-3-(4-chloro-2-nitrophenyl)-2-[(2-methylpropan-2-yl)oxycarbonylamino]prop-2-enoate (compound a-91) under the same conditions as the production example of the compound a-96.

LCMS: m/z 373 $[M+H]^+$

HPLC retention time: 0.76 min (analysis condition A)

Compound a-93 tert-Butyl N-[7-chloro-4-(7-chloro-1H-indazol-4-yl)-2-oxo-1H-quinolin-3-yl]carbamate

[Formula 136]

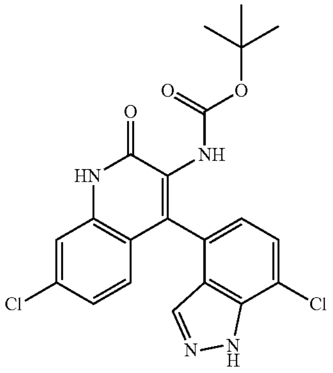

The title compound was synthesized from tert-butyl N-(4-bromo-7-chloro-2-oxo-1H-quinolin-3-yl) carbamate (compound a-92) under the same conditions as the production example of the compound a-100, except that (7-chloro-1H-indazol-4-yl) boronic acid was used instead of (2-methoxypyridin-4-yl) boronic acid used in the production example of the compound a-100.

LCMS: m/z 445 $[M+H]^+$

HPLC retention time: 0.71 min (analysis condition A)

Compound A40

3-Amino-7-chloro-4-(7-chloro-1H-indazol-4-yl)-1H-quinolin-2-one

[Formula 137]

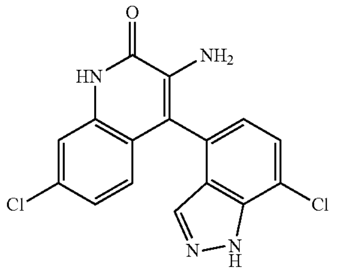

The title compound was synthesized from tert-butyl N-[7-chloro-4-(7-chloro-1H-indazol-4-yl)-2-oxo-1H-quinolin-3-yl]carbamate (compound a-93) under the same conditions as the production example of the compound A33.

LCMS: m/z 345 $[M+H]^+$

HPLC retention time: 0.68 min (analysis condition A)

Compound A49

3-Amino-6-chloro-4-(1H-indazol-6-yl)-1H-quinolin-2-one

[Formula 138]

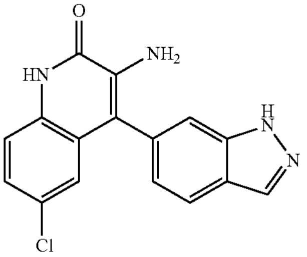

A suspension of tert-butyl N-(4-bromo-6-chloro-2-oxo-1H-quinolin-3-yl) carbamate (compound a-96, 350 mg, 0.937 mmol), 1H-indazol-6-ylboronic acid (455 mg, 2.81 mmol), 1,1'-bis(diphenylphosphino)ferrocene]dichloropalladium(II) (68.54 mg, 0.094 mmol) and cesium carbonate (1.072 g, 3.279 mmol) in THF/water (4/1, 7 mL) in a reaction vessel was heated at 70° C. under nitrogen atmosphere for 2.5 hours. The reaction solution was cooled to room temperature, water was added, and the mixture was extracted with ethyl acetate. The organic layer was dried over anhydrous sodium sulfate, the drying agent was filtered off, and then the filtrate was concentrated under reduced pressure. The obtained residue was suspended in ethyl acetate/petroleum ether (1/4), and the solid was collected by filtration. The obtained solid was dissolved in DCM (4 mL), a 4 M hydrogen chloride dioxane solution (6 mL) was added, and the mixture was stirred at room temperature for 2.5 hours. The reaction mixture was concentrated under reduced pressure and then dissolved in DMF, and a saturated aqueous sodium bicarbonate solution was added thereto to adjust the mixed solution to pH 8. The produced solid was collected by filtration and purified by reversed phase column chromatography to obtain the title compound (33.9 mg) as a grayish solid.

LCMS: m/z 311 $[M+H]^+$

HPLC retention time: 0.60 min (analysis condition A)

Compound A41

3-Amino-6-chloro-4-(3-hydroxyphenyl)-1H-quinolin-2-one

[Formula 139]

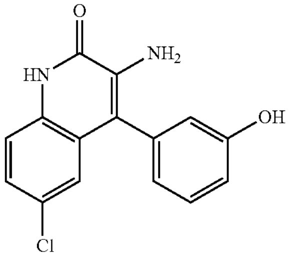

The title compound was synthesized from tert-butyl N-(4-bromo-6-chloro-2-oxo-1H-quinolin-3-yl) carbamate (compound a-96) under the same conditions as the production example of the compound A49, except that 3-hydroxyphenyl boronic acid was used instead of 1H-indazol-6-ylboronic acid used in the production example of the compound A49.

LCMS: m/z 287 $[M+H]^+$

HPLC retention time: 0.62 min (analysis condition A)

Compound A42

3-Amino-6-chloro-4-(3-methoxyphenyl)-1H-quinolin-2-one

[Formula 140]

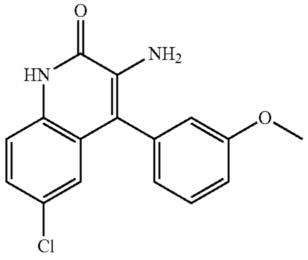

The title compound was synthesized from tert-butyl N-(4-bromo-6-chloro-2-oxo-1H-quinolin-3-yl) carbamate (compound a-96) under the same conditions as the production example of the compound A49, except that 3-methoxybenzeneboronic acid was used instead of 1H-indazol-6-ylboronic acid used in the production example of the compound A49.

LCMS: m/z 301 $[M+H]^+$

HPLC retention time: 0.74 min (analysis condition A)

Compound A43

3-Amino-6-chloro-4-(1H-indazol-4-yl)-1H-quinolin-2-one

[Formula 141]

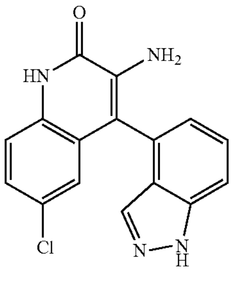

The title compound was synthesized from tert-butyl N-(4-bromo-6-chloro-2-oxo-1H-quinolin-3-yl) carbamate (compound a-96) under the same conditions as the production example of the compound A49, except that (1H-indazol-4-yl) boronic acid was used instead of 1H-indazol-6-ylboronic acid used in the production example of the compound A49.

LCMS: m/z 311 $[M+H]^+$

HPLC retention time: 0.59 min (analysis condition A)

Compound A44

3-Amino-6-chloro-4-pyridin-4-yl-1H-quinolin-2-one

[Formula 142]

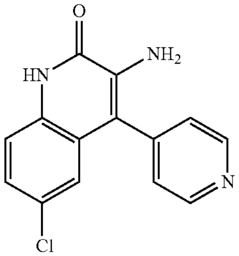

The title compound was synthesized from tert-butyl N-(4-bromo-6-chloro-2-oxo-1H-quinolin-3-yl) carbamate (compound a-96) under the same conditions as the production example of the compound A49, except that 4-pyridylboronic acid was used instead of 1H-indazol-6-ylboronic acid used in the production example of the compound A49.

LCMS: m/z 272 $[M+H]^+$

HPLC retention time: 0.42 min (analysis condition A)

Compound A45

3-Amino-6-chloro-4-pyridin-3-yl-1H-quinolin-2-one

[Formula 143]

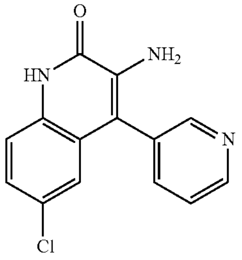

The title compound was synthesized from tert-butyl N-(4-bromo-6-chloro-2-oxo-1H-quinolin-3-yl) carbamate (compound a-96) under the same conditions as the production example of the compound A49, except that 3-pyridylboronic acid was used instead of 1H-indazol-6-ylboronic acid used in the production example of the compound A49.

LCMS: m/z 272 $[M+H]^+$

HPLC retention time: 0.44 min (analysis condition A)

Compound A46

N-[3-(3-amino-6-chloro-2-oxo-1H-quinolin-4-yl) phenyl]methanesulfonamide

[Formula 144]

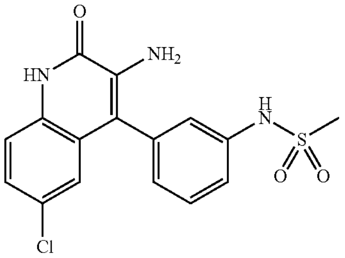

The title compound was synthesized from tert-butyl N-(4-bromo-6-chloro-2-oxo-1H-quinolin-3-yl) carbamate (compound a-96) under the same conditions as the production example of the compound A49, except that 3-(methylsulfonylamino)phenylboronic acid was used instead of 1H-indazol-6-ylboronic acid used in the production example of the compound A49.

LCMS: m/z 364 $[M+H]^+$

HPLC retention time: 0.60 min (analysis condition A)

Compound A47

3-Amino-4-(2-aminopyridin-4-yl)-6-chloro-1H-quinolin-2-one

[Formula 145]

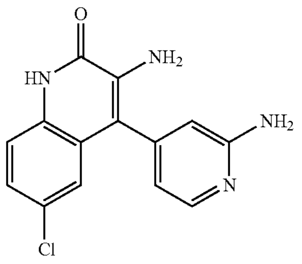

The title compound was synthesized from tert-butyl N-(4-bromo-6-chloro-2-oxo-1H-quinolin-3-yl) carbamate (compound a-96) under the same conditions as the production example of the compound A49, except that 2-aminopyridin-4-boronic acid pinacol ester was used instead of 1H-indazol-6-ylboronic acid used in the production example of the compound A49.

LCMS: m/z 287 $[M+H]^+$

HPLC retention time: 0.38 min (analysis condition A)

Compound A48

3-Amino-4-(3H-benzimidazol-5-yl)-6-chloro-1H-quinolin-2-one

[Formula 146]

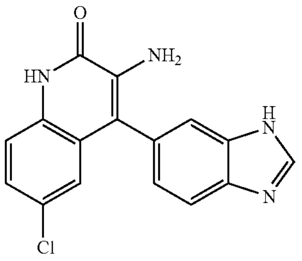

The title compound was synthesized from tert-butyl N-(4-bromo-6-chloro-2-oxo-1H-quinolin-3-yl) carbamate (compound a-96) under the same conditions as the production example of the compound A49, except that 6-(4,4,5,5-tetramethyl-1,3,2-dioxaborolan-2-yl)-1H-benzimidazole, tetrakis (triphenylphosphine)palladium (0), tripotassium phosphate, and 1,2-dimethoxyethane were respectively used instead of 1H-indazol-6-ylboronic acid, 1,1'-bis(diphenylphosphino)ferrocene]dichloropalladium(II), cesium carbonate, and THE used in the production example of the compound A49.

LCMS: m/z 311 $[M+H]^+$

HPLC retention time: 0.40 min (analysis condition A)

Compound A50

3-Amino-6-chloro-4-[3-(difluoromethoxy)phenyl]-1H-quinolin-2-one

[Formula 147]

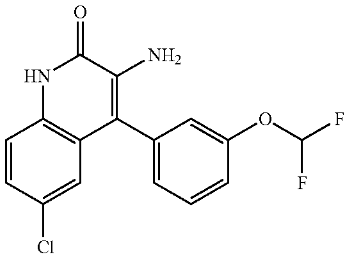

The title compound was synthesized from tert-butyl N-(4-bromo-6-chloro-2-oxo-1H-quinolin-3-yl) carbamate (compound a-96) under the same conditions as the production example of the compound A49, except that 3-(difluoromethoxy)phenylboronic acid was used instead of 1H-indazol-6-ylboronic acid used in the production example of the compound A49.

LCMS: m/z 337 $[M+H]^+$

HPLC retention time: 0.76 min (analysis condition A)

Compound A51

3-Amino-6-chloro-4-[3-(difluoromethyl)phenyl]-1H-quinolin-2-one

[Formula 148]

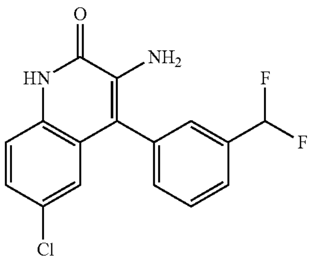

The title compound was synthesized from tert-butyl N-(4-bromo-6-chloro-2-oxo-1H-quinolin-3-yl) carbamate (compound a-96) under the same conditions as the production example of the compound A49, except that 3-(difluoromethyl)phenylboronic acid was used instead of 1H-indazol-6-ylboronic acid used in the production example of the compound A49.

LCMS: m/z 321 $[M+H]^+$

HPLC retention time: 0.74 min (analysis condition A)

Compound A52

3-Amino-6-chloro-4-(1-methyl-2-oxopyridin-4-yl)-1H-quinolin-2-one

[Formula 149]

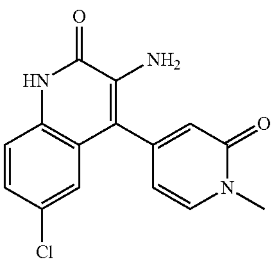

The title compound was synthesized from tert-butyl N-(4-bromo-6-chloro-2-oxo-1H-quinolin-3-yl) carbamate (compound a-96) under the same conditions as the production example of the compound A49, except that 1-methyl-4-(4,4,5,5-tetramethyl-1,3,2-dioxaborolan-2-yl) pyridin-2(1H)-one was used instead of 1H-indazol-6-ylboronic acid used in the production example of the compound A49.

LCMS: m/z 302 $[M+H]^+$

HPLC retention time: 0.48 min (analysis condition A)

Compound A53

3-Amino-6-chloro-4-(1H-indol-4-yl)-1H-quinolin-2-one

[Formula 150]

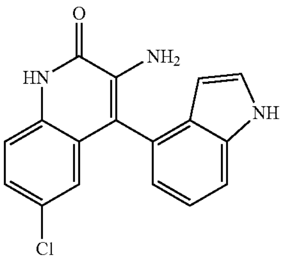

The title compound was synthesized from tert-butyl N-(4-bromo-6-chloro-2-oxo-1H-quinolin-3-yl) carbamate (compound a-96) under the same conditions as the production example of the compound A49, except that 1H-indol-4-ylboronic acid was used instead of 1H-indazol-6-ylboronic acid used in the production example of the compound A49.

LCMS: m/z 310 $[M+H]^+$

HPLC retention time: 0.66 min (analysis condition A)

Compound A55

3-Amino-6-chloro-4-(6-methyl-1H-indazol-4-yl)-1H-quinolin-2-one

[Formula 151]

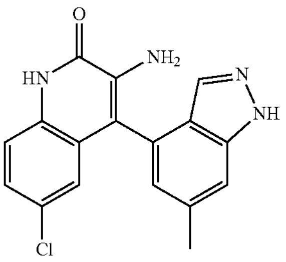

The title compound was synthesized from tert-butyl N-(4-bromo-6-chloro-2-oxo-1H-quinolin-3-yl) carbamate (compound a-96) under the same conditions as the production example of the compound A49, except that 6-methyl-1H-indazol-4-yl-4-boronic acid and 1,4-dioxane were used instead of 1H-indazol-6-ylboronic acid and THE used in the production example of the compound A49.

LCMS: m/z 325 $[M+H]^+$

HPLC retention time: 0.63 min (analysis condition A)

Compound A56

3-Amino-6-chloro-4-(6-fluoro-1H-indazol-4-yl)-1H-quinolin-2-one

[Formula 152]

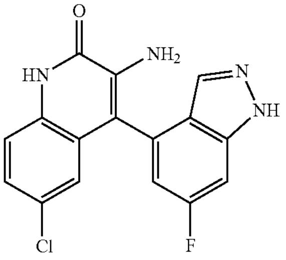

The title compound was synthesized from tert-butyl N-(4-bromo-6-chloro-2-oxo-1H-quinolin-3-yl) carbamate (compound a-96) under the same conditions as the production example of the compound A49, except that 6-fluoro-4-(4,4,5,5-tetramethyl-1,3,2-dioxaborolan-2-yl)-1H-indazole was used instead of 1H-indazol-6-ylboronic acid used in the production example of the compound A49.

LCMS: m/z 329 $[M+H]^+$

HPLC retention time: 0.62 min (analysis condition A)

Compound A57

3-Amino-6-chloro-4-(7-fluoro-1H-indazol-4-yl)-1H-quinolin-2-one

[Formula 153]

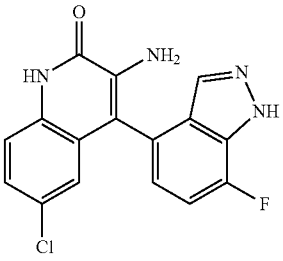

The title compound was synthesized from tert-butyl N-(4-bromo-6-chloro-2-oxo-1H-quinolin-3-yl) carbamate (compound a-96) under the same conditions as the production example of the compound A49, except that (7-fluoro-1H-indazol-4-yl) boronic acid was used instead of 1H-indazol-6-ylboronic acid used in the production example of the compound A49.

LCMS: m/z 329 $[M+H]^+$

HPLC retention time: 0.62 min (analysis condition A)

Compound A58

3-Amino-6-chloro-4-(6-chloro-1H-indazol-4-yl)-1H-quinolin-2-one

[Formula 154]

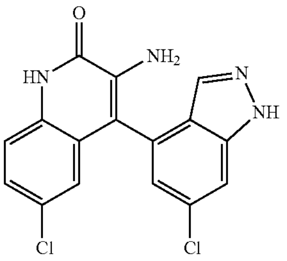

The title compound was synthesized from tert-butyl N-(4-bromo-6-chloro-2-oxo-1H-quinolin-3-yl) carbamate (compound a-96) under the same conditions as the production example of the compound A49, except that 6-chloro-4-(4,4,5,5-tetramethyl-1,3,2-dioxaborolan-2-yl)-1H-indazole and 1,4-dioxane were used instead of 1H-indazol-6-ylboronic acid and THE used in the production example of the compound A49.

LCMS: m/z 345 $[M+H]^+$

HPLC retention time: 0.67 min (analysis condition A)

Compound A59

3-Amino-6-chloro-4-(7-chloro-1H-indazol-4-yl)-1H-quinolin-2-one

[Formula 155]

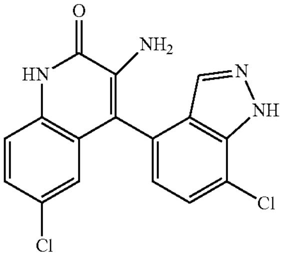

The title compound was synthesized from tert-butyl N-(4-bromo-6-chloro-2-oxo-1H-quinolin-3-yl) carbamate (compound a-96) under the same conditions as the production example of the compound A49, except that 7-chloro-4-(4,4,5,5-tetramethyl-1,3,2-dioxaborolan-2-yl)-1H-indazole and 1,4-dioxane were used instead of 1H-indazol-6-ylboronic acid and THE used in the production example of the compound A49.

LCMS: m/z 345 $[M+H]^+$

HPLC retention time: 0.66 min (analysis condition A)

Compound A60

3-Amino-6-chloro-4-(7-methyl-1H-indazol-4-yl)-1H-quinolin-2-one

[Formula 156]

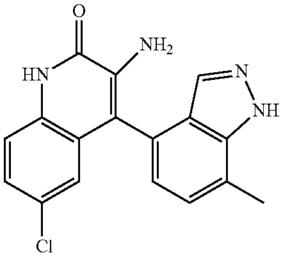

The title compound was synthesized from tert-butyl N-(4-bromo-6-chloro-2-oxo-1H-quinolin-3-yl) carbamate (compound a-96) under the same conditions as the production example of the compound A49, except that 7-methyl-4-(4,4,5,5-tetramethyl-1,3,2-dioxaborolan-2-yl)-1H-indazole and 1,4-dioxane were used instead of 1H-indazol-6-ylboronic acid and THE used in the production example of the compound A49.

LCMS: m/z 325 $[M+H]^+$

HPLC retention time: 0.63 min (analysis condition A)

Compound A61

3-Amino-6-chloro-4-[7-(trifluoromethyl)-1H-indazol-4-yl]-1H-quinolin-2-one

[Formula 157]

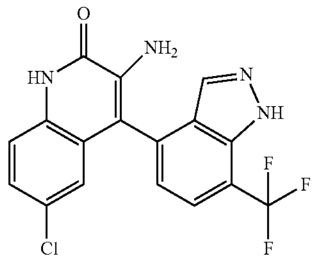

The title compound was synthesized from tert-butyl N-(4-bromo-6-chloro-2-oxo-1H-quinolin-3-yl) carbamate (compound a-96) under the same conditions as the production example of the compound A49, except that 4-(4,4,5,5-tetramethyl-1,3,2-dioxaborolan-2-yl)-7-(trifluoromethyl)-1H-indazole and 1,4-dioxane were used instead of 1H-indazol-6-ylboronic acid and THE used in the production example of the compound A49.

LCMS: m/z 379 $[M+H]^+$

HPLC retention time: 0.70 min (analysis condition A)

Compound A62

3-Amino-6-chloro-4-(3-methyl-1H-indazol-4-yl)-1H-quinolin-2-one

[Formula 158]

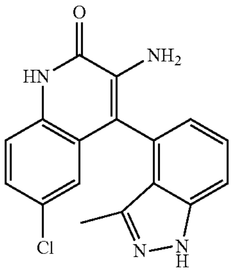

The title compound was synthesized from tert-butyl N-(4-bromo-6-chloro-2-oxo-1H-quinolin-3-yl) carbamate (compound a-96) under the same conditions as the production example of the compound A49, except that 3-methyl-1H-indazol-4-yl) boronic acid, tetrakis (triphenylphosphine)palladium (0), tripotassium phosphate, and 1,2-dimethoxyethane were respectively used instead of 1H-indazol-6-ylboronic acid, 1,1'-bis(diphenylphosphino)ferrocene] dichloropalladium(II), cesium carbonate, and THF used in the production example of the compound A49.

LCMS: m/z 325 $[M+H]^+$

HPLC retention time: 0.59 min (analysis condition A)

Compound A63

3-Amino-6-chloro-4-(5-methyl-1H-indazol-4-yl)-1H-quinolin-2-one

[Formula 159]

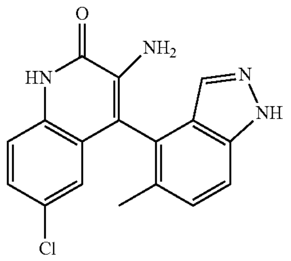

The title compound was synthesized from tert-butyl N-(4-bromo-6-chloro-2-oxo-1H-quinolin-3-yl) carbamate (compound a-96) under the same conditions as the production example of the compound A49, except that [5-methyl-1-(oxan-2-yl)-1H-indazol-4-yl]boronic acid, tris(dibenzylideneacetone) dipalladium (0) chloroform adduct, 4-anthracen-9-yl-3-tert-butyl-2H-1,3-benzooxaphosphole, tripotassium phosphate, and 1,4-dioxane were respectively used instead of 1H-indazol-6-ylboronic acid, 1,1'-bis(diphenylphosphino)ferrocene]dichloropalladium(II), cesium carbonate, and THE used in the production example of the compound A49.

LCMS: m/z 325 $[M+H]^+$

HPLC retention time: 0.60 min (analysis condition A)

Compound A65

3-Amino-6-cyclopropyl-4-(3-hydroxyphenyl)-1H-quinolin-2-one

[Formula 160]

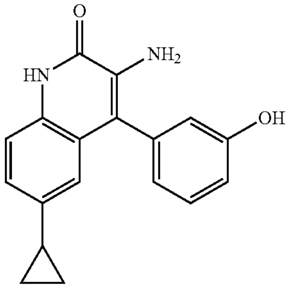

LCMS: m/z 293 $[M+H]^+$

HPLC retention time: 0.61 min (analysis condition A)

Compound A66

3-Amino-4-(3-hydroxyphenyl)-1H-quinolin-2-one

[Formula 161]

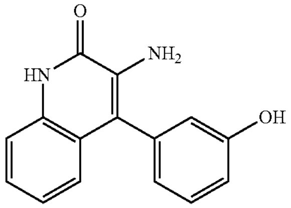

The compound A65 and the compound A66 were synthesized from 3-amino-6-chloro-4-(3-hydroxyphenyl)-1H-quinolin-2-one (compound A41) under the same conditions as the production example of the compound a-62, except that XPhos Pd G4, potassium carbonate, and potassium cyclopropyltrifluoroborate were used instead of tetrakis (triphenylphosphine)palladium (0), cesium carbonate, and potassium propyltrifluoroborate used in the production example of the compound a-62.

LCMS: m/z 253 $[M+H]^+$

HPLC retention time: 0.53 min (analysis condition A)

Compound a-98

(3-Amino-6-chloro-2-oxo-1H-quinolin-4-yl) boronic acid

[Formula 162]

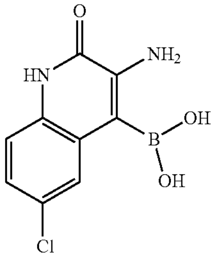

tert-Butyl N-(4-bromo-6-chloro-2-oxo-1H-quinolin-3-yl) carbamate (compound a-96, 1 g, 2.676 mmol) in a reaction vessel, [1,1'-bis(diphenylphosphino)ferrocene]dichloropalladium(II) (0.39 g, 0.535 mmol), bis(pinacolato)diboron (1.36 g, 5.35 mmol), and potassium acetate (1.05 g, 10.706 mmol) were suspended in 1,4-dioxane (30 mL), and the mixture was stirred at 100° C. under nitrogen atmosphere for 5 hours. The reaction mixture was cooled to room temperature, and water was added thereto, and then the mixture was extracted three times with ethyl acetate. The organic layer was dried over anhydrous sodium sulfate, the drying agent was filtered off, and then the filtrate was concentrated under reduced pressure. The obtained residue was purified by reversed phase column chromatography to obtain the title compound (350 mg, yield 54.8%) as a light brown solid.

LCMS: m/z 239 $[M+H]^+$

HPLC retention time: 0.44 min (analysis condition S)

Compound A67

3-Amino-6-chloro-4-(5-fluoro-1H-indazol-4-yl)-1H-quinolin-2-one

[Formula 163]

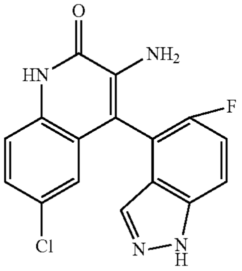

The title compound was synthesized from (3-amino-6-chloro-2-oxo-1H-quinolin-4-yl) boronic acid (compound a-98) and 4-bromo-5-fluoro-1-(tetrahydro-2H-pyran-2-yl)-1H-indazole under the same conditions as the production example of the compound A49, except that tris(dibenzylideneacetone) dipalladium (0) chloroform adduct, 4-anthracen-9-yl-3-tert-butyl-2H-1,3-benzooxaphosphole, tripotassium phosphate, and 1,4-dioxane were respectively used instead of 1,1'-bis(diphenylphosphino)ferrocene]dichloropalladium (II), cesium carbonate, and THF used in the production example of the compound A49.

LCMS: m/z 329 $[M+H]^+$

HPLC retention time: 0.59 min (analysis condition A)

Compound A69

3-Amino-4-(2-aminopyrimidin-4-yl)-6-chloro-1H-quinolin-2-one

[Formula 164]

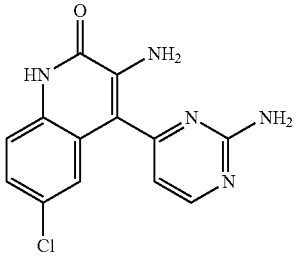

The title compound was synthesized from tert-butyl N-(4-bromo-6-chloro-2-oxo-1H-quinolin-3-yl) carbamate (compound a-96) and 4-(trimethylstannyl)-2-[bis(tert-butoxycarbonyl)amino]pyrimidine under the same conditions as the production example of the compounds a-83 and A22, except that bis(triphenylphosphine)palladium(II) dichloride and tert-butyl N-(tert-butoxycarbonyl)-N-[4-(trimethylstannyl) pyrimidin-2-yl]carbamate were used instead of tetrakis (triphenylphosphine)palladium (0) and tributyl(1-ethoxyvinyl) stannane used in the production example of the compound a-83.

LCMS: m/z 288 $[M+H]^+$

HPLC retention time: 0.46 min (analysis condition A)

Compound A70

3-Amino-4-phenyl-1H-quinolin-2-one

[Formula 165]

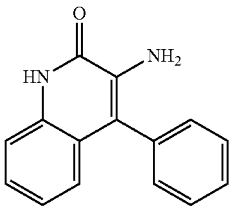

The title compound was synthesized based on the previously reported literature (Tetrahedron 2008, vol. 64, p. 5139-5146 (Non Patent Literature 21)).

LCMS: m/z 237 $[M+H]^+$

HPLC retention time: 0.66 min (analysis condition A)

Compound a-104

6-Bromo-4-hydroxy-3-nitro-1H-quinolin-2-one

[Formula 166]

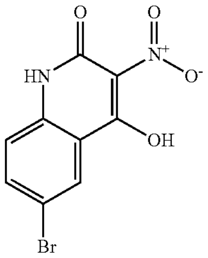

6-Bromo-4-hydroxy-1H-quinolin-2-one (100 mg, 0.417 mmol) in a reaction vessel was suspended in 65% nitric acid (1 mL), and the mixture was stirred at room temperature for 1 hour. The reaction mixture was stirred at 75° C. for 2 hours and cooled to room temperature, then water (5 mL) was added thereto, and the solid was collected by filtration. The obtained solid was washed with water (3 mL) to obtain the title compound (76 mg, yield 64%) as an orange solid.

LCMS: m/z 285 $[M+H]^+$

HPLC retention time: 0.39 min (analysis condition A)

Compound a-105

6-Bromo-4-chloro-3-nitro-1H-quinolin-2-one

[Formula 167]

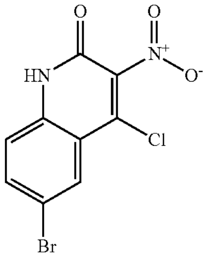

6-Bromo-4-hydroxy-3-nitro-1H-quinolin-2-one (compound a-104, 145 mg, 0.509 mmol) in a reaction vessel was suspended in thionyl chloride (1.45 mL), DMF (47.4 μL, 0.61 mmol) was added thereto, and the mixture was stirred at room temperature for 3 hours. The reaction mixture was concentrated under reduced pressure, and the obtained residue was purified by silica gel column chromatography to obtain the title compound (24.9 mg, yield 16%) as a pale yellow solid.

LCMS: m/z 303 $[M+H]^+$

HPLC retention time: 0.72 min (analysis condition A)

Compound a-106

6-Bromo-4-[3-(hydroxymethyl) piperidin-1-yl]-3-nitro-1H-quinolin-2-one

[Formula 168]

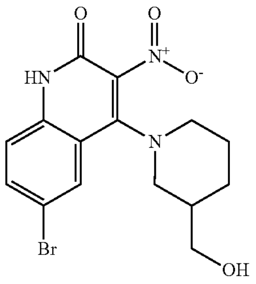

6-Bromo-4-chloro-3-nitro-1H-quinolin-2-one (compound a-105, 21.9 mg, 0.072 mmol) in a reaction vessel was dissolved in DMF (0.44 mL), piperidin-3-ylmethanol (24.9 mg, 0.216 mmol) was added thereto, and the mixture was stirred at room temperature for 1 hour. To the reaction mixture, water (0.9 mL) was added, and then the solid was collected by filtration to obtain the title compound (33 mg) as a yellow solid.

LCMS: m/z 382 $[M+H]^+$

HPLC retention time: 0.62 min (analysis condition A)

Compound A71

3-Amino-6-bromo-4-[3-(hydroxymethyl) piperidin-1-yl]-1H-quinolin-2-one 2,2,2-trifluoroacetate

[Formula 169]

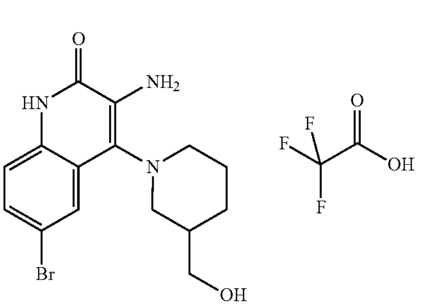

6-Bromo-4-[3-(hydroxymethyl) piperidin-1-yl]-3-nitro-1H-quinolin-2-one (compound a-106, 27 mg, 0.071 mmol) in a reaction vessel was dissolved in EtOH (0.54 mL), iron powder (39.4 mg, 0.706 mmol) and a saturated aqueous ammonium solution (135 μL) were added thereto, and the mixture was stirred at 70° C. for 1 hour. The reaction mixture was cooled to room temperature and then filtered using Celite. The filtrate was concentrated, the obtained residue was purified by reversed phase column chromatography (0.05% aqueous TFA solution/0.05% TFA acetonitrile solution) to obtain the title compound (16 mg, yield 64%) as a pale yellow solid.

LCMS: m/z 352 $[M+H]^+$

HPLC retention time: 0.93 min (analysis condition H)

Compound b-1

Methyl (E)-2-[(2-methylpropan-2-yl)oxycarbonylamino]-3-(1-nitronaphthalen-2-yl) prop-2-enoate

[Formula 170]

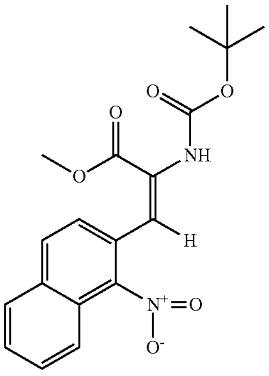

A solution of 2-(tert-butoxycarbonylamino)-2-(dimethoxyphosphoryl)methyl acetate (22.6 g, 76.0 mmol) in DCM (300 mL) in a reaction vessel was cooled to 0° C. under nitrogen atmosphere, 1,8-diazabicyclo[5.4.0]undec-7-ene (19.5 g, 127.9 mmol) was added thereto, and the mixture was stirred for 30 min. To the reaction mixture, 1-nitronaphthalene-2-carbaldehyde (15.6 g, 77.5 mmol) was added, and the mixture was further stirred at room temperature for 30 min. To the reaction mixture, DCM was added, and the mixture was sequentially washed twice with a saturated aqueous ammonium chloride solution and once with brine. The organic layer was dried over anhydrous sodium sulfate, the drying agent was filtered off, and then the obtained filtrate was concentrated under reduced pressure to obtain the crude product of the title compound (29.3 g) as an oily substance.

LCMS: m/z 371 $[M-H]^-$

HPLC retention time: 0.92 min (analysis condition A)

Compound b-3

Methyl (Z)-3-bromo-2-[(2-methylpropan-2-yl)oxycarbonylamino]-3-(1-nitronaphthalen-2-yl) prop-2-enoate

[Formula 171]

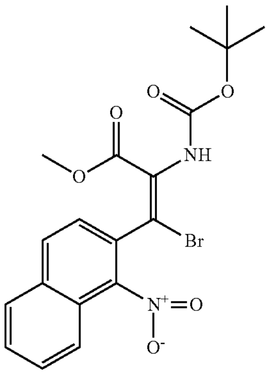

To a solution of 2-(tert-butoxycarbonylamino)-2-dimethoxyphosphoryl-methyl acetate (compound b-1, 5.0 g, 13.4 mmol) in DCM (90 mL) in a reaction vessel, N-bromosuccinimide (3.1 g, 17.4 mmol) was added, and the mixture was stirred at room temperature for 16 hours. To the reaction mixture, 1,4-diazabicyclo[2.2.2]octane (2.3 g, 20.1 mmol) was added, and the mixture was further stirred at room temperature for 16 hours. To the reaction mixture, a saturated aqueous ammonium chloride solution was added, and the mixture was extracted with ethyl acetate. The organic layer was washed with a saturated aqueous ammonium chloride solution, a saturated aqueous sodium bicarbonate solution, and brine. The obtained solution was dried over anhydrous sodium sulfate, the drying agent was filtered off, and then the obtained filtrate was concentrated under reduced pressure. The obtained residue was purified by silica gel column chromatography to obtain the title compound (3.8 g, yield 63%) as a yellow solid.

LCMS: m/z 449 $[M-H]^-$

HPLC retention time: 0.94 min (analysis condition A)

Compound b-4

Methyl (E)-3-(3-methoxyphenyl)-2-[(2-methylpropan-2-yl)oxycarbonylamino]-3-(1-nitronaphthalen-2-yl) prop-2-enoate

[Formula 172]

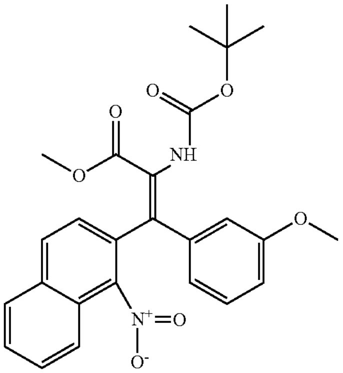

To a mixture of methyl (Z)-3-bromo-2-[(2-methylpropan-2-yl)oxycarbonylamino]-3-(1-nitronaphthalen-2-yl) prop-2-enoate (compound b-3, 1.20 g, 2.67 mmol), 3-methoxybenzeneboronic acid (1.22 g, 8.00 mmol), cesium carbonate (3.04 g, 9.33 mmol), and 1,1'-bis(diphenylphosphino)ferrocene]dichloropalladium(II) (0.29 g, 0.40 mmol) in a reaction vessel, THF (24 mL) and water (24 mL) were added, and the mixture was stirred at 70° C. under nitrogen atmosphere for 2 hours. The reaction mixture was cooled to room temperature, then water was added thereto, and the mixture was extracted with ethyl acetate. The organic layer was dried over anhydrous sodium sulfate, the drying agent was filtered off, and then the obtained filtrate was concentrated under reduced pressure. The obtained residue was purified by silica gel column chromatography to obtain the title compound 0.66 g, yield 52%) as a yellow solid.

LCMS: m/z 477 $[M-H]^-$

HPLC retention time: 2.87 min (analysis condition D)

Compound b-5 tert-Butyl N-[4-(3-methoxyphenyl)-2-oxo-1H-benzo [h]quinolin-3-yl]carbamate

[Formula 173]

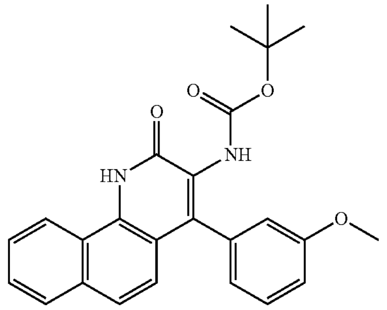

To a solution of methyl (E)-3-(3-methoxyphenyl)-2-[(2-methylpropan-2-yl)oxycarbonylamino]-3-(1-nitronaphthalen-2-yl) prop-2-enoate (compound b-4, 598.6 mg, 1.25 mmol) in EtOH (12 mL) in a reaction vessel, a saturated aqueous ammonium chloride solution (2.99 mL) and iron powder (349 mg, 6.25 mmol) were added, and the mixture was stirred at 70° C. under nitrogen atmosphere for 1 hour. The reaction mixture was filtered using Celite and then washed with a mixed solution of ethyl acetate and DCM. The filtrate was concentrated under reduced pressure to obtain the crude product of the title compound (127 mg, yield 24%).

LCMS: m/z 417 $[M+H]^+$

HPLC retention time: 2.43 min (analysis condition D)

Compound B1

3-Amino-4-(3-methoxyphenyl)-1H-benzo[h]quinolin-2-one

[Formula 174]

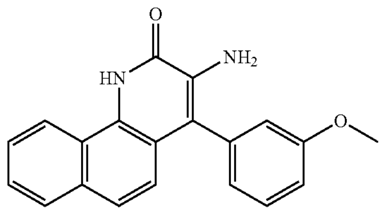

To a solution of tert-butyl N-[4-(3-methoxyphenyl)-2-oxo-1H-benzo[h]quinolin-3-yl]carbamate (compound b-5, 2.00 g, 4.80 mmol) in DCM (40 mL) in a reaction vessel, TFA (10 mL) was added, and the mixture was stirred at room temperature for 30 min. The reaction mixture was concentrated, and the obtained residue was purified by reversed phase column chromatography to obtain the title compound (210 mg, yield 14%) as a yellow solid.

LCMS: 317 $[M+H]^+$

HPLC retention time: 0.79 min (analysis condition A)

Compound B2

3-Amino-4-(3-hydroxyphenyl)-1H-benzo[h]quinolin-2-one

[Formula 175]

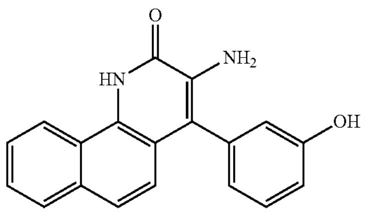

A solution of 3-amino-4-(3-methoxyphenyl)-1H-benzo[h]quinolin-2-one (compound B1, 180 mg, 0.57 mmol) in DCM (8 mL) in a reaction vessel was cooled to 0° C., a 1 M solution of boron tribromide in DCM (3 mL, 3.0 mmol) was added thereto, and the mixture was stirred for 1.5 hours. To the reaction mixture, a saturated aqueous sodium bicarbonate solution was added to adjust the aqueous layer to pH 8, and the mixture was extracted twice with ethyl acetate. The organic layer was dried over anhydrous sodium sulfate, the drying agent was filtered off, and then the obtained filtrate was concentrated under reduced pressure. The obtained residue was purified by reversed phase column chromatography to obtain the title compound (74.5 mg, yield 43%) as a pale yellow solid.

LCMS: m/z 303 $[M+H]^+$

HPLC retention time: 0.65 min (analysis condition A)

Compound b-2

1-Amino-4-bromo-N-methoxy-N-methylnaphthalene-2-carboxamide

[Formula 176]

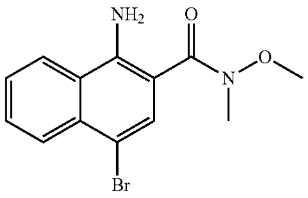

To a solution of 1-amino-4-bromo-naphthalene-2-carboxylic acid (2.00 g, 7.52 mmol) in DMF (20 mL) in a reaction vessel, HATU (3.43 g, 9.02 mmol), N,O-dimethylhydroxylamine hydrochloride (1.25 g, 12.8 mmol), and DIPEA (5.91 mL, 33.8 mmol) were added, and the mixture was stirred at room temperature for 30 min. To the reaction mixture, water was added, and the obtained solid was collected by filtration and washed with a mixed solution (1:1) of EtOH and water to obtain the title compound (1.94 g, yield 83%) as a brown solid.

LCMS: m/z 309 $[M+H]^+$

HPLC retention time: 0.82 min (analysis condition A)

Compound b-6

(1-Amino-4-bromonaphthalen-2-yl)-(3-methoxyphenyl) methanone

[Formula 177]

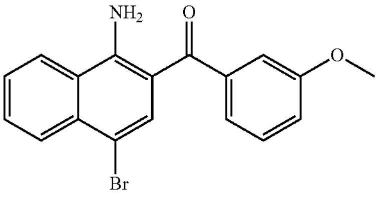

A solution of 1-amino-4-bromo-N-methoxy-N-methylnaphthalene-2-carboxamide (compound b-2, 200 mg, 0.65 mmol) in THF (2 mL) in a reaction vessel was cooled to −20° C., a 1 M solution of 3-methoxyphenylmagnesiumbromide in THF (2.26 mL, 2.26 mmol) was added, and the mixture was stirred for 15 hours. To the reaction mixture, water and 1 M hydrochloric acid was added, and the mixture was extracted with ethyl acetate. The organic layer was concentrated under reduced pressure, and the obtained residue was purified by silica gel column chromatography to obtain the title compound (120 mg, yield 52%) as a yellow solid.

LCMS: m/z 356 $[M+H]^+$

HPLC retention time: 1.09 min (analysis condition A)

Compound b-7

N-[4-bromo-2-(3-methoxybenzoyl) naphthalen-1-yl]-2-chloroacetamide

[Formula 178]

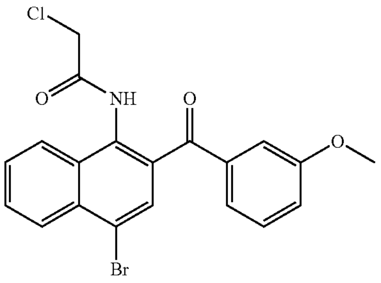

A solution of (1-amino-4-bromonaphthalen-2-yl)-(3-methoxyphenyl) methanone (compound b-6, 429 mg, 1.21 mmol) in DCM (8.59 mL) in a reaction vessel was cooled to 0° C., pyridine (122 μL, 1.51 mmol) and chloroacetyl chloride (115 μL, 1.45 mmol) were added thereto, and the mixture was stirred for 15 hours. The reaction mixture was purified by silica gel column chromatography to obtain the title compound (530 mg) as a colorless solid.

LCMS: m/z 432 $[M+H]^+$

HPLC retention time: 0.96 min (analysis condition A)

Compound b-8

6-Bromo-4-(3-methoxyphenyl)-3-pyridin-1-ium-1-yl-1H-benzo[h]quinolin-2-one: chloride

[Formula 179]

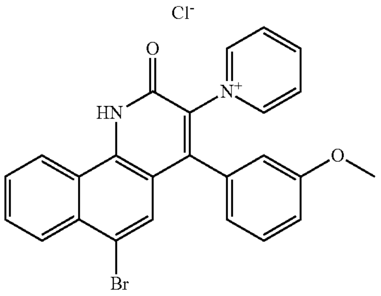

A solution of N-[4-bromo-2-(3-methoxybenzoyl) naphthalen-1-yl]-2-chloroacetamide (compound b-7, 540 mg, 1.25 mmol) in pyridine (16.2 mL) in a reaction vessel was stirred at 70° C. for 15 hours. To the reaction mixture, ethyl acetate was added, and then the solid was collected by filtration to obtain the title compound (520 mg, yield 84%) as a yellow solid.

LCMS: m/z 457 $[M]^+$

HPLC retention time: 0.65 min (analysis condition A)

Compound b-9

3-Amino-6-bromo-4-(3-methoxyphenyl)-1H-benzo[h]quinolin-2-one

[Formula 180]

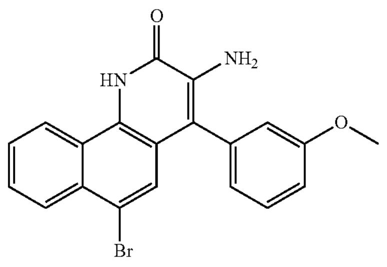

To a solution of 6-bromo-4-(3-methoxyphenyl)-3-pyridin-1-ium-1-yl-1H-benzo[h]quinolin-2-one; chloride (compound b-8, 520 mg, 1.1 mmol) in EtOH (5.2 mL) in a reaction vessel, hydrazine monohydrate (1.04 mL, 21.1 mmol) was added, and the mixture was stirred at 70° C. for 24 hours. To the reaction mixture, water was added, the solid was collected by filtration and then washed with water to obtain the title compound (418 mg, yield 95%) as a yellow solid.

LCMS: m/z 395 $[M+H]^+$

HPLC retention time: 1.03 min (analysis condition A)

Compound B4

3-Amino-6-bromo-4-(3-hydroxyphenyl)-1H-benzo[h]quinolin-2-one

[Formula 181]

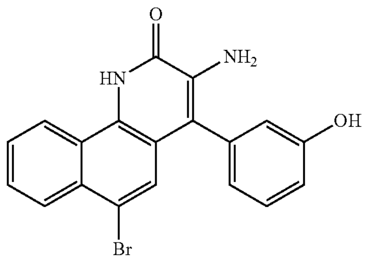

The title compound was synthesized from 3-amino-6-bromo-4-(3-methoxyphenyl)-1H-benzo[h]quinolin-2-one (compound b-9) under the same conditions as the production example of the compound B2.

LCMS: m/z 381 $[M+H]^+$

HPLC retention time: 0.86 min (analysis condition A)

Compound b-10

3-Amino-6-cyclopropyl-4-(3-methoxyphenyl)-1H-benzo[h]quinolin-2-one

[Formula 182]

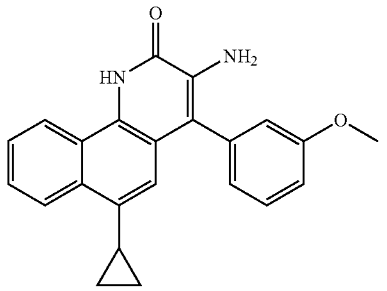

To a mixed solution of 3-amino-6-bromo-4-(3-methoxyphenyl)-1H-benzo[h]quinolin-2-one (compound b-9, 50 mg, 0.13 mmol) in 1,4-dioxane (1 mL) and water (0.1 mL) in a reaction vessel, DPPF Pd G4 (11.9 mg, 0.013 mmol), cesium carbonate (124 mg, 0.38 mmol), and potassium cyclopropyltrifluoroborate (37.4 mg, 0.25 mmol) were added, and the mixture was stirred at 100° C. for 15 hours. To the reaction mixture, ethyl acetate was added, and the mixture was filtered using Celite. The filtrate was concentrated under reduced pressure to obtain the crude product of the title compound.

LCMS: m/z 357.5 $[M+H]^+$

HPLC retention time: 1.00 min (analysis condition A)

Compound B3

3-Amino-6-cyclopropyl-4-(3-hydroxyphenyl)-1H-benzo[h]quinolin-2-one

[Formula 183]

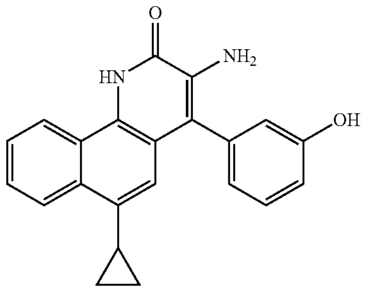

The title compound was synthesized from 3-amino-6-cyclopropyl-4-(3-methoxyphenyl)-1H-benzo[h]quinolin-2-one (compound b-10) under the same conditions as the production example of the compound B2.

LCMS: m/z 343 $[M+H]^+$

HPLC retention time: 0.86 min (analysis condition A)

Compound b-11

3-Amino-4-(3-methoxyphenyl)-6-phenyl-1H-benzo[h]quinolin-2-one

[Formula 184]

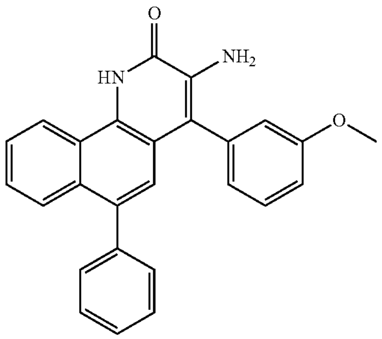

The title compound was synthesized from 3-amino-6-bromo-4-(3-methoxyphenyl)-1H-benzo[h]quinolin-2-one (compound b-9) under the same conditions as the production example of the compound b-10, except that phenylboronic acid was used instead of potassium cyclopropyltrifluoroborate used in the production example of the compound b-10.

LCMS: m/z 393 $[M+H]^+$

HPLC retention time: 1.05 min (analysis condition A)

Compound B5

3-Amino-4-(3-hydroxyphenyl)-6-phenyl-1H-benzo[h]quinolin-2-one

[Formula 185]

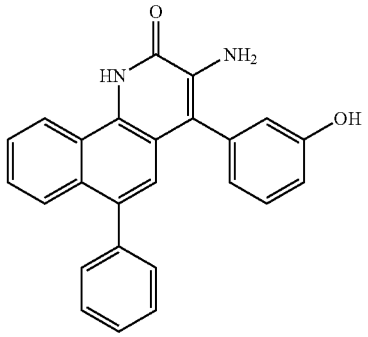

The title compound was synthesized from 3-amino-4-(3-methoxyphenyl)-6-phenyl-1H-benzo[h]quinolin-2-one (compound b-11) under the same conditions as the production example of the compound B2.

LCMS: m/z 379 $[M+H]^+$

HPLC retention time: 0.92 min (analysis condition A)

Compound b-12

3-Amino-4-(3-methoxyphenyl)-6-methyl-1H-benzo[h]quinolin-2-one

[Formula 186]

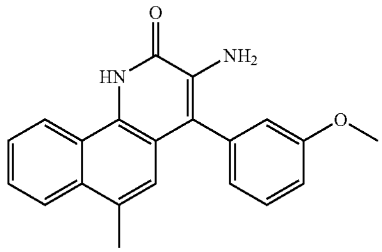

The title compound was synthesized from 3-amino-6-bromo-4-(3-methoxyphenyl)-1H-benzo[h]quinolin-2-one (compound b-9) under the same conditions as the production example of the compound b-10, except that trimethylboroxine was used instead of potassium cyclopropyltrifluoroborate used in the production example of the compound b-10.

LCMS: m/z 331 $[M+H]^+$

HPLC retention time: 0.95 min (analysis condition A)

Compound B6

3-Amino-4-(3-hydroxyphenyl)-6-methyl-1H-benzo[h]quinolin-2-one

[Formula 187]

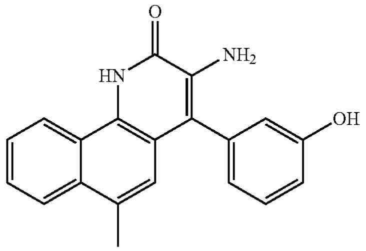

The title compound was synthesized from 3-amino-4-(3-methoxyphenyl)-6-methyl-1H-benzo[h]quinolin-2-one (compound b-12) under the same conditions as the production example of the compound B2.

LCMS: m/z 317 $[M+H]^+$

HPLC retention time: 0.80 min (analysis condition A)

Compound b-13

3-Amino-4-(3-methoxyphenyl)-2-oxo-1H-benzo[h]quinoline-6-carbonitrile

[Formula 188]

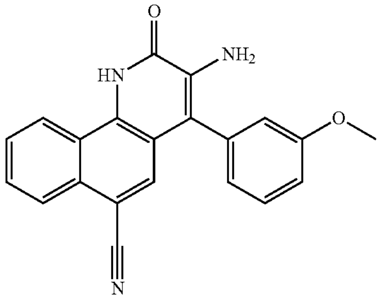

To a solution of 3-amino-6-bromo-4-(3-methoxyphenyl)-1H-benzo[h]quinolin-2-one (compound b-9, 40 mg, 0.10 mmol) in NMP (0.8 mL) in a reaction vessel, copper (I) cyanide (27.2 mg, 0.30 mmol) was added, and the mixture was stirred at 200° C. for 20 min in a sealed tube using a microwave reactor. To the reaction mixture, aqueous ammonia was added, the mixture was extracted with ethyl acetate, and the organic layer was concentrated under reduced pressure. The obtained residue was purified by silica gel column chromatography to obtain the title compound (35.5 mg, yield 83%).

LCMS: m/z 342 $[M+H]^+$

HPLC retention time: 0.75 min (analysis condition A)

Compound b-14

3-Amino-6-chloro-4-(3-methoxyphenyl)-1H-benzo[h]quinolin-2-one

[Formula 189]

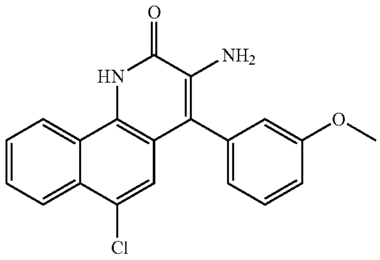

To a solution of 3-amino-6-bromo-4-(3-methoxyphenyl)-1H-benzo[h]quinolin-2-one (compound b-9, 30 mg, 0.08 mmol) in NMP (0.6 mL) in a reaction vessel, copper (I) chloride (30.1 mg, 0.30 mmol) was added, and the mixture was stirred at 120° C. for 2 hours in a sealed tube using a microwave reactor. The reaction mixture was cooled to room temperature and then purified by reversed phase column chromatography to obtain the title compound (25 mg, yield 94%).

LCMS: m/z 351 $[M+H]^+$

HPLC retention time: 0.89 min (analysis condition A)

Compound B7

3-Amino-4-(3-hydroxyphenyl)-2-oxo-1H-benzo[h]quinoline-6-carbonitrile

[Formula 190]

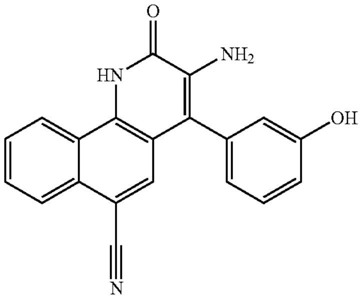

The title compound was synthesized from 3-amino-4-(3-methoxyphenyl)-2-oxo-1H-benzo[h]quinoline-6-carbonitrile (compound b-13) under the same conditions as the production example of the compound B2.

LCMS: m/z 328 $[M+H]^+$

HPLC retention time: 0.64 min (analysis condition A)

Compound B8

3-Amino-6-chloro-4-(3-hydroxyphenyl)-1H-benzo[h]quinolin-2-one

[Formula 191]

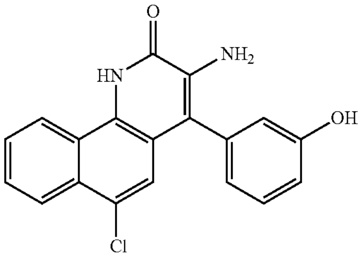

The title compound was synthesized from 3-amino-6-chloro-4-(3-methoxyphenyl)-1H-benzo[h]quinolin-2-one (compound b-14) under the same conditions as the production example of the compound B2.

LCMS: m/z 337 $[M+H]^+$

HPLC retention time: 0.73 min (analysis condition A)

Compound c-3

4-Bromo-7-fluoro-2-(oxan-2-yl)indazole

[Formula 192]

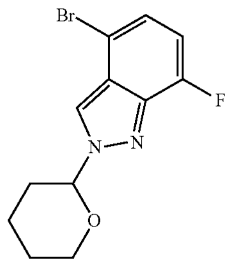

To a solution of 4-bromo-7-fluoro-1H-indazole (15 g, 69.8 mmol) in DCM (349 mL) in a reaction vessel, 3,4-dihydro-2H-pyran (11.74 g, 140 mmol) and pyridinium p-toluenesulfonate (3.51 g, 13.95 mmol) were added, and the mixture was stirred at room temperature for 2 hours. The reaction mixture was concentrated under reduced pressure, and the obtained residue was purified by silica gel column chromatography to obtain the title compound (19.4 g, yield 93%) as a colorless liquid.

LCMS: m/z 299 $[M+H]^+$

HPLC retention time: 1.24 min (analysis condition F)

Compound c-4

(2,4,6-Trichlorophenyl) 7-fluoro-2-(oxan-2-yl)indazole-4-carboxylate

[Formula 193]

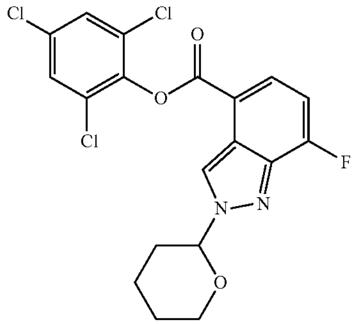

To a mixture of 4-bromo-7-fluoro-2-(oxan-2-yl)indazole (compound c-3, 30.0 g, 100 mmol) and triethylamine (28.0 mL, 201 mmol) in a reaction vessel, toluene (436 mL) was added, and the reaction vessel was degassed under reduced pressure and subjected to nitrogen replacement. To the reaction mixture, palladium(II) acetate (0.68 g, 3.01 mmol) and 4,5-bis(diphenylphosphino)-9,9-dimethylxanthene (3.48 g, 6.02 mmol) were added, the reaction vessel was further degassed under reduced pressure and subjected to nitrogen replacement. To the reaction mixture, a solution of 2,4,6-trichlorophenyl formate (27.1 g, 120 mmol) in toluene (65.1 mL) which was degassed under reduced pressure and subjected to nitrogen replacement was added dropwise at 80° C. The reaction mixture was stirred at 80° C. under nitrogen atmosphere for 30 min and concentrated under reduced pressure to obtain the crude product of the title compound.

LCMS: m/z 443 $[M+H]^+$

HPLC retention time: 1.59 min (analysis condition F)

Compound c-5

7-Fluoro-2-(oxan-2-yl)indazole-4-carboxylic acid

[Formula 194]

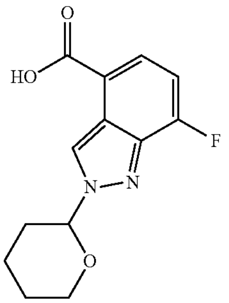

To a suspension of the crude product of (2,4,6-trichlorophenyl) 7-fluoro-2-(oxan-2-yl)indazole-4-carboxylate (compound c-4) in THF (400 mL) in a reaction vessel, a 2.5 M aqueous sodium hydroxide solution (160 mL, 400 mmol) was added, and the mixture was stirred at 60° C. for 3.5 hours. The reaction mixture was cooled to room temperature and filtered using Celite. To the filtrate, a 2.5 M aqueous phosphoric acid solution (400 mmol, 160 mL) was added, and the mixture was extracted with a mixed solution of ethyl acetate and THF. The organic layer was extracted three times with an aqueous sodium carbonate solution and water, and then the obtained aqueous layer was filtered. To the filtrate, a 2.5 M aqueous phosphoric acid solution (400 mmol, 160 mL) was added, and the solid was collected by filtration to obtain the title compound (24.01 g, yield 91%) as a colorless solid.

LCMS: m/z 263 $[M-H]^-$

HPLC retention time: 0.86 min (analysis condition F)

Compound c-6

7-Fluoro-N-methoxy-N-methyl-2-(oxan-2-yl)indazole-4-carboxamide

[Formula 195]

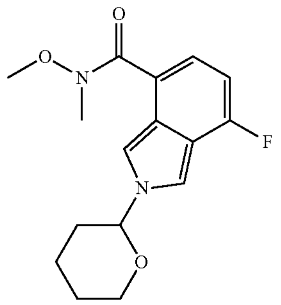

The title compound was synthesized from 7-fluoro-2-(oxan-2-yl)indazole-4-carboxylic acid (compound c-5) under the same conditions as the production example of the compound b-2, except that THF was used instead of DMF used in the production example of the compound b-2.

LCMS: m/z 308 $[M+H]^+$

HPLC retention time: 0.88 min (analysis condition F)

Compound b-24

6-Chloro-2,4-diiodonaphthalen-1-amine

[Formula 196]

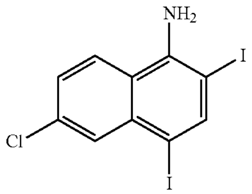

To a solution of 6-chloro-naphthalen-1-ylamine (0.263 g, 1.48 mmol) in DMSO (4.23 mL) in a reaction vessel, N-iodosuccinimide (0.68 g, 3.04 mmol) was added, and the mixture was stirred at room temperature for 20 min. To the reaction mixture, a saturated aqueous sodium thiosulfate solution and DCM were added, and the mixture was washed with a saturated aqueous sodium bicarbonate solution. The organic layer was dried over anhydrous sodium sulfate, the drying agent was filtered off, and then the obtained filtrate was concentrated under reduced pressure to obtain the crude product of the title compound (0.89 g).

LCMS: m/z 429 $[M+H]^+$

HPLC retention time: 1.12 min (analysis condition Q)

Compound b-25

(E)-N'-(6-chloro-2,4-diiodonaphthalen-1-yl)-N,N-dimethylmethanimidamide

[Formula 197]

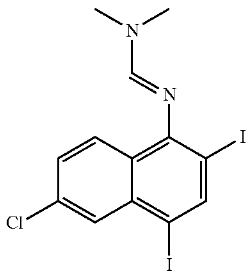

To a mixture of the crude product (0.89 g) of 6-chloro-2,4-diiodonaphthalen-1-amine (compound b-24) and N,N-dimethylformamidedimethylacetal (1.1 mL, 8.26 mmol) in a reaction vessel, EtOH (3.4 mL) was added, and the mixture was stirred at 80° C. for 25 min. The reaction mixture was concentrated under reduced pressure, and the obtained residue was purified by silica gel column chromatography to obtain the title compound (0.69 g, yield 67%) as an oily substance.

LCMS: m/z 485 $[M+H]^+$

HPLC retention time: 0.73 min (analysis condition Q)

Compound b-26

(E)-N'-[6-chloro-2-[7-fluoro-2-(oxan-2-yl)indazole-4-carbonyl]-4-iodonaphthalen-1-yl]-N,N-dimethylmethanimidamide

[Formula 198]

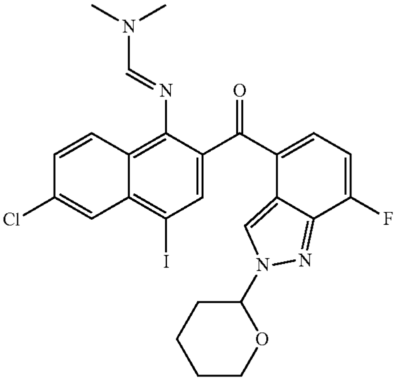

To a mixture of (E)-N'-(6-chloro-2,4-diiodonaphthalen-1-yl)-N,N-dimethylmethanimidamide (compound c-6, 218 mg, 0.709 mmol) and 7-fluoro-N-methoxy-N-methyl-2-(oxan-2-yl)indazole-4-carboxamide (compound b-25, 516 mg, 1.06 mmol) in a reaction vessel, THF (3.55 mL) was added, the mixture was cooled to −40° C., a 1.3 M solution of isopropylmagnesium chloride-lithium chloride complex in THF (928 μL, 1.21 mmol) was added dropwise thereto, and the mixture was stirred at 0° C. for 4 hours. To the reaction mixture, a saturated aqueous ammonium chloride solution was added, and the mixture was extracted three times with DCM. The organic layer was dried over anhydrous sodium sulfate, the drying agent was filtered off, and then the obtained filtrate was concentrated under reduced pressure. The obtained residue was purified by reversed phase column chromatography (0.1% aqueous formic acid solution/0.1% formic acid in acetonitrile solution) to obtain the title compound (370 mg, yield 86%) as a yellow solid.

LCMS: m/z 605 $[M+H]^+$

HPLC retention time: 1.01 min (analysis condition Q)

Compound b-27

(1-Amino-6-chloro-4-iodonaphthalen-2-yl)-[7-fluoro-2-(oxan-2-yl)indazol-4-yl]methanone

[Formula 199]

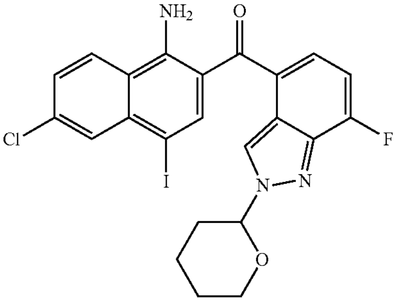

To a solution of (E)-N'-[6-chloro-2-[7-fluoro-2-(oxan-2-yl)indazole-4-carbonyl]-4-iodonaphthalen-1-yl]-N,N-dimethylmethanimidamide (compound b-26, 70 mg, 0.116 mmol) in DMSO (964 μL) in a reaction vessel, a 5 M aqueous sodium hydroxide solution (116 μL, 0.579 mmol) was added, and the mixture was stirred at room temperature for 30 min. The reaction mixture was purified by reversed phase column chromatography (0.1% aqueous formic acid solution/0.1% formic acid in acetonitrile solution) to obtain the title compound (75 mg) as a yellow solid.

LCMS: m/z 550 $[M+H]^+$

HPLC retention time: 1.15 min (analysis condition Q)

Compound b-28

2-Chloro-N-[6-chloro-2-[7-fluoro-2-(oxan-2-yl)indazole-4-carbonyl]-4-iodonaphthalen-1-yl]acetamide

[Formula 200]

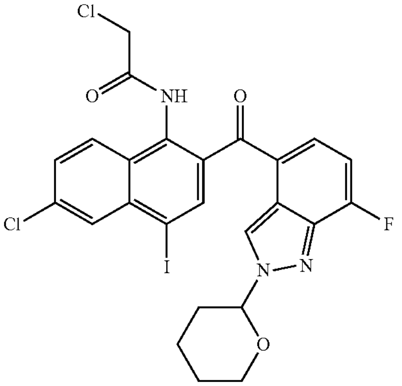

A solution of (1-amino-6-chloro-4-iodonaphthalen-2-yl)-[7-fluoro-2-(oxan-2-yl)indazol-4-yl]methanone (compound b-27, 73.3 mg, 0.133 mmol) in DCM (1.33 mL) in a reaction vessel was cooled to 0° C., chloroacetyl chloride (18.2 μL, 0.23 mmol) and pyridine (21.57 μL, 0.267 mmol) were added thereto, and the mixture was stirred for 20 min to obtain a solution of the title compound in DCM.

LCMS: m/z 626 $[M+H]^+$

HPLC retention time: 1.00 min (analysis condition Q)

Compound b-29

8-Chloro-4-[7-fluoro-2-(oxan-2-yl)indazol-4-yl]-6-iodo-3-pyridin-1-ium-1-yl-1H-benzo[h]quinolin-2-one; chloride

[Formula 201]

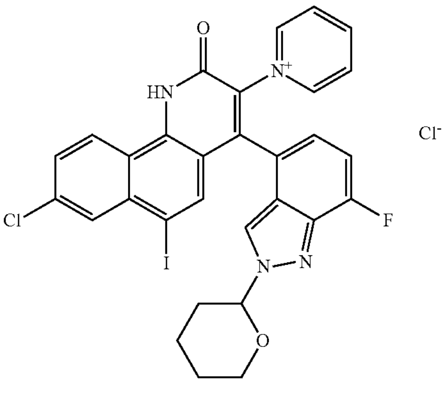

To the solution of 2-chloro-N-[6-chloro-2-[7-fluoro-2-(oxan-2-yl)indazole-4-carbonyl]-4-iodonaphthalen-1-yl]acetamide (compound b-28) in DCM, pyridine (677 μL, 0.133 mmol) was added, DCM was distilled off by concentration under reduced pressure, and the mixture was stirred at 80° C. for 40 min to obtain a solution of the title compound in pyridine.

LCMS: m/z 651 $[M]^+$

HPLC retention time: 0.63 min (analysis condition Q)

Compound b-30

8-Chloro-4-(7-fluoro-1H-indazol-4-yl)-6-iodo-3-pyridin-1-ium-1H-benzo[h]quinolin-2-one; chloride

[Formula 202]

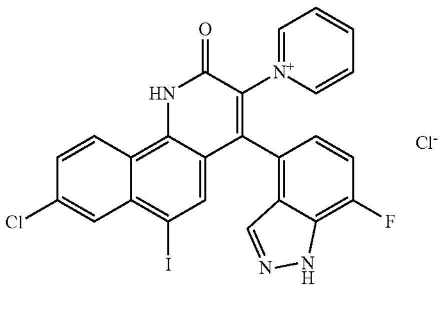

The solution of 8-chloro-4-[7-fluoro-2-(oxan-2-yl)indazol-4-yl]-6-iodo-3-pyridin-1-ium-1-yl-1H-benzo[h]quinolin-2-one; chloride (compound b-29) in pyridine was cooled to 0° C., a 12 M hydrochloric acid (0.11 mL, 1.33 mmol) was added thereto, and the mixture was heated at 90° C. for 50 min. The reaction mixture was purified by reversed phase column chromatography (0.1% aqueous formic acid solution/0.1% formic acid in acetonitrile solution) to obtain the title compound (66 mg, yield 82%) as a yellow solid.

LCMS: m/z 567 $[M]^+$

HPLC retention time: 0.54 min (analysis condition Q)

Compound B13

3-Amino-8-chloro-4-(7-fluoro-1H-indazol-4-yl)-6-iodo-1H-benzo[h]quinolin-2-one

[Formula 203]

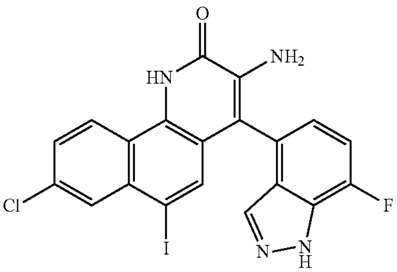

The title compound was synthesized from 8-chloro-4-(7-fluoro-1H-indazol-4-yl)-6-iodo-3-pyridin-1-ium-1H-benzo[h]quinolin-2-one; chloride (compound b-30) under the same conditions as the production example of the compound b-9, except that DMSO was used instead of EtOH used in the production example of the compound b-9.

LCMS: m/z 505 $[M+H]^+$

HPLC retention time: 0.87 min (analysis condition A)

Compound b-31

N'-[6-chloro-4-cyclopropyl-2-[7-fluoro-2-(oxan-2-yl)indazole-4-carbonyl]naphthalen-1-yl]-N,N-dimethylmethanimidamide

[Formula 204]

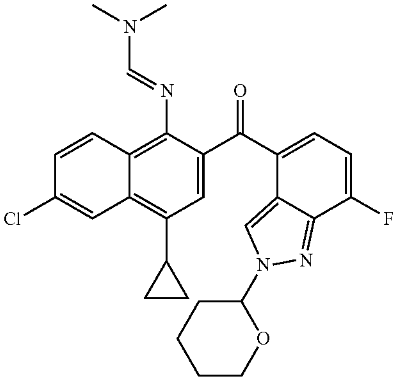

To a solution of (E)-N'-[6-chloro-2-[7-fluoro-2-(oxan-2-yl)indazole-4-carbonyl]-4-iodonaphthalen-1-yl]-N,N-dimethylmethanimidamide (compound b-26, 106 mg, 0.175 mmol) and XPhos Pd G4 (26.7 mg) in DMA (1.75 mL) in a reaction vessel, a 0.5 M solution of cyclopropylzinc bromide in THF (736 μl, 0.368 mmol) was added, and the reaction mixture was stirred at room temperature for 20 min. To the reaction mixture, water was added, and the mixture was extracted with ethyl acetate. The organic layer was washed with brine and dried over anhydrous sodium sulfate, the drying agent was filtered off, and then the obtained filtrate was concentrated under reduced pressure. The obtained residue was purified by reversed phase column chromatography (0.1% aqueous formic acid solution/0.1% formic acid in acetonitrile solution) to obtain the title compound (29.5 mg, yield 32%) as a yellow solid.

LCMS: m/z 519 $[M+H]^+$

HPLC retention time: 0.70 min (analysis condition R)

Compound b-32

(1-Amino-6-chloro-4-cyclopropylnaphthalen-2-yl)-[7-fluoro-2-(oxan-2-yl)indazol-4-yl]methanone

[Formula 205]

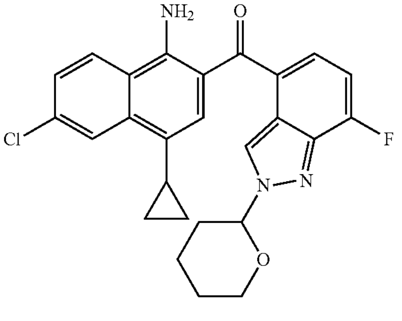

The title compound was synthesized from N'-[6-chloro-4-cyclopropyl-2-[7-fluoro-2-(oxan-2-yl)indazole-4-carbonyl]naphthalen-1-yl]-N,N-dimethylmethanimidamide (compound b-31) under the same conditions as the production example of the compound b-27.

LCMS: m/z 464 $[M+H]^+$

HPLC retention time: 1.09 min (analysis condition R)

Compound B14

3-Amino-8-chloro-6-cyclopropyl-4-(7-fluoro-1H-indazol-4-yl)-1H-benzo[h]quinolin-2-one

[Formula 206]

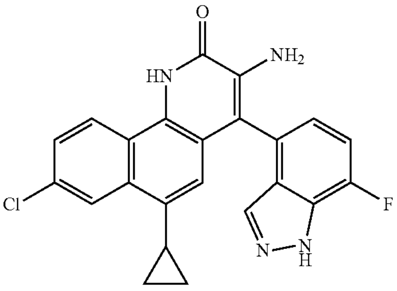

The title compound was synthesized from (1-amino-6-chloro-4-cyclopropylnaphthalen-2-yl)-[7-fluoro-2-(oxan-2-yl)indazol-4-yl]methanone (compound b-32) under the same conditions as the production examples of the compounds b-28, b-29, b-30, and the compound b-9, except that DMSO was used instead of EtOH used in the production example of the compound b-9.

LCMS: m/z 419 $[M+H]^+$

HPLC retention time: 0.82 min (analysis condition A)

Compound b-36

(E)-N'-[6-chloro-2-[7-fluoro-2-(oxan-2-yl)indazole-4-carbonyl]-4-methylnaphthalen-1-yl]-N,N-dimethylmethanimidamide

[Formula 207]

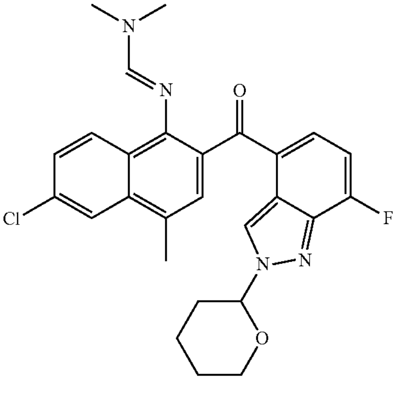

The title compound was synthesized from (E)-N'-[6-chloro-2-[7-fluoro-2-(oxan-2-yl)indazole-4-carbonyl]-4-iodonaphthalen-1-yl]-N,N-dimethylmethanimidamide (compound b-26) under the same conditions as the production example of the compound b-31, except that a 2 M solution of methylzincchloride in THF was used instead of the 0.5 M solution of cyclopropylzinc bromide in THF used in the production example of the compound b-31.

LCMS: m/z 493 $[M+H]^+$

HPLC retention time: 0.64 min (analysis condition Q)

Compound b-37

(1-Amino-6-chloro-4-methylnaphthalen-2-yl)-[7-fluoro-2-(oxan-2-yl)indazol-4-yl]methanone

[Formula 208]

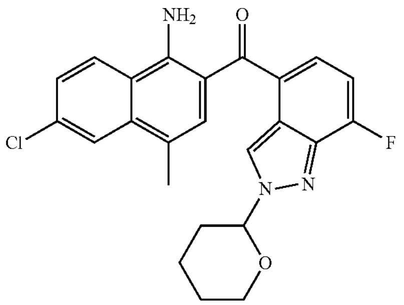

The title compound was synthesized from (E)-N'-[6-chloro-2-[7-fluoro-2-(oxan-2-yl)indazole-4-carbonyl]-4-methylnaphthalen-1-yl]-N,N-dimethylmethanimidamide (compound b-36) under the same conditions as the production example of the compound b-27, except that DMSO was used instead of EtOH used in the production example of the compound b-9.

LCMS: m/z 438 $[M+H]^+$

HPLC retention time: 1.06 min (analysis condition Q)

Compound B15

3-Amino-8-chloro-4-(7-fluoro-1H-indazol-4-yl)-6-methyl-1H-benzo[h]quinolin-2-one

[Formula 209]

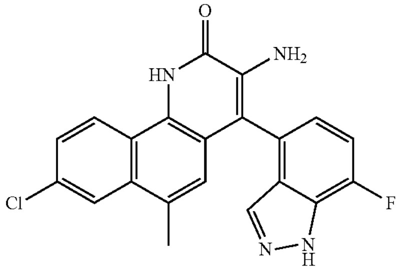

The title compound was synthesized from (1-amino-6-chloro-4-methylnaphthalen-2-yl)-[7-fluoro-2-(oxan-2-yl)indazol-4-yl]methanone (compound b-37) under the same conditions as the production examples of the compounds b-28, b-29, b-30, and the compound b-9, except that DMSO was used instead of EtOH used in the production example of the compound b-9.

LCMS: m/z 393 $[M+H]^+$

HPLC retention time: 0.78 min (analysis condition A)

Compound b-16

7-Chloro-2,4-diiodonaphthalen-1-amine

[Formula 210]

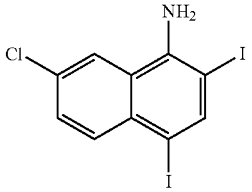

The title compound was synthesized from 7-chloronaphthalen-1-amine hydrochloride under the same conditions as the production example of the compound b-24.

LCMS: m/z 430 $[M+H]^+$

HPLC retention time: 1.11 min (analysis condition Q)

Compound b-17

(E)-N'-(7-chloro-2,4-diiodonaphthalen-1-yl)-N,N-dimethylmethanimidamide

[Formula 211]

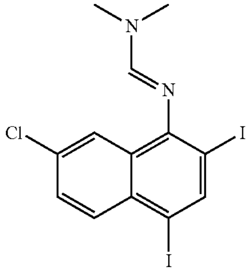

The title compound was synthesized from 7-chloro-2,4-diiodonaphthalen-1-amine (compound b-16) under the same conditions as the production example of the compound b-25.

LCMS: m/z 485 $[M+H]^+$

HPLC retention time: 0.71 min (analysis condition Q)

Compound b-18

(E)-N'-[7-chloro-2-[7-fluoro-2-(oxan-2-yl)indazole-4-carbonyl]-4-iodonaphthalen-1-yl]-N,N-dimethylmethanimidamide

[Formula 212]

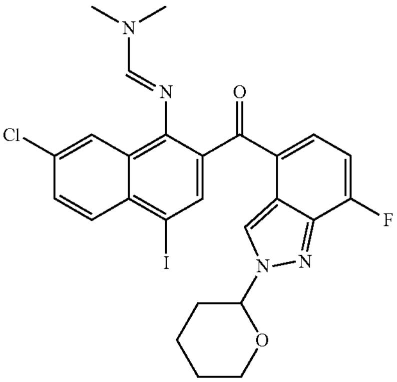

The title compound was synthesized from (E)-N'-(7-chloro-2,4-diiodonaphthalen-1-yl)-N,N-dimethylmethanimidamide (compound b-17) under the same conditions as the production example of the compound b-26.

LCMS: m/z 605 $[M+H]^+$

HPLC retention time: 1.00 min (analysis condition Q)

Compound b-19

(1-Amino-7-chloro-4-iodonaphthalen-2-yl)-[7-fluoro-2-(oxan-2-yl)indazol-4-yl]methanone

[Formula 213]

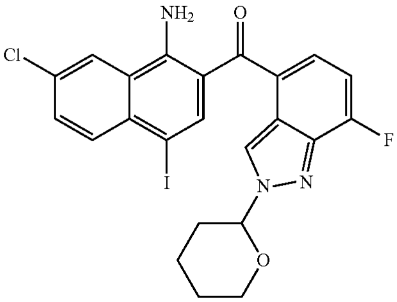

The title compound was synthesized from (E)-N'-[7-chloro-2-[7-fluoro-2-(oxan-2-yl)indazole-4-carbonyl]-4-iodonaphthalen-1-yl]-N,N-dimethylmethanimidamide (compound b-18) under the same conditions as the production example of the compound b-27.

LCMS: m/z 550 $[M+H]^+$

HPLC retention time: 1.15 min (analysis condition Q)

Compound B9

3-Amino-9-chloro-4-(7-fluoro-1H-indazol-4-yl)-6-iodo-1H-benzo[h]quinolin-2-one

[Formula 214]

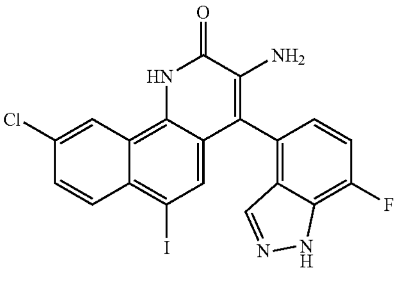

The title compound was synthesized from (1-amino-7-chloro-4-iodonaphthalen-2-yl)-[7-fluoro-2-(oxan-2-yl)indazol-4-yl]methanone (compound b-19) under the same conditions as the production examples of the compounds b-28, b-29, b-30, and the compound b-9, except that DMSO was used instead of EtOH used in the production example of the compound b-9.

LCMS: m/z 505 $[M+H]^+$

HPLC retention time: 0.87 min (analysis condition A)

Compound B10

3-Amino-9-chloro-6-cyclopropyl-4-(7-fluoro-1H-indazol-4-yl)-1H-benzo[h]quinolin-2-one

[Formula 215]

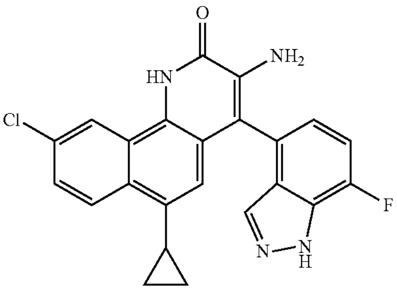

The title compound was synthesized from 3-amino-9-chloro-4-(7-fluoro-1H-indazol-4-yl)-6-iodo-1H-benzo[h]quinolin-2-one (compound B9) under the same conditions as the production example of the compound b-31.

LCMS: m/z 419 $[M+H]^+$

HPLC retention time: 0.83 min (analysis condition A)

Compound B11

3-Amino-9-chloro-4-(7-fluoro-1H-indazol-4-yl)-1H-benzo[h]quinolin-2-one

[Formula 216]

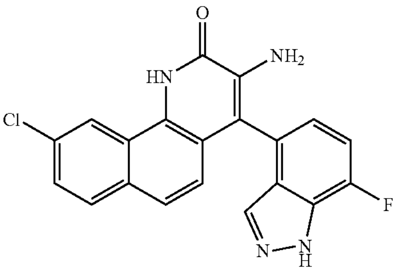

To 3-amino-9-chloro-4-(7-fluoro-1H-indazol-4-yl)-6-iodo-1H-benzo[h]quinolin-2-one (compound B9, 34 mg, 0.067 mmol), Xantphos Pd G4 (6.83 mg, 6.74 µmol), formic acid (5.43 µL, 0.141 mmol), and triethylamine (28.2 µL, 0.20 mmol) in a reaction vessel, DMA (674 µL) was added, and the mixture was heated at 100° C. for 6 hours. The reaction mixture was purified by reversed phase column chromatography (0.1% aqueous formic acid solution/0.1% formic acid in acetonitrile solution) to obtain the title compound (16 mg, yield 63%) as a light brown solid.

LCMS: m/z 379 $[M+H]^+$

HPLC retention time: 0.74 min (analysis condition A)

Compound B12

3-Amino-9-chloro-4-(7-fluoro-1H-indazol-4-yl)-6-methyl-1H-benzo[h]quinolin-2-one

[Formula 217]

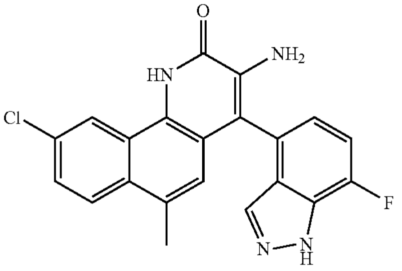

The title compound was synthesized from 3-amino-9-chloro-4-(7-fluoro-1H-indazol-4-yl)-6-iodo-1H-benzo[h]quinolin-2-one (compound B9) under the same conditions as the production example of the compound b-10, except that potassium carbonate, a [1,1'-bis(diphenylphosphino)ferrocene]dichloropalladium(II)-DCM composite, and trimethylboroxine were used instead of cesium carbonate, DPPF Pd G4, and potassium cyclopropyltrifluoroborate used in the production example of the compound b-10.

LCMS: m/z 393 $[M+H]^+$

HPLC retention time: 0.78 min (analysis condition A)

Compound b-59

4-Bromo-2-iodonaphthalen-1-amine

[Formula 218]

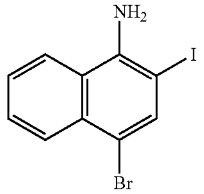

To a solution of 4-bromonaphthalen-1-amine (1.00 g, 4.50 mmol) in DMSO (10 mL) in a reaction vessel, N-iodosuccinimide (1.06 g, 4.73 mmol) was added, and the mixture was stirred at room temperature for 30 min. A 5% aqueous sodium bicarbonate solution (50 mL) was added thereto, and the mixture was extracted three times with ethyl acetate. The organic layer was washed with a 20% aqueous sodium thiosulfate solution and brine and dried over anhydrous sodium sulfate, the drying agent was filtered off, and then the obtained filtrate was concentrated under reduced pressure. The obtained residue was purified by silica gel column chromatography (hexane/ethyl acetate) to obtain the title compound (0.88 g, yield 54%) as a brown solid.

LCMS: m/z 348 $[M+H]^+$

HPLC retention time: 1.00 min (analysis condition A)

Compound b-60

(E)-N'-(4-bromo-2-iodonaphthalen-1-yl)-N,N-dimethylmethanimidamide

[Formula 219]

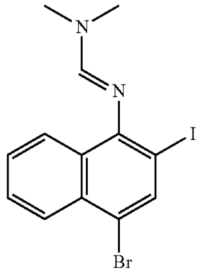

The title compound was synthesized from 4-bromo-2-iodonaphthalen-1-amine (compound b-59) under the same conditions as the production example of the compound b-25.

LCMS: m/z 403 $[M+H]^+$

HPLC retention time: 0.56 min (analysis condition A)

Compound b-61

(E)-N'-[4-bromo-2-[7-fluoro-2-(oxan-2-yl)indazole-4-carbonyl]naphthalen-1-yl]-N,N-dimethylmethanimidamide

[Formula 220]

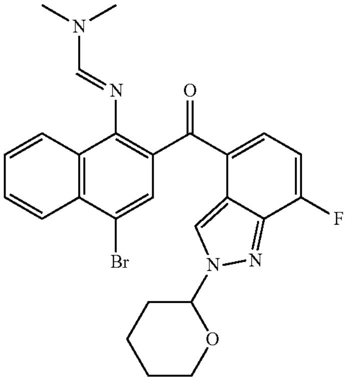

The title compound was synthesized from (E)-N'-(4-bromo-2-iodonaphthalen-1-yl)-N,N-dimethylmethanimidamide (compound b-60) under the same conditions as the production example of the compound b-26.

LCMS: m/z 523 $[M+H]^+$

HPLC retention time: 0.76 min (analysis condition A)

Compound b-62

(1-Amino-4-bromonaphthalen-2-yl)-[7-fluoro-2-(oxan-2-yl)indazol-4-yl]methanone

[Formula 221]

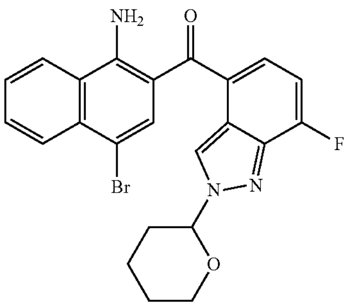

The title compound was synthesized from (E)-N'-[4-bromo-2-[7-fluoro-2-(oxan-2-yl)indazole-4-carbonyl]naphthalen-1-yl]-N,N-dimethylmethanimidamide (compound b-61) under the same conditions as the production example of the compound b-27.

LCMS: m/z 468 $[M+H]^+$

HPLC retention time: 1.06 min (analysis condition A)

Compound b-63

N-[4-bromo-2-[7-fluoro-2-(oxan-2-yl)indazole-4-carbonyl]naphthalen-1-yl]-2-chloroacetamide

[Formula 222]

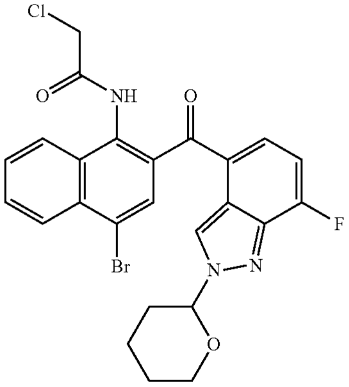

A solution of (1-amino-4-bromonaphthalen-2-yl)-[7-fluoro-2-(oxan-2-yl)indazol-4-yl]methanone (compound b-62, 301 mg, 0.643 mmol) in DCM (4.8 mL) in a reaction vessel was cooled to 0° C., chloroacetyl chloride (0.061 mL, 0.77 mmol) and pyridine (0.067 mL, 0.84 mmol) were added thereto, and the mixture was stirred at 0° C. for 30 min. The reaction mixture was concentrated under reduced pressure to obtain the crude product of the title compound.

LCMS: m/z 544 $[M+H]^+$

HPLC retention time: 0.93 min (analysis condition A)

Compound b-64

6-Bromo-4-[7-fluoro-2-(oxan-2-yl)indazol-4-yl]-3-pyridin-1-ium-1-yl-1H-benzo[h]quinolin-2-one; chloride

[Formula 223]

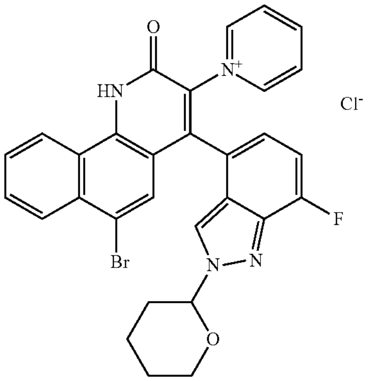

To the crude product of N-[4-bromo-2-[7-fluoro-2-(oxan-2-yl)indazole-4-carbonyl]naphthalen-1-yl]-2-chloroacetamide (compound b-63) in a reaction vessel, pyridine was added, and the mixture was stirred at 80° C. for 1 hour to obtain a solution of the title compound in pyridine.

LCMS: m/z 569 $[M]^+$

HPLC retention time: 0.64 min (analysis condition A)

Compound b-65

3-Amino-6-bromo-4-[7-fluoro-2-(oxan-2-yl)indazol-4-yl]-1H-benzo[h]quinolin-2-one

[Formula 224]

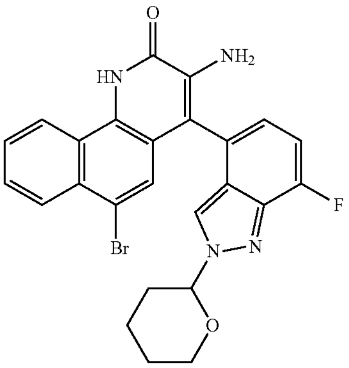

To the solution of 6-bromo-4-[7-fluoro-2-(oxan-2-yl)indazol-4-yl]-3-pyridin-1-ium-1-yl-1H-benzo[h]quinolin-2-one; chloride (compound b-64) in pyridine in a reaction vessel, hydrazine monohydrate (0.32 mL, 6.43 mmol) was added, and the mixture was stirred at 80° C. for 30 min. The reaction mixture was cooled to room temperature and then concentrated under reduced pressure to obtain the crude product of the title compound.

LCMS: m/z 507 $[M+H]^+$

HPLC retention time: 0.95 min (analysis condition A)

Compound B21

3-Amino-6-bromo-4-(7-fluoro-1H-indazol-4-yl)-1H-benzo[h]quinolin-2-one

[Formula 225]

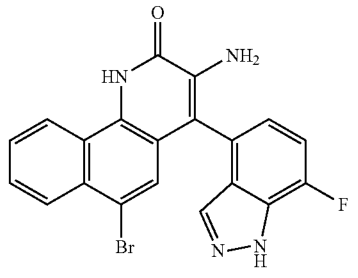

The crude product of 3-amino-6-bromo-4-[7-fluoro-2-(oxan-2-yl)indazol-4-yl]-1H-benzo[h]quinolin-2-one (compound b-65) in a reaction vessel was suspended in DCM (3.9 mL), and the mixture was cooled to 0° C. A 5% solution of hydrogen chloride in MeOH (7.81 mL, 12.9 mL) was added thereto, and the mixture was stirred for 30 min. The reaction mixture was concentrated under reduced pressure, and the obtained residue was purified by reversed phase column chromatography (0.1% aqueous formic acid solution/0.1% formic acid in acetonitrile solution) to obtain the title compound (285 mg, yield 79%) as a light brown solid.

LCMS: m/z 423 $[M+H]^+$

HPLC retention time: 0.77 min (analysis condition A)

Compound b-75

3-Amino-6-bromo-4-[7-fluoro-2-(oxan-2-yl)indazol-4-yl]-1-methylbenzo[h]quinolin-2-one

[Formula 226]

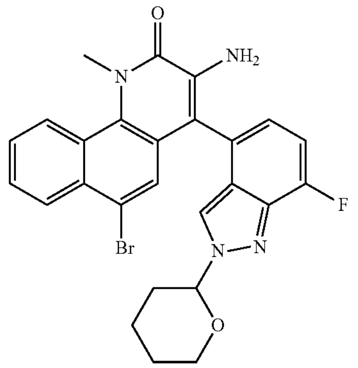

To a solution of 3-amino-6-bromo-4-[7-fluoro-2-(oxan-2-yl)indazol-4-yl]-1H-benzo[h]quinolin-2-one (compound b-65, 50 mg, 0.090 mmol) in DMA (904 μL) in a reaction vessel, potassium carbonate (31.2 mg, 0.226 mmol) and iodomethane (16.9 μL, 0.271 mmol) were added, and the mixture was stirred at room temperature for 15 hours to obtain a solution of the title compound in DMA.

LCMS: m/z 521 $[M+H]^+$

HPLC retention time: 1.20 min (analysis condition A)

Compound B33

3-Amino-6-bromo-4-(7-fluoro-1H-indazol-4-yl)-1-methylbenzo[h]quinolin-2-one

[Formula 227]

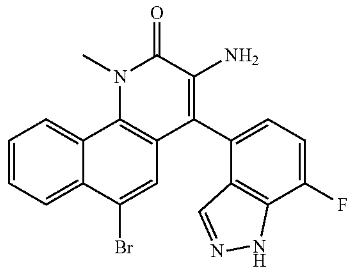

The solution of 3-amino-6-bromo-4-[7-fluoro-2-(oxan-2-yl)indazol-4-yl]-1-methylbenzo[h]quinolin-2-one (compound b-75) in DMA in a reaction vessel was cooled to 0° C., a 5% solution of hydrogen chloride in MeOH (1.37 mL, 2.25 mmol) was added thereto, and the mixture was stirred for 1 hour. A 22% aqueous formic acid solution (0.1 mL) and DMSO were added thereto, and the mixture was filtered. The filtrate was purified by reversed phase column chromatography (0.1% aqueous formic acid solution/0.1% formic acid in acetonitrile solution) to obtain the title compound (1.5 mg, yield 3.8%) as a colorless solid.

LCMS: m/z 437 $[M+H]^+$

HPLC retention time: 0.85 min (analysis condition A)

Compound B22

3-Amino-6-cyclopropyl-4-(7-fluoro-1H-indazol-4-yl)-1H-benzo[h]quinolin-2-one

[Formula 228]

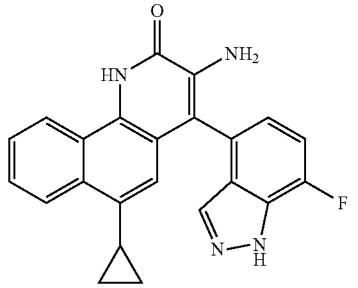

To a solution of 3-amino-6-bromo-4-(7-fluoro-1H-indazol-4-yl)-1H-benzo[h]quinolin-2-one (compound B21, 30 mg, 0.071 mmol) and CPhos Pd G3 (5.72 mg, 7.09 μmol) in DMA (0.35 mL) in a reaction vessel, a 0.5 M solution of cyclopropylzinc bromide in THF (0.58 mL, 0.29 mmol) was added, and the mixture was stirred at room temperature under nitrogen atmosphere for 15 hours. Further, CPhos Pd G3 (2.9 mg, 3.6 μmol) and a 0.5 M solution of cyclopropylzinc bromide in THF (0.29 mL, 0.145 mmol) were added thereto, and the mixture was stirred at room temperature for 3 hours. The reaction mixture was cooled to 0° C., formic acid (0.2 mL) and DMSO were added thereto, and the mixture was filtered. The filtrate was purified by reversed phase column chromatography (0.1% aqueous formic acid solution/0.1% formic acid in acetonitrile solution) to obtain the title compound (8.5 mg, yield 31%) as a light brown solid.

LCMS: m/z 385 $[M+H]^+$

HPLC retention time: 0.76 min (analysis condition A)

Compound B23

3-Amino-6-ethyl-4-(7-fluoro-1H-indazol-4-yl)-1H-benzo[h]quinolin-2-one

[Formula 229]

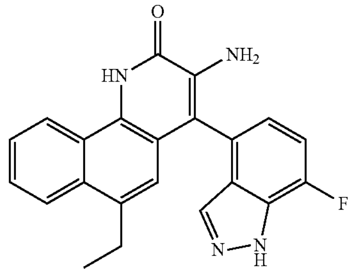

The title compound was synthesized from 3-amino-6-bromo-4-(7-fluoro-1H-indazol-4-yl)-1H-benzo[h]quinolin-2-one (compound B21) under the same conditions as the production example of the compound B22, except that about a 1 M solution of diethylzinc in hexane was used instead of a 0.5 M solution of cyclopropylzinc bromide in THE used in the production example of the compound B22.

LCMS: m/z 373 $[M+H]^+$

HPLC retention time: 0.75 min (analysis condition A)

Compound B24

3-Amino-6-cyclobutyl-4-(7-fluoro-1H-indazol-4-yl)-1H-benzo[h]quinolin-2-one

[Formula 230]

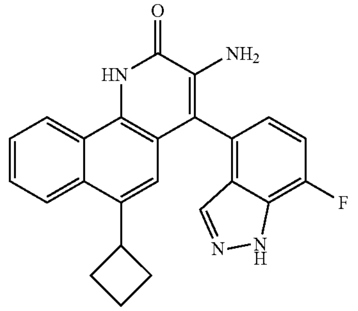

The title compound was synthesized from 3-amino-6-bromo-4-(7-fluoro-1H-indazol-4-yl)-1H-benzo[h]quinolin-2-one (compound B21) under the same conditions as the production example of the compound B22, except that a 0.5 M solution of cyclobutylzinc bromide in hexane was used instead of the 0.5 M solution of cyclopropylzinc bromide in THE used in the production example of the compound B22.

LCMS: m/z 399 $[M+H]^+$

HPLC retention time: 0.82 min (analysis condition A)

Compound B25

3-Amino-6-cyclopentyl-4-(7-fluoro-1H-indazol-4-yl)-1H-benzo[h]quinolin-2-one

[Formula 231]

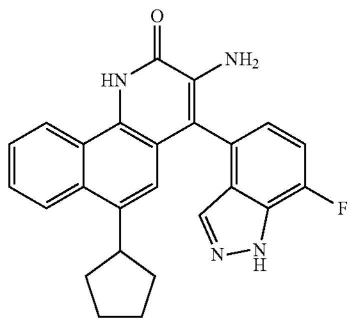

The title compound was synthesized from 3-amino-6-bromo-4-(7-fluoro-1H-indazol-4-yl)-1H-benzo[h]quinolin-2-one (compound B21) under the same conditions as the production example of the compound B22, except that a 0.5 M solution of cyclopentylzinc bromide in THF was used instead of the 0.5 M solution of cyclopropylzinc bromide in THE used in the production example of the compound B22.

LCMS: m/z 413 $[M+H]^+$

HPLC retention time: 0.85 min (analysis condition A)

Compound B26

3-Amino-4-(7-fluoro-1H-indazol-4-yl)-2-oxo-1H-benzo[h]quinoline-6-carbonitrile

[Formula 232]

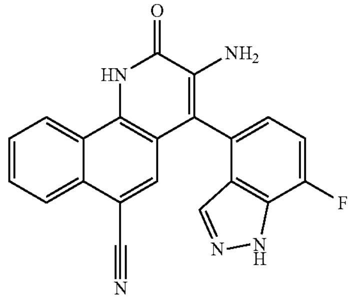

A solution of 3-amino-6-bromo-4-(7-fluoro-1H-indazol-4-yl)-1H-benzo[h]quinolin-2-one (compound B21, 30 mg, 0.071 mmol) in DMA (0.709 mL) was added to a reaction vessel, the reaction vessel was degassed under reduced pressure and subjected to nitrogen replacement, then zinc cyanide (25.0 mg, 0.213 mmol) and tetrakis(triphenylphosphine)palladium (0) (8.2 mg, 7.1 µmol) were added thereto, and the mixture was stirred at 80° C. under nitrogen atmosphere. The reaction mixture was cooled to room temperature, and formic acid (0.1 mL) and water (1.4 mL) were added thereto. The solid was collected by filtration, and then washed with a mixed solvent of DMA/water (1:2) and acetonitrile, MeOH, and DCM. The solid was suspended in acetonitrile while stirring, and the solid collected by filtration was washed with acetonitrile and MeOH to obtain the title compound (18 mg, yield 69%) as a pale yellow solid.

LCMS: m/z 370 $[M+H]^+$

HPLC retention time: 0.66 min (analysis condition A)

Compound B27

3-Amino-4-(7-fluoro-1H-indazol-4-yl)-6-methyl-1H-benzo[h]quinolin-2-one

[Formula 233]

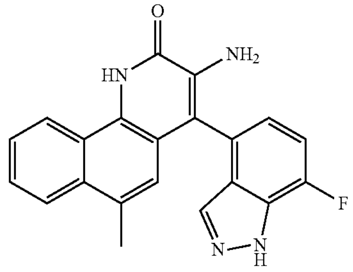

The title compound was synthesized from 3-amino-6-bromo-4-(7-fluoro-1H-indazol-4-yl)-1H-benzo[h]quinolin-2-one (compound B21) under the same conditions as the production example of the compound B22. A 2 M solution of methylzinc chloride in THF was used instead of the 0.5 M solution of cyclopropylzinc bromide in THE used in the production example of the compound B22.

LCMS: m/z 359 $[M+H]^+$

HPLC retention time: 0.71 min (analysis condition A)

Compound B28

3-Amino-4-(7-fluoro-1H-indazol-4-yl)-6-prop-1-inyl-1H-benzo[h]quinolin-2-one

[Formula 234]

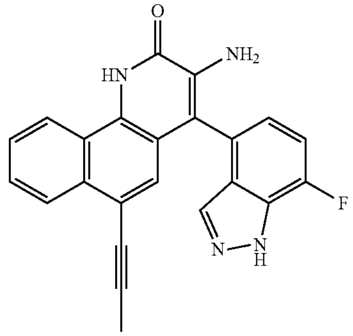

3-Amino-6-bromo-4-(7-fluoro-1H-indazol-4-yl)-1H-benzo[h]quinolin-2-one (compound B21, 20 mg, 0.047 mmol), bis(triphenylphosphine)palladium(II) dichloride (3.32 mg, 4.72 μmol), 1,3-bis(diphenylphosphino) propane (3.9 mg, 9.45 μmol), 2-butynoic acid (4.37 mg, 0.052 mmol), 1,8-diazabicyclo[5.4.0]undec-7-ene (14.25 μL, 0.095 mmol) and degassed DMA (0.709 mL) were added to a reaction vessel, and the reaction vessel was degassed under reduced pressure and subjected to nitrogen replacement. The reaction mixture was stirred at 90° C. for 12 hours, then the reaction mixture was cooled to 0° C., a 22% aqueous formic acid solution (0.1 mL) and DMSO were added thereto, and the mixture was filtered. The obtained filtrate was purified by reversed phase column chromatography (0.1% aqueous formic acid solution/0.1% formic acid in acetonitrile solution) to obtain the title compound (2.5 mg, yield 14%) as a colorless solid.

LCMS: m/z 383 $[M+H]^+$

HPLC retention time: 0.76 min (analysis condition A)

Compound B29

3-Amino-4-(7-fluoro-1H-indazol-4-yl)-6-(1-methylpyrazole-4-yl)-1H-benzo[h]quinolin-2-one

[Formula 235]

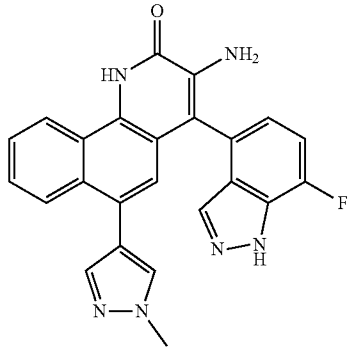

3-Amino-6-bromo-4-(7-fluoro-1H-indazol-4-yl)-1H-benzo[h]quinolin-2-one (compound B21, 20 mg, 0.047 mmol), cesium carbonate (46.2 mg, 0.142 mmol), 1-methyl-1H-pyrazole-4-boronic acid (11.9 mg, 0.095 mmol), XPhos Pd G4 (40.7 mg, 0.047 mmol), and a mixed solution of degassed DMA (315 μL) and degassed water (158 μL) were added to a reaction vessel, and the reaction mixture was stirred at 110° C. for 2 hours. The reaction mixture was cooled to room temperature, then a 22% aqueous formic acid solution (0.1 mL) and DMSO were added thereto, and the mixture was filtered. The obtained filtrate was purified by reversed phase column chromatography (0.1% aqueous formic acid solution/0.1% formic acid in acetonitrile solution) to obtain the title compound (17.2 mg, yield 86%) as a colorless solid.

LCMS: m/z 425 $[M+H]^+$

HPLC retention time: 0.59 min (analysis condition A)

Compound B30

3-Amino-6-ethenyl-4-(7-fluoro-1H-indazol-4-yl)-1H-benzo[h]quinolin-2-one

[Formula 236]

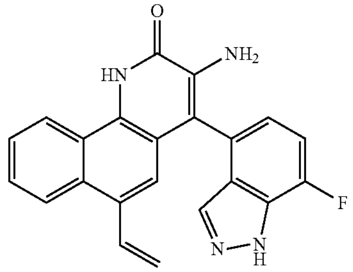

The title compound was synthesized from 3-amino-6-bromo-4-(7-fluoro-1H-indazol-4-yl)-1H-benzo[h]quinolin-2-one (compound B21) under the same conditions as the production example of the compound B29, except that potassium vinyltrifluoroborate was used instead of 1-methyl-1H-pyrazole-4-boronic acid used in the production example of the compound B29.

LCMS: m/z 371 $[M+H]^+$

HPLC retention time: 0.73 min (analysis condition A)

Compound B31

3-Amino-6-dimethylphosphoryl-4-(7-fluoro-1H-indazol-4-yl)-1H-benzo[h]quinolin-2-one

[Formula 237]

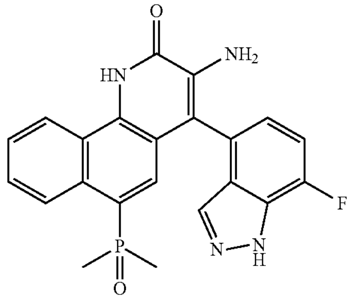

3-Amino-6-bromo-4-(7-fluoro-1H-indazol-4-yl)-1H-benzo[h]quinolin-2-one (compound B21, 20 mg, 0.047 mmol), dimethylphosphineoxide (10 mg, 0.128 mmol), Xantphos Pd G4 (4.55 mg, 4.73 μmol), tripotassium phosphate (25.1 mg, 0.118 mmol), and degassed NMP (0.47 mL) were added to a reaction vessel, and heated at 150° C. for 30 min in a sealed tube using a microwave reactor. To the reaction mixture, a 22% aqueous formic acid solution (0.1 mL) and DMSO were added, and the mixture was filtered. The obtained filtrate was purified by reversed phase column chromatography (0.1% aqueous formic acid solution/0.1% formic acid in acetonitrile solution) to obtain the title compound (12.8 mg, yield 64%) as a white solid.

LCMS: m/z 421 $[M+H]^+$

HPLC retention time: 0.46 min (analysis condition A)

Compound b-66

(E)-N'-[4-bromo-2-[7-chloro-2-(oxan-2-yl)indazole-4-carbonyl]naphthalen-1-yl]-N,N-dimethylmethanimidamide

[Formula 238]

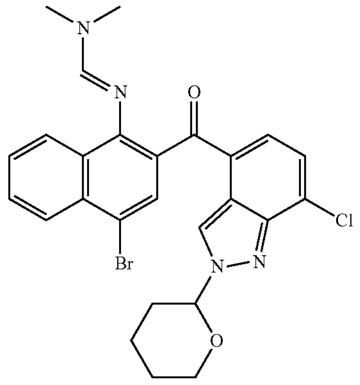

The title compound was synthesized from (E)-N'-(4-bromo-2-iodonaphthalen-1-yl)-N,N-dimethylmethanimidamide (compound b-60) and [7-chloro-2-(oxan-2-yl)indazol-4-yl]-morpholin-4-ylmethanone (compound a-54) under the same conditions as the production example of the compound b-26, except that a 0.75 M solution of isopropylmagnesium bromide in THF was used instead of the 1.3 M solution of isopropylmagnesium chloride-lithium chloride complex in THE used in the production example of the compound b-26.

LCMS: m/z 539 $[M+H]^+$

HPLC retention time: 0.80 min (analysis condition A)

Compound b-67

(1-Amino-4-bromonaphthalen-2-yl)-[7-chloro-2-(oxan-2-yl)indazol-4-yl]methanone

[Formula 239]

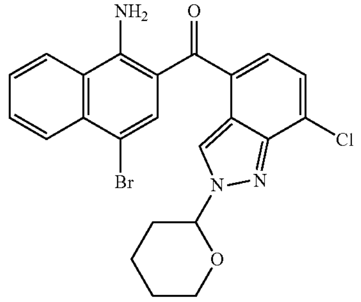

(E)-N'-[4-bromo-2-[7-chloro-2-(oxan-2-yl)indazole-4-carbonyl]naphthalen-1-yl]-N,N-dimethylmethanimidamide (compound b-66, 150 mg, 0.278 mmol) in a reaction vessel was dissolved in a mixed solution of 2-propanol (1.85 mL) and water (0.93 mL), a 1.5 M aqueous lithium hydroxide solution (1.39 mmol, 926 μL) was added thereto, and the mixture was stirred at 80° C. for 24 hours. To the reaction mixture, water (1 mL) was added, and the solid was collected by filtration. The obtained solid was sequentially washed with a mixed solution of isopropanol and water, water, and MeOH to obtain the title compound (108.5 mg, yield 98%) as a yellow solid.

LCMS: m/z 484 $[M+H]^+$

HPLC retention time: 1.09 min (analysis condition A)

Compound B36

3-Amino-6-bromo-4-(7-chloro-1H-indazol-4-yl)-1H-benzo[h]quinolin-2-one

[Formula 240]

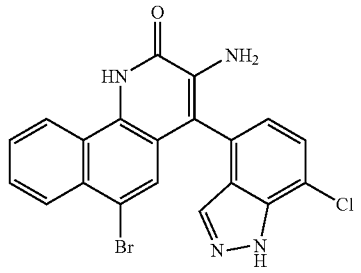

The title compound was synthesized from (1-amino-4-bromonaphthalen-2-yl)-[7-chloro-2-(oxan-2-yl)indazol-4-yl]methanone (compound b-67) under the same conditions as the production examples of the compounds b-63, b-64, b-65, and B21.

LCMS: m/z 439 [M+H]+

HPLC retention time: 0.81 min (analysis condition A)

Compound B37

3-Amino-4-(7-chloro-1H-indazol-4-yl)-6-cyclopropyl-1H-benzo[h]quinolin-2-one

[Formula 241]

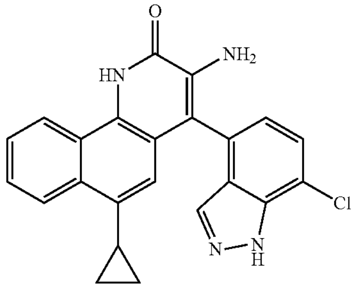

The title compound was synthesized from 3-amino-6-bromo-4-(7-chloro-1H-indazol-4-yl)-1H-benzo[h]quinolin-2-one (compound B36) under the same conditions as the production example of the compound B22.

LCMS: m/z 401 [M+H]+

HPLC retention time: 0.79 min (analysis condition A)

Compound B38

3-Amino-4-(7-chloro-1H-indazol-4-yl)-6-ethyl-1H-benzo[h]quinolin-2-one

[Formula 242]

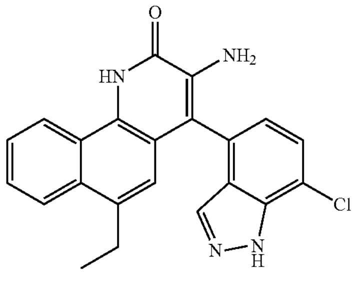

The title compound was synthesized from 3-amino-6-bromo-4-(7-chloro-1H-indazol-4-yl)-1H-benzo[h]quinolin-2-one (compound B36) under the same conditions as the production example of the compound B22, except that about a 1 M solution of diethylzinc in hexane was used instead of a 0.5 M solution of cyclopropylzinc bromide in THE used in the production example of the compound B22.

LCMS: m/z 389 [M+H]+

HPLC retention time: 0.79 min (analysis condition A)

Compound B39

3-Amino-4-(7-chloro-1H-indazol-4-yl)-6-cyclobutyl-1H-benzo[h]quinolin-2-one

[Formula 243]

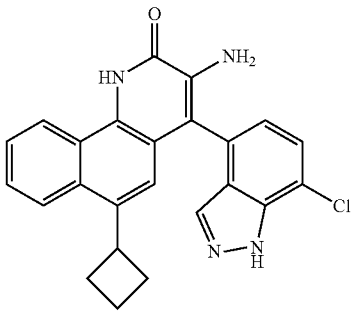

The title compound was synthesized from 3-amino-6-bromo-4-(7-chloro-1H-indazol-4-yl)-1H-benzo[h]quinolin-2-one (compound B36) under the same conditions as the production example of the compound B22, except that a 0.5 M solution of cyclobutylzinc bromide in hexane was used instead of the 0.5 M solution of cyclopropylzinc bromide in THE used in the production example of the compound B22.

LCMS: m/z 415 [M+H]+

HPLC retention time: 0.85 min (analysis condition A)

Compound B40

3-Amino-4-(7-chloro-1H-indazol-4-yl)-6-cyclopentyl-1H-benzo[h]quinolin-2-one

[Formula 244]

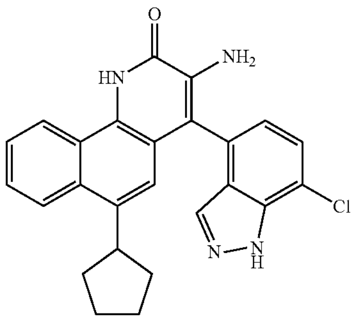

The title compound was synthesized from 3-amino-6-bromo-4-(7-chloro-1H-indazol-4-yl)-1H-benzo[h]quinolin-2-one (compound B36) under the same conditions as the production example of the compound B22, except that a 0.5 M solution of cyclopentylzinc bromide in THF was used instead of the 0.5 M solution of cyclopropylzinc bromide in THE used in the production example of the compound B22.

LCMS: m/z 429 [M+H]+

HPLC retention time: 0.89 min (analysis condition A)

Compound B41

3-Amino-4-(7-chloro-1H-indazol-4-yl)-2-oxo-1H-benzo[h]quinoline-6-carbonitrile

[Formula 245]

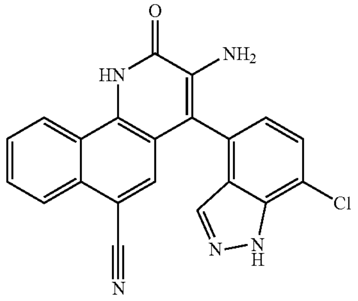

The title compound was synthesized from 3-amino-6-bromo-4-(7-chloro-1H-indazol-4-yl)-1H-benzo[h]quinolin-2-one (compound B36) under the same conditions as the production example of the compound B26.

LCMS: m/z 386 $[M+H]^+$

HPLC retention time: 0.70 min (analysis condition A)

Compound B42

3-Amino-4-(7-cyano-1H-indazol-4-yl)-2-oxo-1H-benzo[h]quinoline-6-carbonitrile

[Formula 246]

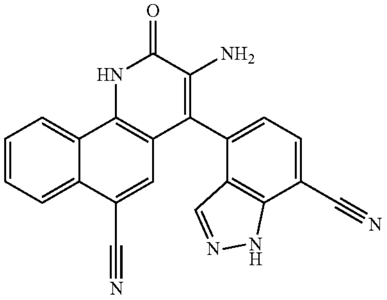

The title compound was synthesized from 3-amino-6-bromo-4-(7-chloro-1H-indazol-4-yl)-1H-benzo[h]quinolin-2-one (compound B36) under the same conditions as the production example of the compound B26, except that XPhos Pd G4 was used instead of tetrakis (triphenylphosphine)palladium (0) used in the production example of the compound B26.

LCMS: m/z 377 $[M+H]^+$

HPLC retention time: 0.64 min (analysis condition A)

Compound B43

3-Amino-4-(7-chloro-1H-indazol-4-yl)-6-methyl-1H-benzo[h]quinolin-2-one

[Formula 247]

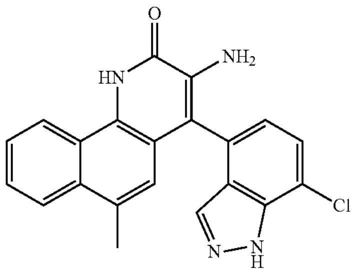

LCMS: m/z 375 $[M+H]^+$

HPLC retention time: 0.75 min (analysis condition A)

Compound B44

3-Amino-4-(7-chloro-1H-indazol-4-yl)-1H-benzo[h]quinolin-2-one

[Formula 248]

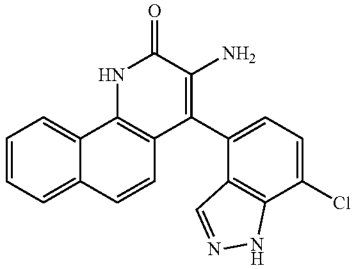

B43 and B44 were synthesized from 3-amino-6-bromo-4-(7-chloro-1H-indazol-4-yl)-1H-benzo[h]quinolin-2-one (compound B36) under the same conditions as the production example of the compound B29, except that tetrakis (triphenylphosphine)palladium (0) and trimethylboroxine were used instead of XPhos Pd G4 and 1-methyl-1H-pyrazole-4-boronic acid used in the production example of the compound B29.

LCMS: m/z 361 $[M+H]^+$

HPLC retention time: 0.72 min (analysis condition A)

Compound B45

3-Amino-6-chloro-4-(7-chloro-1H-indazol-4-yl)-1H-benzo[h]quinolin-2-one

[Formula 249]

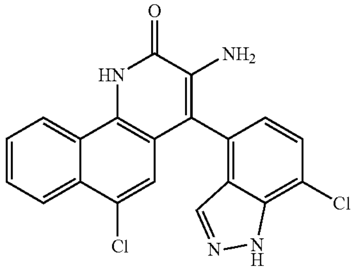

The title compound was synthesized from 3-amino-6-bromo-4-(7-chloro-1H-indazol-4-yl)-1H-benzo[h]quinolin-2-one (compound B36) under the same conditions as the production example of the compound b-14, except that the microwave reactor used in the production example of the compound b-14 was not used, and heating and stirring were carried out.

LCMS: m/z 395 $[M+H]^+$

HPLC retention time: 0.80 min (analysis condition A)

Compound b-76

4-Chloro-2-iodonaphthalen-1-amine

[Formula 250]

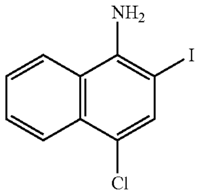

LCMS: m/z 304 $[M+H]^+$

HPLC retention time: 0.99 min (analysis condition A)

Compound b-77

(E)-N'-(4-chloro-2-iodonaphthalen-1-yl)-N,N-dimethylmethanimidamide

[Formula 251]

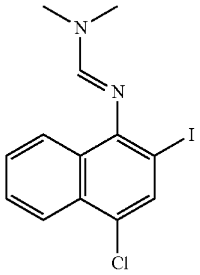

(1) To a solution of 4-chloronaphthalen-1-amine (300 mg, 1.689 mmol) in DMSO (3 mL) in a reaction vessel, N-iodosuccinimide (399 mg, 1.77 mmol) was added, and the mixture was stirred at room temperature for 30 min to obtain a solution of 4-chloro-2-iodonaphthalen-1-amine (compound b-76) in DMSO.

(2) To a solution of the obtained compound b-76 in DMSO, N,N-dimethylformamidedimethylacetal (0.905 mL, 6.76 mmol) was added, and the mixture was stirred at 80° C. for 1 hour. To the reaction mixture, a 22% aqueous formic acid solution and acetonitrile were added, and the mixture was filtered. The filtrate was purified by reversed phase column chromatography (0.1% aqueous formic acid solution/0.1% formic acid in acetonitrile solution) to obtain (E)-N'-(4-chloro-2-iodonaphthalen-1-yl)-N,N-dimethylmethanimidamide (compound b-77, 564 mg, yield 93%) as an oily substance.

LCMS: m/z 359 $[M+H]^+$

HPLC retention time: 0.55 min (analysis condition A)

Compound b-78

(E)-N'-[4-chloro-2-[7-fluoro-2-(oxan-2-yl)indazole-4-carbonyl]naphthalen-1-yl]-N,N-dimethylmethanimidamide

[Formula 252]

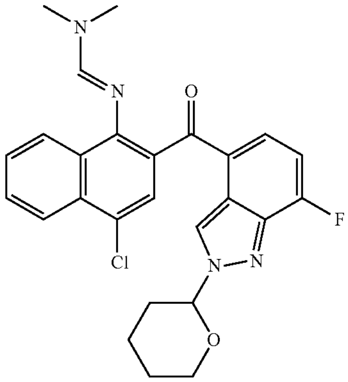

The title compound was synthesized from (E)-N'-(4-chloro-2-iodonaphthalen-1-yl)-N,N-dimethylmethanimidamide (compound b-77) under the same conditions as the production example of the compound b-26, except that toluene was used instead of THE used in the production example of the compound b-26.

LCMS: m/z 479 $[M+H]^+$

HPLC retention time: 0.73 min (analysis condition A)

Compound b-79

(1-Amino-4-chloronaphthalen-2-yl)-[7-fluoro-2-(oxan-2-yl)indazol-4-yl]methanone

[Formula 253]

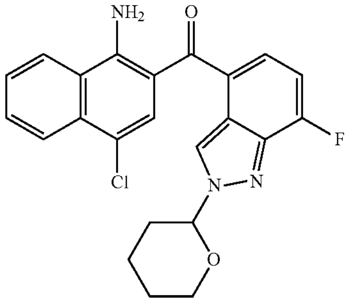

The title compound was synthesized from (E)-N'-[4-chloro-2-[7-fluoro-2-(oxan-2-yl)indazole-4-carbonyl]naphthalen-1-yl]-N,N-dimethylmethanimidamide (compound b-78) under the same conditions as the production example of the compound b-27.

LCMS: m/z 424 $[M+H]^+$

HPLC retention time: 1.04 min (analysis condition A)

Compound B34

3-Amino-6-chloro-4-(7-fluoro-1H-indazol-4-yl)-1H-benzo[h]quinolin-2-one

[Formula 254]

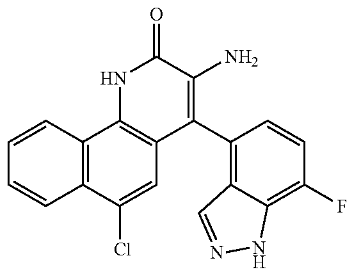

The title compound was synthesized from (1-amino-4-chloronaphthalen-2-yl)-[7-fluoro-2-(oxan-2-yl)indazol-4-yl]methanone (compound b-79) under the same conditions as the production examples of the compounds b-63, b-64, b-65, and B21.

LCMS: m/z 379 $[M+H]^+$

HPLC retention time: 0.77 min (analysis condition A)

Compound b-83

4-Fluoro-2-iodonaphthalen-1-amine

[Formula 255]

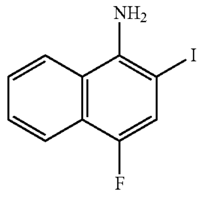

To a solution of 4-fluoronaphthalen-1-amine (600 mg, 3.72 mmol) in DMSO (6 mL) in a reaction vessel, TFA (315 μL, 4.09 mmol) and N-iodosuccinimide (854 mg, 3.8 mmol) were added, and the mixture was stirred at room temperature for 15 min to obtain a solution of the title compound in DMSO.

LCMS: m/z 288 $[M+H]^+$

HPLC retention time: 0.90 min (analysis condition B)

Compound b-84

(E)-N'-(4-fluoro-2-iodonaphthalen-1-yl)-N,N-dimethylmethanimidamide

[Formula 256]

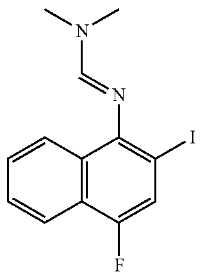

To the solution of compound b-83 in DMSO, N,N-dimethylformamidedimethylacetal (3.97 mL, 29.8 mmol) was added, and the mixture was stirred at 80° C. for 3 hours. The reaction mixture was purified by reversed phase column chromatography and silica gel column chromatography to obtain the title compound (971 mg, yield 76%).

LCMS: m/z 343 $[M+H]^+$

HPLC retention time: 0.51 min (analysis condition B)

Compound b-85

(E)-N'-[4-fluoro-2-[7-fluoro-2-(oxan-2-yl)indazole-4-carbonyl]naphthalen-1-yl]-N,N-dimethylmethanimidamide

[Formula 257]

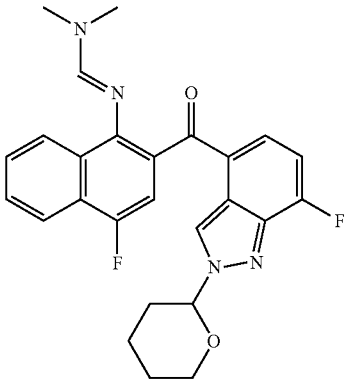

The title compound was synthesized from (E)-N'-(4-fluoro-2-iodonaphthalen-1-yl)-N,N-dimethylmethanimidamide (compound b-84) under the same conditions as the production example of the compound b-26, except that toluene was used instead of THE used in the production example of the compound b-26.

LCMS: m/z 463 $[M+H]^+$

HPLC retention time: 0.65 min (analysis condition B)

Compound b-86

(1-Amino-4-fluoronaphthalen-2-yl)-[7-fluoro-2-(oxan-2-yl)indazol-4-yl]methanone

[Formula 258]

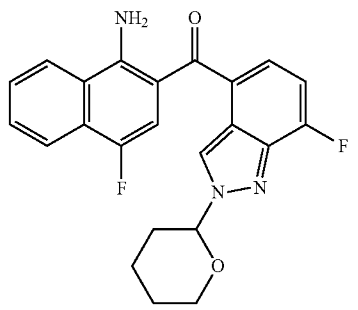

The title compound was synthesized from (E)-N'-[4-fluoro-2-[7-fluoro-2-(oxan-2-yl)indazole-4-carbonyl]naphthalen-1-yl]-N,N-dimethylmethanimidamide (compound b-85) under the same conditions as the production example of the compound b-27, except that a 1.5 M aqueous lithium hydroxide solution was used instead of the 5 M aqueous sodium hydroxide solution used in the production example of the compound b-27.

LCMS: m/z 408 $[M+H]^+$

HPLC retention time: 0.97 min (analysis condition B)

Compound B35

3-Amino-6-fluoro-4-(7-fluoro-1H-indazol-4-yl)-1H-benzo[h]quinolin-2-one

[Formula 259]

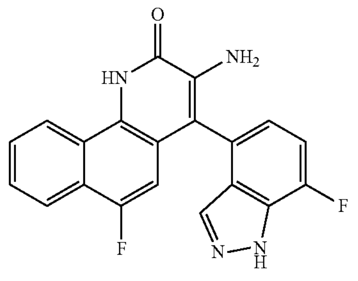

The title compound was synthesized from (1-amino-4-fluoronaphthalen-2-yl)-[7-fluoro-2-(oxan-2-yl)indazol-4-yl]methanone (compound b-86) under the same conditions as the production examples of the compounds b-63, b-64, b-65, and B21.

LCMS: m/z 363 $[M+H]^+$

HPLC retention time: 0.70 min (analysis condition B)

Compound b-90

Methyl 2-[[1-(oxan-2-yl)indazole-4-carbonyl]amino]acetate

[Formula 260]

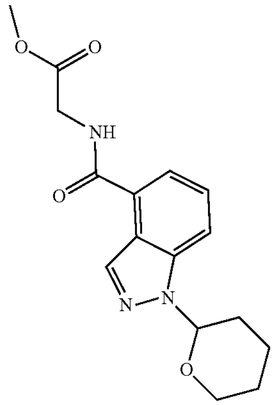

The title compound was synthesized from 1-(tetrahydropyran-2-yl)-1H-indazole-4-carboxylic acid under the same conditions as the production example of the compound b-2, except that glycine methyl ester hydrochloride was used instead of N,O-dimethylhydroxylamine hydrochloride used in the production example of the compound b-2.

LCMS: m/z 318 $[M+H]^+$

HPLC retention time: 0.80 min (analysis condition F)

Compound b-91

Methyl 2-[(2-methylpropan-2-yl)oxycarbonyl-[1-(oxan-2-yl)indazole-4-carbonyl]amino]acetate

[Formula 261]

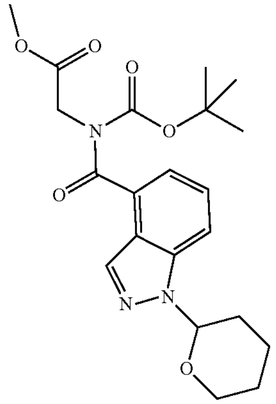

To a solution of methyl 2-[[1-(oxan-2-yl)indazole-4-carbonyl]amino]acetate (compound b-90, 105 g, 332 mmol) in THF (1.1 L) in a reaction vessel, di-tert-butyl dicarbonate (145 g, 663 mmol) and 4-dimethylaminopyridine (4.05 g, 33.2 mmol) were added, and the mixture was stirred at room temperature for 1 hour. To the mixed reaction solution, ethyl acetate (525 mL) was added, and the mixture was sequentially washed with 1 M hydrochloric acid, a saturated aqueous sodium bicarbonate solution, and 13% brine, and concentrated under reduced pressure. To the obtained residue, hexane (1.58 L) was added, and the mixture was stirred for 2 hours. The precipitated solid was collected by filtration and washed with hexane (315 mL) to obtain the title compound (136 g, yield 98%) as a light brown solid.

LCMS: m/z 418 $[M+H]^+$

HPLC retention time: 1.20 min (analysis condition F)

Compound b-92

Methyl 2-[(2-methylpropan-2-yl)oxycarbonylamino]-3-[1-(oxan-2-yl)indazol-4-yl]-3-oxopropanoate

[Formula 262]

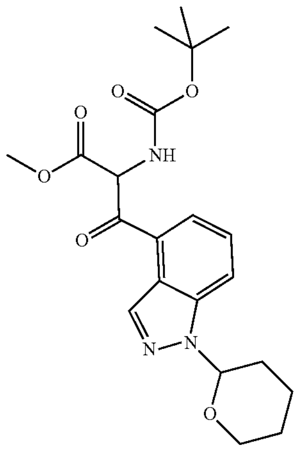

A solution of methyl 2-[(2-methylpropan-2-yl)oxycarbonyl-[1-(oxan-2-yl)indazole-4-carbonyl]amino]acetate (compound b-91, 10 g, 23.95 mmol) in THF (150 mL) in a reaction vessel was cooled to 0° C., a 1 M solution of potassium tert-butoxide in THF (2.4 mL, 2.4 mmol) and a 1 M solution of LiHMDS in THF (25.2 mL, 25.2 mmol) were added thereto, and the mixture was stirred for 30 min to obtain a solution of the title compound in THF.

LCMS: m/z 418 $[M+H]^+$

HPLC retention time: 2.67 min (analysis condition E)

Compound b-93

Methyl (E)-3-(4-methylphenyl) sulfonyloxy-2-[(2-methylpropan-2-yl)oxycarbonylamino]-3-[1-(oxan-2-yl)indazol-4-yl]prop-2-enoate

[Formula 263]

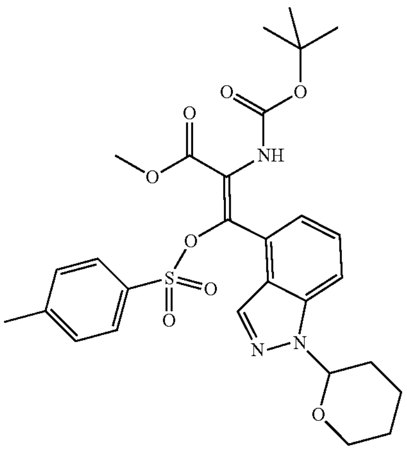

To a solution of methyl 2-[(2-methylpropan-2-yl)oxycarbonylamino]-3-[1-(oxan-2-yl)indazol-4-yl]-3-oxopropanoate (compound b-92) in THF in a reaction vessel, a solution of p-toluenesulfonic anhydride (8.6 g, 26.3 mmol) in THF (50 mL) was added, and the mixture was stirred for 5 hours. To the reaction mixture, a 10% aqueous formic acid solution was added, and the mixture was extracted with ethyl acetate. The organic layer was washed with a saturated aqueous sodium bicarbonate solution and brine and concentrated. The obtained residue was purified by silica gel column chromatography to obtain the title compound (10.6 g, yield 78%).

LCMS: m/z 572 $[M+H]^+$

HPLC retention time: 3.04 min (analysis condition E)

Compound b-99

4-Cyclopropyl-6-fluoronaphthalen-1-amine

[Formula 264]

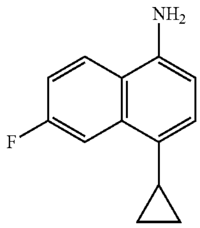

The title compound was synthesized from 4-bromo-6-fluoronaphthalen-1-amine under the same conditions as the production example of the compound b-31, except that CPhos Pd G3 was used instead of XPhos Pd G4 used in the production example of the compound b-31.

LCMS: m/z 202 $[M+H]^+$

HPLC retention time: 0.74 min (analysis condition A)

Compound b-100

2-Bromo-4-cyclopropyl-6-fluoronaphthalen-1-amine

[Formula 265]

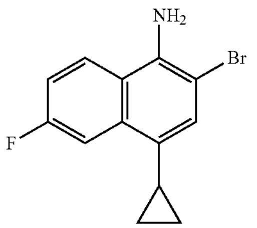

A solution of 4-cyclopropyl-6-fluoronaphthalen-1-amine (compound b-99, 218 mg, 1.08 mmol) in DMF (4.36 mL) in a reaction vessel was cooled to 0° C., N-bromosuccinimide (174 mg, 1.68 mmol) was added thereto, and the mixture was stirred for 1 hour. Further, N-bromosuccinimide (19.28 mg, 0.108 mmol) was added thereto, and the mixture was stirred for 30 min. The reaction mixture was purified by reversed phase column chromatography to obtain the title compound (239 mg, yield 79%).

LCMS: m/z 280 $[M+H]^+$

HPLC retention time: 0.99 min (analysis condition B)

Compound b-101

4-Cyclopropyl-6-fluoro-2-(4,4,5,5-tetramethyl-1,3,2-dioxaborolan-2-yl) naphthalen-1-amine

[Formula 266]

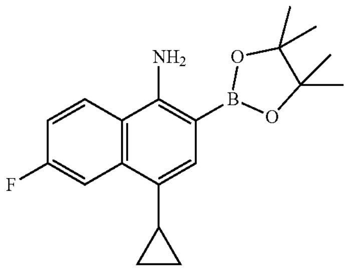

To a solution of 2-bromo-4-cyclopropyl-6-fluoronaphthalen-1-amine (compound b-100, 235 mg, 0.839 mmol) in toluene (4.7 mL) in a reaction vessel, acetic acid (101 μL, 1.762 mmol), bis(pinacolato)diboron (320 mg, 1.26 mmol), and potassium carbonate (232 mg, 1.68 mmol) were added thereto, and the mixture was stirred for 5 min. To the reaction mixture, [1,4-bis(diphenylphosphino)butane]palladium(II) dichloride (50.7 mg, 0.084 mmol) was added, and the mixture was stirred at 100° C. under nitrogen atmosphere for 2 hours. The reaction mixture was cooled to room temperature and then filtered, and the obtained filtrate was purified by silica gel column chromatography to obtain the title compound (195.8 mg, yield 71%).

LCMS: m/z 328 $[M+H]^+$

HPLC retention time: 1.09 min (analysis condition B)

Compound b-102 tert-Butyl N-[6-cyclopropyl-8-fluoro-4-[1-(oxan-2-yl)indazol-4-yl]-2-oxo-1H-benzo[h]quinolin-3-yl] carbamate

[Formula 267]

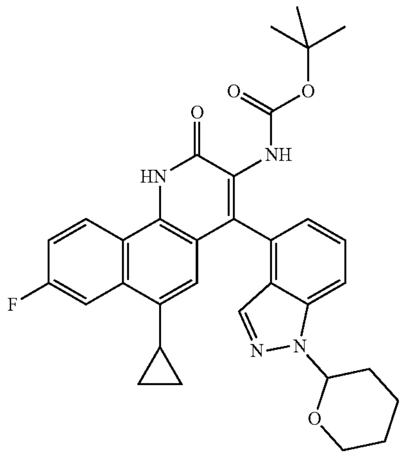

To a mixed solution of methyl (E)-3-(4-methylphenyl) sulfonyloxy-2-[(2-methylpropan-2-yl)oxycarbonylamino]-3-[1-(oxan-2-yl)indazol-4-yl]prop-2-enoate (compound b-93, 120 mg, 0.21 mmol) in 4-methyltetrahydropyran (2.4 mL) and water (360 μL) in a reaction vessel, 4-cyclopropyl-6-fluoro-2-(4,4,5,5-tetramethyl-1,3,2-dioxaborolan-2-yl) naphthalen-1-amine (compound b-101, 68.7 mg, 0.21 mmol), sodium carbonate (44.5 mg, 0.42 mmol), 1,4-bis (diphenylphosphino)butane]palladium(II) dichloride (12.67 mg, 0.021 mmol) were added, and the mixture was stirred at 100° C. under nitrogen atmosphere for 1 hour. To the mixed reaction solution, water was added, the mixture was extracted with ethyl acetate, and the organic layer was concentrated under reduced pressure. The obtained residue was purified by silica gel column chromatography to obtain the title compound (72 mg, yield 60%).

LCMS: m/z 569 $[M+H]^+$

HPLC retention time: 0.98 min (analysis condition B)

Compound B48

3-Amino-6-cyclopropyl-8-fluoro-4-(1H-indazol-4-yl)-1H-benzo[h]quinolin-2-one; hydrochloride

[Formula 268]

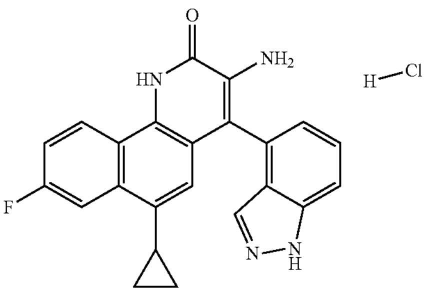

To tert-butyl N-[6-cyclopropyl-8-fluoro-4-[1-(oxan-2-yl) indazol-4-yl]-2-oxo-1H-benzo[h]quinolin-3-yl]carbamate (compound b-102, 72 mg, 0.127 mmol) in a reaction vessel, a 5% solution of hydrogen chloride in MeOH was added, and the mixture was stirred at room temperature for 24 hours. To the reaction mixture, TBME was added, and the mixture was stirred. The solid was collected by filtration and washed with TBME to obtain the title compound (34.3 mg, yield 64.4%) as a yellow solid.

LCMS: m/z 385 $[M+H]^+$

HPLC retention time: 0.74 min (analysis condition B)

Compound b-94

4-Bromo-7-fluoronaphthalen-1-amine

[Formula 269]

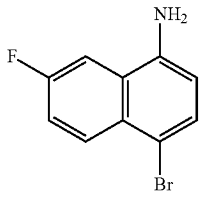

The title compound was synthesized from 7-fluoronaphthalen-1-amine under the same conditions as the production example of the compound b-100.

LCMS: m/z 240 $[M+H]^+$

HPLC retention time: 1.02 min (analysis condition B)

Compound b-95

4-Cyclopropyl-7-fluoronaphthalen-1-amine

[Formula 270]

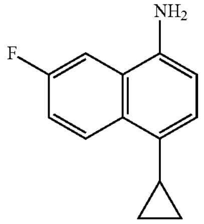

The title compound was synthesized from 4-bromo-7-fluoronaphthalen-1-amine (compound b-94) under the same conditions as the production example of the compound B22, except that 2-dicyclohexylphosphino-2',6'-bis(N,N-dimethylamino) biphenyl and palladium(II) acetate were used instead of CPhos Pd G3 used in the production example of the compound B22.

LCMS: m/z 202 $[M+H]^+$

HPLC retention time: 0.88 min (analysis condition B)

Compound b-96

2-Bromo-4-cyclopropyl-7-fluoronaphthalen-1-amine

[Formula 271]

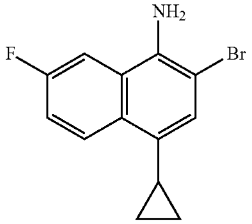

The title compound was synthesized from 4-cyclopropyl-7-fluoronaphthalen-1-amine (compound b-95) under the same conditions as the production example of the compound b-100.

LCMS: m/z 280 $[M+H]^+$

HPLC retention time: 0.99 min (analysis condition B)

Compound b-97

4-Cyclopropyl-7-fluoro-2-(4,4,5,5-tetramethyl-1,3,2-dioxaborolan-2-yl) naphthalen-1-amine

[Formula 272]

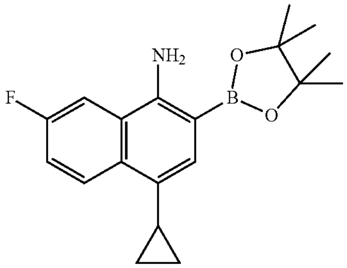

The title compound was synthesized from 2-bromo-4-cyclopropyl-7-fluoronaphthalen-1-amine (compound b-96) under the same conditions as the production example of the compound b-101.

LCMS: m/z 328 $[M+H]^+$

HPLC retention time: 1.08 min (analysis condition B)

Compound b-98 tert-Butyl N-[6-cyclopropyl-9-fluoro-4-[1-(oxan-2-yl)indazol-4-yl]-2-oxo-1H-benzo[h]quinolin-3-yl] carbamate

[Formula 273]

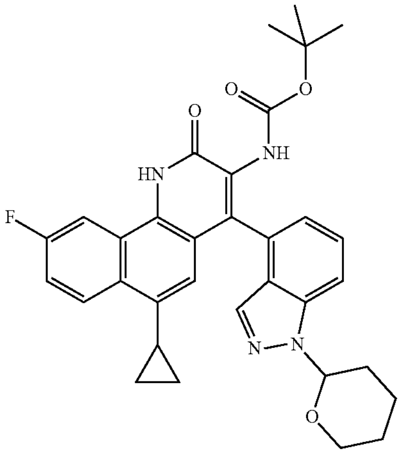

The title compound was synthesized from 4-cyclopropyl-7-fluoro-2-(4,4,5,5-tetramethyl-1,3,2-dioxaborolan-2-yl) naphthalen-1-amine (compound b-97) under the same conditions as the production example of the compound b-102.

LCMS: m/z 569 $[M+H]^+$

HPLC retention time: 0.98 min (analysis condition B)

Compound B47

3-Amino-6-cyclopropyl-9-fluoro-4-(1H-indazol-4-yl)-1H-benzo[h]quinolin-2-one

[Formula 274]

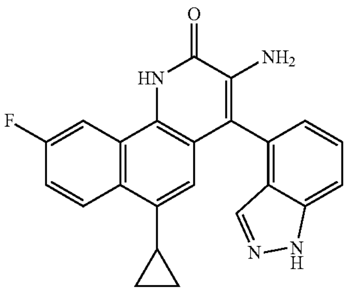

The title compound was synthesized from tert-butyl N-[6-cyclopropyl-9-fluoro-4-[1-(oxan-2-yl)indazol-4-yl]-2-oxo-1H-benzo[h]quinolin-3-yl]carbamate (compound b-98) under the same conditions as the production example of the compound B48.

LCMS: m/z 385 $[M+H]^+$

HPLC retention time: 0.75 min (analysis condition B)

Compound b-103

2-Bromo-4-cyclopropylnaphthalen-1-amine

[Formula 275]

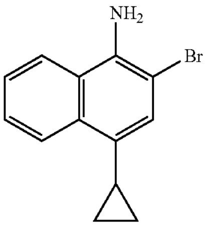

The title compound was synthesized from 4-cyclopropylnaphthalen-1-amine under the same conditions as the production example of the compound b-100, except that NMP was used instead of DMF used in the production example of the compound b-100.

LCMS: m/z 262 $[M+H]^+$

HPLC retention time: 0.95 min (analysis condition A)

Compound b-104

4-Cyclopropyl-2-(4,4,5,5-tetramethyl-1,3,2-dioxaborolan-2-yl) naphthalen-1-amine

[Formula 276]

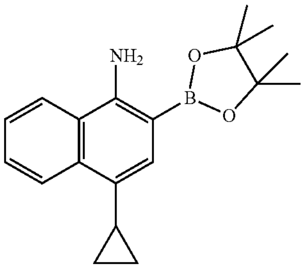

The title compound was synthesized from 2-bromo-4-cyclopropylnaphthalen-1-amine (compound b-103) under the same conditions as the production example of the compound b-101, except that 1,1'-bis(diphenylphosphino) ferrocene]dichloropalladium(II) and potassium acetate were used instead of [1,4-bis(diphenylphosphino)butane]palladium(II) dichloride, potassium carbonate, and acetic acid used in the production example of the compound b-101.

LCMS: m/z 310 $[M+H]^+$

HPLC retention time: 1.05 min (analysis condition A)

Compound b-105 tert-Butyl N-[6-cyclopropyl-4-[1-(oxan-2-yl)indazol-4-yl]-2-oxo-1H-benzo[h]quinolin-3-yl]carbamate

[Formula 277]

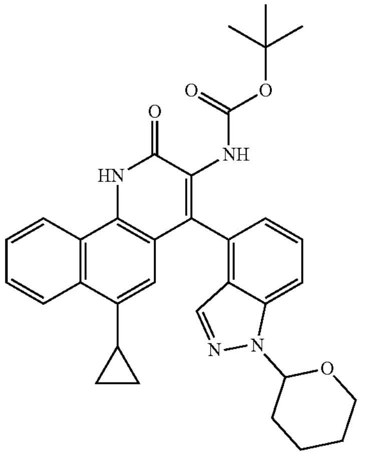

The title compound was synthesized from 4-cyclopropyl-2-(4,4,5,5-tetramethyl-1,3,2-dioxaborolan-2-yl) naphthalen-1-amine (compound b-104) under the same conditions as the production example of the compound b-102, except that palladium(II) acetate and 1,4-bis(diphenylphosphino) butane were used instead of [1,4-bis(diphenylphosphino) butane]palladium(II) dichloride used in the production example of the compound b-102.

LCMS: m/z 551 $[M+H]^+$

HPLC retention time: 0.95 min (analysis condition A)

Compound B49

3-Amino-6-cyclopropyl-4-(1H-indazol-4-yl)-1H-benzo[h]quinolin-2-one

[Formula 278]

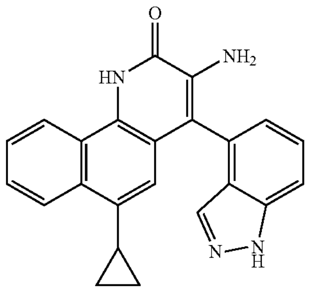

To a solution of tert-butyl N-[6-cyclopropyl-4-[1-(oxan-2-yl)indazol-4-yl]-2-oxo-1H-benzo[h]quinolin-3-yl]carbamate (compound b-105, 30 mg, 0.054 mmol) in TFE (0.9 mL) in a reaction vessel, trimethylsilyl chloride (21 μL, 0.16 mmol) was added, and the mixture was stirred at room temperature for 8 hours. The reaction mixture was concentrated under reduced pressure, and the obtained residue was purified by reversed phase column chromatography to obtain the title compound (13.3 mg, yield 66%) as a grayish solid.

LCMS: m/z 367 $[M+H]^+$

HPLC retention time: 0.72 min (analysis condition A)

Compound b-41

5-Chloro-2-iodonaphthalen-1-amine

[Formula 279]

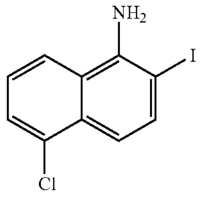

The title compound was synthesized from 5-chloronaphthalen-1-amine under the same conditions as the production example of the compound b-59, except that NMP was used instead of DMSO used in the production example of the compound b-59. LCMS: m/z 304 $[M+H]^+$ HPLC retention time: 0.97 min (analysis condition Q)

Compound b-42

4-Bromo-5-chloro-2-iodonaphthalen-1-amine

[Formula 280]

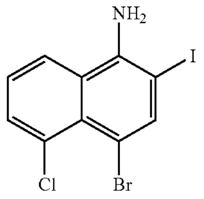

The title compound was synthesized from 5-chloro-2-iodonaphthalen-1-amine (b-41) under the same conditions as the production example of the compound b-100, except that NMP was used instead of DMF used in the production example of the compound b-100.

HPLC retention time: 1.05 min (analysis condition Q)

Compound b-43

(E)-N'-(4-bromo-5-chloro-2-iodonaphthalen-1-yl)-N,N-dimethylmethanimidamide

[Formula 281]

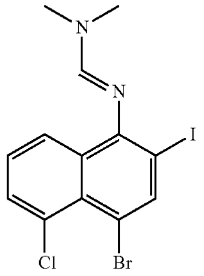

The title compound was synthesized from 4-bromo-5-chloro-2-iodonaphthalen-1-amine (compound b-42) under the same conditions as the production example of the compound b-25.

LCMS: m/z 437 $[M+H]^+$

HPLC retention time: 0.69 min (analysis condition Q)

Compound b-44

(E)-N'-[4-bromo-5-chloro-2-[7-fluoro-2-(oxan-2-yl) indazole-4-carbonyl]naphthalen-1-yl]-N,N-dimethyl-methanimidamide

[Formula 282]

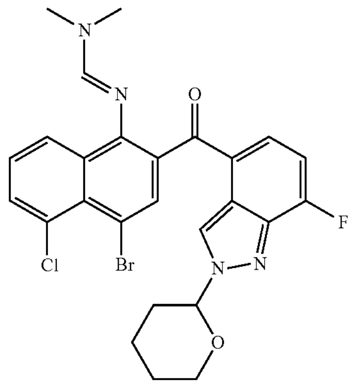

The title compound was synthesized from (E)-N'-(4-bromo-5-chloro-2-iodonaphthalen-1-yl)-N,N-dimethyl-methanimidamide (b-43) under the same conditions as the production example of the compound b-26.

LCMS: m/z 557 $[M+H]^+$

HPLC retention time: 0.92 min (analysis condition Q)

Compound b-45

(1-Amino-4-bromo-5-chloronaphthalen-2-yl)-[7-fluoro-2-(oxan-2-yl)indazol-4-yl]methanone

[Formula 283]

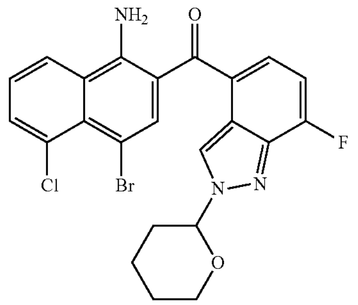

The title compound was synthesized from (E)-N'-[4-bromo-5-chloro-2-[7-fluoro-2-(oxan-2-yl)indazole-4-carbonyl]naphthalen-1-yl]-N,N-dimethylmethanimidamide (compound b-44) under the same conditions as the production example of the compound b-27.

LCMS: m/z 502 $[M+H]^+$

HPLC retention time: 1.09 min (analysis condition Q)

Compound B16

3-Amino-6-bromo-7-chloro-4-(7-fluoro-1H-indazol-4-yl)-1H-benzo[h]quinolin-2-one

[Formula 284]

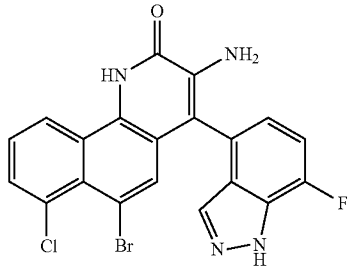

The title compound was synthesized from (1-amino-4-bromo-5-chloronaphthalen-2-yl)-[7-fluoro-2-(oxan-2-yl)indazol-4-yl]methanone (compound b-45) under the same conditions as the production examples of the compounds b-28, b-29, b-30, and the compound b-9, except that DMSO was used instead of EtOH used in the production example of the compound b-9.

LCMS: m/z 457 $[M+H]^+$

HPLC retention time: 0.80 min (analysis condition A)

Compound B19

3-Amino-7-chloro-4-(7-fluoro-1H-indazol-4-yl)-6-methyl-1H-benzo[h]quinolin-2-one

[Formula 285]

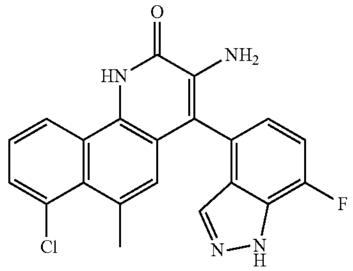

LCMS: m/z 393 $[M+H]^+$

HPLC retention time: 0.79 min (analysis condition A)

Compound B18

3-Amino-7-chloro-4-(7-fluoro-1H-indazol-4-yl)-1H-benzo[h]quinolin-2-one

[Formula 286]

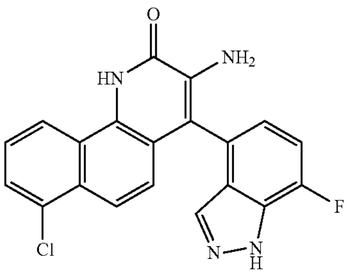

The compound B18 and the compound B19 were synthesized from 3-amino-6-bromo-7-chloro-4-(7-fluoro-1H-indazol-4-yl)-1H-benzo[h]quinolin-2-one (compound B16) under the same conditions as the production example of the compound b-10, except that potassium carbonate, a [1,1'-bis(diphenylphosphino)ferrocene]dichloropalladium(II)-DCM composite, and trimethylboroxine were used instead of cesium carbonate, DPPF Pd G4, and potassium cyclopropyltrifluoroborate used in the production example of the compound b-10.

LCMS: m/z 379 $[M+H]^+$

HPLC retention time: 0.75 min (analysis condition A)

Compound b-111

(E)-N'-[5-chloro-4-cyclopropyl-2-[7-fluoro-2-(oxan-2-yl)indazole-4-carbonyl]naphthalen-1-yl]-N,N-dimethylmethanimidamide

[Formula 287]

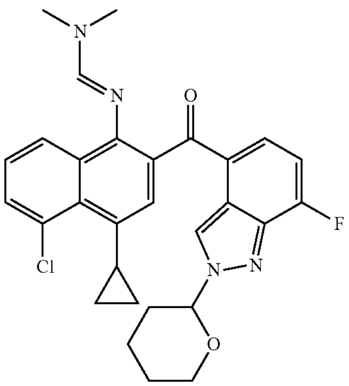

The title compound was synthesized from (E)-N'-[4-bromo-5-chloro-2-[7-fluoro-2-(oxan-2-yl)indazole-4-carbonyl]naphthalen-1-yl]-N,N-dimethylmethanimidamide (compound b-44) under the same conditions as the production example of the compound b-31.

LCMS: m/z 519 $[M+H]^+$

HPLC retention time: 0.68 min (analysis condition Q)

Compound b-112

(1-Amino-5-chloro-4-cyclopropylnaphthalen-2-yl)-[7-fluoro-2-(oxan-2-yl)indazol-4-yl]methanone

[Formula 288]

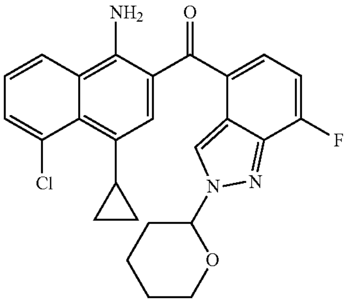

The title compound was synthesized from (E)-N'-[5-chloro-4-cyclopropyl-2-[7-fluoro-2-(oxan-2-yl)indazole-4-carbonyl]naphthalen-1-yl]-N,N-dimethylmethanimidamide (compound b-111) under the same conditions as the production example of the compound b-27.

LCMS: m/z 464 $[M+H]^+$

HPLC retention time: 1.12 min (analysis condition Q)

Compound B17

3-Amino-7-chloro-6-cyclopropyl-4-(7-fluoro-1H-indazol-4-yl)-1H-benzo[h]quinolin-2-one

[Formula 289]

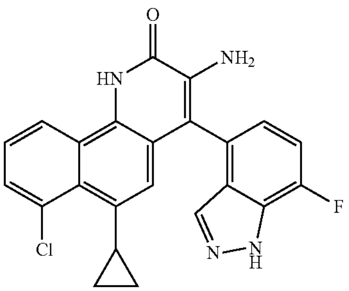

The title compound was synthesized from (1-amino-5-chloro-4-cyclopropylnaphthalen-2-yl)-[7-fluoro-2-(oxan-2-yl)indazol-4-yl]methanone (compound b-112) under the same conditions as the production examples of the compounds b-28, b-29, b-30, and b-9, except that DMSO was used instead of EtOH used in the production example of the compound b-9.

LCMS: m/z 419 $[M+H]^+$

HPLC retention time: 0.84 min (analysis condition B)

Compound b-51

8-Chloro-2,4-diiodonaphthalen-1-amine

[Formula 290]

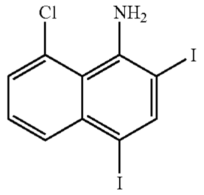

The title compound was synthesized from 8-chloronaphthalen-1-amine under the same conditions as the production example of the compound b-24.

LCMS: m/z 430 $[M+H]^+$

HPLC retention time: 1.17 min (analysis condition Q)

Compound b-52

(E)-N'-(8-chloro-2,4-diiodonaphthalen-1-yl)-N,N-dimethylmethanimidamide

[Formula 291]

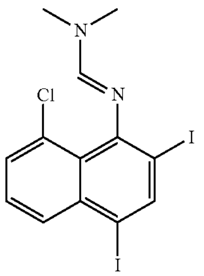

The title compound was synthesized from 8-chloro-2,4-diiodonaphthalen-1-amine (compound b-51) under the same conditions as the production example of the compound b-25.

LCMS: m/z 485 $[M+H]^+$

HPLC retention time: 0.52 min (analysis condition Q)

Compound b-53

(E)-N'-[8-chloro-2-[7-fluoro-2-(oxan-2-yl)indazole-4-carbonyl]-4-iodonaphthalen-1-yl]-N,N-dimethylmethanimidamide

[Formula 292]

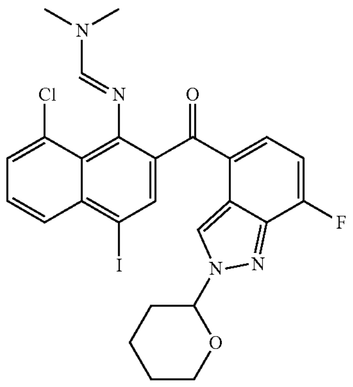

The title compound was synthesized from (E)-N'-(8-chloro-2,4-diiodonaphthalen-1-yl)-N,N-dimethylmethanimidamide (compound b-52) under the same conditions as the production example of the compound b-26.

LCMS: m/z 605 $[M+H]^+$

HPLC retention time: 0.71 min (analysis condition Q)

Compound b-54

(E)-N'-[8-chloro-4-cyclopropyl-2-[7-fluoro-2-(oxan-2-yl)indazole-4-carbonyl]naphthalen-1-yl]-N,N-dimethylmethanimidamide

[Formula 293]

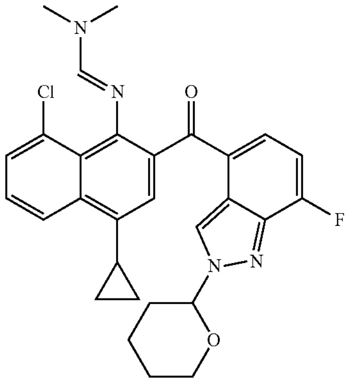

The title compound was synthesized from (E)-N'-[8-chloro-2-[7-fluoro-2-(oxan-2-yl)indazole-4-carbonyl]-4-iodonaphthalen-1-yl]-N,N-dimethylmethanimidamide (compound b-53) under the same conditions as the production example of the compound b-31.

LCMS: m/z 519 $[M+H]^+$

HPLC retention time: 0.58 min (analysis condition Q)

Compound b-55

(1-Amino-8-chloro-4-cyclopropylnaphthalen-2-yl)-[7-fluoro-2-(oxan-2-yl)indazol-4-yl]methanone

[Formula 294]

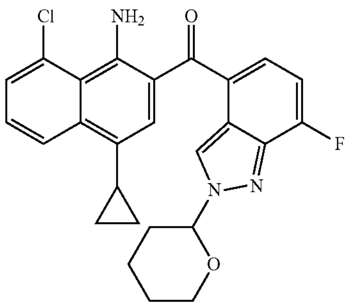

The title compound was synthesized from (E)-N'-[8-chloro-4-cyclopropyl-2-[7-fluoro-2-(oxan-2-yl)indazole-4-carbonyl]naphthalen-1-yl]-N,N-dimethylmethanimidamide (compound b-54) under the same conditions as the production example of the compound b-27.

LCMS: m/z 464 [M+H]

HPLC retention time: 1.15 min (analysis condition Q) $^+$

Compound b-56

2-Chloro-N-[8-chloro-4-cyclopropyl-2-[7-fluoro-2-(oxan-2-yl)indazole-4-carbonyl]naphthalen-1-yl] acetamide

[Formula 295]

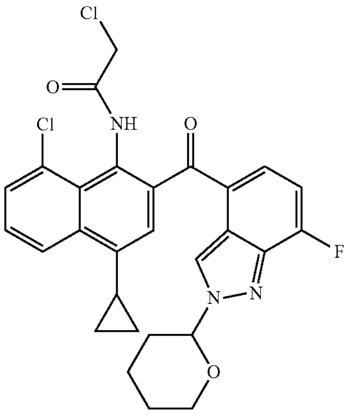

(1-Amino-8-chloro-4-cyclopropylnaphthalen-2-yl)-[7-fluoro-2-(oxan-2-yl)indazol-4-yl]methanone (compound b-55, 57 mg, 0.123 mmol) and 2-chloroacetic acid (58.1 mg, 0.614 mmol) were dissolved in ethyl acetate (1.23 mL) in a reaction vessel, a 50% solution of propylphosphonic acid anhydride in ethyl acetate (439 μL, 0.737 mmol) and pyridine (199 μL, 2.457 mmol) were added, and the mixture was stirred at 80° C. for 1 hour. The reaction mixture was purified by reversed phase column chromatography (0.1% aqueous formic acid solution/0.1% formic acid in acetonitrile solution) to obtain the title compound (41 mg, yield 62%) as a grayish solid.

LCMS: m/z 540 $[M+H]^+$

HPLC retention time: 0.91 min (analysis condition Q)

Compound b-57

10-Chloro-6-cyclopropyl-4-[7-fluoro-2-(oxan-2-yl) indazol-4-yl]-3-pyridin-1-ium-1-yl-1H-benzo[h] quinolin-2-one; chloride

[Formula 296]

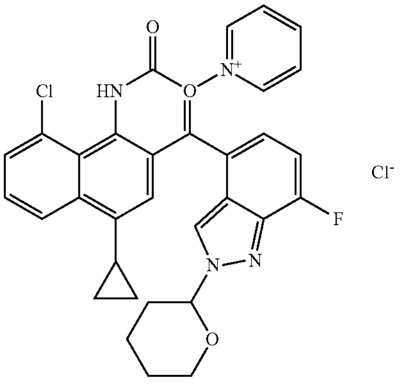

To 2-chloro-N-[8-chloro-4-cyclopropyl-2-[7-fluoro-2-(oxan-2-yl)indazole-4-carbonyl]naphthalen-1-yl]acetamide (compound b-56, 54.7 mg, 0.101 mmol) in a reaction vessel, pyridine (1.0 mL) was added, and the mixture was stirred at 90° C. for 12 hours to obtain a solution of the title compound in pyridine.

LCMS: m/z 565 $[M]^+$

HPLC retention time: 0.55 min (analysis condition Q)

Compound b-58

10-Chloro-6-cyclopropyl-4-(7-fluoro-1H-indazol-4-yl)-3-pyridin-1-ium-1-yl-1H-benzo[h]quinolin-2-one; chloride

[Formula 297]

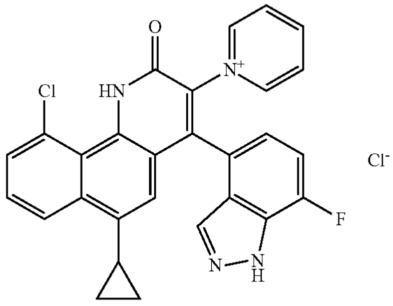

To the solution of 10-chloro-6-cyclopropyl-4-[7-fluoro-2-(oxan-2-yl)indazol-4-yl]-3-pyridin-1-ium-1-yl-1H-benzo [h]quinolin-2-one; chloride (compound b-57) in pyridine, 12 M hydrochloric acid (166 μL, 2.20 mmol) was added, and the mixture was stirred at 90° C. for 2 hours. The reaction mixture was purified by reversed phase column chromatography (0.1% aqueous formic acid solution/0.1% formic acid in acetonitrile solution) to obtain the title compound (36.6 mg, yield 75%) as a yellow solid.

LCMS: m/z 481 $[M]^+$

HPLC retention time: 0.48 min (analysis condition Q)

Compound B20

3-Amino-10-chloro-6-cyclopropyl-4-(7-fluoro-1H-indazol-4-yl)-1H-benzo[h]quinolin-2-one

[Formula 298]

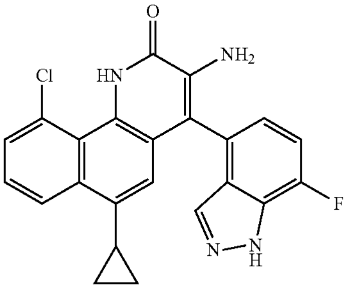

The title compound was synthesized from 10-chloro-6-cyclopropyl-4-(7-fluoro-1H-indazol-4-yl)-3-pyridin-1-ium-1-yl-1H-benzo[h]quinolin-2-one; chloride (compound b-58) under the same conditions as the production example of the compound b-9, except that DMSO was used instead of EtOH used in the production example of the compound b-9.

LCMS: m/z 419 $[M+H]^+$

HPLC retention time: 0.84 min (analysis condition A)

Compound b-110

7-Fluoro-2-(oxan-2-yl)-4-(4,4,5,5-tetramethyl-1,3,2-dioxaborolan-2-yl)indazole

[Formula 299]

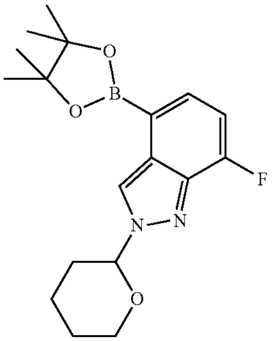

The title compound was synthesized from 7-fluoro-1H-indazole-4-boronic acid pinacol ester under the same conditions as the production example of the compound c-3.

LCMS: m/z 347 $[M+H]^+$

HPLC retention time: 1.06 min (analysis condition C)

Compound b-71

Methyl (E)-3-[7-fluoro-2-(oxan-2-yl)indazol-4-yl]-2-[(2-methylpropan-2-yl)oxycarbonylamino]-3-(1-nitronaphthalen-2-yl) prop-2-enoate

[Formula 300]

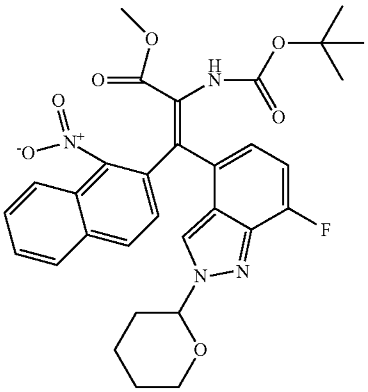

The title compound was synthesized from 7-fluoro-2-(oxan-2-yl)-4-(4,4,5,5-tetramethyl-1,3,2-dioxaborolan-2-yl) indazole (compound b-110) under the same conditions as the production example of the compound b-4, except that toluene was used instead of THF used in the production example of the compound b-4.

LCMS: m/z 591 $[M+H]^+$

HPLC retention time: 2.24 min (analysis condition C)

Compound b-72 tert-Butyl N-[4-[7-fluoro-2-(oxan-2-yl)indazol-4-yl]-2-oxo-1H-benzo[h]quinolin-3-yl]carbamate

[Formula 301]

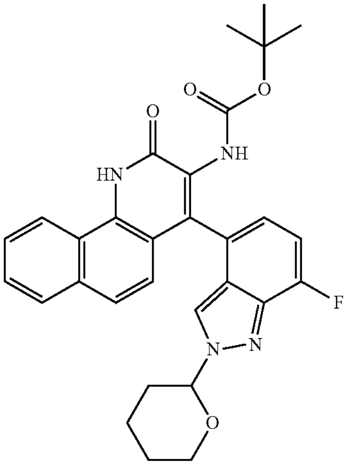

To a solution of methyl (E)-3-[7-fluoro-2-(oxan-2-yl) indazol-4-yl]-2-[(2-methylpropan-2-yl)oxycarbonylamino]-3-(1-nitronaphthalen-2-yl) prop-2-enoate (compound b-71, 66 mg, 0.112 mmol) in ethyl acetate (1.98 mL) in a reaction vessel, 20% palladium hydroxide on carbon (62.8 mg) was added, the reaction vessel was degassed under reduced pressure and then subjected to hydrogen replacement, and the mixture was stirred at room temperature for 15 hours. The reaction mixture was filtered using Celite, and the filtrate was concentrated. The obtained residue was purified by reversed phase column chromatography to obtain the title compound (35 mg, yield 34%) as a yellow solid.

LCMS: m/z 529 $[M+H]^+$

HPLC retention time: 2.37 min (analysis condition C)

Compound B32

3-Amino-4-(7-fluoro-1H-indazol-4-yl)-1H-benzo[h]quinolin-2-one

[Formula 302]

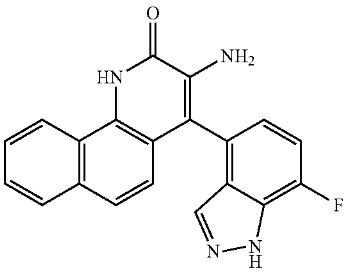

The title compound was synthesized from tert-butyl N-[4-[7-fluoro-2-(oxan-2-yl)indazol-4-yl]-2-oxo-1H-benzo[h]quinolin-3-yl]carbamate (compound b-72) under the same conditions as the production example of the compound B48.

LCMS: m/z 345 [M+H]$^+$

HPLC retention time: 1.81 min (analysis condition C)

Compound b-73

Methyl (E)-2-[(2-methylpropan-2-yl)oxycarbonylamino]-3-(1-nitronaphthalen-2-yl)-3-[1-(oxan-2-yl)indazol-4-yl]prop-2-enoate

[Formula 303]

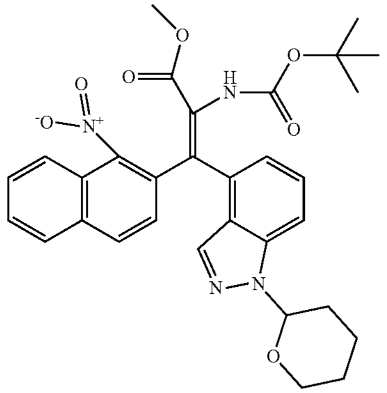

The title compound was synthesized from 1-(tetrahydro-2H-pyran-2-yl)-4-(4,4,5,5-tetramethyl-1,3,2-dioxaborolan-2-yl)-1H-indazole under the same conditions as the production example of the compound b-4, except that toluene and DPPF Pd G4 were used instead of THF and 1,1'-bis(diphenylphosphino)ferrocene]dichloropalladium(II) used in the production example of the compound b-4.

LCMS: m/z 573.5 [M+H]$^+$

HPLC retention time: 2.95 min (analysis condition D)

Compound b-74 tert-Butyl N-[4-[1-(oxan-2-yl)indazol-4-yl]-2-oxo-1H-benzo[h]quinolin-3-yl]carbamate

[Formula 304]

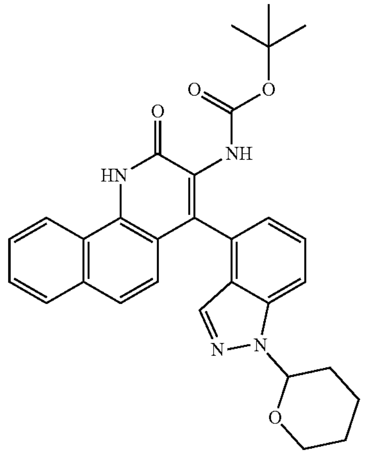

The title compound was synthesized from methyl (E)-2-[(2-methylpropan-2-yl)oxycarbonylamino]-3-(1-nitronaphthalen-2-yl)-3-[1-(oxan-2-yl)indazol-4-yl]prop-2-enoate (compound b-73) under the same conditions as the production example of the compound b-72, except that TFE was used instead of ethyl acetate used in the production example of the compound b-72.

LCMS: m/z 511 [M+H]$^+$

HPLC retention time: 0.84 min (analysis condition A)

Compound B46

3-Amino-4-(1H-indazol-4-yl)-1H-benzo[h]quinolin-2-one

[Formula 305]

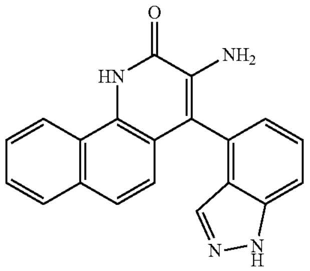

The title compound was synthesized from tert-butyl N-[4-[1-(oxan-2-yl)indazol-4-yl]-2-oxo-1H-benzo[h]quinolin-3-yl]carbamate (compound b-74) under the same conditions as the production example of the compound B49.

LCMS: m/z 327 [M+H]$^+$

HPLC retention time: 0.62 min (analysis condition A)

Compound b-108

Methyl (E)-3-(3-fluorophenyl)-2-[(2-methylpropan-2-yl)oxycarbonylamino]-3-(1-nitronaphthalen-2-yl)prop-2-enoate

[Formula 306]

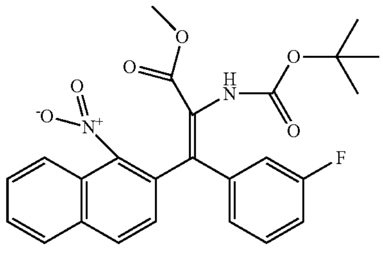

The title compound was synthesized from 3-fluorophenylboronic acid under the same conditions as the production example of the compound b-4, except that toluene and DPPF Pd G4 were used instead of THF and 1,1'-bis(diphenylphosphino)ferrocene]dichloropalladium(II) used in the production example of the compound b-4.

LCMS: m/z 467.5 [M+H]$^+$

HPLC retention time: 0.94 min (analysis condition A)

Compound b-109 tert-Butyl N-[4-(3-fluorophenyl)-2-oxo-1H-benzo[h]quinolin-3-yl]carbamate

[Formula 307]

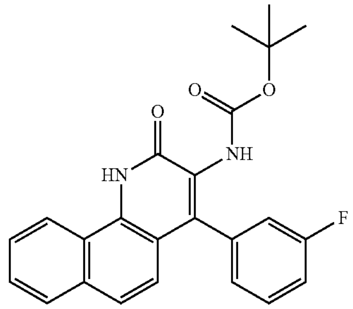

The title compound was synthesized from methyl (E)-3-(3-fluorophenyl)-2-[(2-methylpropan-2-yl)oxycarbonylamino]-3-(1-nitronaphthalen-2-yl) prop-2-enoate (compound b-108) under the same conditions as the production example of the compound b-5.

LCMS: m/z 405 $[M+H]^+$

HPLC retention time: 2.51 min (analysis condition D)

Compound B50

3-Amino-4-(3-fluorophenyl)-1H-benzo[h]quinolin-2-one; hydrochloride

[Formula 308]

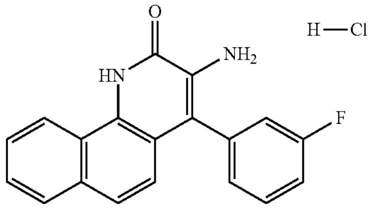

The title compound was synthesized from tert-butyl N-[4-(3-fluorophenyl)-2-oxo-1H-benzo[h]quinolin-3-yl]carbamate (compound b-109) under the same conditions as the production example of the compound B49.

LCMS: m/z 305 $[M+H]^+$

HPLC retention time: 0.80 min (analysis condition A)

Compound c-1

8-Bromo-6-iodoquinolin-5-amine

[Formula 309]

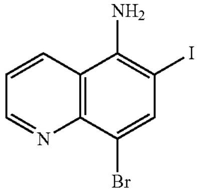

A suspension of 5-amino-8-bromoquinoline (49.7 g, 223 mmol) in acetonitrile (446 mL) in a reaction vessel was cooled to 0° C., TFA (18.02 mL, 234 mmol) was added thereto, then N-iodosuccinimide (52.6 g, 234 mmol) was added, and the mixture was stirred for 1.5 hours. The reaction mixture was poured into a 3% aqueous sodium bicarbonate solution (1.25 L), and then a 10% aqueous sodium thiosulfate solution (250 mL) was added thereto. The solid was collected by filtration and washed with water (650 mL) to obtain the title compound (66.78 g, yield 86%).

LCMS: m/z 349 $[M+H]^+$

HPLC retention time: 0.97 min (analysis condition F)

Compound c-2

(E)-N'-(8-bromo-6-iodoquinolin-5-yl)-N,N-dimethylmethanimidamide

[Formula 310]

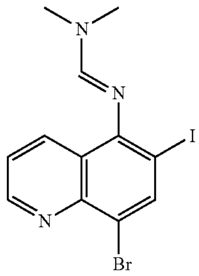

To a suspension of 8-bromo-6-iodoquinolin-5-amine (compound c-1, 51.86 g, 149 mmol) in EtOH (248 mL) in a reaction vessel, N,N-dimethylformamidedimethylacetal (80 mL, 594 mmol) was added, and the mixture was stirred at 80° C. under nitrogen atmosphere for 2.5 hours. The reaction mixture was cooled to room temperature, and ethyl acetate (1.0 L), a 10% aqueous sodium thiosulfate solution (260 mL), and brine (260 mL) were added thereto. The obtained mixture was filtered through amino silica gel (104 g), and washed with ethyl acetate (260 mL). The organic layer was separated from the filtrate, and the aqueous layer was extracted with ethyl acetate (260 mL). The obtained organic layer was combined, washed with 13% saline, dried over anhydrous magnesium sulfate, the drying agent was filtered off, and then the filtrate was concentrated under reduced pressure. To the obtained residue, TBME (50 mL) and hexane (100 mL) were added, the mixture was stirred at room temperature for 15 min, then hexane (100 mL) was further added thereto, and the mixture was stirred for 30 min. The solid was collected by filtration and washed with hexane (500 mL) to obtain the title compound (56.08 g, yield 93%).

LCMS: m/z 404 $[M+H]^+$

HPLC retention time: 0.62 min (analysis condition F)

Compound c-7

(E)-N'-[8-bromo-6-[7-fluoro-2-(oxan-2-yl)indazole-4-carbonyl]quinolin-5-yl]-N,N-dimethylmethanimidamide

[Formula 311]

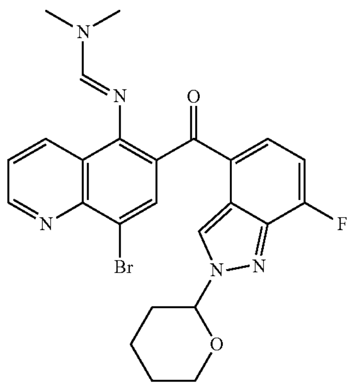

A solution of (E)-N'-(8-bromo-6-iodoquinolin-5-yl)-N,N-dimethylmethanimidamide (c-2, 41.2 g, 102 mmol) and 7-fluoro-N-methoxy-N-methyl-2-(oxan-2-yl)indazole-4-carboxamide (c-6, 34.5 g, 112 mmol) in toluene (638 mL) in a reaction vessel was cooled to −40° C., a 1.3 M isopropylmagnesium chloride-lithium chloride complex solution (110 mL, 143 mmol) was added thereto, and the mixture was stirred at −40° C. for 30 min, and then stirred at 0° C. for 3.5 hours. To the reaction mixture, a saturated aqueous ammonium chloride solution was added, and the mixture was extracted with ethyl acetate. The organic layer was washed with brine and dried over anhydrous sodium sulfate, the drying agent was filtered off, and then the filtrate was concentrated under reduced pressure. To the residue, acetonitrile (350 mL) was added, the mixture was stirred for 1 hour, then water (88 mL) was added thereto, and the mixture was further stirred for 1 hour. The solid was collected by filtration and washed with a mixed solution of acetonitrile (20 mL) and water (80 mL) to obtain the title compound (44.39 g, yield 77%) as a yellow solid.

LCMS: m/z 524 $[M+H]^+$

HPLC retention time: 0.91 min (analysis condition F)

Compound c-8

(5-Amino-8-bromoquinolin-6-yl)-[7-fluoro-2-(oxan-2-yl)indazol-4-yl]methanone

[Formula 312]

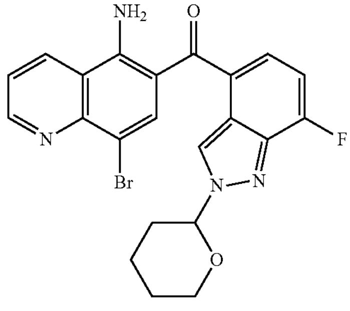

To a suspension of (E)-N'-[8-bromo-6-[7-fluoro-2-(oxan-2-yl)indazole-4-carbonyl]quinolin-5-yl]-N,N-dimethylmethanimidamide (compound c-7, 22.65 g, 43.2 mmol) in DMSO (216 mL) in a reaction vessel, a 5 M aqueous sodium hydroxide solution (25.9 mL, 130 mmol) was added, and the mixture was stirred at room temperature for 3 hours. To the reaction mixture, a saturated aqueous ammonium chloride solution was added, and the mixture was extracted with ethyl acetate. The obtained organic layer was washed with an aqueous saturated sodium chloride solution and dried over anhydrous sodium sulfate, the drying agent was filtered off, and then the filtrate was concentrated under reduced pressure. The obtained residue was purified by silica gel column chromatography (hexane/ethyl acetate) to obtain the title compound (18.3 g, yield 90%) as a yellow solid.

LCMS: m/z 469 $[M+H]^+$

HPLC retention time: 1.15 min (analysis condition F)

Compound C1

3-Amino-6-bromo-4-(7-fluoro-1H-indazol-4-yl)-1H-1,7-phenanthrolin-2-one

[Formula 313]

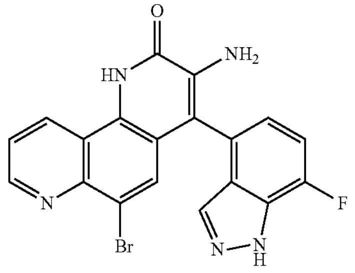

The title compound was synthesized from (5-amino-8-bromoquinolin-6-yl)-[7-fluoro-2-(oxan-2-yl)indazol-4-yl]methanone (compound c-8) under the same conditions as the production examples of the compounds b-28, b-29, b-30, and the compound b-9.

LCMS: m/z 424 $[M+H]^+$

HPLC retention time: 0.56 min (analysis condition A)

Compound c-12

6-Bromo-4-(7-fluoro-1-methylindazol-4-yl)-2-methoxy-1,7-phenanthrolin-3-amine

[Formula 314]

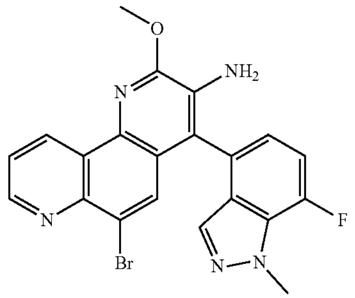

To a suspension of 3-amino-6-bromo-4-(7-fluoro-1H-indazol-4-yl)-1H-1,7-phenanthrolin-2-one (compound C1, 20 mg, 0.047 mmol) in DMF (400 μL) in a reaction vessel, potassium carbonate (39.1 mg, 0.283 mmol) and iodomethane (12.97 μL, 0.207 mmol) were added, and the mixture was stirred at room temperature for 15 hours. The reaction mixture was purified by reversed phase column chromatography to obtain the title compound (11.4 mg, yield 53.5%) as a yellow solid.

LCMS: m/z 452 $[M+H]^+$

HPLC retention time: 0.89 min (analysis condition A)

Compound C2

3-Amino-6-bromo-4-(7-fluoro-1-methylindazol-4-yl)-1H-1,7-phenanthrolin-2-one

[Formula 315]

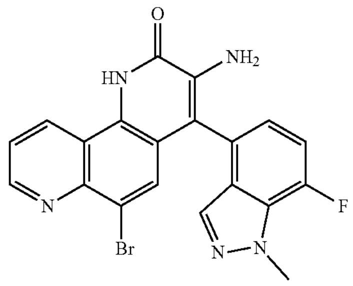

To a solution of 6-bromo-4-(7-fluoro-1-methylindazol-4-yl)-2-methoxy-1,7-phenanthrolin-3-amine (compound c-12, 8.7 mg, 0.019 mmol) in NMP (200 μL) in a reaction vessel, lithium chloride (8.15 mg, 0.192 mmol) and p-toluenesulfonic acid monohydrate (36.6 mg, 0.192 mmol) were added, and the mixture was stirred at 120° C. for 5 hours. The reaction mixture was purified by reversed phase column chromatography to obtain the title compound (2.2 mg, yield 20%) as a colorless solid.

LCMS: m/z 438 $[M+H]^+$

HPLC retention time: 0.66 min (analysis condition A)

Compound c-9

N-[8-bromo-6-[7-fluoro-2-(oxan-2-yl)indazole-4-carbonyl]quinolin-5-yl]-2-chloroacetamide

[Formula 316]

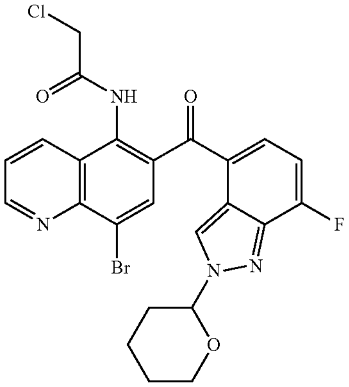

A solution of (5-amino-8-bromoquinolin-6-yl)-[7-fluoro-2-(oxan-2-yl)indazol-4-yl]methanone (compound c-8, 17.12 g, 36.5 mmol) in DMA (137 mL) in a reaction vessel was cooled to 0° C., N,N-dimethylaniline (27.6 mL, 219 mmol) and chloroacetyl chloride (5.8 mL, 73 mmol) were added thereto, and the mixture was stirred at room temperature for 30 min to obtain a solution of the title compound in DMA.

LCMS: m/z 545 $[M+H]^+$

HPLC retention time: 1.08 min (analysis condition F)

Compound c-10

6-Bromo-4-[7-fluoro-2-(oxan-2-yl)indazol-4-yl]-3-pyridin-1-ium-1-yl-1H-1,7-phenanthrolin-2-one; chloride

[Formula 317]

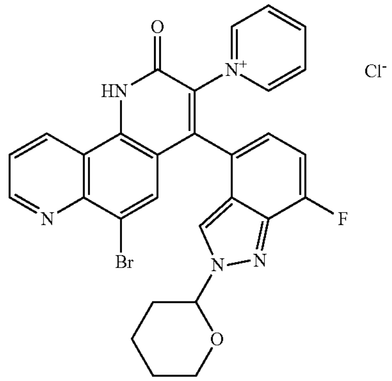

To the solution of N-[8-bromo-6-[7-fluoro-2-(oxan-2-yl)indazole-4-carbonyl]quinolin-5-yl]-2-chloroacetamide (compound c-9) in DMA, pyridine (137 mL) was added, and the mixture was stirred at 60° C. for 4 hours to obtain a suspension of the title compound in DMA/pyridine.

LCMS: m/z 570 $[M]^+$

HPLC retention time: 0.78 min (analysis condition F)

Compound c-13

3-Amino-6-bromo-4-[7-fluoro-2-(oxan-2-yl)indazol-4-yl]-1H-1,7-phenanthrolin-2-one

[Formula 318]

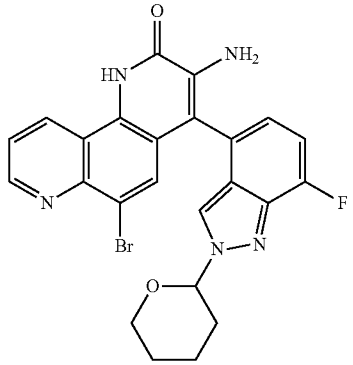

The suspension of 6-bromo-4-[7-fluoro-2-(oxan-2-yl)indazol-4-yl]-3-pyridin-1-ium-1-yl-1H-1,7-phenanthrolin-2-one; chloride (compound c-10) in DMA/pyridine was cooled to room temperature, hydrazine monohydrate (17.7 mL) was added thereto, and the mixture was stirred at 60° C. for 2 hours. The reaction mixture was cooled to room temperature, water (170 mL) was added thereto, and the mixture was further stirred. The solid was collected by filtration and washed with EtOH/water (1/1). The obtained solid was suspended in EtOH (255 mL), hexane (85 mL) was added thereto, and the mixture was stirred at 50° C. for 30 min. The mixture was cooled to room temperature, hexane (170 mL) was added thereto, and the mixture was further stirred for 1 hour. The solid was collected by filtration and washed with hexane to obtain the title compound (16.93 g, yield 86%) as a pale yellow solid.

LCMS: m/z 508 $[M+H]^+$

HPLC retention time: 1.01 min (analysis condition F)

Compound c-14

6-Bromo-4-[7-fluoro-2-(oxan-2-yl)indazol-4-yl]-2-[(4-methoxyphenyl)methoxy]-1,7-phenanthrolin-3-amine

[Formula 319]

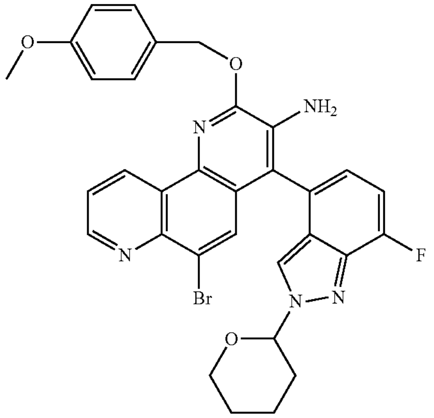

To a solution of 3-amino-6-bromo-4-[7-fluoro-2-(oxan-2-yl)indazol-4-yl]-1H-1,7-phenanthrolin-2-one (compound c-13, 2.11 g, 4.15 mmol) in NMP (20.75 mL) in a reaction vessel, potassium carbonate (1.147 g, 8.3 mmol) and 4-methoxybenzylchloride (678 μL, 4.98 mmol) were added, and the mixture was stirred at 70° C. for 2.5 hours. The reaction mixture was cooled to room temperature, water (30 mL) was added thereto, and the mixture was further stirred at room temperature for 1.5 hours. The solid was collected by filtration and washed with water to obtain the title compound (2.55 g, yield 98%).

LCMS: m/z 628 $[M+H]^+$

HPLC retention time: 1.49 min (analysis condition F)

Compound c-15

3-Amino-4-[7-fluoro-2-(oxan-2-yl)indazol-4-yl]-2-[(4-methoxyphenyl)methoxy]-1,7-phenanthrolin-6-ol

[Formula 320]

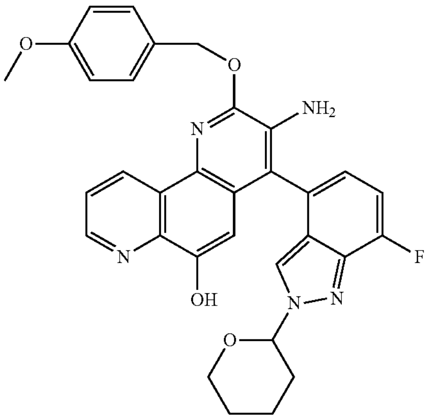

6-Bromo-4-[7-fluoro-2-(oxan-2-yl)indazol-4-yl]-2-[(4-methoxyphenyl)methoxy]-1,7-phenanthrolin-3-amine (compound c-14, 3.43 g, 5.46 mmol) in a reaction vessel and a 8 M aqueous potassium hydrate solution (3.41 mL, 27.3 mmol) were suspended in a 1,4-dioxane solution (54.6 mL), and then the reaction vessel was degassed under reduced pressure and subjected to nitrogen replacement. To the mixture, tBuBrettPhos Pd G3 (350 mg, 0.409 mmol) was added, the reaction vessel was degassed under reduced pressure and subjected to nitrogen replacement, and then the mixture was heated at 100° C. for 5.5 hours. The reaction mixture was cooled to 0° C. A 0.26 M aqueous phosphoric acid solution (21.8 mmol, 83 mL) was added to the reaction mixture, and the mixture was stirred at room temperature for 1.5 hours. The solid was collected by filtration and sequentially washed with a mixed solvent of water and acetonitrile/water (1/1) to obtain the title compound (3.08 g) as an orange solid.

LCMS: m/z 566 $[M+H]^+$

HPLC retention time: 1.19 min (analysis condition G)

Compound C3

3-Amino-4-(7-fluoro-1H-indazol-4-yl)-6-hydroxy-1H-1,7-phenanthrolin-2-one

[Formula 321]

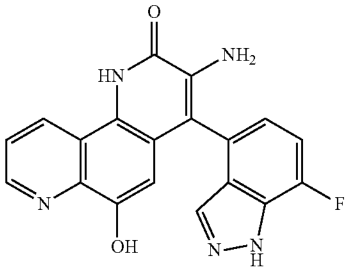

To a solution of 3-amino-4-[7-fluoro-2-(oxan-2-yl)indazol-4-yl]-2-[(4-methoxyphenyl)methoxy]-1,7-phenanthrolin-6-ol (compound c-15, 5 mg, 8.84 μmol) in EtOH (100 μL) in a reaction vessel, anisole (2.9 μL, 26.5 μmol) and 12 M hydrochloric acid (3.68 μL, 44.4 μmol) were added, and the mixture was stirred at room temperature for 1 hour. The mixture was combined with other samples, concentrated, and then purified by reversed phase column chromatography to obtain the title compound (2.5 mg) as a yellow solid.

LCMS: m/z 362 $[M+H]^+$

HPLC retention time: 0.40 min (analysis condition A)

Compound c-16

4-[7-Fluoro-2-(oxan-2-yl)indazol-4-yl]-6-methoxy-2-[(4-methoxyphenyl)methoxy]-1,7-phenanthrolin-3-amine

[Formula 322]

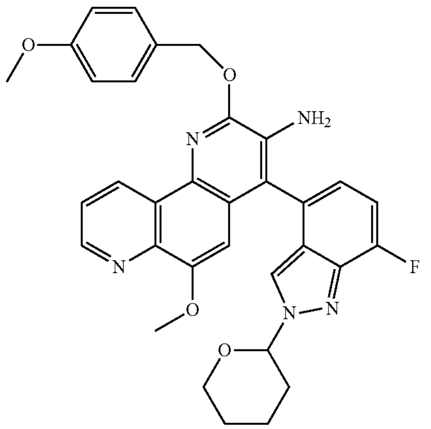

To a solution of 3-amino-4-[7-fluoro-2-(oxan-2-yl)indazol-4-yl]-2-[(4-methoxyphenyl)methoxy]-1,7-phenanthrolin-6-ol (compound c-15, 200 mg, 0.354 mmol) in THF (2 mL) in a reaction vessel, MeOH (50 μL, 1.237 mmol) and a 0.5 M solution of cyanomethylenetrimethylphosphorane in THF (2.1 mL, 1.05 mmol) were added, and the mixture was stirred at 70° C. for 2 hours. Water (200 μL) was added, and the mixture was further stirred at 70° C. for 1 hour. The reaction solution was cooled to room temperature, water was added, and the mixture was extracted with ethyl acetate. The organic layer was dried over anhydrous sodium sulfate, the drying agent was filtered off, and then the filtrate was concentrated under reduced pressure. The obtained residue was purified by silica gel column chromatography (ethyl acetate/DCM) to obtain the title compound (120 mg, yield 59%).

LCMS: m/z 580.5 $[M+H]^+$

HPLC retention time: 0.72 min (analysis condition A)

Compound C4

3-Amino-4-(7-fluoro-1H-indazol-4-yl)-6-methoxy-1H-1,7-phenanthrolin-2-one

[Formula 323]

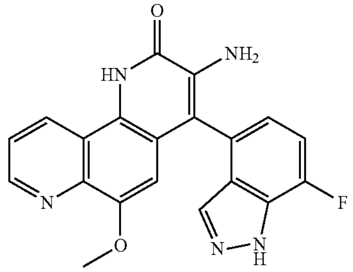

To a solution of 4-[7-fluoro-2-(oxan-2-yl)indazol-4-yl]-6-methoxy-2-[(4-methoxyphenyl)methoxy]-1,7-phenanthrolin-3-amine (compound c-16, 722 mg, 1.246 mmol) in DCM (7.2 mL) in a reaction vessel, triethylsilane (0.995 mL, 6.23 mmol) and TFA (7.2 mL) were added, and the mixture was stirred at room temperature for 2 hours. The reaction mixture was concentrated, the obtained residue was combined with a reaction mixture of another lot obtained by the same operation, and the mixture was purified by reversed phase column chromatography (0.05% aqueous TFA solution/0.05% TFA acetonitrile solution). The collected fraction was concentrated and neutralized with a 5% aqueous sodium bicarbonate solution. The solid was collected by filtration and washed with water to obtain the title compound (531.8 mg) as a yellow solid.

LCMS: m/z 376.5 $[M+H]^+$

HPLC retention time: 0.38 min (analysis condition A)

Compound C29

3-Amino-4-(7-fluoro-1H-indazol-4-yl)-6-((1s,3s)-3-methoxycyclobutoxy)-1,7-phenanthrolin-2(1H)-one

[Formula 324]

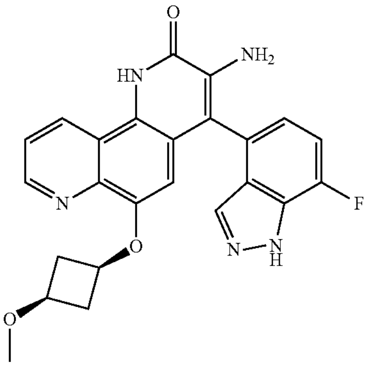

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 446 $[M+H]^+$

HPLC retention time: 0.43 min (analysis condition A)

Compound C30

3-Amino-4-(7-fluoro-1H-indazol-4-yl)-6-((1r,3r)-3-methoxycyclobutoxy)-1,7-phenanthrolin-2(1H)-one

[Formula 325]

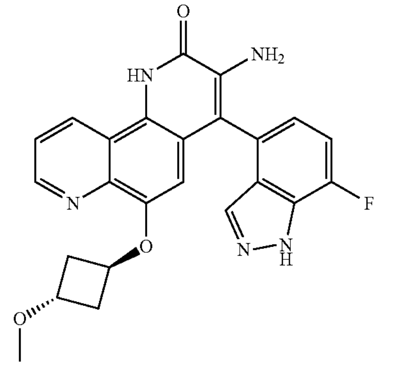

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and B49, except that 10 equivalents of triethylsilane were used based on the raw material, in addition to the conditions of the production example of the compound B49.

LCMS: m/z 446 $[M+H]^+$

HPLC retention time: 0.43 min (analysis condition A)

Compound C31

(1r,3r)-3-[[3-Amino-4-(7-fluoro-1H-indazol-4-yl)-2-oxo-1H-1,7-phenanthrolin-6-yl]oxy]cyclobutane-1-carbonitrile

[Formula 326]

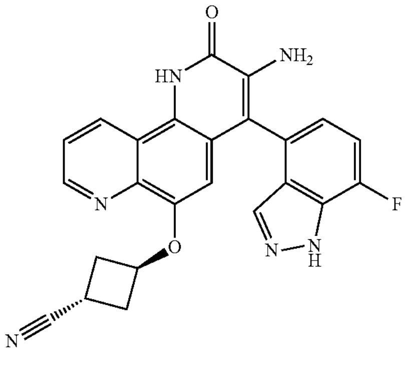

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 441 $[M+H]^+$

HPLC retention time: 0.43 min (analysis condition A)

Compound C32

3-Amino-6-(3,3-difluoropropoxy)-4-(7-fluoro-1H-indazol-4-yl)-1H-1,7-phenanthrolin-2-one

[Formula 327]

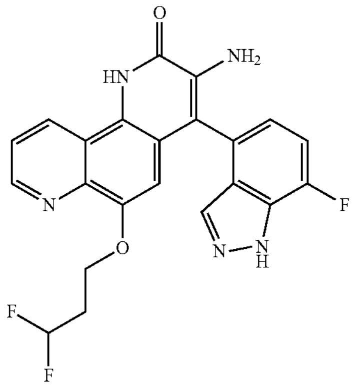

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4, except that trifluoromethanesulfonic acid was used instead of TFA used in the production example of the compound C4.

LCMS: m/z 440 $[M+H]^+$

HPLC retention time: 0.46 min (analysis condition A)

Compound C33

(1s,3s)-3-[[3-Amino-4-(7-fluoro-1H-indazol-4-yl)-2-oxo-1H-1,7-phenanthrolin-6-yl]oxy]cyclobutane-1-carbonitrile

[Formula 328]

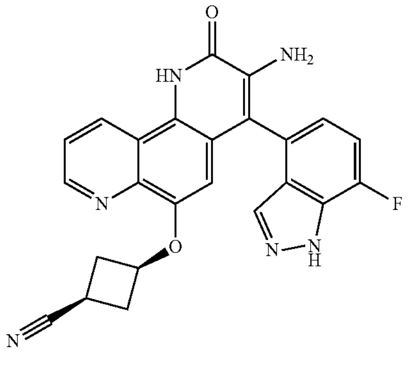

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 441 $[M+H]^+$

HPLC retention time: 0.43 min (analysis condition A)

Compound C34

3-Amino-6-[(2S)-butan-2-yl]oxy-4-(7-fluoro-1H-indazol-4-yl)-1H-1,7-phenanthrolin-2-one

[Formula 329]

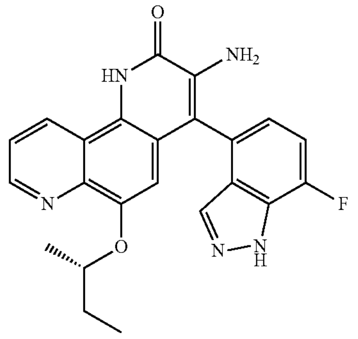

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 418 $[M+H]^+$

HPLC retention time: 0.46 min (analysis condition A)

Compound C35

3-Amino-4-(7-fluoro-1H-indazol-4-yl)-6-[[(2R)-oxolan-2-yl]methoxy]-1H-1,7-phenanthrolin-2-one

[Formula 330]

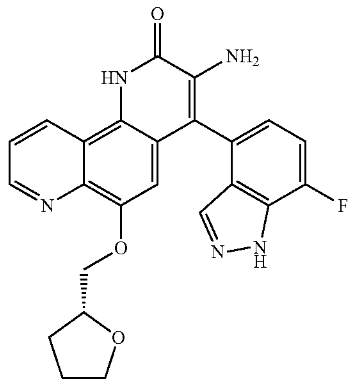

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 446 $[M+H]^+$

HPLC retention time: 0.43 min (analysis condition A)

Compound C36

3-Amino-6-[(2R)-butan-2-yl]oxy-4-(7-fluoro-1H-indazol-4-yl)-3,4-dihydro-1H-1,7-phenanthrolin-2-one

[Formula 331]

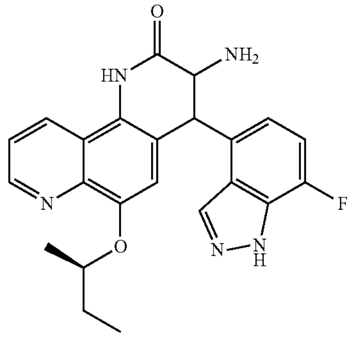

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 418 $[M+H]^+$

HPLC retention time: 0.47 min (analysis condition A)

Compound C37

3-Amino-4-(7-fluoro-1H-indazol-4-yl)-6-[[(2S)-oxolan-2-yl]methoxy]-1H-1,7-phenanthrolin-2-one

[Formula 332]

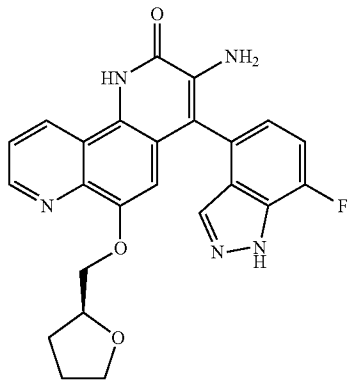

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 446 $[M+H]^+$

HPLC retention time: 0.43 min (analysis condition A)

Compound C38

3-Amino-6-[(1-fluorocyclopropyl)methoxy]-4-(7-fluoro-1H-indazol-4-yl)-1H-1,7-phenanthrolin-2-one

[Formula 333]

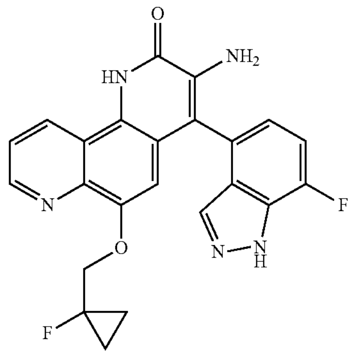

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 434 $[M+H]^+$

HPLC retention time: 0.47 min (analysis condition A)

Compound C39

3-Amino-6-[(3,3-difluorocyclobutyl)methoxy]-4-(7-fluoro-1H-indazol-4-yl)-1H-1,7-phenanthrolin-2-one

[Formula 334]

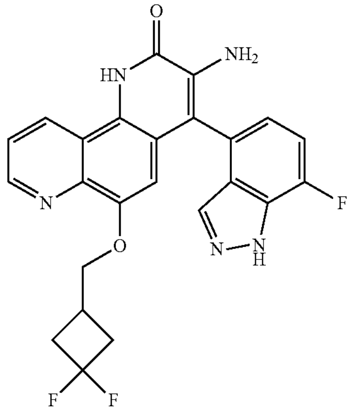

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 466 $[M+H]^+$

HPLC retention time: 0.51 min (analysis condition A)

Compound C40

3-Amino-4-(7-fluoro-1H-indazol-4-yl)-6-[(3-fluorooxetan-3-yl)methoxy]-1H-1,7-phenanthrolin-2-one

[Formula 335]

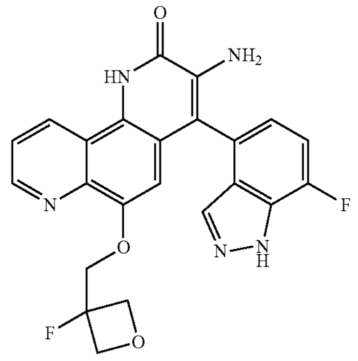

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4, except that TFA (2 v/w) was used instead of TFA (10 v/w) used in the production example of the compound C4.

LCMS: m/z 450 $[M+H]^+$

HPLC retention time: 0.43 min (analysis condition A)

Compound C41

3-Amino-4-(7-fluoro-1H-indazol-4-yl)-6-(2-oxaspiro[3,3]heptan-6-yloxy)-1H-1,7-one

[Formula 336]

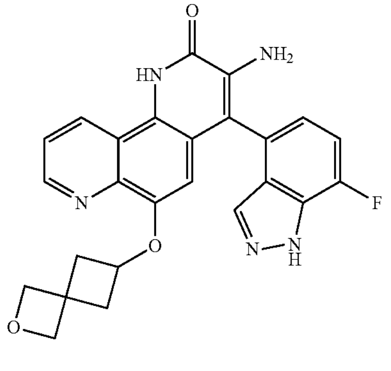

Ine title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4, except that TFA (2 v/w) was used instead of TFA (10 v/w) used in the production example of the compound C4.

LCMS: m/z 458 $[M+H]^+$

HPLC retention time: 0.42 min (analysis condition A)

Compound c-55

4-[7-Fluoro-2-(oxan-2-yl)indazol-4-yl]-2-[(4-methoxyphenyl)methoxy]-6-[2-(trifluoromethoxy)ethoxy]-1,7-phenanthrolin-3-amine

[Formula 337]

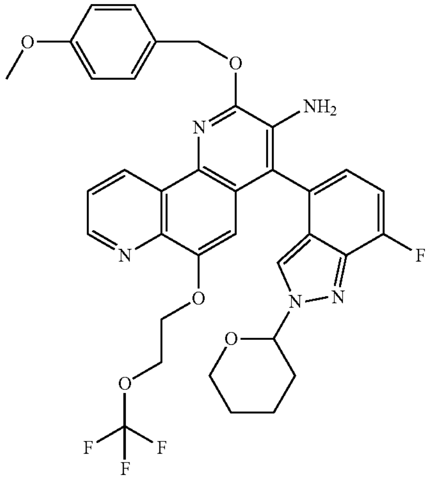

To a solution of 3-amino-4-[7-fluoro-2-(oxan-2-yl)indazol-4-yl]-2-[(4-methoxyphenyl)methoxy]-1,7-phenanthrolin-6-ol (compound c-15, 30 mg, 0.053 mmol) in THF (600 μL) in a reaction vessel, 2-(trifluoromethoxy) ethanol (10.3 μL, 0.106 mmol), triphenylphosphine (27.8 mg, 0.106 mmol), and diisopropyl azodiformate (55.8 μL, 0.106 mmol) were added, and the mixture was stirred at room temperature for 15 hours. To the reaction mixture, 2-(trifluoromethoxy) ethanol (10.3 μL, 0.106 mmol), triphenylphosphine (27.8 mg, 0.106 mmol), and diisopropyl azodiformate (55.8 μL, 0.106 mmol) were added, and the mixture was further stirred for 15 hours. The reaction mixture was concentrated under reduced pressure, and the obtained residue was purified by silica gel column chromatography (DCM/acetone) to obtain the title compound (41 mg).

LCMS: m/z 678 $[M+H]^+$

HPLC retention time: 0.86 min (analysis condition A)

Compound C43

3-Amino-4-(7-fluoro-1H-indazol-4-yl)-6-[2-(trifluoromethoxy)ethoxy]-1H-1,7-phenanthrolin-2-one

[Formula 338]

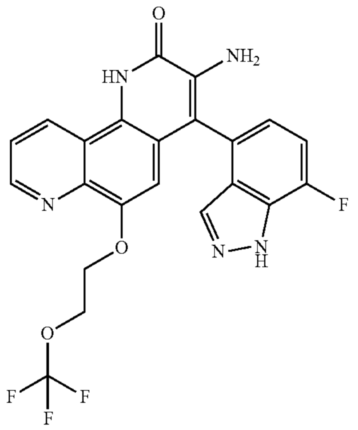

The title compound was synthesized from 4-[7-fluoro-2-(oxan-2-yl)indazol-4-yl]-2-[(4-methoxyphenyl)methoxy]-6-[2-(trifluoromethoxy)ethoxy]-1,7-phenanthrolin-3-amine (compound c-55) under the same conditions as the production example of the compound C4.

LCMS: m/z 474 $[M+H]^+$

HPLC retention time: 0.52 min (analysis condition A)

Compound C44

3-Amino-4-(7-fluoro-1H-indazol-4-yl)-6-[[1-(trifluoromethyl)cyclopropyl]methoxy]-1H-1,7-one

[Formula 339]

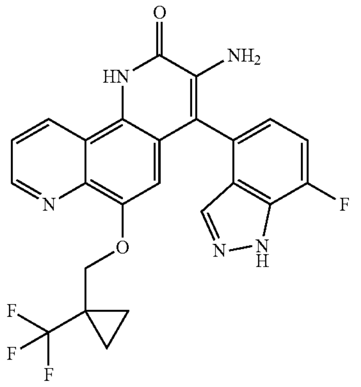

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 484 $[M+H]^+$

HPLC retention time: 0.55 min (analysis condition A)

Compound C45

3-Amino-4-(7-fluoro-1H-indazol-4-yl)-6-[(2S)-2-methoxypropoxy]-1H-1,7-phenanthrolin-2-one

[Formula 340]

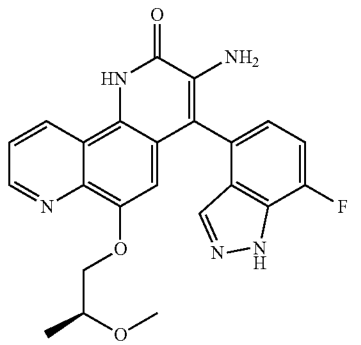

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 434 $[M+H]^+$

HPLC retention time: 0.43 min (analysis condition A)

Compound C46

3-Amino-4-(7-fluoro-1H-indazol-4-yl)-6-[(3R)-oxan-3-yl]oxy-1H-1,7-phenanthrolin-2-one

[Formula 341]

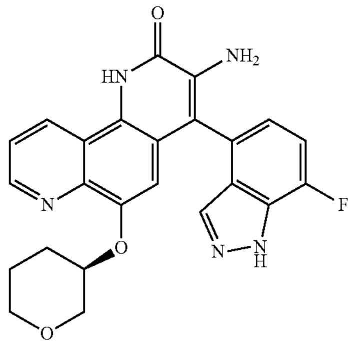

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 446 $[M+H]^+$

HPLC retention time: 0.43 min (analysis condition A)

Compound C47

3-Amino-6-(1,1-dioxothian-4-yl)oxy-4-(7-fluoro-1H-indazol-4-yl)-1H-1,7-phenanthrolin-2-one

[Formula 342]

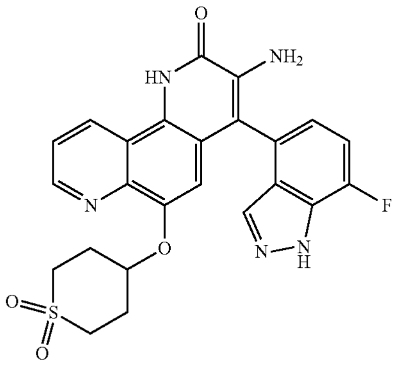

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 494 $[M+H]^+$

HPLC retention time: 0.41 min (analysis condition A)

Compound C48

3-Amino-6-(4,4-difluorocyclohexyl)oxy-4-(7-fluoro-1H-indazol-4-yl)-1H-1,7-phenanthrolin-2-one

[Formula 343]

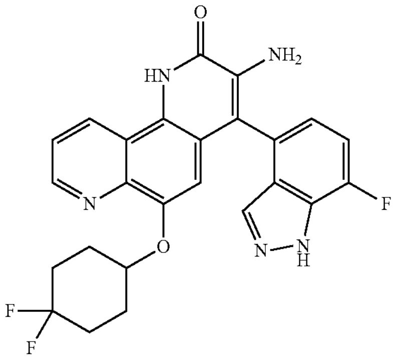

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 480 $[M+H]^+$

HPLC retention time: 0.53 min (analysis condition A)

Compound C49

3-Amino-6-(1-bicyclo[1.1.1]pentanylmethoxy)-4-(7-fluoro-1H-indazol-4-yl)-1H-1,7-phenanthrolin-2-one

[Formula 344]

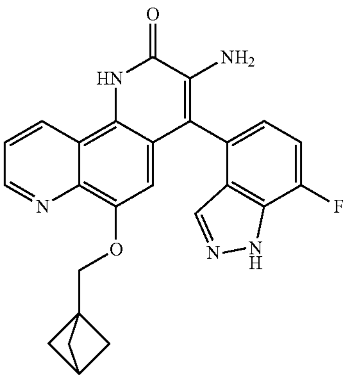

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 442 $[M+H]^+$

HPLC retention time: 0.53 min (analysis condition A)

Compound C50

3-Amino-4-(7-fluoro-1H-indazol-4-yl)-6-[(2R)-2-methoxypropoxy]-1H-1,7-phenanthrolin-2-one

[Formula 345]

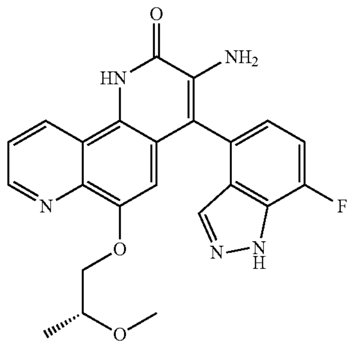

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 434 $[M+H]^+$

HPLC retention time: 0.43 min (analysis condition A)

Compound C51

3-Amino-4-(7-fluoro-1H-indazol-4-yl)-6-[(3S)-oxan-3-yl]oxy-1H-1,7-phenanthrolin-2-one

[Formula 346]

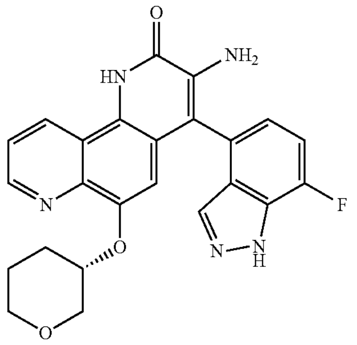

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4.

LCMS: m/z 446 $[M+H]^+$

HPLC retention time: 0.42 min (analysis condition A)

Compound C52

3-Amino-6-[(3,3-difluoro-1-methylcyclobutyl)methoxy]-4-(7-fluoro-1H-indazol-4-yl)-1H-1,7-one

[Formula 347]

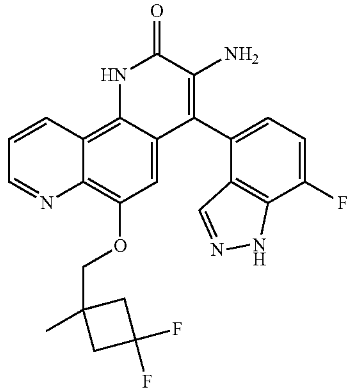

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4, except that anisole was used instead of triethylsilane used in the production example of the compound C4.

LCMS: m/z 480 $[M+H]^+$

HPLC retention time: 0.55 min (analysis condition A)

Compound C53

3-Amino-4-(7-fluoro-1H-indazol-4-yl)-6-[(1-methoxycyclopropyl)methoxy]-1H-1,7-phenanthrolin-2-one

[Formula 348]

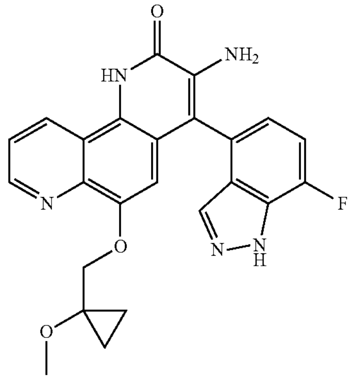

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4, except that anisole was used instead of triethylsilane used in the production example of the compound C4.

LCMS: m/z 446 $[M+H]^+$

HPLC retention time: 0.44 min (analysis condition A)

Compound C54

1-[[3-Amino-4-(7-fluoro-1H-indazol-4-yl)-2-oxo-1H-1,7-phenanthrolin-6-yl]oxymethyl]cyclopropane-1-carbonitrile

[Formula 349]

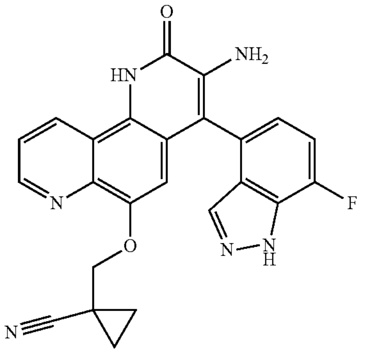

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4, except that anisole was used instead of triethylsilane used in the production example of the compound C4.

LCMS: m/z 441 $[M+H]^+$

HPLC retention time: 0.44 min (analysis condition A)

Compound C55

1-[[3-Amino-4-(7-fluoro-1H-indazol-4-yl)-2-oxo-1H-1,7-phenanthrolin-6-yl]oxymethyl]cyclobutane-1-carbonitrile

[Formula 350]

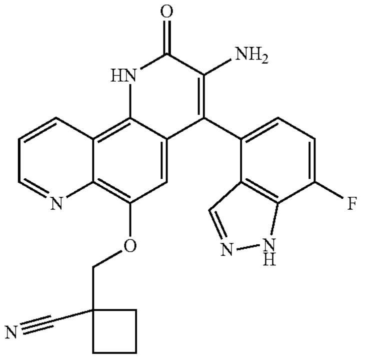

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4, except that anisole was used instead of triethylsilane used in the production example of the compound C4.

LCMS: m/z 455 $[M+H]^+$

HPLC retention time: 0.48 min (analysis condition A)

Compound C56

3-Amino-6-[(1-fluorocyclobutyl)methoxy]-4-(7-fluoro-1H-indazol-4-yl)-1H-1,7-phenanthrolin-2-one

[Formula 351]

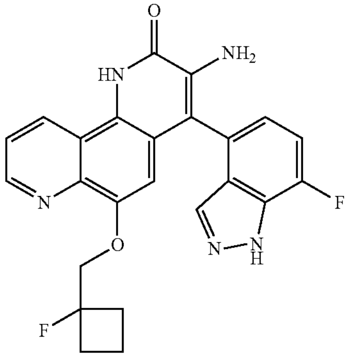

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4, except that anisole was used instead of triethylsilane used in the production example of the compound C4.

LCMS: m/z 448 $[M+H]^+$

HPLC retention time: 0.49 min (analysis condition A)

Compound C57

3-Amino-4-(7-fluoro-1H-indazol-4-yl)-6-[3-(trifluoromethyl)cyclobutyl]oxy-1H-1,7-one

[Formula 352]

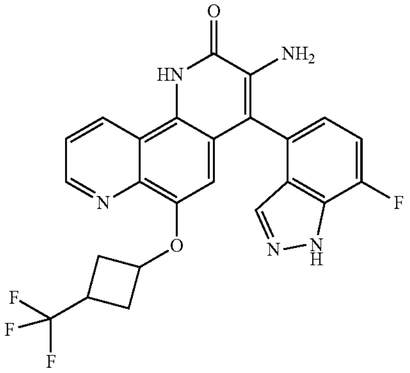

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4, except that anisole was used instead of triethylsilane used in the production example of the compound C4.

LCMS: m/z 484 $[M+H]^+$

HPLC retention time: 0.53 min (analysis condition A)

Compound C58

3-Amino-6-[3-(difluoromethyl)cyclobutyl]oxy-4-(7-fluoro-1H-indazol-4-yl)-1H-1,7-phenanthrolin-2-one

[Formula 353]

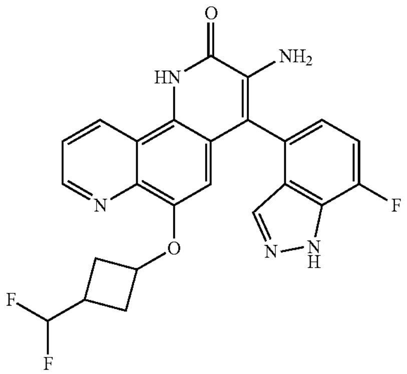

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4, except that anisole was used instead of triethylsilane used in the production example of the compound C4.

LCMS: m/z 466 $[M+H]^+$

HPLC retention time: 0.49 min (analysis condition A)

Compound C59

3-Amino-4-(7-fluoro-1H-indazol-4-yl)-6-(3,3,3-trifluoro-2,2-dimethylpropoxy)-1H-1,7-one

[Formula 354]

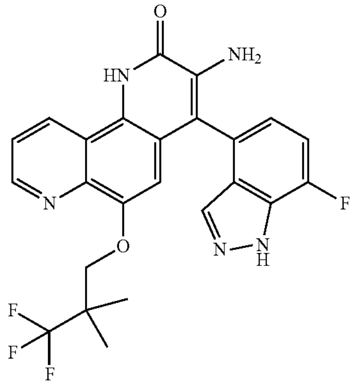

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4, except that the mixture was heated at 150° C. for 3 hours in a sealed tube using a microwave reactor under the same conditions as the production example of the compound c-16. In addition, anisole was used instead of triethylsilane used in the production example of the compound C4.

LCMS: m/z 486 $[M+H]^+$

HPLC retention time: 0.59 min (analysis condition A)

Compound C60

3-Amino-4-(7-fluoro-1H-indazol-4-yl)-6-propoxy-1H-1,7-phenanthrolin-2-one

[Formula 355]

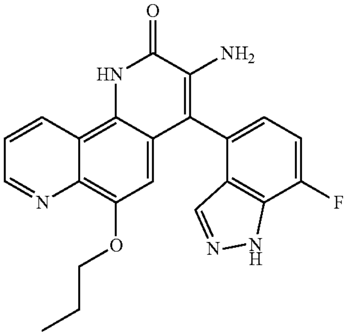

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4, except that anisole was used instead of triethylsilane used in the production example of the compound C4.

LCMS: m/z 404 $[M+H]^+$

HPLC retention time: 0.47 min (analysis condition A)

Compound C61

(R)-3-amino-4-(7-fluoro-1H-indazol-4-yl)-6-(2-fluoropropoxy)-1,7-phenanthrolin-2(1H)-one

[Formula 356]

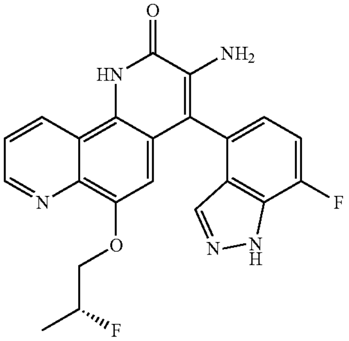

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-16 and C4, except that anisole was used instead of triethylsilane used in the production example of the compound C4.

LCMS: m/z 422 $[M+H]^+$

HPLC retention time: 0.43 min (analysis condition A)

Compound c-17

4-[7-Fluoro-2-(oxan-2-yl)indazol-4-yl]-2-[(4-methoxyphenyl)methoxy]-6-[(3R)-oxolan-3-yl]oxy-1,7-phenanthrolin-3-amine

[Formula 357]

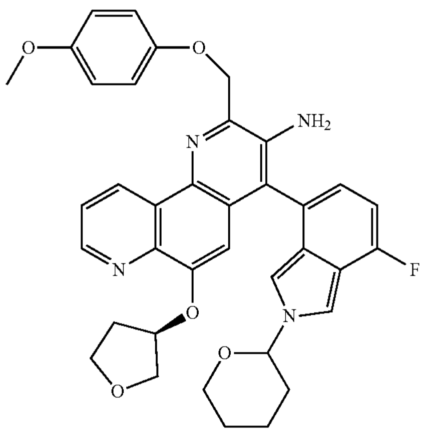

To a solution of 3-amino-4-[7-fluoro-2-(oxan-2-yl)indazol-4-yl]-2-[(4-methoxyphenyl)methoxy]-1,7-phenanthrolin-6-ol (compound c-15, 30 mg, 0.053 mmol) in toluene (900 μL) in a reaction vessel, (S)-3-hydroxytetrahydrofuran (12.63 μL, 0.159 mmol) and cyanomethylenetributylphosphorane (41.7 μL, 0.159 mmol) were added, the mixture was stirred at 60° C. for 3 hours to obtain a solution of the title compound in toluene.

LCMS: m/z 636 $[M+H]^+$

HPLC retention time: 2.11 min (analysis condition D)

Compound C5

3-Amino-4-(7-fluoro-1H-indazol-4-yl)-6-[(3R)-oxolan-3-yl]oxy-1H-1,7-phenanthrolin-2-one

[Formula 358]

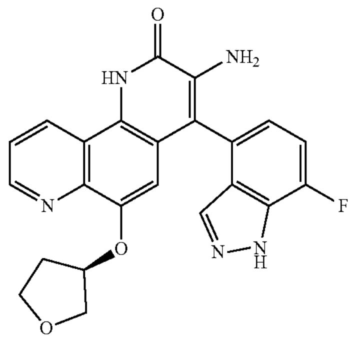

The solution of 4-[7-fluoro-2-(oxan-2-yl)indazol-4-yl]-2-[(4-methoxyphenyl)methoxy]-6-[(3R)-oxolan-3-yl]oxy-1,7-phenanthrolin-3-amine (compound c-17) in toluene in a reaction vessel was cooled to room temperature, anisole (57.9 μL, 0.53 mmol) and TFA (300 μL) were added thereto, and the mixture was stirred at room temperature for 15 hours. The reaction mixture was concentrated under reduced pressure, potassium acetate (15.62 mg, 0.159 mmol) was added thereto, and then the mixture was purified by reversed phase column chromatography to obtain the title compound (12.63 mg, yield 55.2%) as a pale yellow solid.

LCMS: m/z 432 $[M+H]^+$

HPLC retention time: 0.40 min (analysis condition A)

Compound C6

3-Amino-6-cyclopentyloxy-4-(7-fluoro-1H-indazol-4-yl)-1H-1,7-phenanthrolin-2-one

[Formula 359]

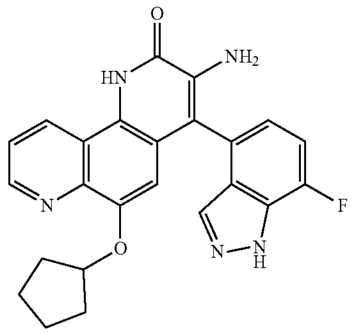

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-17 and C5.

LCMS: m/z 430 $[M+H]^+$

HPLC retention time: 0.48 min (analysis condition A)

Compound C7

3-Amino-4-(7-fluoro-1H-indazol-4-yl)-6-(oxan-4-yloxy)-1H-1,7-phenanthrolin-2-one

[Formula 360]

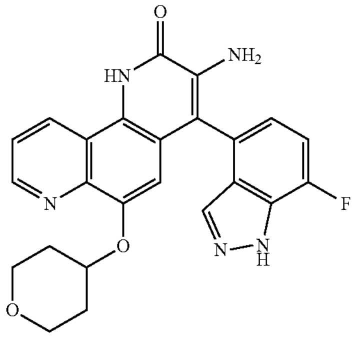

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-17 and C5.

LCMS: m/z 446 $[M+H]^+$

HPLC retention time: 0.40 min (analysis condition A)

Compound C8

3-Amino-6-ethoxy-4-(7-fluoro-1H-indazol-4-yl)-1H-1,7-phenanthrolin-2-one

[Formula 361]

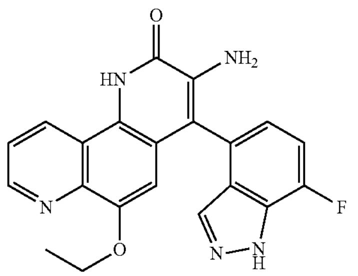

The title compound was synthesized from 3-amino-4-[7-fluoro-2-(oxan-2-yl)indazol-4-yl]-2-[(4-methoxyphenyl) methoxy]-1,7-phenanthrolin-6-ol (compound c-15) and a corresponding alcohol under the same conditions as the production examples of the compounds c-17 and C5.

LCMS: m/z 390 $[M+H]^+$

HPLC retention time: 0.41 min (analysis condition A)

Compound C9

3-Amino-6-(cyclobutylmethoxy)-4-(7-fluoro-1H-indazol-4-yl)-1H-1,7-phenanthrolin-2-one

[Formula 362]

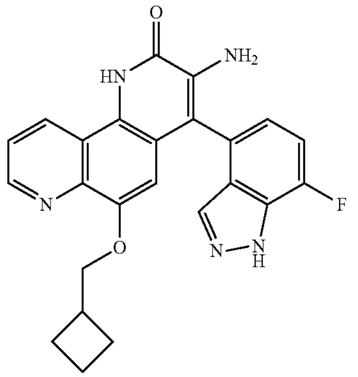

The title compound was synthesized from 3-amino-4-[7-fluoro-2-(oxan-2-yl)indazol-4-yl]-2-[(4-methoxyphenyl) methoxy]-1,7-phenanthrolin-6-ol (compound c-15) and a corresponding alcohol under the same conditions as the production examples of the compounds c-17 and C5.

LCMS: m/z 430 $[M+H]^+$

HPLC retention time: 0.51 min (analysis condition A)

Compound C10

3-Amino-4-(7-fluoro-1H-indazol-4-yl)-6-(3-methyl-butoxy)-1H-1,7-phenanthrolin-2-one

[Formula 363]

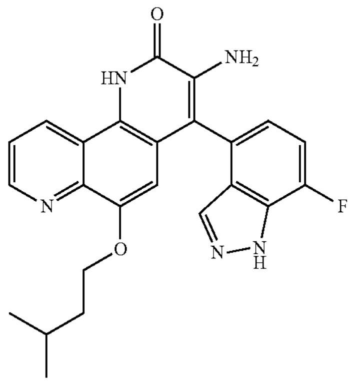

The title compound was synthesized from 3-amino-4-[7-fluoro-2-(oxan-2-yl)indazol-4-yl]-2-[(4-methoxyphenyl) methoxy]-1,7-phenanthrolin-6-ol (compound c-15) and a corresponding alcohol under the same conditions as the production examples of the compounds c-17 and C5.

LCMS: m/z 432 $[M+H]^+$

HPLC retention time: 0.53 min (analysis condition A)

Compound C11

3-Amino-6-(cyclopropylmethoxy)-4-(7-fluoro-1H-indazol-4-yl)-1H-1,7-phenanthrolin-2-one

[Formula 364]

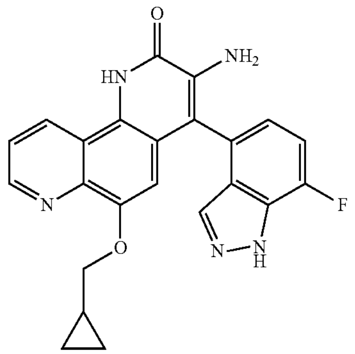

The title compound was synthesized from 3-amino-4-[7-fluoro-2-(oxan-2-yl)indazol-4-yl]-2-[(4-methoxyphenyl) methoxy]-1,7-phenanthrolin-6-ol (compound c-15) and a corresponding alcohol under the same conditions as the production examples of the compounds c-17 and C5.

LCMS: m/z 416 $[M+H]^+$

HPLC retention time: 0.46 min (analysis condition A)

Compound C12

3-Amino-4-(7-fluoro-1H-indazol-4-yl)-6-[(3S)-oxolan-3-yl]oxy-1H-1,7-phenanthrolin-2-one

[Formula 365]

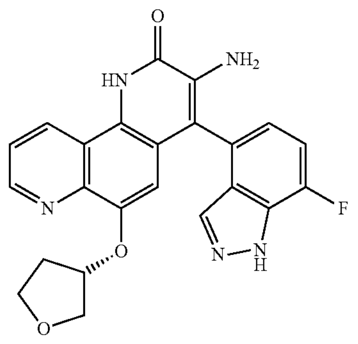

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-17 and C5.

LCMS: m/z 432 $[M+H]^+$

HPLC retention time: 0.40 min (analysis condition A)

Compound C17

3-Amino-6-cyclohexyloxy-4-(7-fluoro-1H-indazol-4-yl)-1H-1,7-phenanthrolin-2-one

[Formula 366]

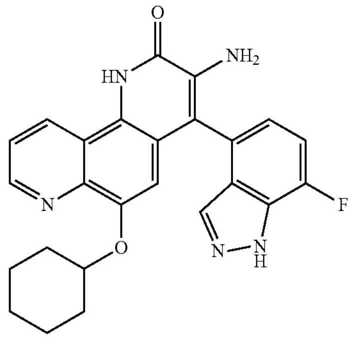

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-17 and C5.

LCMS: m/z 444 $[M+H]^+$

HPLC retention time: 0.51 min (analysis condition A)

Compound C18

3-Amino-6-cyclobutyloxy-4-(7-fluoro-1H-indazol-4-yl)-1H-1,7-phenanthrolin-2-one

[Formula 367]

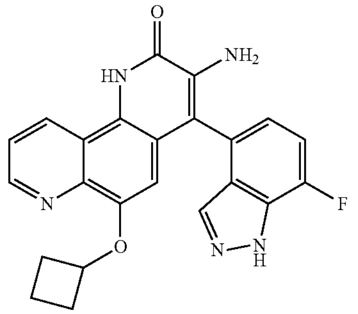

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-17 and C5.

LCMS: m/z 416 $[M+H]^+$

HPLC retention time: 0.46 min (analysis condition A)

Compound C19

3-Amino-4-(7-fluoro-1H-indazol-4-yl)-6-(3-fluoropropoxy)-1H-1,7-phenanthrolin-2-one

[Formula 368]

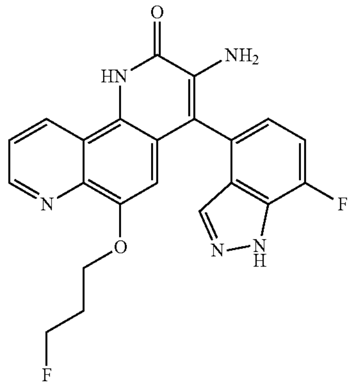

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-17 and C5.

LCMS: m/z 422 $[M+H]^+$

HPLC retention time: 0.43 min (analysis condition A)

Compound C20

3-Amino-4-(7-fluoro-1H-indazol-4-yl)-6-(3-hydroxy-3-methylbutoxy)-1H-1,7-phenanthrolin-2-one

[Formula 369]

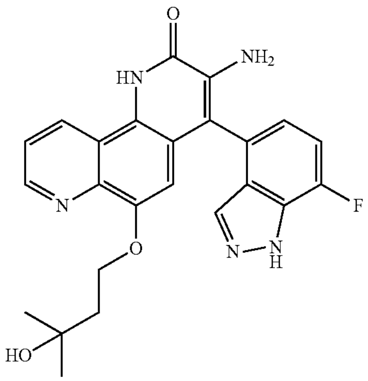

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-17 and C5.

LCMS: m/z 448 $[M+H]^+$

HPLC retention time: 0.94 min (analysis condition D)

Compound C24

3-Amino-4-(7-fluoro-1H-indazol-4-yl)-6-(2-hydroxy-2-methylpropoxy)-1H-1,7-phenanthrolin-2-one

[Formula 370]

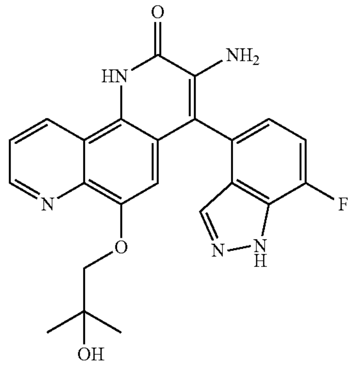

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and a corresponding alcohol under the same conditions as the production examples of the compounds c-17 and C5.

LCMS: m/z 434 $[M+H]^+$

HPLC retention time: 0.43 min (analysis condition A)

Compound c-75

[(2R)-1,1,1-trifluoropropan-2-yl]1,1,2,2,3,3,4,4,4-nonafluorobutane-1-sulfonate

[Formula 371]

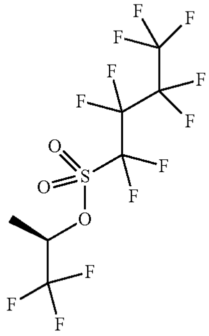

A solution of (R)-1,1,1-trifluoro-2-propanol (300 mg, 2.63 mmol) in THF (3 mL) in a reaction vessel was cooled to 0° C., triethylamine (367 μL, 2.63 mmol) and nonafluoro-1-butanesulfonyl fluoride (614 μL, 3.42 mmol) were added thereto, and the mixture was stirred at room temperature for 15 hours. The reaction mixture was concentrated, and the obtained residue was purified by silica gel column chromatography (DCM) to obtain the title compound (746 mg, yield 72%) as a colorless liquid.

$^1$H-NMR ($CDCl_3$) δ: 5.20-5.11 (1H, m), 1.68 (3H, d, J=6.7 Hz)

Compound c-76

(3,3-Difluorocyclobutyl)1,1,2,2,3,3,4,4,4-nonafluorobutane-1-sulfonate

[Formula 372]

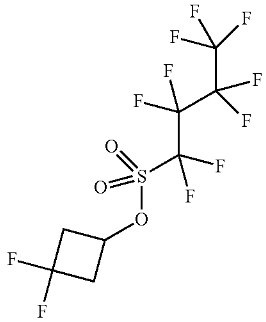

The title compound was synthesized using a corresponding alcohol under the same conditions as the production example of the compound c-75.

$^1$H-NMR ($CDCl_3$) δ: 5.30-5.23 (1H, m), 3.24-3.14 (2H, m), 3.09-2.97 (2H, m)

Compound c-77

2,2-Difluoropropyl 1,1,2,2,3,3,4,4,4-nonafluorobutane-1-sulfonate

[Formula 373]

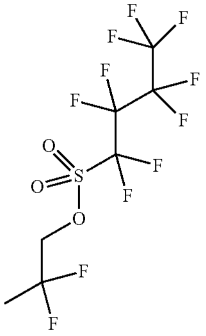

The title compound was synthesized using a corresponding alcohol under the same conditions as the production example of the compound c-75.

$^1$H-NMR ($CDCl_3$) δ: 4.54 (2H, t, J=10.8 Hz), 1.76 (3H, t, J=18.5 Hz)

Compound c-78

(2,2-Difluoro-3-methoxypropyl) 1,1,2,2,3,3,4,4,4-nonafluorobutane-1-sulfonate

[Formula 374]

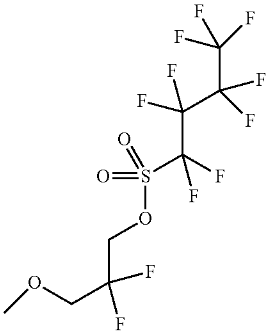

The title compound was synthesized using a corresponding alcohol under the same conditions as the production example of the compound c-75.

$^1$H-NMR ($CDCl_3$) δ: 4.68 (2H, t, J=11.5 Hz), 3.71 (2H, t, J=12.0 Hz), 3.46 (3H, s)

Compound c-79

[(2S)-1,1,1-trifluoropropan-2-yl]1,1,2,2,3,3,4,4,4-nonafluorobutane-1-sulfonate

[Formula 375]

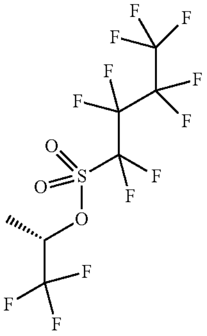

The title compound was synthesized using a corresponding alcohol under the same conditions as the production example of the compound c-75.

$^1$H-NMR ($CDCl_3$) δ: 5.20-5.11 (1H, m), 1.68 (3H, d, J=6.7 Hz)

Compound c-80

(1r,3r)-3-Fluorocyclobutyl trifluoromethanesulfonate

[Formula 375]

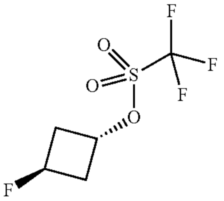

The title compound was synthesized using a corresponding alcohol under the same conditions as the production example of the compound a-102.

$^1$H-NMR ($d_6$-DMSO) δ: 4.91-4.71 (1H, m), 4.63-4.55 (1H, m), 3.01-2.92 (2H, m), 2.49-2.35 (2H, m)

Compound c-25

4-[7-Fluoro-2-(oxan-2-yl)indazol-4-yl]-2-[(4-methoxyphenyl)methoxy]-6-propan-2-yloxy-1,7-phenanthrolin-3-amine

[Formula 377]

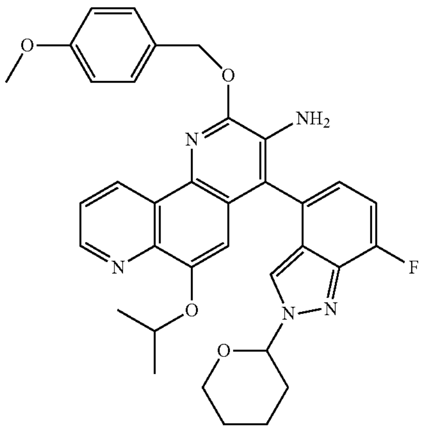

To a solution of 3-amino-4-[7-fluoro-2-(oxan-2-yl)indazol-4-yl]-2-[(4-methoxyphenyl)methoxy]-1,7-phenanthrolin-6-ol (compound c-15, 30 mg, 0.053 mmol) in DMA (265 μL) in a reaction vessel, potassium carbonate (29.3 mg, 0.212 mmol) and 2-iodopropane (15.91 μL, 0.159 mmol) were added, and the mixture was stirred at 80° C. for 15 hours. The reaction mixture was cooled to room temperature, a 20% aqueous sodium chloride solution was added thereto, and the mixture was extracted three times with ethyl acetate. The organic layer was dried over anhydrous sodium sulfate, the drying agent was filtered off, and then the filtrate was concentrated under reduced pressure to obtain the crude product of the title compound (44.6 mg).

LCMS: m/z 609 $[M+H]^+$

HPLC retention time: 0.74 min (analysis condition A)

Compound C13

3-Amino-4-(7-fluoro-1H-indazol-4-yl)-6-propan-2-yloxy-1H-1,7-phenanthrolin-2-one

[Formula 378]

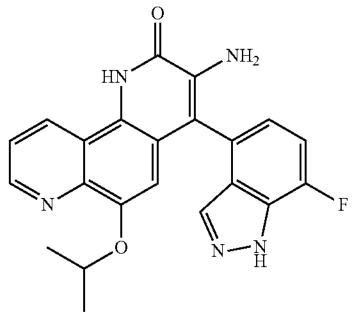

The title compound was synthesized from 4-[7-fluoro-2-(oxan-2-yl)indazol-4-yl]-2-[(4-methoxyphenyl)methoxy]-6-propan-2-yloxy-1,7-phenanthrolin-3-amine (compound c-25) under the same conditions as the production example of the compound B49, except that anisole was used in an amount of 3 equivalents based on the raw material, in addition to the conditions of the production example of the compound B49.

LCMS: m/z 404 $[M+H]^+$

HPLC retention time: 0.43 min (analysis condition A)

Compound C22

3-Amino-4-(7-fluoro-1H-indazol-4-yl)-6-[(2S)-1,1,1-trifluoropropan-2-yl]oxy-1H-1,7-phenanthrolin-2-one

[Formula 379]

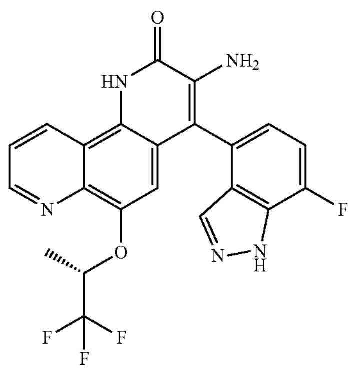

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and [(2R)-1,1,1-trifluoropropan-2-yl]1,1,2,2,3,3,4,4,4-nonafluorobutane-1-sulfonate (compound c-75) under the same conditions as the compounds c-25 and B49, except that 10 equivalents of anisole were used based on the raw material, in addition to the conditions of the production example of the compound B49.

LCMS: m/z 458 $[M+H]^+$

HPLC retention time: 0.57 min (analysis condition A)

Compound C23

3-Amino-6-(3,3-difluorocyclobutyl)oxy-4-(7-fluoro-1H-indazol-4-yl)-1H-1,7-phenanthrolin-2-one

[Formula 380]

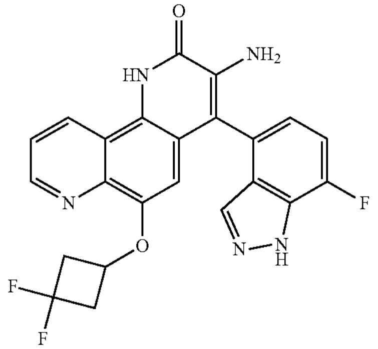

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and (3,3-difluorocyclobutyl) 1,1,2,2,3,3,4,4,4-nonafluorobutane-1-sulfonate (compound c-76) under the same conditions as the compounds c-25 and B49, except that 10 equivalents of anisole were used based on the raw material, in addition to the conditions of the production example of the compound B49.

LCMS: m/z 452 $[M+H]^+$

HPLC retention time: 0.50 min (analysis condition A)

Compound C25

3-Amino-6-(2,2-difluoropropoxy)-4-(7-fluoro-1H-indazol-4-yl)-1H-1,7-phenanthrolin-2-one

[Formula 381]

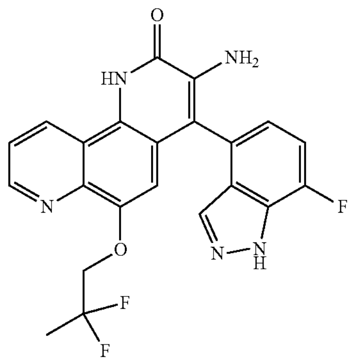

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and 2,2-difluoropropyl 1,1,2,2,3,3,4,4,4-nonafluorobutane-1-sulfonate (compound c-77) under the same conditions as the compounds c-25 and C4, except that anisole and toluene were used instead of triethylsilane and DCM used under the conditions of the production example of the compound C4.

LCMS: m/z 440 $[M+H]^+$

HPLC retention time: 0.49 min (analysis condition A)

Compound C27

3-Amino-4-(7-fluoro-1H-indazol-4-yl)-6-[(2R)-1,1,1-trifluoropropan-2-yl]oxy-1H-1,7-phenanthrolin-2-one

[Formula 382]

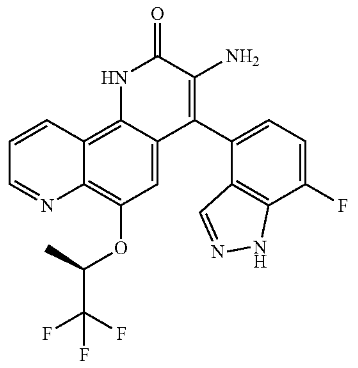

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and [(2S)-1,1,1-trifluoropropan-2-yl]1,1,2,2,3,3,4,4,4-nonafluorobutane-1-sulfonate (compound c-79) under the same conditions as the compounds c-25 and B49, except that triethylsilane was used in an amount of 10 equivalents based on the raw material, in addition to the conditions of the production example of the compound B49.

LCMS: m/z 458 $[M+H]^+$

HPLC retention time: 0.57 min (analysis condition A)

Compound c-28

6-(2,2-Difluoroethoxy)-4-[7-fluoro-2-(oxan-2-yl)indazol-4-yl]-2-[(4-methoxyphenyl)methoxy]-1,7-phenanthrolin-3-amine

[Formula 383]

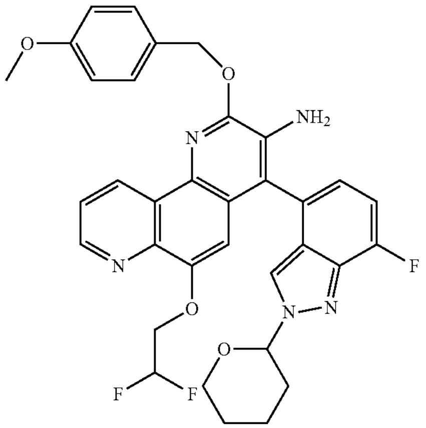

To a solution of 3-amino-4-[7-fluoro-2-(oxan-2-yl)indazol-4-yl]-2-[(4-methoxyphenyl)methoxy]-1,7-phenanthrolin-6-ol (compound c-15, 30 mg, 0.053 mmol) in DMA (265 μL) in a reaction vessel, potassium carbonate (29.3 mg, 0.212 mmol) and 2,2-difluoroethyltriflate (21.1 μL, 0.159 mmol) were added, and the mixture was stirred at room temperature for 15 hours. To the reaction mixture, water was added, and the mixture was extracted with ethyl acetate. The organic layer was dried over anhydrous sodium sulfate, the drying agent was filtered off, and then the filtrate was concentrated under reduced pressure. The obtained residue was purified by silica gel column chromatography to obtain the title compound (22.4 mg, yield 67%).

LCMS: m/z 630.5 $[M+H]^+$

HPLC retention time: 0.83 min (analysis condition A)

Compound C16

3-Amino-6-(2,2-difluoroethoxy)-4-(7-fluoro-1H-indazol-4-yl)-1H-1,7-phenanthrolin-2-one

[Formula 384]

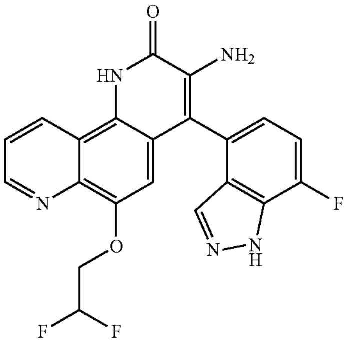

The title compound was synthesized from 6-(2,2-difluoroethoxy)-4-[7-fluoro-2-(oxan-2-yl)indazol-4-yl]-2-[(4-methoxyphenyl)methoxy]-1,7-phenanthrolin-3-amine (compound c-28) under the same conditions as the production example of the compound B49, except that anisole was used in an amount of 3 equivalents based on the raw material, in addition to the conditions of the production example of the compound B49.

LCMS: m/z 426 $[M+H]^+$

HPLC retention time: 0.46 min (analysis condition A)

Compound C14

3-Amino-4-(7-fluoro-1H-indazol-4-yl)-6-(2-methoxyethoxy)-1H-1,7-phenanthrolin-2-one

[Formula 385]

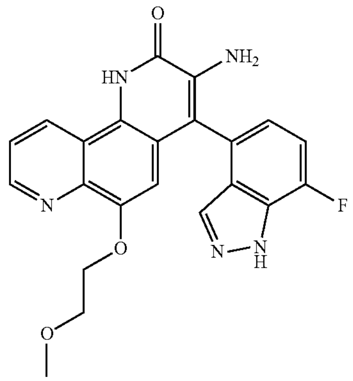

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and 1-bromo-2-methoxyethane under the same conditions as the compounds c-28 and B49, except that anisole was used in an amount of 3 equivalents based on the raw material, in addition to the conditions of the production example of the compound B49.

LCMS: m/z 420 $[M+H]^+$

HPLC retention time: 0.40 min (analysis condition A)

Compound C15

3-Amino-4-(7-fluoro-1H-indazol-4-yl)-6-(2,2,2-trifluoroethoxy)-1H-1,7-phenanthrolin-2-one

[Formula 386]

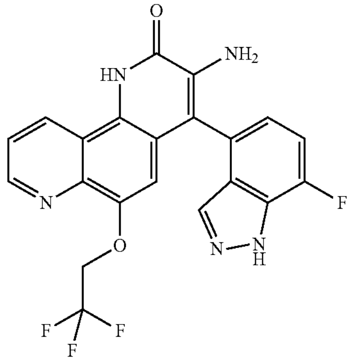

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and 2,2,2-trifluoroethyltriflate under the same conditions as the compounds c-28 and B49, except that anisole was used in an amount of 3 equivalents based on the raw material, in addition to the conditions of the production example of the compound B49.

LCMS: m/z 444 $[M+H]^+$

HPLC retention time: 0.53 min (analysis condition A)

Compound C26

3-Amino-6-(2,2-difluoro-3-methoxypropoxy)-4-(7-fluoro-1H-indazol-4-yl)-1H-1,7-phenanthrolin-2-one

[Formula 387]

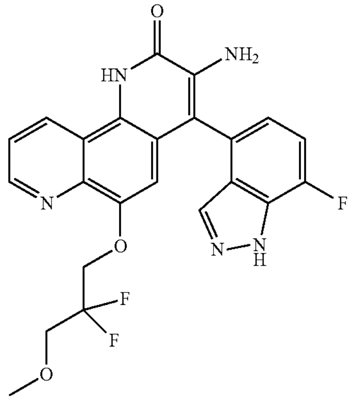

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and (2,2-difluoro-3-methoxypropyl) 1,1,2,2,3,3,4,4,4-nonafluorobutane-1-sulfonate (compound c-78) under the same conditions as the compounds c-28 and B49, except that triethylsilane was used in an amount of 7 equivalents based on the raw material, in addition to the conditions of the production example of the compound B49.

LCMS: m/z 470 $[M+H]^+$

HPLC retention time: 0.49 min (analysis condition A)

Compound C28

3-Amino-4-(7-fluoro-1H-indazol-4-yl)-6-((1s,3s)-3-fluorocyclobutoxy)-1,7-phenanthrolin-2(1H)-one

[Formula 388]

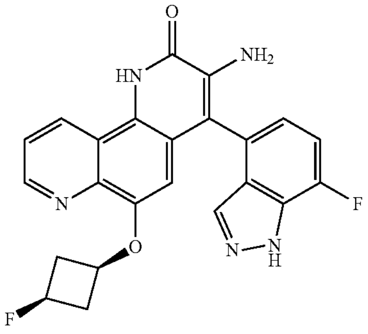

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and (1r,3r)-3-fluorocyclobutyl trifluoromethanesulfonate (compound c-80) under the same conditions as the compounds c-28 and C4, except that anisole was used instead of triethylsilane used under the conditions of the production example of the compound C4.

LCMS: m/z 434 $[M+H]^+$

HPLC retention time: 0.47 min (analysis condition A)

Compound C42

3-Amino-6-((1r,3r)-3-fluorocyclobutyl)oxy-4-(7-fluoro-1H-indazol-4-yl)-1H-1,7-phenanthrolin-2-one

[Formula 389]

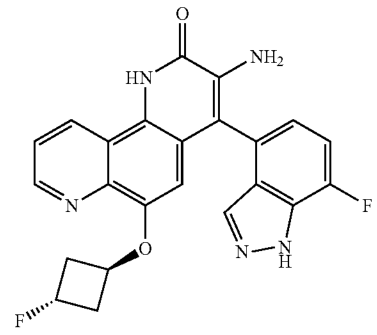

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and (1s,3s)-3-fluorocyclobutyl trifluoromethanesulfonate (compound a-102) under the same conditions as the compounds c-28 and C4.

LCMS: m/z 434 $[M+H]^+$

HPLC retention time: 0.46 min (analysis condition A)

Compound C62

2-[[3-Amino-4-(7-fluoro-1H-indazol-4-yl)-2-oxo-1H-1,7-phenanthrolin-6-yl]oxy]acetonitrile

[Formula 390]

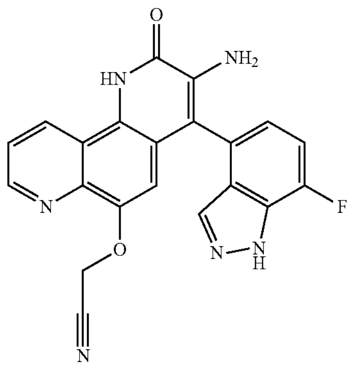

The title compound was synthesized from 3-amino-4-[7-fluoro-2-(oxan-2-yl)indazol-4-yl]-2-[(4-methoxyphenyl)methoxy]-1,7-phenanthrolin-6-ol (compound c-15) and 2-bromoacetonitrile under the same conditions as the compounds c-28 and C4, except that anisole was used instead of triethylsilane used under the conditions of the production example of the compound C4.

LCMS: m/z 401 $[M+H]^+$

HPLC retention time: 0.43 min (analysis condition A)

Compound c-89

2-Ethylhexyl 3-[[3-amino-4-[7-fluoro-2-(oxan-2-yl)indazol-4-yl]-2-[(4-methoxyphenyl)methoxy]-1,7-phenanthrolin-6-yl]sulfanyl]propanoate

[Formula 391]

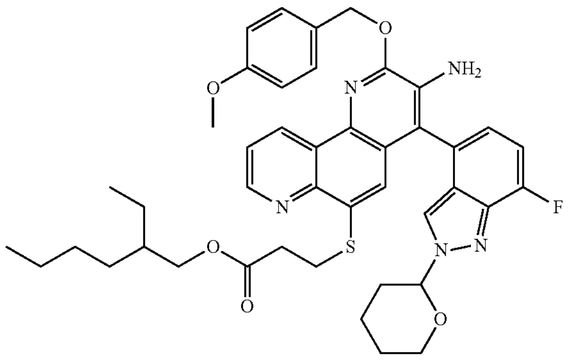

6-Bromo-4-[7-fluoro-2-(oxan-2-yl)indazol-4-yl]-2-[(4-methoxyphenyl)methoxy]-1,7-phenanthrolin-3-amine (compound c-14, 151 mg, 0.24 mmol) in a reaction vessel and Xantphos Pd G3 (22.76 mg, 0.024 mmol) were suspended in 1,4-dioxane (2.4 mL), DIPEA (210 UL, 1.2 mmol) and 2-ethylhexyl 3-mercaptopropionic acid (109 μL, 0.48 mmol) were added, and the mixture was stirred at 100° C. under nitrogen atmosphere for 5 hours. The reaction mixture was cooled to room temperature and concentrated under reduced pressure. The obtained residue was purified by reversed phase column chromatography (0.1% aqueous formic acid solution/0.1% formic acid in acetonitrile solution) to obtain the title compound (205.6 mg) as a light brown solid.

LCMS: m/z 766 $[M+H]^+$

HPLC retention time: 1.78 min (analysis condition F)

Compound c-91

6-(Difluoromethylsulfanyl)-4-[7-fluoro-2-(oxan-2-yl)indazol-4-yl]-2-[(4-methoxyphenyl)methoxy]-1,7-phenanthrolin-3-amine

[Formula 392]

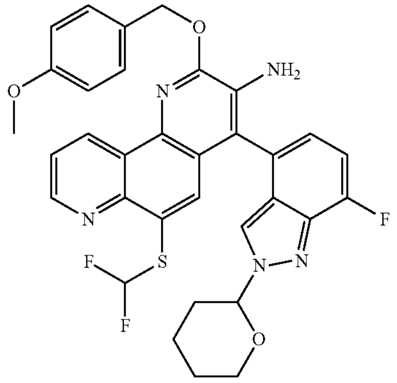

To a solution of 2-ethylhexyl 3-[[3-amino-4-[7-fluoro-2-(oxan-2-yl)indazol-4-yl]-2-[(4-methoxyphenyl)methoxy]-1,7-phenanthrolin-6-yl]sulfanyl]propanoate (compound c-89, 50 mg, 0.065 mmol) and 3-mercaptopropionic acid (17.82 μL, 0.078 mmol) in DMF (435 μL) in a reaction vessel, a 1 M solution of lithium tert-butoxide in THF (150 μL, 0.15 mmol) was added, and the mixture was stirred at room temperature for 40 min. The mixed reaction solution was cooled to −40° C., then an 8 M aqueous potassium hydrate solution (163 μL, 1.306 mmol) and diethyl (bromodifluoromethyl)phosphonate (27.9 μL, 0.157 mmol) were added, and the mixture was stirred at 0° C. for 1 hour. To the reaction mixture, diethyl (bromodifluoromethyl)phosphonate (46.5 μL, 0.261 mmol) was further added, and the mixture was stirred at 0° C. for 45 min. To the reaction mixture, diethyl (bromodifluoromethyl)phosphonate (151 μL, 0.849 mmol) was further added, and the mixture was stirred at 20° C. for 12 hours. The reaction mixture was purified by reversed phase column chromatography (0.1% aqueous formic acid solution/0.1% formic acid in acetonitrile solution) to obtain the title compound (26.2 mg, yield 64%) as a yellow solid.

LCMS: m/z 632 $[M+H]^+$

HPLC retention time: 1.50 min (analysis condition F)

Compound C63

3-Amino-6-(difluoromethylsulfanyl)-4-(7-fluoro-1H-indazol-4-yl)-1H-1,7-phenanthrolin-2-one

[Formula 393]

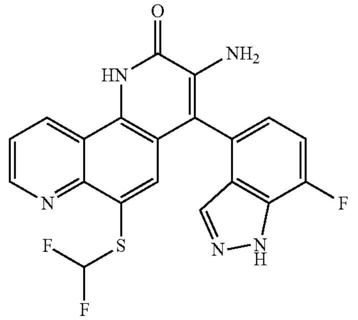

The title compound was synthesized from 6-(difluoromethylsulfanyl)-4-[7-fluoro-2-(oxan-2-yl)indazol-4-yl]-2-[(4-methoxyphenyl)methoxy]-1,7-phenanthrolin-3-amine (compound c-91) under the same conditions as the production example of the compound C4, except that the reaction was carried out without using triethylsilane used in the production example of the compound C4.

LCMS: m/z 428 $[M+H]^+$

HPLC retention time: 0.87 min (analysis condition F)

Compound c-33

6-(Difluoromethoxy)-4-[7-fluoro-2-(oxan-2-yl)indazol-4-yl]-2-[(4-methoxyphenyl)methoxy]-1,7-phenanthrolin-3-amine

[Formula 394]

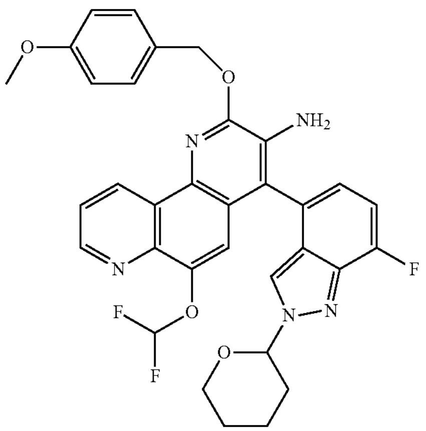

To a solution of 3-amino-4-[7-fluoro-2-(oxan-2-yl)indazol-4-yl]-2-[(4-methoxyphenyl)methoxy]-1,7-phenanthrolin-6-ol (compound c-15, 30 mg, 0.053 mmol) in acetonitrile (600 μL) in a reaction vessel, a 4 M aqueous sodium hydroxide solution (265 μL) and diethyl (bromodifluoromethyl)phosphonate (18.85 μL, 0.106 mmol) were added, and the mixture was stirred at 80° C. for 3 hours. To the reaction mixture, water was added, and the mixture was extracted with ethyl acetate to obtain the crude product of the title compound.

LCMS: m/z 616 $[M+H]^+$

HPLC retention time: 3.04 min (analysis condition D)

Compound C21

3-Amino-6-(difluoromethoxy)-4-(7-fluoro-1H-indazol-4-yl)-1H-1,7-phenanthrolin-2-one

[Formula 395]

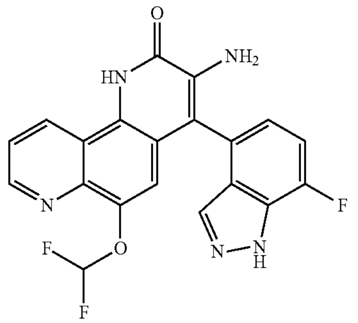

The title compound was synthesized from the crude product of 6-(difluoromethoxy)-4-[7-fluoro-2-(oxan-2-yl)indazol-4-yl]-2-[(4-methoxyphenyl)methoxy]-1,7-phenanthrolin-3-amine (compound c-33) under the same conditions as the production example of the compound B49, except that anisole was used in an amount of 10 equivalents based on the raw material, in addition to the conditions of the production example of the compound B49.

LCMS: m/z 412 $[M+H]^+$

HPLC retention time: 0.54 min (analysis condition A)

Compound c-83

(E)-N'-[6-iodo-8-(trifluoromethoxy)quinolin-5-yl]-N,N-dimethylmethanimidamide

[Formula 396]

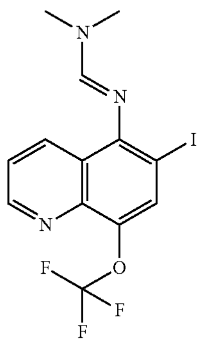

The title compound was synthesized from 5-amino-8-trifluoromethoxyquinoline under the same conditions as the production examples of the compounds b-76 and b-77.

LCMS: m/z 410 $[M+H]^+$

HPLC retention time: 0.45 min (analysis condition A)

Compound c-84

(E)-N'-[6-[7-fluoro-2-(oxan-2-yl)indazole-4-carbonyl]-8-(trifluoromethoxy)quinolin-5-yl]-N,N-dimethylmethanimidamide

[Formula 397]

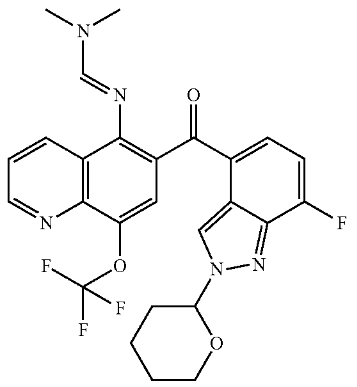

The title compound was synthesized from the compound (E)-N'-[6-iodo-8-(trifluoromethoxy)quinolin-5-yl]-N,N-dimethylmethanimidamide (c-83) under the same conditions as the production example of the compound b-26, except that toluene was used instead of THE used in the production example of the compound b-26.

LCMS: m/z 530 $[M+H]^+$

HPLC retention time: 0.69 min (analysis condition A)

Compound c-85

[5-Amino-8-(trifluoromethoxy)quinolin-6-yl]-[7-fluoro-2-(oxan-2-yl)indazol-4-yl]methanone

[Formula 398]

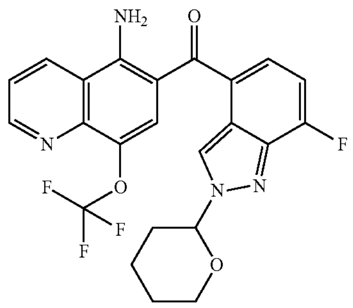

The title compound was synthesized from (E)-N'-[6-[7-fluoro-2-(oxan-2-yl)indazole-4-carbonyl]-8-(trifluoromethoxy)quinolin-5-yl]-N,N-dimethylmethanimidamide (compound c-84) under the same conditions as the production example of the compound b-27.

LCMS: m/z 475 $[M+H]^+$

HPLC retention time: 0.85 min (analysis condition A)

Compound c-86

2-Chloro-N-[6-[7-fluoro-2-(oxan-2-yl)indazole-4-carbonyl]-8-(trifluoromethoxy)quinolin-5-yl]acetamide

[Formula 399]

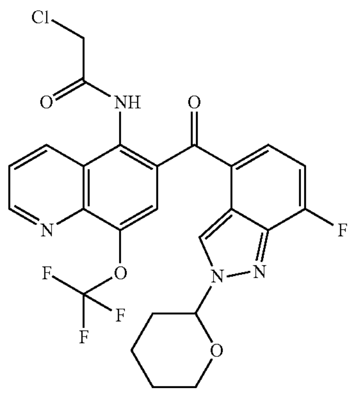

To a solution of [5-amino-8-(trifluoromethoxy)quinolin-6-yl]-[7-fluoro-2-(oxan-2-yl)indazol-4-yl]methanone (compound c-85, 133 mg, 0.28 mmol) in DMA (2.66 mL) in a reaction vessel, chloroacetyl chloride (33.7 μL, 0.42 mmol) was added, and the mixture was stirred for 30 min to obtain a solution of the title compound in DMA.

LCMS: m/z 551 $[M+H]^+$

HPLC retention time: 0.79 min (analysis condition A)

Compound c-87

4-[7-Fluoro-2-(oxan-2-yl)indazol-4-yl]-3-pyridin-1-ium-1-yl-6-(trifluoromethoxy)-1H-1,7-phenanthrolin-2-one; chloride

[Formula 400]

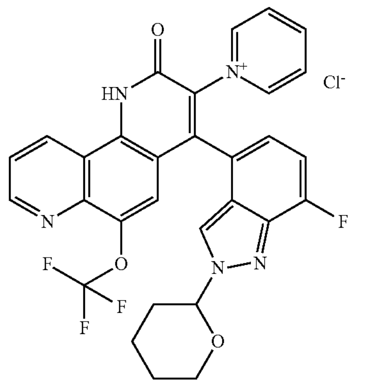

To the solution of 2-chloro-N-[6-[7-fluoro-2-(oxan-2-yl)indazole-4-carbonyl]-8-(trifluoromethoxy)quinolin-5-yl]acetamide (compound c-86) in DMA in a reaction vessel, pyridine (1.33 mL) was added, and the mixture was stirred at 70° C. for 1 hour to obtain a mixed solution of the title compound in DMA/pyridine.

LCMS: m/z 576.5 $[M]^+$

HPLC retention time: 0.52 min (analysis condition A)

Compound c-88

4-(7-Fluoro-1H-indazol-4-yl)-3-pyridin-1-ium-1-yl-6-(trifluoromethoxy)-1H-1,7-phenanthrolin-2-one; chloride

[Formula 401]

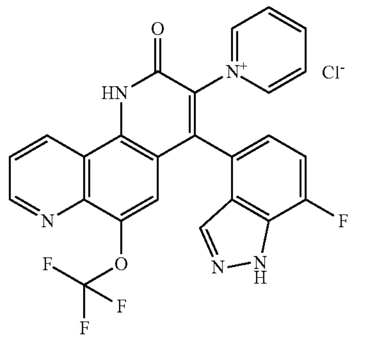

The mixed solution of 4-[7-fluoro-2-(oxan-2-yl)indazol-4-yl]-3-pyridin-1-ium-1-yl-6-(trifluoromethoxy)-1H-1,7-phenanthrolin-2-one; chloride (compound c-87) in DMA/pyridine in a reaction vessel was cooled to room temperature, 12 M hydrochloric acid (234 μL, 2.8 mmol) was added thereto, and the mixture was stirred at 70° C. for 1 hour and further stirred at 80° C. for 1.5 hours to obtain a mixed solution of the title compound in DMA/pyridine.

LCMS: m/z 492 $[M]^+$

HPLC retention time: 0.42 min (analysis condition A)

Compound C188

3-Amino-4-(7-fluoro-1H-indazol-4-yl)-6-(trifluoromethoxy)-1H-1,7-phenanthrolin-2-one

[Formula 402]

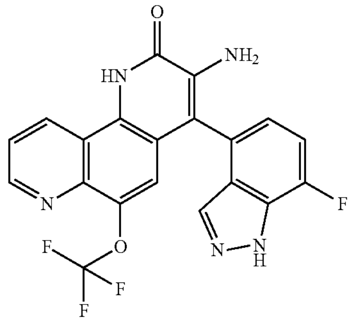

The mixed solution of 4-(7-fluoro-1H-indazol-4-yl)-3-pyridin-1-ium-1-yl-6-(trifluoromethoxy)-1H-1,7-phenanthrolin-2-one; chloride (compound c-88) in DMA/pyridine in a reaction vessel was cooled to room temperature, hydrazine monohydrate (139 μL, 2.8 mmol) was added thereto, and the mixture was stirred at 90° C. for 30 min. The reaction mixture was cooled to room temperature, and 15 mL of water was added thereto. The obtained solid was collected by filtration and sequentially washed with water and acetonitrile/water (1/4) to obtain the title compound (75.4 mg, yield 62.6%) as a brown solid.

LCMS: m/z 430 $[M+H]^+$

HPLC retention time: 0.59 min (analysis condition A)

Compound c-99

4-Bromo-6,7-difluoro-1-(oxan-2-yl)indazole

[Formula 403]

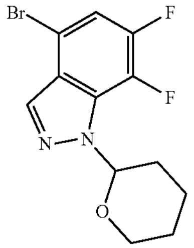

To a solution of 4-bromo-6,7-difluoro-1H-indazole (6.38 g, 27.4 mmol) in DCM (128 mL) in a reaction vessel, 3,4-dihydro-2H-pyran (7.49 mL, 82 mmol) and p-toluenesulfonic acid monohydrate (0.521 g, 2.74 mmol) were added, and the mixture was stirred at room temperature for 15 hours. The reaction mixture was washed with a saturated aqueous sodium bicarbonate solution, the organic layer was dried over anhydrous sodium sulfate, the drying agent was filtered off, and then the filtrate was concentrated under reduced pressure. The obtained residue was purified by silica gel column chromatography (ethyl acetate/hexane) to obtain the title compound (6.68 g, yield 77%) as a colorless solid.

LCMS: m/z 317 $[M+H]^+$

HPLC retention time: 0.97 min (analysis condition A)

Compound c-100

(2,4,6-Trichlorophenyl) 6,7-difluoro-1-(oxan-2-yl) indazole-4-carboxylate

[Formula 404]

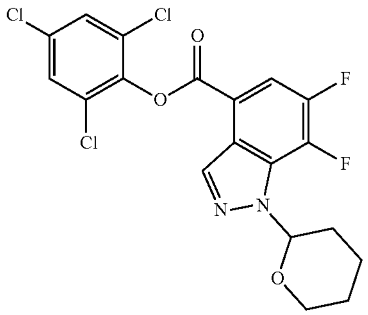

The title compound was synthesized from 4-bromo-6,7-difluoro-1-(oxan-2-yl)indazole (compound c-99) under the same conditions as the production example of the compound c-4.

LCMS: m/z 461 $[M+H]^+$

HPLC retention time: 1.03 min (analysis condition U)

Compound c-101

6,7-Difluoro-1-(oxan-2-yl)indazole-4-carboxylic acid

[Formula 405]

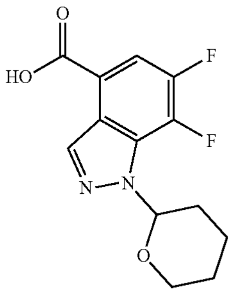

The title compound was synthesized from (2,4,6-trichlorophenyl) 6,7-difluoro-1-(oxan-2-yl)indazole-4-carboxylate (compound c-100) under the same conditions as the production example of the compound c-5.

LCMS: m/z 283 $[M+H]^+$

HPLC retention time: 0.69 min (analysis condition A)

Compound c-102

6,7-Difluoro-N-methoxy-N-methyl-1-(oxan-2-yl) indazole-4-carboxamide

[Formula 406]

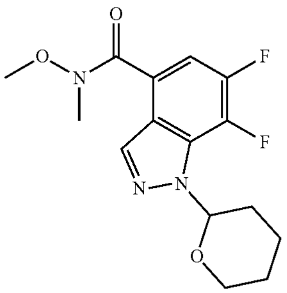

The title compound was synthesized from 6,7-difluoro-1-(oxan-2-yl)indazole-4-carboxylic acid (compound c-101) under the same conditions as the production example of the compound b-2, except that THF and triethylamine were used instead of DMF and DIPEA used in the production example of the compound b-2.

LCMS: m/z 326 $[M+H]^+$

HPLC retention time: 0.72 min (analysis condition A)

Compound c-103

(E)-N'-[8-bromo-6-[6,7-difluoro-1-(oxan-2-yl)indazole-4-carbonyl]quinolin-5-yl]-N,N-dimethylmethanimidamide

[Formula 407]

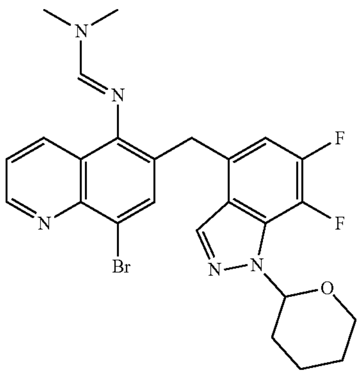

The title compound was synthesized from 6,7-difluoro-N-methoxy-N-methyl-1-(oxan-2-yl)indazole-4-carboxamide (compound c-102) and (E)-N'-(8-bromo-6-iodoquinolin-5-yl)-N,N-dimethylmethanimidamide (compound c-2) under the same conditions as the production example of the compound b-26, except that toluene was used instead of THE used in the production example of the compound b-26.

LCMS: m/z 542 $[M+H]^+$

HPLC retention time: 0.85 min (analysis condition A)

Compound c-104

(5-Amino-8-bromoquinolin-6-yl)-[6,7-difluoro-1-(oxan-2-yl)indazol-4-yl]methanone

[Formula 408]

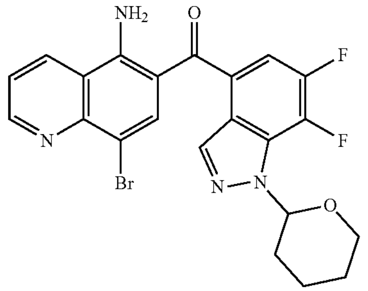

The title compound was synthesized from (E)-N'-[8-bromo-6-[6,7-difluoro-1-(oxan-2-yl)indazole-4-carbonyl]quinolin-5-yl]-N,N-dimethylmethanimidamide (compound c-103) under the same conditions as the production example of the compound b-27.

LCMS: m/z 487 $[M+H]^+$

HPLC retention time: 0.90 min (analysis condition A)

Compound c-105

N-[8-bromo-6-[6,7-difluoro-1-(oxan-2-yl)indazole-4-carbonyl]quinolin-5-yl]-2-chloroacetamide

[Formula 409]

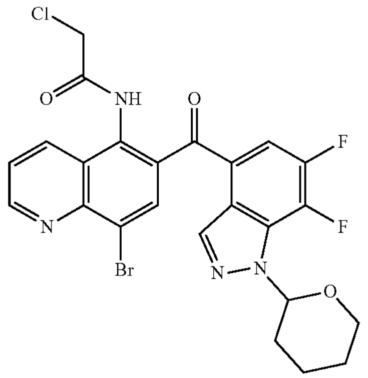

LCMS: m/z 563 $[M+H]^+$

HPLC retention time: 0.83 min (analysis condition A)

Compound c-106

6-Bromo-4-[6,7-difluoro-1-(oxan-2-yl)indazol-4-yl]-3-pyridin-1-ium-1-yl-1H-1,7-phenanthrolin-2-one; chloride

[Formula 410]

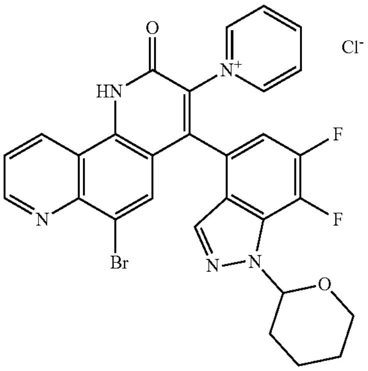

LCMS: m/z 588 $[M]^+$

HPLC retention time: 0.54 min (analysis condition A)

Compound c-107

3-Amino-6-bromo-4-[6,7-difluoro-1-(oxan-2-yl)indazol-4-yl]-1H-1,7-phenanthrolin-2-one

[Formula 411]

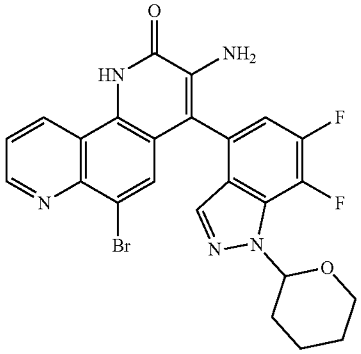

The compound c-105, the compound c-106, and the compound c-107 were synthesized from (5-amino-8-bromoquinolin-6-yl)-[6,7-difluoro-1-(oxan-2-yl)indazol-4-yl]methanone (compound c-104) under the same conditions as the production examples of the compounds c-9, c-10, and c-13, except that the reaction was carried out without using N,N-dimethylaniline used in the production example of the compound c-9.

LCMS: m/z 526 $[M+H]^+$

HPLC retention time: 0.81 min (analysis condition A)

Compound C66

3-Amino-6-bromo-4-(6,7-difluoro-1H-indazol-4-yl)-1H-1,7-phenanthrolin-2-one

[Formula 412]

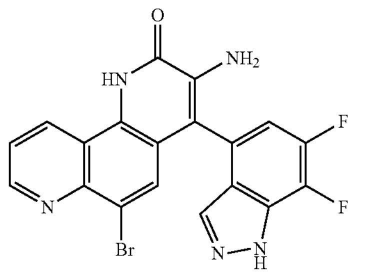

The title compound was synthesized from 3-amino-6-bromo-4-[6,7-difluoro-1-(oxan-2-yl)indazol-4-yl]-1H-1,7-phenanthrolin-2-one (compound c-107) under the same conditions as the production example of the compound B49.

LCMS: m/z. 442 $[M+H]^+$

HPLC retention time: 0.59 min (analysis condition A)

Compound c-108

3-Amino-4-[6,7-difluoro-1-(oxan-2-yl)indazol-4-yl]-6-methoxy-1H-1,7-phenanthrolin-2-one

[Formula 413]

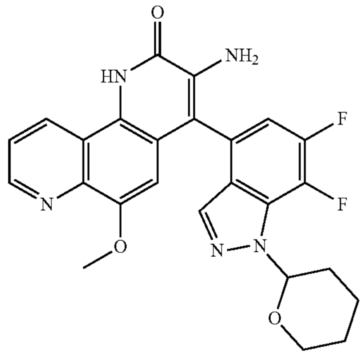

A solution of 3-amino-6-bromo-4-[6,7-difluoro-1-(oxan-2-yl)indazol-4-yl]-1H-1,7-phenanthrolin-2-one (compound c-107, 25 mg, 0.047 mmol) and tBuBrettPhos Pd G3 (4.06 mg, 4.75 μmol) in 1,4-dioxane (317 μL) in a reaction vessel was cooled to 0° C., and a 5 M solution of sodium methoxide in methanol (66.5 μL, 0.332 mmol) was added thereto. Nitrogen gas was blown into the mixed suspension, and then the mixture was stirred at room temperature for 3.5 hours. The reaction mixture was purified by reversed phase column chromatography (0.1% aqueous formic acid solution/0.1% formic acid in acetonitrile solution) to obtain the title compound (18.8 mg, yield 83%) as a brown solid.

LCMS: m/z 478 $[M+H]^+$

HPLC retention time: 0.56 min (analysis condition A)

Compound C65

3-Amino-4-(6,7-difluoro-1H-indazol-4-yl)-6-methoxy-1H-1,7-phenanthrolin-2-one

[Formula 414]

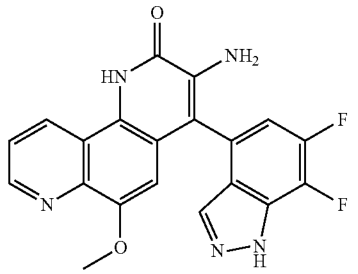

The title compound was synthesized from 3-amino-4-[6,7-difluoro-1-(oxan-2-yl)indazol-4-yl]-6-methoxy-1H-1,7-phenanthrolin-2-one (compound c-108) under the same conditions as the production example of the compound B49.

LCMS: m/z 394 $[M+H]^+$

HPLC retention time: 0.41 min (analysis condition A)

Compound c-109

6-Bromo-4-[6,7-difluoro-1-(oxan-2-yl)indazol-4-yl]-2-[(4-methoxyphenyl)methoxy]-1,7-phenanthrolin-3-amine

[Formula 415]

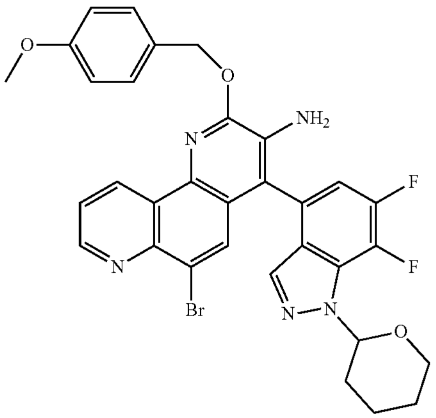

The title compound was synthesized from 3-amino-6-bromo-4-[6,7-difluoro-1-(oxan-2-yl)indazol-4-yl]-1H-1,7-phenanthrolin-2-one (compound c-107) under the same conditions as the production example of the compound c-14.

LCMS: m/z 646 $[M+H]^+$

HPLC retention time: 5.66 min (analysis condition J)

Compound c-110

3-Amino-4-[6,7-difluoro-1-(oxan-2-yl)indazol-4-yl]-2-[(4-methoxyphenyl)methoxy]-1,7-phenanthrolin-6-ol

[Formula 416]

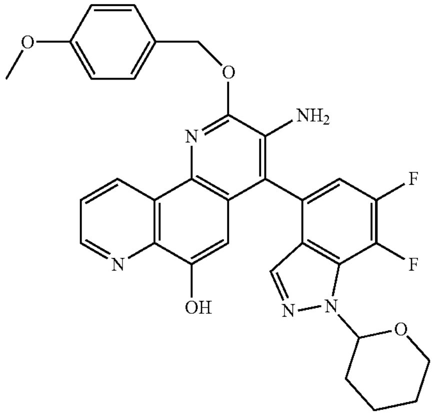

The title compound was synthesized from 6-bromo-4-[6,7-difluoro-1-(oxan-2-yl)indazol-4-yl]-2-[(4-methoxyphenyl)methoxy]-1,7-phenanthrolin-3-amine (compound c-109) under the same conditions as the production example of the compound c-15.

LCMS: m/z 584.5 $[M+H]^+$

HPLC retention time: 0.92 min (analysis condition A)

Compound C67

3-Amino-4-(6,7-difluoro-1H-indazol-4-yl)-6-ethoxy-1H-1,7-phenanthrolin-2-one

[Formula 417]

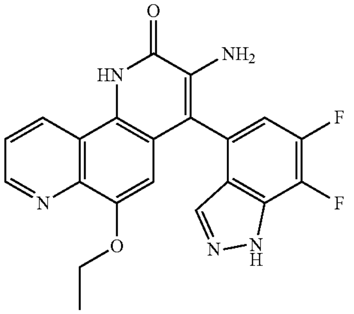

The title compound was synthesized from 3-amino-4-[6,7-difluoro-1-(oxan-2-yl)indazol-4-yl]-2-[(4-methoxyphenyl)methoxy]-1,7-phenanthrolin-6-ol (compound c-110) under the same conditions as the production examples of the compounds c-28 and C4, except that iodoethane and DMF were used instead of 2,2-difluoroethyltriflate and DMA used in the production example of the compound c-28. In addition, anisole was used instead of triethylsilane used in the production example of the compound C4.

LCMS: m/z 408 $[M+H]^+$

HPLC retention time: 0.44 min (analysis condition A)

Compound C68

3-Amino-6-(2,2-difluoroethoxy)-4-(6,7-difluoro-1H-indazol-4-yl)-1H-1,7-phenanthrolin-2-one

[Formula 418]

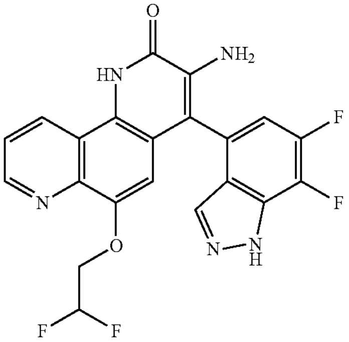

The title compound was synthesized from 3-amino-4-[6,7-difluoro-1-(oxan-2-yl)indazol-4-yl]-2-[(4-methoxyphenyl)methoxy]-1,7-phenanthrolin-6-ol (compound c-110) under the same conditions as the production examples of the compounds c-28 and C4, except that DMF was used instead of DMA used in the production example of the compound c-28. In addition, anisole was used instead of triethylsilane used in the production example of the compound C4.

LCMS: m/z 444 $[M+H]^+$

HPLC retention time: 0.49 min (analysis condition A)

Compound C69

3-Amino-4-(6,7-difluoro-1H-indazol-4-yl)-6-propan-2-yloxy-1H-1,7-phenanthrolin-2-one

[Formula 419]

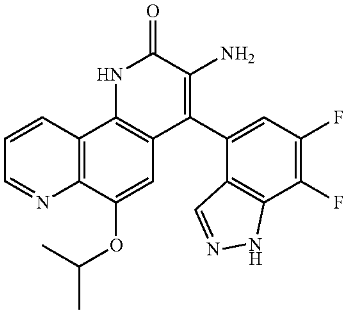

The title compound was synthesized from 3-amino-4-[6,7-difluoro-1-(oxan-2-yl)indazol-4-yl]-2-[(4-methoxyphenyl)methoxy]-1,7-phenanthrolin-6-ol (compound c-110) under the same conditions as the production examples of the compounds c-28 and C4, except that 2-iodopropane and DMF were used instead of 2,2-difluoroethyltriflate and DMA used in the production example of the compound c-28. In addition, anisole was used instead of triethylsilane used in the production example of the compound C4.

LCMS: m/z 422 $[M+H]^+$

HPLC retention time: 0.46 min (analysis condition A)

Compound C70

3-Amino-6-(cyclopropylmethoxy)-4-(6,7-difluoro-1H-indazol-4-yl)-1H-1,7-phenanthrolin-2-one

[Formula 420]

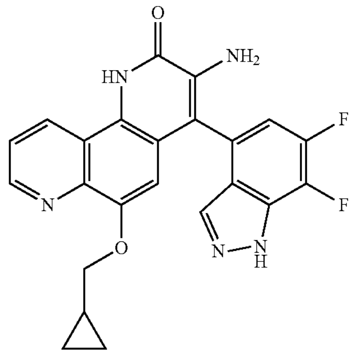

The title compound was synthesized from 3-amino-4-[6,7-difluoro-1-(oxan-2-yl)indazol-4-yl]-2-[(4-methoxyphenyl)methoxy]-1,7-phenanthrolin-6-ol (compound c-110) and a corresponding alcohol under the same conditions as the production examples of the compounds c-16 and C4, except that anisole was used instead of triethylsilane used in the production example of the compound C4.

LCMS: m/z 434 [M+H]$^+$

HPLC retention time: 0.49 min (analysis condition A)

Compound C71

3-Amino-4-(6,7-difluoro-1H-indazol-4-yl)-6-[(1-fluorocyclopropyl)methoxy]-1H-1,7-one

[Formula 421]

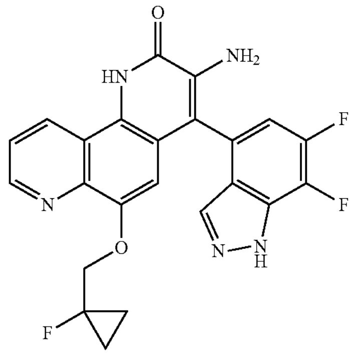

The title compound was synthesized from 3-amino-4-[6,7-difluoro-1-(oxan-2-yl)indazol-4-yl]-2-[(4-methoxyphenyl)methoxy]-1,7-phenanthrolin-6-ol (compound c-110) and a corresponding alcohol under the same conditions as the production examples of the compounds c-16 and C4, except that anisole was used instead of triethylsilane used in the production example of the compound C4.

LCMS: m/z 452 [M+H]$^+$

HPLC retention time: 0.49 min (analysis condition A)

Compound c-116

(E)-N'-[6-[6,7-difluoro-1-(oxan-2-yl)indazole-4-carbonyl]-8-(trifluoromethoxy)quinolin-5-yl]-N,N-dimethylmethanimidamide

[Formula 422]

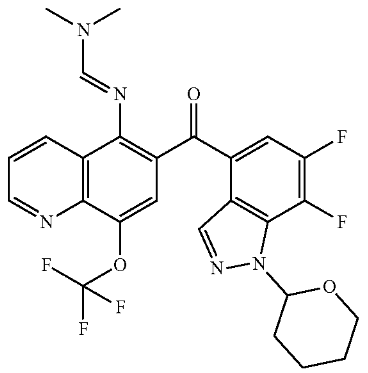

The title compound was synthesized from (E)-N'-[6-iodo-8-(trifluoromethoxy)quinolin-5-yl]-N,N-dimethylmethanimidamide (compound c-83) and 6,7-difluoro-N-methoxy-N-methyl-1-(oxan-2-yl)indazole-4-carboxamide (compound c-102) under the same conditions as the production example of the compound b-26, except that toluene was used instead of THE used in the production example of the compound b-26.

LCMS: m/z 548 [M+H]$^+$

HPLC retention time: 0.90 min (analysis condition A)

Compound c-117

[5-Amino-8-(trifluoromethoxy)quinolin-6-yl]-[6,7-difluoro-1-(oxan-2-yl)indazol-4-yl]methanone

[Formula 423]

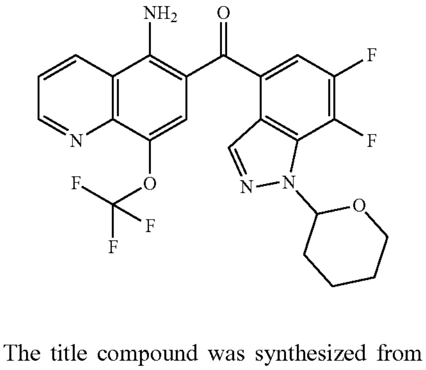

The title compound was synthesized from (E)-N'-[6-[6,7-difluoro-1-(oxan-2-yl)indazole-4-carbonyl]-8-(trifluoromethoxy)quinolin-5-yl]-N,N-dimethylmethanimidamide (compound c-116) under the same conditions as the production example of the compound b-27.

LCMS: m/z 493 [M+H]$^+$

HPLC retention time: 0.93 min (analysis condition A)

Compound C72

3-Amino-4-(6,7-difluoro-1H-indazol-4-yl)-6-(trifluoromethoxy)-1H-1,7-phenanthrolin-2-one

[Formula 424]

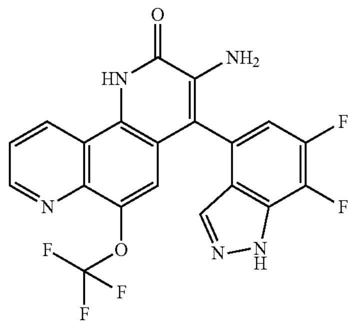

The title compound was synthesized from [5-amino-8-(trifluoromethoxy)quinolin-6-yl]-[6,7-difluoro-1-(oxan-2-yl)indazol-4-yl]methanone (compound c-117) under the same conditions as the production examples of the compounds c-9, c-10, c-13, and B49, except that the reaction was carried out without using N,N-dimethylaniline used in the production example of the compound c-9.

LCMS: m/z 448 [M+H]$^+$

HPLC retention time: 0.63 min (analysis condition A)

Compound c-246

6-Iodo-8-(trifluoromethyl)quinoline-5-amine

[Formula 425]

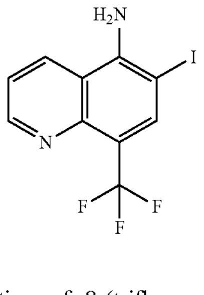

To a solution of 8-(trifluoromethyl)quinoline-5-amine (250 mg, 1.178 mmol) in DMSO (1.96 mL) in a reaction vessel, TFA (91 μL, 1.178 mmol) was added, and the mixture was cooled to 0° C. To the mixture, N-iodosuccinimide (270 mg, 1.20 mmol) was added, and the mixture was stirred at 0° C. for 1 hour to obtain a solution of the title compound in DMSO.

LCMS: m/z 339 [M+H]$^+$

HPLC retention time: 0.78 min (analysis condition A)

Compound c-247

(E)-N'-[6-iodo-8-(trifluoromethyl)quinolin-5-yl]-N,N-dimethylmethanimidamide

[Formula 426]

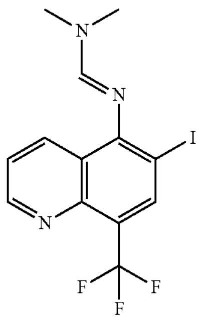

The solution of 6-iodo-8-(trifluoromethyl)quinoline-5-amine (compound c-246) in DMSO was heated to room temperature, N,N-dimethylformamidedimethylacetal (1.25 mL, 9.42 mmol) was added thereto, and the mixture was stirred at room temperature for 15 hours. The reaction mixture was purified by reversed phase column chromatography (0.1% aqueous formic acid solution/0.1% formic acid in acetonitrile solution) to obtain the title compound (330 mg, yield 71%) as a pale yellow solid.

LCMS: m/z 394 [M+H]$^+$

HPLC retention time: 0.62 min (analysis condition A)

Compound c-248

(E)-N'-[6-[7-fluoro-2-(oxan-2-yl)indazole-4-carbonyl]-8-(trifluoromethyl)quinolin-5-yl]-N,N-dimethylmethanimidamide

[Formula 427]

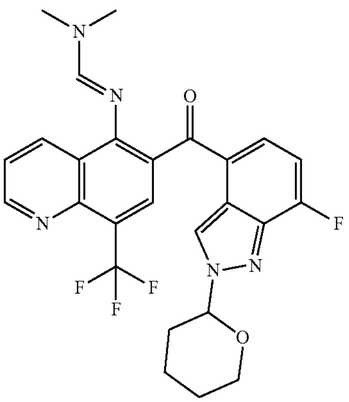

The title compound was synthesized from (E)-N'-[6-iodo-8-(trifluoromethyl)quinolin-5-yl]-N,N-dimethylmethanimidamide (compound c-247) under the same conditions as the production example of the compound b-26.

LCMS: m/z 514 [M+H]$^+$

HPLC retention time: 0.88 min (analysis condition A)

Compound c-249

[5-Amino-8-(trifluoromethyl)quinolin-6-yl]-[7-fluoro-2-(oxan-2-yl)indazol-4-yl]methanone

[Formula 428]

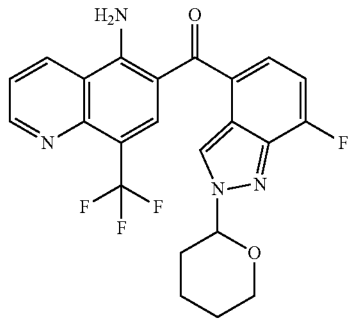

The title compound was synthesized from (E)-N'-[6-[7-fluoro-2-(oxan-2-yl)indazole-4-carbonyl]-8-(trifluoromethyl)quinolin-5-yl]-N,N-dimethylmethanimidamide (compound c-248) under the same conditions as the production example of the compound b-27.

LCMS: m/z 459 $[M+H]^+$

HPLC retention time: 0.89 min (analysis condition A)

Compound C187

3-Amino-4-(7-fluoro-1H-indazol-4-yl)-6-(trifluoromethyl)-1H-1,7-phenanthrolin-2-one

[Formula 429]

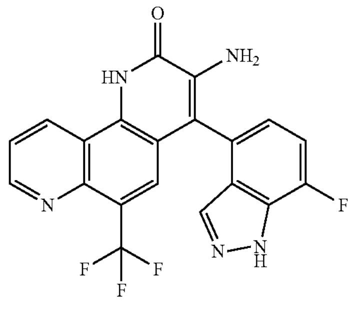

The title compound was synthesized from [5-amino-8-(trifluoromethyl)quinolin-6-yl]-[7-fluoro-2-(oxan-2-yl)indazol-4-yl]methanone (compound c-249) under the same conditions as the production examples of the compounds b-63, b-64, b-65, and B21.

LCMS: m/z 414 $[M+H]^+$

HPLC retention time: 0.62 min (analysis condition A)

Compound c-93

(E)-N'-(8-fluoro-6-iodoquinolin-5-yl)-N,N-dimethylmethanimidamide

[Formula 430]

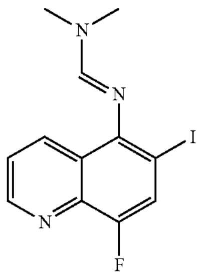

The title compound was synthesized from 8-fluoroquinolin-5-amine under the same conditions as the production examples of the compounds c-246 and c-247.

LCMS: m/z 344 $[M+H]^+$

HPLC retention time: 0.85 min (analysis condition H)

Compound c-94

(E)-N'-[8-fluoro-6-[7-fluoro-2-(oxan-2-yl)indazole-4-carbonyl]quinolin-5-yl]-N,N-dimethylmethanimidamide

[Formula 431]

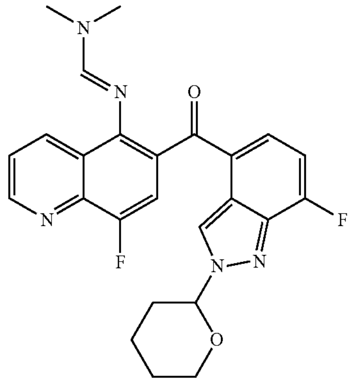

The title compound was synthesized from (E)-N'-(8-fluoro-6-iodoquinolin-5-yl)-N,N-dimethylmethanimidamide (compound c-93) under the same conditions as the production example of the compound b-26.

LCMS: m/z 464 $[M+H]^+$

HPLC retention time: 0.54 min (analysis condition A)

Compound c-95

(5-Amino-8-fluoroquinolin-6-yl)-[7-fluoro-2-(oxan-2-yl)indazol-4-yl]methanone

[Formula 432]

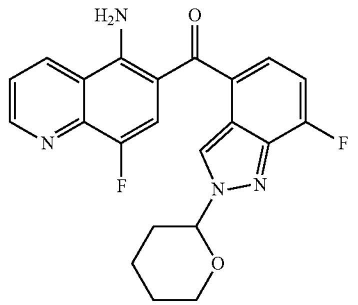

The title compound was synthesized from (E)-N'-[8-fluoro-6-[7-fluoro-2-(oxan-2-yl)indazole-4-carbonyl]quinolin-5-yl]-N,N-dimethylmethanimidamide (compound c-94) under the same conditions as the production example of the compound b-27.

LCMS: m/z 409 $[M+H]^+$

HPLC retention time: 0.74 min (analysis condition A)

Compound C64

3-Amino-6-fluoro-4-(7-fluoro-1H-indazol-4-yl)-1H-1,7-phenanthrolin-2-one

[Formula 433]

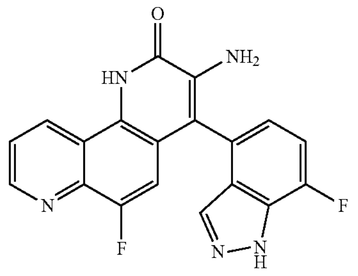

The title compound was synthesized from (5-amino-8-bromoquinolin-6-yl)-[7-fluoro-2-(oxan-2-yl)indazol-4-yl]methanone (compound c-95) under the same conditions as the production examples of the compounds b-28, b-29, b-30, and the compound b-9.

LCMS: m/z 364 $[M+H]^+$

HPLC retention time: 0.51 min (analysis condition A)

Compound c-123

(E)-N'-[8-bromo-6-[7-chloro-2-(oxan-2-yl)indazole-4-carbonyl]quinolin-5-yl]-N,N-dimethylmethanimidamide

[Formula 434]

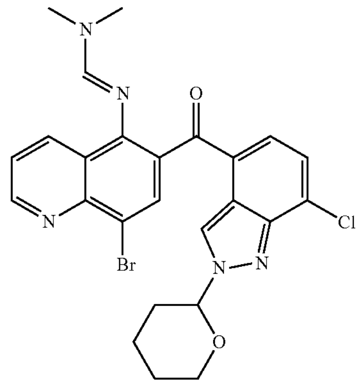

The title compound was synthesized from (E)-N'-(8-bromo-6-iodoquinolin-5-yl)-N,N-dimethylmethanimidamide (compound c-2) and 7-chloro-N-methoxy-N-methyl-2-(oxan-2-yl)indazole-4-carboxamide (compound a-4) under the same conditions as the production example of the compound b-26, except that toluene was used instead of THE used in the production example of the compound b-26.

LCMS: m/z 540 $[M+H]^+$

HPLC retention time: 0.69 min (analysis condition A)

Compound c-124

(5-Amino-8-bromoquinolin-6-yl)-[7-chloro-2-(oxan-2-yl)indazol-4-yl]methanone

[Formula 435]

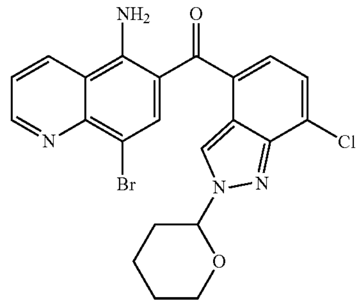

The title compound was synthesized from (E)-N'-[8-bromo-6-[7-chloro-2-(oxan-2-yl)indazole-4-carbonyl]quinolin-5-yl]-N,N-dimethylmethanimidamide (compound c-123) under the same conditions as the production example of the compound b-27.

LCMS: m/z 485 $[M+H]^+$

HPLC retention time: 0.86 min (analysis condition A)

Compound c-177

3-Amino-6-bromo-4-[7-chloro-2-(oxan-2-yl)indazol-4-yl]-1H-1,7-phenanthrolin-2-one

[Formula 436]

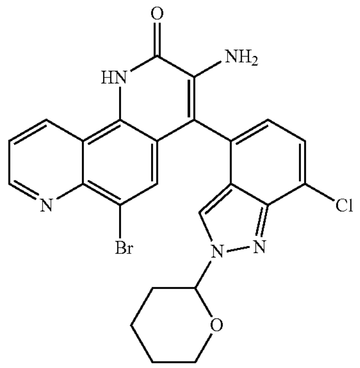

The title compound was synthesized from (5-amino-8-bromoquinolin-6-yl)-[7-chloro-2-(oxan-2-yl)indazol-4-yl]methanone (compound c-124) under the same conditions as the production examples of the compounds c-9, c-10, and c-13, except that the reaction was carried out without using N,N-dimethylaniline used in the production example of the compound c-9.

LCMS: m/z 524 $[M+H]^+$

HPLC retention time: 0.76 min (analysis condition A)

Compound C73

3-Amino-6-bromo-4-(7-chloro-1H-indazol-4-yl)-1H-1,7-phenanthrolin-2-one

[Formula 437]

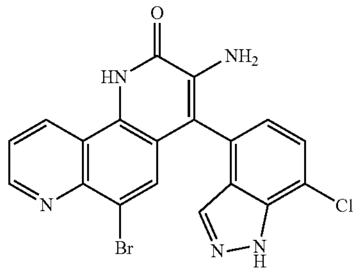

The title compound was synthesized from 3-amino-6-bromo-4-[7-chloro-2-(oxan-2-yl)indazol-4-yl]-1H-1,7-phenanthrolin-2-one (compound c-177) under the same conditions as the production example of the compound C4.

LCMS: m/z 440 $[M+H]^+$

HPLC retention time: 0.61 min (analysis condition A)

Compound C74

3-Amino-4-(7-chloro-1H-indazol-4-yl)-6-methoxy-1H-1,7-phenanthrolin-2-one

[Formula 438]

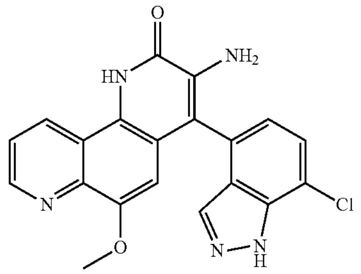

The title compound was synthesized from 3-amino-6-bromo-4-(7-chloro-1H-indazol-4-yl)-1H-1,7-phenanthrolin-2-one (compound C73) under the same conditions as the production example of the compound c-108, except that NMP was used instead of 1,4-dioxane used in the production example of the compound c-108.

LCMS: m/z 392 $[M+H]^+$

HPLC retention time: 0.41 min (analysis condition A)

Compound c-122

(E)-N'-(8-chloro-6-iodoquinolin-5-yl)-N,N-dimethylmethanimidamide

[Formula 439]

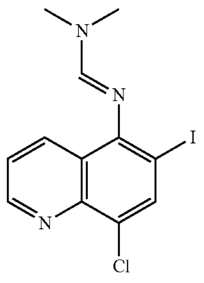

The title compound was synthesized from 8-chloroquinolin-5-amine under the same conditions as the production examples of the compounds c-1 and b-25.

LCMS: m/z 360 $[M+H]^+$

HPLC retention time: 0.81 min (analysis condition H)

Compound c-133

(5-Amino-8-chloroquinolin-6-yl)-[7-chloro-2-(oxan-2-yl)indazol-4-yl]methanone

[Formula 440]

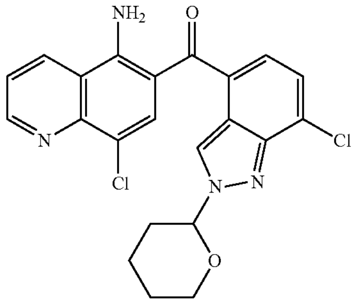

The title compound was synthesized from (E)-N'-(8-chloro-6-iodoquinolin-5-yl)-N,N-dimethylmethanimidamide (compound c-122) and [7-chloro-2-(oxan-2-yl)indazol-4-yl]-morpholin-4-ylmethanone (compound a-54) under the same conditions as the production examples of the compounds b-26 and b-27.

LCMS: m/z 441 $[M+H]^+$

HPLC retention time: 0.84 min (analysis condition A)

Compound C77

3-Amino-6-chloro-4-(7-chloro-1H-indazol-4-yl)-1H-1,7-phenanthrolin-2-one

[Formula 441]

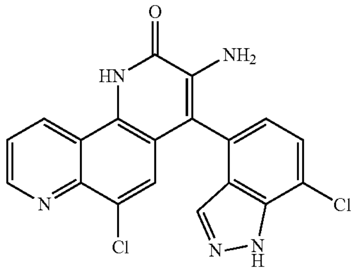

The title compound was synthesized from the compound (5-amino-8-chloroquinolin-6-yl)-[7-chloro-2-(oxan-2-yl)indazol-4-yl]methanone (compound c-133) under the same conditions as the production examples of the compounds b-63, c-64, b-65, and B21, except that 12 M hydrochloric acid was used instead of the 5% solution of hydrogen chloride in MeOH used in the production example of the compound B21.

LCMS: m/z 396 $[M+H]^+$

HPLC retention time: 0.59 min (analysis condition A)

Compound c-134

(E)-N'-[8-chloro-6-[7-fluoro-2-(oxan-2-yl)indazole-4-carbonyl]quinolin-5-yl]-N,N-dimethylmethanimidamide

[Formula 442]

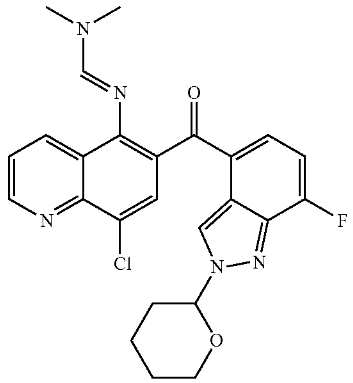

The title compound was synthesized from (E)-N'-(8-chloro-6-iodoquinolin-5-yl)-N,N-dimethylmethanimidamide (c-122) and 7-fluoro-N-methoxy-N-methyl-2-(oxan-2-yl)indazole-4-carboxamide (compound c-6) under the same conditions as the production example of the compound b-26.

LCMS: m/z 480 $[M+H]^+$

HPLC retention time: 0.62 min (analysis condition A)

Compound c-135

(5-Amino-8-chloroquinolin-6-yl)-[7-fluoro-2-(oxan-2-yl)indazol-4-yl]methanone

[Formula 443]

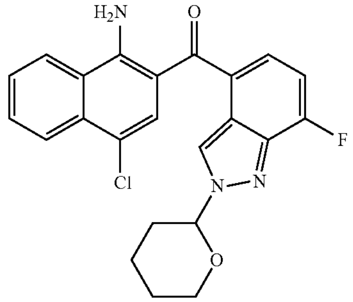

The title compound was synthesized from (E)-N'-[8-chloro-6-[7-fluoro-2-(oxan-2-yl)indazole-4-carbonyl]quinolin-5-yl]-N,N-dimethylmethanimidamide (compound c-134) under the same conditions as the production example of the compound b-27.

LCMS: m/z 425 $[M+H]^+$

HPLC retention time: 0.75 min (analysis condition A)

Compound C78

3-Amino-6-chloro-4-(7-fluoro-1H-indazol-4-yl)-1H-1,7-phenanthrolin-2-one

[Formula 444]

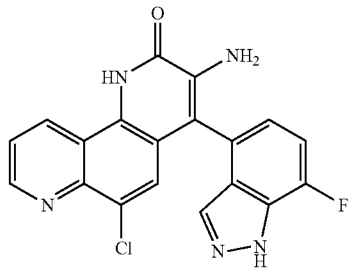

The title compound was synthesized from 5-amino-8-chloroquinolin-6-yl)-[7-fluoro-2-(oxan-2-yl)indazol-4-yl] methanone (compound c-135) under the same conditions as the production examples of the compounds b-28, b-29, b-30, and b-9, except that hydrazine monohydrochloride was used instead of 12 M hydrochloric acid used in the production example of the compound b-30.

LCMS: m/z 380 $[M+H]^+$

HPLC retention time: 0.53 min (analysis condition B)

Compound c-137

N-Methoxy-N-methyl-1-(oxan-2-yl)indazole-4-carboxamide

[Formula 445]

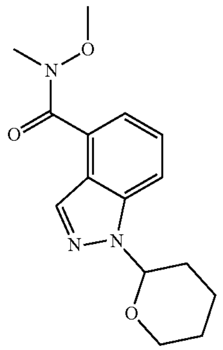

The title compound was synthesized from 1-(tetrahydro-2H-pyran-2-yl)-1H-indazole-4-carboxylic acid under the same conditions as the production example of the compound b-2.

LCMS: m/z 290 $[M+H]^+$

HPLC retention time: 0.58 min (analysis condition A)

Compound c-138

(E)-N'-[8-chloro-6-[1-(oxan-2-yl)indazole-4-carbonyl]quinolin-5-yl]-N,N-dimethylmethanimidamide

[Formula 446]

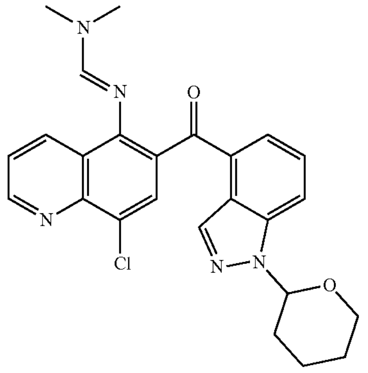

The title compound was synthesized from N-methoxy-N-methyl-1-(oxan-2-yl)indazole-4-carboxamide (compound c-137) and (E)-N'-(8-chloro-6-iodoquinolin-5-yl)-N,N-dimethylmethanimidamide (compound c-122) under the same conditions as the production example of the compound b-26, except that a 0.75 M solution of isopropylmagnesium chloride in THF was used instead of the 1.3 M solution of isopropylmagnesium chloride-lithium chloride complex in THE used in the production example of the compound b-26.

LCMS: m/z 462 $[M+H]^+$

HPLC retention time: 0.61 min (analysis condition A)

Compound c-139

(5-Amino-8-chloroquinolin-6-yl)-[1-(oxan-2-yl)indazol-4-yl]methanone

[Formula 447]

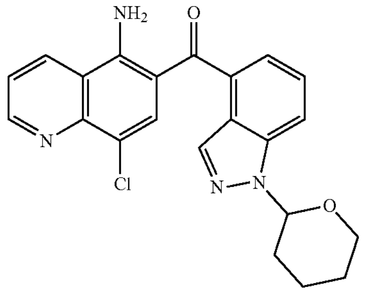

The title compound was synthesized from (E)-N'-[8-chloro-6-[1-(oxan-2-yl)indazole-4-carbonyl]quinolin-5-yl]-N,N-dimethylmethanimidamide (compound c-138) under the same conditions as the production example of the compound b-67.

LCMS: m/z 407 $[M+H]^+$

HPLC retention time: 0.77 min (analysis condition A)

Compound C79

3-Amino-6-chloro-4-(1H-indazol-4-yl)-1H-1,7-phenanthrolin-2-one

[Formula 448]

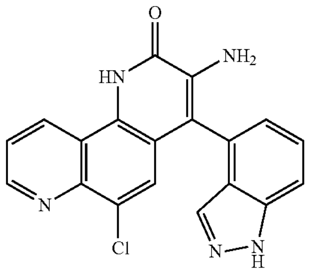

The title compound was synthesized from (5-amino-8-chloroquinolin-6-yl)-[1-(oxan-2-yl)indazol-4-yl]methanone (compound c-139) under the same conditions as the production examples of the compounds b-7, b-8, b-9, and B48.

LCMS: m/z 362 $[M+H]^+$

HPLC retention time: 0.50 min (analysis condition A)

Compound c-126

4-Bromo-7-chloro-6-fluoro-2-(oxan-2-yl)indazole

[Formula 449]

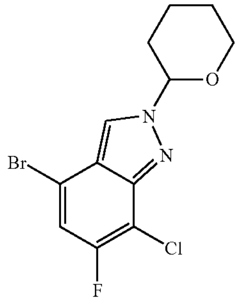

The title compound was synthesized from 4-bromo-7-chloro-6-fluoro-1H-indazole under the same conditions as the production example of the compound c-3.

LCMS: m/z 333 $[M+H]^+$

HPLC retention time: 0.96 min (analysis condition A)

Compound c-127

(2,4,6-Trichlorophenyl) 7-chloro-6-fluoro-2-(oxan-2-yl)indazole-4-carboxylate

[Formula 450]

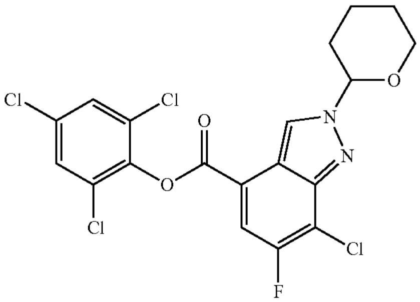

The title compound was synthesized from 4-bromo-7-chloro-6-fluoro-2-(oxan-2-yl)indazole (compound c-126) under the same conditions as the production example of the compound c-4.

LCMS: m/z 477 $[M+H]^+$

HPLC retention time: 1.20 min (analysis condition A)

Compound c-128

7-Chloro-6-fluoro-2-(oxan-2-yl)indazole-4-carboxylic acid

[Formula 451]

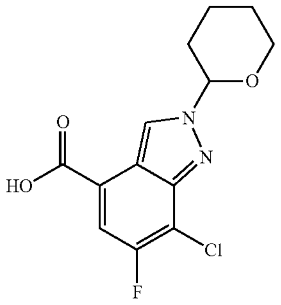

The title compound was synthesized from (2,4,6-trichlorophenyl) 7-chloro-6-fluoro-2-(oxan-2-yl)indazole-4-carboxylate (compound c-127) under the same conditions as the production example of the compound c-5.

LCMS: m/z 299 $[M+H]^+$

HPLC retention time: 0.68 min (analysis condition A)

Compound c-129

7-Chloro-6-fluoro-N-methoxy-N-methyl-2-(oxan-2-yl)indazole-4-carboxamide

[Formula 452]

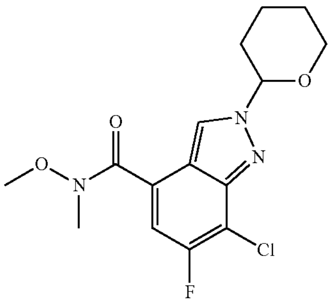

The title compound was synthesized from 7-chloro-6-fluoro-2-(oxan-2-yl)indazole-4-carboxylic acid (compound c-128) under the same conditions as the production example of the compound b-2, except that triethylamine was used instead of DIPEA used in the production example of the compound b-2.

LCMS: m/z 342 $[M+H]^+$

HPLC retention time: 0.71 min (analysis condition A)

Compound c-130

(E)-N'-[8-bromo-6-[7-chloro-6-fluoro-2-(oxan-2-yl)indazole-4-carbonyl]quinolin-5-yl]-N,N-dimethyl-methanimidamide

[Formula 453]

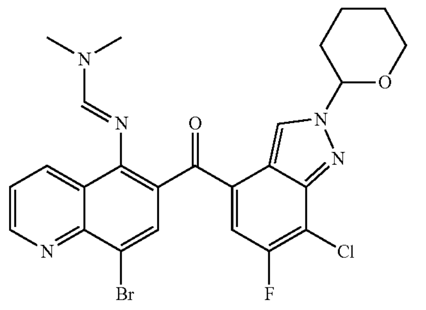

The title compound was synthesized from (E)-N'-(8-bromo-6-iodoquinolin-5-yl)-N,N-dimethylmethanimidamide (compound c-2) and 7-chloro-6-fluoro-N-methoxy-N-methyl-2-(oxan-2-yl)indazole-4-carboxamide (compound c-129) under the same conditions as the production example of the compound b-26, except that toluene was used instead of THF used in the production example of the compound b-26.

LCMS: m/z 558 $[M+H]^+$

HPLC retention time: 0.81 min (analysis condition A)

Compound c-131

(5-Amino-8-bromoquinolin-6-yl)-[7-chloro-6-fluoro-2-(oxan-2-yl)indazol-4-yl]methanone

[Formula 454]

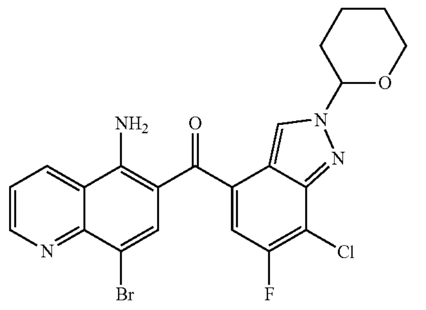

The title compound was synthesized from (E)-N'-[8-bromo-6-[7-chloro-6-fluoro-2-(oxan-2-yl)indazole-4-carbonyl]quinolin-5-yl]-N,N-dimethylmethanimidamide (compound c-130) under the same conditions as the production example of the compound b-27.

LCMS: m/z 503 $[M+H]^+$

HPLC retention time: 0.88 min (analysis condition A)

Compound C75

3-Amino-6-bromo-4-(7-chloro-6-fluoro-1H-indazol-4-yl)-1H-1,7-phenanthrolin-2-one

[Formula 455]

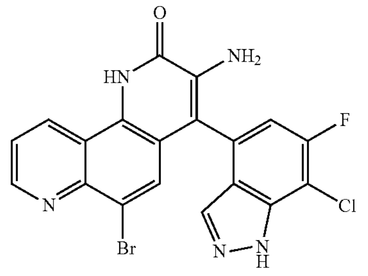

The title compound was synthesized from (5-amino-8-bromoquinolin-6-yl)-[7-chloro-6-fluoro-2-(oxan-2-yl)indazol-4-yl]methanone (compound c-131) under the same conditions as the production examples of the compounds c-86, c-87, c-88, and C188.

LCMS: m/z 458 $[M+H]^+$

HPLC retention time: 0.62 min (analysis condition A)

Compound C76

3-Amino-4-(7-chloro-6-fluoro-1H-indazol-4-yl)-6-methoxy-1H-1,7-phenanthrolin-2-one

[Formula 456]

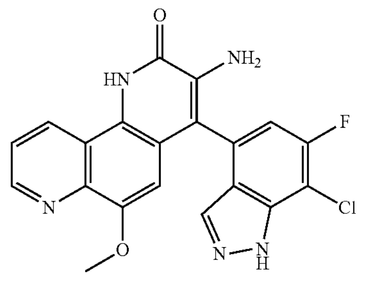

The title compound was synthesized from 3-amino-6-bromo-4-(7-chloro-6-fluoro-1H-indazol-4-yl)-1H-1,7-phenanthrolin-2-one (compound C75) under the same conditions as the production example of the compound c-108, except that NMP was used instead of 1,4-dioxane used in the production example of the compound c-108.

LCMS: m/z 410 $[M+H]^+$

HPLC retention time: 0.44 min (analysis condition A)

Compound c-143

3-Amino-6-bromo-4-[7-chloro-6-fluoro-2-(oxan-2-yl)indazol-4-yl]-1H-1,7-phenanthrolin-2-one

[Formula 457]

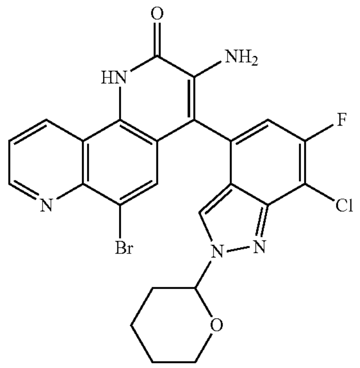

The title compound was synthesized from (5-amino-8-bromoquinolin-6-yl)-[7-chloro-6-fluoro-2-(oxan-2-yl)indazol-4-yl]methanone (compound c-131) under the same conditions as the production examples of the compounds c-9, c-10, and c-13.

LCMS: m/z 542 $[M+H]^+$

HPLC retention time: 0.78 min (analysis condition A)

Compound c-144

6-Bromo-4-[7-chloro-6-fluoro-2-(oxan-2-yl)indazol-4-yl]-2-[(4-methoxyphenyl)methoxy]-1,7-phenanthrolin-3-amine

[Formula 458]

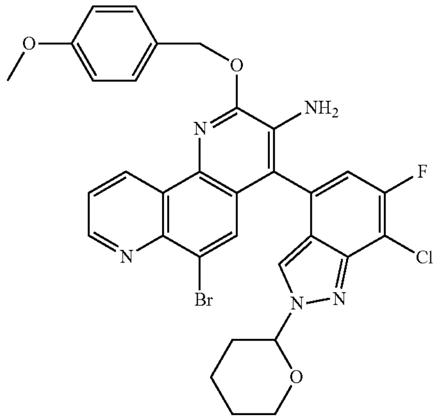

The title compound was synthesized from 3-amino-6-bromo-4-[7-chloro-6-fluoro-2-(oxan-2-yl)indazol-4-yl]-1H-1,7-phenanthrolin-2-one (compound c-143) under the same conditions as the production example of the compound c-14.

LCMS: m/z 662 $[M+H]^+$

HPLC retention time: 1.10 min (analysis condition A)

Compound c-145

3-Amino-4-[7-chloro-6-fluoro-2-(oxan-2-yl)indazol-4-yl]-2-[(4-methoxyphenyl)methoxy]-1,7-phenanthrolin-6-ol

[Formula 459]

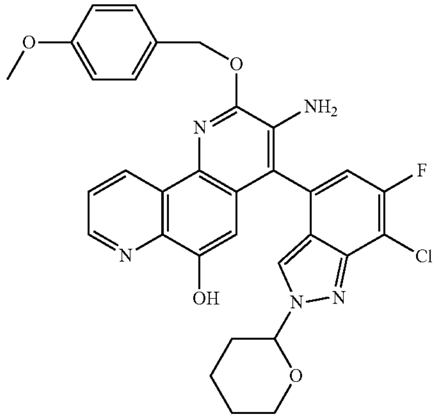

The title compound was synthesized from 6-bromo-4-[7-chloro-6-fluoro-2-(oxan-2-yl)indazol-4-yl]-2-[(4-methoxyphenyl)methoxy]-1,7-phenanthrolin-3-amine (compound c-144) under the same conditions as the production example of the compound c-15.

LCMS: m/z 601 $[M+H]^+$

HPLC retention time: 0.93 min (analysis condition A)

Compound C193

3-Amino-4-(7-chloro-6-fluoro-1H-indazol-4-yl)-6-ethoxy-1H-1,7-phenanthrolin-2-one

[Formula 460]

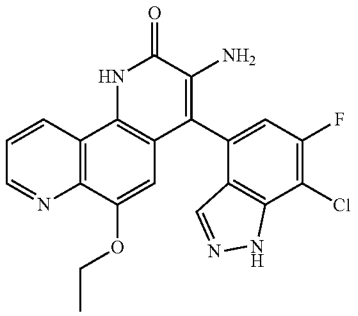

The title compound was synthesized from 3-amino-4-[7-chloro-6-fluoro-2-(oxan-2-yl)indazol-4-yl]-2-[(4-methoxyphenyl)methoxy]-1,7-phenanthrolin-6-ol (compound c-145) and a corresponding alcohol under the same conditions as the production examples of the compounds c-16 and C4, except that anisole was used instead of triethylsilane used in the production example of the compound C4.

LCMS: m/z 424 $[M+H]^+$

HPLC retention time: 0.47 min (analysis condition A)

Compound C194

3-Amino-4-(7-chloro-6-fluoro-1H-indazol-4-yl)-6-propan-2-yloxy-1H-1,7-phenanthrolin-2-one

[Formula 461]

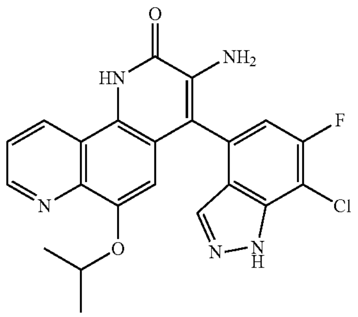

The title compound was synthesized from 3-amino-4-[7-chloro-6-fluoro-2-(oxan-2-yl)indazol-4-yl]-2-[(4-methoxyphenyl)methoxy]-1,7-phenanthrolin-6-ol (compound c-145) and a corresponding alcohol under the same conditions as the production examples of the compounds c-16 and C4, except that anisole was used instead of triethylsilane used in the production example of the compound C4.

LCMS: m/z 438 $[M+H]^+$

HPLC retention time: 0.48 min (analysis condition A)

Compound c-147

Methyl 1-(oxan-2-yl)pyrazolo[3,4-c]pyridine-4-carboxylate

[Formula 462]

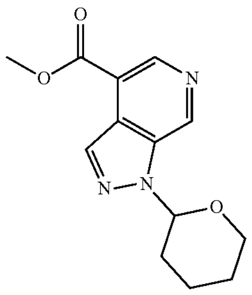

The title compound was synthesized from methyl 1H-pyrazolo[3,4-c]pyridine-4-carboxylate under the same conditions as the production example of the compound c-99, except that the reaction was carried out by heating the reaction mixture to 80° C. for 2 hours.

LCMS: m/z 262 $[M+H]^+$

HPLC retention time: 0.52 min (analysis condition A)

Compound c-148

1-(Oxan-2-yl)pyrazolo[3,4-c]pyridine-4-carboxylic acid

[Formula 463]

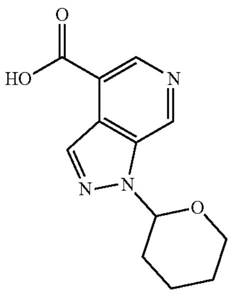

The title compound was synthesized from methyl 1-(oxan-2-yl)pyrazolo[3,4-c]pyridine-4-carboxylate (compound c-147) under the same conditions as the production example of the compound c-5, except that MeOH was used instead of THE used in the production example of the compound c-5, and the reaction was carried out by stirring the reaction mixture at room temperature for 1 hour.

LCMS: m/z 248 $[M+H]^+$

HPLC retention time: 0.34 min (analysis condition A)

Compound c-149

N-Methoxy-N-methyl-1-(oxan-2-yl)pyrazolo[3,4-c]pyridine-4-carboxamide

[Formula 464]

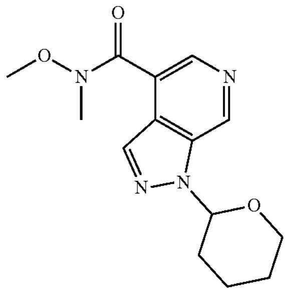

The title compound was synthesized from 1-(oxan-2-yl)pyrazolo[3,4-c]pyridine-4-carboxylic acid (compound c-148) under the same conditions as the production example of the compound b-2, except that triethylamine was used instead of DIPEA used in the production example of the compound b-2.

LCMS: m/z 291.5 $[M+H]^+$

HPLC retention time: 0.40 min (analysis condition A)

Compound c-150

(E)-N'-[8-bromo-6-[1-(oxan-2-yl)pyrazolo[3,4-c]pyridine-4-carbonyl]quinolin-5-yl]-N,N-dimethylmethanimidamide

[Formula 465]

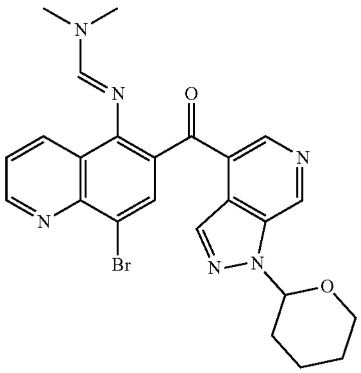

The title compound was synthesized from (E)-N'-(8-bromo-6-iodoquinolin-5-yl)-N,N-dimethylmethanimidamide (compound c-2) and N-methoxy-N-methyl-1-(oxan-2-yl)pyrazolo[3,4-c]pyridine-4-carboxamide (compound c-149) under the same conditions as the production example of the compound b-26.

LCMS: m/z 507.5 $[M+H]^+$

HPLC retention time: 0.55 min (analysis condition A)

Compound c-151

(5-Amino-8-bromoquinolin-6-yl)-[1-(oxan-2-yl)pyrazolo[3,4-c]pyridin-4-yl]methanone

[Formula 466]

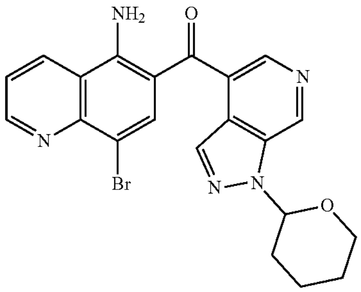

The title compound was synthesized from (E)-N'-[8-bromo-6-[1-(oxan-2-yl)pyrazolo[3,4-c]pyridine-4-carbonyl]quinolin-5-yl]-N,N-dimethylmethanimidamide (compound c-150) under the same conditions as the production example of the compound b-27.

LCMS: m/z 452 $[M+H]^+$

HPLC retention time: 0.59 min (analysis condition A)

Compound C80

3-Amino-6-bromo-4-(1H-pyrazolo[3,4-c]pyridin-4-yl)-1H-1,7-phenanthrolin-2-one

[Formula 467]

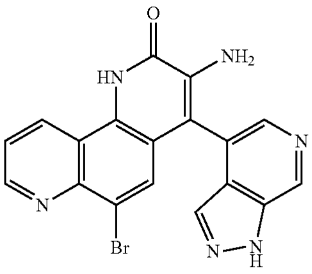

The title compound was synthesized from (5-amino-8-bromoquinolin-6-yl)-[1-(oxan-2-yl)pyrazolo[3,4-c]pyridin-4-yl]methanone (compound c-151) under the same conditions as the production examples of the compounds b-28, b-29, b-30, and b-9. DMSO was used instead of EtOH used in the production example of the compound b-9.

LCMS: m/z 407 $[M+H]^+$

HPLC retention time: 0.38 min (analysis condition A)

Compound c-156

N-methoxy-N-methyl-1H-pyrazolo[3,4-b]pyridine-4-carboxamide

[Formula 468]

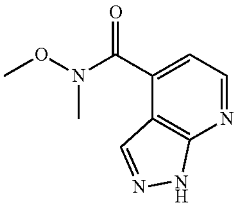

The title compound was synthesized from 1H-pyrazolo[3,4-b]pyridine-4-carboxylic acid under the same conditions as the production example of the compound b-2, except that triethylamine was used instead of DIPEA used in the production example of the compound b-2.

LCMS: m/z 207 $[M+H]^+$

HPLC retention time: 0.34 min (analysis condition A)

Compound c-157

N-methoxy-N-methyl-1-(oxan-2-yl)pyrazolo[3,4-b]pyridine-4-carboxamide

[Formula 469]

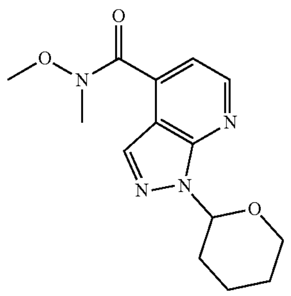

The title compound was synthesized from N-methoxy-N-methyl-1H-pyrazolo[3,4-b]pyridine-4-carboxamide (compound c-156) under the same conditions as the production example of the compound c-99, except that THF was used instead of DCM used in the production example of the compound c-99, and the reaction was carried out by heating the reaction mixture at 60° C. for 2 hours.

LCMS: m/z 292 $[M+H]^+$

HPLC retention time: 0.52 min (analysis condition A)

Compound c-158

(E)-N'-[8-bromo-6-[1-(oxan-2-yl)pyrazolo[3,4-b]pyridine-4-carbonyl]quinolin-5-yl]-N,N-dimethyl-methanimidamide

[Formula 470]

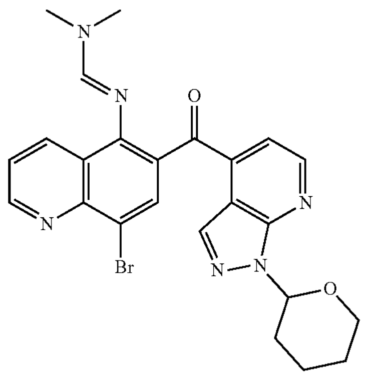

The title compound was synthesized from (E)-N'-(8-bromo-6-iodoquinolin-5-yl)-N,N-dimethylmethanimidamide (compound c-2) and N-methoxy-N-methyl-1-(oxan-2-yl)pyrazolo[3,4-b]pyridine-4-carboxamide (compound c-157) under the same conditions as the production example of the compound b-26.

LCMS: m/z 507.5 $[M+H]^+$

HPLC retention time: 0.71 min (analysis condition A)

Compound c-159

(5-Amino-8-bromoquinolin-6-yl)-[1-(oxan-2-yl)pyrazolo[3,4-b]pyridin-4-yl]methanone

[Formula 471]

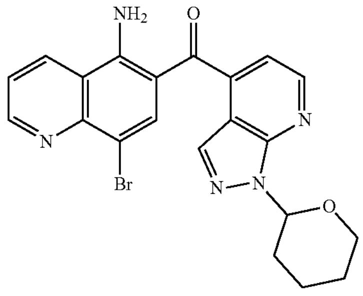

The title compound was synthesized from (E)-N'-[8-bromo-6-[1-(oxan-2-yl)pyrazolo[3,4-b]pyridine-4-carbonyl]quinolin-5-yl]-N,N-dimethylmethanimidamide (compound c-158) under the same conditions as the production example of the compound b-27.

LCMS: m/z 452 $[M+H]^+$

HPLC retention time: 0.73 min (analysis condition A)

Compound C81

3-Amino-6-bromo-4-(1H-pyrazolo[3,4-b]pyridin-4-yl)-1H-1,7-phenanthrolin-2-one

[Formula 472]

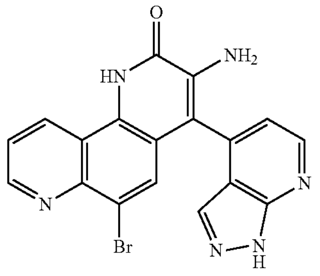

The title compound was synthesized from (5-amino-8-bromoquinolin-6-yl)-[1-(oxan-2-yl)pyrazolo[3,4-b]pyridin-4-yl]methanone (compound c-159) under the same conditions as the production examples of the compounds b-28, b-29, b-30, and b-9, except that DCM was used instead of DMA used in the production example of the compound b-28, and the reaction was carried out by adding pyridine. In addition, DMSO was used instead of EtOH used in the production example of the compound b-9.

LCMS: m/z 407 $[M+H]^+$

HPLC retention time: 0.47 min (analysis condition A)

Compound C82

3-Amino-6-cyclopropyl-4-(1H-pyrazolo[3,4-b]pyridin-4-yl)-1H-1,7-phenanthrolin-2-one

[Formula 473]

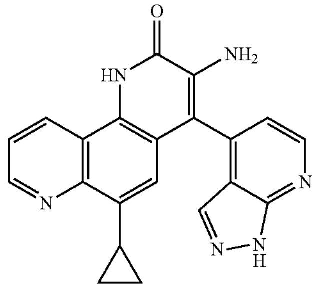

The title compound was synthesized from 3-amino-6-bromo-4-(1H-pyrazolo[3,4-b]pyridin-4-yl)-1H-1,7-phenanthrolin-2-one (compound C81) under the same conditions as the production example of the compound B22, except that XPhos Pd G4 was used instead of CPhos Pd G3 used in the production example of the compound B22.

LCMS: m/z 369.5 $[M+H]^+$

HPLC retention time: 0.40 min (analysis condition A)

Compound C84

3-Amino-6-cyclopropyl-4-(7-fluoro-1H-indazol-4-yl)-1H-1,7-phenanthrolin-2-one

[Formula 474]

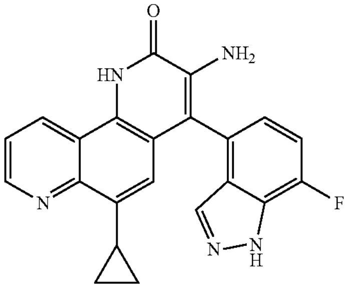

The title compound was synthesized from 3-amino-6-bromo-4-(7-fluoro-1H-indazol-4-yl)-1H-1,7-phenanthrolin-2-one (compound C1) under the same conditions as the production example of the compound B22.

LCMS: m/z 386 $[M+H]^+$

HPLC retention time: 0.49 min (analysis condition A)

Compound c-259

(5-Amino-8-cyclopropylquinolin-6-yl)-[7-fluoro-2-(oxan-2-yl)indazol-4-yl]methanone

[Formula 475]

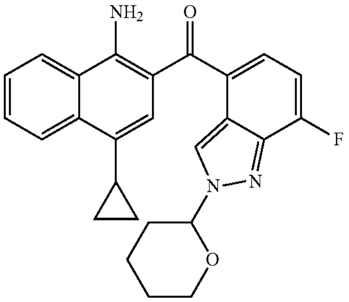

A solution of (5-amino-8-bromoquinolin-6-yl)-[7-fluoro-2-(oxan-2-yl)indazol-4-yl]methanone (compound c-8, 15 g, 32 mmol) in DMA (128 mL) in a reaction vessel was degassed under reduced pressure and subjected to nitrogen replacement, and then XPhos Pd G4 (0.825 g, 0.959 mmol) was added thereto. To the mixture, a 0.5 M solution of cyclopropylzinc bromide in THF (211 mL, 105 mmol) was added, and the mixture was stirred at room temperature under nitrogen atmosphere for 45 min. The reaction mixture was combined with that of another lot, then a saturated aqueous ammonium chloride solution was added thereto, and the mixture was extracted with ethyl acetate. The organic layer was washed with an aqueous saturated sodium chloride solution and then dried over anhydrous sodium sulfate, the drying agent was filtered off, and then the filtrate was concentrated under reduced pressure. The obtained residue was purified by silica gel column chromatography (hexane/ethyl acetate) to obtain the title compound (20.1 g) as an orange solid.

LCMS: m/z 431 $[M+H]^+$

HPLC retention time: 0.94 min (analysis condition F)

Compound c-260

2-Chloro-N-[8-cyclopropyl-6-[7-fluoro-2-(oxan-2-yl)indazole-4-carbonyl]quinolin-5-yl]acetamide

[Formula 476]

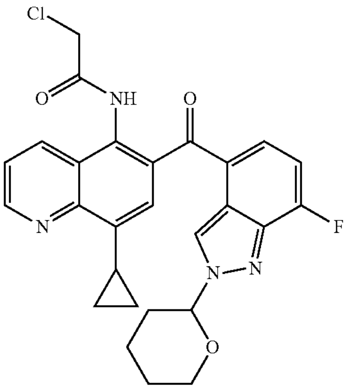

A solution of (5-amino-8-cyclopropylquinolin-6-yl)-[7-fluoro-2-(oxan-2-yl)indazol-4-yl]methanone (compound c-259, 19.52 g, 45.3 mmol) in DCM (302 mL) in a reaction vessel was cooled to 0° C., then chloroacetyl chloride (6.14 mL, 77 mmol) and pyridine (7.31 mL, 91 mmol) were added thereto, and the mixture was stirred at 0° C. under nitrogen atmosphere for 1 hour. The reaction mixture was concentrated under reduced pressure to obtain the crude product of the title compound.

LCMS: m/z 507 $[M+H]^+$

HPLC retention time: 1.10 min (analysis condition F)

Compound c-261

6-Cyclopropyl-4-[7-fluoro-2-(oxan-2-yl)indazol-4-yl]-3-pyridin-1-ium-1-yl-1H-1,7-phenanthrolin-2-one; chloride

[Formula 477]

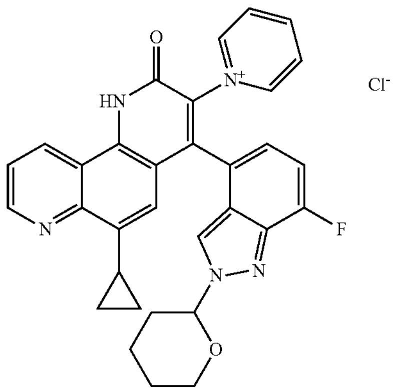

To the crude product of 2-chloro-N-[8-cyclopropyl-6-[7-fluoro-2-(oxan-2-yl)indazole-4-carbonyl]quinolin-5-yl]acetamide (compound c-260) in a reaction vessel, pyridine (230 mL) was added, and the mixture was stirred at 80° C. for 1 hour. The reaction mixture was cooled to room temperature to obtain a solution of the title compound in pyridine.

LCMS: m/z 532 $[M]^+$

HPLC retention time: 0.79 min (analysis condition F)

Compound c-262

6-Cyclopropyl-4-(7-fluoro-1H-indazol-4-yl)-3-pyridin-1-ium-1-yl-1H-1,7-phenanthrolin-2-one; chloride

[Formula 478]

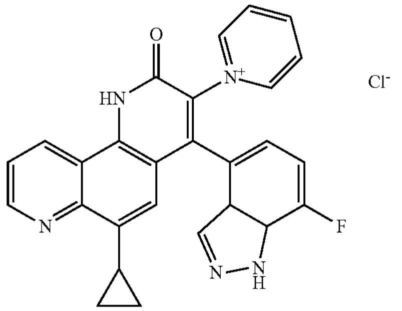

To the solution of 6-cyclopropyl-4-[7-fluoro-2-(oxan-2-yl)indazol-4-yl]-3-pyridin-1-ium-1-yl-1H-1,7-phenanthrolin-2-one; chloride (compound c-261) in pyridine in a reaction vessel, 12 M hydrochloric acid (38.9 mL, 453 mmol) was added, and the mixture was stirred at 80° C. for 8 hours. The reaction mixture was cooled to room temperature, and acetonitrile (257 mL) was added thereto. The solid was collected by filtration and then washed three times with acetonitrile (257 mL) to obtain the title compound (19.18 g, yield 87%).

LCMS: m/z 448 $[M]^+$

HPLC retention time: 0.66 min (analysis condition F)

Compound C84

3-Amino-6-cyclopropyl-4-(7-fluoro-1H-indazol-4-yl)-1H-1,7-phenanthrolin-2-one

[Formula 479]

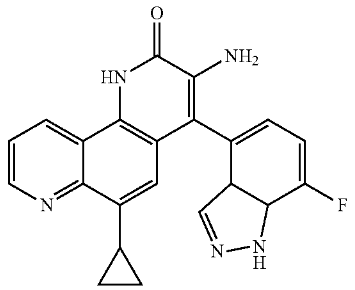

To 6-cyclopropyl-4-(7-fluoro-1H-indazol-4-yl)-3-pyridin-1-ium-1-yl-1H-1,7-phenanthrolin-2-one; chloride (compound c-262, 19.18 g, 39.6 mmol) in a reaction vessel, DMSO (189 mL) and hydrazine monohydrate (19.64 mL, 396 mmol) were added, and the mixture was heated at 80° C. for 1 hour. The reaction mixture was cooled to room temperature, and water (253 mL) was added thereto. The solid was collected by filtration and washed twice with water (200 mL) to obtain the title compound (11.63 g, yield 76%).

LCMS: m/z 386 $[M+H]^+$

HPLC retention time: 0.49 min (analysis condition A)

Compound C85

3-Amino-4-(7-fluoro-1H-inadazol-4-yl)-6-methyl-1H-1,7-phenanthrolin-2-one

[Formula 480]

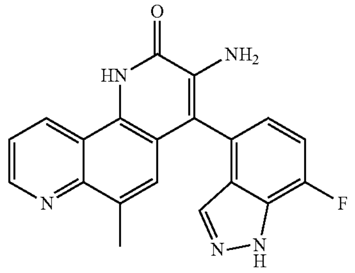

The title compound was synthesized from 3-amino-6-bromo-4-(7-fluoro-1H-indazol-4-yl)-1H-1,7-phenanthrolin- 2-one (compound C1) under the same conditions as the production example of the compound B22, except that a 2 M solution of methylzincchloride in THF was used instead of the 0.5 M solution of cyclopropylzinc bromide in THE used in the production example of the compound B22.

LCMS: m/z 360 $[M+H]^+$

HPLC retention time: 0.48 min (analysis condition A)

Compound c-255

(5-Amino-8-methylquinolin-6-yl)-[7-fluoro-2-(oxan-2-yl)indazol-4-yl]methanone

[Formula 481]

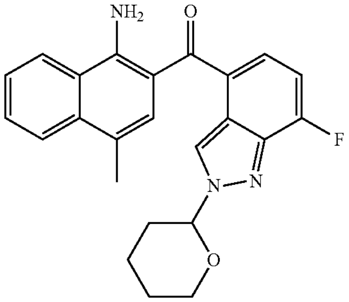

To (5-amino-8-bromoquinolin-6-yl)-[7-fluoro-2-(oxan-2-yl)indazol-4-yl]methanone (compound c-8, 10 g, 21.31 mmol) and XPhos Pd G4 (0.55 g, 0.639 mmol) in a reaction vessel, DMA (107 mL) was added, the reaction vessel was degassed under reduced pressure and subjected to nitrogen replacement, then a 2 M solution of methylzinc chloride in THF (42.6 mL, 85 mmol) was added thereto, and the mixture was stirred at room temperature for 1 hour. The reaction mixture was cooled to 0° C., water (100 mL), a saturated aqueous ammonium chloride solution (200 mL), and ethyl acetate (400 mL) were added thereto, the mixture was filtered using Celite, and then the organic layer was separated. The organic layer was washed with an aqueous saturated sodium chloride solution (50 mL) and then dried over anhydrous magnesium sulfate, the drying agent was filtered off, and then the filtrate was concentrated under reduced (hexane/ethyl acetate) to obtain the title compound (8.4 g, yield 97%) as an orange solid.

LCMS: m/z 405 $[M+H]^+$

HPLC retention time: 0.96 min (analysis condition F)

Compound c-256

2-Chloro-N-[6-[7-fluoro-2-(oxan-2-yl)indazole-4-carbonyl]-8-methylquinolin-5-yl]acetamide

[Formula 482]

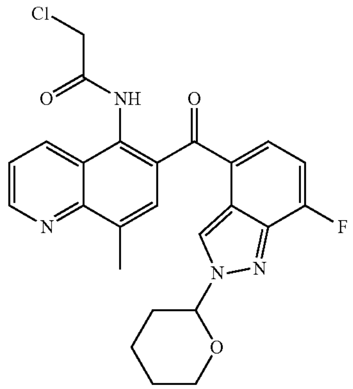

Into a reaction vessel, a solution of (5-amino-8-methylquinolin-6-yl)-[7-fluoro-2-(oxan-2-yl)indazol-4-yl]methanone (compound c-255, 8.4 g, 20.77 mmol) in DMA (69.2 mL) was added, and the reaction vessel was degassed under reduced pressure and subjected to nitrogen replacement, the reaction solution was cooled to 0° C., then N,N-dimethylaniline (15.73 mL, 125 mmol) and chloroacetyl chloride (3.3 mL, 41.5 mmol) were added thereto, and the mixture was stirred at room temperature for 30 min to obtain a solution of the title compound in DMA.

LCMS: m/z 481 $[M+H]^+$

HPLC retention time: 1.04 min (analysis condition F)

Compound c-257

4-[7-Fluoro-2-(oxan-2-yl)indazol-4-yl]-6-methyl-3-pyridin-1-ium-1-yl-1H-1,7-phenanthrolin-2-one; chloride

[Formula 483]

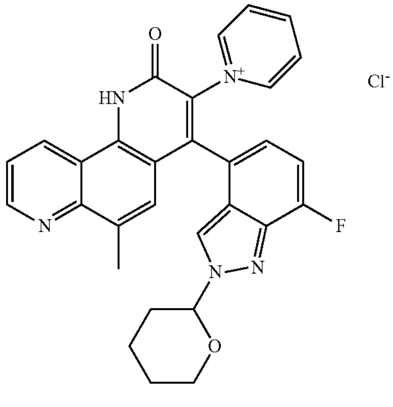

To a solution of 2-chloro-N-[6-[7-fluoro-2-(oxan-2-yl)indazole-4-carbonyl]-8-methylquinolin-5-yl]acetamide (compound c-256) in DMA in a reaction vessel, pyridine (78 mL) was added, and the mixture was stirred at 60° C. for 7 hours. The reaction mixture was cooled to room temperature to obtain a solution of the title compound in DMA/pyridine.

LCMS: m/z 506 $[M]^+$

HPLC retention time: 0.77 min (analysis condition F)

Compound c-258

3-Amino-4-[7-fluoro-2-(oxan-2-yl)indazol-4-yl]-6-methyl-1H-1,7-phenanthrolin-2-one

[Formula 484]

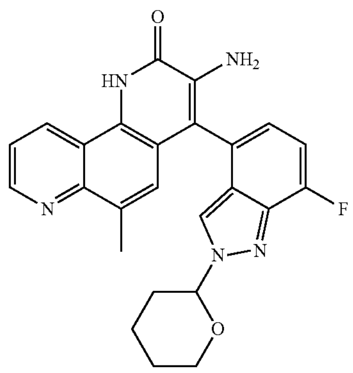

To a solution of the compound c-257 in DMA/pyridine, hydrazine monohydrate (10.1 mL, 208 mmol) was added, and the mixture was stirred at 60° C. under nitrogen atmosphere for 2 hours. The reaction mixture was cooled to room temperature, water (165 mL) was added thereto, and the mixture was further stirred for 30 min. The solid was collected by filtration and washed with EtOH/water (1/1, 56 mL) to obtain the title compound (compound c-258, 9.5 g).

LCMS: m/z 444 $[M+H]^+$

HPLC retention time: 0.87 min (analysis condition F)

Compound C85

[Formula 485]

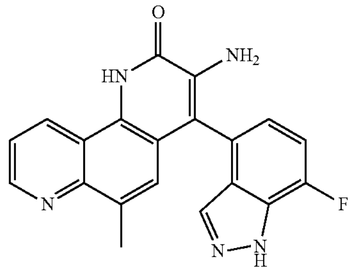

To a solution of 3-amino-4-[7-fluoro-2-(oxan-2-yl)indazol-4-yl]-6-methyl-1H-1,7-phenanthrolin-2-one (compound c-258, 11.56 g, 26.1 mmol) in TFE (116 mL) in a reaction vessel, triethylsilane (8.33 mL, 52.1 mmol) was added, the reaction solution was cooled to 0° C., then trimethylsilyl chloride (9.99 mL, 78 mmol) was added thereto, and the mixture was stirred at room temperature for 30 min. The reaction mixture was combined with that of another lot, a saturated aqueous sodium bicarbonate solution (240 mL) was added thereto, and the mixture was stirred at room temperature for 30 min. The solid was collected by filtration and washed with water (60 mL) and acetonitrile/water (1/4, 60 mL). The obtained solid was suspended in acetonitrile (120 mL), and the mixture was stirred at room temperature for 30 min. The solid was collected by filtration, and washed with acetonitrile (60 mL). The obtained solid was combined with that of another lot, the solids were suspended in acetonitrile (260 mL), and the mixture was stirred at room temperature for 30 min. The solid was collected by filtration, and washed with acetonitrile (65 mL). The obtained solid was dissolved in DMSO (39 mL), a 9% aqueous sodium bicarbonate solution (13 mL) and water (13 mL) were added thereto, and the mixture was stirred at room temperature for 30 min. The solid was collected by filtration, washed twice with water (65 mL), and then dried to obtain the title compound (8.69 g).

LCMS: m/z 360 $[M+H]^+$

HPLC retention time: 0.48 min (analysis condition A)

Compound C86

3-Amino-6-ethyl-4-(7-fluoro-1H-indazol-4-yl)-1H-1,7-phenanthrolin-2-one

[Formula 484]

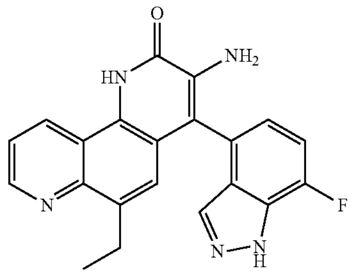

The title compound was synthesized from 3-amino-6-bromo-4-(7-fluoro-1H-indazol-4-yl)-1H-1,7-phenanthrolin-2-one (compound C1) under the same conditions as the production example of the compound B22, except that a 1 M solution of diethylzinc in hexane was used instead of the 0.5 M solution of cyclopropylzinc bromide in THE used in the production example of the compound B22.

LCMS: m/z 374 $[M+H]^+$

HPLC retention time: 0.54 min (analysis condition A)

Compound C91

3-Amino-6-cyclobutyl-4-(7-fluoro-1H-indazol-4-yl)-1H-1,7-phenanthrolin-2-one

[Formula 487]

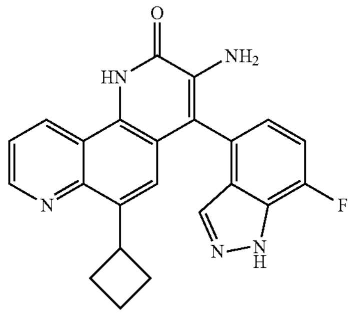

The title compound was synthesized from 3-amino-6-bromo-4-(7-fluoro-1H-indazol-4-yl)-1H-1,7-phenanthrolin- 2-one (compound C1) under the same conditions as the production example of the compound B22, except that a 0.5 M solution of cyclobutylzinc bromide in THF was used instead of the 0.5 M solution of cyclopropylzinc bromide in THF used in the production example of the compound B22.

LCMS: m/z 400 [M+H]+

HPLC retention time: 0.62 min (analysis condition A)

Compound C92

3-Amino-6-cyclopentyl-4-(7-fluoro-1H-indazol-4-yl)-1H-1,7-phenanthrolin-2-one

[Formula 488]

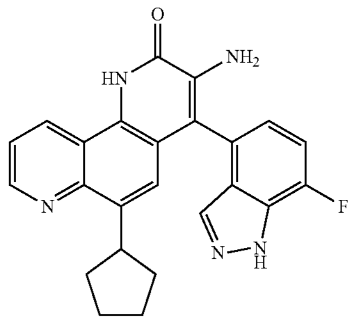

The title compound was synthesized from 3-amino-6-bromo-4-(7-fluoro-1H-indazol-4-yl)-1H-1,7-phenanthrolin-2-one (compound C1) under the same conditions as the production example of the compound B22, except that a 0.5 M solution of cyclopentylzinc bromide in THF was used instead of the 0.5 M solution of cyclopropylzinc bromide in THF used in the production example of the compound B22.

LCMS: m/z 414 [M+H]+

HPLC retention time: 0.67 min (analysis condition A)

Compound C96

3-Amino-4-(7-fluoro-1H-indazol-4-yl)-6-(oxolan-2-yl)-1H-1,7-phenanthrolin-2-one

[Formula 489]

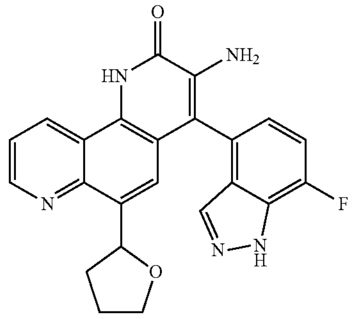

The title compound was synthesized from 3-amino-6-bromo-4-(7-fluoro-1H-indazol-4-yl)-1H-1,7-phenanthrolin-2-one (compound C1) under the same conditions as the production example of the compound B22, except that XPhos Pd G4 was used instead of CPhos Pd G3 used in the production example of the compound B22.

LCMS: m/z 416 [M+H]+

HPLC retention time: 0.59 min (analysis condition A)

Compound C97 tert-Butyl 3-[3-amino-4-(7-fluoro-1H-indazol-4-yl)-2-oxo-1H-1,7-phenanthrolin-6-yl]azetidine-1-carboxylate

[Formula 490]

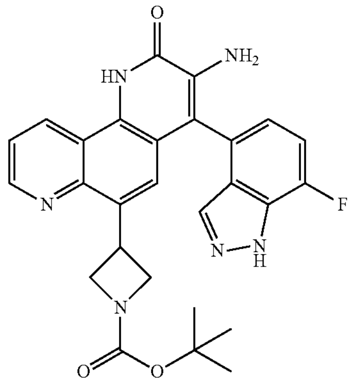

The title compound was synthesized from 3-amino-6-bromo-4-(7-fluoro-1H-indazol-4-yl)-1H-1,7-phenanthrolin-2-one (compound C1) under the same conditions as the production example of the compound B22, except that XPhos Pd G4 and a solution of 1-tert-butoxycarbonylazetidin-3-ylzinc iodide in DMA were respectively used instead of CPhos Pd G3 and the 0.5 M solution of cyclopropylzinc bromide in THE used in the production example of the compound B22.

LCMS: m/z 501.5 [M+H]+

HPLC retention time: 0.68 min (analysis condition A)

Compound C98

3-Amino-4-(7-fluoro-1H-indazol-4-yl)-6-(oxan-4-yl)-1H-1,7-phenanthrolin-2-one

[Formula 491]

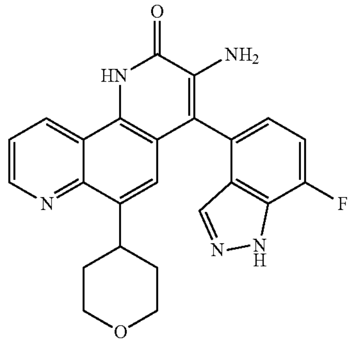

The title compound was synthesized from 3-amino-6-bromo-4-(7-fluoro-1H-indazol-4-yl)-1H-1,7-phenanthrolin-2-one (compound C1) under the same conditions as the production example of the compound B22, except that tris(dibenzylideneacetone)dipalladium(0)-chloroform adduct and a solution of 2-dicyclohexylphosphino-2',4',6'- triisopropylbiphenyl and (tetrahydropyran-4-yl) zinc iodide in DMA were respectively used instead of CPhos Pd G3 and the 0.5 M solution of cyclopropylzinc bromide in THE used in the production example of the compound B22, and the reaction was carried out by heating the reaction solution to 80° C.

LCMS: m/z 430.6 $[M+H]^+$

HPLC retention time: 0.53 min (analysis condition A)

Compound C99 tert-Butyl 4-[3-amino-4-(7-fluoro-1H-indazol-4-yl)-2-oxo-1H-1,7-phenanthrolin-6-yl]piperidine-1-carboxylate

[Formula 492]

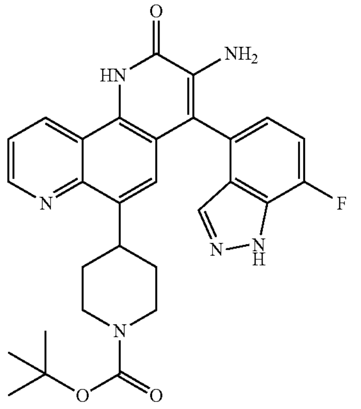

The title compound was synthesized from 3-amino-6-bromo-4-(7-fluoro-1H-indazol-4-yl)-1H-1,7-phenanthrolin-2-one (compound C1) under the same conditions as the production example of the compound B22, except that XPhos Pd G4 and a solution of [1-(tert-butoxycarbonyl) piperidin-4-yl]zinc iodide in DMA were respectively used instead of CPhos Pd G3 and the 0.5 M solution of cyclopropylzinc bromide in THF used in the production example of the compound B22.

LCMS: m/z 529.6 $[M+H]^+$

HPLC retention time: 0.71 min (analysis condition A)

Compound C100

3-Amino-4-(7-fluoro-1H-indazol-4-yl)-6-[(E)-4-hydroxybut-1-enyl]-1H-1,7-phenanthrolin-2-one

[Formula 493]

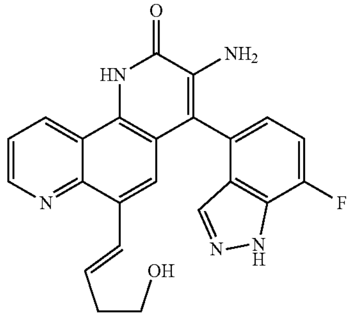

The title compound was synthesized from 3-amino-6-bromo-4-(7-fluoro-1H-indazol-4-yl)-1H-1,7-phenanthrolin-2-one (compound C1) under the same conditions as the production example of the compound B22, except that XPhos Pd G4 and a solution of (tetrahydrofuran-3-yl) zinc iodide in DMA were respectively used instead of CPhos Pd G3 and the 0.5 M solution of cyclopropylzinc bromide in THE used in the production example of the compound B22.

LCMS: m/z 416.5 $[M+H]^+$

HPLC retention time: 0.43 min (analysis condition A)

Compound C101

3-Amino-6-(1,4-dioxaspiro[4.5]decan-8-yl)-4-(7-fluoro-1H-indazol-4-yl)-1H-1,7-phenanthrolin-2-one 2,2,2-trifluoroacetate

[Formula 494]

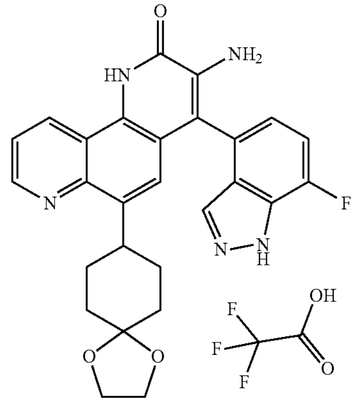

The title compound was synthesized from 3-amino-6-bromo-4-(7-fluoro-1H-indazol-4-yl)-1H-1,7-phenanthrolin-2-one (compound C1) under the same conditions as the production example of the compound B22, except that XPhos Pd G4 and (1,4-dioxaspiro[4.5]decan-8-yl) zinc iodide were used instead of CPhos Pd G3 and the 0.5 M solution of cyclopropylzinc bromide in THE used in the production example of the compound B22. In addition, the reaction was carried out by heating the reaction solution to 80° C.

LCMS: m/z 486 $[M+H]^+$

HPLC retention time: 0.56 min (analysis condition A)

Compound C104

3-Amino-4-(7-fluoro-1H-indazol-4-yl)-6-propan-2-yl-1H-1,7-phenanthrolin-2-one

[Formula 495]

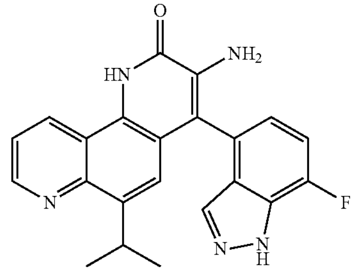

The title compound was synthesized from 3-amino-6-bromo-4-(7-fluoro-1H-indazol-4-yl)-1H-1,7-phenanthrolin-2-one (compound C1) under the same conditions as the production example of the compound B22. Xantphos Pd G4 and a 0.5 M solution of 2-propylzincbromide in THF were used instead of CPhos Pd G3 and the 0.5 M solution of cyclopropylzinc bromide in THF used in the production example of the compound B22.

LCMS: m/z 388.5 $[M+H]^+$

HPLC retention time: 0.59 min (analysis condition A)

Compound C105

3-Amino-4-(7-fluoro-1H-indazol-4-yl)-6-(2-methyl-propyl)-1H-1,7-phenanthrolin-2-one

[Formula 496]

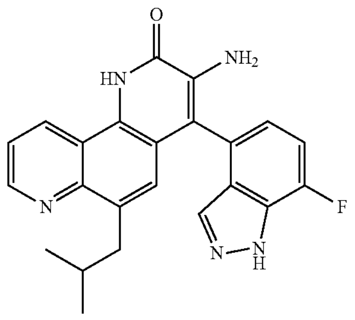

The title compound was synthesized from 3-amino-6-bromo-4-(7-fluoro-1H-indazol-4-yl)-1H-1,7-phenanthrolin-2-one (compound C1) under the same conditions as the production example of the compound B22, except that XPhos Pd G4 and a 0.5 M solution of 2-methylpropylzinc bromide in THF were respectively used instead of CPhos Pd G3 and the 0.5 M solution of cyclopropylzinc bromide in THE used in the production example of the compound B22.

LCMS: m/z 402.5 $[M+H]^+$

HPLC retention time: 0.64 min (analysis condition A)

Compound C106

3-Amino-4-(7-fluoro-1H-indazol-4-yl)-6-propyl-1H-1,7-phenanthrolin-2-one

[Formula 497]

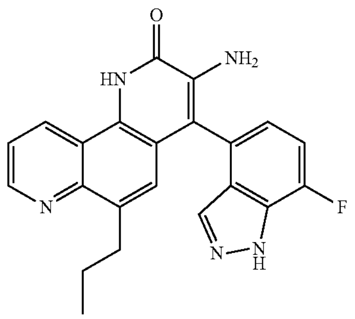

The title compound was synthesized from 3-amino-6-bromo-4-(7-fluoro-1H-indazol-4-yl)-1H-1,7-phenanthrolin-2-one (compound C1) under the same conditions as the production example of the compound B22, except that XPhos Pd G4 and a 0.5 M solution of propylzinc bromide in THF were respectively used instead of CPhos Pd G3 and the 0.5 M solution of cyclopropylzinc bromide in THE used in the production example of the compound B22.

LCMS: m/z 388.5 $[M+H]^+$

HPLC retention time: 0.57 min (analysis condition A)

Compound C107

3-Amino-4-(7-fluoro-1H-indazol-4-yl)-6-(3-methyl-butyl)-1H-1,7-phenanthrolin-2-one

[Formula 498]

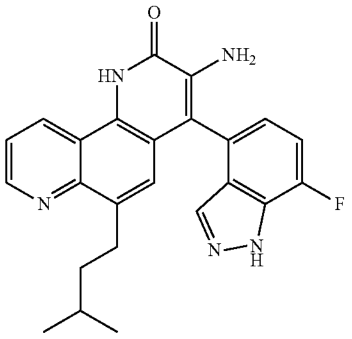

The title compound was synthesized from 3-amino-6-bromo-4-(7-fluoro-1H-indazol-4-yl)-1H-1,7-phenanthrolin-2-one (compound C1) under the same conditions as the production example of the compound B22, except that XPhos Pd G4 and a 0.5 M solution of 3-methylbutylzinc bromide in THF were respectively used instead of CPhos Pd G3 and the 0.5 M solution of cyclopropylzinc bromide in THE used in the production example of the compound B22.

LCMS: m/z 416.5 $[M+H]^+$

HPLC retention time: 0.70 min (analysis condition A)

Compound C108

3-Amino-4-(7-fluoro-1H-indazol-4-yl)-6-pentan-3-yl-1H-1,7-phenanthrolin-2-one

[Formula 499]

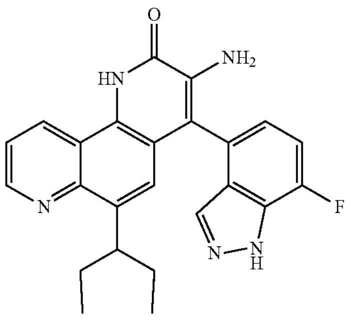

The title compound was synthesized from 3-amino-6-bromo-4-(7-fluoro-1H-indazol-4-yl)-1H-1,7-phenanthrolin-2-one (compound C1) under the same conditions as the production example of the compound B22, Xantphos Pd G4 and a 0.5 M solution of 1-ethylpropylzinc bromide in THF were used instead of CPhos Pd G3 and the 0.5 M solution of cyclopropylzinc bromide in THE used in the production example of the compound B22.

LCMS: m/z 416.5 $[M+H]^+$

HPLC retention time: 0.69 min (analysis condition A)

Compound C109

3-Amino-6-butan-2-yl-4-(7-fluoro-1H-indazol-4-yl)-1H-1,7-phenanthrolin-2-one

[Formula 500]

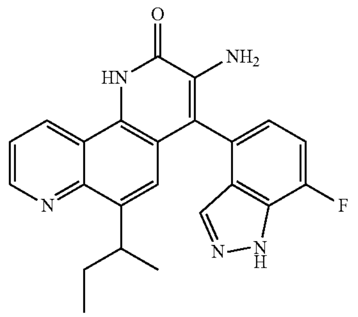

The title compound was synthesized from 3-amino-6-bromo-4-(7-fluoro-1H-indazol-4-yl)-1H-1,7-phenanthrolin-2-one (compound C1) under the same conditions as the production example of the compound B22, Xantphos Pd G4 and a 0.5 M solution of sec-butylzinc bromide in THF were used instead of CPhos Pd G3 and the 0.5 M solution of cyclopropylzinc bromide in THF used in the production example of the compound B22.

LCMS: m/z 402.5 $[M+H]^+$

HPLC retention time: 0.64 min (analysis condition A)

Compound C114

3-Amino-4-(7-fluoro-1H-indazol-4-yl)-6-(4-methylpiperazin-1-yl)-1H-1,7-phenanthrolin-2-one

[Formula 501]

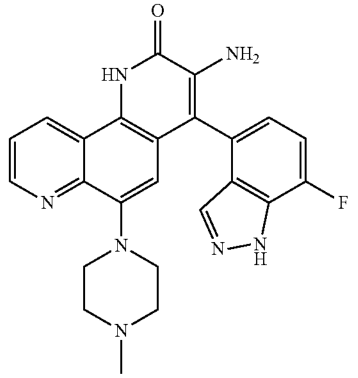

To a solution of 3-amino-6-bromo-4-(7-fluoro-1H-indazol-4-yl)-1H-1,7-phenanthrolin-2-one (compound C1, 20 mg, 0.047 mmol), copper (I) iodide (8.98 mg, 0.047 mmol), tripotassium phosphate (30 mg, 0.141 mmol), and [(2,6-dimethylphenyl)amino](oxo)acetic acid (18.22 mg, 0.094 mmol) in DMSO (471 μL) in a reaction vessel, 1-methylpiperazine (15.74 μL, 0.141 mmol) was added, the reaction vessel was degassed under reduced pressure and subjected to nitrogen replacement, and then the mixture was heated at 110° C. for 18 hours. The reaction mixture was purified by reversed phase column chromatography (10 mM aqueous ammonium hydrogencarbonate solution/MeOH) to obtain the title compound (3.6 mg, yield 17%) as a pale yellow solid.

LCMS: m/z 444.6 $[M+H]^+$

HPLC retention time: 0.31 min (analysis condition A)

Compound C113

3-Amino-4-(7-fluoro-1H-indazol-4-yl)-6-pyrrolidin-1-yl-1H-1,7-phenanthrolin-2-one

[Formula 502]

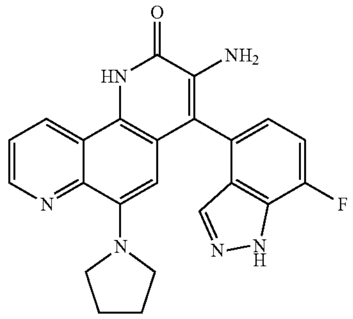

The title compound was synthesized from 3-amino-6-bromo-4-(7-fluoro-1H-indazol-4-yl)-1H-1,7-phenanthrolin-2-one (compound C1) and a corresponding amine under the same conditions as the production example of the compound C114.

LCMS: m/z 415.6 $[M+H]^+$

HPLC retention time: 0.42 min (analysis condition A)

Compound C115

3-Amino-6-(3,3-difluoropyrrolidin-1-yl)-4-(7-fluoro-1H-indazol-4-yl)-1H-1,7-phenanthrolin-2-one

[Formula 503]

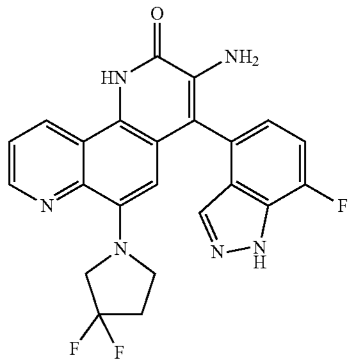

The title compound was synthesized from 3-amino-6-bromo-4-(7-fluoro-1H-indazol-4-yl)-1H-1,7-phenanthrolin-2-one (compound C1) and a corresponding amine under the same conditions as the production example of the compound C114.

LCMS: m/z 451.5 [M+H]+

HPLC retention time: 0.64 min (analysis condition A)

Compound C116

3-Amino-4-(7-fluoro-1H-indazol-4-yl)-6-(3-hydroxypyrrolidin-1-yl)-1H-1,7-phenanthrolin-2-one

[Formula 504]

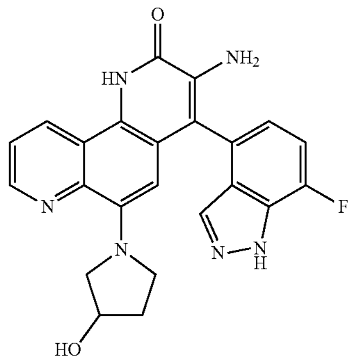

The title compound was synthesized from 3-amino-6-bromo-4-(7-fluoro-1H-indazol-4-yl)-1H-1,7-phenanthrolin-2-one (compound C1) and a corresponding amine under the same conditions as the production example of the compound C114.

LCMS: m/z 431.6 [M+H]+

HPLC retention time: 0.38 min (analysis condition A)

Compound C117

3-Amino-4-(7-fluoro-1H-indazol-4-yl)-6-(4-morpholin-4-ylpiperidin-1-yl)-1H-1,7-one

[Formula 505]

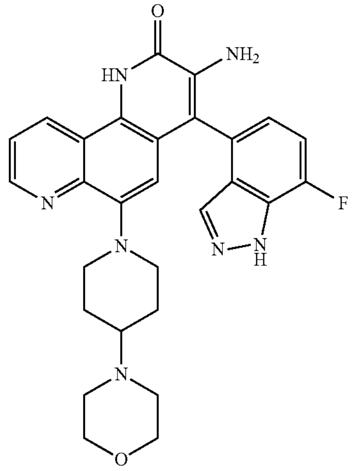

The title compound was synthesized from 3-amino-6-bromo-4-(7-fluoro-1H-indazol-4-yl)-1H-1,7-phenanthrolin-2-one (compound C1) and a corresponding amine under the same conditions as the production example of the compound C114.

LCMS: m/z 514.6 [M+H]+

HPLC retention time: 0.34 min (analysis condition A)

Compound C118

3-Amino-4-(7-fluoro-1H-indazol-4-yl)-6-(2-oxa-6-azaspiro[3,3]heptan-6-yl)-1H-1,7-one

[Formula 506]

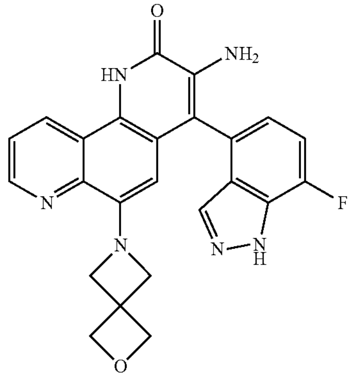

The title compound was synthesized from 3-amino-6-bromo-4-(7-fluoro-1H-indazol-4-yl)-1H-1,7-phenanthrolin-2-one (compound C1) and a corresponding amine under the same conditions as the production example of the compound C114.

LCMS: m/z 443.5 [M+H]+

HPLC retention time: 0.52 min (analysis condition A)

Compound C119

3-Amino-4-(7-fluoro-1H-indazol-4-yl)-6-(4-pyrrolidin-1-ylpiperidin-1-yl)-1H-1,7-phenanthrolin-2-one

[Formula 507]

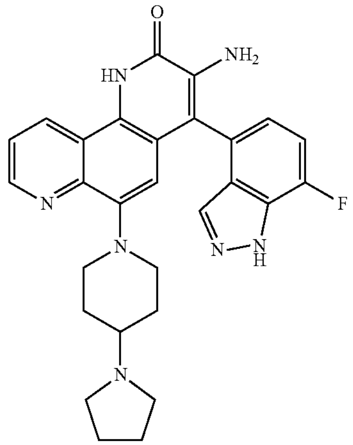

The title compound was synthesized from 3-amino-6-bromo-4-(7-fluoro-1H-indazol-4-yl)-1H-1,7-phenanthrolin-2-one (compound C1) and a corresponding amine under the same conditions as the production example of the compound C114.

LCMS: m/z 498.6 [M+H]+

HPLC retention time: 0.35 min (analysis condition A)

Compound C120

3-Amino-4-(7-fluoro-1H-indazol-4-yl)-6-(2-oxa-7-azaspiro[3.4]octan-7-yl)-1H-1,7-one

[Formula 508]

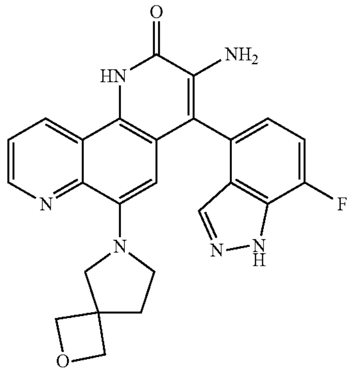

The title compound was synthesized from 3-amino-6-bromo-4-(7-fluoro-1H-indazol-4-yl)-1H-1,7-phenanthrolin-2-one (compound C1) and a corresponding amine under the same conditions as the production example of the compound C114.

LCMS: m/z 457.6 $[M+H]^+$

HPLC retention time: 0.44 min (analysis condition A)

Compound C121

3-Amino-6-(azetidin-1-yl)-4-(7-fluoro-1H-indazol-4-yl)-1H-1,7-phenanthrolin-2-one

[Formula 509]

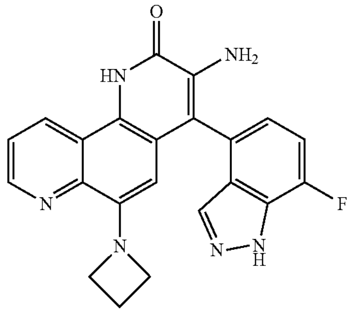

The title compound was synthesized from 3-amino-6-bromo-4-(7-fluoro-1H-indazol-4-yl)-1H-1,7-phenanthrolin-2-one (compound C1) and a corresponding amine under the same conditions as the production example of the compound C114.

LCMS: m/z 401.5 $[M+H]^+$

HPLC retention time: 0.45 min (analysis condition A)

Compound C122

3-Amino-4-(7-fluoro-1H-indazol-4-yl)-6-morpholin-4-yl-1H-1,7-phenanthrolin-2-one 2,2,2-trifluoroacetate

[Formula 510]

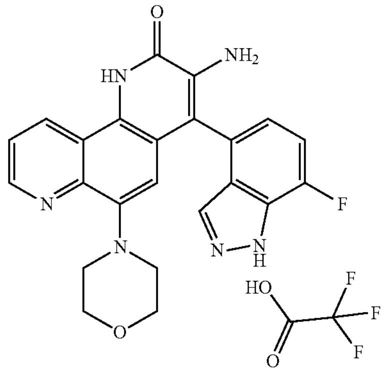

The title compound was synthesized from 3-amino-6-bromo-4-(7-fluoro-1H-indazol-4-yl)-1H-1,7-phenanthrolin-2-one (compound C1) and a corresponding amine under the same conditions as the production example of the compound C114.

LCMS: m/z 431 $[M+H]^+$

HPLC retention time: 0.39 min (analysis condition A)

Compound C123

3-Amino-6-(3,3-difluoroazetidin-1-yl)-4-(7-fluoro-1H-indazol-4-yl)-1H-1,7-phenanthrolin-2-one

[Formula 511]

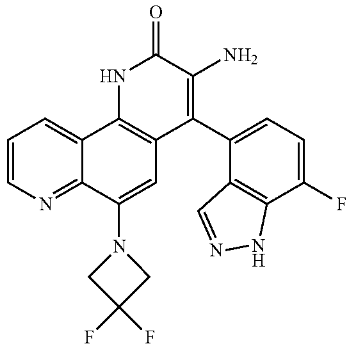

The title compound was synthesized from 3-amino-6-bromo-4-(7-fluoro-1H-indazol-4-yl)-1H-1,7-phenanthrolin-2-one (compound C1) and a corresponding amine under the same conditions as the production example of the compound C114.

LCMS: m/z 437.5 $[M+H]^+$

HPLC retention time: 0.67 min (analysis condition A)

Compound C124

3-Amino-6-(1,1-dioxo-1,4-thiazinan-4-yl)-4-(7-fluoro-1H-indazol-4-yl)-1H-1,7-phenanthrolin-2-one

[Formula 512]

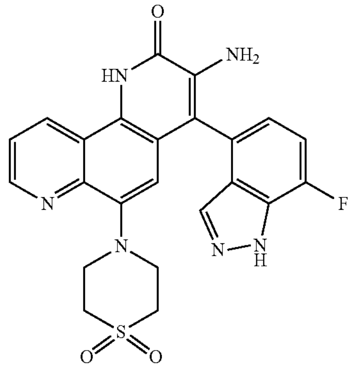

The title compound was synthesized from 3-amino-6-bromo-4-(7-fluoro-1H-indazol-4-yl)-1H-1,7-phenanthrolin-2-one (compound C1) and a corresponding amine under the same conditions as the production example of the compound C114.

LCMS: m/z 479 $[M+H]^+$

HPLC retention time: 0.39 min (analysis condition A)

Compound C125

3-Amino-4-(7-fluoro-1H-indazol-4-yl)-6-piperidin-1-yl-1H-1,7-phenanthrolin-2-one

[Formula 513]

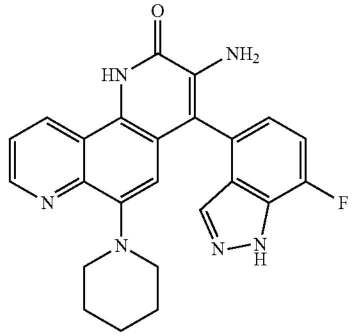

The title compound was synthesized from 3-amino-6-bromo-4-(7-fluoro-1H-indazol-4-yl)-1H-1,7-phenanthrolin-2-one (compound C1) and a corresponding amine under the same conditions as the production example of the compound C114.

LCMS: m/z 429.5 $[M+H]^+$

HPLC retention time: 0.41 min (analysis condition A)

Compound C126

3-Amino-6-(4,4-difluoropiperidin-1-yl)-4-(7-fluoro-1H-indazol-4-yl)-1H-1,7-phenanthrolin-2-one

[Formula 514]

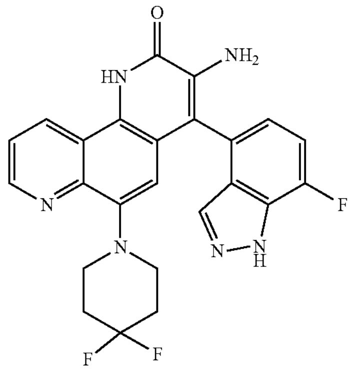

The title compound was synthesized from 3-amino-6-bromo-4-(7-fluoro-1H-indazol-4-yl)-1H-1,7-phenanthrolin-2-one (compound C1) and a corresponding amine under the same conditions as the production example of the compound C114.

LCMS: m/z 465.5 $[M+H]^+$

HPLC retention time: 0.51 min (analysis condition A)

Compound C128

3-Amino-4-(7-fluoro-1H-indazol-4-yl)-6-(6-oxa-3-azabicyclo[3.1.1]heptan-3-yl)-1H-1,7-phenanthrolin-2-one

[Formula 515]

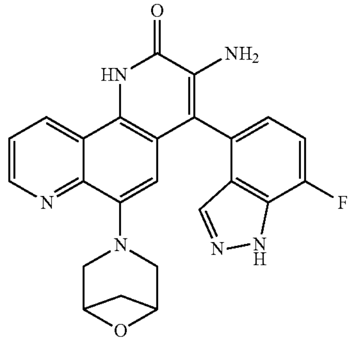

The title compound was synthesized from 3-amino-6-bromo-4-(7-fluoro-1H-indazol-4-yl)-1H-1,7-phenanthrolin-2-one (compound C1) and a corresponding amine under the same conditions as the production example of the compound C114.

LCMS: m/z 443.5 $[M+H]^+$

HPLC retention time: 0.42 min (analysis condition A)

Compound C129

3-Amino-4-(7-fluoro-1H-indazol-4-yl)-6-(3-oxa-6-azabicyclo[3.1.1]heptan-6-yl)-1H-1,7-one

[Formula 516]

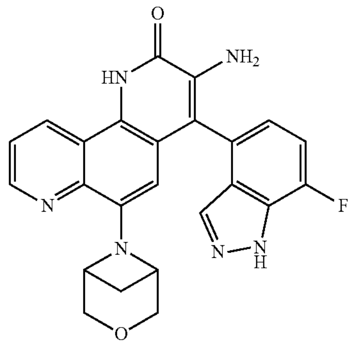

The title compound was synthesized from 3-amino-6-bromo-4-(7-fluoro-1H-indazol-4-yl)-1H-1,7-phenanthrolin-2-one (compound C1) and a corresponding amine under the same conditions as the production example of the compound C114.

LCMS: m/z 443.5 $[M+H]^+$

HPLC retention time: 0.52 min (analysis condition A)

Compound C131

3-Amino-4-(7-fluoro-1H-indazol-4-yl)-6-[4-(trifluoromethyl) piperidin-1-yl]-1H-1,7-phenanthrolin-2-one

[Formula 517]

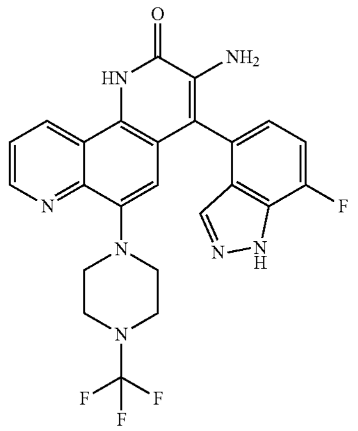

The title compound was synthesized from 3-amino-6-bromo-4-(7-fluoro-1H-indazol-4-yl)-1H-1,7-phenanthrolin-2-one (compound C1) and a corresponding amine under the same conditions as the production example of the compound C114.

LCMS: m/z 497 $[M+H]^+$

HPLC retention time: 0.54 min (analysis condition A)

Compound C83

3-Amino-4-(7-fluoro-1H-indazol-4-yl)-1H-1,7-phenanthrolin-2-one

[Formula 518]

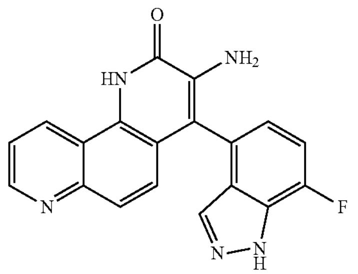

The title compound was synthesized from 3-amino-6-bromo-4-(7-fluoro-1H-indazol-4-yl)-1H-1,7-phenanthrolin-2-one (compound C1) under the same conditions as the production example of the compound B11, except that Xantphos Pd G3 was used instead of Xantphos Pd G4 used in the production example of the compound B11.

LCMS: m/z 346 $[M+H]^+$

HPLC retention time: 0.42 min (analysis condition A)

Compound C87

3-Amino-4-(7-fluoro-1H-indazol-4-yl)-2-oxo-1H-1,7-phenanthroline-6-carbonitrile

[Formula 519]

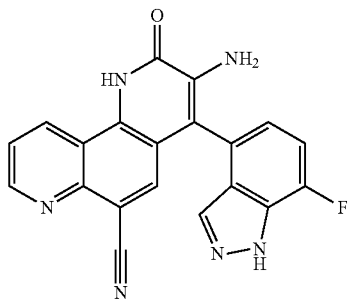

The title compound was synthesized from 3-amino-6-bromo-4-(7-fluoro-1H-indazol-4-yl)-1H-1,7-phenanthrolin-2-one (compound C1) under the same conditions as the production example of the compound B26, except that XPhos Pd G4 was used instead of tetrakis (triphenylphosphine)palladium (0) used in the production example of the compound B26.

LCMS: m/z 371 $[M+H]^+$

HPLC retention time: 0.54 min (analysis condition A)

Compound C88

3-Amino-4-(7-fluoro-1H-indazol-4-yl)-6-(1-methylpyrazol-4-yl)-1H-1,7-phenanthrolin-2-one

[Formula 520]

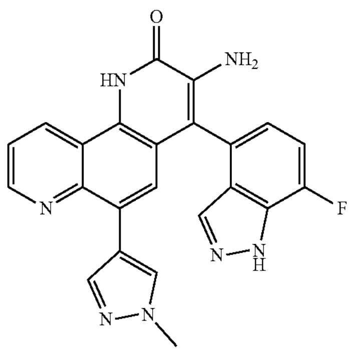

The title compound was synthesized from 3-amino-6-bromo-4-(7-fluoro-1H-indazol-4-yl)-1H-1,7-phenanthrolin-2-one (compound C1) under the same conditions as the production example of the compound B29.

LCMS: m/z 426 $[M+H]^+$

HPLC retention time: 0.50 min (analysis condition A)

Compound C89

3-Amino-6-ethenyl-4-(7-fluoro-1H-indazol-4-yl)-1H-1,7-phenanthrolin-2-one

[Formula 521]

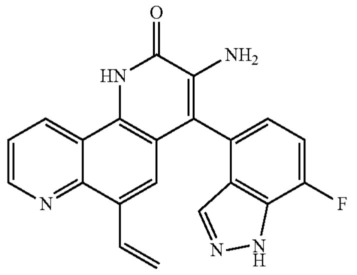

The title compound was synthesized from 3-amino-6-bromo-4-(7-fluoro-1H-indazol-4-yl)-1H-1,7-phenanthrolin-2-one (compound C1) under the same conditions as the production example of the compound B29, except that potassium vinyltrifluoroborate was used instead of 1-methyl-1H-pyrazole-4-boronic acid used in the production example of the compound B29.

LCMS: m/z 372 $[M+H]^+$

HPLC retention time: 0.60 min (analysis condition A)

Compound C90

3-Amino-4-(7-fluoro-1H-indazol-4-yl)-6-prop-1-inyl-1H-1,7-phenanthrolin-2-one

[Formula 522]

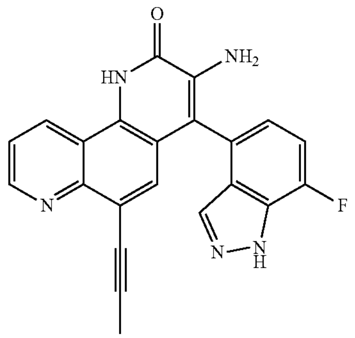

The title compound was synthesized from 3-amino-6-bromo-4-(7-fluoro-1H-indazol-4-yl)-1H-1,7-phenanthrolin-2-one (compound C1) under the same conditions as the production example of the compound B28, except that DMSO was used instead of DMA used in the production example of the compound B28.

LCMS: m/z 384 $[M+H]^+$

HPLC retention time: 0.52 min (analysis condition A)

Compound C93

2-[3-Amino-4-(7-fluoro-1H-indazol-4-yl)-2-oxo-1H-1,7-phenanthrolin-6-yl]-N,N-dimethylacetamide

[Formula 523]

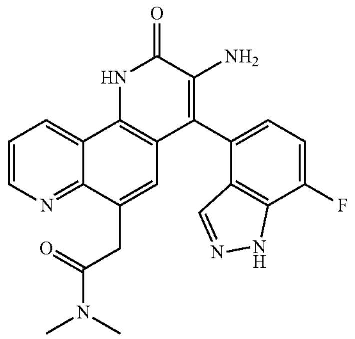

A solution of 3-amino-6-bromo-4-(7-fluoro-1H-indazol-4-yl)-1H-1,7-phenanthrolin-2-one (compound C1, 20 mg, 0.047 mmol) and BINAP Pd G4 (4.74 mg, 4.71 μmol) in DMA (0.471 mL) in a reaction vessel was degassed under reduced pressure and subjected to nitrogen replacement. Cyclopropanecarbonitrile (10.4 μL, 0.141 mmol) and a 1.0 M solution of LiHMDS in THF (0.28 mL, 0.28 mmol) were added thereto, and the mixture was stirred at 150° C. for 30 min using a microwave reactor. The reaction mixture was cooled to room temperature, a 22% aqueous formic acid solution (0.1 mL) and DMSO were added thereto, and the mixture was filtered. The filtrate was purified by reversed phase column chromatography (0.1% aqueous formic acid solution/0.1% formic acid in acetonitrile solution) to obtain the title compound (5 mg, yield 25%) as a light brown solid.

LCMS: m/z 431 $[M+H]^+$

HPLC retention time: 0.49 min (analysis condition A)

Compound C94

3-Amino-6-(2,3-dihydrofuran-4-yl)-4-(7-fluoro-1H-indazol-4-yl)-1H-1,7-phenanthrolin-2-one

[Formula 524]

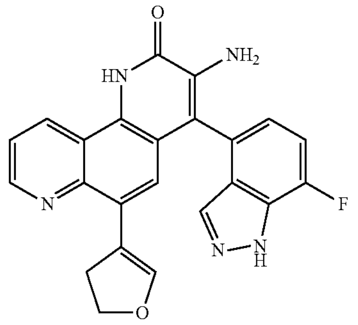

The title compound was synthesized from 3-amino-6-bromo-4-(7-fluoro-1H-indazol-4-yl)-1H-1,7-phenanthrolin-2-one (compound C1) under the same conditions as the production example of the compound B29, except that tripotassium phosphate and 4,5-dihydrofuran-3-boronic acid pinacol ester were used instead of cesium carbonate and 1-methyl-1H-pyrazole-4-boronic acid used in the production example of the compound B29. In addition, the reaction was carried out by heating the reaction solution to 90° C.

LCMS: m/z 414 $[M+H]^+$

HPLC retention time: 0.68 min (analysis condition A)

Compound C95

1-[3-Amino-4-(7-fluoro-1H-indazol-4-yl)-2-oxo-1H-1,7-phenanthrolin-6-yl]cyclopropane-1-carbonitrile

[Formula 525]

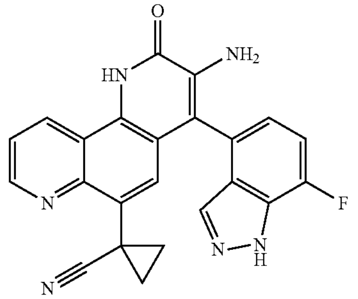

A solution of 3-amino-6-bromo-4-(7-fluoro-1H-indazol-4-yl)-1H-1,7-phenanthrolin-2-one (compound C1, 20 mg, 0.047 mmol), 4,6-bis(diphenylphosphino) phenoxazine (5.2 mg, 9.43 μmol), and tris(dibenzylideneacetone)dipalladium (0) chloroform adduct (4.88 mg, 4.71 μmol) in THF (0.471 mL) in a reaction vessel was degassed under reduced pressure and subjected to nitrogen replacement. Cyclopropanecarbonitrile (10.4 μL, 0.141 mmol) and a 1.0 M solution of LiHMDS in THF (0.28 mL, 0.28 mmol) were added thereto, and the mixture was stirred at 150° C. for 1 hour using a microwave reactor. The reaction mixture was cooled to room temperature, a 22% aqueous formic acid solution (0.1 mL) and DMSO were added thereto, and the mixture was filtered. The filtrate was purified by reversed phase column chromatography (0.1% aqueous formic acid solution/0.1% formic acid in acetonitrile solution) to obtain the title compound (3 mg, yield 16%) as a light brown solid.

LCMS: m/z 411 $[M+H]^+$

HPLC retention time: 0.53 min (analysis condition A)

Compound C200

6-Acetyl-3-amino-4-(7-fluoro-1H-indazol-4-yl)-1H-1,7-phenanthrolin-2-one

[Formula 526]

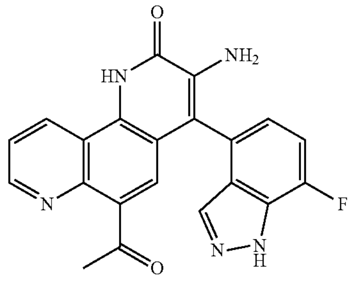

A solution of 3-amino-6-bromo-4-(7-fluoro-1H-indazol-4-yl)-1H-1,7-phenanthrolin-2-one (compound C1, 50 mg, 0.118 mmol) and tetrakis(triphenylphosphine)palladium (0) (13.62 mg, 0.012 mmol) in DMA (0.5 mL) in a reaction vessel was degassed under reduced pressure and subjected to nitrogen replacement. Tributyl(1-ethoxyvinyl) stannane (0.2 mL, 0.598 mmol) was added thereto, and the mixture was stirred at 80° C. for 2 hours. To the reaction mixture, tetrakis (triphenylphosphine)palladium (0) (13.62 mg, 0.012 mmol) and tributyl(1-ethoxyvinyl) stannane (0.2 mL, 0.598 mmol) were added, and the mixture was further stirred at 80° C. for 15 hours. The reaction mixture was cooled to room temperature, 4 M hydrochloric acid was added thereto, and the mixture was stirred for 30 min. To the reaction mixture, a 22% aqueous formic acid solution (0.2 mL) and DMSO were added, and the mixture was filtered. The filtrate was purified by reversed phase column chromatography (0.1% aqueous formic acid solution/0.1% formic acid in acetonitrile solution) to obtain the title compound (16.9 mg, yield 37%) as a light brown solid.

LCMS: m/z 388 $[M+H]^+$

HPLC retention time: 0.42 min (analysis condition B)

Compound C102

3-Amino-4-(7-fluoro-1H-indazol-4-yl)-6-(3-hydroxy-3-methylbut-1-inyl)-1H-1,7-phenanthrolin-2-one

[Formula 527]

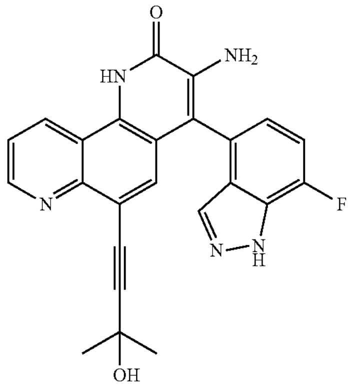

A solution of 3-amino-6-bromo-4-(7-fluoro-1H-indazol-4-yl)-1H-1,7-phenanthrolin-2-one (compound C1, 30 mg, 0.071 mmol) and cesium carbonate (46.1 mg, 0.141 mmol) in DMA (0.354 mL) in a reaction vessel was degassed under reduced pressure and subjected to nitrogen replacement, and then [1,3-bis(2,6-diisopropylphenyl) imidazol-2-ylidene](3-chloropyridyl)palladium(II) dichloride (4.8 mg, 7.07 μmol) and 2-methyl-3-butin-2-ol (10.3 μL, 0.106 mmol) were added, and the mixture was stirred at 80° C. for 15 hours. The reaction mixture was cooled to room temperature and combined with that of another lot, then a 22% aqueous formic acid solution (0.2 mL) and DMSO were added thereto, and the mixture was filtered. The filtrate was purified twice by reversed phase column chromatography (0.1% aqueous formic acid solution/0.1% formic acid in acetonitrile solution) to obtain the title compound (2 mg, yield 3.3%) as a light brown solid.

LCMS: m/z 428 $[M+H]^+$

HPLC retention time: 0.50 min (analysis condition A)

Compound C103

3-Amino-4-(7-fluoro-1H-indazol-4-yl)-6-prop-1-en-2-yl-1H-1,7-phenanthrolin-2-one

[Formula 528]

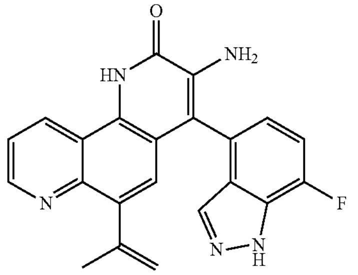

The title compound was synthesized from 3-amino-6-bromo-4-(7-fluoro-1H-indazol-4-yl)-1H-1,7-phenanthrolin-2-one (compound C1) under the same conditions as the production example of the compound b-10, except that XPhos Pd G4, potassium isopropenyltrifluoroborate, and DMA were respectively used instead of DPPF Pd G4, potassium cyclopropyltrifluoroborate, and 1,4-dioxane used in the production example of the compound b-10.

LCMS: m/z 386.5 $[M+H]^+$

HPLC retention time: 0.53 min (analysis condition A)

Compound C110

3-Amino-6-dimethylphosphoryl-4-(7-fluoro-1H-indazol-4-yl)-1H-1,7-phenanthrolin-2-one

[Formula 529]

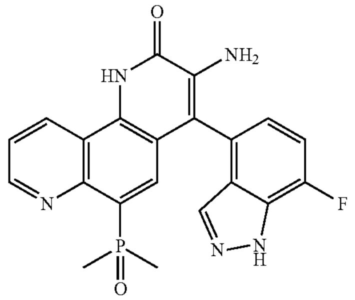

The title compound was synthesized from 3-amino-6-bromo-4-(7-fluoro-1H-indazol-4-yl)-1H-1,7-phenanthrolin-2-one (compound C1) under the same conditions as the production example of the compound B31.

LCMS: m/z 422 $[M+H]^+$

HPLC retention time: 0.45 min (analysis condition A)

Compound C111

3-Amino-4-(7-fluoro-1H-indazol-4-yl)-6-iodo-1H-1,7-phenanthrolin-2-one

[Formula 530]

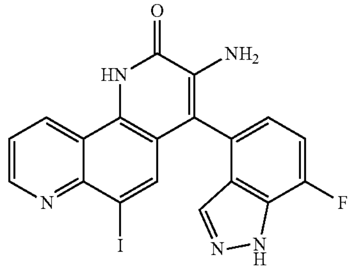

To a suspension of 3-amino-6-bromo-4-(7-fluoro-1H-indazol-4-yl)-1H-1,7-phenanthrolin-2-one (compound C1, 10 mg, 0.024 mmol), sodium iodide (7.07 mg, 0.047 mmol), and copper (I) iodide (2.245 mg, 0.012 mmol) in 1,4-dioxane (0.4 mL) in a reaction vessel, N,N'-dimethylethylenediamine (2.28 μL, 0.021 mmol) was added, the reaction vessel was degassed under reduced pressure and subjected to nitrogen replacement, and then the mixture was stirred at 110° C. for 20 hours. To the reaction mixture, a 22% aqueous formic acid solution, DMSO, and acetonitrile were added, and the mixture was purified by reversed phase column chromatography (0.1% aqueous formic acid solution/0.1% formic acid in acetonitrile solution) to obtain the title compound (8.6 mg, yield 77%) as a pale yellow solid.

LCMS: m/z 472 [M+H]$^+$

HPLC retention time: 0.63 min (analysis condition A)

Compound C112

3-Amino-4-(7-fluoro-1H-indazol-4-yl)-6-(2-oxopyrrolidin-1-yl)-1H-1,7-phenanthrolin-2-one

[Formula 531]

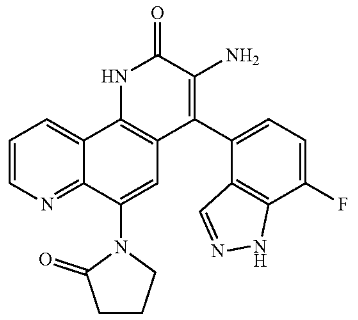

To a suspension of 3-amino-6-iodo-4-(7-fluoro-1H-indazol-4-yl)-1H-1,7-phenanthrolin-2-one (compound C111, 10 mg, 0.021 mmol), potassium carbonate (20.53 mg, 0.149 mmol), (1S,2S)-(+)-N,N'-dimethylcyclohexane-1,2-diamine (18.11 mg, 0.127 mmol), and copper (I) iodide (12.2 mg, 0.064 mmol) in 1,4-dioxane (0.212 mL) in a reaction vessel, pyrrolidine-2-one (6.55 μL, 0.085 mmol) was added, the reaction vessel was degassed under reduced pressure and subjected to nitrogen replacement, and then the mixture was stirred at 110° C. for 20 hours. To the reaction mixture, a 22% aqueous formic acid solution and DMSO were added, and the mixture was filtered. The filtrate was purified by reversed phase column chromatography (0.1% aqueous formic acid solution/0.1% formic acid in acetonitrile solution) to obtain the title compound (1.9 mg, yield 7%) as a pale yellow solid.

LCMS: m/z 429 [M+H]$^+$

HPLC retention time: 0.46 min (analysis condition A)

Compound C127

N-[3-Amino-4-(7-fluoro-1H-indazol-4-yl)-2-oxo-1H-1,7-phenanthrolin-6-yl]methanesulfonamide

[Formula 532]

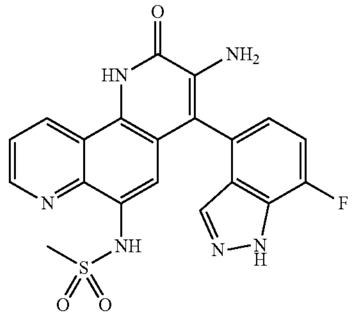

To a suspension of 3-amino-6-bromo-4-(7-fluoro-1H-indazol-4-yl)-1H-1,7-phenanthrolin-2-one (compound C1, 20 mg, 0.047 mmol), tripotassium phosphate (40 mg, 0.189 mmol), and methanesulfonamide (13.45 mg, 0.141 mmol) in 1,4-dioxane (0.471 mL) in a reaction vessel, tBuXPhos Pd G4 (3.75 mg, 4.71 μmol) was added, the reaction vessel was degassed under reduced pressure and subjected to nitrogen replacement, and then the mixture was stirred at 110° C. for 17 hours. To the reaction mixture, a 22% aqueous formic acid solution and DMSO were added, and the mixture was purified by reversed phase column chromatography (0.1% aqueous formic acid solution/0.1% formic acid in acetonitrile solution) to obtain the title compound (3.5 mg, yield 17%) as a pale yellow solid.

LCMS: m/z 439 [M+H]$^+$

HPLC retention time: 0.50 min (analysis condition A)

Compound C130

N-[3-amino-4-(7-fluoro-1H-indazol-4-yl)-2-oxo-1H-1,7-phenanthrolin-6-yl]cyclopropanesulfonamide

[Formula 533]

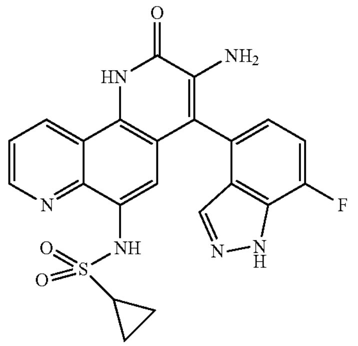

The title compound was synthesized from 3-amino-6-bromo-4-(7-fluoro-1H-indazol-4-yl)-1H-1,7-phenanthrolin-2-one (compound C1) under the same conditions as the production example of the compound C127, except that cyclopropylsulfonamide was used instead of methanesulfonamide used in the production example of the compound C127.

LCMS: m/z 465 [M+H]$^+$

HPLC retention time: 0.55 min (analysis condition A)

Compound C133

3-Amino-4-(7-fluoro-1H-indazol-4-yl)-6-piperidin-4-yl-1H-1,7-phenanthrolin-2-one; hydrochloride

[Formula 534]

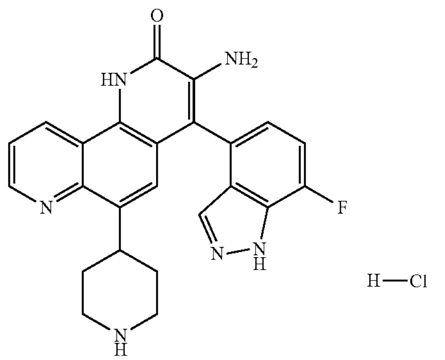

To a solution of tert-butyl 4-[3-amino-4-(7-fluoro-1H-indazol-4-yl)-2-oxo-1H-1,7-phenanthrolin-6-yl]piperidine-1-carboxylate (compound C99, 4.5 mg, 8.51 μmol) in TFE (0.3 mL), trimethylsilyl chloride (5.39 μL, 0.043 mmol) was added, and the mixture was stirred at room temperature for 30 min. The reaction mixture was concentrated, a mixed solution of acetonitrile and water was added thereto, and the mixture was freeze-dried to obtain the title compound (3.8 mg, yield 83%) as an orange solid.

LCMS: m/z 429.5 $[M+H]^+$

HPLC retention time: 0.37 min (analysis condition A)

Compound C132

3-Amino-6-(azetidin-3-yl)-4-(7-fluoro-1H-indazol-4-yl)-1H-1,7-phenanthrolin-2-one; formate

[Formula 535]

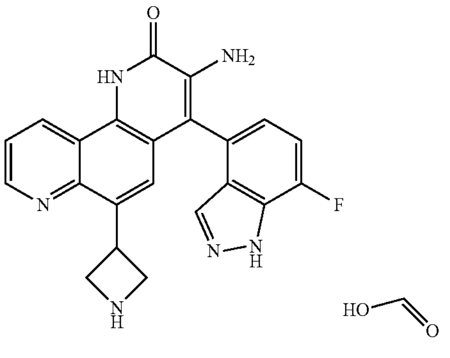

The title compound was synthesized from tert-butyl 3-[3-amino-4-(7-fluoro-1H-indazol-4-yl)-2-oxo-1H-1,7-phenanthrolin-6-yl]azetidine-1-carboxylate (compound C97) under the same conditions as the production example of the compound C133.

LCMS: m/z 401.5 $[M+H]^+$

HPLC retention time: 0.36 min (analysis condition A)

Compound C134

3-Amino-6-(1-cyclobutylpiperidin-4-yl)-4-(7-fluoro-1H-indazol-4-yl)-1H-1,7-phenanthrolin-2-one

[Formula 536]

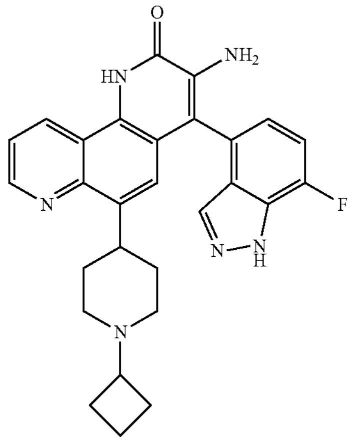

3-Amino-4-(7-fluoro-1H-indazol-4-yl)-6-piperidin-4-yl-1H-1,7-phenanthrolin-2-one; hydrochloride (compound C133, 10.5 mg, 0.02 mmol) was suspended in the mixed solution of THF (0.21 mL) and DMA (0.07 mL), triethylamine (13.61 μL, 0.098 mmol), acetic acid (33.5 μL, 0.586 mmol), cyclobutanone (4.41 μL, 0.059 mmol), and triacetoxysodium borohydride (12.4 mg, 0.059 mmol) were added thereto, and the mixture was stirred at room temperature for 3 hours. To the reaction mixture, a 22% aqueous formic acid solution (0.2 mL) and DMSO were added, and the mixture was filtered. The filtrate was purified by reversed phase column chromatography (0.1% aqueous formic acid solution/0.1% formic acid in acetonitrile solution) to obtain the title compound (4.9 mg, yield 52%) as a grayish solid.

LCMS: m/z 483.5 $[M+H]^+$

HPLC retention time: 0.39 min (analysis condition A)

Compound C135

3-Amino-4-(7-fluoro-1H-indazol-4-yl)-6-[1-(oxetan-3-yl) piperidin-4-yl]-1H-1,7-phenanthrolin-2-one

[Formula 537]

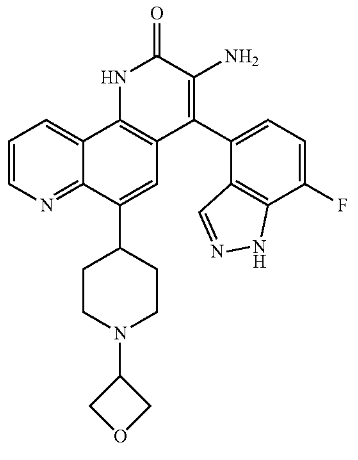

The title compound was synthesized from 3-amino-4-(7-fluoro-1H-indazol-4-yl)-6-piperidin-4-yl-1H-1,7-phenanthrolin-2-one; hydrochloride (compound C133) under the same conditions as the production example of the compound C134, except that 3-oxetanone was used instead of cyclobutanone used in the production example of the compound C134.

LCMS: m/z 485.5 [M+H]$^+$

HPLC retention time: 0.36 min (analysis condition A)

Compound C136

3-Amino-4-(7-fluoro-1H-indazol-4-yl)-6-(1-propan-2-ylpiperidin-4-yl)-1H-1,7-phenanthrolin-2-one; formate

[Formula538]

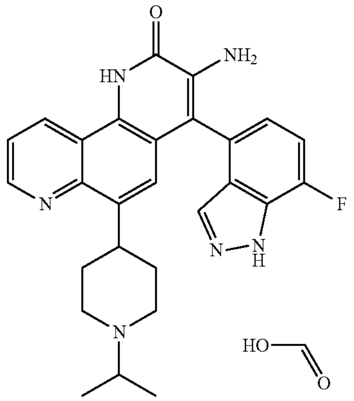

The title compound was synthesized from 3-amino-4-(7-fluoro-1H-indazol-4-yl)-6-piperidin-4-yl-1H-1,7-phenanthrolin-2-one; hydrochloride (compound C133) under the same conditions as the production example of the compound C134, except that acetone was used instead of cyclobutanone used in the production example of the compound C134.

LCMS: m/z 471 [M+H]$^+$

HPLC retention time: 0.39 min (analysis condition A)

Compound C137

3-Amino-4-(7-fluoro-1H-indazol-4-yl)-6-[1-(oxan-4-yl) piperidin-4-yl]-1H-1,7-phenanthrolin-2-one

[Formula 539]

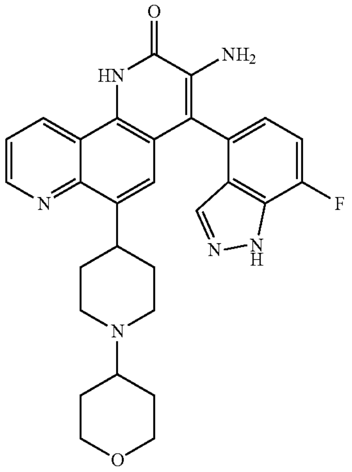

The title compound was synthesized from 3-amino-4-(7-fluoro-1H-indazol-4-yl)-6-piperidin-4-yl-1H-1,7-phenanthrolin-2-one; hydrochloride (compound C133) under the same conditions as the production example of the compound C134, except that tetrahydro-4H-pyran-4-one was used instead of cyclobutanone used in the production example of the compound C134.

LCMS: m/z 513 [M+H]$^+$

HPLC retention time: 0.38 min (analysis condition A)

Compound C138

3-Amino-4-(7-fluoro-1H-indazol-4-yl)-6-(1-methylpiperidin-4-yl)-1H-1,7-phenanthrolin-2-one

[Formula 540]

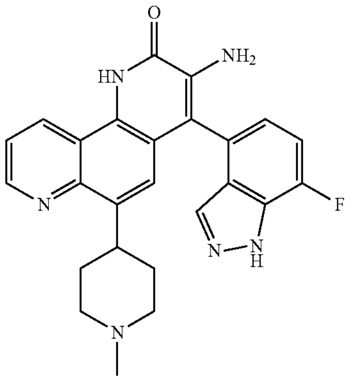

The title compound was synthesized from 3-amino-4-(7-fluoro-1H-indazol-4-yl)-6-piperidin-4-yl-1H-1,7-phenanthrolin-2-one; hydrochloride (compound C133) under the same conditions as the production example of the compound C134, except that formaldehyde was used instead of cyclobutanone used in the production example of the compound C134.

LCMS: m/z 443 $[M+H]^+$

HPLC retention time: 0.38 min (analysis condition A)

Compound C139

3-Amino-4-(7-fluoro-1H-indazol-4-yl)-6-(4-oxocyclohexyl)-1H-1,7-phenanthrolin-2-one

[Formula 541]

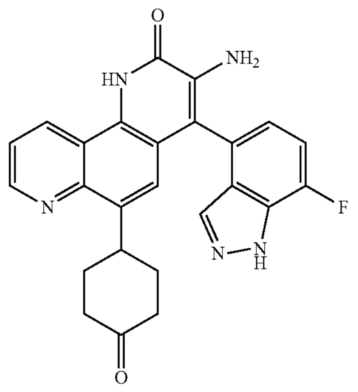

The title compound was synthesized from 3-amino-6-(1,4-dioxaspiro[4.5]decan-8-yl)-4-(7-fluoro-1H-indazol-4-yl)-1H-1,7-phenanthrolin-2-one 2,2,2-trifluoroacetate (compound C101) under the same conditions as the production example of the compound B1.

LCMS: m/z 442 $[M+H]^+$

HPLC retention time: 0.51 min (analysis condition A)

Compound C140

3-Amino-4-(7-fluoro-1H-indazol-4-yl)-6-((1r, 4r)-4-hydroxycyclohexyl)-1H-1,7-phenanthrolin-2-one

[Formula 542]

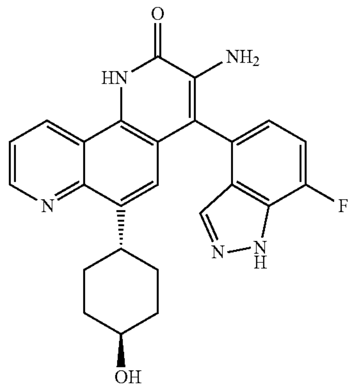

LCMS: m/z 444.5 $[M+H]^+$

HPLC retention time: 0.44 min (analysis condition A)

Compound C141

3-Amino-4-(7-fluoro-1H-indazol-4-yl)-6-((1s, 4s)-4-hydroxycyclohexyl)-1H-1,7-phenanthrolin-2-one

[Formula 543]

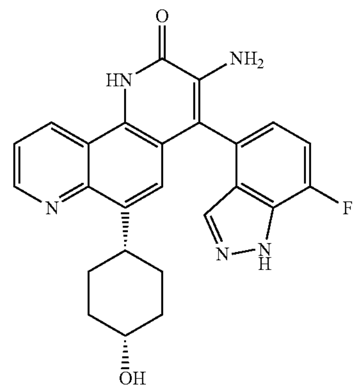

To a solution of 3-amino-4-(7-fluoro-1H-indazol-4-yl)-6-(4-oxocyclohexyl)-1H-1,7-phenanthrolin-2-one (compound C139, 8 mg, 0.018 mmol) in MeOH (0.2 mL), sodium borohydride (5.8 mg, 0.153 mmol) was added, and the mixture was stirred at room temperature for 3.5 hours. To the reaction mixture, a 44% aqueous formic acid solution (200 μL) and DMSO were added, and the mixture was filtered. The filtrate was purified by reversed phase column chromatography (0.1% aqueous formic acid solution/0.1% formic acid in acetonitrile solution) to obtain the compound C140 (6.7 mg, yield 66%) and the compound C141 (0.7 mg, yield 6.9%) as yellow solids.

LCMS: m/z 444.5 $[M+H]^+$

HPLC retention time: 0.48 min (analysis condition A)

Compound c-171 tert-Butyl 3-[bis[(2-methylpropan-2-yl)oxycarbonyl]amino]-4-[7-fluoro-1-[(2-methylpropan-2-yl)oxycarbonyl]indazol-4-yl]-2-oxo-6-prop-1-en-2-yl-1,7-phenanthroline-1-carboxylate

[Formula 544]

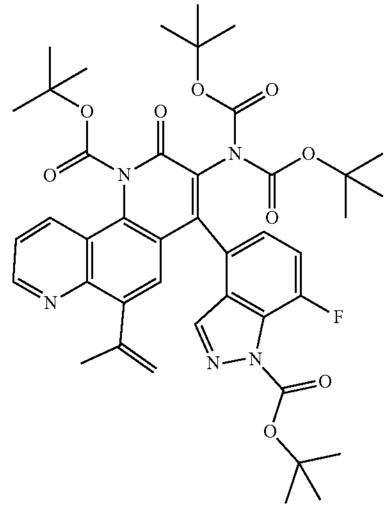

To a solution of 3-amino-4-(7-fluoro-1H-indazol-4-yl)-6-prop-1-en-2-yl-1H-1,7-phenanthrolin-2-one (compound C103, 63.1 mg, 0.164 mmol) in THF (1.7 mL), di-tert-butyl dicarbonate (314 mg, 1.44 mmol) and dimethylaminopyridine (16 mg, 0.131 mmol) were added, and the mixture was stirred at room temperature for 15 hours. The reaction mixture was concentrated, and the obtained residue was purified by silica gel column chromatography (ethyl acetate/hexane) to obtain the title compound (91.2 mg, yield 71%) as a pale yellow solid.

LCMS: m/z 786.7 $[M+H]^+$

HPLC retention time: 1.26 min (analysis condition A)

Compound C142

3-Amino-4-(7-fluoro-1H-indazol-4-yl)-6-(1-methylcyclopropyl)-1H-1,7-phenanthrolin-2-one

[Formula 545]

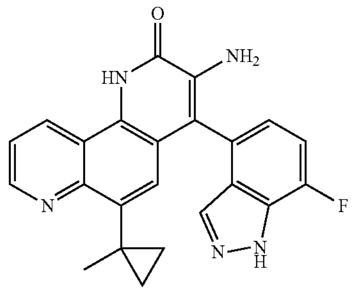

A solution of tert-butyl 3-[bis[(2-methylpropan-2-yl)oxycarbonyl]amino]-4-[7-fluoro-1-[(2-methylpropan-2-yl)oxycarbonyl]indazol-4-yl]-2-oxo-6-prop-1-en-2-yl-1,7-phenanthroline-1-carboxylate (compound c-171, 45 mg, 0.057 mmol) in DCM (1 mL) was cooled to 0° C., then a solution of diiodomethane (18.48 μL, 0.229 mmol) in DCM (1 mL) and a 1 M solution of diethylzinc in toluene (229 μL, 0.229 mmol) were added thereto, and the mixture was stirred at room temperature for 15 hours. The reaction mixture was cooled to 0° C., TFA (500 μL) was added thereto, and then the mixture was stirred at room temperature for 30 min. The reaction mixture was concentrated, potassium acetate (60 mg, 0.611 mmol), DMSO, and water were added thereto, and then the mixture was purified by reversed phase column chromatography (0.1% aqueous formic acid solution/0.1% formic acid in acetonitrile solution) to obtain the title compound (2.5 mg, yield 11%) as an orange solid.

LCMS: m/z 400.5 $[M+H]^+$

HPLC retention time: 0.47 min (analysis condition A)

Compound c-163

3-Amino-6-ethenyl-4-[7-fluoro-2-(oxan-2-yl)indazol-4-yl]-1H-1,7-phenanthrolin-2-one

[Formula 546]

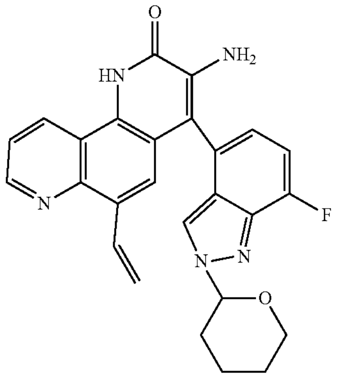

The title compound was synthesized from 3-amino-6-bromo-4-[7-fluoro-2-(oxan-2-yl)indazol-4-yl]-1H-1,7-phenanthrolin-2-one (compound c-13) under the same conditions as the production example of the compound B29, except that potassium vinyltrifluoroborate was used instead of 1-methyl-1H-pyrazole-4-boronic acid used in the production example of the compound B29.

LCMS: m/z 456.5 $[M+H]^+$

HPLC retention time: 0.73 min (analysis condition A)

Compound c-164

5-Ethenyl-7-[7-fluoro-2-(oxan-2-yl)indazol-4-yl]-9-methyl-[1,3]oxazolo[5,4-b][1,7]phenanthroline

[Formula 547]

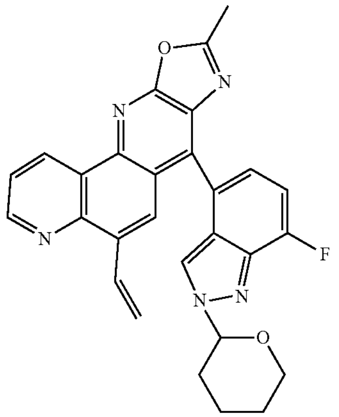

To a solution of 3-amino-6-ethenyl-4-[7-fluoro-2-(oxan-2-yl)indazol-4-yl]-1H-1,7-phenanthrolin-2-one (compound c-163, 59 mg, 0.130 mmol) in NMP (1.18 mL), trimethyl orthoacetate (81 μL, 0.648 mmol) was added, and the mixture was stirred at 150° C. for 30 min. To the reaction mixture, water was added, and the mixture was extracted with ethyl acetate. The organic layer was concentrated under reduced pressure, and the obtained residue was purified by silica gel column chromatography to obtain the title compound (25 mg, yield 40%).

LCMS: m/z 480.5 $[M+H]^+$

HPLC retention time: 1.00 min (analysis condition A)

Compound c-165

5-(2,2-Difluorocyclopropyl)-7-[7-fluoro-2-(oxan-2-yl)indazol-4-yl]-9-methyl-[1,3]oxazolo[5,4-b][1,7]phenanthroline

[Formula 548]

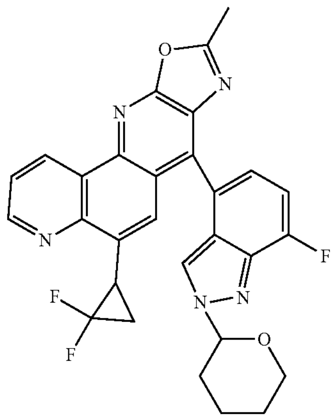

To a solution of 5-ethenyl-7-[7-fluoro-2-(oxan-2-yl)indazol-4-yl]-9-methyl-[1,3]oxazolo[5,4-b][1,7]phenanthroline (compound c-164, 48 mg, 0.1 mmol) in THF (2.4 mL), (trifluoromethyl)trimethylsilane (222 μL, 1.5 mmol) and sodium iodide (3 mg, 0.02 mmol) were added, and the mixture was stirred at 60° C. for 1 hour. (Trifluoromethyl)trimethylsilane (222 μL, 1.5 mmol) was further added thereto, and the mixture was stirred at 60° C. The reaction mixture was concentrated, the obtained residue was combined with that of another lot, and the mixture was purified by silica gel column chromatography to obtain the title compound (56 mg).

LCMS: m/z 530.5 $[M+H]^+$

HPLC retention time: 0.97 min (analysis condition A)

Compound C145

3-Amino-6-(2,2-difluorocyclopropyl)-4-(7-fluoro-1H-indazol-4-yl)-1H-1,7-phenanthrolin-2-one

[Formula 549]

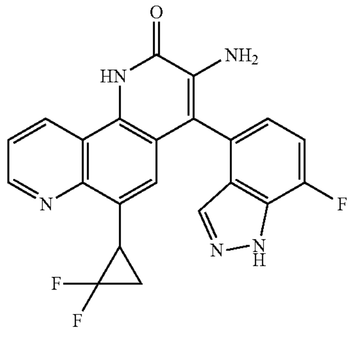

To a solution of 5-(2,2-difluorocyclopropyl)-7-[7-fluoro-2-(oxan-2-yl)indazol-4-yl]-9-methyl-[1,3]oxazolo[5,4-b][1,7]phenanthroline (compound c-165, 45 mg, 0.085 mmol) in EtOH (2.7 mL), 12 M hydrochloric acid (142 μL, 1.7 mmol) was added, and the mixture was stirred at 80° C. for 15 hours. The reaction mixture was combined with the reaction mixture of another lot obtained by the same operation and concentrated, and the obtained residue was purified by reversed phase column chromatography to obtain the title compound (35 mg) as a grayish solid.

LCMS: m/z 422 $[M+H]^+$

HPLC retention time: 0.60 min (analysis condition A)

Compound c-166 tert-Butyl 4-[3-[bis[(2-methylpropan-2-yl)oxycarbonyl]amino]-6-bromo-2-oxo-1H-1,7-phenanthrolin-4-yl]-7-fluoroindazole-1-carboxylate

[Formula 550]

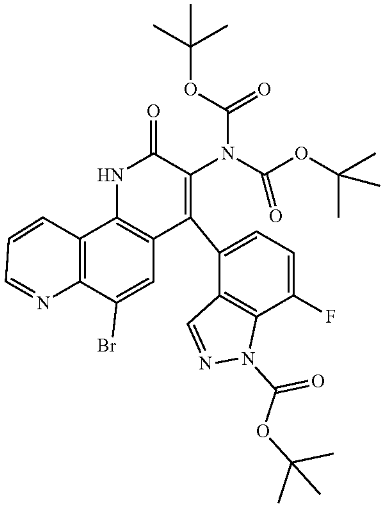

The title compound was synthesized from 3-amino-6-bromo-4-(7-fluoro-1H-indazol-4-yl)-1H-1,7-phenanthrolin-2-one (compound C1) under the same conditions as the production example of the compound c-171.

LCMS: m/z 724 $[M+H]^+$

HPLC retention time: 0.98 min (analysis condition A)

Compound c-167 tert-Butyl 3-[4-(7-fluoro-1H-indazol-4-yl)-3-[(2-methylpropan-2-yl)oxycarbonylamino]-2-oxo-1H-1,7-phenanthrolin-6-yl]pyrrolidine-1-carboxylate

[Formula 551]

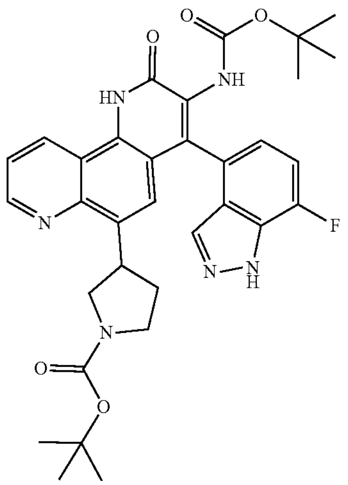

To a solution of tert-butyl 4-[3-[bis[(2-methylpropan-2-yl)oxycarbonyl]amino]-6-bromo-2-oxo-1H-1,7-phenanthrolin-4-yl]-7-fluoroindazole-1-carboxylate (compound c-166, 50 mg, 0.069 mmol) in DMA (0.345 mL), tert-butyl 3-bromopyrrolidine-1-carboxylate (25.9 mg, 0.104 mmol), nickel(II) iodide (4.31 mg, 0.014 mmol), 4,4'-di-tert-butyl-2,2'-dipyridyl (3.7 mg, 0.014 mmol), 4-ethylpyridine (7.85 μL, 0.069 mmol), magnesium chloride (6.57 mg, 0.069 mmol), and manganese (7.58 mg, 0.138 mmol) were added, the reaction mixture was degassed under reduced pressure and subjected to nitrogen replacement, and then the mixture was stirred at 60° C. for 22 hours. To the reaction mixture, a 22% aqueous formic acid solution and DMSO were added, and the mixture was filtered. The filtrate was purified by reversed phase column chromatography (0.1% aqueous formic acid solution/0.1% formic acid in acetonitrile solution) to obtain the title compound (3.4 mg, yield 8%) as a grayish solid.

LCMS: m/z 816 $[M+H]^+$

HPLC retention time: 0.76 min (analysis condition A)

Compound C146

3-Amino-4-(7-fluoro-1H-indazol-4-yl)-6-pyrrolidin-3-yl-1H-1,7-phenanthrolin-2-one; formate

[Formula 552]

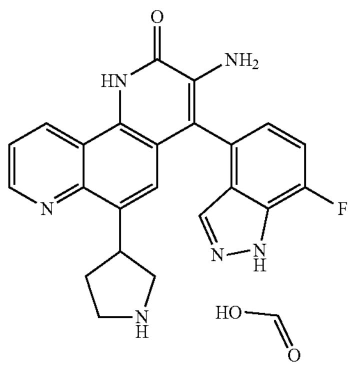

The title compound was synthesized from tert-butyl 3-[4-(7-fluoro-1H-indazol-4-yl)-3-[(2-methylpropan-2-yl)oxycarbonylamino]-2-oxo-1H-1,7-phenanthrolin-6-yl]pyrrolidine-1-carboxylate (compound c-167) under the same conditions as the production example of the compound C133.

LCMS: m/z 415.51 $[M+H]^+$

HPLC retention time: 0.37 min (analysis condition A)

Compound c-168 tert-Butyl 3-[bis[(2-methylpropan-2-yl)oxycarbonyl]amino]-6-bromo-4-[7-fluoro-2-(oxan-2-yl)indazol-4-yl]-2-oxo-1,7-phenanthroline-1-carboxylate

[Formula 553]

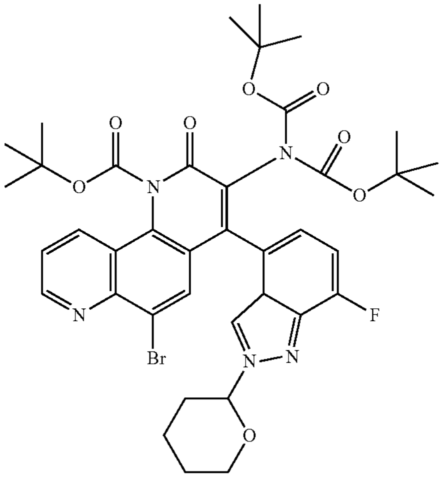

The title compound was synthesized from 3-amino-6-bromo-4-[7-fluoro-2-(oxan-2-yl)indazol-4-yl]-1H-1,7-phenanthrolin-2-one (compound c-13) under the same conditions as the production example of the compound c-171.

LCMS: m/z 808.5 $[M+H]^+$

HPLC retention time: 1.07 min (analysis condition V)

Compound c-169 tert-Butyl 3-[bis[(2-methylpropan-2-yl)oxycarbonyl]amino]-6-bromo-4-[7-fluoro-2-(oxan-2-yl)indazol-4-yl]-2-oxo-9-(4,4,5,5-tetramethyl-1,3,2-dioxaborolan-2-yl)-1,7-phenanthroline-1-carboxylate

[Formula 554]

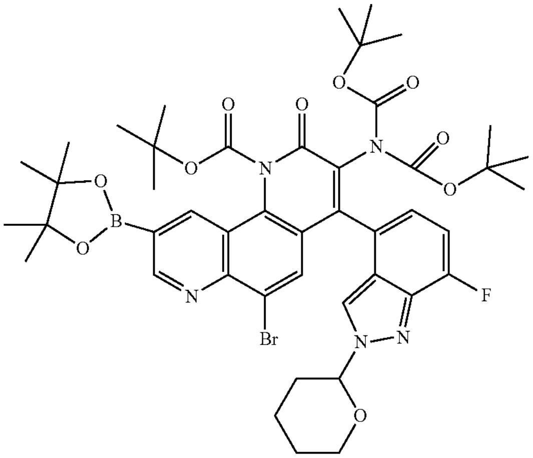

To a solution of tert-butyl 3-[bis[(2-methylpropan-2-yl)oxycarbonyl]amino]-6-bromo-4-[7-fluoro-2-(oxan-2-yl)indazol-4-yl]-2-oxo-1,7-phenanthroline-1-carboxylate (compound c-168, 100 mg), 4,4'-di-tert-butyl-2,2'-dipyridyl (6.64 mg, 0.025 mmol), and bis(pinacolato)diboron (126 mg, 0.495 mmol) in THF (1 mL), di-μ-methoxobis(1,5-cyclooctadiene)diiridium (8.20 mg, 0.012 mol) was added, and the mixture was degassed under reduced pressure, subjected to nitrogen replacement, and then stirred at room temperature for 4 days. The reaction mixture was concentrated, and the obtained residue was purified by silica gel column chromatography to obtain the title compound (68.6 mg, yield 59%).

LCMS: m/z 934.6 $[M+H]^+$

HPLC retention time: 0.89 min (analysis condition W)

Compound c-170 tert-Butyl 3-[bis[(2-methylpropan-2-yl)oxycarbonyl]amino]-4-[7-fluoro-2-(oxan-2-yl)indazol-4-yl]-6-methyl-2-oxo-9-(4,4,5,5-tetramethyl-1,3,2-dioxaborolan-2-yl)-1,7-phenanthroline-1-carboxylate

[Formula 555]

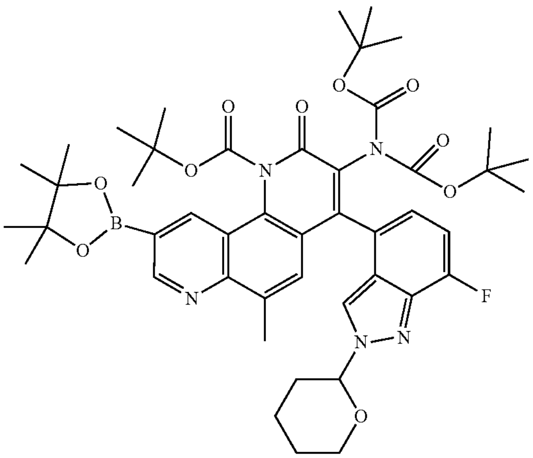

The title compound was synthesized from tert-butyl 3-[bis[(2-methylpropan-2-yl)oxycarbonyl]amino]-6-bromo-4-[7-fluoro-2-(oxan-2-yl)indazol-4-yl]-2-oxo-9-(4,4,5,5-tetramethyl-1,3,2-dioxaborolan-2-yl)-1,7-phenanthroline-1-carboxylate (compound c-169) under the same conditions as the production example of the compound B22, except that a 2 M solution of methylzincchloride in THF was used instead of the 0.5 M solution of cyclopropylzinc bromide in THE used in the production example of the compound B22.

LCMS: m/z 870.8 $[M+H]^+$

HPLC retention time: 0.90 min (analysis condition W)

Compound C189

[3-Amino-4-(7-fluoro-1H-indazol-4-yl)-6-methyl-2-oxo-1H-1,7-phenanthrolin-9-yl]boronic acid

[Formula 556]

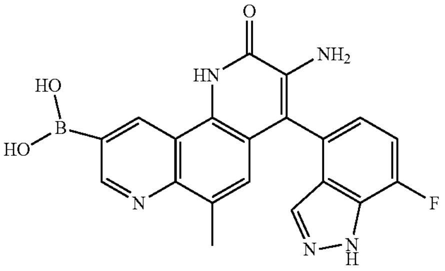

The title compound was synthesized from tert-butyl 3-[bis[(2-methylpropan-2-yl)oxycarbonyl]amino]-4-[7-fluoro-2-(oxan-2-yl)indazol-4-yl]-6-methyl-2-oxo-9-(4,4,5,5-tetramethyl-1,3,2-dioxaborolan-2-yl)-1,7-phenanthroline-1-carboxylate (compound c-170) under the same conditions as the production example of the compound B1.

LCMS: m/z 404.5 $[M+H]^+$

HPLC retention time: 0.41 min (analysis condition A)

Compound c-266

6,7-Difluoro-1H-indazole-4-carboxylic acid

[Formula 557]

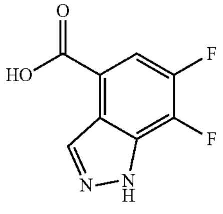

Into a reaction vessel, 4-bromo-6,7-difluoro-1H-indazole (10 g, 42.92 mmol), oxalic acid dihydrate (8.12 g, 64.37 mmol), palladium acetate (0.48 g, 2.15 mmol), and 4,5-bis(diphenylphosphino)-9,9-dimethylxanthene (1.24 g, 2.15 mmol) were added, and the reaction vessel was degassed under reduced pressure and subjected to nitrogen replacement. To this mixture, acetic anhydride (6.09 mL, 64.37 mmol) and DMF (90 mL) were added, and the reaction vessel was degassed under reduced pressure and subjected to nitrogen replacement. The reaction mixture was heated to 80° C., and DIPEA (11.99 mL, 68.66 mmol) was added dropwise thereto over 1 hour. The reaction mixture was stirred at 80° C. for 1 hour, then oxalic acid dihydrate (5.41 g, 42.92 mmol) and acetic anhydride (4.06 mL, 42.92 mmol) were added, and DIPEA (7.5 mL, 42.9 mmol) was added dropwise thereto over 1 hour. The reaction mixture was stirred at 80° C. for 1 hour. The reaction mixture was cooled to 0° C., and then a 5 M aqueous potassium hydrate solution (103 mL, 0.51 mol) was added dropwise thereto. The reaction mixture was stirred at 0° C. for 30 min, and then the mixture was stirred at room temperature for 1 hour. To the reaction mixture, isopropyl acetate (100 mL) was added, and the insoluble matter was filtered off. The organic layer was discarded, the aqueous layer was washed with isopropyl acetate (100 mL), and then concentrated hydrochloric acid was added to the aqueous layer so as to have pH 3-4. The produced solid was collected by filtration and washed twice with water (20 mL). The obtained solid was dried at 50° C. under reduced pressure to obtain the title compound (8.47 g, yield 96%) as a light brown solid.

LCMS: m/z 199 $[M+H]^+$

HPLC retention time: 2.03 min (analysis condition Y)

Compound c-267

6,7-Difluoro-N-methoxy-N-methyl-1H-indazole-4-carboxamide

[Formula 558]

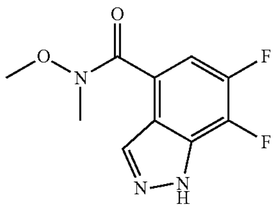

A solution of 6,7-difluoro-1H-indazole-4-carboxylic acid (compound c-266, 3.0 g, 15.14 mmol) in DMF (21 mL) in a reaction vessel was cooled to 0° C., and then N,O-dimethylhydroxylamine hydrochloride (1.77 g, 18.17 mmol) and a 50% solution of propylphosphonic acid anhydride in ethyl acetate (11.7 mL, 19.68 mmol) were added thereto. To this mixture, DIPEA (7.93 mL, 45.4 mmol) was added dropwise over 10 min. The reaction mixture was stirred for 30 min, then a 20% aqueous ammonium chloride solution (21 mL) was added thereto, and the mixture was extracted with ethyl acetate (21 mL). The operation in which ethyl acetate (21 mL) was added to the aqueous layer and the mixture was extracted again was repeated twice. The obtained organic layer was mixed and then sequentially washed with a 5% aqueous sodium bicarbonate solution (30 mL) and a 10% aqueous sodium chloride solution (30 mL), and then the organic layer was concentrated under reduced pressure. The obtained crude product was dissolved in acetone (9 mL) at room temperature, and n-heptane (36 mL) was added thereto. This suspension was cooled to 0° C., then stirred for 1 hour, and collected by filtration, and then the solid was washed with heptane. The obtained solid was dried at 40° C. under reduced pressure to obtain the title compound (2.62 g, yield 72%) as a light brown solid.

LCMS: m/z 242 $[M+H]^+$

HPLC retention time: 1.29 min (analysis condition Y)

Compound c-102

6,7-Difluoro-N-methoxy-N-methyl-1-(oxan-2-yl)indazole-4-carboxamide

[Formula 559]

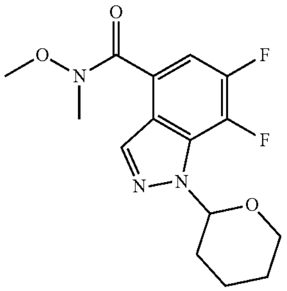

A solution of 6,7-difluoro-N-methoxy-N-methyl-1H-indazole-4-carboxamide (compound c-267, 2 g, 8.29 mmol) in DCM (20 mL) in a reaction vessel was cooled to 10° C., p-toluenesulfonic acid monohydrate (0.158 g, 0.829 mmol) was added thereto, and then 3,4-dihydro-2H-pyran (2.27 mL, 24.88 mmol) was added dropwise thereto. The reaction mixture was heated to 35° C. and stirred for 30 min. The reaction mixture was cooled to 10° C., and a 5% aqueous sodium bicarbonate solution (14 mL) was added thereto. The organic layer was separated and concentrated under reduced pressure, and then toluene (14 mL) was added and azeotroped to obtain the title compound (2.81 g).

LCMS: m/z 326 $[M+H]^+$

HPLC retention time: 0.72 min (analysis condition A)

Compound c-269

6,7-Difluoro-N-methoxy-N-methyl-2-(oxan-2-yl)indazole-4-carboxamide

[Formula 560]

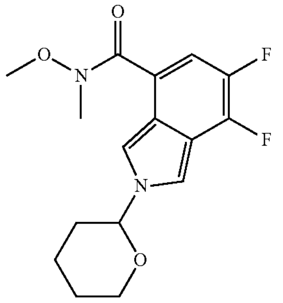

To a solution of 6,7-difluoro-N-methoxy-N-methyl-1H-indazole-4-carboxamide (compound c-267, 14.9 g, 61.7 mmol) in DCM (298 mL) in a reaction vessel, 3,4-dihydro-2H-pyran (16.9 mL, 185 mmol) and pyridinium p-toluenesulfonate (1.55 g, 6.18 mmol) were added, and the mixture was stirred at room temperature for 6 hours. To the reaction mixture, a 20% aqueous sodium bicarbonate solution was added, and the mixture was extracted with DCM. The organic layer was washed with a 10% aqueous sodium chloride solution and then concentrated under reduced pressure. The obtained residue was purified by silica gel column chromatography to obtain the title compound (20 g, yield 100%) as a colorless oily substance.

LCMS: m/z 326 [M+H]$^+$

HPLC retention time: 1.87 min (analysis condition Y)

Compound c-270

6-Iodo-8-methylquinolin-5-amine

[Formula 561]

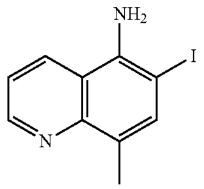

A suspension of 8-methylquinolin-5-amine (3.0 g, 18.96 mmol) in acetonitrile (21.0 mL) in a reaction vessel was cooled with ice, TFA (1.53 mL, 19.91 mmol), N-iodosuccinimide (4.48 g, 19.91 mmol), and acetonitrile (12.0 mL) were added thereto, and the mixture was stirred under ice cooling for 30 min. To the reaction mixture, a 5% aqueous sodium sulfite solution (20.0 mL) was added, and the mixture was stirred at room temperature. A 5% aqueous sodium sulfite solution (15.0 mL) and a 5% aqueous sodium carbonate solution (10.0 mL) were further added thereto, and the mixture was stirred. The solid was collected by filtration and washed with water to obtain the title compound (4.71 g, yield 87%) as a brown solid.

LCMS: m/z 285 [M+H]$^+$

HPLC retention time: 1.09 min (analysis condition Y)

Compound c-271

(E)-N'-(6-iodo-8-methylquinolin-5-yl)-N,N-dimethylmethanimidamide

[Formula 562]

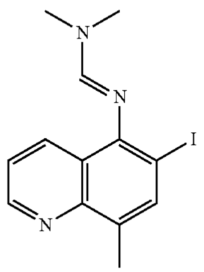

To a suspension of 6-iodo-8-methylquinolin-5-amine (compound c-270, 4.00 g, 14.08 mmol) in ethanol (20.0 mL) in a reaction vessel, N,N-dimethylformamidedimethylacetal (3.77 mL, 28.2 mmol) was added, and the mixture was stirred at 90° C. for 2 hours. The reaction mixture was concentrated under reduced pressure, a 10% aqueous sodium chloride solution (30 mL) was added thereto, and the mixture was extracted with isopropyl acetate (30 mL). The obtained organic layer was concentrated under reduced pressure, TBME and n-heptane were added to the concentrated residue, and the mixture was stirred. The solid was collected by filtration and washed with n-heptane to obtain the title compound (3.8 g, yield 80%) as a light brown solid.

LCMS: m/z 340 [M+H]$^+$

HPLC retention time: 0.77 min (analysis condition Y)

Compound c-272

(E)-N'-[6-[6,7-difluoro-1-(oxan-2-yl)indazole-4-carbonyl]-8-methylquinolin-5-yl]-N,N-dimethylmethanimidamide

[Formula 563]

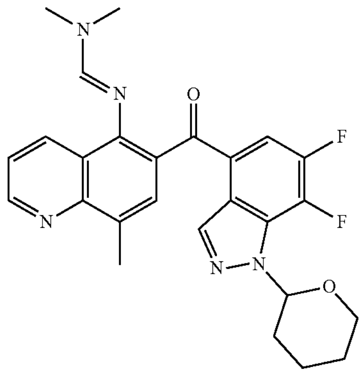

A solution of (E)-N'-(6-iodo-8-methylquinolin-5-yl)-N,N-dimethylmethanimidamide (compound c-271, 146 mg, 0.430 mmol) in toluene (1.5 mL) in a reaction vessel was cooled to −10° C., a 1.3 M solution of isopropylmagnesium chloride-lithium chloride complex in THF (0.355 mL, 0.461 mmol) was added thereto, and the mixture was stirred at −10° C. for 1 hour. To the reaction mixture, a solution of 6,7-difluoro-N-methoxy-N-methyl-1-(oxan-2-yl)indazole-4-carboxamide (compound c-102, 100 mg, 0.307 mmol) in toluene (0.25 mL) was added dropwise. The reaction mixture was stirred at −10° C. for 10 min and then stirred at 0° C. for 30 min. To the reaction mixture, a 17% aqueous ammonium chloride solution was added, and the mixture was extracted with ethyl acetate and concentrated under reduced pressure. To the residue, acetonitrile (1.0 mL) was added, and the mixture was dissolved at 70° C. and then cooled to 35° C. The solid was collected by filtration and washed with acetonitrile (2 mL) to obtain the title compound (36 mg, yield 24%) as a yellow solid.

LCMS: m/z 478 [M+H]$^+$

HPLC retention time: 1.84 min (analysis condition Y)

Compound c-273

(5-Amino-8-methylquinolin-6-yl) (6,7-difluoro-2-(tetrahydro-2H-pyran-2-yl)-1H-indazol-4-yl) methanone

[Formula 564]

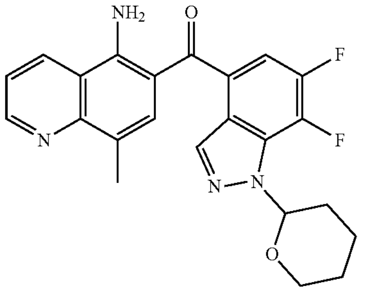

To (E)-N'-[6-[6,7-difluoro-1-(oxan-2-yl)indazole-4-carbonyl]-8-methylquinolin-5-yl]-N,N-dimethylmethanimidamide (compound c-272, 100 mg, 0.21 mmol) in a reaction vessel, a mixed solution (2.2 mL) of DMSO/water (10:1) was added, and the mixture was stirred. This mixed solution was cooled to 10° C., a 50% aqueous potassium hydrate solution (78 μL, 1.05 mmol) was added thereto, and the mixture was stirred for 2 hours 30 min. To the reaction mixture, a 20% aqueous ammonium chloride solution (2 mL) was added dropwise, and the mixture was stirred for 30 min. The solid was collected by filtration and then washed with water (2 mL) to obtain the title compound (82 mg, yield 93%) as a solid.

LCMS: m/z 423 $[M+H]^+$

HPLC retention time: 4.05 min (analysis condition X)

Compound c-274

2-Chloro-N-[6-[6,7-difluoro-1-(oxan-2-yl)indazole-4-carbonyl]-8-methylquinolin-5-yl]acetamide

[Formula 565]

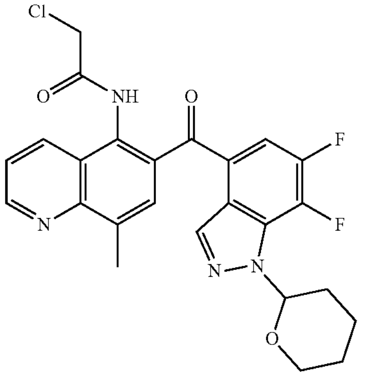

To a solution of (5-amino-8-methylquinolin-6-yl)-[6,7-difluoro-1-(oxan-2-yl)indazol-4-yl]methanone (compound c-273, 1.13 g, 2.67 mmol) in DMA (22.6 mL) in a reaction vessel, chloroacetyl chloride (0.321 mL, 4.01 mmol) was added, and the mixture was stirred at room temperature for 1 hour to obtain a solution of the title compound in DMA.

LCMS: m/z 499 $[M+H]^+$

HPLC retention time: 0.99 min (analysis condition A)

Compound c-275

4-[6,7-Difluoro-1-(oxan-2-yl)indazol-4-yl]-6-methyl-3-pyridin-1-ium-1-yl-1H-1,7-phenanthrolin-2-one; chloride

[Formula 566]

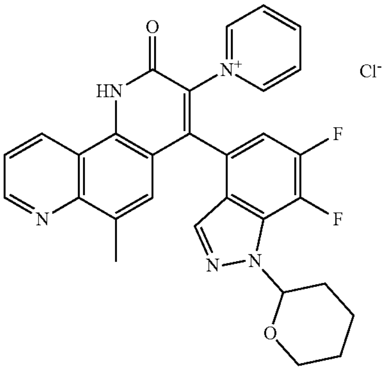

To the solution of 2-chloro-N-[6-[6,7-difluoro-1-(oxan-2-yl)indazole-4-carbonyl]-8-methylquinolin-5-yl]acetamide (compound c-274) in DMA in a reaction vessel, pyridine (11.3 mL) was added, and the mixture was stirred at 65° C. for 2 hours. The reaction mixture was cooled to room temperature to obtain a solution of the title compound in DMA/pyridine.

LCMS: m/z 524 $[M]^+$

HPLC retention time: 0.55 min (analysis condition A)

Compound c-276

3-Amino-4-[6,7-difluoro-1-(oxan-2-yl)indazol-4-yl]-6-methyl-1H-1,7-phenanthrolin-2-one

[Formula 567]

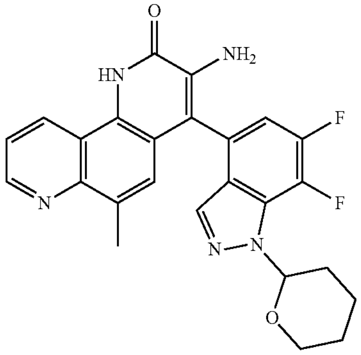

A solution of 4-[6,7-difluoro-1-(oxan-2-yl)indazol-4-yl]-6-methyl-3-pyridin-1-ium-1-yl-1H-1,7-phenanthrolin-2-one; chloride (compound c-275) in DMA/pyridine in a reaction vessel was cooled to 0° C., hydrazine monohydrate (1.3 mL, 26.7 mmol) was added thereto, and the mixture was stirred at 65° C. for 7 hours. Water (100 mL) was added thereto at room temperature, and the produced solid was collected by filtration and washed with a mixed solution (50 mL) of acetonitrile/water (1/4) to obtain the title compound (1.14 g, yield 92%) as a light brown solid.

LCMS: m/z 462 $[M+H]^+$

HPLC retention time: 0.69 min (analysis condition A)

Compound c-277

(E)-N'-[6-[6,7-difluoro-2-(oxan-2-yl)indazole-4-carbonyl]-8-methylquinolin-5-yl]-N,N-dimethyl-methanimidamide

[Formula 568]

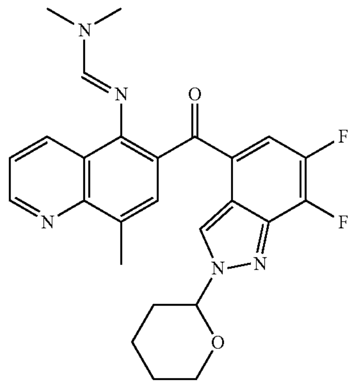

A solution of (E)-N'-(6-iodo-8-methylquinolin-5-yl)-N,N-dimethylmethanimidamide (compound c-271, 416 mg, 1.23 mmol) in toluene (2.0 mL) in a reaction vessel was cooled to −20° C., a 1.3 M solution of isopropylmagnesium chloride-lithium chloride complex in THF (1.01 mL, 1.31 mmol) was added thereto, the mixture was stirred at −20° C. for 45 min, then a 1.3 M solution of isopropylmagnesium chloride-lithium chloride complex in THF (0.2 mL, 0.26 mmol) was added thereto, and the mixture was stirred for 40 min. To the reaction mixture, a solution of 6,7-difluoro-N-methoxy-N-methyl-2-(oxan-2-yl)indazole-4-carboxamide (compound c-269, 285 mg, 0.88 mmol) in toluene (1.5 mL) was added dropwise, and the mixture was stirred at −20° C. for 45 min. To the reaction mixture, a 15% aqueous ammonium chloride solution was added, and the mixture was extracted with ethyl acetate. The organic layer was washed with a 15% aqueous ammonium chloride solution and 10% saline, and concentrated under reduced pressure. To the residue, acetonitrile (2 mL) was added, the mixture was stirred, then water (1.4 mL) was added thereto, and further stirred for 1.5 hours. The solid was collected by filtration and washed with a mixed solution of acetonitrile (2 mL) and water (2 mL) to obtain the title compound (171 mg, yield 41%) as a yellow solid.

LCMS: m/z 478 $[M+H]^+$

HPLC retention time: 1.61 min (analysis condition Y)

Compound c-278

(5-Amino-8-methylquinolin-6-yl) (6,7-difluoro-2-(tetrahydro-2H-pyran-2-yl)-2H-indazol-4-yl) methanone

[Formula 569]

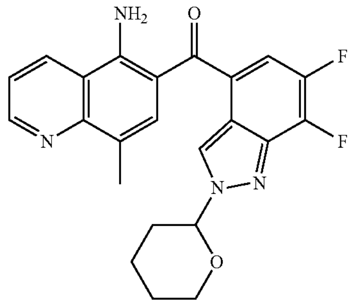

To (E)-N'-[6-[6,7-difluoro-2-(oxan-2-yl)indazole-4-carbonyl]-8-methylquinolin-5-yl]-N,N-dimethylmethanimidamide (compound c-277, 10 mg, 0.02 mmol) in a reaction vessel, a mixed solution (0.22 mL) of DMSO/water (10:1) was added, and the mixture was stirred. This mixed solution was cooled to 10° C., a 50% aqueous potassium hydrate solution (7.8 μL, 0.11 mmol) was added thereto, and the mixture was stirred for 1 hour 30 min. To the reaction mixture, a 20% aqueous ammonium chloride solution (0.2 mL) was added dropwise, and the mixture was stirred for 1 hour. The solid was collected by filtration and then washed with water to obtain the title compound (7.1 mg, yield 80%) as a solid.

LCMS: m/z 423 $[M+H]^+$

HPLC retention time: 2.26 min (analysis condition Y)

Compound c-279

2-Chloro-N-[6-[6,7-difluoro-2-(oxan-2-yl)indazole-4-carbonyl]-8-methylquinolin-5-yl]acetamide

[Formula 570]

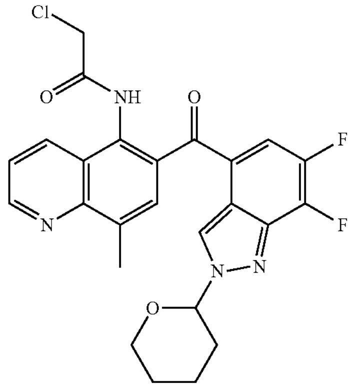

A solution of (5-amino-8-methylquinolin-6-yl)-[6,7-difluoro-2-(oxan-2-yl)indazol-4-yl]methanone (compound c-278, 534 mg, 1.18 mmol) in DMA (8 mL) in a reaction vessel was cooled to 0° C., chloroacetyl chloride (0.14 mL, 1.78 mmol) was added thereto, and the mixture was stirred at room temperature for 1 hour to obtain a solution of the title compound in DMA.

LCMS: m/z 499 $[M+H]^+$

HPLC retention time: 2.38 min (analysis condition Y)

Compound c-280

4-[6,7-Difluoro-2-(oxan-2-yl)indazol-4-yl]-6-methyl-3-pyridin-1-ium-1-yl-1H-1,7-phenanthrolin-2-one; chloride

[Formula 571]

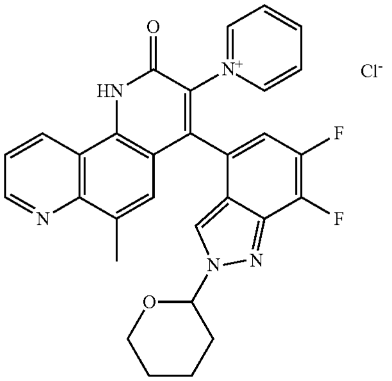

To the solution of 2-chloro-N-[6-[6,7-difluoro-2-(oxan-2-yl)indazole-4-carbonyl]-8-methylquinolin-5-yl]acetamide (compound c-279) in DMA in a reaction vessel, pyridine (5 mL) was added, and the mixture was stirred at 60° C. for 4 hours. The reaction mixture was cooled to room temperature to obtain a solution of the title compound in DMA/pyridine.

LCMS: m/z 524 $[M]^+$

HPLC retention time: 1.48 min (analysis condition Y)

Compound c-281

3-Amino-4-[6,7-difluoro-2-(oxan-2-yl)indazol-4-yl]-6-methyl-1H-1,7-phenanthrolin-2-one

[Formula 572]

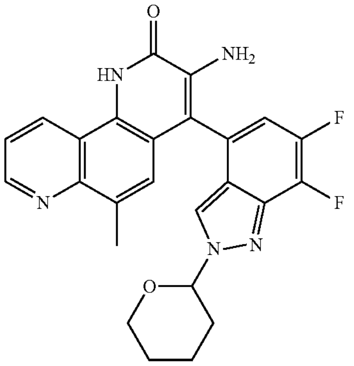

To the solution of the compound c-280 in DMA/pyridine in a reaction vessel, 80% hydrazine monohydrate (0.72 mL, 11.8 mmol) was added, and the mixture was stirred at 60° C. for 1 hour. Water (12.5 mL) was added thereto at room temperature, and the produced solid was collected by filtration and washed with water (5 mL) to obtain the title compound (448.4 mg, yield 76%) as a light brown solid.

LCMS: m/z 462 $[M+H]^+$

HPLC retention time: 2.07 min (analysis condition Y)

Compound C190

3-Amino-4-(6,7-difluoro-1H-indazol-4-yl)-6-methyl-1H-1,7-phenanthrolin-2-one

[Formula 573]

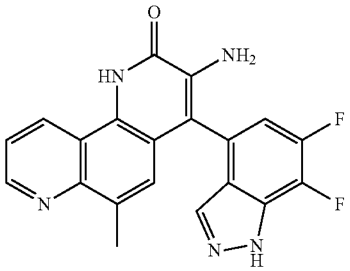

To a solution of 3-amino-6-bromo-4-(6,7-difluoro-1H-indazol-4-yl)-1H-1,7-phenanthrolin-2-one (compound C66, 82.8 mg, 0.187 mmol) in DMA (2.48 mL) in a reaction vessel, a 2 M solution of methylzinc chloride in THF (936 μL, 1.87 mmol) and CPhos Pd G3 (15.1 mg, 0.019 mmol) were added, the reaction vessel was degassed under reduced pressure and subjected to nitrogen replacement, and then the mixture was stirred at room temperature for 1 hour. The reaction mixture was purified by reversed phase column chromatography (0.1% aqueous formic acid solution/0.1% formic acid in acetonitrile solution) to obtain the title compound (58.5 mg, yield 83%) as a grayish solid.

LCMS: m/z 378 $[M+H]^+$

HPLC retention time: 0.50 min (analysis condition A)

Compound C191

3-Amino-6-cyclopropyl-4-(6,7-difluoro-1H-indazol-4-yl)-1H-1,7-phenanthrolin-2-one

[Formula 574]

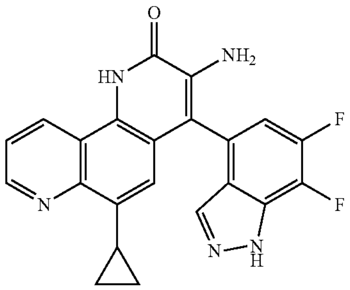

The title compound was synthesized from 3-amino-6-bromo-4-(6,7-difluoro-1H-indazol-4-yl)-1H-1,7-phenanthrolin-2-one (compound C66) under the same conditions as the production example of the compound B22.

LCMS: m/z 404 $[M+H]^+$

HPLC retention time: 0.51 min (analysis condition A)

Compound C192

3-Amino-4-(6,7-difluoro-1H-indazol-4-yl)-6-ethyl-1H-1,7-phenanthrolin-2-one

[Formula 575]

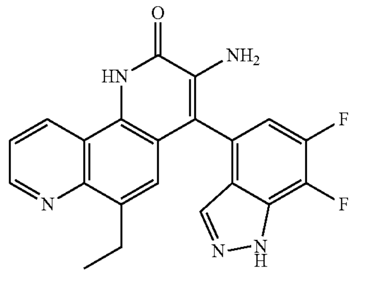

The title compound was synthesized from 3-amino-6-bromo-4-(6,7-difluoro-1H-indazol-4-yl)-1H-1,7-phenanthrolin-2-one (compound C66) under the same conditions as the production example of the compound B22, except that a 1 M solution of diethylzinc in hexane was used instead of the 0.5 M solution of cyclopropylzinc bromide in THE used in the production example of the compound B22.

LCMS: m/z 392 $[M+H]^+$

HPLC retention time: 0.57 min (analysis condition A)

Compound C195

3-Amino-4-(7-chloro-6-fluoro-1H-indazol-4-yl)-6-cyclopropyl-1H-1,7-phenanthrolin-2-one

[Formula 576]

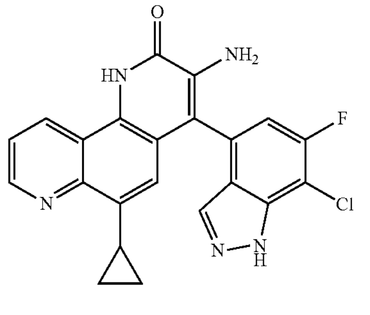

The title compound was synthesized from 3-amino-6-bromo-4-(7-chloro-6-fluoro-1H-indazol-4-yl)-1H-1,7-phenanthrolin-2-one (compound C75) under the same conditions as the production example of the compound B22, except that THF was used instead of DMA used in the production example of the compound B22.

LCMS: m/z 420 $[M+H]^+$

HPLC retention time: 0.56 min (analysis condition A)

Compound C196

3-Amino-4-(7-chloro-6-fluoro-1H-indazol-4-yl)-6-methyl-1H-1,7-phenanthrolin-2-one

[Formula 577]

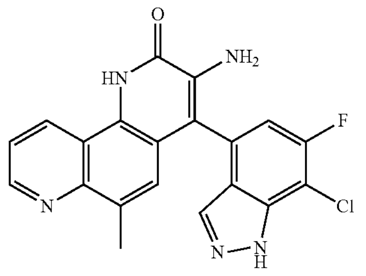

The title compound was synthesized from 3-amino-6-bromo-4-(7-chloro-6-fluoro-1H-indazol-4-yl)-1H-1,7-phenanthrolin-2-one (compound C75) under the same conditions as the production example of the compound B22, except that a 2 M solution of methylzincchloride in THF was used instead of the 0.5 M solution of cyclopropylzinc bromide in THE used in the production example of the compound B22.

LCMS: m/z 394 $[M+H]^+$

HPLC retention time: 0.53 min (analysis condition A)

Compound C143

3-Amino-4-(7-chloro-1H-indazol-4-yl)-6-cyclopropyl-1H-1,7-phenanthrolin-2-one

[Formula 578]

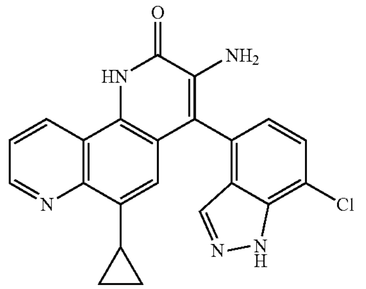

LCMS: m/z 402 $[M+H]^+$

HPLC retention time: 0.53 min (analysis condition A)

Compound C144

3-Amino-4-(7-chloro-1H-indazol-4-yl)-1H-1,7-phenanthrolin-2-one

[Formula 579]

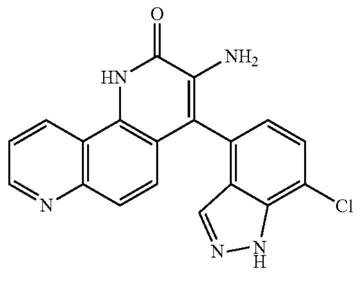

C143 and C144 were synthesized from 3-amino-6-bromo-4-[7-chloro-2-(oxan-2-yl)indazol-4-yl]-1H-1,7-phenanthrolin-2-one (compound c-177) under the same conditions as the production examples of the compounds B22 and B48, except that THF was used instead of DMA used in the production example of the compound B22.

LCMS: m/z 362 $[M+H]^+$

HPLC retention time: 0.45 min (analysis condition A)

Compound C147

3-Amino-4-(7-chloro-1H-indazol-4-yl)-6-cyclobutyl-1H-1,7-phenanthrolin-2-one

[Formula 580]

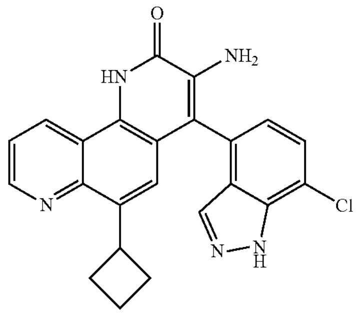

The title compound was synthesized from 3-amino-6-bromo-4-(7-chloro-1H-indazol-4-yl)-1H-1,7-phenanthrolin-2-one (compound C73) under the same conditions as the production example of the compound B22, except that a 0.5 M solution of cyclobutylzinc bromide in THF and THE were used instead of the 0.5 M solution of cyclopropylzinc bromide in THF and DMA used in the production example of the compound B22.

LCMS: m/z 416 $[M+H]^+$

HPLC retention time: 0.66 min (analysis condition A)

Compound C148

3-Amino-4-(7-chloro-1H-indazol-4-yl)-2-oxo-1H-1,7-phenanthroline-6-carbonitrile

[Formula 581]

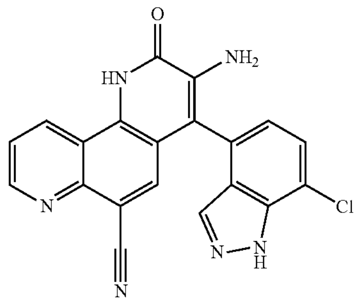

LCMS: m/z 387 $[M+H]^+$

HPLC retention time: 0.56 min (analysis condition A)

Compound C149

3-Amino-4-(7-cyano-1H-indazol-4-yl)-2-oxo-1H-1,7-phenanthroline-6-carbonitrile

[Formula 582]

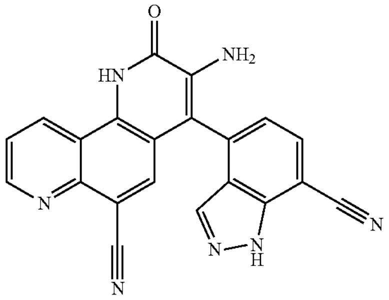

The compound C148 and the compound C149 were synthesized from 3-amino-6-bromo-4-(7-chloro-1H-indazol-4-yl)-1H-1,7-phenanthrolin-2-one (compound C73) under the same conditions as the production example of the compound B26, except that XPhos Pd G4 and DMSO were used instead of tetrakis (triphenylphosphine)palladium (0) and DMA used in the production example of the compound B26.

LCMS: m/z 378 $[M+H]^+$

HPLC retention time: 0.52 min (analysis condition A)

Compound C150

3-Amino-4-(7-chloro-1H-indazol-4-yl)-6-ethyl-1H-1,7-phenanthrolin-2-one

[Formula 583]

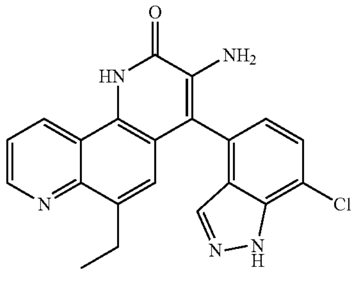

The title compound was synthesized from 3-amino-6-bromo-4-(7-chloro-1H-indazol-4-yl)-1H-1,7-phenanthrolin-2-one (compound C73) under the same conditions as the production example of the compound B22, except that a 1 M solution of diethylzinc in hexane and THF were used instead of the 0.5 M solution of cyclopropylzinc bromide in THF and DMA used in the production example of the compound B22.

LCMS: m/z 390 $[M+H]^+$

HPLC retention time: 0.58 min (analysis condition A)

Compound C151

3-Amino-4-(7-chloro-1H-indazol-4-yl)-6-cyclopentyl-1H-1,7-phenanthrolin-2-one

[Formula 584]

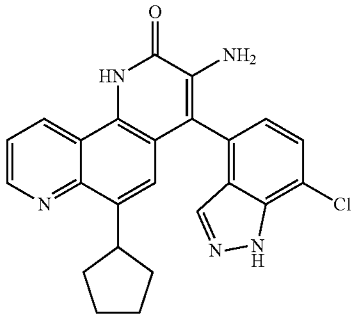

The title compound was synthesized from 3-amino-6-bromo-4-(7-chloro-1H-indazol-4-yl)-1H-1,7-phenanthrolin-2-one (compound C73) under the same conditions as the production example of the compound B22, except that a 0.5 M solution of cyclopentylzinc bromide in THF and THE were used instead of the 0.5 M solution of cyclopropylzinc bromide in THF and DMA used in the production example of the compound B22.

LCMS: m/z 430 $[M+H]^+$

HPLC retention time: 0.71 min (analysis condition A)

Compound C152

3-Amino-4-(7-chloro-1H-indazol-4-yl)-6-methyl-1H-1,7-phenanthrolin-2-one

[Formula 585]

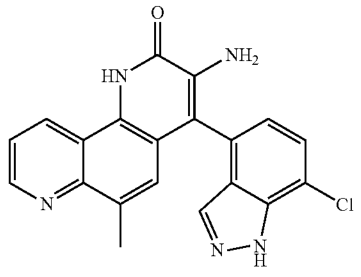

LCMS: m/z 376 $[M+H]^+$

HPLC retention time: 0.50 min (analysis condition A)

Compound C153

3-Amino-6-methyl-4-(7-methyl-1H-indazol-4-yl)-1H-1,7-phenanthrolin-2-one

[Formula 586]

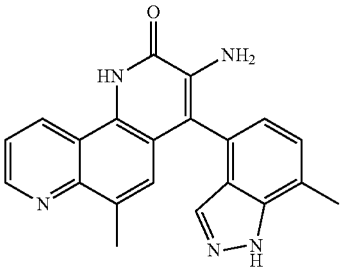

The compound C152 and the compound C153 were synthesized from 3-amino-6-bromo-4-(7-chloro-1H-indazol-4-yl)-1H-1,7-phenanthrolin-2-one (compound C73) under the same conditions as the production example of the compound B22, except that a 2 M solution of methylzinc-chloride in THF was used instead of the 0.5 M solution of cyclopropylzinc bromide in THF used in the production example of the compound B22.

LCMS: m/z 356 $[M+H]^+$

HPLC retention time: 0.47 min (analysis condition A)

Compound c-188

4-Bromo-5-fluoro-2-(oxan-2-yl)indazole

[Formula 587]

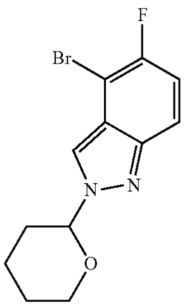

The title compound was synthesized from 4-bromo-5-fluoro-1H-indazole under the same conditions as the production example of the compound c-3.

LCMS: m/z 299 $[M+H]^+$

HPLC retention time: 0.83 min (analysis condition Q)

Compound c-189

(2,4,6-trichlorophenyl) 5-fluoro-2-(oxan-2-yl)indazole-4-carboxylate

[Formula 588]

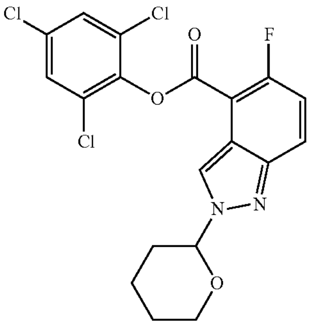

The title compound was synthesized from 4-bromo-5-fluoro-2-(oxan-2-yl)indazole (compound c-188) under the same conditions as the production example of the compound c-4.

LCMS: m/z 443 $[M+H]^+$

HPLC retention time: 1.07 min (analysis condition Q)

Compound c-190

5-Fluoro-2-(oxan-2-yl)indazole-4-carboxylic acid

[Formula 589]

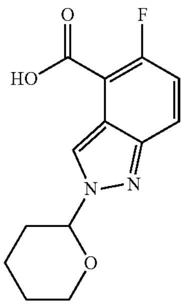

The title compound was synthesized from (2,4,6-trichlorophenyl) 5-fluoro-2-(oxan-2-yl)indazole-4-carboxylate (compound c-189) under the same conditions as the production example of the compound c-5.

LCMS: m/z 265 $[M+H]^+$

HPLC retention time: 0.53 min (analysis condition Q)

Compound c-191

5-Fluoro-N-methoxy-N-methyl-2-(oxan-2-yl)indazole-4-carboxamide

[Formula 590]

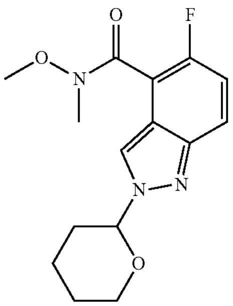

The title compound was synthesized from 5-fluoro-2-(oxan-2-yl)indazole-4-carboxylic acid (compound c-190) under the same conditions as the production example of the compound b-2, except that triethylamine and THF were used instead of DIPEA and DMF used in the production example of the compound b-2.

LCMS: m/z 308 $[M+H]^+$

HPLC retention time: 0.56 min (analysis condition Q)

Compound c-192

(E)-N'-[8-bromo-6-[5-fluoro-2-(oxan-2-yl)indazole-4-carbonyl]quinolin-5-yl]-N,N-dimethylmethanimidamide

[Formula 591]

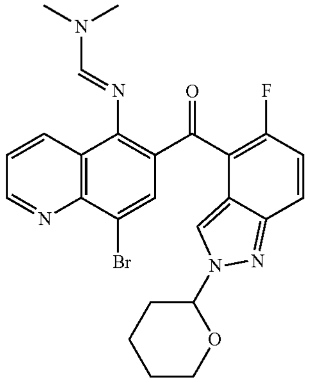

The title compound was synthesized from (E)-N'-(8-bromo-6-iodoquinolin-5-yl)-N,N-dimethylmethanimidamide (compound c-2) and 5-fluoro-N-methoxy-N-methyl-2-(oxan-2-yl)indazole-4-carboxamide (compound c-191) under the same conditions as the production example of the compound b-26.

LCMS: m/z 524 $[M+H]^+$

HPLC retention time: 0.65 min (analysis condition Q)

Compound c-193

(5-Amino-8-bromoquinolin-6-yl)-[5-fluoro-2-(oxan-2-yl)indazol-4-yl]methanone

[Formula 592]

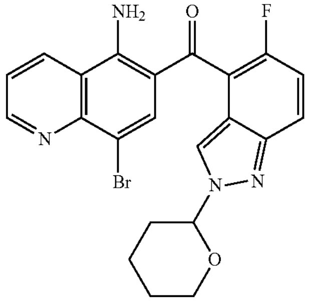

The title compound was synthesized from (E)-N'-[8-bromo-6-[5-fluoro-2-(oxan-2-yl)indazole-4-carbonyl]quinolin-5-yl]-N,N-dimethylmethanimidamide (compound c-192) under the same conditions as the production example of the compound b-27, except that DMF was used instead of DMSO used in the production example of the compound b-27.

LCMS: m/z 469 $[M+H]^+$

HPLC retention time: 0.75 min (analysis condition Q)

Compound C154

3-Amino-6-bromo-4-(5-fluoro-1H-indazol-4-yl)-1H-1,7-phenanthrolin-2-one

[Formula 593]

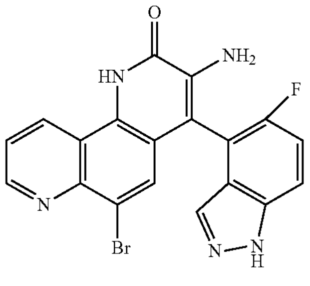

The title compound was synthesized from (5-amino-8-bromoquinolin-6-yl)-[5-fluoro-2-(oxan-2-yl)indazol-4-yl]methanone (compound c-193) under the same conditions as the production examples of the compounds b-28, b-29, b-30, and b-9.

LCMS: m/z 424 $[M+H]^+$

HPLC retention time: 0.54 min (analysis condition A)

Compound C155

3-Amino-4-(5-fluoro-1H-indazol-4-yl)-6-methyl-1H-1,7-phenanthrolin-2-one

[Formula 594]

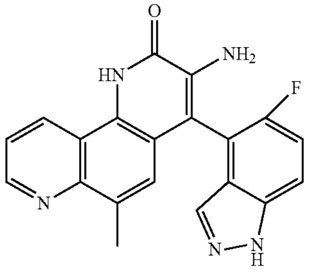

The title compound was synthesized from 3-amino-6-bromo-4-(5-fluoro-1H-indazol-4-yl)-1H-1,7-phenanthrolin-2-one (compound C154) under the same conditions as the production example of the compound B22, except that XPhos Pd G4 and a 2 M solution of methylzinc chloride in THF were used instead of CPhos Pd G3 and the 0.5 M solution of cyclopropylzinc bromide in THE used in the production example of the compound B22.

LCMS: m/z 360 $[M+H]^+$

HPLC retention time: 0.44 min (analysis condition A)

Compound c-198

(5-Amino-8-cyclopropylquinolin-6-yl)-[5-fluoro-2-(oxan-2-yl)indazol-4-yl]methanone

[Formula 595]

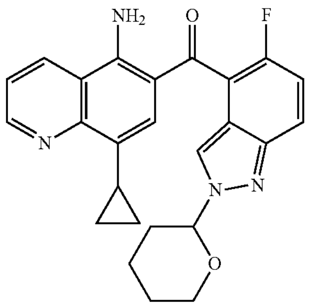

The title compound was synthesized from (5-amino-8-bromoquinolin-6-yl)-[5-fluoro-2-(oxan-2-yl)indazol-4-yl] methanone (compound c-193) under the same conditions as the production example of the compound B22, except that XPhos Pd G4 was used instead of CPhos Pd G3 used in the production example of the compound B22.

LCMS: m/z 431.6 $[M+H]^+$

HPLC retention time: 0.64 min (analysis condition Q)

Compound C156

3-Amino-6-cyclopropyl-4-(5-fluoro-1H-indazol-4-yl)-1H-1,7-phenanthrolin-2-one (racemate)

[Formula 596]

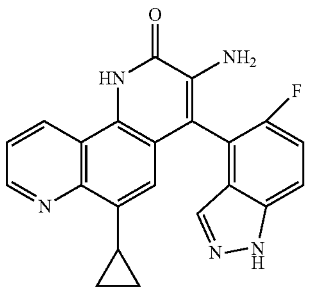

The title compound was synthesized from the compound (5-amino-8-cyclopropylquinolin-6-yl)-[5-fluoro-2-(oxan-2-yl)indazol-4-yl]methanone (c-198) under the same conditions as the production examples of the compounds b-28, b-29, b-30, and b-9.

LCMS: m/z 386.6 $[M+H]^+$

HPLC retention time: 0.45 min (analysis condition A)

Compound C157

(R)-3-amino-6-cyclopropyl-4-(5-fluoro-1H-indazol-4-yl)-1H-1,7-phenanthrolin-2-one

[Formula 597]

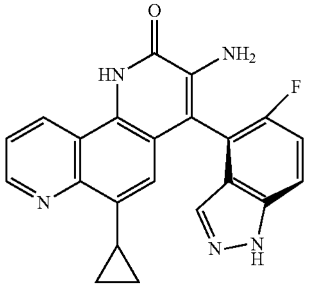

LCMS: m/z 386 $[M+H]^+$

HPLC retention time: 0.45 min (analysis condition A)

Chiral HPLC retention time: 5.48 min (analysis condition P)

Compound C158

(S)-3-amino-6-cyclopropyl-4-(5-fluoro-1H-indazol-4-yl)-1H-1,7-phenanthrolin-2-one

[Formula 598]

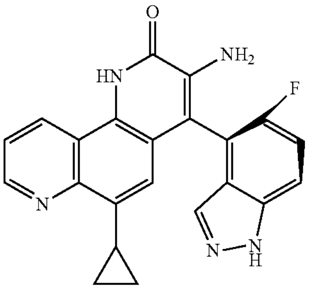

3-Amino-6-cyclopropyl-4-(5-fluoro-1H-indazol-4-yl)-1H-1,7-phenanthrolin-2-one (compound C156) was purified by chiral preparative HPLC (CHIRALCEL OZ-3, 4.6×250 mm, 5 μm, hexane/EtOH) to obtain each of the compound C157 (7.3 mg) and the compound C158 (7.1 mg) as a solid.

LCMS: m/z 386 $[M+H]^+$

HPLC retention time: 0.45 min (analysis condition A)

Chiral HPLC retention time: 8.94 min (analysis condition P)

Compound c-202 tert-Butyl 3-[bis[(2-methylpropan-2-yl)oxycarbonyl]amino]-6-bromo-4-[7-fluoro-1-[(2-methylpropan-2-yl)oxycarbonyl]indazol-4-yl]-2-oxo-1,7-phenanthroline-1-carboxylate

[Formula 599]

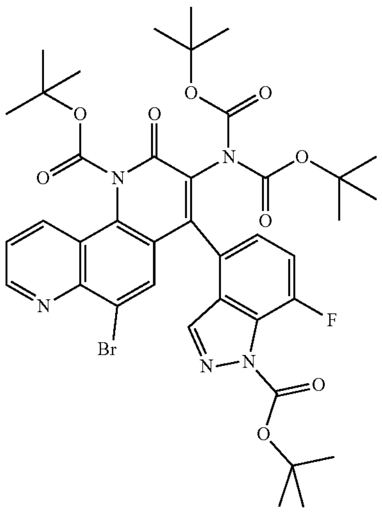

The title compound was synthesized from 3-amino-6-bromo-4-(7-fluoro-1H-indazol-4-yl)-1H-1,7-phenanthrolin-2-one (compound C1) under the same conditions as the production example of the compound c-171.

LCMS: m/z 824 $[M+H]^+$

HPLC retention time: 1.70 min (analysis condition F)

Compound C163

3-Amino-6-(4,4-difluorocyclohexyl)-4-(7-fluoro-1H-indazol-4-yl)-1H-1,7-phenanthrolin-2-one

[Formula 600]

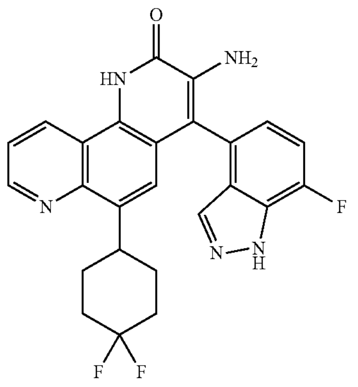

(1) To a suspension of 5,7-di-tert-butyl-3-phenylbenzo[d]oxazol-3-ium tetrafluoroborate (CAS number: 1207294-92-5, 30.7 mg, 0.078 mmol) and 4,4-difluorocyclohexan-1-ol (11.56 mg, 0.085 mmol) in TBME (920 μL) in a reaction vessel, pyridine (6.26 μL, 0.078 mmol) was added, and the mixture was stirred at room temperature under nitrogen atmosphere for 5 minutes.

(2) To tert-butyl 3-[bis[(2-methylpropan-2-yl)oxycarbonyl]amino]-6-bromo-4-[7-fluoro-1-[(2-methylpropan-2-yl)oxycarbonyl]indazol-4-yl]-2-oxo-1,7-phenanthroline-1-carboxylate (compound c-202, 40 mg, 0.049 mmol), $NiBr_2$-dtbbpy (CAS number: 1894189-67-3, 1.77 mg, 3.64 μmol), (4,4'-di-tert-butyl-2,2'-bipyridine)bis[(2-pyridinyl)phenyl]iridium(III) hexafluorophosphate (CAS number: 676525-77-2, 0.78 mg, 0.728 μmol), quinuclidine (9.44 mg, 0.085 mmol), and phthalimide (1.61 mg, 10.91 μmol) in another reaction vessel, DMA (920 μL) was added under nitrogen atmosphere.

(3) The TBME suspension obtained in (1) was filtered, and then added to the DMA solution obtained in (2). The reaction mixture was stirred at 1500 rpm, and irradiated with LED light at a wavelength of 450 nm for 2 hours under nitrogen atmosphere, while air-cooling the reaction vessel by a blower, to cause the photoredox catalysis. To the reaction solution, an aqueous saturated sodium chloride solution was added, and the mixture was extracted with ethyl acetate. The organic layer was washed with an aqueous saturated sodium chloride solution and dried over anhydrous sodium sulfate, the drying agent was filtered off, and then the filtrate was concentrated under reduced pressure.

(4) To the obtained residue, DCM (1 mL) and TFA (0.1 mL) were added, and the mixture was stirred at room temperature for 3 hours. The reaction mixture was concentrated, and the obtained residue was purified by reversed phase column chromatography (0.1% aqueous TFA solution/0.1% TFA acetonitrile solution). The obtained mixed solution of the title compound in water/acetonitrile was concentrated, a saturated aqueous sodium bicarbonate solution was added thereto, and the mixture was extracted with ethyl acetate. The organic layer was dried over anhydrous sodium sulfate, the drying agent was filtered off, and then the filtrate was concentrated under reduced pressure to obtain the title compound (11.3 mg, yield 50%) as a colorless solid.

LCMS: m/z 464 $[M+H]^+$

HPLC retention time: 0.97 min (analysis condition F)

Compound C159

3-Amino-4-(7-fluoro-1H-indazol-4-yl)-6-(oxolan-3-yl)-1H-1,7-phenanthrolin-2-one

[Formula 601]

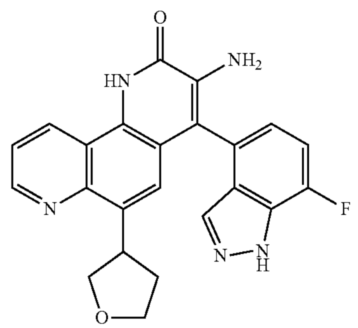

The title compound was synthesized from tert-butyl 3-[bis[(2-methylpropan-2-yl)oxycarbonyl]amino]-6-bromo-4-[7-fluoro-1-[(2-methylpropan-2-yl)oxycarbonyl]indazol-4-yl]-

2-oxo-1,7-phenanthroline-1-carboxylate (compound c-202) under the same conditions as the production example of the compound C163, except that 3-hydroxytetrahydrofuran was used instead of 4,4-difluorocyclohexan-1-ol used in the production example of the compound C163.

LCMS: m/z 416 $[M+H]^+$

HPLC retention time: 0.82 min (analysis condition I)

Compound C160

3-Amino-4-(7-fluoro-1H-indazol-4-yl)-6-(3-fluoropropyl)-1H-1,7-phenanthrolin-2-one

[Formula 602]

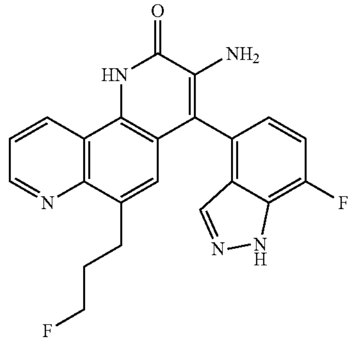

The title compound was synthesized from tert-butyl 3-[bis[(2-methylpropan-2-yl)oxycarbonyl]amino]-6-bromo-4-[7-fluoro-1-[(2-methylpropan-2-yl)oxycarbonyl]indazol-4-yl]-2-oxo-1,7-phenanthroline-1-carboxylate (compound c-202) under the same conditions as the production example of the compound C163, except that 3-fluoropropan-1-ol was used instead of 4,4-difluorocyclohexan-1-ol used in the production example of the compound C163.

LCMS: m/z 406 $[M+H]^+$

HPLC retention time: 0.81 min (analysis condition F)

Compound C161

3-Amino-4-(7-fluoro-1H-indazol-4-yl)-6-(3,3,3-trifluoropropyl)-1H-1,7-phenanthrolin-2-one

[Formula 603]

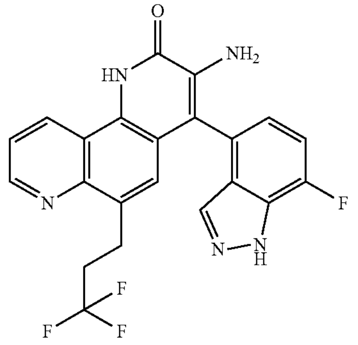

The title compound was synthesized from tert-butyl 3-[bis[(2-methylpropan-2-yl)oxycarbonyl]amino]-6-bromo-4-[7-fluoro-1-[(2-methylpropan-2-yl)oxycarbonyl]indazol-4-yl]-2-oxo-1,7-phenanthroline-1-carboxylate (compound c-202) under the same conditions as the production example of the compound C163, except that 3,3,3-trifluoro-1-propanol was used instead of 4,4-difluorocyclohexan-1-ol used in the production example of the compound C163.

LCMS: m/z 442 $[M+H]^+$

HPLC retention time: 0.99 min (analysis condition F)

Compound C162

3-Amino-6-(3,3-difluorocyclopentyl)-4-(7-fluoro-1H-indazol-4-yl)-1H-1,7-phenanthrolin-2-one

[Formula 604]

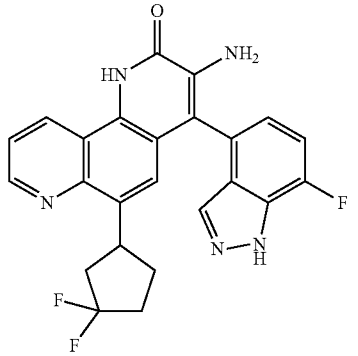

The title compound was synthesized from tert-butyl 3-[bis[(2-methylpropan-2-yl)oxycarbonyl]amino]-6-bromo-4-[7-fluoro-1-[(2-methylpropan-2-yl)oxycarbonyl]indazol-4-yl]-2-oxo-1,7-phenanthroline-1-carboxylate (compound c-202) under the same conditions as the production example of the compound C163, except that 3,3-difluorocyclopentan-1-ol was used instead of 4,4-difluorocyclohexan-1-ol used in the production example of the compound C163.

LCMS: m/z 450 $[M+H]^+$

HPLC retention time: 0.98 min (analysis condition F)

Compound C164

3-Amino-6-(3,3-difluorocyclobutyl)-4-(7-fluoro-1H-indazol-4-yl)-1H-1,7-phenanthrolin-2-one

[Formula 605]

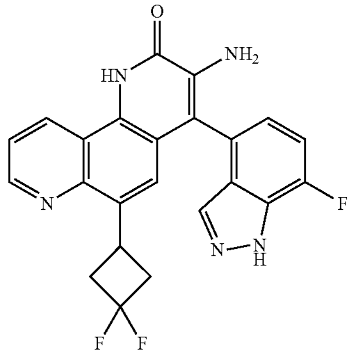

The title compound was synthesized from tert-butyl 3-[bis[(2-methylpropan-2-yl)oxycarbonyl]amino]-6-bromo-4-[7-fluoro-1-[(2-methylpropan-2-yl)oxycarbonyl]indazol-4-yl]-

2-oxo-1,7-phenanthroline-1-carboxylate (compound c-202) under the same conditions as the production example of the compound C163, except that 3,3-difluorocyclobutan-1-ol was used instead of 4,4-difluorocyclohexan-1-ol used in the production example of the compound C163.

LCMS: m/z 436 $[M+H]^+$

HPLC retention time: 0.96 min (analysis condition F)

Compound C166

3-Amino-6-(2,2-difluorospiro[3,3]heptan-6-yl)-4-(7-fluoro-1H-indazol-4-yl)-1H-1,7-phenanthrolin-2-one

[Formula 606]

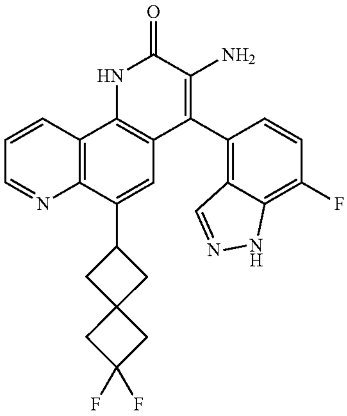

The title compound was synthesized from tert-butyl 3-[bis[(2-methylpropan-2-yl)oxycarbonyl]amino]-6-bromo-4-[7-fluoro-1-[(2-methylpropan-2-yl)oxycarbonyl]indazol-4-yl]-2-oxo-1,7-phenanthroline-1-carboxylate (compound c-202) under the same conditions as the production example of the compound C163, except that 6,6-difluorospiro[3,3]heptan-2-ol was used instead of 4,4-difluorocyclohexan-1-ol used in the production example of the compound C163.

LCMS: m/z 476 $[M+H]^+$

HPLC retention time: 0.99 min (analysis condition F)

Compound C167

3-Amino-6-(3,3-dimethylcyclobutyl)-4-(7-fluoro-1H-indazol-4-yl)-1H-1,7-phenanthrolin-2-one

[Formula 607]

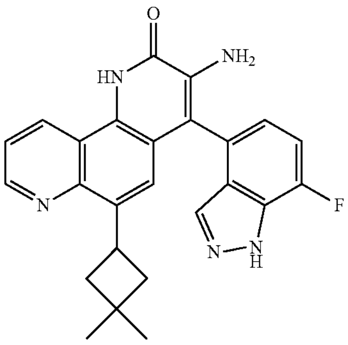

The title compound was synthesized from tert-butyl 3-[bis[(2-methylpropan-2-yl)oxycarbonyl]amino]-6-bromo-4-[7-fluoro-1-[(2-methylpropan-2-yl)oxycarbonyl]indazol-4-yl]-2-oxo-1,7-phenanthroline-1-carboxylate (compound c-202) under the same conditions as the production example of the compound C163, except that 3,3-dimethylcyclobutan-1-ol was used instead of 4,4-difluorocyclohexan-1-ol used in the production example of the compound C163.

LCMS: m/z 428 $[M+H]^+$

HPLC retention time: 1.00 min (analysis condition F)

Compound C168

3-Amino-4-(7-fluoro-1H-indazol-4-yl)-6-(1,1,1-trifluoropropan-2-yl)-1H-1,7-phenanthrolin-2-one

[Formula 608]

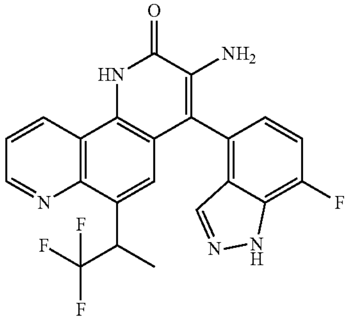

The title compound was synthesized from tert-butyl 3-[bis[(2-methylpropan-2-yl)oxycarbonyl]amino]-6-bromo-4-[7-fluoro-1-[(2-methylpropan-2-yl)oxycarbonyl]indazol-4-yl]-2-oxo-1,7-phenanthroline-1-carboxylate (compound c-202) under the same conditions as the production example of the compound C163, except that 1,1,1-trifluoropropan-2-ol was used instead of 4,4-difluorocyclohexan-1-ol used in the production example of the compound C163.

LCMS: m/z 442 $[M+H]^+$

HPLC retention time: 1.01 min (analysis condition F)

Compound C169

3-Amino-4-(7-fluoro-1H-indazol-4-yl)-6-spiro[3,3]heptan-2-yl-1H-1,7-phenanthrolin-2-one

[Formula 609]

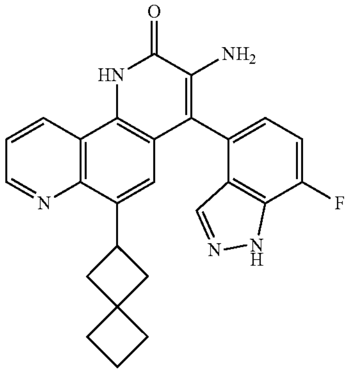

The title compound was synthesized from tert-butyl 3-[bis[(2-methylpropan-2-yl)oxycarbonyl]amino]-6-bromo-4-[7-fluoro-1-[(2-methylpropan-2-yl)oxycarbonyl]indazol-4-yl]-2-oxo-1,7-phenanthroline-1-carboxylate (compound c-202) under the same conditions as the production example of the compound C163, except that spiro[3,3]heptan-2-ol was used instead of 4,4-difluorocyclohexan-1-ol used in the production example of the compound C163.

LCMS: m/z 440 $[M+H]^+$

HPLC retention time: 1.05 min (analysis condition F)

Compound C170

3-Amino-6-(2,2-difluoroethyl)-4-(7-fluoro-1H-indazol-4-yl)-1H-1,7-phenanthrolin-2-one

[Formula 610]

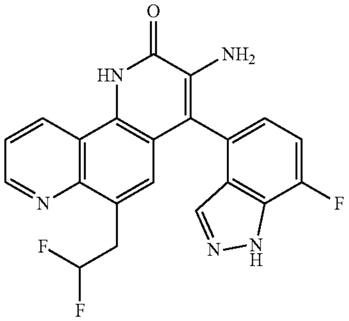

The title compound was synthesized from tert-butyl 3-[bis[(2-methylpropan-2-yl)oxycarbonyl]amino]-6-bromo-4-[7-fluoro-2-(oxan-2-yl)indazol-4-yl]-2-oxo-1,7-phenanthroline-1-carboxylate (compound c-168) under the same conditions as the production example of the compound C163, except that 2,2-difluoroethan-1-ol was used instead of 4,4-difluorocyclohexan-1-ol used in the production example of the compound C163.

LCMS: m/z 410 $[M+H]^+$

HPLC retention time: 0.89 min (analysis condition F)

Compound C171

3-Amino-6-(3,3-difluoropropyl)-4-(7-fluoro-1H-indazol-4-yl)-1H-1,7-phenanthrolin-2-one

[Formula 611]

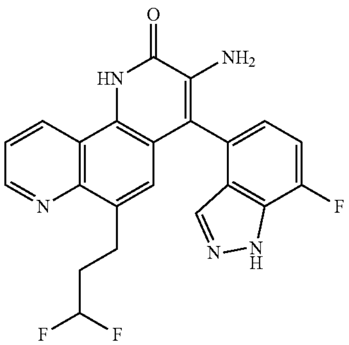

The title compound was synthesized from tert-butyl 3-[bis[(2-methylpropan-2-yl)oxycarbonyl]amino]-6-bromo-4-[7-fluoro-2-(oxan-2-yl)indazol-4-yl]-2-oxo-1,7-phenanthroline-1-carboxylate (compound c-168) under the same conditions as the production example of the compound C163, except that 3,3-difluoropropan-1-ol was used instead of 4,4-difluorocyclohexan-1-ol used in the production example of the compound C163.

LCMS: m/z 424 $[M+H]^+$

HPLC retention time: 0.89 min (analysis condition F)

Compound C173

3-Amino-6-(3-tert-butylcyclobutyl)-4-(7-fluoro-1H-indazol-4-yl)-1H-1,7-phenanthrolin-2-one

[Formula 612]

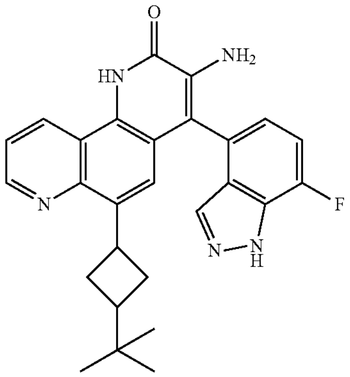

The title compound was synthesized from tert-butyl 3-[bis[(2-methylpropan-2-yl)oxycarbonyl]amino]-6-bromo-4-[7-fluoro-2-(oxan-2-yl)indazol-4-yl]-2-oxo-1,7-phenanthroline-1-carboxylate (compound c-168) under the same conditions as the production example of the compound C163, except that 3-(tert-butyl)cyclobutan-1-ol was used instead of 4,4-difluorocyclohexan-1-ol used in the production example of the compound C163.

LCMS: m/z 456 $[M+H]^+$

HPLC retention time: 1.11 min (analysis condition F)

Compound C174

3-Amino-6-(2,2-dimethylspiro[3,3]heptan-6-yl)-4-(7-fluoro-1H-indazol-4-yl)-1H-1,7-one

[Formula 613]

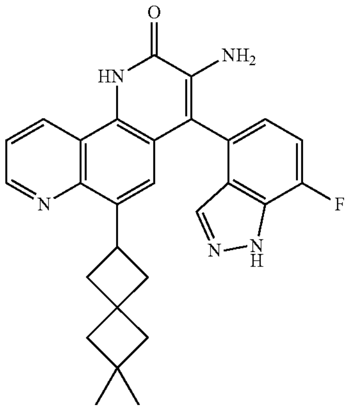

The title compound was synthesized from tert-butyl 3-[bis[(2-methylpropan-2-yl)oxycarbonyl]amino]-6-bromo-4-[7-fluoro-2-(oxan-2-yl)indazol-4-yl]-2-oxo-1,7-phenanthroline-1-carboxylate (compound c-168) under the same conditions as the production example of the compound C163, except that 6,6-dimethylspiro[3,3]heptan-2-ol was used instead of 4,4-difluorocyclohexan-1-ol used in the production example of the compound C163.

LCMS: m/z 468 $[M+H]^+$

HPLC retention time: 1.19 min (analysis condition F)

Compound C175

3-Amino-4-(7-fluoro-1H-indazol-4-yl)-6-spiro[2.3]hexan-5-yl-1H-1,7-phenanthrolin-2-one

[Formula 614]

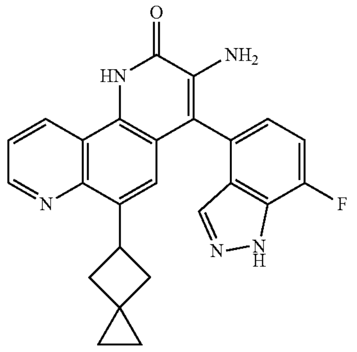

The title compound was synthesized from tert-butyl 3-[bis[(2-methylpropan-2-yl)oxycarbonyl]amino]-6-bromo-4-[7-fluoro-2-(oxan-2-yl)indazol-4-yl]-2-oxo-1,7-phenanthroline-1-carboxylate (compound c-168) under the same conditions as the production example of the compound C163, except that spiro[2.3]hexan-5-ol was used instead of 4,4-difluorocyclohexan-1-ol used in the production example of the compound C163.

LCMS: m/z 426 $[M+H]^+$

HPLC retention time: 0.96 min (analysis condition F)

Compound C176

3-[3-Amino-4-(7-fluoro-1H-indazol-4-yl)-2-oxo-1H-1,7-phenanthrolin-6-yl]cyclobutane-1-carbonitrile

[Formula 615]

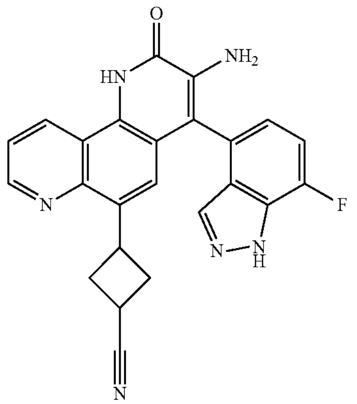

The title compound was synthesized from tert-butyl 3-[bis[(2-methylpropan-2-yl)oxycarbonyl]amino]-6-bromo-4-[7-fluoro-2-(oxan-2-yl)indazol-4-yl]-2-oxo-1,7-phenanthroline-1-carboxylate (compound c-168) under the same conditions as the production example of the compound C163, except that 3-hydroxycyclobutanecarbonitrile was used instead of 4,4-difluorocyclohexan-1-ol used in the production example of the compound C163.

LCMS: m/z 425 $[M+H]^+$

HPLC retention time: 1.57 min (analysis condition F)

Compound C177

1-[[3-Amino-4-(7-fluoro-1H-indazol-4-yl)-2-oxo-1H-1,7-phenanthrolin-6-yl]methyl]cyclopropane-1-carbonitrile

[Formula 616]

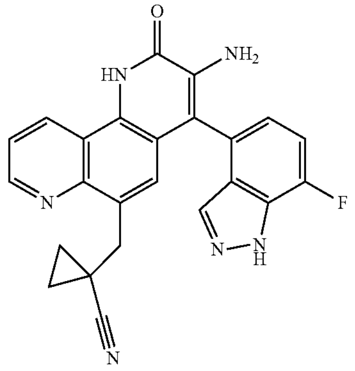

The title compound was synthesized from tert-butyl 3-[bis[(2-methylpropan-2-yl)oxycarbonyl]amino]-6-bromo-4-[7-fluoro-2-(oxan-2-yl)indazol-4-yl]-2-oxo-1,7-phenanthroline-1-carboxylate (compound c-168) under the same conditions as the production example of the compound C163, except that 1-(hydroxymethyl)cyclopropane-1-carbonitrile was used instead of 4,4-difluorocyclohexan-1-ol used in the production example of the compound C163.

LCMS: m/z 425 $[M+H]^+$

HPLC retention time: 1.61 min (analysis condition F)

Compound C178

(1s,3s)-3-[3-Amino-4-(7-fluoro-1H-indazol-4-yl)-2-oxo-1H-1,7-phenanthrolin-6-yl]cyclobutane-1-carbonitrile

[Formula 617]

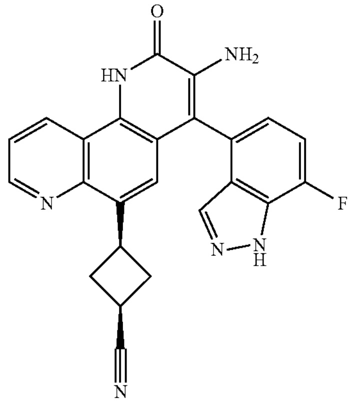

LCMS: m/z 425 $[M+H]^+$

HPLC retention time: 0.55 min (analysis condition A)

Compound C179

(1r,3r)-3-[3-Amino-4-(7-fluoro-1H-indazol-4-yl)-2-oxo-1H-1,7-phenanthrolin-6-yl]cyclobutane-1-carbonitrile

[Formula 618]

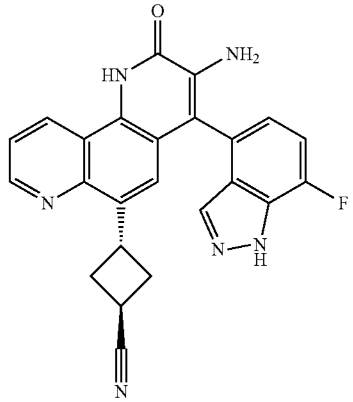

3-[3-Amino-4-(7-fluoro-1H-indazol-4-yl)-2-oxo-1H-1,7-phenanthrolin-6-yl]cyclobutane-1-carbonitrile (compound C176) was purified by preparative HPLC (Xselect CSH C18 19 mm×100 mm, 5 μm, 0.1% aqueous formic acid solution/0.1% formic acid in acetonitrile solution) to obtain the compound C178 (1.96 mg) and the compound C179 (2.12 mg) as yellow solids.

LCMS: m/z 425 $[M+H]^+$

HPLC retention time: 0.56 min (analysis condition A)

Compound c-223

5-Bromo-7-[7-fluoro-2-(oxan-2-yl)indazol-4-yl]-[1,3]oxazolo[5,4-b][1,7]phenanthroline

[Formula 619]

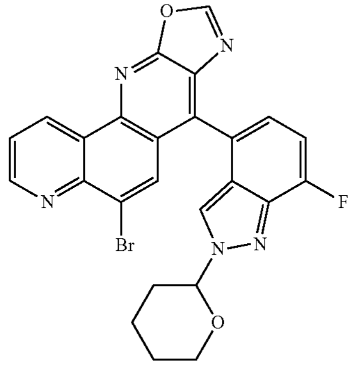

The title compound was synthesized from 3-amino-6-bromo-4-[7-fluoro-2-(oxan-2-yl)indazol-4-yl]-1H-1,7-phenanthrolin-2-one (compound c-13) under the same conditions as the production example of the compound c-164, except that triethyl orthoformate was used instead of trimethyl orthoacetate used in the production example of the compound c-164.

LCMS: m/z 518 $[M+H]^+$

HPLC retention time: 0.90 min (analysis condition A)

Compound C180

3-Amino-8-tert-butyl-4-(7-fluoro-1H-indazol-4-yl)-1H-1,7-phenanthrolin-2-one

[Formula 620]

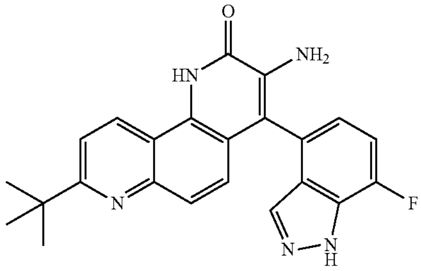

(1) 5-Bromo-7-[7-fluoro-2-(oxan-2-yl)indazol-4-yl]-[1,3]oxazolo[5,4-b][1,7]phenanthroline (compound c-223, 20 mg, 0.039 mmol), sodium carbonate (16.4 mg, 0.154 mmol), and [4,4'-bis(1,1-dimethyl)-2,2'-bipyridine-N1,N1']bis[3,5-difluoro-2-[5-(trifluoromethyl)-2-pyridinyl-N]phenyl-C] iridium(III) hexafluorophosphate (CAS number: 870987-63-6) (0.43 mg, 0.39 μmol) in a reaction vessel were suspended in 1,4-dioxane (0.39 mL) under nitrogen atmosphere, and 2-iodo-2-methylpropane (13.8 μL, 0.116 mmol) and 1,1,1,3,3,3-hexamethyl-2-(trimethylsilyl)trisilane (34.9 μL, 0.116 mmol) were added thereto. To the reaction mixture, a solution of $NiBr_2$·dtbbpy (CAS number: 1894189-67-3, 0.94 mg, 1.93 μmol) in 1,2-dimethoxyethane (1 mL) was added under nitrogen atmosphere. The reaction mixture was stirred at 1500 rpm, and irradiated with LED light at a wavelength of 450 nm for 2 hours under nitrogen atmosphere, while air-cooling it by a blower, to cause the photoredox catalysis.

(2) To the reaction mixture obtained in (1), 12 M hydrochloric acid (200 μL) was added, and the mixture was stirred at room temperature for 1 hour. To the reaction mixture, an aqueous sodium hydroxide solution (300 μL) was added, and the mixture was extracted with ethyl acetate. The organic layer was concentrated under reduced pressure, and the obtained residue was purified by reversed phase column chromatography (0.1% aqueous formic acid solution/0.1% formic acid in acetonitrile solution) to obtain the title compound (1.5 mg, yield 9.7%) as a pale yellow solid.

LCMS: m/z 402 $[M+H]^+$

HPLC retention time: 0.87 min (analysis condition F)

Compound C165

3-Amino-4-(7-fluoro-1H-indazol-4-yl)-6-(2,2,2-trifluoroethyl)-1H-1,7-phenanthrolin-2-one

[Formula 621]

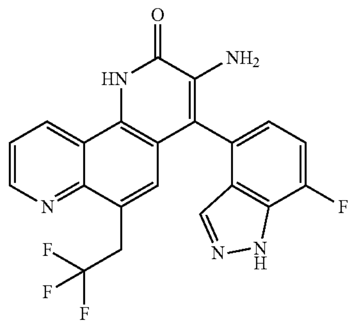

The title compound was synthesized from tert-butyl 3-[bis[(2-methylpropan-2-yl)oxycarbonyl]amino]-6-bromo-4-[7-fluoro-1-[(2-methylpropan-2-yl)oxycarbonyl]indazol-4-yl]-2-oxo-1,7-phenanthroline-1-carboxylate (compound c-202) under the same conditions as the production example of the compound C180, except that 1,1,1-trifluoro-2-iodoethane was used instead of 2-iodo-2-methylpropane used in the production example of the compound C180.

LCMS: m/z 428 $[M+H]^+$

HPLC retention time: 0.94 min (analysis condition F)

Compound c-253

4-Bromo-7-fluoro-1-(oxan-2-yl)indazole

[Formula 622]

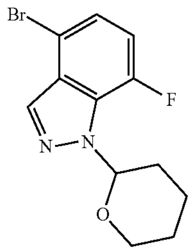

The title compound was synthesized from 4-bromo-7-fluoro-1H-indazole under the same conditions as the production example of the compound c-99.

LCMS: m/z 299 $[M+H]^+$

HPLC retention time: 0.93 min (analysis condition A)

Compound c-254

7-Fluoro-1-(oxan-2-yl)indazole-4-carbaldehyde

[Formula 623]

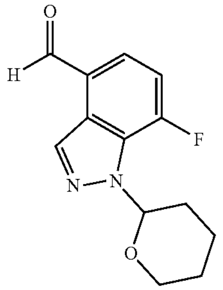

A solution of 4-bromo-7-fluoro-1-(oxan-2-yl)indazole (compound c-253, 16.4 g, 54.8 mmol) in THF (164 mL) in a reaction vessel was cooled to −78° C., a 2.3 M butyllithium cyclohexane solution (31.0 mL, 71.3 mmol) was added dropwise thereto, and the mixture was stirred for 30 min. To the reaction mixture, DMF (12.74 mL, 164 mmol) was added, and then the mixture was stirred for 1 hour. To the reaction mixture, a saturated aqueous ammonium chloride solution was added, and the mixture was extracted with ethyl acetate. The organic layer was dried over anhydrous sodium sulfate, the drying agent was filtered off, and then the filtrate was concentrated under reduced pressure. The obtained residue was purified by silica gel column chromatography to obtain the title compound (8.5 g, yield 63%) as a colorless solid.

LCMS: m/z 249 $[M+H]^+$

HPLC retention time: 0.73 min (analysis condition A)

Compound c-226

(E)-N'-(6,8-diiodo-2-methylquinolin-5-yl)-N,N-dimethylmethanimidamide

[Formula 624]

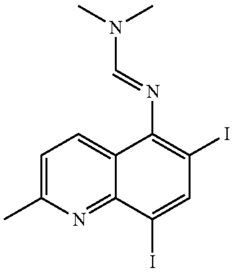

The title compound was synthesized from 2-methylquinolin-5-amine under the same conditions as the production example of the compounds b-24 and b-25, except that a mixed solution of acetonitrile/DMSO (2/1) was used instead of DMSO used in the production example of the compound b-24.

LCMS: m/z 466 $[M+H]^+$

HPLC retention time: 0.54 min (analysis condition A)

Compound c-227

(5-Amino-8-iodo-2-methylquinolin-6-yl)-[7-fluoro-1-(oxan-2-yl)indazol-4-yl]methanol

[Formula 625]

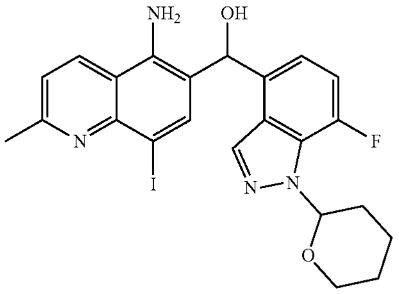

A solution of (E)-N'-(6,8-diiodo-2-methylquinolin-5-yl)-N,N-dimethylmethanimidamide (compound c-226, 206 mg, 0.443 mmol) in THF (1.7 mL) in a reaction vessel was cooled to −40° C., a 1.3 M isopropylmagnesium chloride-lithium chloride complex solution (0.372 mL, 0.483 mmol) was added thereto, and the mixture was stirred for 15 min. To the reaction mixture, a solution of 7-fluoro-1-(oxan-2-yl)indazole-4-carbaldehyde (c-254, 100 mg, 0.403 mmol) in THF (1 mL) was added, and then the mixture was stirred for 30 min. The reaction mixture was heated to 0° C., a saturated aqueous sodium bicarbonate solution was added thereto, and the mixture was extracted with ethyl acetate. The organic layer was washed with brine and concentrated under reduced pressure. The obtained residue was dissolved in acetonitrile (1 mL), a 30% aqueous formic acid solution was added thereto, and the mixture was stirred at room temperature for 30 min. To the reaction mixture, ethylenediamine (0.269 mL, 4.03 mmol) was added, and then the mixture was stirred at 60° C. for 2 hours. The reaction mixture was purified by reversed phase column chromatography (0.1% aqueous formic acid solution/0.1% solution of formic acid in acetonitrile) to obtain the title compound (121 mg, yield 51%).

LCMS: m/z 533 $[M+H]^+$

HPLC retention time: 2.14 min (analysis condition G)

Compound c-228

(5-Amino-8-iodo-2-methylquinolin-6-yl)-[7-fluoro-1-(oxan-2-yl)indazol-4-yl]methanone

[Formula 626]

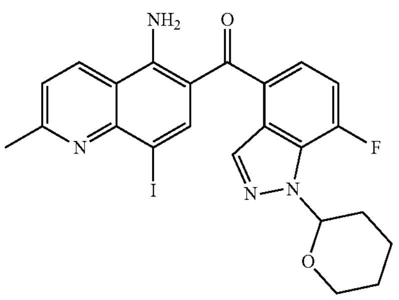

To a solution of (5-amino-8-iodo-2-methylquinolin-6-yl)-[7-fluoro-1-(oxan-2-yl)indazol-4-yl]methanol (compound c-227, 110 mg, 0.207 mmol) in DCM (2.07 mL), manganese oxide (71.9 mg, 0.827 mmol) was added, and the mixture was stirred at room temperature for 32 hours. The reaction mixture was filtered using Celite. The filtrate was concentrated, the obtained residue was purified by silica gel column chromatography (hexane/ethyl acetate) to obtain the title compound (91 mg, yield 83%) as a yellow solid.

LCMS: m/z 531 $[M+H]^+$

HPLC retention time: 2.49 min (analysis condition G)

Compound C181

3-Amino-4-(7-fluoro-1H-indazol-4-yl)-6-iodo-8-methyl-1H-1,7-phenanthrolin-2-one

[Formula 627]

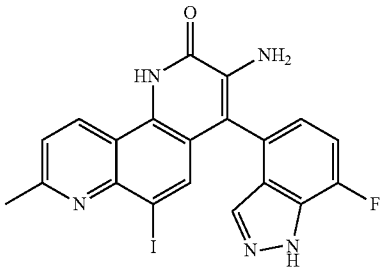

The title compound was synthesized from the compound (5-amino-8-iodo-2-methylquinolin-6-yl)-[7-fluoro-1-(oxan-2-yl)indazol-4-yl]methanone (compound c-228) under the same conditions as the production examples of the compounds b-28, b-29, b-30, and b-9, except that DMSO was used instead of EtOH used in the production example of the compound b-9.

LCMS: m/z 486 $[M+H]^+$

HPLC retention time: 0.70 min (analysis condition A)

Compound C182

3-Amino-6-cyclopropyl-4-(7-fluoro-1H-indazol-4-yl)-8-methyl-1H-1,7-phenanthrolin-2-one

[Formula 628]

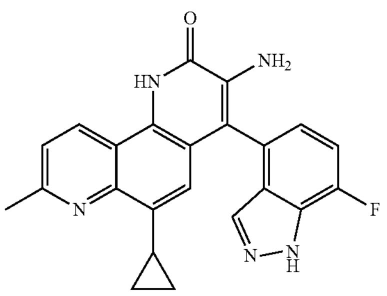

LCMS: m/z 400 $[M+H]^+$

HPLC retention time: 0.49 min (analysis condition A)

Compound C183

3-Amino-4-(7-fluoro-1H-indazol-4-yl)-8-methyl-1H-1,7-phenanthrolin-2-one

[Formula 629]

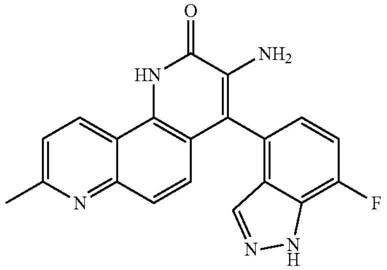

The compound C182 and the compound C183 were synthesized from 3-amino-4-(7-fluoro-1H-indazol-4-yl)-6-iodo-8-methyl-1H-1,7-phenanthrolin-2-one (compound C181) under the same conditions as the production example of the compound B22, except that XPhos Pd G4 was used instead of CPhos Pd G3 used in the production example of the compound B22.

LCMS: m/z 360 $[M+H]^+$

HPLC retention time: 0.38 min (analysis condition A)

Compound c-232

8-Cyclopropylquinolin-5-amine

[Formula 630]

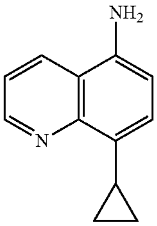

The title compound was synthesized from 8-bromoquinolin-5-amine under the same conditions as the production example of the compound B22, except that XPhos Pd G3 was used instead of CPhos Pd G3 used in the production example of the compound B22.

LCMS: m/z 185 $[M+H]^+$

HPLC retention time: 0.68 min (analysis condition H)

Compound c-233

6-Bromo-8-cyclopropylquinolin-5-amine

[Formula 631]

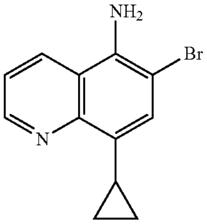

The title compound was synthesized from 8-cyclopropylquinolin-5-amine (compound c-232) under the same conditions as the production example of the compound b-100, except that NMP was used instead of DMF used in the production example of the compound b-100.

LCMS: m/z 263 $[M+H]^+$

HPLC retention time: 0.90 min (analysis condition H)

Compound c-234

8-Cyclopropyl-6-tributylstannylquinolin-5-amine

[Formula 632]

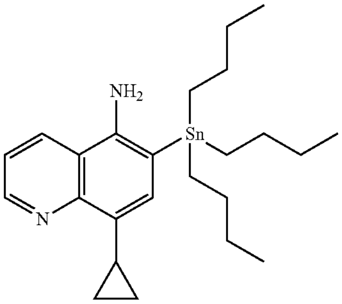

6-Bromo-8-cyclopropylquinolin-5-amine (compound c-233, 200 mg, 0.76 mmol), hexabutyldistannane (750 μL, 1.52 mmol), and tetrakis(triphenylphosphine)palladium (0) (88 mg, 0.076 mmol) in a reaction vessel were dissolved in toluene (3.8 mL), and the reaction vessel was degassed under reduced pressure and subjected to nitrogen replacement. The mixture was stirred at 150° C. for 2 hours using a microwave reactor. The reaction solution was concentrated, and the obtained residue was purified by reversed phase column chromatography to obtain the title compound (79 mg, yield 22%).

LCMS: m/z 475 $[M+H]^+$

HPLC retention time: 1.00 min (analysis condition A)

Compound c-235

3-Amino-6-cyclopropyl-4-[1-(oxan-2-yl)indazol-4-yl]-1H-1,7-phenanthrolin-2-one

[Formula 633]

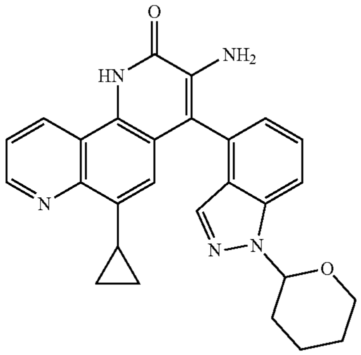

8-Cyclopropyl-6-tributylstannylquinolin-5-amine (compound c-234, 79 mg, 0.168 mmol), methyl (E)-3-(4-methylphenyl) sulfonyloxy-2-[(2-methylpropan-2-yl)oxycarbonylamino]-3-[1-(oxan-2-yl)indazol-4-yl]prop-2-enoate (compound b-93, 48 mg, 0.084 mmol), and tetrakis (triphenylphosphine)palladium (0) (19.4 mg, 0.017 mmol) in a reaction vessel were dissolved in toluene, and the reaction vessel was degassed under reduced pressure and subjected to nitrogen replacement. The mixture was stirred at 150° C. for 30 min using a microwave reactor. The reaction solution was concentrated, and the obtained residue was purified by reversed phase column chromatography to obtain the title compound (11 mg, yield 29%) as a yellow solid.

LCMS: m/z 452 $[M+H]^+$

HPLC retention time: 0.61 min (analysis condition A)

Compound C185

3-Amino-6-cyclopropyl-4-(1H-indazol-4-yl)-1H-1,7-phenanthrolin-2-one

[Formula 634]

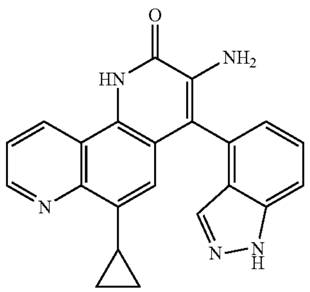

The title compound was synthesized from 3-amino-6-cyclopropyl-4-[1-(oxan-2-yl)indazol-4-yl]-1H-1,7-phenanthrolin-2-one (compound c-235) under the same conditions as the production example of the compound B49.

LCMS: m/z 368 $[M+H]^+$

HPLC retention time: 0.44 min (analysis condition A)

Compound c-243

6-(4,4,5,5-Tetramethyl-1,3,2-dioxaborolan-2-yl)quinolin-5-amine

[Formula 635]

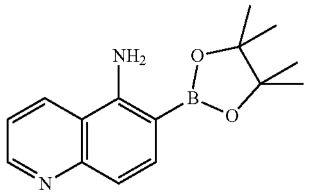

The title compound was synthesized from 6-bromoquinolin-5-amine under the same conditions as the production example of the compound b-101, except that DPPF Pd G4 and potassium acetate were used instead of [1,4-bis(diphenylphosphino)butane]palladium(II) dichloride, potassium carbonate, and acetic acid used in the production example of the compound b-101.

LCMS: m/z 271.5 $[M+H]^+$

HPLC retention time: 0.51 min (analysis condition A)

Compound c-244 tert-Butyl N-[4-[1-(oxan-2-yl)indazol-4-yl]-2-oxo-1H-1,7-phenanthrolin-3-yl]carbamate

[Formula 636]

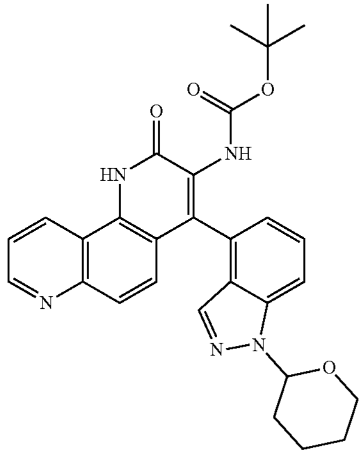

The title compound was synthesized from 6-(4,4,5,5-tetramethyl-1,3,2-dioxaborolan-2-yl)quinolin-5-amine (compound c-243) under the same conditions as the production example of the compound b-102, except that 1,4-bis(diphenylphosphino)butane and palladium(II) acetate were used instead of 1,4-bis(diphenylphosphino)butane]palladium(II) dichloride used in the production example of the compound b-102.

LCMS: m/z 512.7 $[M+H]^+$

HPLC retention time: 0.69 min (analysis condition A)

Compound C186

3-Amino-4-(1H-indazol-4-yl)-1H-1,7-phenanthrolin-2-one

[Formula 637]

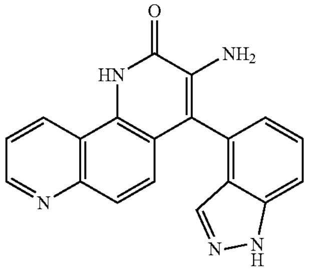

The title compound was synthesized from tert-butyl N-[4-[1-(oxan-2-yl)indazol-4-yl]-2-oxo-1H-1,7-phenanthrolin-3-yl]carbamate (compound c-244) under the same conditions as the production example of the compound B49.

LCMS: m/z 328 $[M+H]^+$

HPLC retention time: 0.39 min (analysis condition A)

Compound c-237

Methyl 2-[(3-methoxybenzoyl)amino]acetate

[Formula 638]

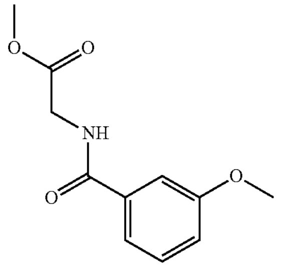

A solution of glycine methyl ester hydrochloride (1.00 g, 7.96 mmol) in THF (5 mL) in a reaction vessel was cooled to 0° C., triethylamine (2.44 mL, 17.5 mmol) and 3-methoxybenzoylchloride (1.09 mL, 7.96 mmol) were added thereto, and the mixture was stirred for 1 hour. The reaction mixture was combined with that of another lot, then water was added thereto, and the mixture was extracted with ethyl acetate. The organic layer was washed with a saturated aqueous sodium bicarbonate solution, and then the mixture was concentrated under reduced pressure to obtain the title compound (1.68 g).

LCMS: m/z 224 $[M+H]^+$

HPLC retention time: 0.49 min (analysis condition A)

Compound c-238

Methyl 2-[(3-methoxybenzoyl)-(2-methylpropan-2-yl)oxycarbonyl]aminolacetate

[Formula 639]

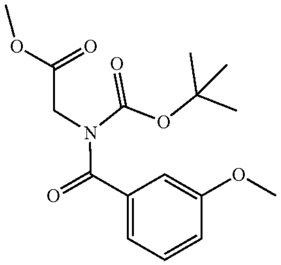

The title compound was synthesized from methyl 2-[(3-methoxybenzoyl)amino]acetate (compound c-237) under the same conditions as the production example of the compound b-91.

LCMS: m/z 324 $[M+H]^+$

HPLC retention time: 0.81 min (analysis condition A)

Compound c-240

Methyl (E)-3-(3-methoxyphenyl)-3-(4-methylphenyl) sulfonyloxy-2-[(2-methylpropan-2-yl)oxycarbonylamino]prop-2-enoate

[Formula 640]

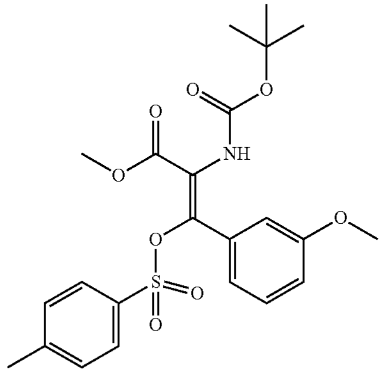

The title compound was synthesized from methyl 2-[(3-methoxybenzoyl)-[(2-methylpropan-2-yl)oxycarbonyl] amino]acetate (compound c-238) under the same conditions as the production example of the compounds b-92 and b-93.

LCMS: m/z 478.5 $[M+H]^+$

HPLC retention time: 0.87 min (analysis condition A)

Compound c-241 tert-Butyl N-[4-(3-methoxyphenyl)-2-oxo-1H-1,7-phenanthrolin-3-yl]carbamate

[Formula 641]

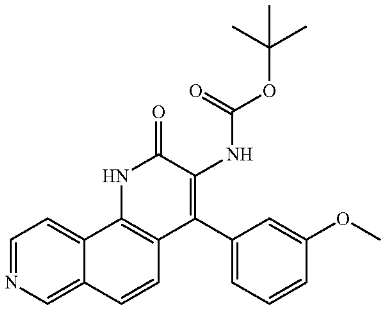

The title compound was synthesized from methyl (E)-3-(3-methoxyphenyl)-3-(4-methylphenyl) sulfonyloxy-2-[(2-methylpropan-2-yl)oxycarbonylamino]prop-2-enoate (compound c-240) and 6-(4,4,5,5-tetramethyl-1,3,2-dioxaborolan-2-yl)quinolin-5-amine (compound c-243) under the same conditions as the production example of the compound b-102, except that DPPF Pd G4 and toluene were used instead of 1,4-bis(diphenylphosphino)butane]palladium(II) dichloride and 4-methyltetrahydropyran used in the production example of the compound b-102.

LCMS: m/z 418.6 $[M+H]^+$

HPLC retention time: 0.63 min (analysis condition A)

Compound C184

3-Amino-4-(3-hydroxyphenyl)-1H-1,7-phenanthrolin-2-one; hydrobromide

[Formula 642]

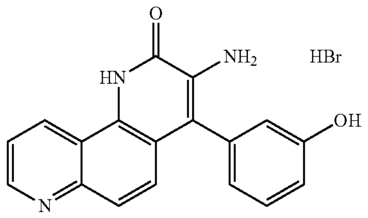

To tert-butyl N-[4-(3-methoxyphenyl)-2-oxo-1H-1,7-phenanthrolin-3-yl]carbamate (compound c-241, 21 mg, 0.050 mmol), 47% hydrobromic acid (210 μL) was added, and the mixture was stirred at room temperature for 2 hours. The solid was collected by filtration and washed with THE to obtain the title compound (14.2 mg, yield 61%) as an orange solid.

LCMS: m/z 304.5 $[M+H]^+$

HPLC retention time: 0.38 min (analysis condition A)

Compound C197

3-Amino-4-(6,7-difluoro-1H-indazol-4-yl)-1H-1,7-phenanthrolin-2-one

[Formula 643]

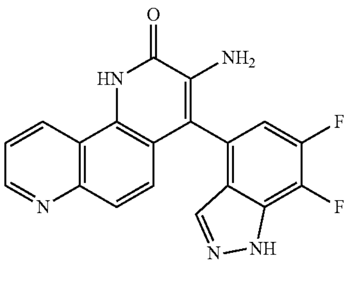

The title compound was synthesized from 3-amino-6-bromo-4-(6,7-difluoro-1H-indazol-4-yl)-1H-1,7-phenanthrolin-2-one (compound C66) under the same conditions as the production example of the compound B11, except that XPhos Pd G4 was used instead of Xantphos Pd G4 used in the production example of the compound B11.

LCMS: m/z 364 $[M+H]^+$

HPLC retention time: 0.43 min (analysis condition A)

Compound C198

3-Amino-6-chloro-4-(6,7-difluoro-1H-indazol-4-yl)-1H-1,7-phenanthrolin-2-one

[Formula 644]

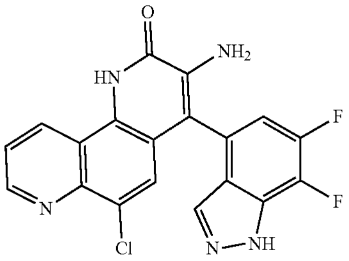

The title compound was synthesized from 3-amino-6-bromo-4-(6,7-difluoro-1H-indazol-4-yl)-1H-1,7-phenanthrolin-2-one (compound C66) under the same conditions as the production example of the compound b-14.

LCMS: m/z 398 $[M+H]^+$

HPLC retention time: 0.57 min (analysis condition A)

Compound C199

3-Amino-4-(6,7-difluoro-1H-indazol-4-yl)-6-hydroxy-1H-1,7-phenanthrolin-2-one

[Formula 645]

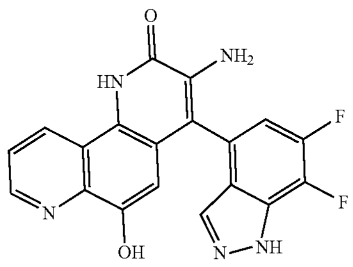

The title compound was synthesized from 3-amino-4-[6,7-difluoro-1-(oxan-2-yl)indazol-4-yl]-2-[(4-methoxyphenyl)methoxy]-1,7-phenanthrolin-6-ol (c-110) under the same conditions as the production example of the compound C4, except that anisole was used instead of triethylsilane used in the production example of C4.

LCMS: m/z 380 $[M+H]^+$

HPLC retention time: 0.45 min (analysis condition A)

Compound C215

3-Amino-4-(6,7-difluoro-1H-indazol-4-yl)-6-pyridin-3-yl-1H-1,7-phenanthrolin-2-one

[Formula 646]

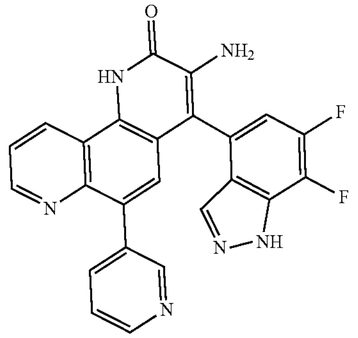

The title compound was synthesized from 3-amino-6-bromo-4-[6,7-difluoro-1-(oxan-2-yl)indazol-4-yl]-1H-1,7-phenanthrolin-2-one (compound c-107) under the same conditions as the production examples of the compounds B29 and C4, except that 3-pyridineboronic acid was used instead of 1-methyl-1H-pyrazole-4-boronic acid used in the production example of the compound B29. In addition, anisole was used instead of triethylsilane used in the production example of C4.

LCMS: m/z 441 $[M+H]^+$

HPLC retention time: 0.41 min (analysis condition A)

Compound C201

3-Amino-6-cyclobutyl-4-(6,7-difluoro-1H-indazol-4-yl)-1H-1,7-phenanthrolin-2-one

[Formula 647]

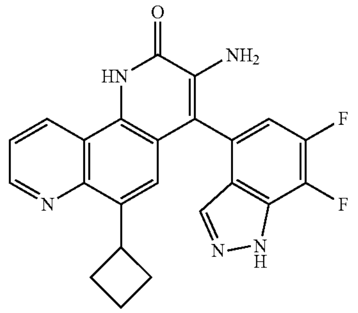

The title compound was synthesized from 3-amino-6-bromo-4-[6,7-difluoro-1-(oxan-2-yl)indazol-4-yl]-1H-1,7-phenanthrolin-2-one (compound c-107) under the same conditions as the production examples of the compounds B22 and C4, except that XPhos Pd G4 and a 0.5 M solution of cyclobutylzinc bromide in THF were used instead of CPhos Pd G3 and the 0.5 M solution of cyclopropylzinc bromide in THE used in the production example of the compound B22. In addition, anisole was used instead of triethylsilane used in the production example of C4.

LCMS: m/z 418 $[M+H]^+$

HPLC retention time: 0.65 min (analysis condition A)

Compound C202

3-Amino-6-cyclopentyl-4-(6,7-difluoro-1H-indazol-4-yl)-1H-1,7-phenanthrolin-2-one

[Formula 648]

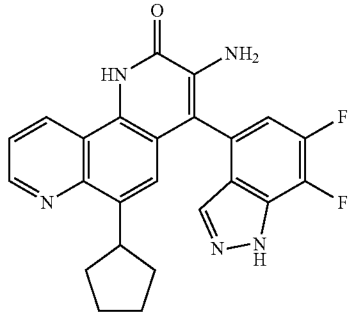

The title compound was synthesized from 3-amino-6-bromo-4-[6,7-difluoro-1-(oxan-2-yl)indazol-4-yl]-1H-1,7-phenanthrolin-2-one (compound c-107) under the same conditions as the production examples of the compounds B22 and C4, except that XPhos Pd G4 and a 0.5 M solution of cyclopentylzinc bromide in THF were used instead of CPhos Pd G3 and the 0.5 M solution of cyclopropylzinc bromide in THE used in the production example of the compound B22. In addition, anisole was used instead of triethylsilane used in the production example of C4.

LCMS: m/z 432 $[M+H]^+$

HPLC retention time: 0.70 min (analysis condition A)

Compound C203

3-Amino-4-(6,7-difluoro-1H-indazol-4-yl)-6-(2-methylpropyl)-1H-1,7-phenanthrolin-2-one

[Formula 649]

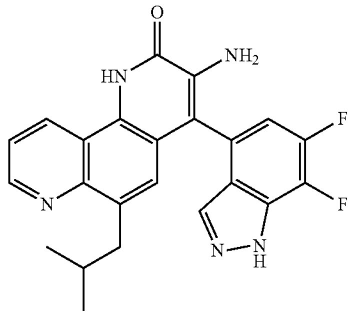

The title compound was synthesized from 3-amino-6-bromo-4-[6,7-difluoro-1-(oxan-2-yl)indazol-4-yl]-1H-1,7-phenanthrolin-2-one (compound c-107) under the same conditions as the production examples of the compounds B22 and C4, except that XPhos Pd G4 and a 0.5 M solution of isobutylzinc bromide in THF were used instead of CPhos Pd G3 and the 0.5 M solution of cyclopropylzinc bromide in THE used in the production example of the compound B22. In addition, anisole was used instead of triethylsilane used in the production example of C4.

LCMS: m/z 420 [M+H]$^+$

HPLC retention time: 0.68 min (analysis condition A)

Compound C204

3-Amino-4-(6,7-difluoro-1H-indazol-4-yl)-6-ethenyl-1H-1,7-phenanthrolin-2-one

[Formula 650]

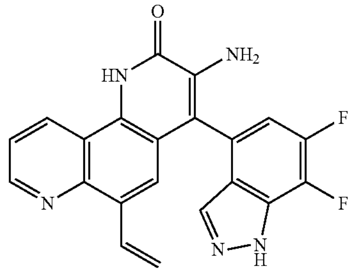

The title compound was synthesized from 3-amino-6-bromo-4-[6,7-difluoro-1-(oxan-2-yl)indazol-4-yl]-1H-1,7-phenanthrolin-2-one (compound c-107) under the same conditions as the production examples of the compounds B29 and C4, except that potassium vinyltrifluoroborate was used instead of 1-methyl-1H-pyrazole-4-boronic acid used in the production example of the compound B29. In addition, anisole was used instead of triethylsilane used in the production example of C4.

LCMS: m/z 390 [M+H]$^+$

HPLC retention time: 0.62 min (analysis condition A)

Compound C205

3-Amino-4-(6,7-difluoro-1H-indazol-4-yl)-6-(difluoromethoxy)-1H-1,7-phenanthrolin-2-one

[Formula 651]

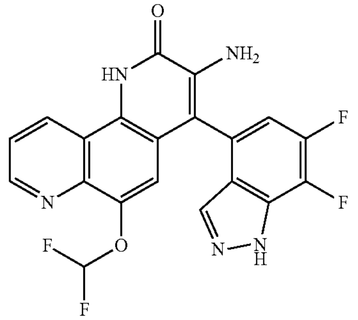

The title compound was synthesized from 3-amino-4-[6,7-difluoro-1-(oxan-2-yl)indazol-4-yl]-2-[(4-methoxyphenyl)methoxy]-1,7-phenanthrolin-6-ol (c-110) under the same conditions as the production examples of the compounds c-33 and C4, except that anisole was used instead of triethylsilane used in the production example of C4.

LCMS: m/z 430 [M+H]$^+$

HPLC retention time: 0.58 min (analysis condition A)

Compound C206

3-Amino-6-cyclobutyloxy-4-(6,7-difluoro-1H-indazol-4-yl)-1H-1,7-phenanthrolin-2-one

[Formula 652]

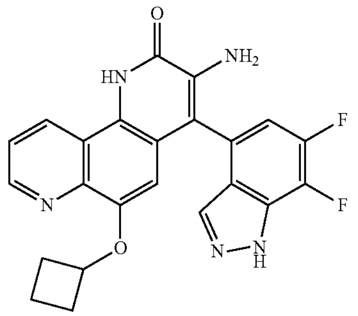

The title compound was synthesized from 3-amino-4-[6,7-difluoro-1-(oxan-2-yl)indazol-4-yl]-2-[(4-methoxyphenyl)methoxy]-1,7-phenanthrolin-6-ol (c-110) under the same conditions as the production examples of the compounds c-28 and C4, except that bromocyclobutane was used instead of 2,2-difluoroethyltriflate used in the production example of the compound c-28, and the reaction was carried out by heating the reaction mixture to 70° C. In addition, anisole was used instead of triethylsilane used in the production example of the compound C4.

LCMS: m/z 434 [M+H]$^+$

HPLC retention time: 0.50 min (analysis condition A)

Compound C207

3-Amino-4-(6,7-difluoro-1H-indazol-4-yl)-6-(1-methylpyrazol-4-yl)-1H-1,7-phenanthrolin-2-one

[Formula 653]

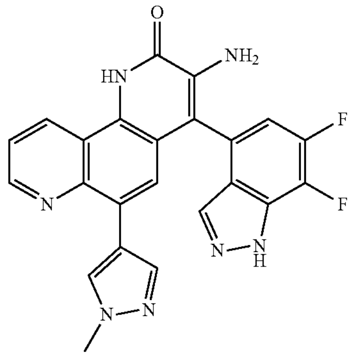

The title compound was synthesized from 3-amino-6-bromo-4-(6,7-difluoro-1H-indazol-4-yl)-1H-1,7-phenanthrolin-2-one (compound C66) under the same conditions as the production example of the compound B29.

LCMS: m/z 444 [M+H]$^+$

HPLC retention time: 0.51 min (analysis condition A)

Compound c-264

3-Amino-4-[6,7-difluoro-1-(oxan-2-yl)indazol-4-yl]-6-(4-methylpiperazin-1-yl)-1H-1,7-one

[Formula 654]

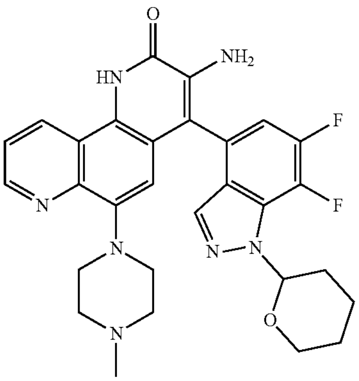

3-Amino-6-bromo-4-[6,7-difluoro-1-(oxan-2-yl)indazol-4-yl]-1H-1,7-phenanthrolin-2-one (compound c-107, 100 mg, 0.19 mmol) and sodium tert-butoxide (220 mg, 2.29 mmol) in a reaction vessel were suspended in 1,4-dioxane (2 mL). To the reaction mixture, 1-methylpiperazine (62.8 μL, 0.571 mmol) and XPhos Pd G4 (49.7 mg, 0.0579 mmol) were added, and the reaction mixture was degassed under reduced pressure, subjected to nitrogen replacement, and then stirred at 150° C. for 2 hours. The reaction mixture was cooled to room temperature and mixed with the reaction mixture of another lot obtained by the same operation, and then the mixture was purified by reversed phase column chromatography (0.1% aqueous formic acid solution/0.1% solution of formic acid in acetonitrile) to obtain the title compound (22 mg).

LCMS: m/z 546 $[M+H]^+$

HPLC retention time: 2.50 min (analysis condition J)

Compound C209

3-Amino-4-(6,7-difluoro-1H-indazol-4-yl)-6-(4-methylpiperazin-1-yl)-1H-1,7-phenanthrolin-2-one

[Formula 655]

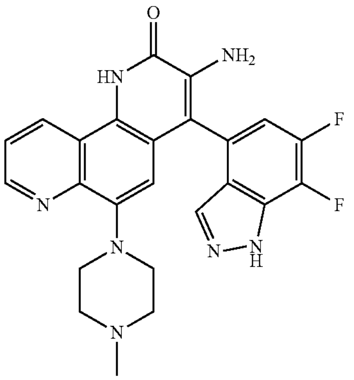

The title compound was synthesized from 3-amino-4-[6,7-difluoro-1-(oxan-2-yl)indazol-4-yl]-6-(4-methylpiperazin-1-yl)-1H-1,7-phenanthrolin-2-one (compound c-264) under the same conditions as the production example of the compound C4, except that anisole was used instead of triethylsilane used in the production example of C4.

LCMS: m/z 462 $[M+H]^+$

HPLC retention time: 0.32 min (analysis condition A)

Compound C208

3-Amino-4-(6,7-difluoro-1H-indazol-4-yl)-6-morpholin-4-yl-1H-1,7-phenanthrolin-2-one

[Formula 656]

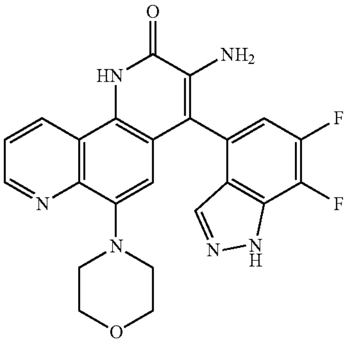

The title compound was synthesized from 3-amino-6-bromo-4-[6,7-difluoro-1-(oxan-2-yl)indazol-4-yl]-1H-1,7-phenanthrolin-2-one (compound c-107) and a corresponding amine under the same conditions as the production examples of the compounds c-264 and C4, except that anisole was used instead of triethylsilane used in the production example of the compound C4.

LCMS: m/z 449 $[M+H]^+$

HPLC retention time: 0.44 min (analysis condition A)

Compound C210

3-Amino-4-(6,7-difluoro-1H-indazol-4-yl)-6-((1r,3r)-3-fluorocyclobutyl)oxy-1H-1,7-phenanthrolin-2-one

[Formula 657]

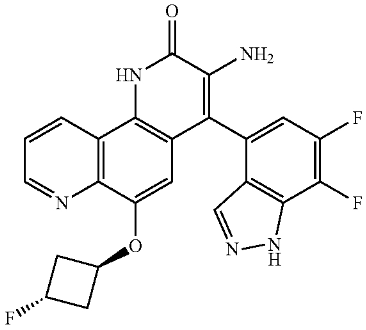

The title compound was synthesized from 3-amino-4-[6,7-difluoro-1-(oxan-2-yl)indazol-4-yl]-2-[(4-methoxyphenyl)methoxy]-1,7-phenanthrolin-6-ol (compound c-110) under the same conditions as the production examples of the compounds c-28 and C4, except that (1s,3s)-3-fluorocyclobutyl trifluoromethanesulfonate (compound a-102) was used instead of 2,2-difluoroethyltriflate used in the production example of the compound c-28. In addition, anisole was used instead of triethylsilane used in the production example of the compound C4.

LCMS: m/z 452 $[M+H]^+$

HPLC retention time: 0.49 min (analysis condition A)

Compound C211

(1r,3r)-3-[[3-Amino-4-(6,7-difluoro-1H-indazol-4-yl)-2-oxo-1H-1,7-phenanthrolin-6-yl]oxy]cyclobutane-1-carbonitrile

[Formula 658]

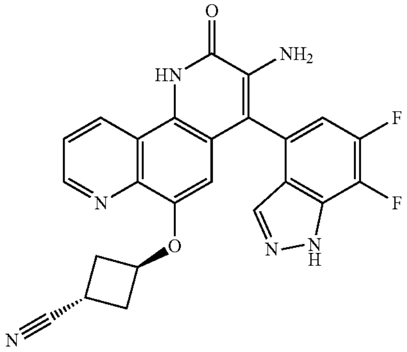

The title compound was synthesized from 3-amino-4-[6,7-difluoro-1-(oxan-2-yl)indazol-4-yl]-2-[(4-methoxyphenyl)methoxy]-1,7-phenanthrolin-6-ol (compound c-110) under the same conditions as the production examples of the compounds c-28 and C4, except that (1s,3s)-3-cyanocyclobutyl trifluoromethanesulfonate (compound a-103) was used instead of 2,2-difluoroethyltriflate used in the production example of the compound c-28. In addition, anisole was used instead of triethylsilane used in the production example of the compound C4.

LCMS: m/z 459 $[M+H]^+$

HPLC retention time: 0.47 min (analysis condition A)

Compound C212

(1s,3s)-3-[[3-Amino-4-(6,7-difluoro-1H-indazol-4-yl)-2-oxo-1H-1,7-phenanthrolin-6-yl]oxy]cyclobutane-1-carbonitrile

[Formula 659]

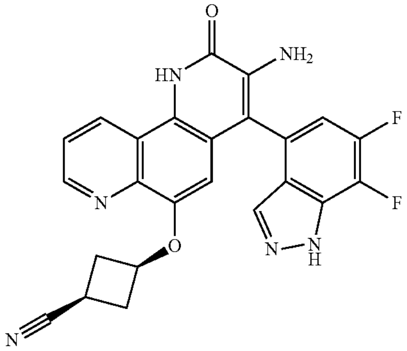

The title compound was synthesized from 3-amino-4-[6,7-difluoro-1-(oxan-2-yl)indazol-4-yl]-2-[(4-methoxyphenyl)methoxy]-1,7-phenanthrolin-6-ol (compound c-110) and (1r,3r)-3-hydroxycyclobutylcarbonitrile under the same conditions as the production examples of the compounds a-102, c-28, and C4, except that anisole was used instead of triethylsilane used in the production example of the compound C4.

LCMS: m/z 452 $[M+H]^+$

HPLC retention time: 0.49 min (analysis condition A)

Compound C213

3-Amino-4-(6,7-difluoro-1H-indazol-4-yl)-6-((1s,3s)-3-fluorocyclobutyl)oxy-1H-1,7-phenanthrolin-2-one

[Formula 660]

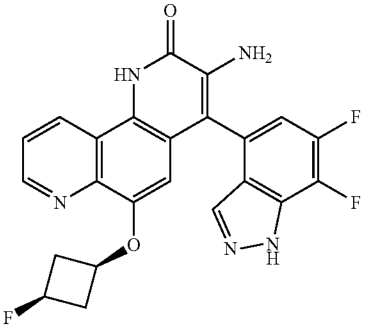

The title compound was synthesized from 3-amino-4-[6,7-difluoro-1-(oxan-2-yl)indazol-4-yl]-2-[(4-methoxyphenyl)methoxy]-1,7-phenanthrolin-6-ol (compound c-110) under the same conditions as the production examples of the compounds c-28 and C4, except that (1r,3r)-3-fluorocyclobutyl trifluoromethanesulfonate (compound a-80) was used instead of 2,2-difluoroethyltriflate used in the production example of the compound c-28. In addition, anisole was used instead of triethylsilane used in the production example of the compound C4.

LCMS: m/z 459 $[M+H]^+$

HPLC retention time: 0.46 min (analysis condition A)

Compound C214

3-Amino-4-(6,7-difluoro-1H-indazol-4-yl)-6-(3,3-difluoropropoxy)-1H-1,7-phenanthrolin-2-one

[Formula 661]

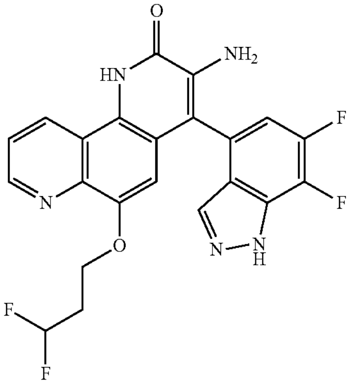

The title compound was synthesized from 3-amino-4-[6,7-difluoro-1-(oxan-2-yl)indazol-4-yl]-2-[(4-methoxyphenyl)methoxy]-1,7-phenanthrolin-6-ol (compound c-110) under the same conditions as the production examples of the compounds c-16 and C4, except that 3,3-difluoropropanol was used instead of MeOH used in the production example of the compound c-16. In addition, anisole was used instead of triethylsilane used in the production example of the compound C4.

LCMS: m/z 458 [M+H]$^+$

HPLC retention time: 0.50 min (analysis condition A)

Compound d-2

(E)-N'-(5-bromo-7-iodoquinolin-8-yl)-N,N-dimethylmethanimidamide

[Formula 662]

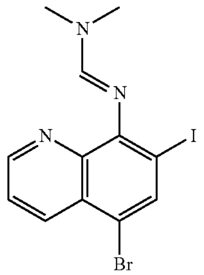

The title compound was synthesized from 5-bromoquinolin-8-amine under the same conditions as the production examples of the compounds c-1 and b-25.

LCMS: m/z 404 [M+H]$^+$

HPLC retention time: 0.38 min (analysis condition Q)

Compound d-3

(E)-N'-[5-bromo-7-[7-fluoro-2-(oxan-2-yl)indazole-4-carbonyl]quinolin-8-yl]-N,N-dimethylmethanimidamide

[Formula 663]

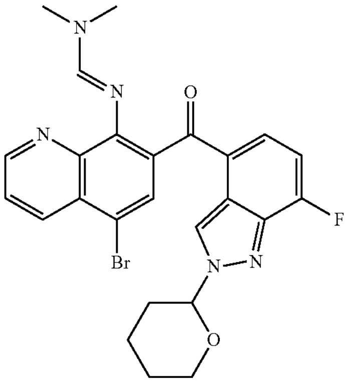

The title compound was synthesized from (E)-N'-(5-bromo-7-iodoquinolin-8-yl)-N,N-dimethylmethanimidamide (compound d-2) under the same conditions as the production example of the compound b-26.

LCMS: m/z 524 [M+H]$^+$

HPLC retention time: 0.53 min (analysis condition Q)

Compound d-4

(8-Amino-5-bromoquinolin-7-yl)-[7-fluoro-2-(oxan-2-yl)indazol-4-yl]methanone

[Formula 664]

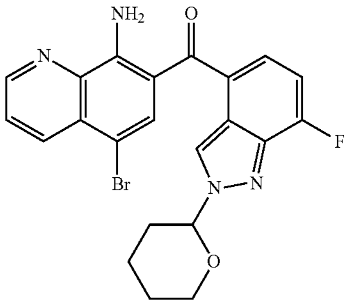

The title compound was synthesized from (E)-N'-[5-bromo-7-[7-fluoro-2-(oxan-2-yl)indazole-4-carbonyl]quinolin-8-yl]-N,N-dimethylmethanimidamide (compound d-3) under the same conditions as the production example of the compound b-27.

LCMS: m/z 471 [M+H]$^+$

HPLC retention time: 1.04 min (analysis condition Q)

Compound D1

3-Amino-6-bromo-4-(7-fluoro-1H-indazol-4-yl)-1H-1,10-phenanthrolin-2-one

[Formula 665]

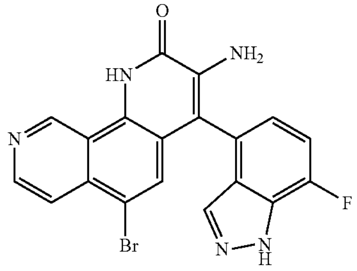

The title compound was synthesized from (8-amino-5-bromoquinolin-7-yl)-[7-fluoro-2-(oxan-2-yl)indazol-4-yl]methanone (compound d-4) under the same conditions as the production examples of the compounds b-28, b-29, b-30, and b-9, except that DIPEA was used instead of pyridine used in the production example of the compound b-28. In addition, DMSO was used instead of EtOH used in the production example of the compound b-9.

LCMS: m/z 424 [M+H]$^+$

HPLC retention time: 0.72 min (analysis condition A)

Compound D2

3-Amino-6-cyclopropyl-4-(7-fluoro-1H-indazol-4-yl)-1H-1,10-phenanthrolin-2-one

[Formula 666]

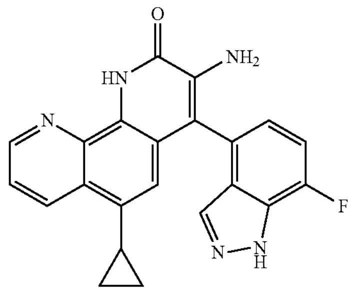

The title compound was synthesized from 3-amino-6-bromo-4-(7-fluoro-1H-indazol-4-yl)-1H-1,10-phenanthrolin-2-one (compound D1) under the same conditions as the production example of the compound B22, except that Xphos Pd G4 was used instead of CPhos Pd G3 used in the production example of the compound B22.

LCMS: m/z 386 $[M+H]^+$

HPLC retention time: 0.71 min (analysis condition A)

Compound D3

3-Amino-4-(7-fluoro-1H-indazol-4-yl)-6-methyl-1H-1,10-phenanthrolin-2-one

[Formula 667]

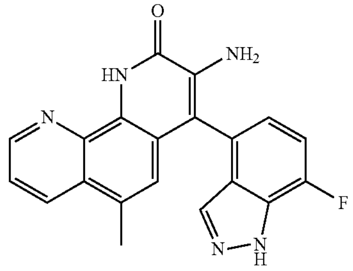

The title compound was synthesized from 3-amino-6-bromo-4-(7-fluoro-1H-indazol-4-yl)-1H-1,10-phenanthrolin-2-one (compound D1) under the same conditions as the production example of the compound B22, except that XPhos Pd G4 and a 2 M solution of methylzinc chloride in THF were used instead of CPhos Pd G3 and the 0.5 M solution of cyclopropylzinc bromide in THF used in the production example of the compound B22.

LCMS: m/z 360 $[M+H]^+$

HPLC retention time: 0.65 min (analysis condition A)

Compound D4

3-Amino-4-(7-fluoro-1H-indazol-4-yl)-1H-1,10-phenanthrolin-2-one

[Formula 668]

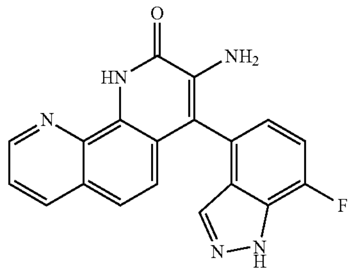

The title compound was synthesized from 3-amino-6-bromo-4-(7-fluoro-1H-indazol-4-yl)-1H-1,10-phenanthrolin-2-one (compound D1) under the same conditions as the production example of the compound B11, except that XPhos Pd G4 was used instead of Xantphos Pd G4 used in the production example of the compound B11.

LCMS: m/z 346 $[M+H]^+$

HPLC retention time: 0.61 min (analysis condition A)

Compound D5

3-Amino-6-ethyl-4-(7-fluoro-1H-indazol-4-yl)-1H-1,10-phenanthrolin-2-one

[Formula 669]

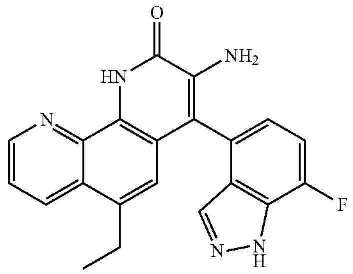

The title compound was synthesized from 3-amino-6-bromo-4-(7-fluoro-1H-indazol-4-yl)-1H-1,10-phenanthrolin-2-one (compound D1) under the same conditions as the production example of the compound B22, except that CPhos Pd G2 and a 1 M solution of diethylzinc in hexane were used instead of XPhos Pd G4 and the 0.5 M solution of cyclopropylzinc bromide in THF used in the production example of the compound B22.

LCMS: m/z 374 $[M+H]^+$

HPLC retention time: 0.69 min (analysis condition A)

Compound D6

3-Amino-4-(7-fluoro-1H-indazol-4-yl)-6-(4-methylpiperazin-1-yl)-1H-1,10-phenanthrolin-2-one

[Formula 670]

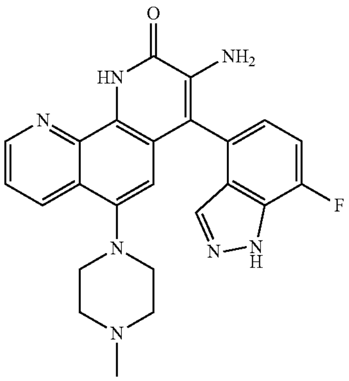

To a mixture of tris(dibenzylideneacetone)dipalladium(0) (32.4 mg, 0.035 mmol) and 2-(dicyclohexylphosphino)-3,6-dimethoxy-2',4',6'-triisopropyl-1,1'-biphenyl (38.0 mg, 0.070 mmol) in a reaction vessel, 1,4-dioxane (1.18 mL) was added, the reaction vessel was degassed under reduced pressure and subjected to argon gas replacement, and the mixture was stirred at 110° C. for 3 minutes. To the reaction mixture, 3-amino-6-bromo-4-(7-fluoro-1H-indazol-4-yl)-1H-1,10-phenanthrolin-2-one (compound D1, 50 mg, 0.118 mmol), 1-methylpiperazine (0.0389 mL, 0.351 mmol), and sodium tert-butoxide (136 mg, 1.42 mmol) were added, the reaction vessel was degassed under reduced pressure and subjected to argon gas replacement, and the reaction mixture was stirred at 150° C. for 1 hour. The reaction mixture was combined with that of another lot, and ethyl acetate and water were added to the reaction mixture. The mixture was filtered using Celite, and the filtrate was extracted twice with ethyl acetate. The organic layer was dried over anhydrous sodium sulfate, the drying agent was filtered off, and then the obtained filtrate was concentrated under reduced pressure. The obtained residue was purified by silica gel column chromatography to obtain the title compound (0.164 g) as a yellow solid.

LCMS: m/z 444.5 $[M+H]^+$

HPLC retention time: 0.38 min (analysis condition A)

Compound D7

3-Amino-4-(7-fluoro-1H-indazol-4-yl)-6-(4-morpholin-4-ylpiperidin-1-yl)-1H-1,10-phenanthrolin-2-one

[Formula 671]

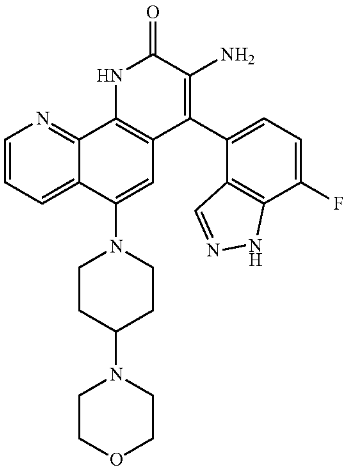

The title compound was synthesized from 3-amino-6-bromo-4-(7-fluoro-1H-indazol-4-yl)-1H-1,10-phenanthrolin-2-one (compound D1) and a corresponding amine under the same conditions as the production example of the compound D6.

LCMS: m/z 514.6 $[M+H]^+$

HPLC retention time: 0.40 min (analysis condition A)

Compound D8

3-Amino-6-(3,3-difluoropyrrolidin-1-yl)-4-(7-fluoro-1H-indazol-4-yl)-1H-1,10-phenanthrolin-2-one

[Formula 672]

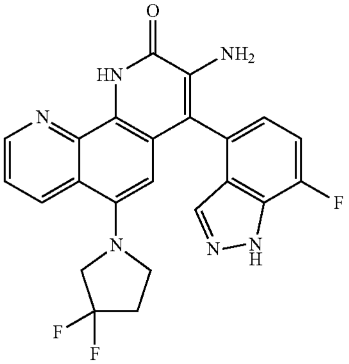

The title compound was synthesized from 3-amino-6-bromo-4-(7-fluoro-1H-indazol-4-yl)-1H-1,10-phenanthrolin-2-one (compound D1) and hydrochloride of a corresponding amine under the same conditions as the production example of the compound D6, except that Xantphos Pd G4 was used instead of tris(dibenzylideneacetone)dipalladium (0) and 2-(dicyclohexylphosphino)-3,6-dimethoxy-2',4',6'-triisopropyl-1,1'-biphenyl used in the production example of the compound D6. In addition, the reaction was carried out by heating the reaction mixture to 100° C.

LCMS: m/z 451.5 [M+H]+

HPLC retention time: 0.70 min (analysis condition A)

Compound D9

3-Amino-4-(7-fluoro-1H-indazol-4-yl)-6-morpholin-4-yl-1H-1,10-phenanthrolin-2-one

[Formula 673]

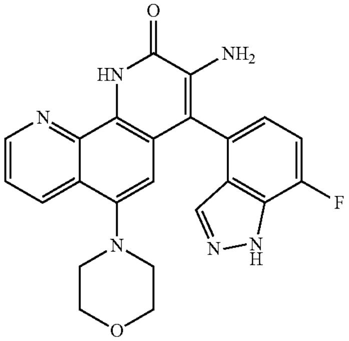

The title compound was synthesized from 3-amino-6-bromo-4-(7-fluoro-1H-indazol-4-yl)-1H-1,10-phenanthrolin-2-one (compound D1) and a corresponding amine under the same conditions as the production example of the compound D6.

LCMS: m/z 431 [M+H]+

HPLC retention time: 0.60 min (analysis condition A)

Compound D10

3-Amino-4-(7-fluoro-1H-indazol-4-yl)-6-(2-oxa-6-azaspiro[3,3]heptan-6-yl)-1H-1,10-one

[Formula 674]

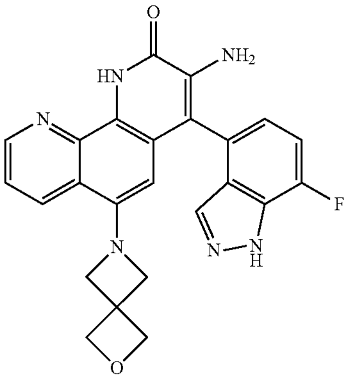

The title compound was synthesized from 3-amino-6-bromo-4-(7-fluoro-1H-indazol-4-yl)-1H-1,10-phenanthrolin-2-one (compound D1) and a corresponding amine under the same conditions as the production example of the compound D6, except that Xantphos Pd G4 was used instead of tris(dibenzylideneacetone)dipalladium(0) and 2-(dicyclohexylphosphino)-3,6-dimethoxy-2',4',6'-triisopropyl-1,1'-biphenyl used in the production example of the compound D6. In addition, the reaction was carried out by heating the reaction mixture to 110° C.

LCMS: m/z 443.5 [M+H]+

HPLC retention time: 0.54 min (analysis condition A)

Compound D11

3-Amino-6-[3-(3,3-difluoroazetidin-1-yl) azetidin-1-yl]-4-(7-fluoro-1H-indazol-4-yl)-1H-1,10-phenanthrolin-2-one

[Formula 675]

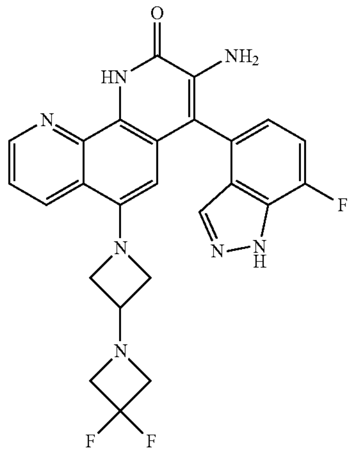

The title compound was synthesized from 3-amino-6-bromo-4-(7-fluoro-1H-indazol-4-yl)-1H-1,10-phenanthrolin-2-one (compound D1) and hydrochloride of a corresponding amine under the same conditions as the production example of the compound D6, except that Xantphos Pd G4 was used instead of tris(dibenzylideneacetone)dipalladium (0) and 2-(dicyclohexylphosphino)-3,6-dimethoxy-2',4',6'-triisopropyl-1,1'-biphenyl used in the production example of the compound D6. In addition, the reaction was carried out by heating the reaction mixture to 100° C.

LCMS: m/z 492.5 [M+H]+

HPLC retention time: 0.55 min (analysis condition A)

Compound D12

6-[(9aR)-3,4,6,7,9,9a-hexahydro-1H-pyrazino[2,1-c][1,4]oxazin-8-yl]-3-amino-4-(7-fluoro-1H-indazol-4-yl)-1H-1,10-phenanthrolin-2-one

[Formula 676]

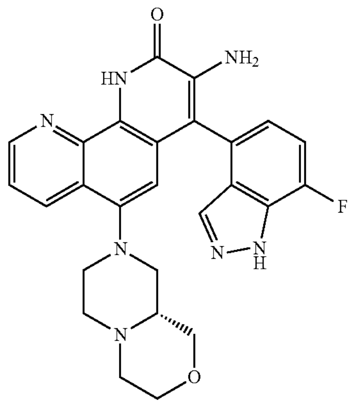

The title compound was synthesized from 3-amino-6-bromo-4-(7-fluoro-1H-indazol-4-yl)-1H-1,10-phenanthrolin-2-one (compound D1) and a corresponding amine under the same conditions as the production example of the compound D6, except that Xantphos Pd G4 was used instead of tris(dibenzylideneacetone)dipalladium(0) and 2-(dicyclohexylphosphino)-3,6-dimethoxy-2',4',6'-triisopropyl-1,1'-biphenyl used in the production example of the compound D6. In addition, the reaction was carried out by heating the reaction mixture to 110° C.

LCMS: m/z 486.5 $[M+H]^+$

HPLC retention time: 0.38 min (analysis condition A)

Compound D13

6-[(9aS)-3,4,6,7,9,9a-hexahydro-1H-pyrazino[2,1-c][1,4]oxazin-8-yl]-3-amino-4-(7-fluoro-1H-indazol-4-yl)-1H-1,10-phenanthrolin-2-one

[Formula 677]

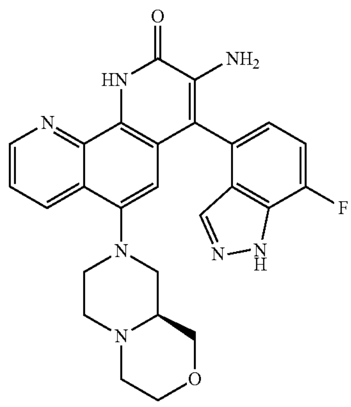

The title compound was synthesized from 3-amino-6-bromo-4-(7-fluoro-1H-indazol-4-yl)-1H-1,10-phenanthrolin-2-one (compound D1) and a corresponding amine under the same conditions as the production example of the compound D6, In addition, the reaction was carried out by heating the reaction mixture to 150° C., except that Xantphos Pd G4 was used instead of tris(dibenzylideneacetone)dipalladium(0) and 2-(dicyclohexylphosphino)-3,6-dimethoxy-2',4',6'-triisopropyl-1,1'-biphenyl used in the production example of the compound D6.

LCMS: m/z 486.5 $[M+H]^+$

HPLC retention time: 0.39 min (analysis condition A)

Compound D14

3-Amino-6-[4-(2,2-difluoroethyl) piperazin-1-yl]-4-(7-fluoro-1H-indazol-4-yl)-1H-1,10-phenanthrolin-2-one

[Formula 678]

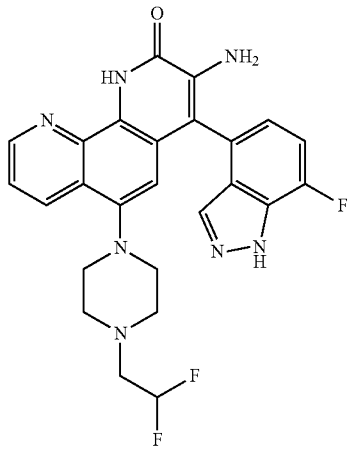

The title compound was synthesized from 3-amino-6-bromo-4-(7-fluoro-1H-indazol-4-yl)-1H-1,10-phenanthrolin-2-one (compound D1) and a corresponding amine under the same conditions as the production example of the compound D6, except that Xantphos Pd G4 was used instead of tris(dibenzylideneacetone)dipalladium(0) and 2-(dicyclohexylphosphino)-3,6-dimethoxy-2',4',6'-triisopropyl-1,1'-biphenyl used in the production example of the compound D6. In addition, the reaction was carried out by heating the reaction mixture to 105° C.

LCMS: m/z 494.5 $[M+H]^+$

HPLC retention time: 0.49 min (analysis condition A)

Compound D15

3-Amino-4-(7-fluoro-1H-indazol-4-yl)-6-[4-(2,2,2-trifluoroethyl) piperazin-1-yl]-1H-1,10-phenanthrolin-2-one

[Formula 679]

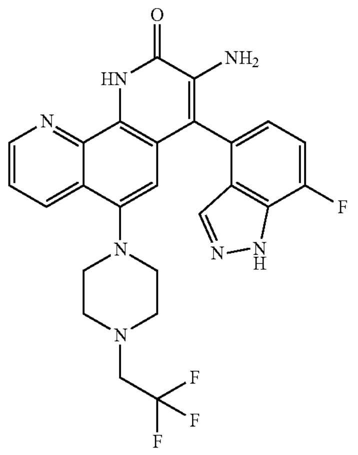

The title compound was synthesized from 3-amino-6-bromo-4-(7-fluoro-1H-indazol-4-yl)-1H-1,10-phenanthrolin-2-one (compound D1) and a corresponding amine under the same conditions as the production example of the compound D6, except that Xantphos Pd G4 was used instead of tris(dibenzylideneacetone)dipalladium(0) and 2-(dicyclohexylphosphino)-3,6-dimethoxy-2',4',6'-triisopropyl-1,1'-biphenyl used in the production example of the compound D6. In addition, the reaction was carried out by heating the reaction mixture to 105° C.

LCMS: m/z 512.5 $[M+H]^+$

HPLC retention time: 0.75 min (analysis condition A)

Compound D16

N-[8-Amino-7-(7-fluoro-1H-indazol-4-yl)-9-oxo-10H-1,10-phenanthroline-5-yl]methanesulfonamide

[Formula 680]

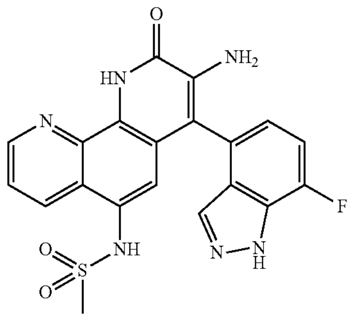

The title compound was synthesized from 3-amino-6-bromo-4-(7-fluoro-1H-indazol-4-yl)-1H-1,10-phenanthrolin-2-one (compound D1) under the same conditions as the production example of the compound C127. In addition, the reaction was carried out by heating the reaction mixture to 150° C.

LCMS: m/z 439 $[M+H]^+$

HPLC retention time: 0.49 min (analysis condition A)

Compound D17

N-[8-amino-7-(7-fluoro-1H-indazol-4-yl)-9-oxo-10H-1,10-phenanthrolin-5-yl]cyclopropanesulfonamide

[Formula 681]

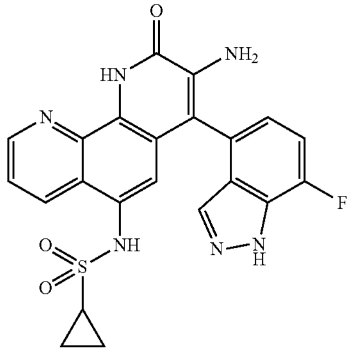

The title compound was synthesized from 3-amino-6-bromo-4-(7-fluoro-1H-indazol-4-yl)-1H-1,10-phenanthrolin-2-one (compound D1) under the same conditions as the production example of the compound C127, except that cyclopropanesulfonamide was used instead of methanesulfonamide used in the production example of the compound C127. In addition, the reaction was carried out by heating the reaction mixture to 150° C.

LCMS: m/z 465 $[M+H]^+$

HPLC retention time: 0.53 min (analysis condition A)

Compound D18

3-Amino-4-(7-fluoro-1H-indazol-4-yl)-6-methoxy-1H-1,10-phenanthrolin-2-one

[Formula 682]

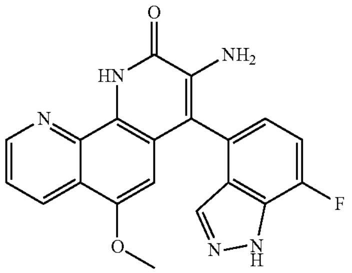

The title compound was synthesized from 3-amino-6-bromo-4-(7-fluoro-1H-indazol-4-yl)-1H-1,10-phenanthrolin-2-one (compound D1) under the same conditions as the production example of the compound c-108, except that tBuXPhos Pd G3 was used instead of tBuBrettPhos Pd G3 used in the production example of the compound c-108.

LCMS: m/z 376 $[M+H]^+$

HPLC retention time: 0.64 min (analysis condition A)

Compound D19

N-[8-amino-7-(7-fluoro-1H-indazol-4-yl)-9-oxo-10H-1,10-phenanthrolin-5-yl]acetamide

[Formula 683]

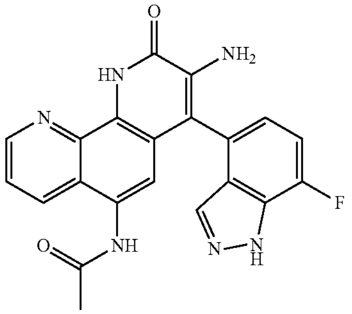

The title compound was synthesized from 3-amino-6-bromo-4-(7-fluoro-1H-indazol-4-yl)-1H-1,10-phenanthrolin-2-one (compound D1) under the same conditions as the production example of the compound D6, except that tBuXPhos Pd G3 and acetamide were used instead of tris(dibenzylideneacetone)dipalladium(0) and 2-(dicyclohexylphosphino)-3,6-dimethoxy-2',4',6'-triisopropyl-1,1'-biphenyl and 1-methylpiperazine used in the production example of the compound D6.

LCMS: m/z 403 $[M+H]^+$

HPLC retention time: 0.44 min (analysis condition A)

Compound D20

3-Amino-4-(7-fluoro-1H-indazol-4-yl)-6-(propan-2-ylamino)-1H-1,10-phenanthrolin-2-one

[Formula 684]

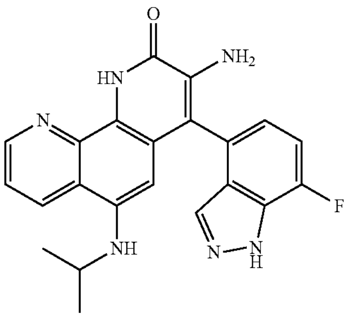

The title compound was synthesized from 3-amino-6-bromo-4-(7-fluoro-1H-indazol-4-yl)-1H-1,10-phenanthrolin-2-one (compound D1) and a corresponding amine under the same conditions as the production example of the compound D6, except that tBuXPhos Pd G3 and isopropylamine were used instead of tris(dibenzylideneacetone) dipalladium(0), 2-(dicyclohexylphosphino)-3,6-dimethoxy-2',4',6'-triisopropyl-1,1'-biphenyl and 1-methylpiperazine used in the production example of the compound D6. In addition, the reaction was carried out by heating the reaction mixture to 150° C.

LCMS: m/z 403 $[M+H]^+$

HPLC retention time: 0.59 min (analysis condition A)

Compound d-6 tert-Butyl 4-[8-amino-7-(7-fluoro-1H-indazol-4-yl)-9-oxo-10H-1,10-phenanthrolin-5-yl]piperidine-1-carboxylate

[Formula 685]

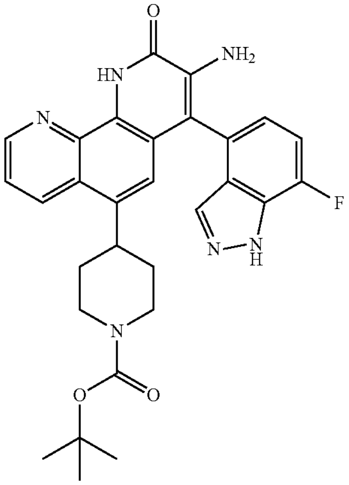

The title compound was synthesized from 3-amino-6-bromo-4-(7-fluoro-1H-indazol-4-yl)-1H-1,10-phenanthrolin-2-one (compound D1) under the same conditions as the production example of the compound B22, except that a solution of [1-(tert-butoxycarbonyl) piperidin-4-yl]zinc iodide in DMA was used instead of the 0.5 M solution of cyclopropylzinc bromide in THF used in the production example of the compound B22.

LCMS: m/z 529 $[M+H]^+$

HPLC retention time: 4.28 min (analysis condition J)

Compound d-7 tert-Butyl 3-[8-amino-7-(7-fluoro-1H-indazol-4-yl)-9-oxo-10H-1,10-phenanthrolin-5-yl]azetidine-1-carboxylic acid

[Formula 686]

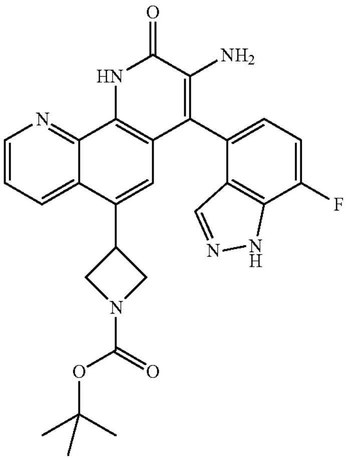

The title compound was synthesized from 3-amino-6-bromo-4-(7-fluoro-1H-indazol-4-yl)-1H-1,10-phenanthrolin-2-one (compound D1) under the same conditions as the production example of the compound B22, except that CPhos Pd G2 and a solution of 1-tert-butoxycarbonylazetidin-3-ylzinc iodide in DMA were respectively used instead of CPhos Pd G3 and the 0.5 M solution of cyclopropylzinc bromide in THE used in the production example of the compound B22.

LCMS: m/z 501 $[M+H]^+$

HPLC retention time: 3.97 min (analysis condition J)

Compound D21

3-Amino-4-(7-fluoro-1H-indazol-4-yl)-6-piperidin-4-yl-1H-1,10-phenanthrolin-2-one

[Formula 687]

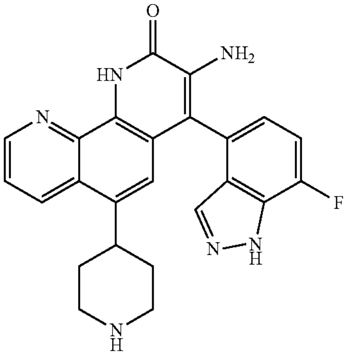

The title compound was synthesized from tert-butyl 4-[8-amino-7-(7-fluoro-1H-indazol-4-yl)-9-oxo-10H-1,10-phenanthrolin-5-yl]piperidine-1-carboxylate (compound d-6) under the same conditions as the production example of the compound C133.

LCMS: m/z 429.5 $[M+H]^+$

HPLC retention time: 0.38 min (analysis condition A)

Compound D28

3-Amino-6-(azetidin-3-yl)-4-(7-fluoro-1H-indazol-4-yl)-1H-1,10-phenanthrolin-2-one

[Formula 688]

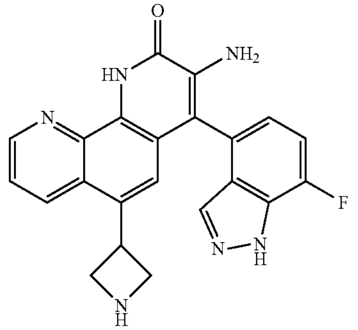

The title compound was synthesized from tert-butyl 3-[8-amino-7-(7-fluoro-1H-indazol-4-yl)-9-oxo-10H-1,10-phenanthrolin-5-yl]azetidine-1-carboxylic acid (compound d-7) under the same conditions as the production example of the compound C133.

LCMS: m/z 401.5 $[M+H]^+$

HPLC retention time: 0.35 min (analysis condition A)

Compound D22

3-Amino-4-(7-fluoro-1H-indazol-4-yl)-6-(1-methylpiperidin-4-yl)-1H-1,10-phenanthrolin-2-one

[Formula 689]

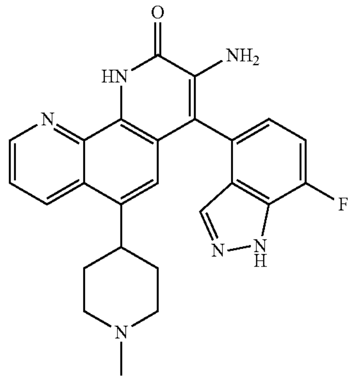

The title compound was synthesized from 3-amino-4-(7-fluoro-1H-indazol-4-yl)-6-piperidin-4-yl-1H-1,10-phenanthrolin-2-one (compound D21) under the same conditions as the production example of the compound C134, except that formalin was used instead of cyclobutanone used in the production example of the compound C134.

LCMS: m/z 443.5 $[M+H]^+$

HPLC retention time: 0.38 min (analysis condition A)

Compound D23

3-Amino-4-(7-fluoro-1H-indazol-4-yl)-6-(1-propan-2-ylpiperidin-4-yl)-1H-1,10-phenanthrolin-2-one

[Formula 690]

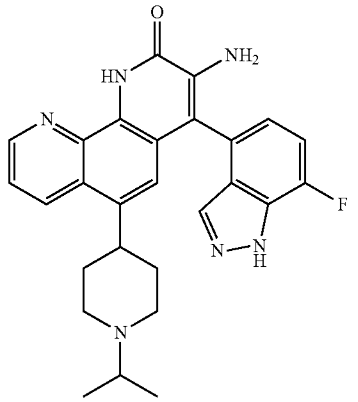

The title compound was synthesized from 3-amino-4-(7-fluoro-1H-indazol-4-yl)-6-piperidin-4-yl-1H-1,10-phenanthrolin-2-one (compound D21) under the same conditions as the production example of the compound C134, except that acetone was used instead of cyclobutanone used in the production example of the compound C134.

LCMS: m/z 471.5 $[M+H]^+$

HPLC retention time: 0.41 min (analysis condition A)

Compound D24

3-Amino-6-(1-cyclobutylpiperidin-4-yl)-4-(7-fluoro-1H-indazol-4-yl)-1H-1,10-phenanthrolin-2-one

[Formula 691]

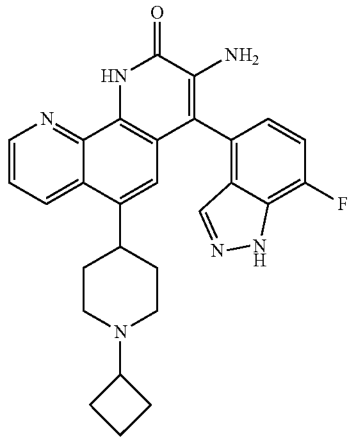

The title compound was synthesized from 3-amino-4-(7-fluoro-1H-indazol-4-yl)-6-piperidin-4-yl-1H-1,10-phenanthrolin-2-one (compound D21) under the same conditions as the production example of the compound C134.

LCMS: m/z 483.5 $[M+H]^+$

HPLC retention time: 0.42 min (analysis condition A)

Compound D25

3-Amino-4-(7-fluoro-1H-indazol-4-yl)-6-[1-(oxan-4-yl) piperidin-4-yl]-1H-1,10-phenanthrolin-2-one

[Formula 692]

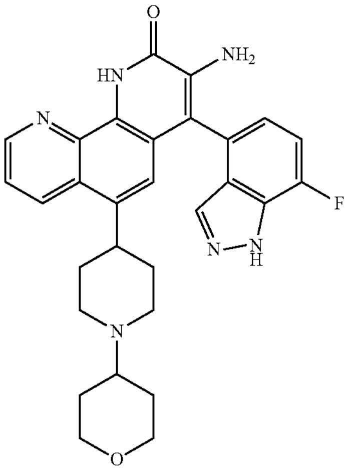

The title compound was synthesized from 3-amino-4-(7-fluoro-1H-indazol-4-yl)-6-piperidin-4-yl-1H-1,10-phenanthrolin-2-one (compound D21) under the same conditions as the production example of the compound C134, except that tetrahydro-4H-pyran-4-one was used instead of cyclobutanone used in the production example of the compound C134.

LCMS: m/z 513.5 $[M+H]^+$

HPLC retention time: 0.39 min (analysis condition A)

Compound D26

3-Amino-6-(1-ethylpiperidin-4-yl)-4-(7-fluoro-1H-indazol-4-yl)-1H-1,10-phenanthrolin-2-one

[Formula 693]

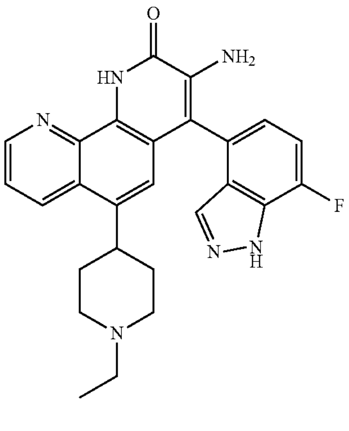

The title compound was synthesized from 3-amino-4-(7-fluoro-1H-indazol-4-yl)-6-piperidin-4-yl-1H-1,10-phenanthrolin-2-one (compound D21) under the same conditions as the production example of the compound C134, except that acetaldehyde was used instead of cyclobutanone used in the production example of the compound C134.

LCMS: m/z 457.5 $[M+H]^+$

HPLC retention time: 0.39 min (analysis condition A)

Compound D27

3-Amino-4-(7-fluoro-1H-indazol-4-yl)-6-[1-(oxetan-3-yl) piperidin-4-yl]-1H-1,10-phenanthrolin-2-one

[Formula 694]

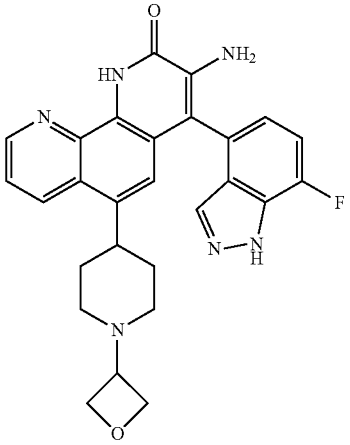

The title compound was synthesized from 3-amino-4-(7-fluoro-1H-indazol-4-yl)-6-piperidin-4-yl-1H-1,10-phenanthrolin-2-one (compound D21) under the same conditions as the production example of the compound C134, except that 3-oxetanone was used instead of cyclobutanone used in the production example of the compound C134.

LCMS: m/z 485.5 $[M+H]^+$

HPLC retention time: 0.37 min (analysis condition A)

Compound D29

3-Amino-4-(7-fluoro-1H-indazol-4-yl)-6-(1-propan-2-ylazetidin-3-yl)-1H-1,10-phenanthrolin-2-one

[Formula 695]

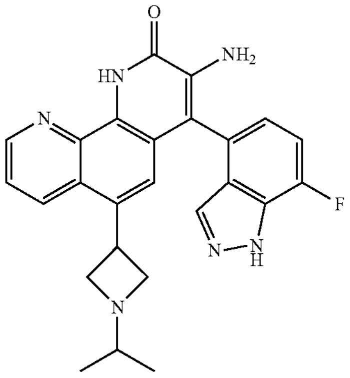

The title compound was synthesized from 3-amino-6-(azetidin-3-yl)-4-(7-fluoro-1H-indazol-4-yl)-1H-1,10-phenanthrolin-2-one (compound D28) under the same conditions as the production example of the compound C134, except that acetone was used instead of cyclobutanone used in the production example of the compound C134.

LCMS: m/z 443.5 $[M+H]^+$

HPLC retention time: 0.38 min (analysis condition A)

Compound D30

3-Amino-4-(7-fluoro-1H-indazol-4-yl)-6-(1-methyl-azetidin-3-yl)-1H-1,10-phenanthrolin-2-one

[Formula 696]

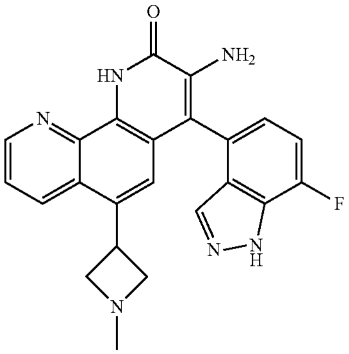

The title compound was synthesized from 3-amino-6-(azetidin-3-yl)-4-(7-fluoro-1H-indazol-4-yl)-1H-1,10-phenanthrolin-2-one (compound D28) under the same conditions as the production example of the compound C134, except that formalin was used instead of cyclobutanone used in the production example of the compound C134.

LCMS: m/z 415.5 $[M+H]^+$

HPLC retention time: 0.35 min (analysis condition A)

Compound e-1

3-Amino-4-[1-(oxan-2-yl)indazol-4-yl]chromen-2-one

[Formula 697]

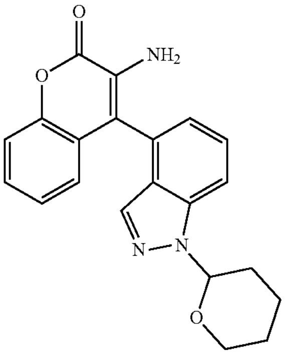

The title compound was synthesized from 3-amino-4-bromo-2H-chromen-2-one under the same conditions as the production example of the compound b-4, except that DPPF Pd G4, 1-(tetrahydropyran-2-yl)-4-(4,4,5,5-tetramethyl[1,3,2]dioxaborolan-2-yl)-1H-indazole, and DMA were respectively used instead of [1,1'-bis(diphenylphosphino)ferrocene]dichloropalladium(II), 3-methoxybenzeneboronic acid, and THF used in the production example of the compound b-4.

LCMS: m/z 362.5 $[M+H]^+$

HPLC retention time: 0.84 min (analysis condition A)

Compound E1

3-Amino-4-(1H-indazol-4-yl) chromen-2-one

[Formula 698]

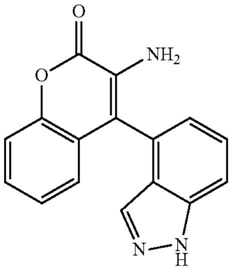

The title compound was synthesized from 3-amino-4-[1-(oxan-2-yl)indazol-4-yl]chromen-2-one (compound e-1) under the same conditions as the production example of the compound B49.

LCMS: m/z 278 $[M+H]^+$

HPLC retention time: 0.64 min (analysis condition A)

Compound e-2

3-Hydroxy-4-[1-(oxan-2-yl)indazol-4-yl]-1H-quinolin-2-one

[Formula 699]

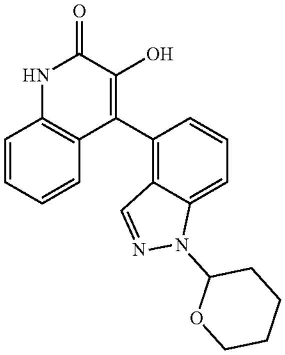

The title compound was synthesized from 4-bromo-3-hydroxyquinolin-2(1H)-one under the same conditions as the production example of the compound b-4, except that XPhos Pd G4, 1-(tetrahydropyran-2-yl)-4-(4,4,5,5-tetramethyl[1,3,2]dioxaborolan-2-yl)-1H-indazole, and DMA were respectively used instead of [1,1'-bis(diphenylphosphino)ferrocene]dichloropalladium(II), 3-methoxybenzeneboronic acid, and THF used in the production example of the compound b-4.

LCMS: m/z 362 $[M+H]^+$

HPLC retention time: 0.70 min (analysis condition A)

Compound E2

3-Hydroxy-4-(1H-indazol-4-yl)-1H-quinolin-2-one

[Formula 700]

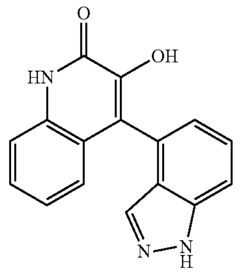

The title compound was synthesized from 3-hydroxy-4-[1-(oxan-2-yl)indazol-4-yl]-1H-quinolin-2-one (compound e-2) under the same conditions as the production example of the compound B49.

LCMS: m/z 278 [M+H]+

HPLC retention time: 0.52 min (analysis condition A)

Compound f-1

8-Bromo-3-fluoroquinolin-5-amine

[Formula 701]

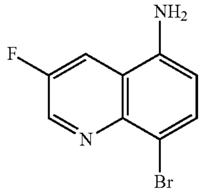

The title compound was synthesized from 3-fluoroquinolin-5-amine under the same conditions as the production example of the compound b-100, except that THF was used instead of DMF used in the production example of the compound b-100.

LCMS: m/z 241 [M+H]+

HPLC retention time: 0.59 min (analysis condition A)

Compound f-2

8-Bromo-3-fluoro-6-iodoquinolin-5-amine

[Formula 702]

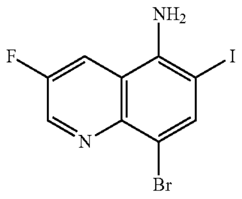

The title compound was synthesized from 8-bromo-3-fluoroquinolin-5-amine (compound f-1) under the same conditions as the production example of the compound c-1, except that a mixed solvent of acetonitrile/DMSO (2/1) was used instead of acetonitrile used in the production example of the compound c-1.

LCMS: m/z 367 [M+H]+

HPLC retention time: 0.80 min (analysis condition A)

Compound f-3

(E)-N'-(8-bromo-3-fluoro-6-iodoquinolin-5-yl)-N,N-dimethylmethanimidamide

[Formula 703]

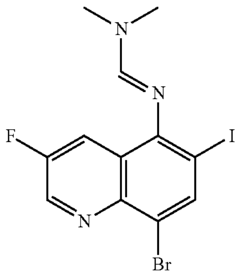

The title compound was synthesized from 8-bromo-3-fluoro-6-iodoquinolin-5-amine (compound f-2) under the same conditions as the production example of the compound b-25, except that the reaction was carried out by heating the reaction mixture to 60° C.

LCMS: m/z 422 [M+H]+

HPLC retention time: 0.48 min (analysis condition A)

Compound f-4

(E)-N'-[8-bromo-3-fluoro-6-[7-fluoro-2-(oxan-2-yl)indazole-4-carbonyl]quinolin-5-yl]-N,N-dimethylmethanimidamide

[Formula 704]

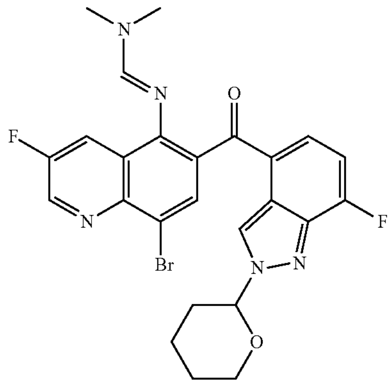

The title compound was synthesized from (E)-N'-(8-bromo-3-fluoro-6-iodoquinolin-5-yl)-N,N-dimethylmethanimidamide (compound f-3) under the same conditions as the production example of the compound b-26.

LCMS: m/z 542 [M+H]+

HPLC retention time: 0.79 min (analysis condition A)

Compound f-5

(5-Amino-8-bromo-3-fluoroquinolin-6-yl)-[7-fluoro-2-(oxan-2-yl)indazol-4-yl]methanone

[Formula 705]

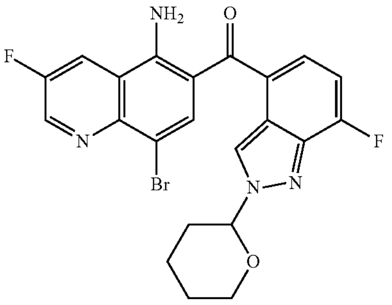

The title compound was synthesized from (E)-N'-[8-bromo-3-fluoro-6-[7-fluoro-2-(oxan-2-yl)indazole-4-carbonyl]quinolin-5-yl]-N,N-dimethylmethanimidamide (compound f-4) under the same conditions as the production example of the compound b-27.

LCMS: m/z 487 $[M+H]^+$

HPLC retention time: 0.90 min (analysis condition A)

Compound f-8

3-Amino-6-bromo-9-fluoro-4-[7-fluoro-2-(oxan-2-yl)indazol-4-yl]-1H-1,7-phenanthrolin-2-one

[Formula 706]

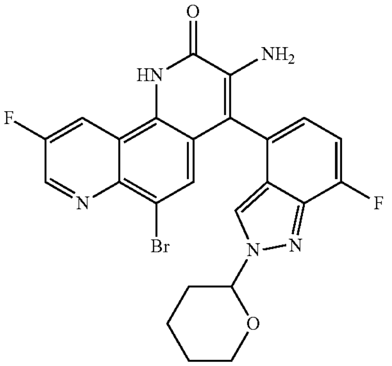

The title compound was synthesized from (5-amino-8-bromo-3-fluoroquinolin-6-yl)-[7-fluoro-2-(oxan-2-yl)indazol-4-yl]methanone (compound f-5) under the same conditions as the production examples of the compounds c-9, c-10, and c-13.

LCMS: m/z 526 $[M+H]^+$

HPLC retention time: 0.79 min (analysis condition A)

Compound f-9

(E)-N'-[8-bromo-6-[6,7-difluoro-1-(oxan-2-yl)indazole-4-carbonyl]-3-fluoroquinolin-5-yl]-N,N-dimethylmethanimidamide

[Formula 707]

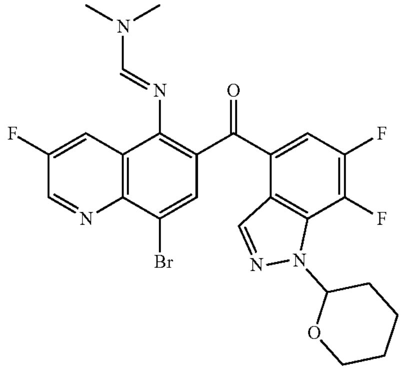

The title compound was synthesized from 6,7-difluoro-N-methoxy-N-methyl-1-(oxan-2-yl)indazole-4-carboxamide (compound c-102) and (E)-N'-(8-bromo-3-fluoro-6-iodoquinolin-5-yl)-N,N-dimethylmethanimidamide (compound f-3) under the same conditions as the production example of the compound b-26.

LCMS: m/z 560 $[M+H]^+$

HPLC retention time: 0.98 min (analysis condition A)

Compound f-10

(5-Amino-8-bromo-3-fluoroquinolin-6-yl)-[6,7-difluoro-1-(oxan-2-yl)indazol-4-yl]methanone

[Formula 708]

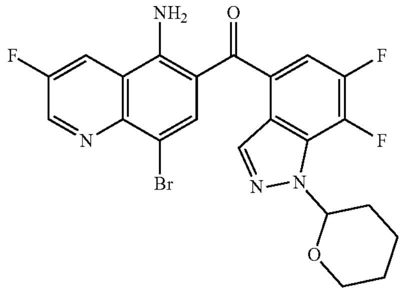

The title compound was synthesized from (E)-N'-[8-bromo-6-[6,7-difluoro-1-(oxan-2-yl)indazole-4-carbonyl]-3-fluoroquinolin-5-yl]-N,N-dimethylmethanimidamide (compound f-9) under the same conditions as the production example of the compound b-27.

LCMS: m/z 505 $[M+H]^+$

HPLC retention time: 0.98 min (analysis condition A)

Compound f-13

3-Amino-6-bromo-4-[6,7-difluoro-1-(oxan-2-yl) indazol-4-yl]-9-fluoro-1H-1,7-phenanthrolin-2-one

[Formula 709]

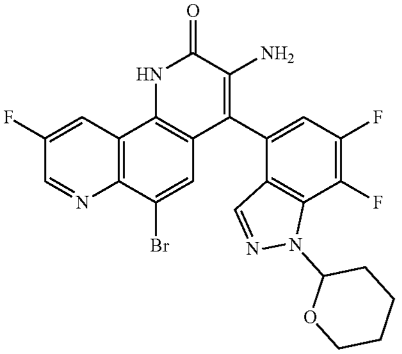

The title compound was synthesized from (5-amino-8-bromo-3-fluoroquinolin-6-yl)-[6,7-difluoro-1-(oxan-2-yl) indazol-4-yl]methanone (compound f-10) under the same conditions as the production examples of the compounds c-9, c-10, and c-13. The reaction was carried out without using N,N-dimethylaniline used in the production example of the compound c-9.

LCMS: m/z 544 $[M+H]^+$

HPLC retention time: 0.87 min (analysis condition A)

Compound F1

3-Amino-6-bromo-9-fluoro-4-(7-fluoro-1H-indazol-4-yl)-1H-1,7-phenanthrolin-2-one

[Formula 710]

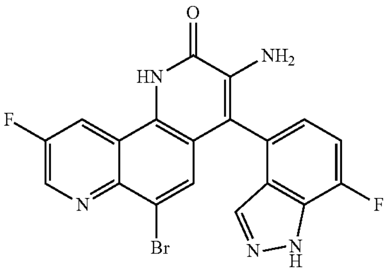

The title compound was synthesized from 3-amino-6-bromo-9-fluoro-4-[7-fluoro-2-(oxan-2-yl)indazol-4-yl]-1H-1,7-phenanthrolin-2-one (compound f-8) under the same conditions as the compound B49, except that triethylsilane was used in an amount of 5 equivalents based on the raw material, in addition to the conditions of the production example of the compound B49. In addition, hexafluoropropan-2-ol was used instead of TFE.

LCMS: m/z 442 $[M+H]^+$

HPLC retention time: 0.64 min (analysis condition A)

Compound F2

3-Amino-9-fluoro-4-(7-fluoro-1H-indazol-4-yl)-6-methoxy-1H-1,7-phenanthrolin-2-one

[Formula 711]

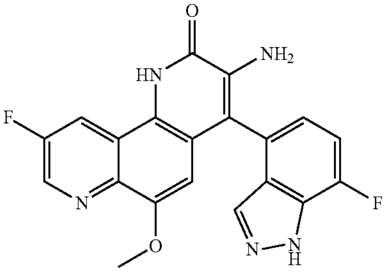

The title compound was synthesized from 3-amino-6-bromo-9-fluoro-4-(7-fluoro-1H-indazol-4-yl)-1H-1,7-phenanthrolin-2-one (compound F1) under the same conditions as the production example of the compound c-108, except that NMP was used instead of 1,4-dioxane used in the production example of the compound c-108.

LCMS: m/z 394 $[M+H]^+$

HPLC retention time: 0.51 min (analysis condition A)

Compound F3

3-Amino-9-fluoro-4-(7-fluoro-1H-indazol-4-yl)-6-methyl-1H-1,7-phenanthrolin-2-one

[Formula 712]

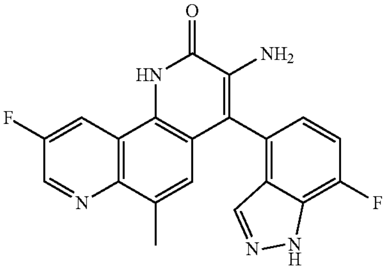

The title compound was synthesized from 3-amino-6-bromo-9-fluoro-4-(7-fluoro-1H-indazol-4-yl)-1H-1,7-phenanthrolin-2-one (compound F1) under the same conditions as the production example of the compound B22, except that a 2 M solution of methylzincchloride in THF was used instead of the 0.5 M solution of cyclopropylzinc bromide in THE used in the production example of the compound B22.

LCMS: m/z 378.5 $[M+H]^+$

HPLC retention time: 0.64 min (analysis condition A)

Compound F4

3-Amino-6-bromo-4-(6,7-difluoro-1H-indazol-4-yl)-9-fluoro-1H-1,7-phenanthrolin-2-one

[Formula 713]

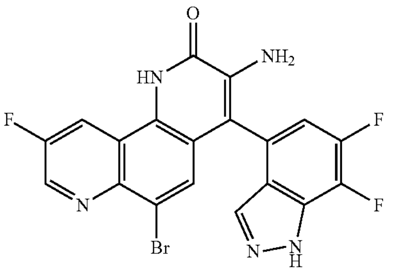

The title compound was synthesized from 3-amino-6-bromo-4-[6,7-difluoro-1-(oxan-2-yl)indazol-4-yl]-9-fluoro-1H-1,7-phenanthrolin-2-one (compound f-13) under the same conditions as the compound B49, except that anisole was used in an amount of 5 equivalents based on the raw material, in addition to the conditions of the production example of the compound B49.

LCMS: m/z 460 $[M+H]^+$

HPLC retention time: 0.67 min (analysis condition A)

Compound F5

3-Amino-4-(6,7-difluoro-1H-indazol-4-yl)-9-fluoro-6-methoxy-1H-1,7-phenanthrolin-2-one

[Formula 714]

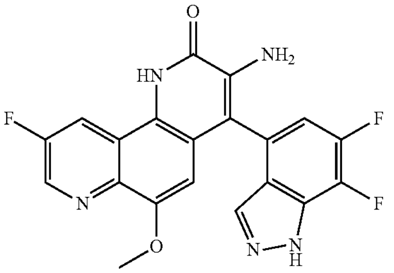

The title compound was synthesized from 3-amino-6-bromo-4-(6,7-difluoro-1H-indazol-4-yl)-9-fluoro-1H-1,7-phenanthrolin-2-one (compound F4) under the same conditions as the production example of the compound c-108, except that NMP was used instead of 1,4-dioxane used in the production example of the compound c-108.

LCMS: m/z 412.5 $[M+H]^+$

HPLC retention time: 0.54 min (analysis condition A)

Compound F6

3-Amino-4-(6,7-difluoro-1H-indazol-4-yl)-9-fluoro-6-methyl-1H-1,7-phenanthrolin-2-one

[Formula 715]

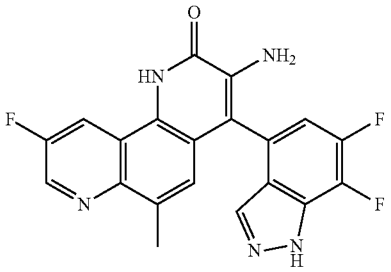

The title compound was synthesized from 3-amino-6-bromo-4-(6,7-difluoro-1H-indazol-4-yl)-9-fluoro-1H-1,7-phenanthrolin-2-one (compound F4) under the same conditions as the production example of the compound B22, except that a 2 M solution of methylzincchloride in THF was used instead of the 0.5 M solution of cyclopropylzinc bromide in THF used in the production example of the compound B22.

LCMS: m/z 396.5 $[M+H]^+$

HPLC retention time: 0.67 min (analysis condition A)

Compound g-1

8-Bromo-6-iodoquinoxalin-5-amine

[Formula 716]

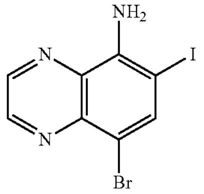

The title compound was synthesized from 8-bromoquinoxalin-5-amine under the same conditions as the production example of the compound b-59.

LCMS: m/z 350 $[M+H]^+$

HPLC retention time: 0.79 min (analysis condition A)

Compound g-2

(E)-N'-(8-bromo-6-iodoquinoxalin-5-yl)-N,N-dimethylmethanimidamide

[Formula 717]

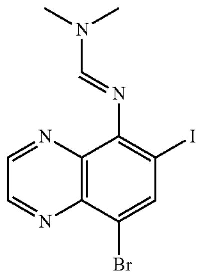

The title compound was synthesized from 8-bromo-6-iodoquinoxalin-5-amine (compound g-1) under the same conditions as the production example of the compound b-25, except that DMSO was used instead of EtOH used in the production example of the compound b-25.

LCMS: m/z 405 $[M+H]^+$

HPLC retention time: 0.39 min (analysis condition A)

Compound g-3

(5-Amino-8-bromoquinoxalin-6-yl)-[7-fluoro-1-(oxan-2-yl)indazol-4-yl]methanol

[Formula 718]

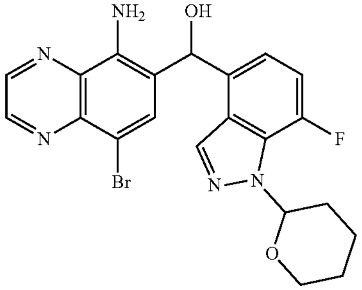

The title compound was synthesized from (E)-N'-(8-bromo-6-iodoquinoxalin-5-yl)-N,N-dimethylmethanimidamide (g-2) and 7-fluoro-1-(oxan-2-yl)indazole-4-carbaldehyde (compound c-254) under the same conditions as the production example of the compound c-227, except that 20 equivalents of N,N'-dimethylpropylene urea were used in addition to the production example of the compound c-227.

LCMS: m/z 472.5 $[M+H]^+$

HPLC retention time: 0.79 min (analysis condition A)

Compound g-4

(5-Amino-8-bromoquinoxalin-6-yl)-[7-fluoro-1-(oxan-2-yl)indazol-4-yl]methanone

[Formula 719]

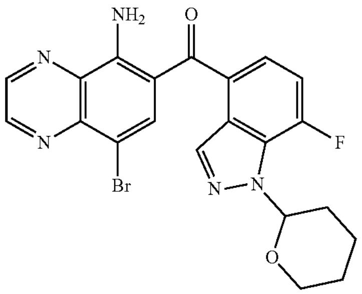

The title compound was synthesized from (5-amino-8-bromoquinoxalin-6-yl)-[7-fluoro-1-(oxan-2-yl)indazol-4-yl]methanol (g-3) under the same conditions as the production example of the compound c-228.

LCMS: m/z 470 $[M+H]^+$

HPLC retention time: 0.95 min (analysis condition A)

Compound G2

5-Bromo-8-chloro-7-(7-fluoro-1H-indazol-4-yl)-10H-pyrido[2,3-f]quinoxalin-9-one

[Formula 720]

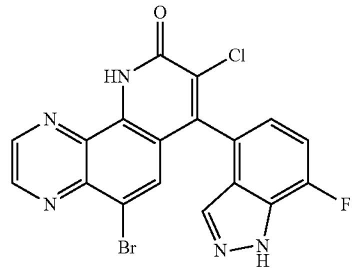

A solution of (5-amino-8-bromoquinoxalin-6-yl)-[7-fluoro-1-(oxan-2-yl)indazol-4-yl]methanone (compound g-4, 56 mg, 0.119 mmol) in DCM (1.12 mL) in a reaction vessel was cooled to 0° C., chloroacetyl chloride (28.6 μL, 0.357 mmol) and DIPEA (83 μL, 0.476 mmol) were added thereto, and the mixture was stirred at room temperature for 1 hour. Further, chloroacetyl chloride (57.2 μL, 0.714 mmol) and DIPEA (166 μL, 0.953 mmol) were added thereto, and the mixture was stirred at room temperature for 1 hour. To the obtained reaction mixture, pyridine (1.12 mL) was added, and the mixture was stirred at 60° C. for 2 hours and then cooled to room temperature. To the reaction mixture, hydrazine monohydrate (74.7 μL, 2.38 mmol) was added, and the mixture was further stirred at 60° C. for 1 hour. The reaction mixture was cooled to room temperature and purified by reversed phase column chromatography. To the obtained crude product, a 5% solution of hydrogen chloride in MeOH (7.81 mL, 12.9 mL) was added, and the mixture was stirred for 30 min. The reaction mixture was concentrated under reduced pressure, and the obtained residue was purified by reversed phase column chromatography (0.1% aqueous formic acid solution/0.1% solution of formic acid in acetonitrile) to obtain the title compound (compound B21, 15 mg, yield 29%) as a colorless solid.

LCMS: m/z 444 $[M+H]^+$

HPLC retention time: 0.64 min (analysis condition A)

Compound g-8

8-Amino-5-bromo-7-[7-fluoro-1-(oxan-2-yl)indazol-4-yl]-10H-pyrido[2,3-f]quinoxalin-9-one

[Formula 721]

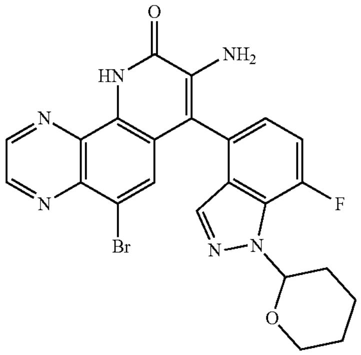

The title compound was synthesized from (5-amino-8-bromoquinoxalin-6-yl)-[7-fluoro-1-(oxan-2-yl)indazol-4-yl]methanone (compound g-4) under the same conditions as the production examples of the compounds c-9, c-10, and c-13, except that N,N-dimethylaniline used in the production example of the compound c-13 was not used.

LCMS: m/z 509 $[M+H]^+$

HPLC retention time: 4.32 min (analysis condition J)

Compound G1

8-Amino-5-bromo-7-(7-fluoro-1H-indazol-4-yl)-10H-pyrido[2,3-f]quinoxalin-9-one

[Formula 720]

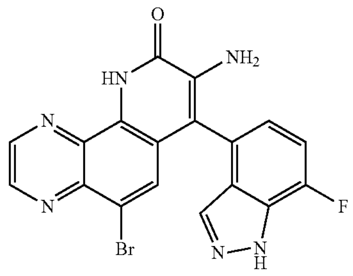

The title compound was synthesized from 8-amino-5-bromo-7-[7-fluoro-1-(oxan-2-yl)indazol-4-yl]-10H-pyrido[2,3-f]quinoxalin-9-one (compound g-8) under the same conditions as the production example of the compound B48.

LCMS: m/z 425 $[M+H]^+$

HPLC retention time: 0.62 min (analysis condition A)

Compound G3

8-Amino-7-(7-fluoro-1H-indazol-4-yl)-5-methyl-10H-pyrido[2,3-f]quinoxalin-9-one

[Formula 723]

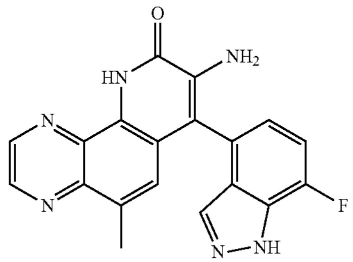

The title compound was synthesized from 8-amino-5-bromo-7-(7-fluoro-1H-indazol-4-yl)-10H-pyrido[2,3-f]quinoxalin-9-one (compound G1) under the same conditions as the production example of the compound B22, except that a 2 M solution of methylzincchloride in THF was used instead of the 0.5 M solution of cyclopropylzinc bromide in THE used in the production example of the compound B22.

LCMS: m/z 361.5 $[M+H]^+$

HPLC retention time: 0.61 min (analysis condition A)

Compound G4

8-Amino-5-cyclopropyl-7-(7-fluoro-1H-indazol-4-yl)-10H-pyrido[2,3-f]quinoxalin-9-one

[Formula 724]

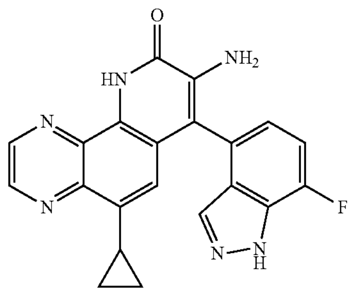

The title compound was synthesized from 8-amino-5-bromo-7-(7-fluoro-1H-indazol-4-yl)-10H-pyrido[2,3-f]quinoxalin-9-one (compound G1) under the same conditions as the production example of the compound B22.

LCMS: m/z 385 $[M-H]^-$

HPLC retention time: 0.63 min (analysis condition A)

Compound G5

N-[8-amino-7-(7-fluoro-1H-indazol-4-yl)-9-oxo-10H-pyrido[2,3-f]quinoxalin-5-yl]methanesulfonamide

[Formula 725]

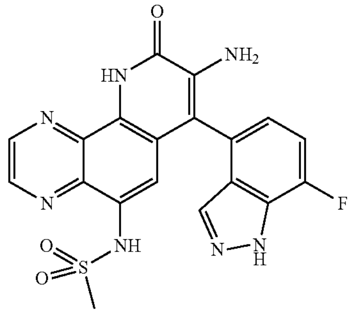

The title compound was synthesized from 8-amino-5-bromo-7-(7-fluoro-1H-indazol-4-yl)-10H-pyrido[2,3-f]quinoxalin-9-one (compound G1) under the same conditions as the production example of the compound C127, except that sodium tert-butoxide was used instead of tripotassium phosphate used in the production example of the compound C127. In addition, the reaction was carried out by heating the reaction mixture to 150° C.

LCMS: m/z 440 $[M+H]^+$

HPLC retention time: 0.48 min (analysis condition A)

Compound G6

N-[8-amino-7-(7-fluoro-1H-indazol-4-yl)-9-oxo-10H-pyrido[2,3-f]quinoxalin-5-yl]cyclopropanesulfonamide

[Formula 726]

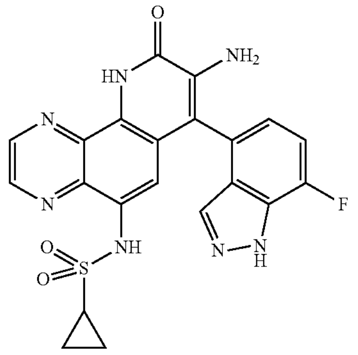

The title compound was synthesized from 8-amino-5-bromo-7-(7-fluoro-1H-indazol-4-yl)-10H-pyrido[2,3-f]quinoxalin-9-one (compound G1) under the same conditions as the production example of the compound C127, except that cyclopropylsulfonamide and sodium tert-butoxide were respectively used instead of methanesulfonamide and tripotassium phosphate used in the production example of the compound C127. In addition, the reaction was carried out by heating the reaction mixture to 150° C.

LCMS: m/z 466 $[M+H]^+$

HPLC retention time: 0.53 min (analysis condition A)

Compound G7

8-Amino-7-(7-fluoro-1H-indazol-4-yl)-5-(4-methylpiperazin-1-yl)-10H-pyrido[2,3-f]quinoxalin-9-one

[Formula 727]

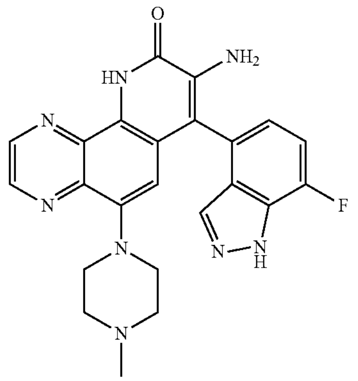

A suspension of 8-amino-5-bromo-7-(7-fluoro-1H-indazol-4-yl)-10H-pyrido[2,3-f]quinoxalin-9-one (compound G1, 120 mg, 0.282 mmol), sodium tert-butoxide (326 mg, 3.39 mmol), tBuXPhos Pd G3 (67.3 mg, 0.0847 mmol), and 1-methylpiperazine (93.2 μL, 0.847 mmol)) in 1,4-dioxane (2.82 mL) in a reaction vessel was degassed under reduced pressure, subjected to argon replacement, and then stirred at 150° C. for 1 hour. The reaction mixture was cooled to room temperature, TFA and DMSO were added thereto, and the mixture was purified by reversed phase column chromatography and silica gel column chromatography to obtain the title compound (19.9 mg, yield 16%) as a yellow solid.

LCMS: m/z 445.5 $[M+H]^+$

HPLC retention time: 0.33 min (analysis condition A)

Compound G8

N-[8-amino-7-(7-fluoro-1H-indazol-4-yl)-9-oxo-10H-pyrido[2,3-f]quinoxalin-5-yl]acetamide

[Formula 728]

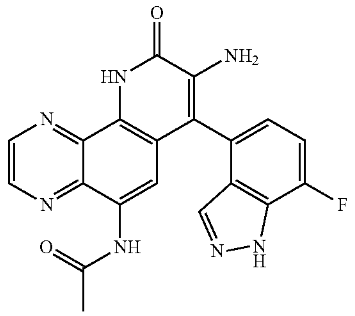

A suspension of 8-amino-5-bromo-7-(7-fluoro-1H-indazol-4-yl)-10H-pyrido[2,3-f]quinoxalin-9-one (compound G1, 120 mg, 0.282 mmol), sodium tert-butoxide (326 mg, 3.39 mmol), tBuXPhos Pd G3 (67.3 mg, 0.0847 mmol), and acetamide (50 mg, 0.846 mmol) in 1,4-dioxane (2.82 mL) in a reaction vessel was degassed under reduced pressure, subjected to argon replacement, and then stirred at 150° C. for 1 hour. To the reaction mixture, TFA and DMSO were added, and the mixture was purified by reversed phase column chromatography (0.1% aqueous TFA solution/0.05% solution of TFA in acetonitrile). The fractions containing the title compound were concentrated and neutralized with a saturated aqueous sodium bicarbonate solution, and the solid was collected by filtration to obtain the title compound (29 mg, yield 25%) as a yellow solid.

LCMS: m/z 404 $[M+H]^+$

HPLC retention time: 0.64 min (analysis condition A)

Compound G9

8-Amino-7-(7-fluoro-1H-indazol-4-yl)-5-(propan-2-ylamino)-10H-pyrido[2,3-f]quinoxalin-9-one

[Formula 729]

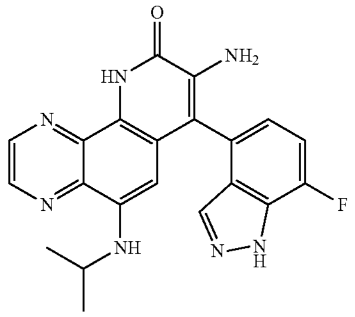

The title compound was synthesized from 8-amino-5-bromo-7-(7-fluoro-1H-indazol-4-yl)-10H-pyrido[2,3-f]quinoxalin-9-one (compound G1) under the same conditions as the production example of the compound G7, except that isopropylamine was used instead of 1-methylpiperazine used in the production example of the compound G7.

LCMS: m/z 404 [M+H]$^+$

HPLC retention time: 0.47 min (analysis condition A)

Compound G10

8-Amino-7-(7-fluoro-1H-indazol-4-yl)-5-methoxy-10H-pyrido[2,3-f]quinoxalin-9-one

[Formula 730]

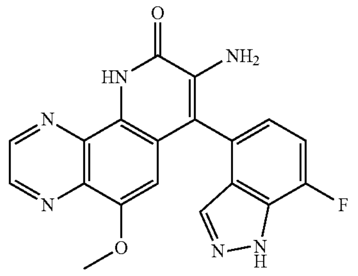

The title compound was synthesized from 8-amino-5-bromo-7-(7-fluoro-1H-indazol-4-yl)-10H-pyrido[2,3-f]quinoxalin-9-one (compound G1) under the same conditions as the production example of the compound c-108.

LCMS: m/z 377 [M+H]$^+$

HPLC retention time: 0.48 min (analysis condition A)

Compound g-9

5-Bromo-7-[7-fluoro-1-(2-trimethylsilylethoxymethyl)indazol-4-yl]-9-(2-trimethylsilylethoxymethoxy)pyrido[2,3-f]quinoxalin-8-amine

[Formula 731]

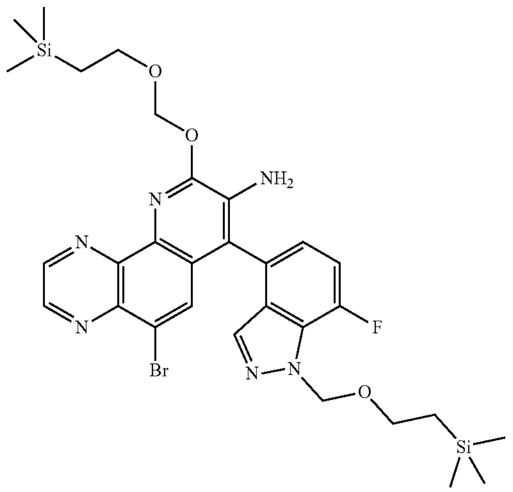

To a solution of 8-amino-5-bromo-7-(7-fluoro-1H-indazol-4-yl)-10H-pyrido[2,3-f]quinoxalin-9-one (compound G1, 50 mg, 0.118 mmol) in DMA (0.75 mL) in a reaction vessel, potassium carbonate (65 mg, 0.47 mmol) and 2-(trimethylsilyl)ethoxymethyl chloride (64 μL, 0.353 mmol) were added, and the reaction mixture was stirred at 80° C. for 2 hours and at room temperature overnight. To the reaction mixture, potassium carbonate (65 mg, 0.47 mmol) and 2-(trimethylsilyl)ethoxymethyl chloride (64 μL, 0.353 mmol) were further added, and the mixture was stirred at 80° C. for 2 hours and at room temperature overnight. To the reaction mixture, water was added, and the mixture was extracted with ethyl acetate. The organic layer was dried over anhydrous sodium sulfate, the drying agent was filtered off, and then the filtrate was concentrated under reduced pressure. The obtained residue was purified by silica gel column chromatography to obtain the title compound (19 mg, yield 23.56%).

LCMS: m/z 685 [M+H]$^+$

HPLC retention time: 1.18 min (analysis condition A)

Compound g-10

8-Amino-7-[7-fluoro-1-(2-trimethylsilylethoxymethyl)indazol-4-yl]-9-(2-trimethylsilylethoxymethoxy)pyrido[2,3-f]quinoxalin-5-ol

[Formula 732]

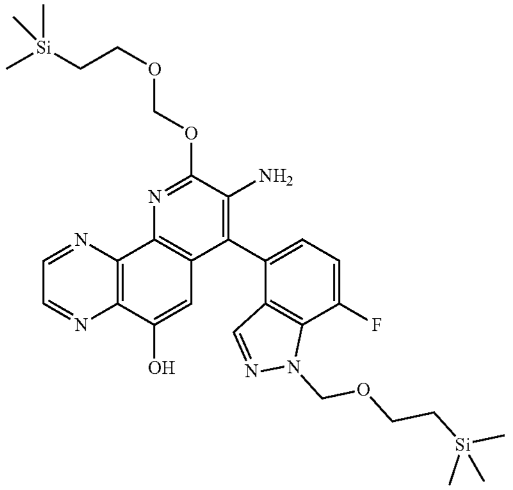

The title compound was synthesized from 5-bromo-7-[7-fluoro-1-(2-trimethylsilylethoxymethyl)indazol-4-yl]-9-(2-trimethylsilyl ethoxymethoxy)pyrido[2,3-f]quinoxalin-8-amine (compound g-9) under the same conditions as the production example of the compound c-15.

LCMS: m/z 623.5 [M+H]$^+$

HPLC retention time: 1.08 min (analysis condition A)

Compound g-11

5-(3,3-Difluoropropoxy)-7-[7-fluoro-1-(2-trimethylsilylethoxymethyl)indazol-4-yl]-9-(2-trimethylsilylethoxymethoxy)pyrido[2,3-f]quinoxalin-8-amine

[Formula 733]

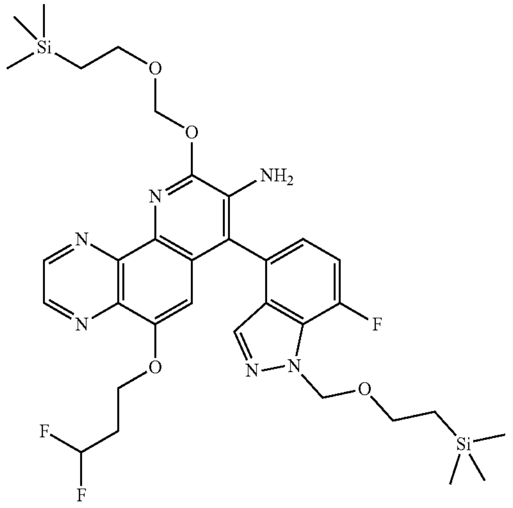

The title compound was synthesized from 8-amino-7-[7-fluoro-1-(2-trimethylsilylethoxymethyl)indazol-4-yl]-9-(2-trimethylsilylethoxymethoxy)pyrido[2,3-f]quinoxalin-5-ol (compound g-10) and a corresponding alcohol under the same conditions as the production example of the compound c-16. The reaction was carried out by heating the reaction mixture to 80° C.

LCMS: m/z 701.6 $[M+H]^+$

HPLC retention time: 1.09 min (analysis condition A)

Compound G18

8-Amino-5-(3,3-difluoropropoxy)-7-(7-fluoro-1H-indazol-4-yl)-10H-pyrido[2,3-f]quinoxalin-9-one

[Formula 734]

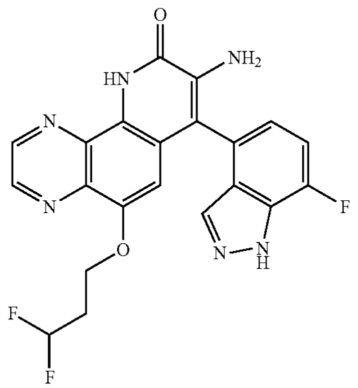

To 5-(3,3-difluoropropoxy)-7-[7-fluoro-1-(2-trimethylsilylethoxymethyl)indazol-4-yl]-9-(2-trimethylsilylethoxymethoxy)pyrido[2,3-f]quinoxalin-8-amine (compound g-11, 12.9 mg, 0.018 mmol) in a reaction vessel, a 5% solution of hydrogen chloride in MeOH (500 μL, 0.823 mmol) was added, and the reaction mixture was stirred at 60° C. for 5 hours. The reaction mixture was concentrated, then neutralized with an aqueous potassium acetate solution, and purified by reversed phase column chromatography to obtain the title compound (5.5 mg, yield 62%) as a pale yellow solid.

LCMS: m/z 441 $[M+H]^+$

HPLC retention time: 0.56 min (analysis condition A)

Compound g-14

5-Bromo-7-[7-fluoro-1-(oxan-2-yl)indazol-4-yl]-9-[(4-methoxyphenyl)methoxy]pyrido[2,3-f]quinoxalin-8-amine

[Formula 735]

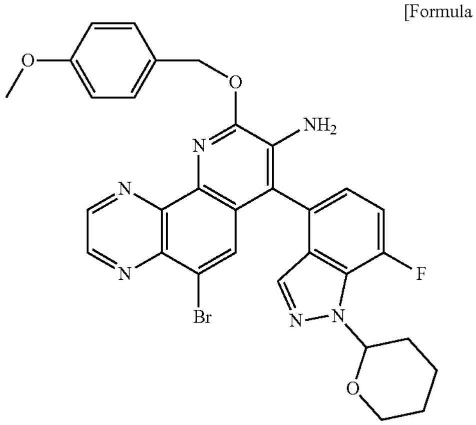

The title compound was synthesized from 8-amino-5-bromo-7-[7-fluoro-1-(oxan-2-yl)indazol-4-yl]-10H-pyrido[2,3-f]quinoxalin-9-one (compound g-8) under the same conditions as the production example of the compound c-14.

LCMS: m/z 629 $[M+H]^+$

HPLC retention time: 5.54 min (analysis condition J)

Compound g-15

8-Amino-7-[7-fluoro-1-(oxan-2-yl)indazol-4-yl]-9-[(4-methoxyphenyl)methoxy]pyrido[2,3-f]quinoxalin-5-ol

[Formula 736]

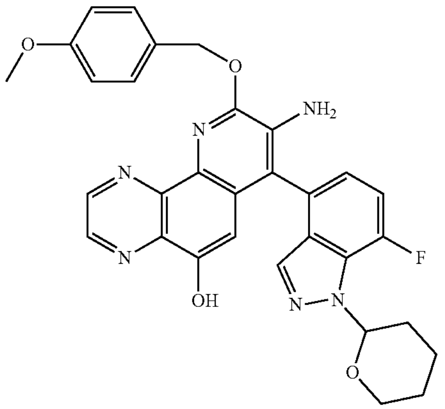

The title compound was synthesized from 5-bromo-7-[7-fluoro-1-(oxan-2-yl)indazol-4-yl]-9-[(4-methoxyphenyl)methoxy]pyrido[2,3-f]quinoxalin-8-amine (compound g-14) under the same conditions as the production example of the compound c-15.

LCMS: m/z 567.5 $[M+H]^+$

HPLC retention time: 0.88 min (analysis condition A)

Compound G11

8-Amino-5-(cyclopropylmethoxy)-7-(7-fluoro-1H-indazol-4-yl)-10H-pyrido[2,3-f]quinoxalin-9-one

[Formula 737]

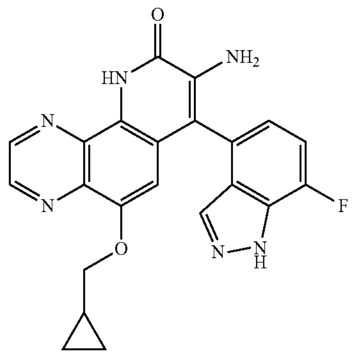

The title compound was synthesized from 8-amino-7-[7-fluoro-1-(oxan-2-yl)indazol-4-yl]-9-[(4-methoxyphenyl)methoxy]pyrido[2,3-f]quinoxalin-5-ol (compound g-15) under the same conditions as the production examples of the compounds c-16 and C4, except that cyclopropanemethanol and anisole were respectively used instead of MeOH and triethylsilane used in the production examples of the compounds c-16 and C4.

LCMS: m/z 417 $[M+H]^+$

HPLC retention time: 1.52 min (analysis condition D)

Compound G12

(1r,3r)-3-[[8-Amino-7-(7-fluoro-1H-indazol-4-yl)-9-oxo-10H-pyrido[2,3-f]quinoxalin-5-yl]oxy]cyclobutane-1-carbonitrile

[Formula 738]

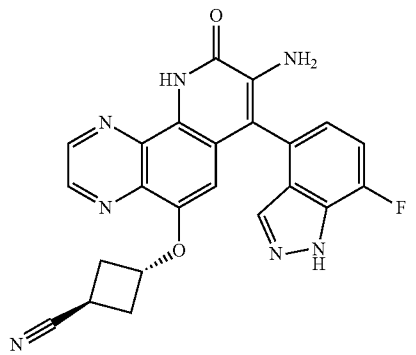

The title compound was synthesized from 8-amino-7-[7-fluoro-1-(oxan-2-yl)indazol-4-yl]-9-[(4-methoxyphenyl)methoxy]pyrido[2,3-f]quinoxalin-5-ol (compound g-15) under the same conditions as the production examples of the compounds c-28 and C4, except that (1s,3s)-3-cyanocyclobutyl trifluoromethanesulfonate (compound a-103) and anisole were respectively used instead of 2,2-difluoroethyl-triflate and triethylsilane used in the production example of the compounds c-28 and C4.

LCMS: m/z 442.5 $[M+H]^+$

HPLC retention time: 0.51 min (analysis condition A)

Compound G13

8-Amino-5-[(2S)-butan-2-yl]oxy-7-(7-fluoro-1H-indazol-4-yl)-10H-pyrido[2,3-f]quinoxalin-9-one

[Formula 739]

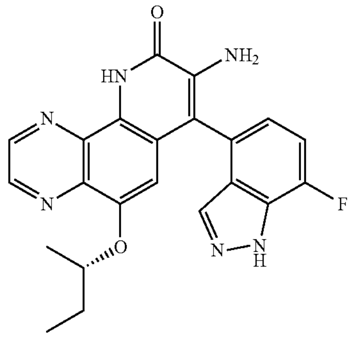

The title compound was synthesized from 8-amino-7-[7-fluoro-1-(oxan-2-yl)indazol-4-yl]-9-[(4-methoxyphenyl)methoxy]pyrido[2,3-f]quinoxalin-5-ol (compound g-15) under the same conditions as the production examples of the compounds c-16 and C4, except that (R)-butan-2-ol and anisole were respectively used instead of MeOH and triethylsilane used in the production examples of the compounds c-16 and C4.

LCMS: m/z 419.5 $[M+H]^+$

HPLC retention time: 0.60 min (analysis condition A)

Compound G14

8-Amino-5-[(2R)-butan-2-yl]oxy-7-(7-fluoro-1H-indazol-4-yl)-10H-pyrido[2,3-f]quinoxalin-9-one

[Formula 740]

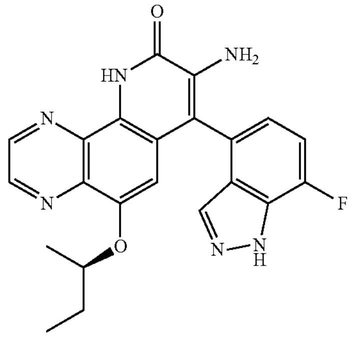

The title compound was synthesized from 8-amino-7-[7-fluoro-1-(oxan-2-yl)indazol-4-yl]-9-[(4-methoxyphenyl)

methoxy]pyrido[2,3-f]quinoxalin-5-ol (compound g-15) under the same conditions as the production examples of the compounds c-16 and C4, except that(S)-butan-2-ol and anisole were respectively used instead of MeOH and triethylsilane used in the production examples of the compounds c-16 and C4.

LCMS: m/z 419.5 $[M+H]^+$

HPLC retention time: 0.60 min (analysis condition A)

Compound g-20

7-[7-Fluoro-1-(oxan-2-yl)indazol-4-yl]-9-[(4-methoxyphenyl)methoxy]-5-propan-2-yloxypyrido[2,3-f]quinoxalin-8-amine

[Formula 741]

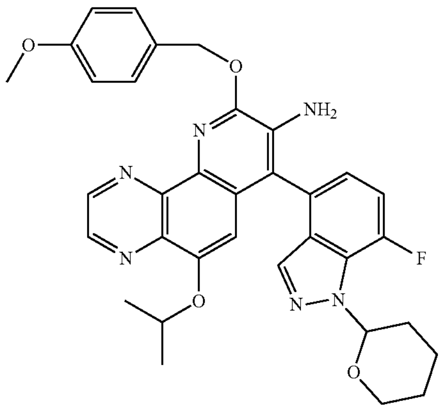

The title compound was synthesized from 8-amino-7-[7-fluoro-1-(oxan-2-yl)indazol-4-yl]-9-[(4-methoxyphenyl)methoxy]pyrido[2,3-f]quinoxalin-5-ol (compound g-15) under the same conditions as the production example of the compound c-28, except that 2-iodopropane was used instead of 2,2-difluoroethyltriflate used in the production example of the compound c-28. In addition, the reaction was carried out by heating the reaction mixture to 40° C.

LCMS: m/z 619.6 $[M+H]^+$

HPLC retention time: 0.95 min (analysis condition A)

Compound g-23

8-Amino-7-(7-fluoro-1H-indazol-4-yl)-5-propan-2-yloxy-2,3,4,10-tetrahydro-1H-pyrido[2,3-f]quinoxalin-9-one

[Formula 742]

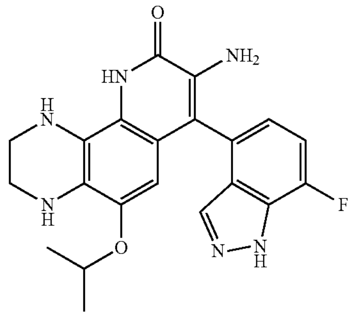

To a solution of 7-[7-fluoro-1-(oxan-2-yl)indazol-4-yl]-9-[(4-methoxyphenyl)methoxy]-5-propan-2-yloxypyrido[2,3-f]quinoxalin-8-amine (compound g-20, 40.2 mg, 0.066 mmol) in DCM (0.3 mL) in a reaction vessel, triethylsilane (0.105 mL, 0.66 mmol) and TFA (0.3 mL) were added, and the reaction mixture was stirred at room temperature for 1.5 hours. The reaction mixture was concentrated, and the obtained residue was dissolved in MeOH. The obtained solution was desalted with an anion exchange resin (PL-HCO3 MP resin), and then the obtained solution was concentrated under reduced pressure to obtain the crude product of the title compound (59.3 mg).

LCMS: m/z 409.5 $[M+H]^+$

HPLC retention time: 0.48 min (analysis condition A)

Compound G15

8-Amino-7-(7-fluoro-1H-indazol-4-yl)-5-propan-2-yloxy-10H-pyrido[2,3-f]quinoxalin-9-one

[Formula 743]

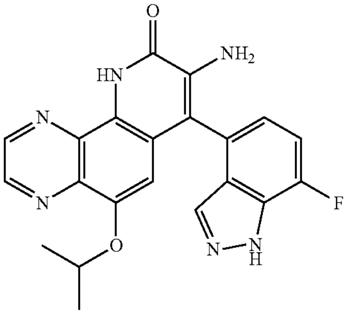

To a solution of the crude product (27 mg) of 8-amino-7-(7-fluoro-1H-indazol-4-yl)-5-propan-2-yloxy-2,3,4,10-tetrahydro-1H-pyrido[2,3-f]quinoxalin-9-one (compound g-23) in 1,1,1,3,3,3-hexafluoro-2-propanol (0.66 mL) in a reaction vessel, a 35% hydrogen peroxide solution (0.058 mL, 0.66 mmol) was added, and the reaction mixture was stirred at room temperature for 1 hour. The reaction mixture was filtered using Celite. The filtrate was concentrated under reduced pressure, the obtained residue was combined with that of another lot, and the mixture was purified by reversed phase column chromatography (0.1% aqueous FA solution/0.1% solution of FA in acetonitrile) to obtain the title compound (17 mg, yield 64%) as a light brown solid.

LCMS: m/z 405 $[M+H]^+$

HPLC retention time: 1.43 min (analysis condition D)

Compound G16

8-Amino-5-((1,3r)-3-fluorocyclobutyl)oxy-7-(7-fluoro-1H-indazol-4-yl)-10H-pyrido[2,3-f]quinoxalin-9-one

[Formula 744]

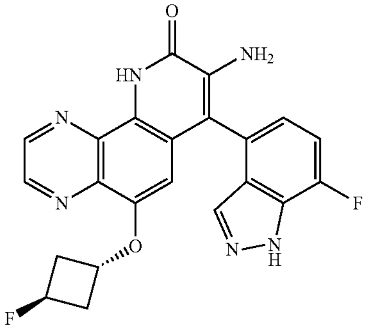

The title compound was synthesized from 8-amino-7-[7-fluoro-1-(oxan-2-yl)indazol-4-yl]-9-[(4-methoxyphenyl)methoxy]pyrido[2,3-f]quinoxalin-5-ol (compound g-15) under the same conditions as the production example of the compounds c-28, g-23, and the compound G15, except that (1s,3s)-3-fluorocyclobutyl trifluoromethanesulfonate (compound a-102) was used instead of 2,2-difluoroethyltriflate used in the production example of the compound c-28.

LCMS: m/z 435 $[M+H]^+$

HPLC retention time: 1.43 min (analysis condition D)

Compound G17

8-Amino-5-((1s,3s)-3-fluorocyclobutyl)oxy-7-(7-fluoro-1H-indazol-4-yl)-10H-pyrido[2,3-f]quinoxalin-9-one

[Formula 745]

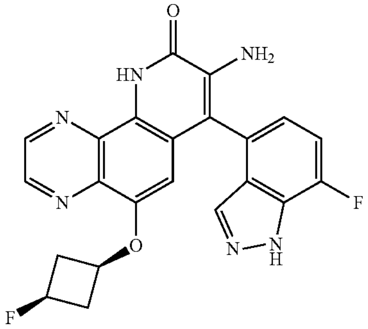

The title compound was synthesized from 8-amino-7-[7-fluoro-1-(oxan-2-yl)indazol-4-yl]-9-[(4-methoxyphenyl)methoxy]pyrido[2,3-f]quinoxalin-5-ol (compound g-15) under the same conditions as the production examples of the compounds c-28, g-23, and the compound G15, except that (1r,3r)-3-fluorocyclobutyl trifluoromethanesulfonate (compound c-80) was used instead of 2,2-difluoroethyltriflate used in the production example of the compound c-28.

LCMS: m/z 435 $[M+H]^+$

HPLC retention time: 1.42 min (analysis condition D)

Compound h-1

4-Bromo-1,2-benzothiazol-7-amine

[Formula 746]

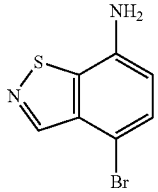

The title compound was synthesized from benzo[d]isothiazol-7-amine under the same conditions as the production example of the compound b-100, except that THF was used instead of DMF used in the production example of the compound b-100.

LCMS: m/z 229 $[M+H]^+$

HPLC retention time: 0.68 min (analysis condition A)

Compound h-3

(E)-N'-(4-bromo-6-iodo-1,2-benzothiazol-7-yl)-N,N-dimethylmethanimidamide

[Formula 747]

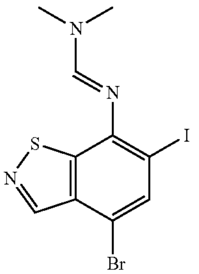

The title compound was synthesized from 4-bromo-1,2-benzothiazol-7-amine (compound h-1) under the same conditions as the production examples of the compounds c-246 and c-247.

LCMS: m/z 410 $[M+H]^+$

HPLC retention time: 0.79 min (analysis condition A)

Compound h-4

(E)-N'-[4-bromo-6-[7-fluoro-2-(oxan-2-yl)indazole-4-carbonyl]-1,2-benzothiazol-7-yl]-N,N-dimethylmethanimidamide

[Formula 748]

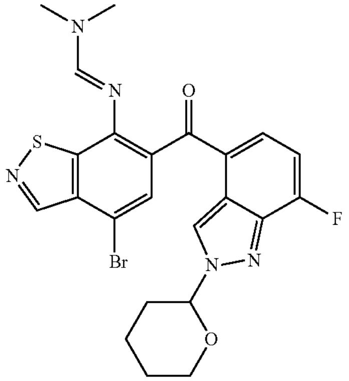

The title compound was synthesized from (E)-N'-(4-bromo-6-iodo-1,2-benzothiazol-7-yl)-N,N-dimethylmethanimidamide (compound h-3) under the same conditions as the production example of the compound b-26, except that toluene was used instead of THE used in the production example of the compound c-26.

LCMS: m/z 530 $[M+H]^+$

HPLC retention time: 0.97 min (analysis condition A)

Compound h-5

(7-Amino-4-bromo-1,2-benzothiazol-6-yl)-[7-fluoro-2-(oxan-2-yl)indazol-4-yl]methanone

[Formula 749]

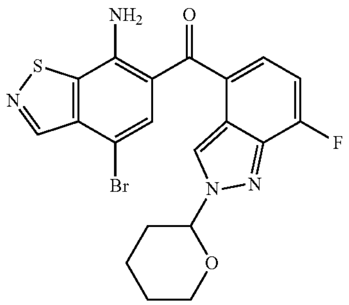

The title compound was synthesized from (E)-N'-[4-bromo-6-[7-fluoro-2-(oxan-2-yl)indazole-4-carbonyl]-1,2-benzothiazol-7-yl]-N,N-dimethylmethanimidamide (compound h-4) under the same conditions as the production example of the compound b-27.

LCMS: m/z 475 $[M+H]^+$

HPLC retention time: 0.98 min (analysis condition A)

Compound H1

7-Amino-4-bromo-6-(7-fluoro-1H-indazol-4-yl)-9H-[1,2]thiazolo[4,5-h]quinolin-8-one

[Formula 750]

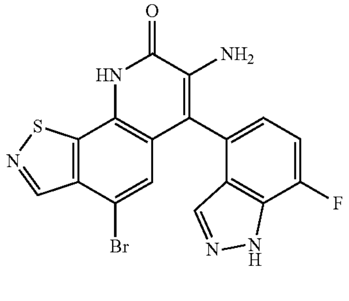

The title compound was synthesized from (7-amino-4-bromo-1,2-benzothiazol-6-yl)-[7-fluoro-2-(oxan-2-yl)indazol-4-yl]methanone (compound h-5) under the same conditions as the production examples of the compounds c-9, c-10, c-13, and the compound B49, except that the reaction was carried out without using N,N-dimethylaniline used in the production example of the compound c-9.

LCMS: m/z 430 $[M+H]^+$

HPLC retention time: 0.67 min (analysis condition A)

Compound H2

7-Amino-6-(7-fluoro-1H-indazol-4-yl)-4-methyl-9H-[1.2]thiazolo[4,5-h]quinolin-8-one

[Formula 751]

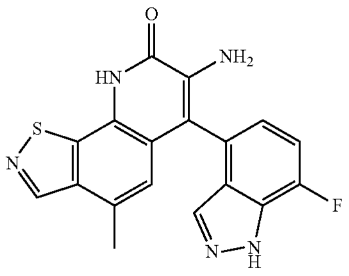

The title compound was synthesized from 7-amino-4-bromo-6-(7-fluoro-1H-indazol-4-yl)-9H-[1,2]thiazolo[4,5-h]quinolin-8-one (compound H1) under the same conditions as the production example of the compound B22, except that a 2 M solution of methylzincchloride in THF was used instead of the 0.5 M solution of cyclopropylzinc bromide in THF used in the production example of the compound B22.

LCMS: m/z 366 $[M+H]^+$

HPLC retention time: 0.59 min (analysis condition A)

Compound H3

7-Amino-4-cyclopropyl-6-(7-fluoro-1H-indazol-4-yl)-9H-[1,2]thiazolo[4,5-h]quinolin-8-one

[Formula 752]

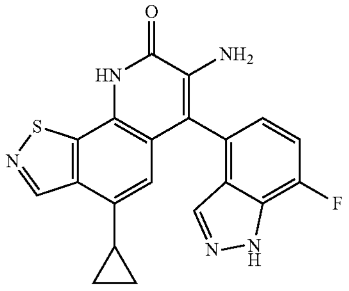

The title compound was synthesized from 7-amino-4-bromo-6-(7-fluoro-1H-indazol-4-yl)-9H-[1,2]thiazolo[4,5-h]quinolin-8-one (compound H1) under the same conditions as the production example of the compound B22.

LCMS: m/z 392 $[M+H]^+$

HPLC retention time: 0.63 min (analysis condition A)

Compound i-1

4-Bromo-1-methylindazol-7-amine

[Formula 753]

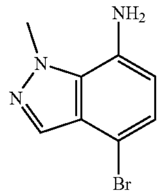

The title compound was synthesized from 1-methyl-1H-indazol-7-amine under the same conditions as the production example of the compound b-100, except that THF was used instead of DMF used in the production example of the compound b-100.

LCMS: m/z 226 $[M+H]^+$

HPLC retention time: 0.61 min (analysis condition A)

Compound i-3

(E)-N'-(4-bromo-6-iodo-1-methylindazol-7-yl)-N,N-dimethylmethanimidamide

[Formula 754]

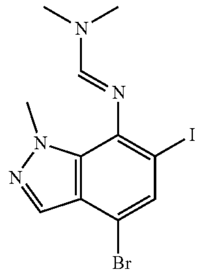

The title compound was synthesized from the 4-bromo-1-methylindazol-7-amine compound (compound i-1) under the same conditions as the production examples of the compounds c-246 and c-247.

LCMS: m/z 407 $[M+H]^+$

HPLC retention time: 0.53 min (analysis condition A)

Compound i-4

(E)-N'-[4-bromo-6-[7-fluoro-2-(oxan-2-yl)indazole-4-carbonyl]-1-methylindazol-7-yl]-N,N-dimethyl-methanimidamide

[Formula 755]

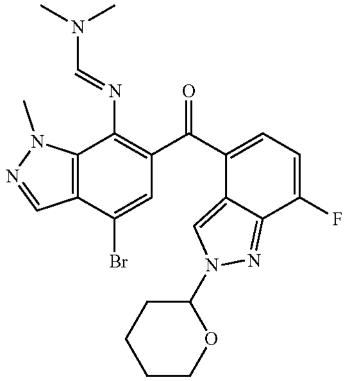

The title compound was synthesized from (E)-N'-(4-bromo-6-iodo-1-methylindazol-7-yl)-N,N-dimethylmethanimidamide (compound i-3) under the same conditions as the production example of the compound b-26.

LCMS: m/z 527.5 $[M+H]^+$

HPLC retention time: 0.80 min (analysis condition A)

Compound i-5

(7-Amino-4-bromo-1-methylindazol-6-yl)-[7-fluoro-2-(oxan-2-yl)indazol-4-yl]methanone

[Formula 756]

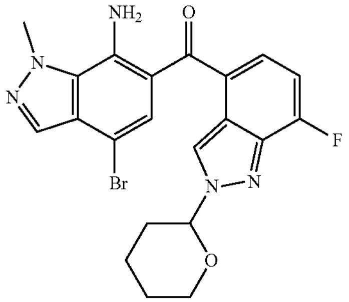

The title compound was synthesized from (E)-N'-[4-bromo-6-[7-fluoro-2-(oxan-2-yl)indazole-4-carbonyl]-1-methylindazol-7-yl]-N,N-dimethylmethanimidamide (compound i-4) under the same conditions as the production example of the compound b-27.

LCMS: m/z 472 $[M+H]^+$

HPLC retention time: 0.92 min (analysis condition A)

Compound I1

7-Amino-4-bromo-6-(7-fluoro-1H-indazol-4-yl)-1-methyl-9H-pyrazolo[4,3-h]quinolin-8-one

[Formula 757]

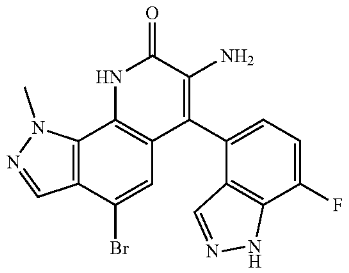

The title compound was synthesized from (7-amino-4-bromo-1-methylindazol-6-yl)-[7-fluoro-2-(oxan-2-yl)indazol-4-yl]methanone (compound i-5) under the same conditions as the production examples of the compounds b-28, b-29, b-30, and b-9, except that DMA was used instead of DCM and pyridine used in the production example of the compound b-30. In addition, EtOH used in the production example of the compound b-9 was not used.

LCMS: m/z 427 [M+H]+

HPLC retention time: 0.64 min (analysis condition A)

Compound I2

7-Amino-6-(7-fluoro-1H-indazol-4-yl)-1,4-dimethyl-9H-pyrazolo[4,3-h]quinolin-8-one

[Formula 758]

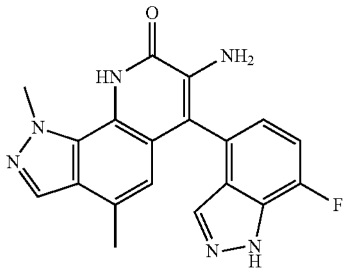

The title compound was synthesized from 7-amino-4-bromo-6-(7-fluoro-1H-indazol-4-yl)-1-methyl-9H-pyrazolo[4,3-h]quinolin-8-one (compound I1) under the same conditions as the production example of the compound B22, except that a 2 M solution of methylzincchloride in THF was used instead of the 0.5 M solution of cyclopropylzinc bromide in THE used in the production example of the compound B22.

LCMS: m/z 363 [M+H]+

HPLC retention time: 0.56 min (analysis condition A)

Compound I3

7-Amino-4-cyclopropyl-6-(7-fluoro-1H-indazol-4-yl)-1-methyl-9H-pyrazolo[4,3-h]quinolin-8-one

[Formula 759]

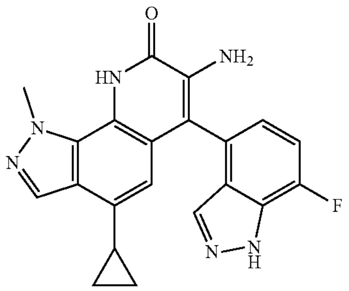

The title compound was synthesized from 7-amino-4-bromo-6-(7-fluoro-1H-indazol-4-yl)-1-methyl-9H-pyrazolo[4,3-h]quinolin-8-one (compound I1) under the same conditions as the production example of the compound B22.

LCMS: m/z 389.5 [M+H]+

HPLC retention time: 0.61 min (analysis condition A)

Compound j-1

5-Bromoquinazolin-8-amine

[Formula 760]

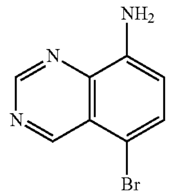

The title compound was synthesized from quinazolin-8-amine under the same conditions as the production example of the compound b-100, except that THF was used instead of DMF used in the production example of the compound b-100.

LCMS: m/z 224 [M+H]+

HPLC retention time: 0.61 min (analysis condition A)

Compound j-3

(E)-N'-(5-bromo-7-iodoquinazolin-8-yl)-N,N-dimethylmethanimidamide

[Formula 761]

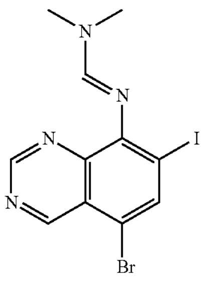

The title compound was synthesized from 5-bromoquinazolin-8-amine (compound j-1) under the same conditions as the production examples of the compounds b-76 and b-77.

LCMS: m/z 405 $[M+H]^+$

HPLC retention time: 0.39 min (analysis condition A)

Compound j-4

(8-Amino-5-bromoquinazolin-7-yl)-[7-fluoro-1-(oxan-2-yl)indazol-4-yl]methanol

[Formula 762]

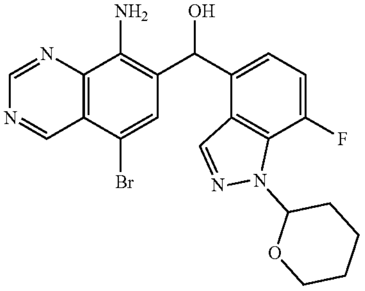

The title compound was synthesized from (E)-N'-(5-bromo-7-iodoquinazolin-8-yl)-N,N-dimethylmethanimidamide (compound j-3) under the same conditions as the production example of the compound c-227, except that the reaction was carried out by cooling the reaction mixture to −78° C.

LCMS: m/z 472.5 $[M+H]^+$

HPLC retention time: 0.82 min (analysis condition A)

Compound j-5

(8-Amino-5-bromoquinazolin-7-yl)-[7-fluoro-1-(oxan-2-yl)indazol-4-yl]methanone

[Formula 763]

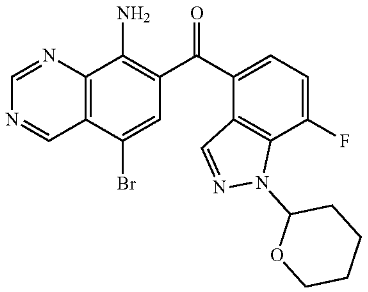

The title compound was synthesized from (8-amino-5-bromoquinazolin-7-yl)-[7-fluoro-1-(oxan-2-yl)indazol-4-yl]methanol (compound j-4) under the same conditions as the production example of the compound c-228.

LCMS: m/z 470 $[M+H]^+$

HPLC retention time: 1.00 min (analysis condition A)

Compound J1

8-Amino-5-bromo-7-(7-fluoro-1H-indazol-4-yl)-10H-pyrido[3,2-h]quinazolin-9-one

[Formula 764]

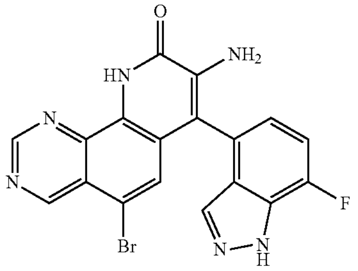

The title compound was synthesized from (8-amino-5-bromoquinazolin-7-yl)-[7-fluoro-1-(oxan-2-yl)indazol-4-yl]methanone (compound j-5) under the same conditions as the production examples of the compounds c-9, c-10, c-13, and B48, except that the reaction was carried out without using N,N-dimethylaniline used in the production example of the compound c-9.

LCMS: m/z 425 $[M+H]^+$

HPLC retention time: 0.61 min (analysis condition A)

Compound J2

8-Amino-7-(7-fluoro-1H-indazol-4-yl)-5-methyl-10H-pyrido[3,2-h]quinazolin-9-one

[Formula 765]

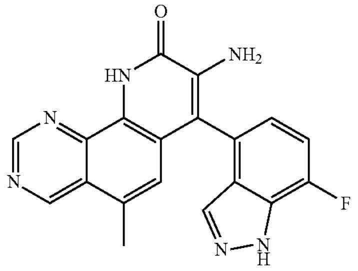

The title compound was synthesized from 8-amino-5-bromo-7-(7-fluoro-1H-indazol-4-yl)-10H-pyrido[3,2-h]quinazolin-9-one (compound J1) under the same conditions as the production example of the compound B22, except that a 2 M solution of methylzincchloride in THF was used instead of the 0.5 M solution of cyclopropylzinc bromide in THE used in the production example of the compound B22.

LCMS: m/z 361 $[M+H]^+$

HPLC retention time: 0.53 min (analysis condition A)

Compound J3

8-Amino-5-cyclopropyl-7-(7-fluoro-1H-indazol-4-yl)-10H-pyrido[3,2-h]quinazolin-9-one

[Formula 766]

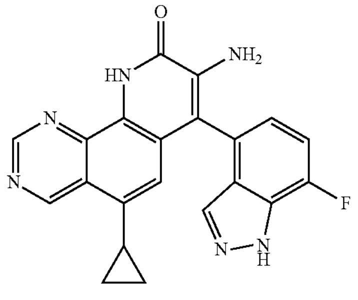

The title compound was synthesized from 8-amino-5-bromo-7-(7-fluoro-1H-indazol-4-yl)-10H-pyrido[3,2-h]quinazolin-9-one (compound J1) under the same conditions as the production example of the compound B22.

LCMS: m/z 387.6 $[M+H]^+$

HPLC retention time: 0.60 min (analysis condition A)

Compound k-1

4-Bromo-6-iodo-1,3-benzothiazol-7-amine

[Formula 767]

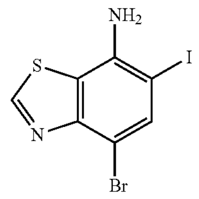

The title compound was synthesized from 4-bromobenzo[d]thiazol-7-amine under the same conditions as the production example of the compound b-59.

LCMS: m/z 355 $[M+H]^+$

HPLC retention time: 0.74 min (analysis condition A)

Compound k-2

(E)-N'-(4-bromo-6-iodo-1,3-benzothiazol-7-yl)-N,N-dimethylmethanimidamide

[Formula 768]

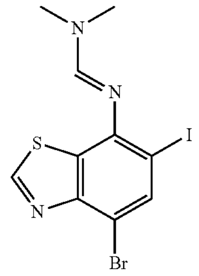

The title compound was synthesized from 4-bromo-6-iodo-1,3-benzothiazol-7-amine (compound k-1) under the same conditions as the production example of the compound b-25, except that THF was used instead of EtOH used in the production example of the compound b-25. In addition, the reaction was carried out by adding 0.2 equivalent amounts of acetic acid based on the raw material.

LCMS: m/z 410 $[M+H]^+$

HPLC retention time: 1.07 min (analysis condition D)

Compound k-3

(7-Amino-4-bromo-1,3-benzothiazol-6-yl)-[7-fluoro-1-(oxan-2-yl)indazol-4-yl]methanol

[Formula 769]

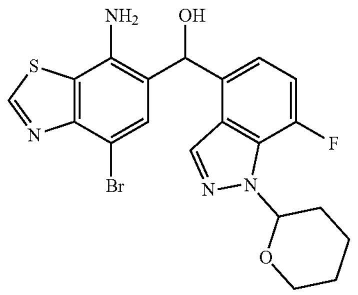

The title compound was synthesized from (E)-N'-(4-bromo-6-iodo-1,3-benzothiazol-7-yl)-N,N-dimethylmethanimidamide (compound k-2) under the same conditions as the production example of the compound c-227, except that the reaction was carried out by cooling the reaction mixture to −78° C.

LCMS: m/z 479 $[M+H]^+$

HPLC retention time: 0.75 min (analysis condition A)

Compound k-4

(7-Amino-4-bromo-1,3-benzothiazol-6-yl)-[7-fluoro-1-(oxan-2-yl)indazol-4-yl]methanone

[Formula 770]

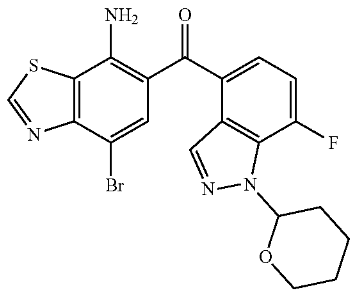

The title compound was synthesized from (7-amino-4-bromo-1,3-benzothiazol-6-yl)-[7-fluoro-1-(oxan-2-yl)indazol-4-yl]methanol (compound k-3) under the same conditions as the production example of the compound c-228.

LCMS: m/z 475 $[M+H]^+$

HPLC retention time: 0.90 min (analysis condition A)

Compound K1

7-Amino-4-bromo-6-(7-fluoro-1H-indazol-4-yl)-9H-[1,3]thiazolo[4,5-h]quinolin-8-one

[Formula 771]

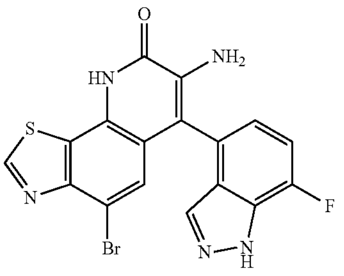

The title compound was synthesized from (7-amino-4-bromo-1,3-benzothiazol-6-yl)-[7-fluoro-1-(oxan-2-yl)indazol-4-yl]methanone (compound k-4) under the same conditions as the production examples of the compounds c-9, c-10, c-13, and B49, except that the reaction was carried out without using N,N-dimethylaniline used in the production example of the compound c-9. In addition, the reaction was carried out by heating the mixed reaction solution at 40° C., in the production example of c-13.

LCMS: m/z 428 $[M-H]^-$

HPLC retention time: 0.57 min (analysis condition A)

Compound K2

7-Amino-6-(7-fluoro-1H-indazol-4-yl)-4-methyl-9H-[1,3]thiazolo[4,5-h]quinolin-8-one

[Formula 772]

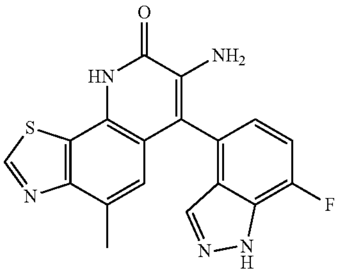

The title compound was synthesized from 7-amino-4-bromo-6-(7-fluoro-1H-indazol-4-yl)-9H-[1,3]thiazolo[4,5-h]quinolin-8-one (compound K1) under the same conditions as the production example of the compound B22, except that a 2 M solution of methylzincchloride in THF was used instead of the 0.5 M solution of cyclopropylzinc bromide in THE used in the production example of the compound B22.

LCMS: m/z 366 $[M+H]^+$

HPLC retention time: 0.56 min (analysis condition A)

Compound K3

7-Amino-4-cyclopropyl-6-(7-fluoro-1H-indazol-4-yl)-9H-[1,3]thiazolo[4,5-h]quinolin-8-one

[Formula 773]

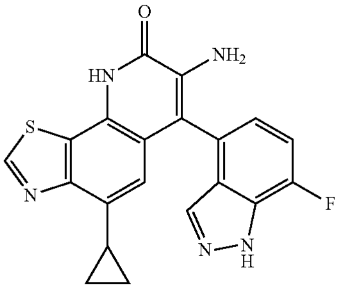

The title compound was synthesized from 7-amino-4-bromo-6-(7-fluoro-1H-indazol-4-yl)-9H-[1,3]thiazolo[4,5-h]quinolin-8-one (compound K1) under the same conditions as the production example of the compound B22.

LCMS: m/z 392.5 $[M+H]^+$

HPLC retention time: 0.60 min (analysis condition A)

Compound k-8

(E)-N'-[4-bromo-6-[7-fluoro-2-(oxan-2-yl)indazole-4-carbonyl]-1,3-benzothiazol-7-yl]-N,N-dimethyl-methanimidamide

[Formula 774]

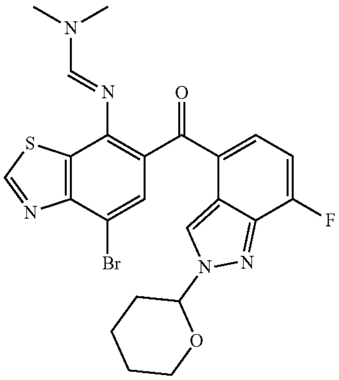

The title compound was synthesized from (E)-N'-(4-bromo-6-iodo-1,3-benzothiazol-7-yl)-N,N-dimethylmethanimidamide (compound k-2) under the same conditions as the production example of the compound b-26.

LCMS: m/z 530 $[M+H]^+$

HPLC retention time: 0.74 min (analysis condition A)

Compound k-9

(7-Amino-4-bromo-1,3-benzothiazol-6-yl)-[7-fluoro-2-(oxan-2-yl)indazol-4-yl]methanone

[Formula 775]

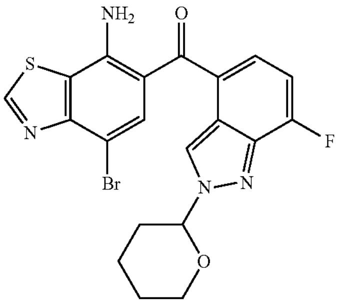

The title compound was synthesized from (E)-N'-[4-bromo-6-[7-fluoro-2-(oxan-2-yl)indazole-4-carbonyl]-1,3-benzothiazol-7-yl]-N,N-dimethylmethanimidamide (compound k-8) under the same conditions as the production example of the compound b-27.

LCMS: m/z 475 $[M+H]^+$

HPLC retention time: 0.84 min (analysis condition A)

Compound k-10

(7-Amino-4-methyl-1,3-benzothiazol-6-yl)-[7-fluoro-2-(oxan-2-yl)indazol-4-yl]methanone

[Formula 776]

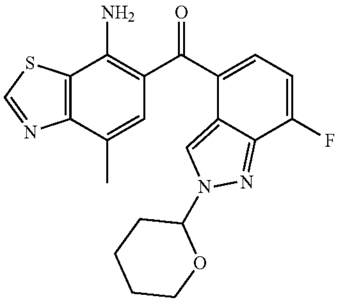

The title compound was synthesized from (7-amino-4-bromo-1,3-benzothiazol-6-yl)-[7-fluoro-2-(oxan-2-yl)indazol-4-yl]methanone (compound k-9) under the same conditions as the production example of the compound B22, except that a 2 M solution of methylzincchloride in THF was used instead of the 0.5 M solution of cyclopropylzinc bromide in THE used in the production example of the compound B22.

LCMS: m/z 411 $[M+H]^+$

HPLC retention time: 0.82 min (analysis condition A)

Compound k-13

7-Amino-6-[7-fluoro-2-(oxan-2-yl)indazol-4-yl]-4-methyl-9H-[1,3]thiazolo[4,5-h]quinolin-8-one

[Formula 777]

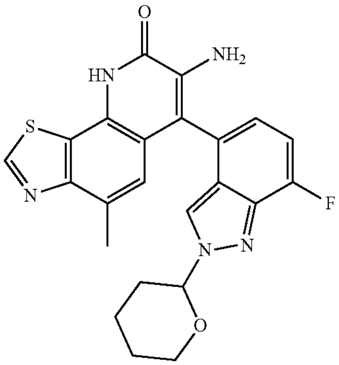

The title compound was synthesized from (7-amino-4-methyl-1,3-benzothiazol-6-yl)-[7-fluoro-2-(oxan-2-yl)indazol-4-yl]methanone (compound k-10) under the same conditions as the production examples of the compounds c-9, c-10, and c-13.

LCMS: m/z 450.5 $[M+H]^+$

HPLC retention time: 0.68 min (analysis condition A)

Compound k-14

3,7-Diamino-4-[7-fluoro-2-(oxan-2-yl)indazol-4-yl]-6-methyl-8-sulfanyl-1H-quinolin-2-one

[Formula 778]

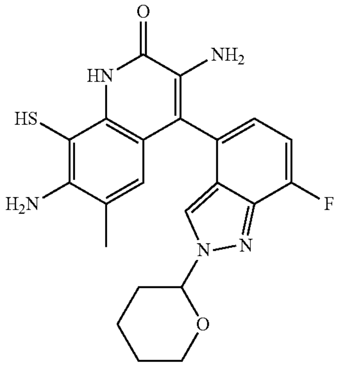

To a solution of 7-amino-6-[7-fluoro-2-(oxan-2-yl)indazol-4-yl]-4-methyl-9H-[1,3]thiazolo[4,5-h]quinolin-8-one (compound k-13, 20 mg, 0.044 mmol) in NMP (200 μL) in a reaction vessel, hydrazine monohydrate (22.03 μL, 0.445 mmol) was added, and the mixture was stirred at 80° C. for 1 hour and at 100° C. for 30 min. The reaction mixture was cooled to room temperature, and an aqueous dithiothreitol solution (20.59 mg, 0.133 mmol) (200 μL) was added thereto. The mixture was purified by reversed phase column chromatography to obtain the title compound (17 mg, yield 87%).

LCMS: m/z 440 $[M+H]^+$

HPLC retention time: 0.62 min (analysis condition A)

Compound K4

7-Amino-6-(7-fluoro-1H-indazol-4-yl)-2,4-dimethyl-9H-[1,3]thiazolo[4,5-h]quinolin-8-one

[Formula 780]

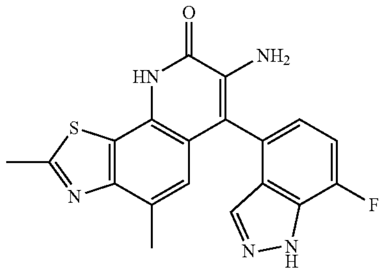

To a solution of 3,7-diamino-4-[7-fluoro-2-(oxan-2-yl)indazol-4-yl]-6-methyl-8-sulfanyl-1H-quinolin-2-one (compound k-14, 4 mg, 9.1 μmol) in DMA (80 μL) in a reaction vessel, dithiothreitol (1.4 mg, 9.1 μmol) and acetylchloride (0.78 μL, 10.92 μmol) were added, and the mixture was stirred at room temperature for 5 min. The reaction mixture was combined with that of another lot, then 12 M hydrochloric acid (6.83 μL, 82 μmol) was added thereto, and the mixture was stirred at room temperature for 3 hours. The reaction mixture was purified by reversed phase column chromatography (0.1% aqueous formic acid solution/0.1% solution of formic acid in acetonitrile) to obtain the title compound (5.6 mg) as a colorless solid.

LCMS: m/z 380 $[M+H]^+$

HPLC retention time: 0.57 min (analysis condition A)

Compound 1-2

(E)-N'-(4-bromo-6-iodo-1-benzothiophen-7-yl)-N,N-dimethylmethanimidamide

[Formula 780]

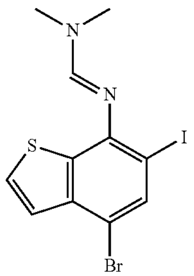

The title compound was synthesized from 4-bromobenzo[b]thiophene-7-amine under the same conditions as the production examples of the compounds c-246 and c-247.

LCMS: m/z 409 $[M+H]^+$

HPLC retention time: 0.61 min (analysis condition A)

Compound 1-3

(E)-N'-[4-bromo-6-[7-fluoro-2-(oxan-2-yl)indazole-4-carbonyl]-1-benzothiophen-7-yl]-N,N-dimethyl-methanimidamide

[Formula 781]

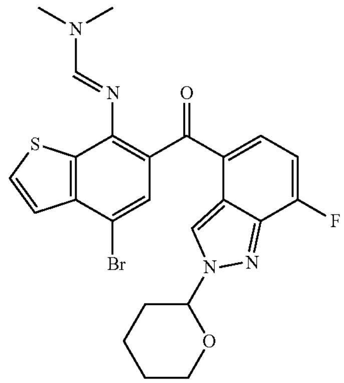

The title compound was synthesized from (E)-N'-(4-bromo-6-iodo-1-benzothiophen-7-yl)-N,N-dimethylmethanimidamide (compound 1-2) under the same conditions as the production example of the compound b-26.

LCMS: m/z 529 $[M+H]^+$

HPLC retention time: 0.83 min (analysis condition A)

Compound 1-4

(7-amino-4-bromo-1-benzothiophen-6-yl)-[7-fluoro-2-(oxan-2-yl)indazol-4-yl]methanone

[Formula 782]

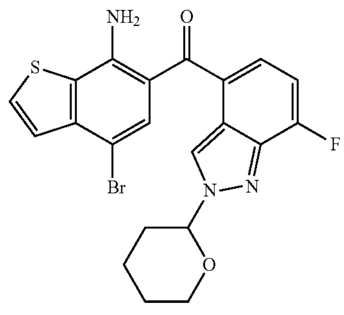

The title compound was synthesized from (E)-N'-[4-bromo-6-[7-fluoro-2-(oxan-2-yl)indazole-4-carbonyl]-1-benzothiophen-7-yl]-N,N-dimethylmethanimidamide (compound 1-3) under the same conditions as the production example of the compound b-27.

LCMS: m/z 474 $[M+H]^+$

HPLC retention time: 1.01 min (analysis condition A)

Compound 1-5

N-[4-bromo-6-[7-fluoro-2-(oxan-2-yl)indazole-4-carbonyl]-1-benzothiophen-7-yl]-2-chloroacetamide

[Formula 783]

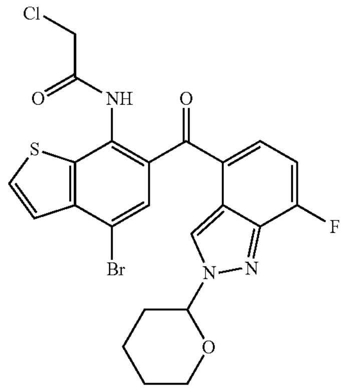

To a solution of (7-amino-4-bromo-1-benzothiophen-6-yl)-[7-fluoro-2-(oxan-2-yl)indazol-4-yl]methanone (compound 1-4, 54 mg, 0.114 mmol) in DMA (540 μL) in a reaction vessel, chloroacetyl chloride (18.24 μL, 0.228 mmol) was added. The reaction mixture was stirred at room temperature for 30 min to obtain a solution of N-[4-bromo-6-[7-fluoro-2-(oxan-2-yl)indazole-4-carbonyl]-1-benzothiophen-7-yl]-2-chloroacetamide (compound 1-5) in DMA.

LCMS: m/z 550 $[M+H]^+$

HPLC retention time: 0.91 min (analysis condition A)

Compound 1-7

4-Bromo-6-(7-fluoro-1H-indazol-4-yl)-7-pyridin-1-ium-1-yl-9H-thieno[3,2-h]quinolin-8-one; chloride

[Formula 784]

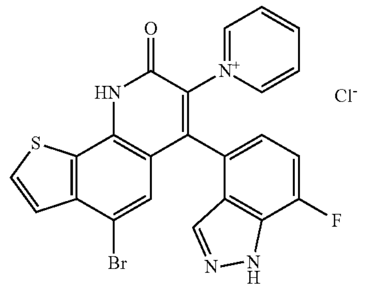

To the solution of the compound 1-5 in DMA in a reaction vessel, pyridine (162 μL, 2 mmol) was added. The reaction mixture was stirred at 60° C. for 4 hours to obtain a solution of 4-bromo-6-(7-fluoro-1H-indazol-4-yl)-7-pyridin-1-ium-1-yl-9H-thieno[3,2-h]quinolin-8-one; chloride (compound 1-7) in DMA/pyridine.

LCMS: m/z 491 $[M]^+$

HPLC retention time: 0.48 min (analysis condition A)

Compound L1

7-Amino-4-bromo-6-(7-fluoro-1H-indazol-4-yl)-9H-thieno[3,2-h]quinolin-8-one

[Formula 785]

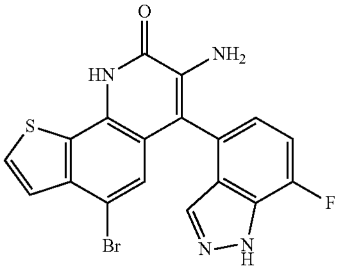

The solution of the compound 1-7 in DMA/pyridine in a reaction vessel, hydrazine monohydrate (56.4 μL, 1.138 mmol) was added, and the mixture was heated at 60° C. for 2 hours. The reaction mixture was cooled to room temperature and purified by reversed phase column chromatography (0.05% aqueous TFA solution/0.05% solution of TFA in acetonitrile) to obtain the title compound (compound L1, 44 mg, yield 90%) as a light brown solid.

LCMS: m/z 429 $[M+H]^+$

HPLC retention time: 0.71 min (analysis condition A)

Compound L2

7-Amino-6-(7-fluoro-1H-indazol-4-yl)-4-methyl-9H-thieno[3,2-h]quinolin-8-one

[Formula 786]

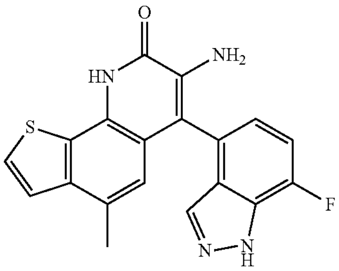

The title compound was synthesized from 7-amino-4-bromo-6-(7-fluoro-1H-indazol-4-yl)-9H-thieno[3,2-h]quinolin-8-one (compound L1) under the same conditions as the production example of the compound B22, except that a 2 M solution of methylzincchloride in THF was used instead of the 0.5 M solution of cyclopropylzinc bromide in THE used in the production example of the compound B22.

LCMS: m/z 365 $[M+H]^+$

HPLC retention time: 0.65 min (analysis condition A)

Compound L3

7-Amino-4-cyclopropyl-6-(7-fluoro-1H-indazol-4-yl)-9H-thieno[3,2-h]quinolin-8-one

[Formula 787]

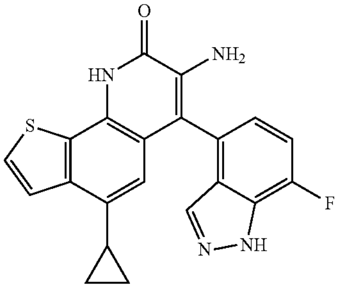

The title compound was synthesized from 7-amino-4-bromo-6-(7-fluoro-1H-indazol-4-yl)-9H-thieno[3,2-h]quinolin-8-one (compound L1) under the same conditions as the production example of the compound B22.

LCMS: m/z 391 $[M+H]^+$

HPLC retention time: 0.69 min (analysis condition A)

Compound m-1

7-Bromo-1-methylbenzimidazol-4-amine

[Formula 788]

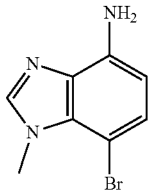

The title compound was synthesized from 1-methyl-1H-benzo[d]imidazol-4-amine under the same conditions as the production example of the compound b-100, except that THF was used instead of DMF used in the production example of the compound b-100.

LCMS: m/z 226 $[M+H]^+$

HPLC retention time: 0.73 min (analysis condition H)

Compound m-3

(E)-N'-(7-bromo-5-iodo-1-methylbenzimidazol-4-yl)-N,N-dimethylmethanimidamide

[Formula 789]

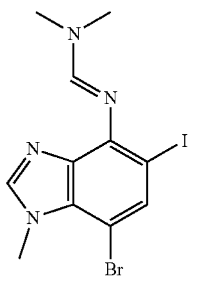

The title compound was synthesized from 7-bromo-1-methylbenzimidazol-4-amine (compound m-1) under the same conditions as the production examples of the compounds b-76 and b-77.

LCMS: m/z 407 $[M+H]^+$

HPLC retention time: 0.99 min (analysis condition H)

Compound m-4

(E)-N'-[7-bromo-5-[7-fluoro-2-(oxan-2-yl)indazole-4-carbonyl]-1-methylbenzimidazol-4-yl]-N,N-dimethylmethanimidamide

[Formula 790]

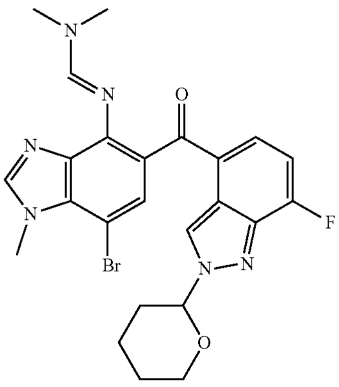

The title compound was synthesized from (E)-N'-(7-bromo-5-iodo-1-methylbenzimidazol-4-yl)-N,N-dimethylmethanimidamide (compound m-3) under the same conditions as the production example of the compound b-26, except that toluene was used instead of THE used in the production example of the compound b-26.

LCMS: m/z 527 $[M+H]^+$

HPLC retention time: 0.55 min (analysis condition A)

Compound m-5

(4-Amino-7-bromo-1-methylbenzimidazol-5-yl)-[7-fluoro-2-(oxan-2-yl)indazol-4-yl]methanone

[Formula 791]

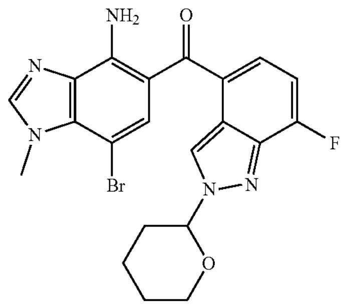

The title compound was synthesized from (E)-N'-[7-bromo-5-[7-fluoro-2-(oxan-2-yl)indazole-4-carbonyl]-1-methylbenzimidazol-4-yl]-N,N-dimethylmethanimidamide (compound m-4) under the same conditions as the production example of the compound b-27.

LCMS: m/z 472 $[M+H]^+$

HPLC retention time: 0.81 min (analysis condition A)

Compound M1

7-Amino-4-bromo-6-(7-fluoro-1H-indazol-4-yl)-3-methyl-9H-imidazo[4,5-h]quinolin-8-one

[Formula 792]

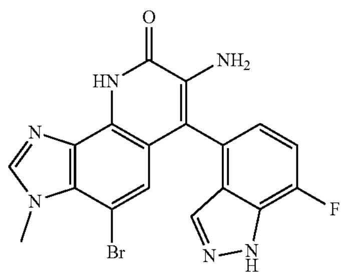

The title compound was synthesized from (4-amino-7-bromo-1-methylbenzimidazol-5-yl)-[7-fluoro-2-(oxan-2-yl)indazol-4-yl]methanone (compound m-5) under the same conditions as the production examples of the compounds b-28, b-29, b-30, and b-9, except that DMA was used instead of DCM and pyridine used in the production example of the compound b-30.

LCMS: m/z 427 $[M+H]^+$

HPLC retention time: 0.57 min (analysis condition A)

Compound M3

7-Amino-6-(7-fluoro-1H-indazol-4-yl)-3-methyl-9H-imidazo[4,5-h]quinolin-8-one

[Formula 793]

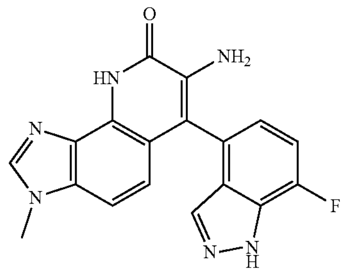

LCMS: m/z 349 $[M+H]^+$

HPLC retention time: 0.42 min (analysis condition A)

Compound M2

7-Amino-6-(7-fluoro-1H-indazol-4-yl)-3,4-dimethyl-9H-imidazo[4,5-h]quinolin-8-one

[Formula 794]

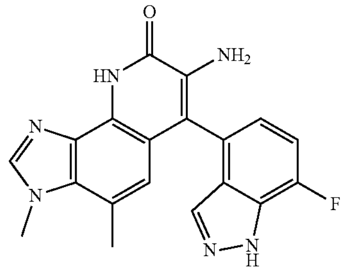

The compound M2 and the compound M3 were synthesized from 7-amino-4-bromo-6-(7-fluoro-1H-indazol-4-yl)-3-methyl-9H-imidazo[4,5-h]quinolin-8-one (compound M1) under the same conditions as the production example of the compound B22, except that a 2 M solution of methylzincchloride in THF was used instead of the 0.5 M solution of cyclopropylzinc bromide in THF used in the production example of the compound B22.

LCMS: m/z 363 $[M+H]^+$

HPLC retention time: 0.45 min (analysis condition A)

Compound M4

7-Amino-4-cyclopropyl-6-(7-fluoro-1H-indazol-4-yl)-3-methyl-9H-imidazo[4,5-h]quinolin-8-one

[Formula 795]

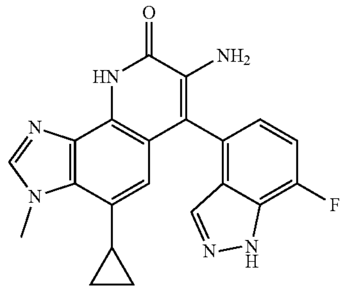

The title compound was synthesized from 7-amino-4-bromo-6-(7-fluoro-1H-indazol-4-yl)-3-methyl-9H-imidazo[4,5-h]quinolin-8-one (compound M1) under the same conditions as the production example of the compound B22.

LCMS: m/z 389.5 $[M+H]^+$

HPLC retention time: 0.50 min (analysis condition A)

Compound n-2

(E)-N'-(7-bromo-5-iodo-1,3-benzothiazol-4-yl)-N,N-dimethylmethanimidamide

[Formula 796]

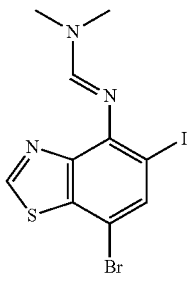

The title compound was synthesized from 7-bromobenzo[d]thiazol-4-amine under the same conditions as the production examples of the compounds b-76 and b-77, except that the reaction was carried out at room temperature.

LCMS: m/z 410 $[M+H]^+$

HPLC retention time: 0.46 min (analysis condition A)

Compound n-3

(E)-N'-[7-bromo-5-[7-fluoro-2-(oxan-2-yl)indazole-4-carbonyl]-1,3-benzothiazol-4-yl]-N,N-dimethyl-methanimidamide

[Formula 797]

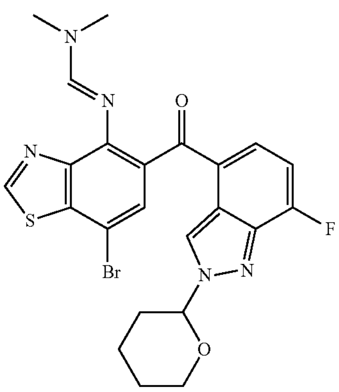

The title compound was synthesized from (E)-N'-(7-bromo-5-iodo-1,3-benzothiazol-4-yl)-N,N-dimethylmethanimidamide (compound n-2) under the same conditions as the production example of the compound b-26, except that toluene was used instead of THE used in the production example of the compound b-26.

LCMS: m/z 530 $[M+H]^+$

HPLC retention time: 1.06 min (analysis condition H)

Compound n-4

(4-Amino-7-bromo-1,3-benzothiazol-5-yl)-[7-fluoro-2-(oxan-2-yl)indazol-4-yl]methanone

[Formula 798]

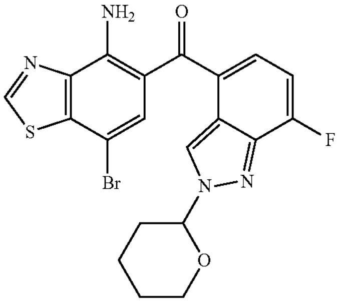

The title compound was synthesized from (E)-N'-[7-bromo-5-[7-fluoro-2-(oxan-2-yl)indazole-4-carbonyl]-1,3-benzothiazol-4-yl]-N,N-dimethylmethanimidamide (compound n-3) under the same conditions as the production example of the compound b-27, except that a 2 M aqueous lithium hydroxide solution was used instead of the 5 M aqueous sodium hydroxide solution used in the production example of the compound b-27.

LCMS: m/z 475 $[M+H]^+$

HPLC retention time: 0.98 min (analysis condition A)

Compound N1

7-Amino-4-bromo-6-(7-fluoro-1H-indazol-4-yl)-9H-[1,3]thiazolo[5,4-h]quinolin-8-one

[Formula 799]

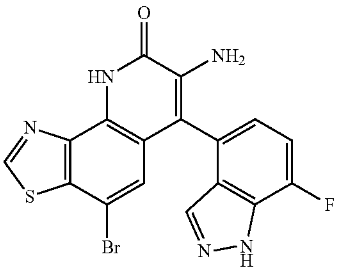

The title compound was synthesized from (4-amino-7-bromo-1,3-benzothiazol-5-yl)-[7-fluoro-2-(oxan-2-yl)indazol-4-yl]methanone (compound n-4) under the same conditions as the production examples of the compounds b-28, b-29, b-30, and b-9, except that DMA was used instead of DCM and pyridine used in the production example of the compound b-28.

LCMS: m/z 430 $[M+H]^+$

HPLC retention time: 0.66 min (analysis condition A)

Compound N2

7-Amino-4-cyclopropyl-6-(7-fluoro-1H-indazol-4-yl)-9H-[1,3]thiazolo[5,4-h]quinolin-8-one

[Formula 800]

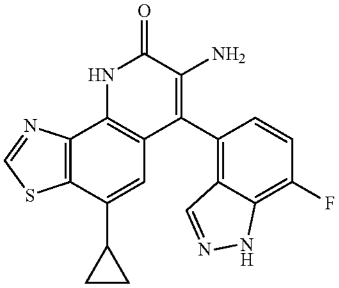

The title compound was synthesized from 7-amino-4-bromo-6-(7-fluoro-1H-indazol-4-yl)-9H-[1,3]thiazolo[5,4-h]quinolin-8-one (compound N1) under the same conditions as the production example of the compound B22.

LCMS: m/z 392 $[M+H]^+$

HPLC retention time: 0.66 min (analysis condition A)

Compound o-1

8-Methyl-5-nitro-1,7-naphthyridine

[Formula 801]

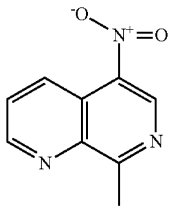

The title compound was synthesized from 8-chloro-5-nitro-1,7-naphthyridine under the same conditions as the production example of the compound B22, except that XPhos Pd G4 and a 2 M solution of methylzinc chloride in THF were used instead of CPhos Pd G3 and the 0.5 M solution of cyclopropylzinc bromide in THE used in the production example of the compound B22.

LCMS: m/z 190.7 $[M+H]^+$

HPLC retention time: 0.56 min (analysis condition A)

Compound o-2

8-Methyl-1,7-naphthyridin-5-amine

[Formula 802]

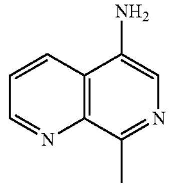

To a solution of 8-methyl-5-nitro-1,7-naphthyridine (compound o-1, 230 mg, 1.216 mmol) in EtOH (6.9 mL) in a reaction vessel, iron powder (340 mg, 6.08 mmol) and 12 M hydrochloric acid (2.3 mL) were added, and the mixture was stirred at 80° C. for 30 min. The reaction mixture was cooled to room temperature and filtered, and then the insoluble matter was washed with EtOH. The filtrate was concentrated, and a saturated aqueous sodium bicarbonate solution was added thereto. The mixture was purified by reversed phase column chromatography (10 mM aqueous ammonium hydrogencarbonate solution/acetonitrile) to obtain the title compound (79.5 mg, yield 41%).

LCMS: m/z 160 $[M+H]^+$

HPLC retention time: 0.47 min (analysis condition H)

Compound o-4

(E)-N'-(6-iodo-8-methyl-1,7-naphthyridin-5-yl)-N,N-dimethylmethanimidamide

[Formula 803]

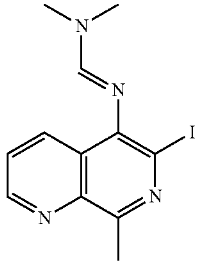

The title compound was synthesized from 8-methyl-1,7-naphthyridin-5-amine (compound 0-2) under the same conditions as the production examples of the compounds c-246 and c-247, except that a mixed solution of acetonitrile/DMSO (2/1) was used instead of DMSO used in the production example of the compound b-24. In addition, the reaction was carried out by heating the reaction solution to 60° C.

LCMS: m/z 341 $[M+H]^+$

HPLC retention time: 0.74 min (analysis condition H)

Compound o-5

(E)-N'-[6-[7-fluoro-2-(oxan-2-yl)indazole-4-carbonyl]-8-methyl-1,7-naphthyridin-5-yl]-N,N-dimethylmethanimidamide

[Formula 804]

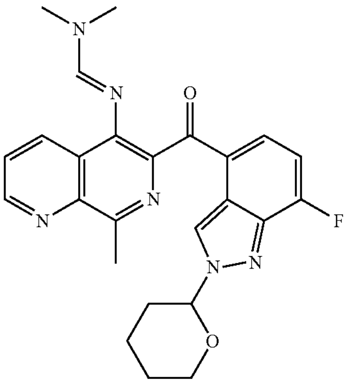

The title compound was synthesized from (E)-N'-(6-iodo-8-methyl-1,7-naphthyridin-5-yl)-N,N-dimethylmethanimidamide (compound o-4) under the same conditions as the production example of the compound b-26, except that toluene was used instead of THE used in the production example of the compound b-26.

LCMS: m/z 461.5 $[M+H]^+$

HPLC retention time: 0.87 min (analysis condition H)

Compound o-6

(5-Amino-8-methyl-1,7-naphthyridin-6-yl)-[7-fluoro-2-(oxan-2-yl)indazol-4-yl]methanone

[Formula 805]

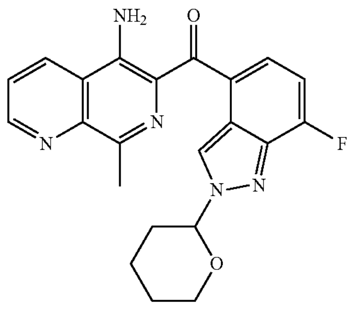

The title compound was synthesized from (E)-N'-[6-[7-fluoro-2-(oxan-2-yl)indazole-4-carbonyl]-8-methyl-1,7-naphthyridin-5-yl]-N,N-dimethylmethanimidamide (compound o-5) under the same conditions as the production example of the compound b-27.

LCMS: m/z 406.5 $[M+H]^+$

HPLC retention time: 0.94 min (analysis condition H)

Compound O1

3-Amino-4-(7-fluoro-1H-indazol-4-yl)-6-methyl-1H-pyrido[2,3-h][1,5]naphthyridin-2-one

[Formula 806]

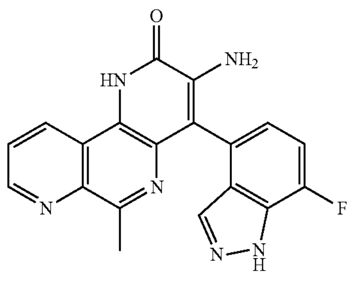

The title compound was synthesized from (5-amino-8-methyl-1,7-naphthyridin-6-yl)-[7-fluoro-2-(oxan-2-yl)indazol-4-yl]methanone (compound o-6) under the same conditions as the production examples of the compounds c-9, c-10, c-13, and B49, except that the reaction was carried out without using N,N-dimethylaniline used in the production example of the compound c-9. In addition, hexafluoro-2-propanol was used instead of TFE used in the production example of the compound B49, and anisole was used in an amount of 5 equivalents based on the raw material.

LCMS: m/z 361 $[M+H]^+$

HPLC retention time: 0.48 min (analysis condition A)

Compound p-1

8-Cyclopropylisoquinolin-5-amine

[Formula 807]

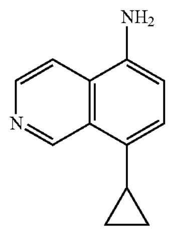

The title compound was synthesized from 8-bromoisoquinolin-5-amine under the same conditions as the production example of the compound b-10, except that 1,1'-bis(diphenylphosphino)ferrocene]dichloropalladium(II) was used instead of DPPF Pd G4 used in the production example of the compound b-10.

LCMS: m/z 185 $[M+H]^+$

HPLC retention time: 0.29 min (analysis condition J)

Compound p-2

6-Bromo-8-cyclopropylisoquinolin-5-amine

[Formula 808]

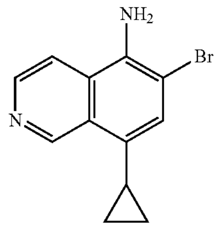

The title compound was synthesized from 8-cyclopropylisoquinolin-5-amine (compound p-1) under the same conditions as the production example of the compound b-100, except that NMP was used instead of DMF used in the production example of the compound b-100.

LCMS: m/z 263 $[M+H]^+$

HPLC retention time: 0.44 min (analysis condition A)

Compound P1

3-Amino-6-cyclopropyl-4-(1H-indazol-4-yl)-1H-1,8-phenanthrolin-2-one

[Formula 809]

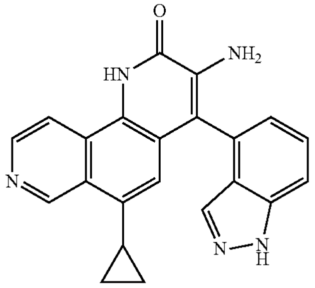

The title compound was synthesized from 6-bromo-8-cyclopropylisoquinolin-5-amine (compound p-2) under the same conditions as the production example of the compounds c-234, c-235, and B49.

LCMS: m/z 368 $[M+H]^+$

HPLC retention time: 0.84 min (analysis condition H)

Compound p-5

6-Iodo-1-methylisoquinolin-5-amine

[Formula 810]

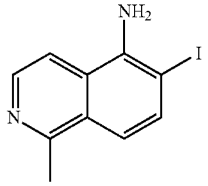

The title compound was synthesized from 1-methylisoquinolin-5-amine under the same conditions as the production example of the compound c-1, except that DMSO was used instead of acetonitrile used in the production example of the compound c-2.

LCMS: m/z 285 $[M+H]^+$

HPLC retention time: 0.88 min (analysis condition H)

Compound p-6

8-Bromo-6-iodo-1-methylisoquinolin-5-amine

[Formula 811]

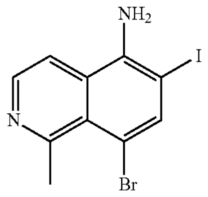

The title compound was synthesized from 6-iodo-1-methylisoquinolin-5-amine (compound p-5) under the same conditions as the production example of the compound b-100, except that DMSO was used instead of DMF used in the production example of the compound b-100.

LCMS: m/z 363 $[M+H]^+$

HPLC retention time: 1.09 min (analysis condition H)

Compound p-7

(E)-N'-(8-bromo-6-iodo-1-methylisoquinolin-5-yl)-N,N-dimethylmethanimidamide

[Formula 812]

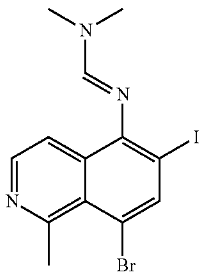

The title compound was synthesized from 8-bromo-6-iodo-1-methylisoquinolin-5-amine (compound p-6) under the same conditions as the production example of the compound b-25, except that DMSO was used instead of EtOH used in the production example of the compound b-25.

LCMS: m/z 418 $[M+H]^+$

HPLC retention time: 1.10 min (analysis condition H)

Compound p-8

(5-Amino-8-bromo-1-methylisoquinolin-6-yl)-[7-fluoro-1-(oxan-2-yl)indazol-4-yl]methanol

[Formula 813]

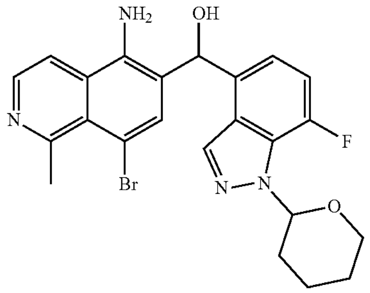

The title compound was synthesized from (E)-N'-(8-bromo-6-iodo-1-methylisoquinolin-5-yl)-N,N-dimethylmethanimidamide (compound p-7) under the same conditions as the production example of the compound c-227.

LCMS: m/z 485 $[M+H]^+$

HPLC retention time: 0.52 min (analysis condition A)

Compound p-9

(5-Amino-8-bromo-1-methylisoquinolin-6-yl)-[7-fluoro-1-(oxan-2-yl)indazol-4-yl]methanone

[Formula 814]

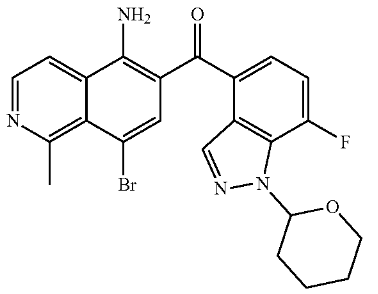

To a solution of (5-amino-8-bromo-1-methylisoquinolin-6-yl)-[7-fluoro-1-(oxan-2-yl)indazol-4-yl]methanol (compound p-8, 34 mg, 0.07 mmol) in DMF (701 μL) in a reaction vessel, copper(II) chloride (0.942 mg, 7.01 μmol) and potassium carbonate (19.36 mg, 0.14 mmol) were added, and the reaction solution was stirred at 60° C. for 3 hours while blowing air thereinto. The reaction mixture was purified by reversed phase column chromatography to obtain the title compound (19 mg, yield 56%).

LCMS: m/z 483 $[M+H]^+$

HPLC retention time: 0.85 min (analysis condition A)

Compound P2

3-Amino-6-bromo-4-(7-fluoro-1H-indazol-4-yl)-7-methyl-1H-1,8-phenanthrolin-2-one

[Formula 815]

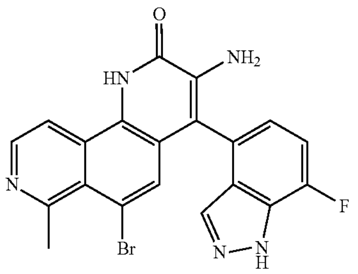

The title compound was synthesized from (5-amino-8-bromo-1-methylisoquinolin-6-yl)-[7-fluoro-1-(oxan-2-yl) indazol-4-yl]methanone (compound p-9) under the same conditions as the production examples of the compounds b-28, b-29, b-30, and b-9, except that DMSO was used instead of EtOH used in the production example of the compound b-9.

LCMS: m/z 438 $[M+H]^+$

HPLC retention time: 0.46 min (analysis condition A)

Compound p-11

(E)-N'-(8-bromo-6-iodoisoquinolin-5-yl)-N,N-dimethylmethanimidamide

[Formula 816]

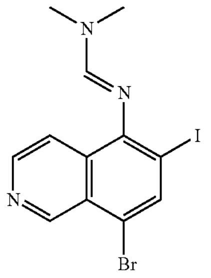

The title compound was synthesized from 8-bromoisoquinolin-5-amine under the same conditions as the production examples of the compounds b-76 and b-77.

LCMS: m/z 404 $[M+H]^+$

HPLC retention time: 0.48 min (analysis condition A)

Compound p-12

(E)-N'-[8-bromo-6-[7-fluoro-2-(oxan-2-yl)indazole-4-carbonyl]isoquinolin-5-yl]-N,N-dimethylmethanimidamide

[Formula 817]

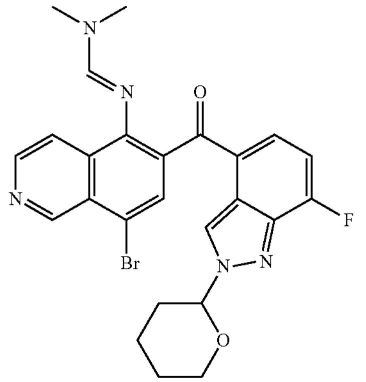

The title compound was synthesized from (E)-N'-(8-bromo-6-iodoisoquinolin-5-yl)-N,N-dimethylmethanimidamide (compound p-11) under the same conditions as the production example of the compound b-26.

LCMS: m/z 524 $[M+H]^+$

HPLC retention time: 0.70 min (analysis condition A)

Compound p-13

(5-Amino-8-bromoisoquinolin-6-yl)-[7-fluoro-2-(oxan-2-yl)indazol-4-yl]methanone

[Formula 818]

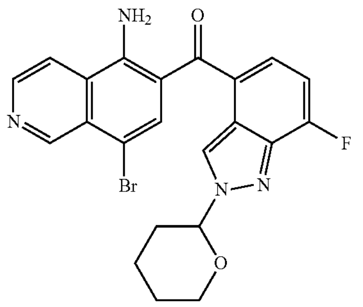

The title compound was synthesized from (E)-N'-[8-bromo-6-[7-fluoro-2-(oxan-2-yl)indazole-4-carbonyl]isoquinolin-5-yl]-N,N-dimethylmethanimidamide (compound p-12) under the same conditions as the production example of the compound b-27.

LCMS: m/z 469 $[M+H]^+$

HPLC retention time: 0.80 min (analysis condition A)

Compound p-15

6-Bromo-4-(7-fluoro-1H-indazol-4-yl)-3-pyridin-1-ium-1-yl-1H-1,8-phenanthrolin-2-one; chloride

[Formula 819]

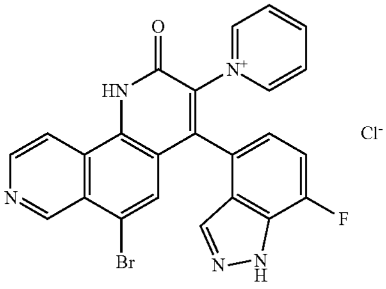

To a solution of (5-amino-8-bromoisoquinolin-6-yl)-[7-fluoro-2-(oxan-2-yl)indazol-4-yl]methanone (compound p-13, 100 mg, 0.213 mmol) in NMP (1 mL) in a reaction vessel, 2-chloroacetic acid (101 mg, 1.07 mmol), 1.7 M solution of propylphosphonic acid anhydride in ethyl acetate (901 μL, 1.53 mmol), and pyridine (345 μL, 4.26 mmol) were added, and the mixture was stirred at 60° C. for 15 hours to obtain a solution of the title compound in pyridine.

LCMS: m/z 486 $[M]^+$

HPLC retention time: 1.60 min (analysis condition G)

Compound P3

3-Amino-6-bromo-4-(7-fluoro-1H-indazol-4-yl)-1H-1,8-phenanthrolin-2-one

[Formula 820]

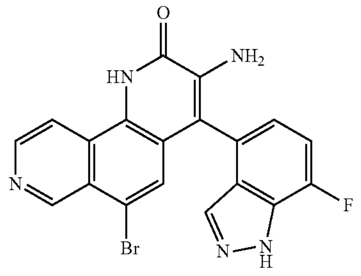

To the solution of 6-bromo-4-(7-fluoro-1H-indazol-4-yl)-3-pyridin-1-ium-1-yl-1H-1,8-phenanthrolin-2-one; chloride (compound p-15) in pyridine in a reaction vessel, hydrazine monohydrate (0.317 mL, 6.39 mmol) was added, and the mixture was stirred at 60° C. for 3 hours. The reaction mixture was cooled to room temperature and then concentrated under reduced pressure, and the obtained residue was purified by reversed phase column chromatography (0.1% aqueous formic acid solution/0.1% solution of formic acid in acetonitrile) to obtain the title compound (10.2 mg, yield 11%) as a brown solid.

LCMS: m/z 424 $[M+H]^+$

HPLC retention time: 1.83 min (analysis condition G)

Compound P4

3-Amino-6-cyclopropyl-4-(7-fluoro-1H-indazol-4-yl)-1H-1,8-phenanthrolin-2-one 2,2,2-trifluoroacetate

[Formula 821]

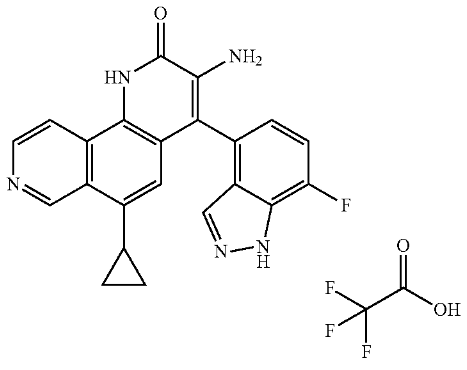

The title compound was synthesized from 3-amino-6-bromo-4-(7-fluoro-1H-indazol-4-yl)-1H-1,8-phenanthrolin-2-one (compound P3) under the same conditions as the production example of the compound b-31.

LCMS: m/z 386 $[M+H]^+$

HPLC retention time: 1.80 min (analysis condition G)

Compound p-17

Methyl (E)-2-[(2-methylpropan-2-yl)oxycarbonylamino]-3-(5-nitroisoquinolin-6-yl) prop-2-enoate

[Formula 822]

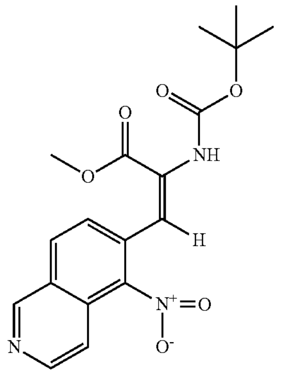

The title compound was synthesized from 5-nitroisoquinoline-6-carbaldehyde under the same conditions as the production example of the compound b-1.

LCMS: m/z 374 [M+H]$^+$

HPLC retention time: 0.78 min (analysis condition A)

Compound p-18

Methyl (Z)-3-bromo-2-[(2-methylpropan-2-yl)oxycarbonylamino]-3-(5-nitroisoquinolin-6-yl) prop-2-enoate

[Formula 823]

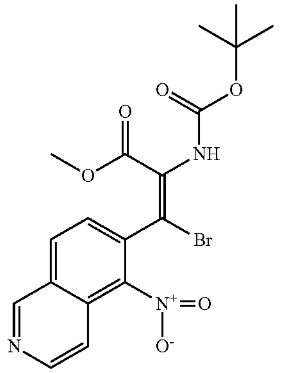

The title compound was synthesized from methyl (E)-2-[(2-methylpropan-2-yl)oxycarbonylamino]-3-(5-nitroisoquinolin-6-yl) prop-2-enoate (compound p-17) under the same conditions as the production example of the compound b-3.

LCMS: m/z 452 [M+H]$^+$

HPLC retention time: 0.75 min (analysis condition A)

Compound p-19

Methyl (E)-3-(3-methoxyphenyl)-2-[(2-methylpropan-2-yl)oxycarbonylamino]-3-(5-nitroisoquinolin-6-yl) prop-2-enoate

[Formula 824]

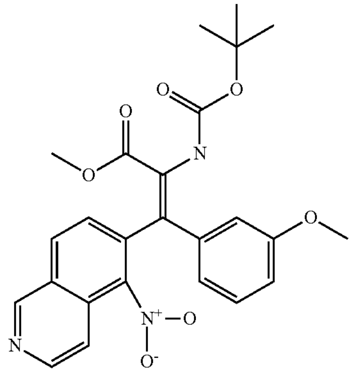

The title compound was synthesized from methyl (Z)-3-bromo-2-[(2-methylpropan-2-yl)oxycarbonylamino]-3-(5-nitroisoquinolin-6-yl) prop-2-enoate (compound p-18) under the same conditions as the production example of the compound b-4, except that Aphos Pd G3 was used instead of [1,1'-bis(diphenylphosphino)ferrocene]dichloropalladium (II) used in the production example of the compound b-4. In addition, the reaction was carried out at room temperature.

LCMS: m/z 480 [M+H]$^+$

HPLC retention time: 0.78 min (analysis condition A)

Compound p-20 tert-Butyl N-[4-(3-methoxyphenyl)-2-oxo-1H-1,8-phenanthrolin-3-yl]carbamate

[Formula 825]

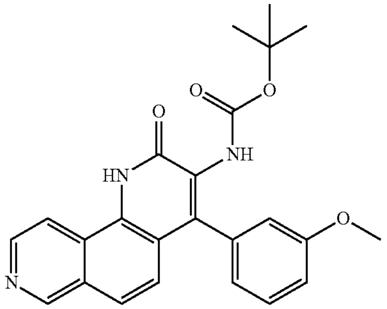

The title compound was synthesized from methyl (E)-3-(3-methoxyphenyl)-2-[(2-methylpropan-2-yl)oxycarbonylamino]-3-(5-nitroisoquinolin-6-yl) prop-2-enoate (compound p-19) under the same conditions as the production example of the compound b-5.

LCMS: m/z 418 [M+H]$^+$

HPLC retention time: 0.59 min (analysis condition A)

Compound P5

3-Amino-4-(3-hydroxyphenyl)-1H-1,8-phenanthrolin-2-one; hydrobromide

[Formula 826]

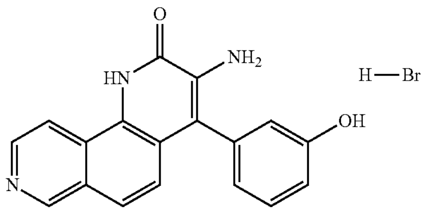

The title compound was synthesized from tert-butyl N-[4-(3-methoxyphenyl)-2-oxo-1H-1,8-phenanthrolin-3-yl]carbamate (compound p-20) under the same conditions as the production example of the compound C184.

LCMS: m/z 304 [M+H]$^+$

HPLC retention time: 0.36 min (analysis condition A)

Compound q-2

5-Cyclopropylisoquinolin-8-amine

[Formula 827]

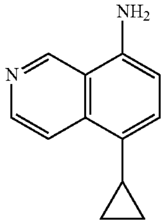

The title compound was synthesized from 5-bromoisoquinolin-8-amine under the same conditions as the production example of the compound b-10, except that 1,1'-bis(diphenylphosphino)ferrocene]dichloropalladium(II) was used instead of DPPF Pd G4 used in the production example of the compound b-10.

LCMS: m/z 185 [M+H]$^+$

HPLC retention time: 0.39 min (analysis condition A)

Compound q-3

7-Bromo-5-cyclopropylisoquinolin-8-amine

[Formula 828]

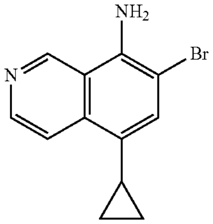

The title compound was synthesized from 5-cyclopropylisoquinolin-8-amine (compound q-2) under the same conditions as the production example of the compound b-100, except that NMP was used instead of DMF used in the production example of the compound b-100.

LCMS: m/z 263 [M+H]$^+$

HPLC retention time: 1.15 min (analysis condition A)

Compound Q1

3-Amino-6-cyclopropyl-4-(1H-indazol-4-yl)-1H-1,9-phenanthrolin-2-one

[Formula 829]

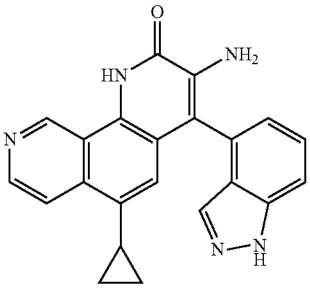

The title compound was synthesized from 7-bromo-5-cyclopropylisoquinolin-8-amine (compound q-3) under the same conditions as the production examples of the compounds c-234, c-235, and B49.

LCMS: m/z 368 [M+H]$^+$

HPLC retention time: 0.45 min (analysis condition A)

Compound r-3

(E)-N'-(3-iodoquinolin-4-yl)-N,N-dimethylmethanimidamide

[Formula 830]

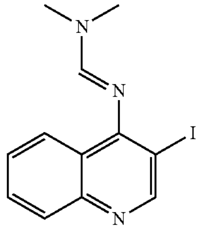

The title compound was synthesized from 3-iodoquinolin-4-amine under the same conditions as the production example of the compound b-25.

LCMS: m/z 326 [M+H]$^+$

HPLC retention time: 0.41 min (analysis condition Q)

Compound r-4

(E)-N'-[3-[7-fluoro-2-(oxan-2-yl)indazole-4-carbonyl]quinolin-4-yl]-N,N-dimethylmethanimidamide

[Formula 831]

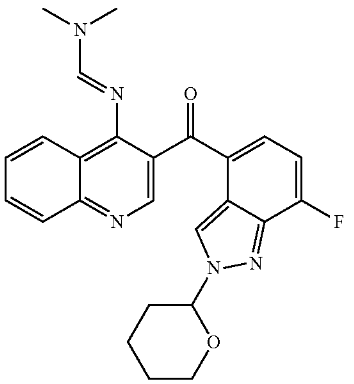

The title compound was synthesized from (E)-N'-(3-iodoquinolin-4-yl)-N,N-dimethylmethanimidamide (compound r-3) under the same conditions as the production example of the compound b-26.

LCMS: m/z 446 $[M+H]^+$

HPLC retention time: 0.47 min (analysis condition Q)

Compound r-5

(4-Aminoquinolin-3-yl)-[7-fluoro-2-(oxan-2-yl)indazol-4-yl]methanone

[Formula 832]

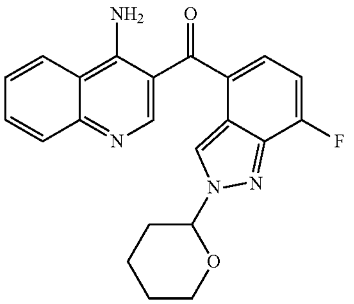

The title compound was synthesized from (E)-N'-[3-[7-fluoro-2-(oxan-2-yl)indazole-4-carbonyl]quinolin-4-yl]-N,N-dimethylmethanimidamide (compound r-4) under the same conditions as the production example of the compound b-27.

LCMS: m/z 391 $[M+H]^+$

HPLC retention time: 0.42 min (analysis condition Q)

Compound R1

3-Amino-4-(7-fluoro-1H-indazol-4-yl)-1H-benzo[h][1,6]naphthyridin-2-one

[Formula 833]

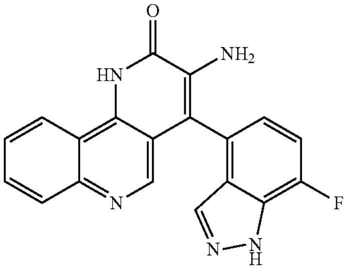

The title compound was synthesized from (4-aminoquinolin-3-yl)-[7-fluoro-2-(oxan-2-yl)indazol-4-yl]methanone (compound r-5) under the same conditions as the production examples of the compounds b-28, b-29, b-30, and b-9, except that DIPEA was used instead of pyridine used in the production example of the compound b-28, and DMSO was used instead of EtOH used in the production example of the compound b-9.

LCMS: m/z 346 $[M+H]^+$

HPLC retention time: 0.36 min (analysis condition A)

Compound s-1

8-Bromo-3-methylcinnolin-5-amine

[Formula 834]

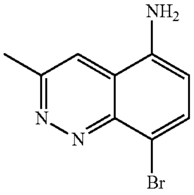

The title compound was synthesized from 3-methylcinnolin-5-amine under the same conditions as the production example of the compound b-100, except that acetonitrile/DMSO (5/3) was used instead of DMF used in the production example of the compound b-100.

LCMS: m/z 238 $[M+H]^+$

HPLC retention time: 0.45 min (analysis condition A)

Compound s-3

(E)-N'-(8-bromo-6-iodo-3-methylcinnolin-5-yl)-N,N-dimethylmethanimidamide

[Formula 835]

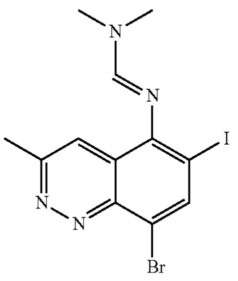

The title compound was synthesized from 8-bromo-3-methylcinnolin-5-amine (compound s-1) under the same conditions as the production examples of the compounds b-76 and b-77.

LCMS: m/z 419 $[M+H]^+$

HPLC retention time: 0.45 min (analysis condition A)

Compound s-4

(5-Amino-8-bromo-3-methylcinnolin-6-yl)-[7-fluoro-1-(oxan-2-yl)indazol-4-yl]methanol

[Formula 836]

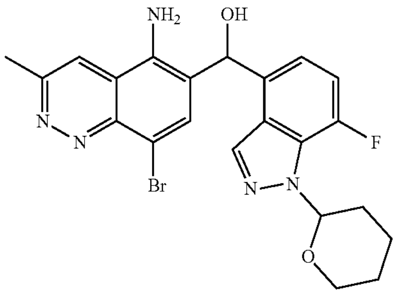

The title compound was synthesized from (E)-N'-(8-bromo-6-iodo-3-methylcinnolin-5-yl)-N,N-dimethylmethanimidamide (compound s-3) under the same conditions as the production example of the compound c-227, except that MeOH was used instead of acetonitrile used in the production example of the compound c-227.

LCMS: m/z 486 $[M+H]^+$

HPLC retention time: 1.72 min (analysis condition G)

Compound s-5

(5-Amino-8-bromo-3-methylcinnolin-6-yl)-[7-fluoro-1-(oxan-2-yl)indazol-4-yl]methanone

[Formula 837]

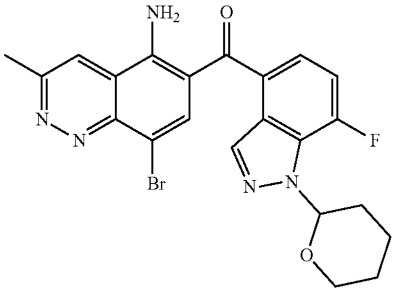

The title compound was synthesized from (5-amino-8-bromo-3-methylcinnolin-6-yl)-[7-fluoro-1-(oxan-2-yl)indazol-4-yl]methanol (compound s-4) under the same conditions as the production example of the compound c-228.

LCMS: m/z 484 $[M+H]^+$

HPLC retention time: 2.05 min (analysis condition G)

Compound s-8

3-Amino-6-bromo-4-[7-fluoro-1-(oxan-2-yl)indazol-4-yl]-9-methyl-1H-pyrido[2,3-f]cinnolin-2-one

[Formula 838]

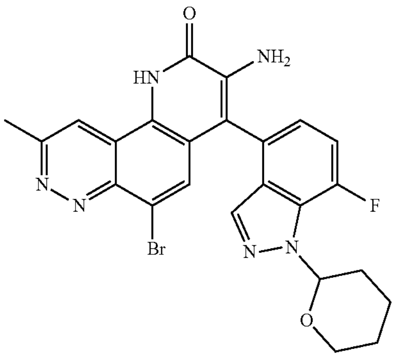

The title compound was synthesized from (5-amino-8-bromo-3-methylcinnolin-6-yl)-[7-fluoro-1-(oxan-2-yl)indazol-4-yl]methanone (compound s-5) under the same conditions as the production examples of the compounds c-9, c-10, and c-13, except that DIPEA and DCM were used instead of N,N-dimethylaniline and DMA used in the production example of the compound c-9.

LCMS: m/z 523 $[M+H]^+$

HPLC retention time: 1.83 min (analysis condition G)

Compound S1

3-Amino-6-bromo-4-(7-fluoro-1H-indazol-4-yl)-9-methyl-1H-pyrido[2,3-f]cinnolin-2-one

[Formula 839]

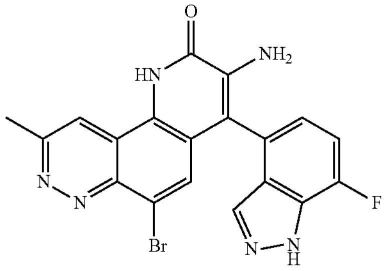

The title compound was synthesized from 3-amino-6-bromo-4-[7-fluoro-1-(oxan-2-yl)indazol-4-yl]-9-methyl-1H-pyrido[2,3-f]cinnolin-2-one (compound s-8) under the same conditions as the production example of the compound B48.

LCMS: m/z 439 $[M+H]^+$

HPLC retention time: 1.36 min (analysis condition G)

Compound t-1

8-Bromo-2-methoxyquinolin-5-amine

[Formula 840]

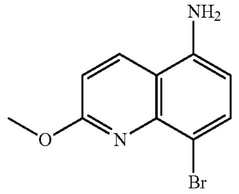

The title compound was synthesized from 2-methoxyquinolin-5-amine under the same conditions as the production example of the compound b-100, except that THF was used instead of DMF used in the production example of the compound b-100.

LCMS: m/z 253 $[M+H]^+$

HPLC retention time: 0.74 min (analysis condition A)

Compound t-3

(E)-N'-(8-bromo-6-iodo-2-methoxyquinolin-5-yl)-N,N-dimethylmethanimidamide

[Formula 841]

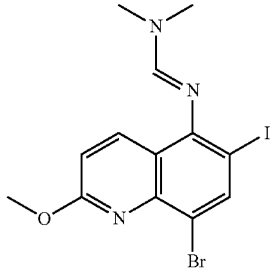

The title compound was synthesized from 8-bromo-2-methoxyquinolin-5-amine (compound t-1) under the same conditions as the production examples of the compounds c-246 and c-247.

LCMS: m/z 434 $[M+H]^+$

HPLC retention time: 0.56 min (analysis condition A)

Compound t-4

(E)-N'-[8-bromo-6-[7-fluoro-2-(oxan-2-yl)indazole-4-carbonyl]-2-methoxyquinolin-5-yl]-N,N-dimethylmethanimidamide

[Formula 842]

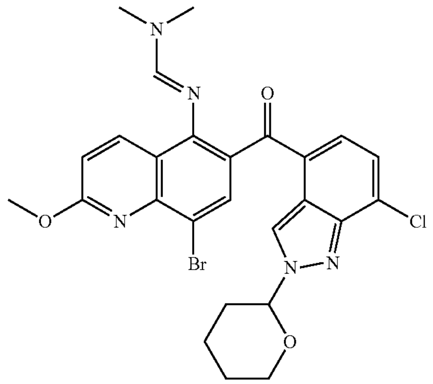

The title compound was synthesized from (E)-N'-(8-bromo-6-iodo-2-methoxyquinolin-5-yl)-N,N-dimethylmethanimidamide (compound t-3) under the same conditions as the production example of the compound b-26, except that toluene was used instead of THE used in the production example of the compound b-26.

LCMS: m/z 554 $[M+H]^+$

HPLC retention time: 0.75 min (analysis condition A)

Compound t-5

(5-Amino-8-bromo-2-methoxyquinolin-6-yl)-[7-fluoro-2-(oxan-2-yl)indazol-4-yl]methanone

[Formula 843]

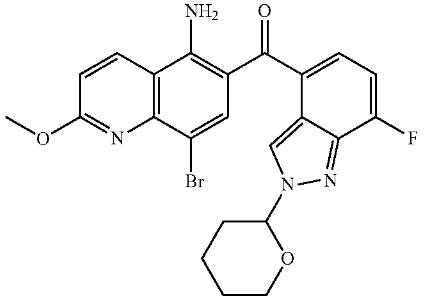

The title compound was synthesized from (E)-N'-[8-bromo-6-[7-fluoro-2-(oxan-2-yl)indazole-4-carbonyl]-2-methoxyquinolin-5-yl]-N,N-dimethylmethanimidamide (compound t-4) under the same conditions as the production example of the compound b-27.

LCMS: m/z 499 $[M+H]^+$

HPLC retention time: 1.02 min (analysis condition A)

Compound t-8

3-Amino-6-bromo-4-[7-fluoro-2-(oxan-2-yl)indazol-4-yl]-8-methoxy-1H-1,7-phenanthrolin-2-one

[Formula 844]

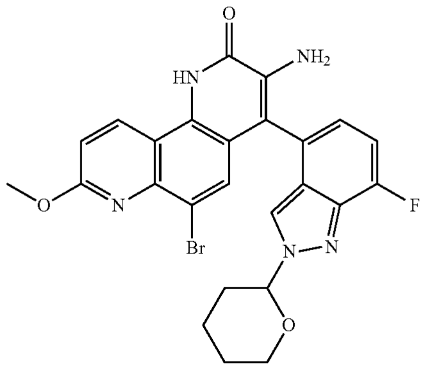

The title compound was synthesized from (5-amino-8-bromo-2-methoxyquinolin-6-yl)-[7-fluoro-2-(oxan-2-yl)indazol-4-yl]methanone (compound t-5) under the same conditions as the production examples of the compounds c-9, c-10, and c-13.

LCMS: m/z 538 [M+H]$^+$

HPLC retention time: 0.91 min (analysis condition A)

Compound t-9

6-Bromo-4-[7-fluoro-2-(oxan-2-yl)indazol-4-yl]-8-methoxy-2-[(4-methoxyphenyl)methoxy]-1,7-phenanthrolin-3-amine

[Formula 845]

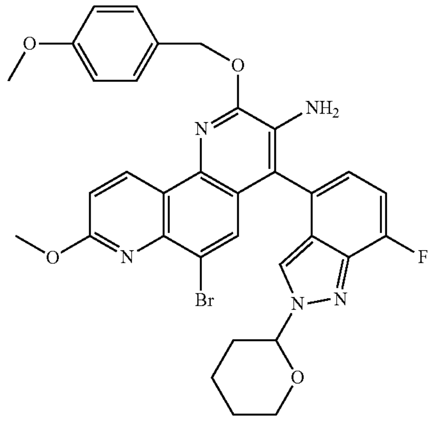

The title compound was synthesized from 3-amino-6-bromo-4-[7-fluoro-2-(oxan-2-yl)indazol-4-yl]-8-methoxy-1H-1,7-phenanthrolin-2-one (compound t-8) under the same conditions as the production example of the compound c-14.

LCMS: m/z 658 [M+H]$^+$

HPLC retention time: 1.22 min (analysis condition A)

Compound t-10

3-Amino-4-[7-fluoro-2-(oxan-2-yl)indazol-4-yl]-8-methoxy-2-[(4-methoxyphenyl)methoxy]-1,7-phenanthrolin-6-ol

[Formula 846]

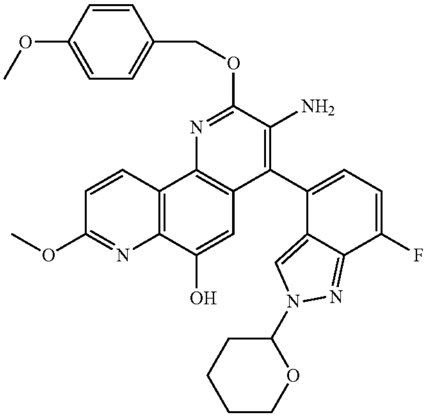

The title compound was synthesized from 6-bromo-4-[7-fluoro-2-(oxan-2-yl)indazol-4-yl]-8-methoxy-2-[(4-methoxyphenyl)methoxy]-1,7-phenanthrolin-3-amine (compound t-9) under the same conditions as the production example of the compound c-15.

LCMS: m/z 596.5 [M+H]$^+$

HPLC retention time: 1.09 min (analysis condition A)

Compound T1

3-Amino-4-(7-fluoro-1H-indazol-4-yl)-6,8-dimethoxy-1H-1,7-phenanthrolin-2-one

[Formula 847]

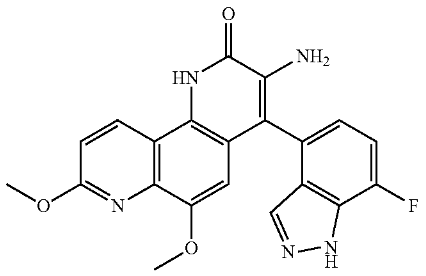

The title compound was synthesized from 3-amino-4-[7-fluoro-2-(oxan-2-yl)indazol-4-yl]-8-methoxy-2-[(4-methoxyphenyl)methoxy]-1,7-phenanthrolin-6-ol (compound t-10) under the same conditions as the production examples of the compounds c-16 and C4, except that anisole was used instead of triethylsilane used in the production example of C4.

LCMS: m/z 406.5 [M+H]$^+$

HPLC retention time: 0.56 min (analysis condition A)

Compound T4

3-Amino-4-(7-fluoro-1H-indazol-4-yl)-6-methoxy-1,7-dihydro-1,7-phenanthroline-2,8-dione

[Formula 848]

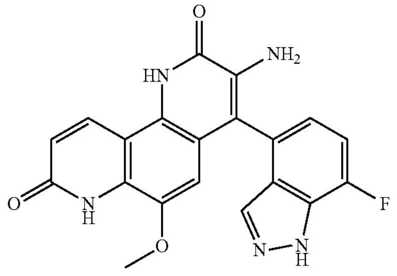

The title compound was synthesized from 3-amino-4-(7-fluoro-1H-indazol-4-yl)-6,8-dimethoxy-1H-1,7-phenanthrolin-2-one (compound T1) under the same conditions as the production example of the compound C184, except that EtOH (20 v/w) was used, in addition to the conditions of the production example of the compound C184.

LCMS: m/z 392.5 $[M+H]^+$

HPLC retention time: 0.44 min (analysis condition A)

Compound T2

3-Amino-4-(7-fluoro-1H-indazol-4-yl)-8-methoxy-6-propan-2-yloxy-1H-1,7-phenanthrolin-2-one

[Formula 849]

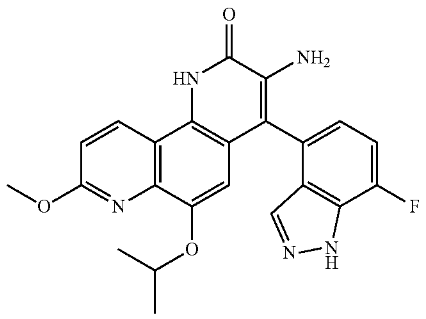

The title compound was synthesized from 3-amino-4-[7-fluoro-2-(oxan-2-yl)indazol-4-yl]-8-methoxy-2-[(4-methoxyphenyl)methoxy]-1,7-phenanthrolin-6-ol (compound t-10) under the same conditions as the production examples of the compounds c-16 and C4, except that 2-propanol and anisole were respectively used instead of MeOH and triethylsilane used in the production examples of c-16 and C4.

LCMS: m/z 434.5 $[M+H]^+$

HPLC retention time: 0.68 min (analysis condition A)

Compound T5

3-Amino-4-(7-fluoro-1H-indazol-4-yl)-6-propan-2-yloxy-1,7-dihydro-1,7-phenanthroline-2,8-dione

[Formula 850]

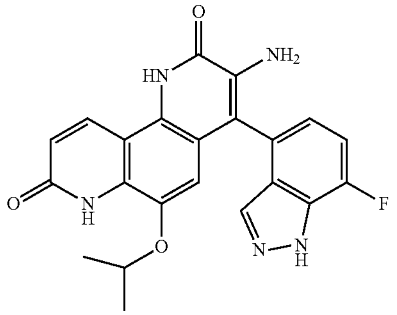

The title compound was synthesized from 3-amino-4-(7-fluoro-1H-indazol-4-yl)-8-methoxy-6-propan-2-yloxy-1H-1,7-phenanthrolin-2-one (compound T2) under the same conditions as the production example of the compound C184, except that EtOH (20 v/w) was used, in addition to the conditions of the production example of the compound C184.

LCMS: m/z 420.5 $[M+H]^+$

HPLC retention time: 0.51 min (analysis condition A)

Compound T3

3-Amino-6-ethoxy-4-(7-fluoro-1H-indazol-4-yl)-8-methoxy-1H-1,7-phenanthrolin-2-one

[Formula 851]

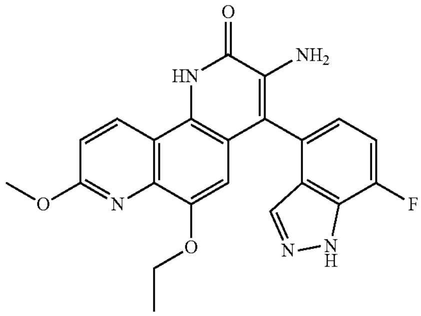

The title compound was synthesized from 3-amino-4-[7-fluoro-2-(oxan-2-yl)indazol-4-yl]-8-methoxy-2-[(4-methoxyphenyl)methoxy]-1,7-phenanthrolin-6-ol (compound t-10) under the same conditions as the production examples of the compounds c-16 and C4, except that EtOH and anisole were respectively used instead of MeOH and triethylsilane used in the production examples of c-16 and C4.

LCMS: m/z 420.5 $[M+H]^+$

HPLC retention time: 0.62 min (analysis condition A)

Compound T6

3-Amino-6-ethoxy-4-(7-fluoro-1H-indazol-4-yl)-1,7-dihydro-1,7-phenanthroline-2,8-dione

[Formula 852]

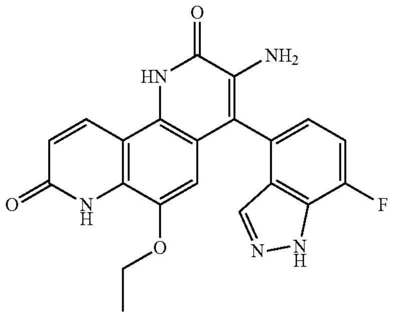

The title compound was synthesized from 3-amino-6-ethoxy-4-(7-fluoro-1H-indazol-4-yl)-8-methoxy-1H-1,7-phenanthrolin-2-one (compound T3) under the same conditions as the production example of the compound C184, except that EtOH (20 v/w) was used, in addition to the conditions of the production example of the compound C184.

LCMS: m/z 406.5 $[M+H]^+$

HPLC retention time: 0.48 min (analysis condition A)

Compound c-263

3-Amino-4-[7-fluoro-2-(oxan-2-yl)indazol-4-yl]-6-methoxy-1H-1,7-phenanthrolin-2-one

[Formula 853]

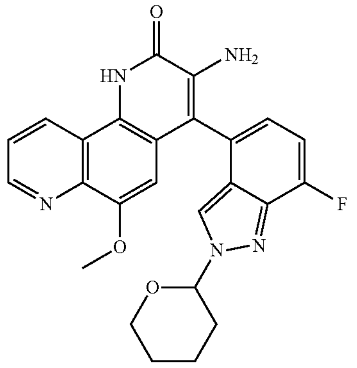

A solution of 3-amino-6-bromo-4-[7-fluoro-2-(oxan-2-yl)indazol-4-yl]-1H-1,7-phenanthrolin-2-one (compound c-13, 27.97 g, 55 mmol) in DMA (367 mL) in a reaction vessel was cooled to 0° C., sodium methoxide (14.86 g, 275 mmol) and tBuBrettPhos Pd G3 (4.7 g, 5.5 mmol) were added thereto, and then the reaction mixture was stirred for 5.5 hours. To the reaction mixture, an 18% aqueous ammonium chloride solution (82 mL) was added over 12 min, and the mixture was stirred for 5 min. To the reaction mixture, N-acetylcysteine (4.49 g, 27.5 mmol) and water (560 mL) were further added, and then the mixture was stirred at room temperature for 20 min. The produced solid was collected by filtration and washed with water (280 mL) and a mixed solution (280 mL) of cyclopentylmethyl ether/water (1/10) to obtain the crude product (36.8 g) of the compound c-263 as a light brown solid.

LCMS: m/z 460 $[M+H]^+$

HPLC retention time: 1.25 min (analysis condition D)

Compound C4

3-Amino-4-(7-fluoro-1H-indazol-4-yl)-6-methoxy-1H-1,7-phenanthrolin-2-one

[Formula 854]

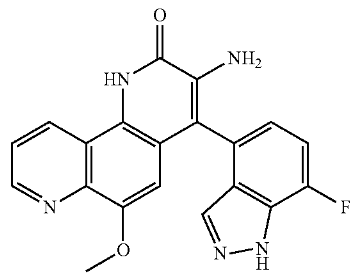

To the crude product of 3-amino-4-[7-fluoro-2-(oxan-2-yl)indazol-4-yl]-6-methoxy-1H-1,7-phenanthrolin-2-one (compound c-263) in a reaction vessel, TFE (455 mL) and water (51 mL) were added. To the reaction mixture, triisopropylsilane (90 mL, 440 mmol) and trimethylsilyl chloride (34.9 mL, 275 mmol) were added, and the mixture was stirred at room temperature for 18 hours. To the reaction mixture, trimethylsilyl chloride (6.97 mL, 55 mmol) was added, and the mixture was further stirred at room temperature for 27 hours. To the reaction mixture, a 5% aqueous sodium bicarbonate solution (595 mL) was added, and the produced solid was collected by filtration. The solid was washed with water (51 mL) and hexane (253 mL). To the obtained solid, DMSO (152 mL) was added, and then a 5% aqueous sodium bicarbonate solution (25.3 mL) and water (278 mL) was added thereto. The produced solid was collected by filtration, and sequentially washed with water (126 mL), a mixed solution (177 mL) of EtOH/water (1/3), and a mixed solution (253 mL) of EtOH/hexane (1/1). The obtained solid was dried to obtain the title compound (14.2 g, yield 69%) as a pale yellow solid.

LCMS: m/z 376.5 $[M+H]^+$

HPLC retention time: 0.38 min (analysis condition A)

Compound c-282

8-Bromo-7-methylquinolin-5-amine

[Formula 855]

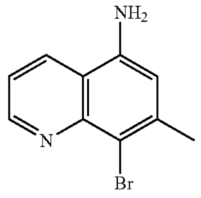

The title compound was synthesized from 7-methylquinolin-5-amine under the same conditions as in the production example of compound b-100, except that THF was used instead of DMF used in the production example of compound b-100.

LCMS: m/z 237 $[M+H]^+$

HPLC retention time: 3.35 min (analysis condition Z)

Compound c-283

8-Bromo-6-iodo-7-methylquinolin-5-amine

[Formula 856]

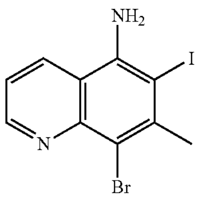

The title compound was synthesized from 8-bromo-7-methylquinolin-5-amine (compound c-282) under the same conditions as in the production example of compound c-1.

LCMS: m/z 363 $[M+H]^+$

HPLC retention time: 2.94 min (analysis condition J)

Compound c-284

N'-(8-Bromo-6-iodo-7-methylquinolin-5-yl)-N,N-dimethylmethanimidamide

[Formula 857]

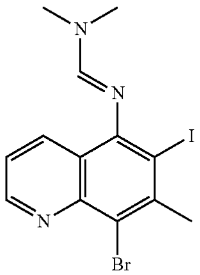

The title compound was synthesized from 8-bromo-6-iodo-7-methylquinolin-5-amine (compound c-283) under the same conditions as in the production example of compound b-25.

LCMS: m/z 418 $[M+H]^+$

HPLC retention time: 2.52 min (analysis condition J)

Compound c-285

N'-[8-Bromo-6-[6,7-difluoro-1-(oxan-2-yl)indazole-4-carbonyl]-7-methylquinolin-5-yl]-N,N-dimethylmethanimidamide

[Formula 858]

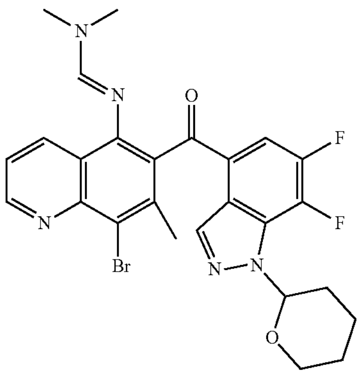

The title compound was synthesized from N'-(8-bromo-6-iodo-7-methylquinolin-5-yl)-N,N-dimethylmethanimidamide (compound c-284) under the same conditions as in the production example of compound b-26, except that toluene and 6,7-difluoro-N-methoxy-N-methyl-1-(oxan-2-yl)indazole-4-carboxamide (compound c-102) were used instead of THF and 7-fluoro-N-methoxy-N-methyl-2-(oxan-2-yl)indazole-4-carboxamide (compound b-25), respectively, used in the production example of compound b-26.

LCMS: m/z 556 $[M+H]^+$

HPLC retention time: 3.68 min (analysis condition J)

Compound c-286

(5-Amino-8-bromo-7-methylquinolin-6-yl)-(6,7-difluoro-1H-indazol-4-yl) methanone

[Formula 859]

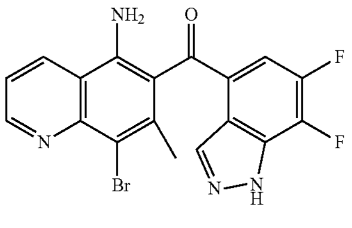

To a solution of N'-[8-bromo-6-[6,7-difluoro-1-(oxan-2-yl)indazole-4-carbonyl]-7-methylquinolin-5-yl]-N,N-dimethylmethanimidamide (compound c-285, 417 mg, 0.749 mmol) in ethanol (8 mL) in a reaction container, zinc chloride (1.53 g, 11.2 mmol) was added at room temperature, and the mixture was stirred at 80° C. for 3 hours and then stirred at 100° C. for 17 hours. The reaction mixture was cooled to room temperature, combined with other lots, and then concentrated under reduced pressure. To the obtained residue, a saturated aqueous solution of sodium bicarbonate and water were added, followed by extraction with ethyl acetate. The aqueous layer was further subjected to extraction with ethyl acetate twice. The obtained organic layers were each washed with saturated saline, then combined, and dried over anhydrous sodium sulfate, and the desiccant was filtered our followed by concentration under reduced pressure. To the obtained residue, ethyl acetate (1.6 mL) was added, and a solid was collected by filtration. The obtained solid was washed twice with ethyl acetate (0.8 mL) to obtain the title compound (121 mg) as a yellow solid.

LCMS: m/z 417 $[M+H]^+$

HPLC retention time: 2.98 min (analysis condition J)

Compound c-287

N-[8-Bromo-6-(6,7-difluoro-1H-indazole-4-carbonyl)-7-methylquinolin-5-yl]-2-chloroacetamide

[Formula 860]

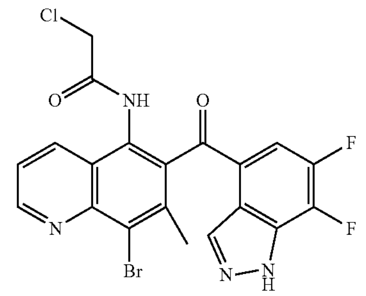

A solution of (5-amino-8-bromo-7-methylquinolin-6-yl)-(6,7-difluoro-1H-indazol-4-yl) methanone (compound c-286, 251 mg, 0.601 mmol) in DMA (4 mL) in a reaction container was cooled to 0° C. Chloroacetyl chloride (72 μL, 0.9 mmol) was added thereto, and the mixture was stirred at room temperature for 50 minutes. Chloroacetyl chloride (36 μL, 0.45 mmol) was added thereto, and the mixture was further stirred at room temperature for 30 minutes to obtain a solution of the title compound in DMA.

LCMS: m/z 493 $[M+H]^+$

HPLC retention time: 3.43 min (analysis condition J)

Compound c-288

6-Bromo-4-(6,7-difluoro-1H-indazol-4-yl)-5-methyl-3-pyridin-1-ium-1-yl-1H-1,7-phenanthrolin-2-one; chloride

[Formula 861]

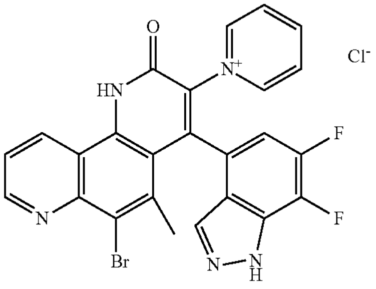

To a solution of N-[8-bromo-6-(6,7-difluoro-1H-indazole-4-carbonyl)-7-methylquinolin-5-yl]-2-chloroacetamide (compound c-287) in DMA in a reaction container, pyridine (2.51 mL) was added, and the mixture was stirred at 60° C. for 4 hours and then cooled to room temperature to obtain a suspension of the title compound in DMA/pyridine.

LCMS: m/z 518 $[M]^+$

HPLC retention time: 2.70 min (analysis condition J)

Compound c-289

3-Amino-6-bromo-4-(6,7-difluoro-1H-indazol-4-yl)-5-methyl-1H-1,7-phenanthrolin-2-one

[Formula 862]

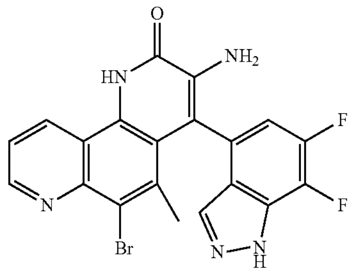

To a suspension of 6-bromo-4-(6,7-difluoro-1H-indazol-4-yl)-5-methyl-3-pyridin-1-ium-1-yl-1H-1,7-phenanthrolin-2-one; chloride (compound c-288) in DMA/pyridine in a reaction container, hydrazine monohydrate (79% aqueous solution) (370 μL, 6.0 mmol) was added, and the mixture was then stirred at 60° C. for 1 hour. The reaction mixture was cooled to room temperature. Water (6 mL) was added thereto, and the mixture was further stirred for 40 minutes. Water (12 mL) was further added thereto, and a solid was collected by filtration and washed twice with water (6 mL). The obtained solid was purified by reverse-phase column chromatography (0.1% aqueous FA solution/0.1% solution of FA in acetonitrile). Fractions containing the title compound were combined and freeze-dried to obtain the title compound (137.8 mg) as yellow-brown solid.

LCMS: m/z 456 $[M+H]^+$

HPLC retention time: 3.09 min (analysis condition J)

Compound C216

3-Amino-4-(6,7-difluoro-1H-indazol-4-yl)-5,6-dimethyl-1H-1,7-phenanthrolin-2-one

[Formula 863]

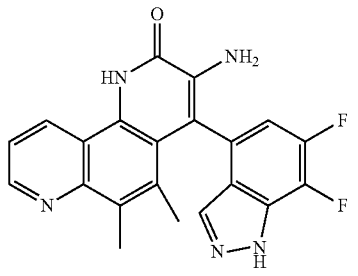

The title compound was synthesized from 3-amino-6-bromo-4-(6,7-difluoro-1H-indazol-4-yl)-5-methyl-1H-1,7-phenanthrolin-2-one (compound c-289) under the same conditions as in the production example of compound B22, except that XPhos Pd G4 and a 2 M solution of methylzinc chloride in THF were used instead of CPhos Pd G3 and a 0.5 M solution of cyclopropylzinc bromide in THF, respectively, used in the production example of compound B22.

LCMS: m/z 392 $[M+H]^+$

HPLC retention time: 0.55 min (analysis condition A)

Compound C217

3-Amino-6-cyclopropyl-4-(6,7-difluoro-1H-indazol-4-yl)-5-methyl-1H-1,7-phenanthrolin-2-one

[Formula 864]

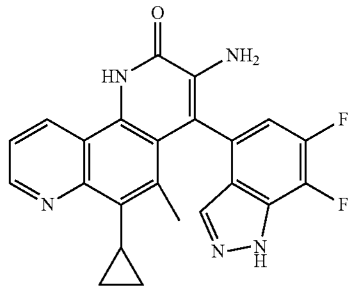

The title compound was synthesized from 3-amino-6-bromo-4-(6,7-difluoro-1H-indazol-4-yl)-5-methyl-1H-1,7-phenanthrolin-2-one (compound c-289) under the same conditions as in the production example of compound B22.

LCMS: m/z 418 $[M+H]^+$

HPLC retention time: 0.48 min (analysis condition A)

Compound C218

3-Amino-4-(6,7-difluoro-1H-indazol-4-yl)-5-methyl-1H-1,7-phenanthrolin-2-one

[Formula 865]

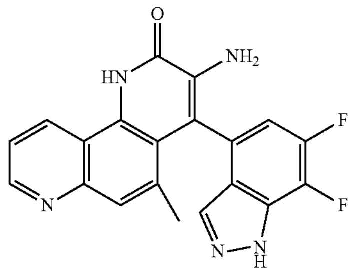

The title compound was synthesized from 3-amino-6-bromo-4-(6,7-difluoro-1H-indazol-4-yl)-5-methyl-1H-1,7-phenanthrolin-2-one (compound c-289) under the same conditions as in the production example of compound B22.

LCMS: m/z 378 $[M+H]^+$

HPLC retention time: 0.47 min (analysis condition A)

Compound c-290

8-Bromo-7-fluoroquinolin-5-amine

[Formula 866]

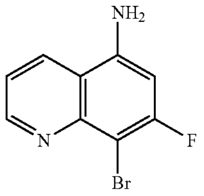

The title compound was synthesized from 7-fluoroquinolin-5-amine under the same conditions as in the production example of compound b-100, except that THF was used instead of DMF used in the production example of compound b-100.

LCMS: m/z 241 $[M+H]^+$

HPLC retention time: 3.43 min (analysis condition Z)

Compound c-291

8-Bromo-7-fluoro-6-iodoquinolin-5-amine

[Formula 867]

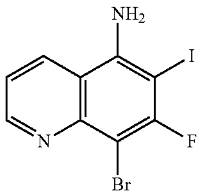

The title compound was synthesized from 8-bromo-7-fluoroquinolin-5-amine (compound c-290) under the same conditions as in the production example of compound c-1.

LCMS: m/z 367 $[M+H]^+$

HPLC retention time: 3.42 min (analysis condition J)

Compound c-292

N'-(8-Bromo-7-fluoro-6-iodoquinolin-5-yl)-N,N-dimethylmethanimidamide

[Formula 868]

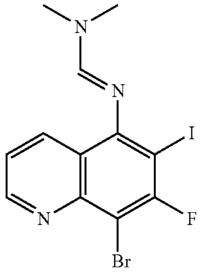

The title compound was synthesized from 8-bromo-7-fluoro-6-iodoquinolin-5-amine (compound c-291) under the same conditions as in the production example of compound b-25.

LCMS: m/z 422 $[M+H]^+$

HPLC retention time: 2.48 min (analysis condition J)

Compound c-293

N'-[8-Bromo-6-[6,7-difluoro-1-(oxan-2-yl)indazole-4-carbonyl]-7-fluoroquinolin-5-yl]-N,N-dimethyl-methanimidamide

[Formula 869]

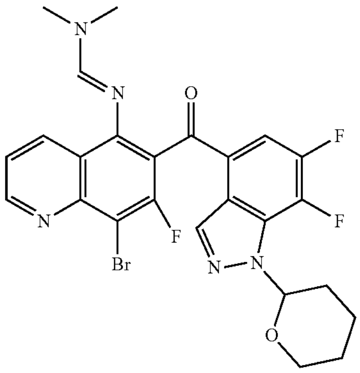

The title compound was synthesized from N'-(8-bromo-7-fluoro-6-iodoquinolin-5-yl)-N,N-dimethylmethanimidamide (compound c-292) under the same conditions as in the production example of compound b-26. Toluene and 6,7-difluoro-N-methoxy-N-methyl-1-(oxan-2-yl)indazole-4-carboxamide (compound c-102) were used instead of THF and 7-fluoro-N-methoxy-N-methyl-2-(oxan-2-yl)indazole-4-carboxamide (compound b-25), respectively, used in the production example of compound b-26.

LCMS: m/z 560 $[M+H]^+$

HPLC retention time: 4.13 min (analysis condition J)

Compound c-294

(5-Amino-8-bromo-7-fluoroquinolin-6-yl)-[6,7-difluoro-1-(oxan-2-yl)indazol-4-yl]methanone

[Formula 870]

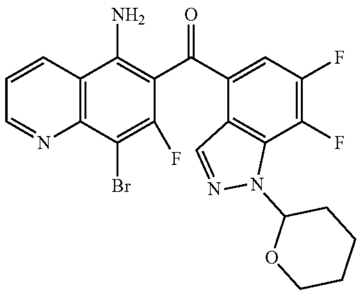

The title compound was obtained from N'-[8-bromo-6-[6,7-difluoro-1-(oxan-2-yl)indazole-4-carbonyl]-7-fluoroquinolin-5-yl]-N,N-dimethylmethanimidamide (compound c-293) under the same conditions as in compound c-286, except that reaction was performed by the addition of 20 equivalents of pyridine to the starting material.

LCMS: m/z 505 $[M+H]^+$

HPLC retention time: 4.88 min (analysis condition J)

Compound c-297

3-Amino-6-bromo-4-[6,7-difluoro-1-(oxan-2-yl)indazol-4-yl]-5-fluoro-1H-1,7-phenanthrolin-2-one

[Formula 871]

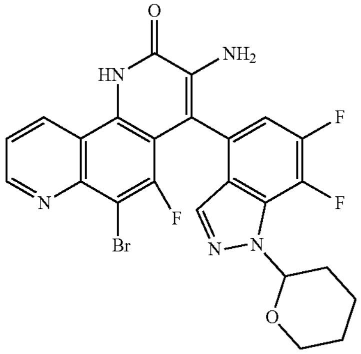

The title compound was synthesized from (5-amino-8-bromo-7-fluoroquinolin-6-yl)-[6,7-difluoro-1-(oxan-2-yl)indazol-4-yl]methanone (compound c-294) under the same conditions as in the production examples of compounds c-9, c-10, and c-13, except that reaction was performed without the use of N,N-dimethylaniline used in the production example of compound c-9.

LCMS: m/z 544 $[M+H]^+$

HPLC retention time: 4.40 min (analysis condition J)

Compound c-298

3-Amino-4-[6,7-difluoro-1-(oxan-2-yl)indazol-4-yl]-5-fluoro-6-methyl-1H-1,7-phenanthrolin-2-one

[Formula 872]

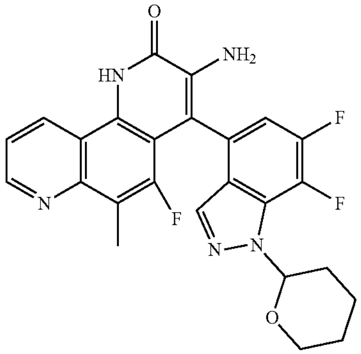

The title compound was synthesized from 3-amino-6-bromo-4-[6,7-difluoro-1-(oxan-2-yl)indazol-4-yl]-5-fluoro-1H-1,7-phenanthrolin-2-one (compound c-297) under the same conditions as in the production example of compound B22, except that XPhos Pd G4 and a 2 M solution of methylzinc chloride in THF were used instead of CPhos Pd G3 and a 0.5 M solution of cyclopropylzinc bromide in THF, respectively, used in the production example of compound B22.

LCMS: m/z 480 $[M+H]^+$

HPLC retention time: 3.76 min (analysis condition J)

Compound c-299

3-Amino-6-cyclopropyl-4-[6,7-difluoro-1-(oxan-2-yl)indazol-4-yl]-5-fluoro-1H-1,7-phenanthrolin-2-one

[Formula 873]

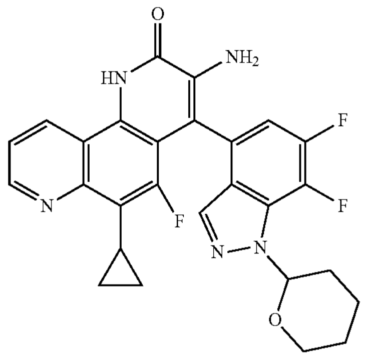

The title compound was synthesized from 3-amino-6-bromo-4-[6,7-difluoro-1-(oxan-2-yl)indazol-4-yl]-5-fluoro-1H-1,7-phenanthrolin-2-one (compound c-297) under the same conditions as in the production example of compound B22.

LCMS: m/z 506 $[M+H]^+$

HPLC retention time: 3.48 min (analysis condition J)

Compound c-300

3-Amino-4-[6,7-difluoro-1-(oxan-2-yl)indazol-4-yl]-5-fluoro-1H-1,7-phenanthrolin-2-one

[Formula 874]

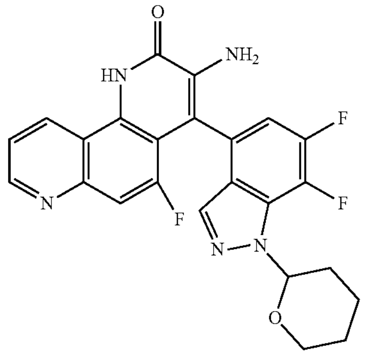

The title compound was synthesized from 3-amino-6-bromo-4-[6,7-difluoro-1-(oxan-2-yl)indazol-4-yl]-5-fluoro-1H-1,7-phenanthrolin-2-one (compound c-297) under the same conditions as in the production example of compound B11, except that tBuXPhos Pd G3 was used instead of Xantphos Pd G4 used in the production example of compound B11.

LCMS: m/z 466 $[M+H]^+$

HPLC retention time: 3.28 min (analysis condition J)

Compound C219

3-Amino-4-(6,7-difluoro-1H-indazol-4-yl)-5-fluoro-6-methyl-1H-1,7-phenanthrolin-2-one

[Formula 875]

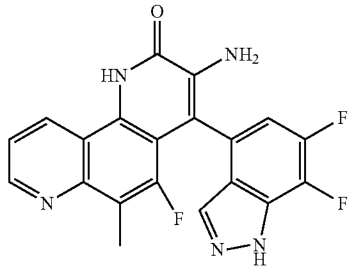

The title compound was synthesized from 3-amino-4-[6,7-difluoro-1-(oxan-2-yl)indazol-4-yl]-5-fluoro-6-methyl-1H-1,7-phenanthrolin-2-one (compound c-298) under the same conditions as in the production example of compound C4, except that anisole was used instead of triethylsilane used in the production example of compound C4.

LCMS: m/z 396 $[M+H]^+$

HPLC retention time: 0.62 min (analysis condition A)

Compound C220

3-Amino-6-cyclopropyl-4-(6,7-difluoro-1H-indazol-4-yl)-5-fluoro-1H-1,7-phenanthrolin-2-one

[Formula 876]

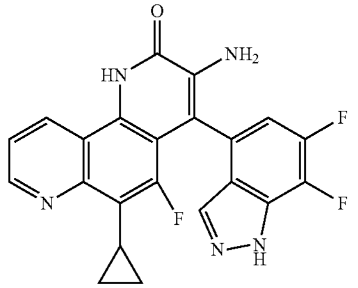

The title compound was synthesized from 3-amino-6-cyclopropyl-4-[6,7-difluoro-1-(oxan-2-yl)indazol-4-yl]-5-fluoro-1H-1,7-phenanthrolin-2-one (compound c-299) under the same conditions as in the production example of compound C4, except that anisole was used instead of triethylsilane used in the production example of compound C4.

LCMS: m/z 422 $[M+H]^+$

HPLC retention time: 0.58 min (analysis condition A)

Compound C221

3-Amino-4-(6,7-difluoro-1H-indazol-4-yl)-5-fluoro-1H-1,7-phenanthrolin-2-one

[Formula 877]

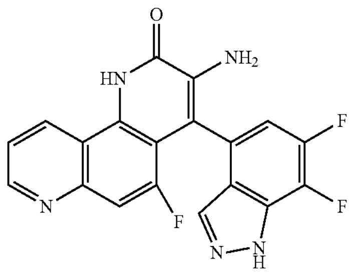

The title compound was synthesized from 3-amino-4-[6,7-difluoro-1-(oxan-2-yl)indazol-4-yl]-5-fluoro-1H-1,7-phenanthrolin-2-one (compound c-300) under the same conditions as in the production example of compound C4, except that anisole was used instead of triethylsilane used in the production example of compound C4.

LCMS: m/z 382 $[M+H]^+$

HPLC retention time: 0.53 min (analysis condition A)

Compound c-301

4-Bromo-5,7-difluoro-1H-indazole

[Formula 878]

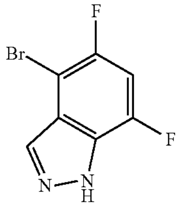

To a solution of 2-bromo-3,5,6-trifluorobenzaldehyde (363 mg, 1.51 mmol) in 1,4-dioxane (10 mL) in a reaction container, hydrazine monohydrate (230 μL, 4.55 mmol) was added, and the mixture was stirred at 120° C. for 4 hours in a sealed tube using a microwave reaction apparatus. The reaction solution was cooled to room temperature, and water was then added thereto, followed by extraction with DCM. The obtained DCM solution was combined with other lots obtained by the same operation as above, and then concentrated. The obtained solid was washed with water to obtain the title compound (218.6 mg).

LCMS: m/z 233 $[M+H]^+$

HPLC retention time: 3.54 min (analysis condition J)

Compound c-302

4-Bromo-5,7-difluoro-1-(oxan-2-yl)indazole

[Formula 879]

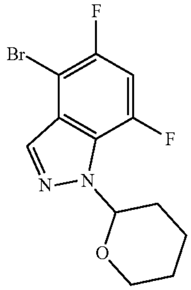

The title compound was synthesized from 4-bromo-5,7-difluoro-1H-indazole (compound c-301) under the same conditions as in the production example of compound c-99.

LCMS: m/z 317 $[M+H]^+$

HPLC retention time: 5.03 min (analysis condition J)

Compound c-303

(2,4,6-Trichlorophenyl) 5,7-difluoro-1-(oxan-2-yl) indazole-4-carboxylate

[Formula 880]

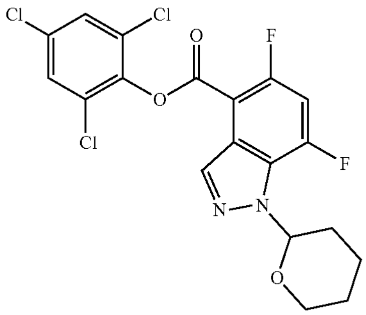

The title compound was synthesized from 4-bromo-5,7-difluoro-1-(oxan-2-yl)indazole (compound c-302) under the same conditions as in the production example of compound c-4.

LCMS: m/z 461 $[M+H]^+$

HPLC retention time: 4.69 min (analysis condition K)

Compound c-304

5,7-Difluoro-1-(oxan-2-yl)indazole-4-carboxylic acid

[Formula 881]

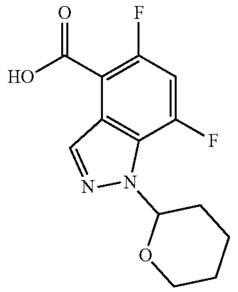

The title compound was synthesized from (2,4,6-trichlorophenyl) 5,7-difluoro-1-(oxan-2-yl)indazole-4-carboxylate (compound c-303) under the same conditions as in the production example of compound c-5, except that reaction was performed under reflux.

LCMS: m/z 283 [M+H]$^+$

HPLC retention time: 3.36 min (analysis condition J)

Compound c-305

5,7-Difluoro-N-methoxy-N-methyl-1-(oxan-2-yl)indazole-4-carboxamide

[Formula 882]

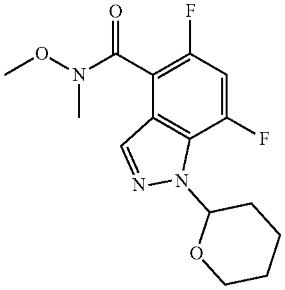

The title compound was synthesized from 5,7-difluoro-1-(oxan-2-yl)indazole-4-carboxylic acid (compound c-304) under the same conditions as in the production example of compound b-2, except that THF was used instead of DMF used in the production example of compound b-2.

LCMS: m/z 326 [M+H]$^+$

HPLC retention time: 3.55 min (analysis condition J)

Compound c-306

N'-[6-[5,7-Difluoro-1-(oxan-2-yl)indazole-4-carbonyl]-8-methylquinolin-5-yl]-N,N-dimethylmethanimidamide

[Formula 883]

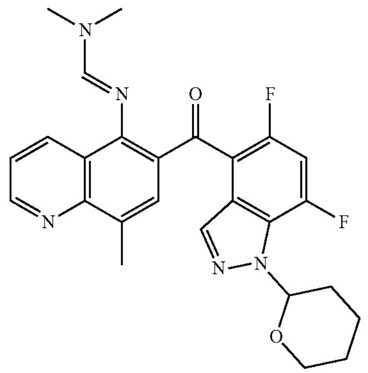

The title compound was synthesized from 5,7-difluoro-N-methoxy-N-methyl-1-(oxan-2-yl)indazole-4-carboxamide (compound c-305) under the same conditions as in the production example of compound b-26, except that toluene and (E)-N'-(6-iodo-8-methylquinolin-5-yl)-N,N-dimethylmethanimidamide (compound c-271) were used instead of THF and (E)-N'-(6-chloro-2,4-diiodonaphthalen-1-yl)-N,N-dimethylmethanimidamide (compound c-6), respectively, used in the production example of compound b-26.

LCMS: m/z 478 [M+H]$^+$

HPLC retention time: 3.19 min (analysis condition J)

Compound c-307

(5-Amino-8-methylquinolin-6-yl)-[5,7-difluoro-1-(oxan-2-yl)indazol-4-yl]methanone

[Formula 884]

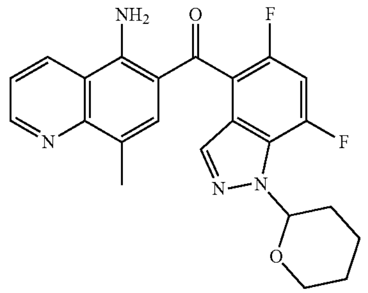

The title compound was obtained from N'-[6-[5,7-difluoro-1-(oxan-2-yl)indazole-4-carbonyl]-8-methylquinolin-5-yl]-N,N-dimethylmethanimidamide (compound c-306) under the same conditions as in compound c-286.

LCMS: m/z 423 [M+H]$^+$

HPLC retention time: 3.48 min (analysis condition J)

Compound c-310

3-Amino-4-[5,7-difluoro-1-(oxan-2-yl)indazol-4-yl]-6-methyl-1H-1,7-phenanthrolin-2-one

[Formula 885]

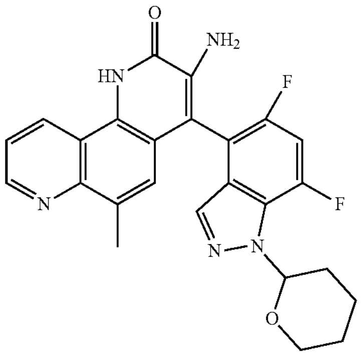

The title compound was synthesized from (5-amino-8-methylquinolin-6-yl)-[5,7-difluoro-1-(oxan-2-yl)indazol-4-yl]methanone (compound c-307) under the same conditions as in the production examples of compounds c-9, c-10, and c-13, except that reaction was performed without the use of N,N-dimethylaniline used in the production example of compound c-9.

LCMS: m/z 462 $[M+H]^+$

HPLC retention time: 3.08 min (analysis condition J)

Compound C222

3-Amino-4-(5,7-difluoro-1H-indazol-4-yl)-6-methyl-1H-1,7-phenanthrolin-2-one

[Formula 886]

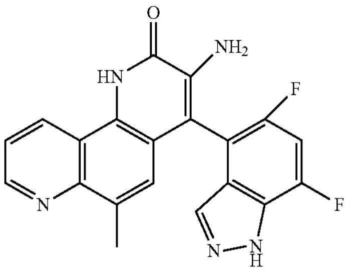

The title compound was synthesized from 3-amino-4-[5,7-difluoro-1-(oxan-2-yl)indazol-4-yl]-6-methyl-1H-1,7-phenanthrolin-2-one (compound c-310) under the same conditions as in the production example of compound C4, except that anisole was used instead of triethylsilane used in the production example of compound C4.

LCMS: m/z 378 $[M+H]^+$

HPLC retention time: 0.53 min (analysis condition A)

Compound c-311

1-(Oxan-2-yl)pyrazolo[4,3-c]pyridine-4-carboxylic acid

[Formula 887]

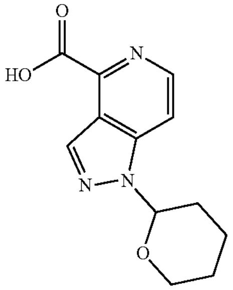

The title compound was synthesized from pyrazolo[4,3-c]pyridine-4-carboxylic acid under the same conditions as in the production example of compound c-99.

LCMS: m/z 248 $[M+H]^+$

HPLC retention time: 2.98 min (analysis condition Z)

Compound c-312

N-Methoxy-N-methyl-1-(oxan-2-yl)pyrazolo[4,3-c]pyridine-4-carboxamide

[Formula 888]

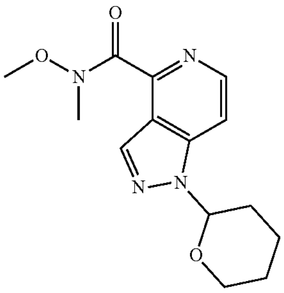

The title compound was synthesized from 1-(oxan-2-yl)pyrazolo[4,3-c]pyridine-4-carboxylic acid (compound c-311) under the same conditions as in the production example of compound b-2, except that THF was used instead of DMF used in the production example of compound b-2.

LCMS: m/z 291 $[M+H]^+$

HPLC retention time: 2.53 min (analysis condition J)

Compound c-313

N,N-Dimethyl-N'-[8-methyl-6-[1-(oxan-2-yl)pyrazolo[4,3-c]pyridine-4-carbonyl]quinolin-5-yl]methanimidamide

[Formula 889]

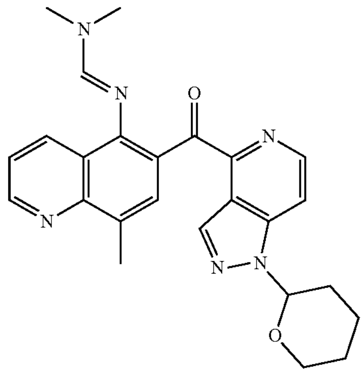

The title compound was synthesized from N-methoxy-N-methyl-1-(oxan-2-yl)pyrazolo[4,3-c]pyridine-4-carboxamide (compound c-312) under the same conditions as in the production example of compound b-26, except that toluene and (E)-N'-(6-iodo-8-methylquinolin-5-yl)-N,N-dimethylmethanimidamide (compound c-271) were used instead of THF and (E)-N'-(6-chloro-2,4-diiodonaphthalen-1-yl)-N,N-dimethylmethanimidamide (compound c-6), respectively, used in the production example of compound b-26.

LCMS: m/z 443 $[M+H]^+$

HPLC retention time: 2.77 min (analysis condition J)

Compound c-314

(5-Amino-8-methylquinolin-6-yl)-[1-(oxan-2-yl)pyrazolo[4,3-c]pyridin-4-yl]methanone

[Formula 890]

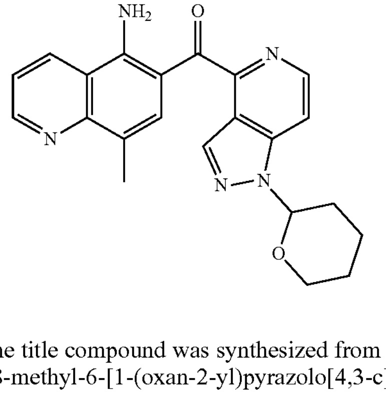

The title compound was synthesized from N,N-dimethyl-N'-[8-methyl-6-[1-(oxan-2-yl)pyrazolo[4,3-c]pyridine-4-carbonyl]quinolin-5-yl]methanimidamide (compound c-313) under the same conditions as in the production example of compound b-27.

LCMS: m/z 388 $[M+H]^+$

HPLC retention time: 2.69 min (analysis condition J)

Compound c-317

3-Amino-6-methyl-4-[1-(oxan-2-yl)pyrazolo[4,3-c]pyridin-4-yl]-1H-1,7-phenanthrolin-2-one

[Formula 891]

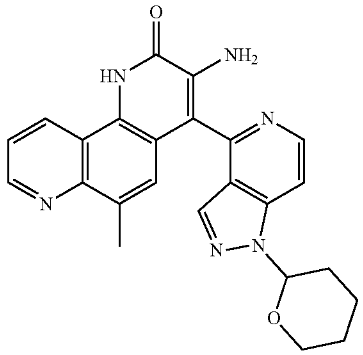

The title compound was synthesized from (5-amino-8-methylquinolin-6-yl)-[1-(oxan-2-yl)pyrazolo[4,3-c]pyridin-4-yl]methanone (compound c-314) under the same conditions as in the production examples of compounds c-9, c-10, and c-13, except that reaction was performed without the use of N,N-dimethylaniline used in the production example of compound c-9.

LCMS: m/z 427 $[M+H]^+$

HPLC retention time: 2.41 min (analysis condition J)

Compound C223

3-Amino-6-methyl-4-(1H-pyrazolo[4,3-c]pyridin-4-yl)-1H-1,7-phenanthrolin-2-one

[Formula 892]

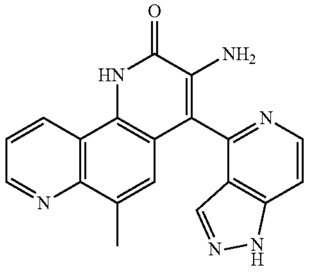

The title compound was synthesized from 3-amino-6-methyl-4-[1-(oxan-2-yl)pyrazolo[4,3-c]pyridin-4-yl]-1H-1,7-phenanthrolin-2-one (compound c-317) under the same conditions as in the production example of compound C4, except that anisole was used instead of triethylsilane used in the production example of compound C4.

LCMS: m/z 343 $[M+H]^+$

HPLC retention time: 0.33 min (analysis condition A)

Compound c-318

1-(Oxan-2-yl)benzotriazole-4-carboxylic acid

[Formula 893]

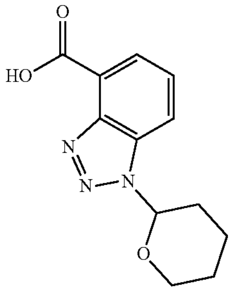

The title compound was synthesized from benzotriazole-4-carboxylic acid under the same conditions as in the production example of compound c-99.

LCMS: m/z 248 $[M+H]^+$

HPLC retention time: 2.66 min (analysis condition J)

Compound c-319

N-Methoxy-N-methyl-1-(oxan-2-yl)benzotriazole-4-carboxamide

[Formula 894]

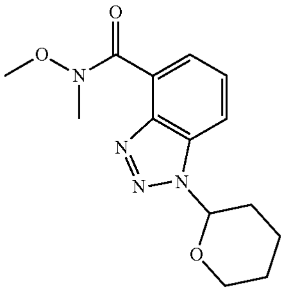

The title compound was synthesized from 1-(oxan-2-yl) benzotriazole-4-carboxylic acid (compound c-318) under the same conditions as in the production example of compound b-2, except that THF was used instead of DMF used in the production example of compound b-2.

LCMS: m/z 291 $[M+H]^+$

HPLC retention time: 2.82 min (analysis condition J)

Compound c-320

N,N-Dimethyl-N'-[8-methyl-6-[1-(oxan-2-yl)benzotriazole-4-carbonyl]quinolin-5-yl]methanimidamide

[Formula 895]

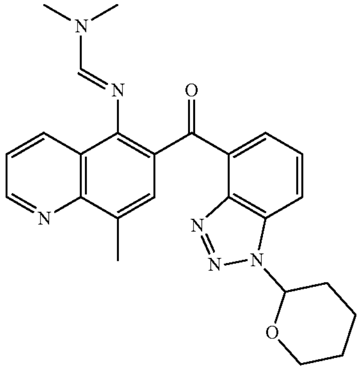

The title compound was synthesized from N-methoxy-N-methyl-1-(oxan-2-yl)benzotriazole-4-carboxamide (compound c-319) under the same conditions as in the production example of compound b-26, except that toluene and (E)-N'-(6-iodo-8-methylquinolin-5-yl)-N,N-dimethylmethanimidamide (compound c-271) were used instead of THF and (E)-N'-(6-chloro-2,4-diiodonaphthalen-1-yl)-N,N-dimethylmethanimidamide (compound c-6), respectively, used in the production example of compound b-26.

LCMS: m/z 443 $[M+H]^+$

HPLC retention time: 2.77 min (analysis condition J)

Compound c-321

(5-Amino-8-methylquinolin-6-yl)-[1-(oxan-2-yl) benzotriazol-4-yl]methanone

[Formula 896]

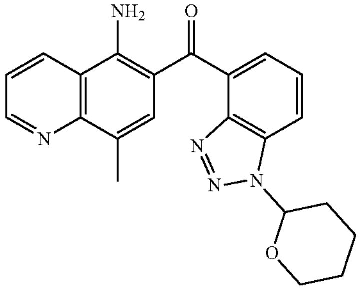

The title compound was synthesized from N,N-dimethyl-N'-[8-methyl-6-[1-(oxan-2-yl)benzotriazole-4-carbonyl] quinolin-5-yl]methanimidamide (compound c-320) under the same conditions as in the production example of compound b-27.

LCMS: m/z 388 $[M+H]^+$

HPLC retention time: 2.89 min (analysis condition J)

Compound c-324

3-Amino-6-methyl-4-[1-(oxan-2-yl)benzotriazol-4-yl]-1H-1,7-phenanthrolin-2-one

[Formula 897]

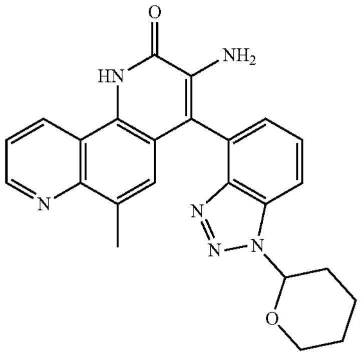

The title compound was synthesized from (5-amino-8-methylquinolin-6-yl)-[1-(oxan-2-yl)benzotriazol-4-yl] methanone (compound c-321) under the same conditions as in the production examples of compounds c-9, c-10, and c-13, except that reaction was performed without the use of N,N-dimethylaniline used in the production example of compound c-9.

LCMS: m/z 427 $[M+H]^+$

HPLC retention time: 2.67 min (analysis condition J)

Compound C224

3-Amino-4-(1H-benzotriazol-4-yl)-6-methyl-1H-1,7-phenanthrolin-2-one

[Formula 898]

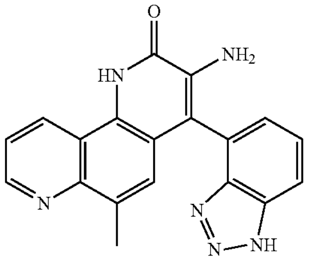

The title compound was synthesized from 3-amino-6-methyl-4-[1-(oxan-2-yl)benzotriazol-4-yl]-1H-1,7-phenanthrolin-2-one (compound c-324) under the same conditions as in the production example of compound C4, except that anisole was used instead of triethylsilane used in the production example of compound C4.

LCMS: m/z 343 $[M+H]^+$

HPLC retention time: 0.43 min (analysis condition A)

Compound C225

3-Amino-6-(tert-butyl)-4-(7-fluoro-1H-indazol-4-yl)-1H-1,7-phenanthrolin-2-one

[Formula 899]

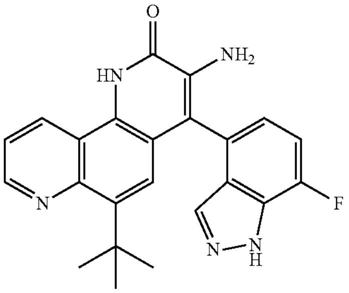

To tert-butyl 3-[bis[(2-methylpropan-2-yl)oxycarbonyl] amino]-6-bromo-4-[7-fluoro-2-(oxan-2-yl)indazol-4-yl]-2-oxo-1,7-phenanthroline-1-carboxylate (compound c-168, 61 mg, 0.075 mmol), potassium tert-butyl trifluoroborate (25 mg, 0.15 mmol), nickel(II) bis(2,2,6,6-tetramethyl-3,5-heptanedionate) (3.2 mg, 7.5 μmol), (2,2'-pyridine)bis[3,5-difluoro-2-[5-(trifluoromethyl)-2-pyridinyl]phenyl]iridium(III) hexafluorophosphate (CAS No: 1092775-62-6, 0.76 mg, 0.75 μmol), zinc bromide (1.7 mg, 7.5 μmol), and dipotassium phosphate (13 mg, 0.075 mmol) in a reaction container, DMA (0.75 mL) was added. The mixture was stirred at 1500 rpm, and photoredox catalysis reaction was performed through irradiation with LED light at 450 nm for 16 hours in a nitrogen atmosphere while the reaction solution was cooled in air with a blower. To the reaction solution, a saturated aqueous solution of sodium chloride was added, followed by extraction with ethyl acetate. The organic layer was washed with a saturated aqueous solution of sodium chloride and dried over anhydrous sodium sulfate, and the desiccant was filtered out Then, the filtrate was concentrated under reduced pressure. To the obtained residue, DCM (3.5 mL) and TFA (1.2 mL) were added, and the mixture was stirred at room temperature for 1 hour. The reaction mixture was concentrated, and the obtained residue was purified by reverse-phase column chromatography (0.1% aqueous FA solution/0.1% solution of FA in acetonitrile). Fractions containing the title compound were combined and freeze-dried to obtain the title compound (2.8 mg, 9%) as a colorless solid.

LCMS: m/z 402 $[M+H]^+$

HPLC retention time: 1.11 min (analysis condition F)

Hydrochloride Monohydrate of Compound C190

3-Amino-4-(6,7-difluoro-1H-indazol-4-yl)-6-methyl-1H-1,7-phenanthrolin-2-one hydrochloride monohydrate

[Formula 900]

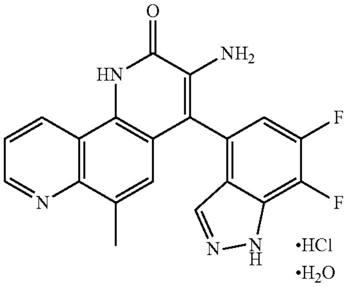

(1) Preparation of Hydrochloride Monohydrate of Compound C190

Figure 9:
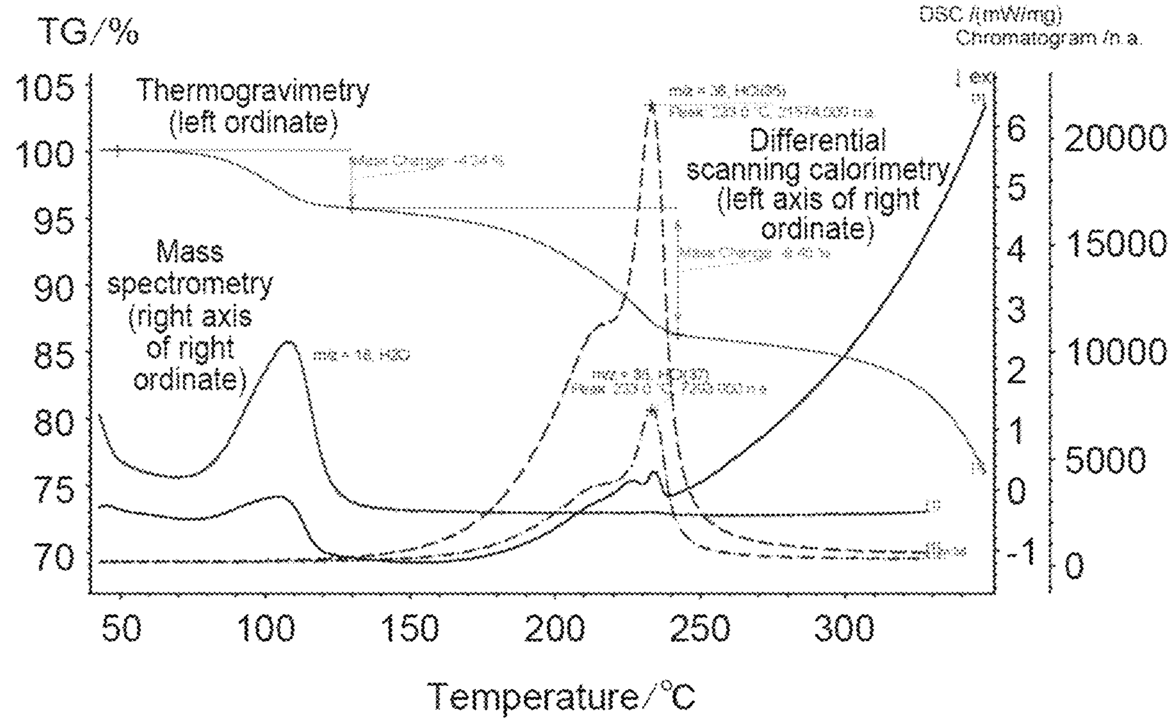
FIG. 9 shows results of simultaneous measurement of thermogravimetry, differential scanning calorimetry and mass spectrometry of sample A. The abscissa depicts a temperature (C). The left ordinate depicts change (%) in weight of the sample in thermogravimetric analysis. The right ordinate depicts heat flow (mW/mg) observed in differential thermal analysis (left) and peak intensity observed in mass spectrometry (right).

To 3-amino-4-(6,7-difluoro-1H-indazol-4-yl)-6-methyl-1H-1,7-phenanthrolin-2-one (compound C190, 342.5 mg) in a reaction container, DMSO (1.7 mL) was added, and the compound was dissolved therein at room temperature. To this solution, 2 M hydrochloric acid (2.57 mL) and water (0.86 mL) were added, and the mixture was stirred at room temperature for 6 minutes. To the reaction container, a wet solid of hydrochloride of compound C190 (sample A-2 mentioned later) was added, and the mixture was stirred at room temperature for 23 hours. Then, a solid was collected by filtration and washed with 2-propanol (4.3 mL). The obtained solid was dried in vacuum for 4 days to obtain a solid of the title compound (sample A). FIG. 9 shows results of simultaneous measurement of thermogravimetry, differential scanning calorimetry and mass spectrometry of the obtained solid. Ion peaks corresponding to m/z of water and HCl were detected around 100° C. and around 230° C., respectively, and the value of decrease in weight corresponded to the amounts of one molecule of water and one molecule of HCl per molecule of compound C190. As a result of conducting the quantitative analysis of a chloride ion by ultra-high performance liquid chromatography, the quantitative value was 7.87±0.19%, which corresponded to hydrochloride monohydrate. Thus, the obtained solid was confirmed to be hydrochloride monohydrate of compound C190.

(2) Preparation of Sample A-1

Figure 10:
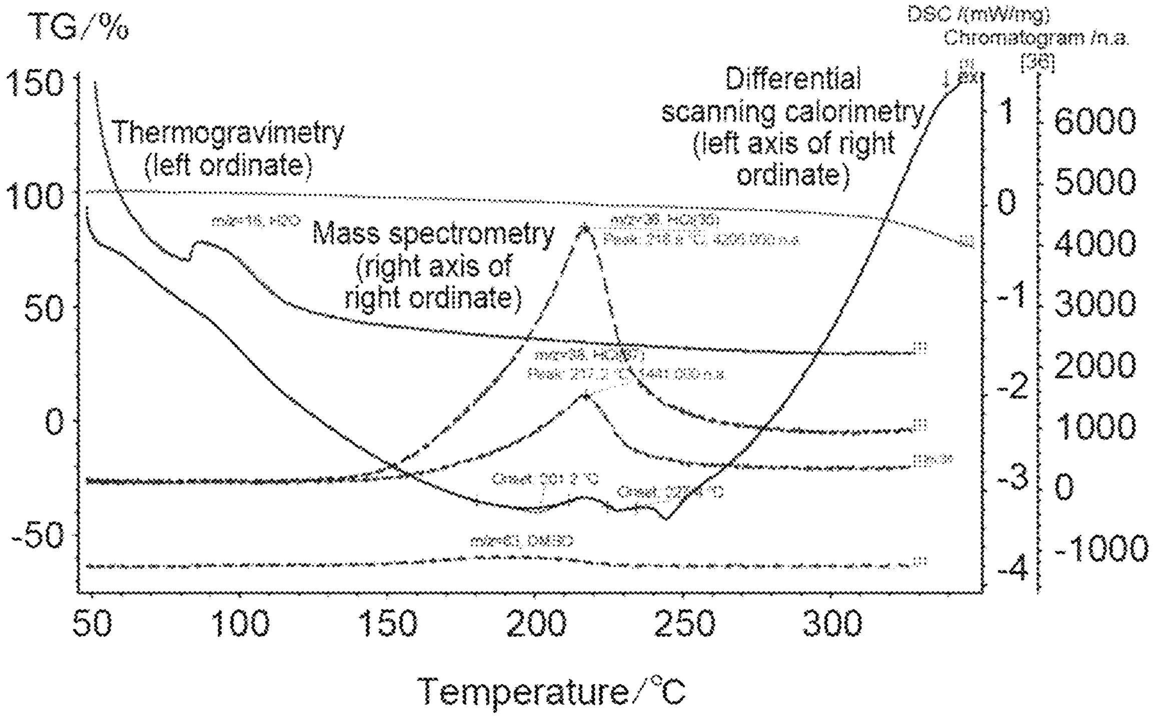
FIG. 10 shows results of simultaneous measurement of thermogravimetry, differential scanning calorimetry and mass spectrometry of sample A-1. The abscissa depicts a temperature (° C.). The left ordinate depicts change (%) in weight of the sample in thermogravimetric analysis (this result is a reference value because the sample filtered through a mesh and dried was measured directly). The right ordinate depicts heat flow (mW/mg) observed in differential scanning calorimetry (left) and peak intensity observed in mass spectrometry (right).

To 3-amino-4-(6,7-difluoro-1H-indazol-4-yl)-6-methyl-1H-1,7-phenanthrolin-2-one (compound C190, 71.7 mg) in a reaction container, 2 M hydrochloric acid (0.10 mL) and DMSO (0.30 mL) were added, and the mixture was stirred at room temperature for approximately 1 minute. Subsequently, DMSO (0.40 mL) was added thereto, and the mixture was stirred at room temperature for 1 minute. Subsequently, DMSO (0.40 mL) was added thereto, and the mixture was stirred at room temperature for 1 minute. The obtained suspension (0.045 mL) was freeze-dried at −20° C. for 3 days. To the obtained freeze-dried product, water (0.015 mL) was added, and the mixture was stirred by shaking at room temperature for 7 days to obtain a solid of hydrochloride hydrate of compound C190 (sample A-1). FIG. 10 shows results of simultaneous measurement of thermogravimetry, differential scanning calorimetry and mass spectrometry of the obtained solid. The solid was confirmed to be hydrochloride hydrate of compound C190.

(3) Preparation of Sample A-2

Figure 11:
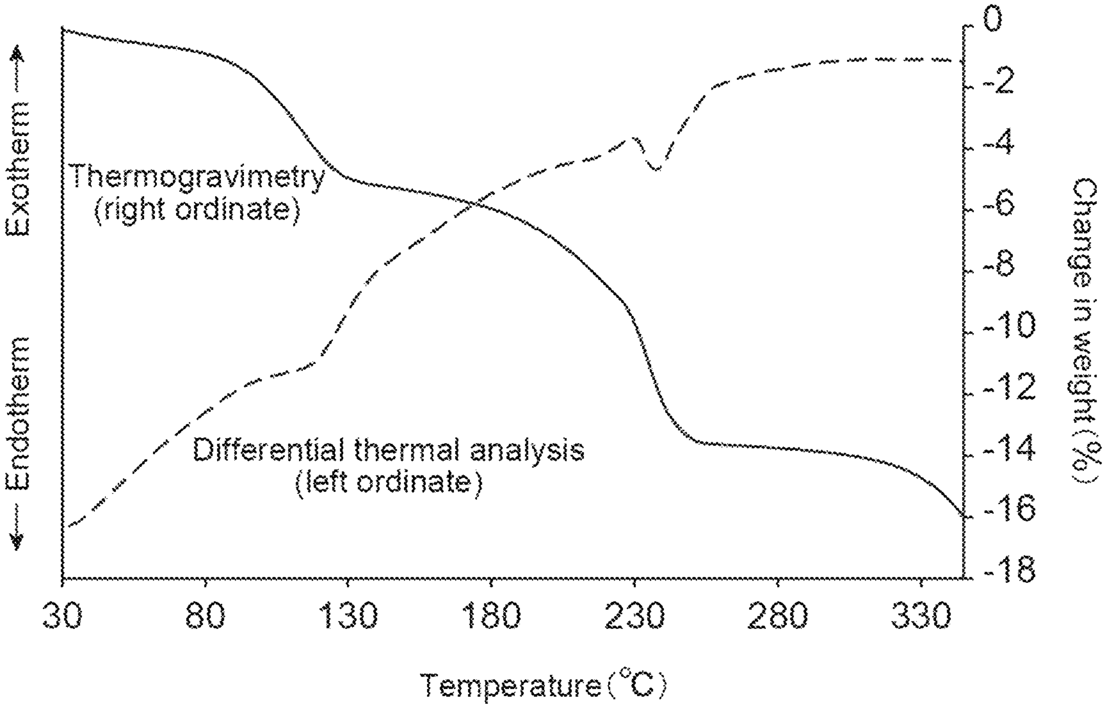
FIG. 11 shows results of simultaneous measurement of thermogravimetry, differential thermal analysis of sample A-2. The abscissa depicts a temperature (° C.). The right ordinate depicts change (%) in weight of the sample in thermogravimetric analysis. The left ordinate depicts heat flow (μV) observed in differential thermal analysis.

To 3-amino-4-(6,7-difluoro-1H-indazol-4-yl)-6-methyl-1H-1,7-phenanthrolin-2-one (compound C190, 30.0 mg) in a reaction container, DMSO (0.15 mL) was added, and the compound was dissolved therein at room temperature. To this solution, 2 M hydrochloric acid (0.23 mL) and water (0.075 mL) were added, and the mixture was stirred at room temperature for 3 minutes. To the reaction container, a wet solid (sample A-1 mentioned above) of hydrochloride of compound C190 was added, and the mixture was stirred at room temperature for 23 hours. Then, a solid was collected by filtration and washed with 2-propanol (0.15 mL). The obtained solid was dried in vacuum overnight to obtain a wet solid of hydrochloride of compound C190. The same operation as above was repeated twice using the obtained solid to obtain a wet solid of hydrochloride of compound C190 (sample A-2). FIG. 11 shows results of simultaneous measurement of thermogravimetry and differential thermal analysis of the obtained solid. The solid was confirmed to be hydrochloride hydrate of compound C190.

Hydrochloride Monohydrate of Compound C85

3-Amino-4-(7-fluoro-1H-indazol-4-yl)-6-methyl-1H-1,7-phenanthrolin-2-one hydrochloride monohydrate

[Formula 901]

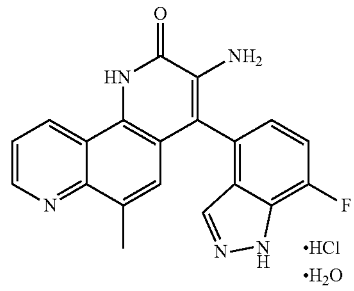

(1) Preparation of Hydrochloride Monohydrate of Compound C85

Figure 12:
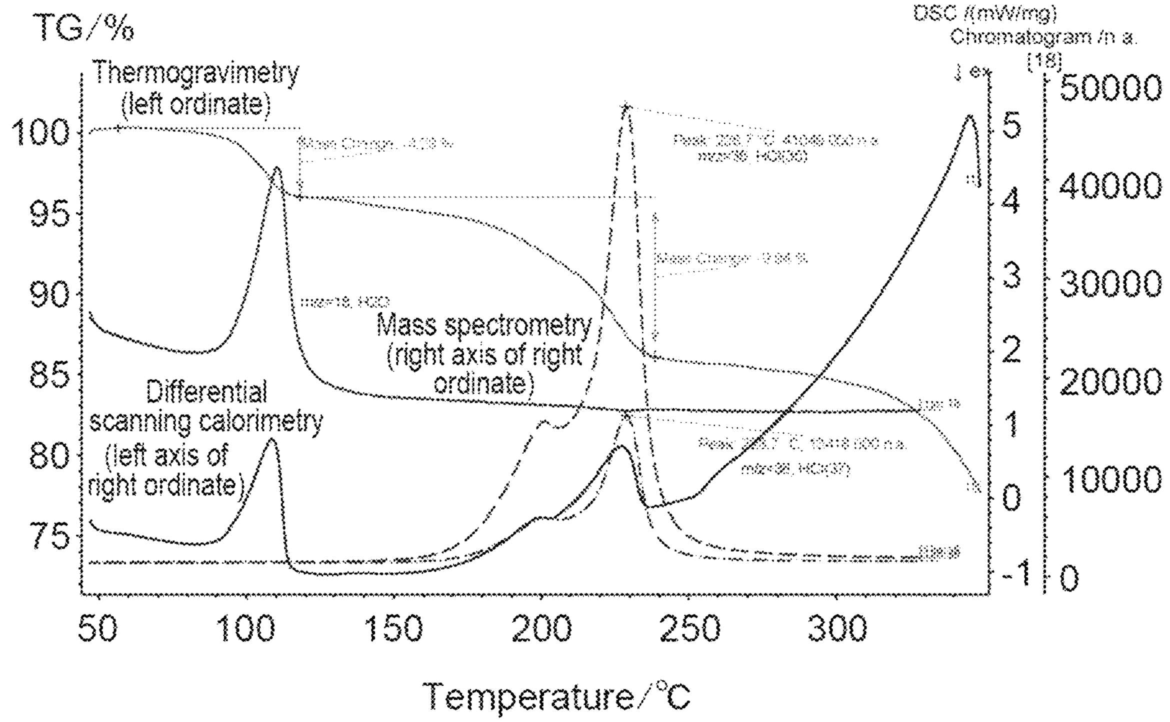
FIG. 12 shows results of simultaneous measurement of thermogravimetry, differential scanning calorimetry and mass spectrometry of sample B. The abscissa depicts a temperature (° C.). The left ordinate depicts change (%) in weight of the sample in thermogravimetric analysis. The right ordinate depicts heat flow (mW/mg) observed in differential scanning calorimetry (left) and peak intensity observed in mass spectrometry (right).

To 3-amino-4-(7-fluoro-1H-indazol-4-yl)-6-methyl-1H-1,7-phenanthrolin-2-one (compound C85, 29.7 mg) in a reaction container, DMSO (0.15 mL) was added, and the compound was dissolved therein at room temperature. To this solution, 2 M hydrochloric acid (0.23 mL) and water (0.074 mL) were added, and the mixture was stirred at room temperature for 5 minutes. To the reaction container, a wet solid (sample B-3 mentioned later) of hydrochloride hydrate of compound C85 was added, and the mixture was stirred at room temperature for 3 days. Then, a solid was collected by filtration and washed with 2-propanol (0.15 mL). The obtained solid was dried in vacuum overnight to obtain a solid of the title compound (sample B). FIG. 12 shows results of simultaneous measurement of thermogravimetry, differential scanning calorimetry and mass spectrometry of the obtained solid. Ion peaks corresponding to m/z of water and HCl were detected around 100° C. and around 230° C., respectively, and the value of decrease in weight corresponded to the amounts of one molecule of water and one molecule of HCl per molecule of compound C85. As a result of conducting the quantitative analysis of a chloride ion by ultra-high performance liquid chromatography, the quantitative value was 9.42±0.15%, which corresponded to hydrochloride monohydrate. Thus, the obtained solid was confirmed to be hydrochloride monohydrate of compound C85.

(2) Preparation of Sample B-1

To 3-amino-4-(7-fluoro-1H-indazol-4-yl)-6-methyl-1H-1,7-phenanthrolin-2-one (compound C85, 68.3 mg) in a reaction container, 2 M hydrochloric acid (0.10 mL) and DMSO (0.28 mL) were added, and the mixture was stirred at room temperature for approximately 1 minute. Subsequently, DMSO (0.38 mL) was added thereto, and the mixture was stirred at room temperature for 1 minute. The obtained suspension (0.030 mL) was freeze-dried at −20° C. for 2 days. To the obtained freeze-dried product, water (0.015 mL) was added, and the mixture was stirred by shaking at room temperature for 8 days to obtain a wet solid (sample B-1).

(3) Preparation of Sample B-2

Figure 13:
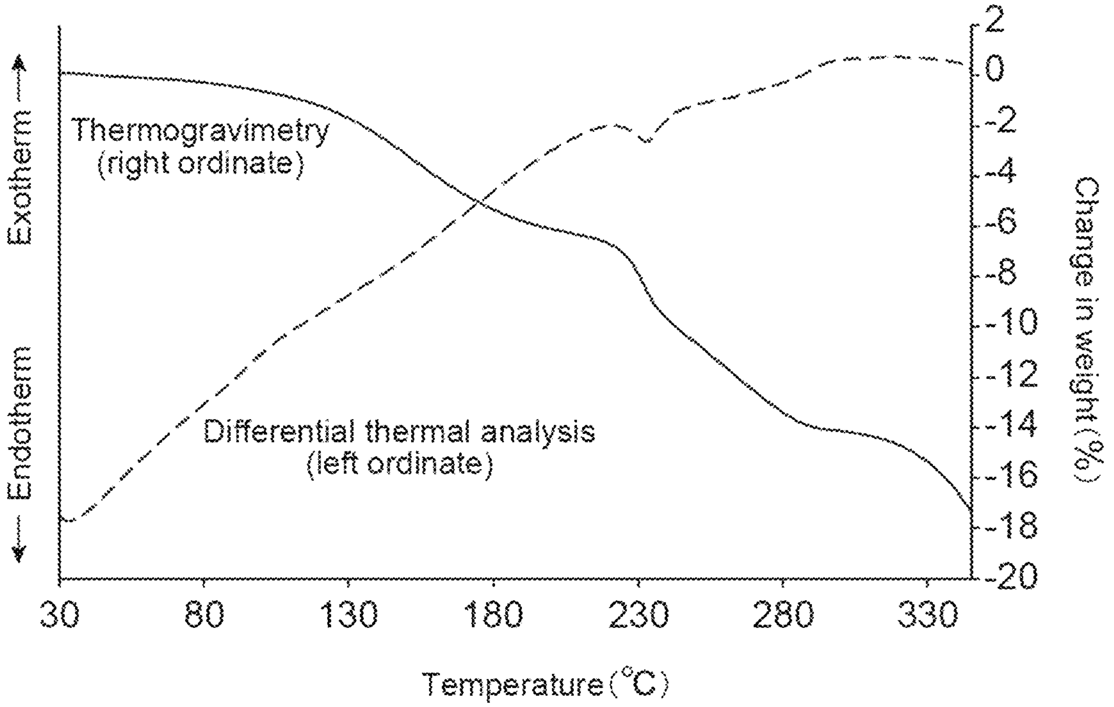
FIG. 13 shows results of simultaneous measurement of thermogravimetry, differential thermal analysis of sample B-2. The abscissa depicts a temperature (° C.). The right ordinate depicts change (%) in weight of the sample in thermogravimetric analysis. The left ordinate depicts heat flow observed in differential thermal analysis.

To 3-amino-4-(7-fluoro-1H-indazol-4-yl)-6-methyl-1H-1,7-phenanthrolin-2-one (compound C85, 301 mg) in a reaction container, 5 M hydrochloric acid (0.90 mL) and water (3.60 mL) were added, and the mixture was stirred at room temperature for 6 minutes. To the reaction container, a wet solid of sample B-1 was added, and the mixture was stirred at room temperature for 5 days. Then, a solid was collected by filtration, and the obtained solid was dried in air over two nights to obtain a solid of hydrochloride hydrate of compound C85 (sample B-2). FIG. 13 shows results of simultaneous measurement of thermogravimetry and differential thermal analysis of the obtained solid. The obtained solid was confirmed to be hydrochloride hydrate of compound C85.

(4) Preparation of Sample B-3

Figure 14:
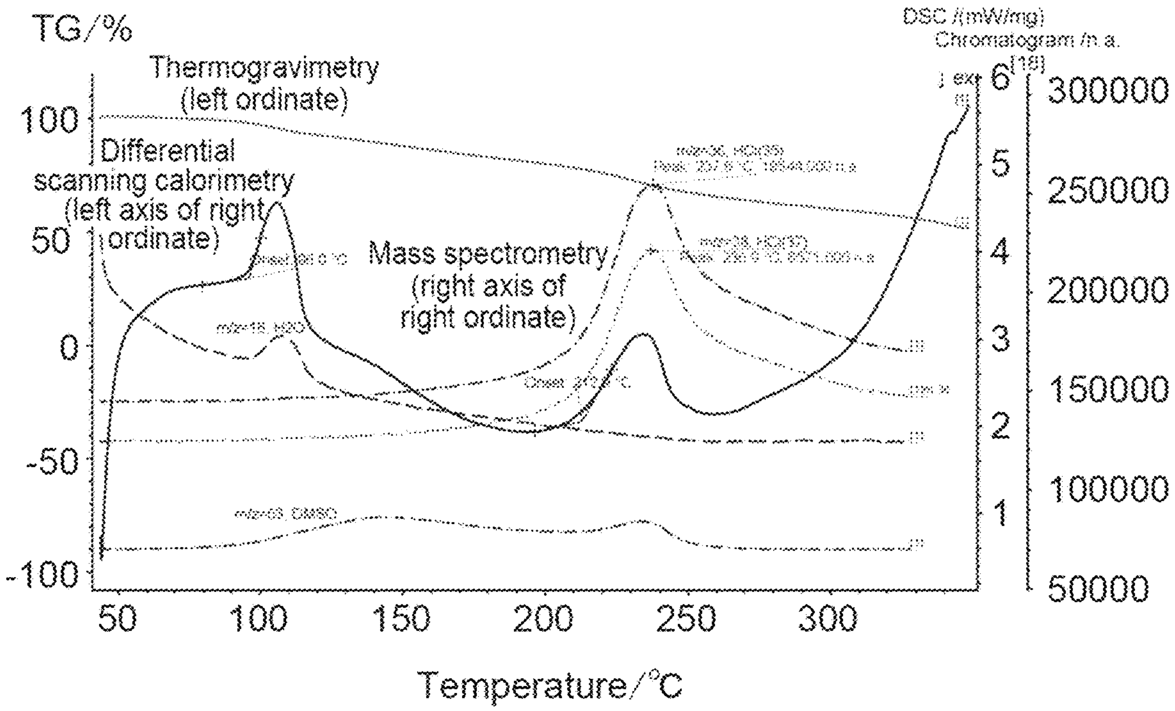
FIG. 14 shows results of simultaneous measurement of thermogravimetry, differential scanning calorimetry and mass spectrometry of sample B-3. The abscissa depicts a temperature (° C.). The left ordinate depicts change (%) in weight of the sample in thermogravimetric analysis (this result is a reference value because the sample filtered through a mesh and dried was measured directly). The right ordinate depicts heat flow (mW/mg) observed in differential scanning calorimetry (left) and peak intensity observed in mass spectrometry (right).

To 3-amino-4-(7-fluoro-1H-indazol-4-yl)-6-methyl-1H-1,7-phenanthrolin-2-one (compound C85, 6.3 mg) in a reaction container, DMSO (0.032 mL) was added, and the compound was dissolved therein at room temperature. To this solution, 2 M hydrochloric acid (0.047 mL) was added, and the mixture was stirred at room temperature for 10 minutes. To the resulting pale yellow suspension, water (0.016 mL) was added, and the mixture was stirred at room temperature for 15 minutes. To the reaction container, a wet solid of sample B-2 was added, and the mixture was stirred at room temperature for 18 hours to obtain a wet solid of hydrochloride hydrate of compound C85 (sample B-3). FIG. 14 shows results of simultaneous measurement of thermogravimetry, differential scanning calorimetry and mass spectrometry of the obtained wet solid. The obtained wet solid was confirmed to be hydrochloride hydrate of compound C85.

Hydrochloride of Compound c-263

3-Amino-4-(7-fluoro-1H-indazol-4-yl)-6-methoxy-1H-1,7-phenanthrolin-2-one hydrochloride

[Formula 902]

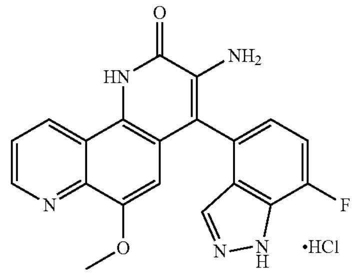

(1) Preparation of Hydrochloride of Compound c-263

Figure 15:
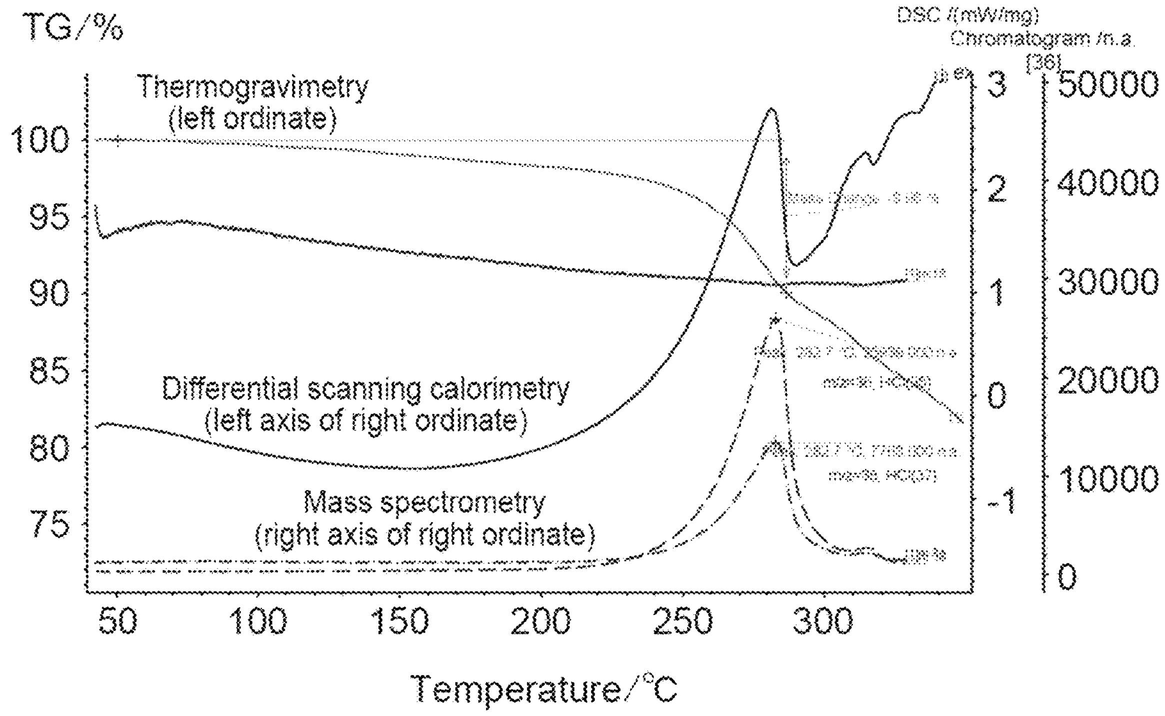
FIG. 15 shows results of simultaneous measurement of thermogravimetry, differential scanning calorimetry and mass spectrometry of sample C. The abscissa depicts a temperature (° C.). The left ordinate depicts change (%) in weight of the sample in thermogravimetric analysis. The right ordinate depicts heat flow (mW/mg) observed in differential scanning calorimetry (left) and peak intensity observed in mass spectrometry (right).

To 3-amino-4-(7-fluoro-1H-indazol-4-yl)-6-methoxy-1H-1,7-phenanthrolin-2-one (compound c-263, 99.7 mg) in a reaction container, DMSO (0.50 mL) was added, and the compound was dissolved therein at room temperature. To this solution, 2 M hydrochloric acid (0.75 mL) and water (0.25 mL) were added, and the mixture was stirred at room temperature for 5 minutes. A wet solid (sample C-2 mentioned later) of hydrochloride of compound c-263 was added, and the mixture was stirred at room temperature for 18 hours. Then, a solid was collected by filtration and washed with 2-propanol (0.50 mL). The obtained solid was dried in vacuum overnight to obtain a solid of the title compound (sample C). FIG. 15 shows results of simultaneous measurement of thermogravimetry, differential scanning calorimetry and mass spectrometry of the obtained solid. An ion peak corresponding to m/z of HCl was detected around 280° C., and the value of decrease in weight corresponded to the amount of one molecule of HCl per molecule of compound c-263. As a result of conducting the quantitative analysis of a chloride ion by ultra-high performance liquid chromatography, the quantitative value was 7.88±1.43%, which corresponded to hydrochloride. Thus, the obtained solid was confirmed to be hydrochloride of compound c-263.

(2) Preparation of Sample C-1

Figure 16:
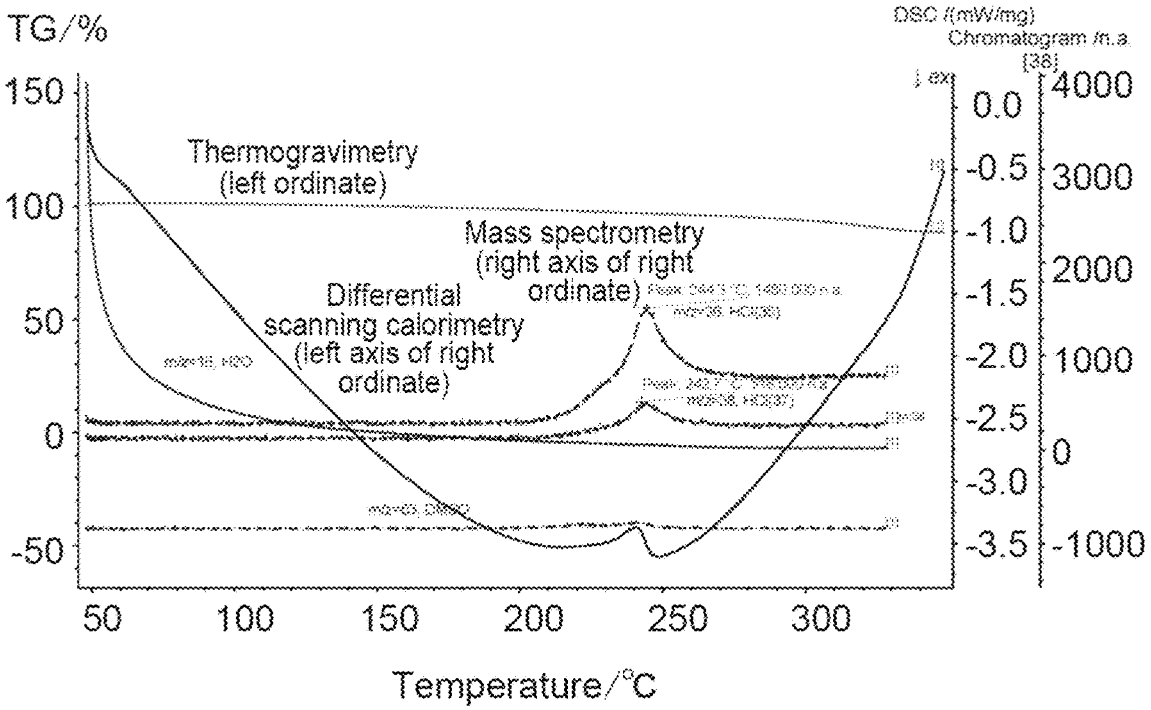
FIG. 16 shows results of simultaneous measurement of thermogravimetry, differential scanning calorimetry and mass spectrometry of sample C-1. The abscissa depicts a temperature (° C.). The left ordinate depicts change (%) in weight of the sample in thermogravimetric analysis (this result is a reference value because the sample filtered through a mesh and dried was measured directly). The right ordinate depicts heat flow (mW/mg) observed in differential scanning calorimetry (left) and peak intensity observed in mass spectrometry (right).

To 3-amino-4-[7-fluoro-2-(oxan-2-yl)indazol-4-yl]-6-methoxy-1H-1,7-phenanthrolin-2-one (compound c-263, 25.3 mg) in a reaction container, 2 M hydrochloric acid (0.035 mL) and DMSO (0.10 mL) were added, and the mixture was stirred at room temperature for approximately 1 minute. Subsequently, DMSO (0.14 mL) was added thereto, and the mixture was stirred at room temperature for 1 minute. Subsequently, DMSO (0.14 mL) was added thereto, and the mixture was stirred at room temperature for 1 minute. The obtained suspension (0.045 mL) was freeze-dried at −20° C. for 3 days. To the obtained freeze-dried product, water (0.015 mL) was added, and the mixture was stirred by shaking at room temperature for 7 days to obtain a solid of hydrochloride of compound c-263 (sample C-1). FIG. 16 shows results of simultaneous measurement of thermogravimetry-differential scanning calorimetry and mass spectrometry of the obtained solid. The obtained solid was confirmed to be hydrochloride of compound c-263.

(3) Preparation of Sample C-2

Figure 17:
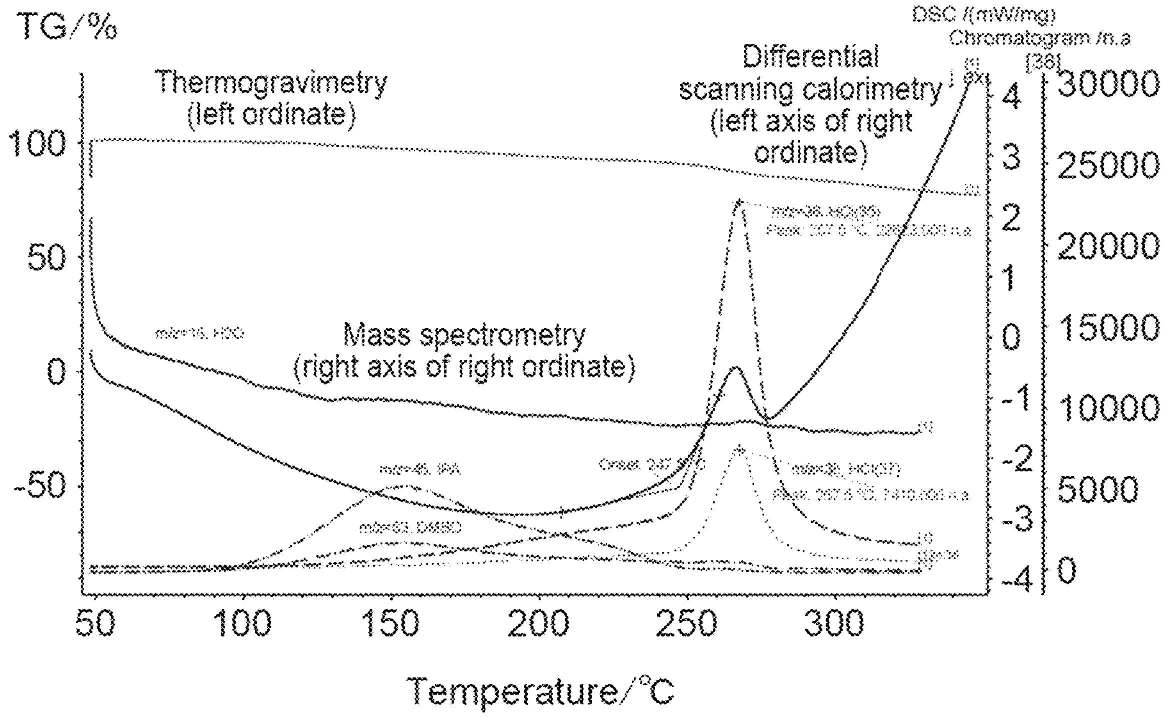
FIG. 17 shows results of simultaneous measurement of thermogravimetry, differential scanning calorimetry and mass spectrometry of sample C-2. The abscissa depicts a temperature (° C.). The left ordinate depicts change (%) in weight of the sample in thermogravimetric analysis (this result is a reference value because the sample filtered through a mesh and dried was measured directly). The right ordinate depicts heat flow (mW/mg) observed in differential scanning calorimetry (left) and peak intensity observed in mass spectrometry (right).

To 3-amino-4-[7-fluoro-2-(oxan-2-yl)indazol-4-yl]-6-methoxy-1H-1,7-phenanthrolin-2-one (compound c-263, 30.0 mg) in a reaction container, DMSO (0.15 mL) was added, and the compound was dissolved therein at room temperature. To this solution, 2 M hydrochloric acid (0.23 mL) and water (0.075 mL) were added, and the mixture was stirred at room temperature for 3 minutes. A wet solid (sample C-1) of hydrochloride of compound c-263 was added thereto, and the mixture was stirred at room temperature for 23 hours, then filtered, and washed with 2-propanol (0.15 mL). The resultant was dried in vacuum overnight to obtain a solid of hydrochloride of compound c-263 (sample C-2). FIG. 17 shows results of simultaneous measurement of thermogravimetry, differential scanning calorimetry and mass spectrometry of the obtained solid. The obtained solid was confirmed to be hydrochloride of compound c-263.

Solvate of Compound C84

3-Amino-6-cyclopropyl-4-(7-fluoro-1H-indazol-4-yl)-1H-1,7-phenanthrolin-2-one solvate

[Formula 903]

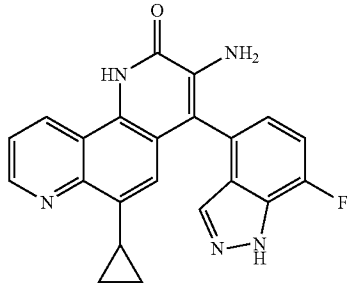

Figure 18:
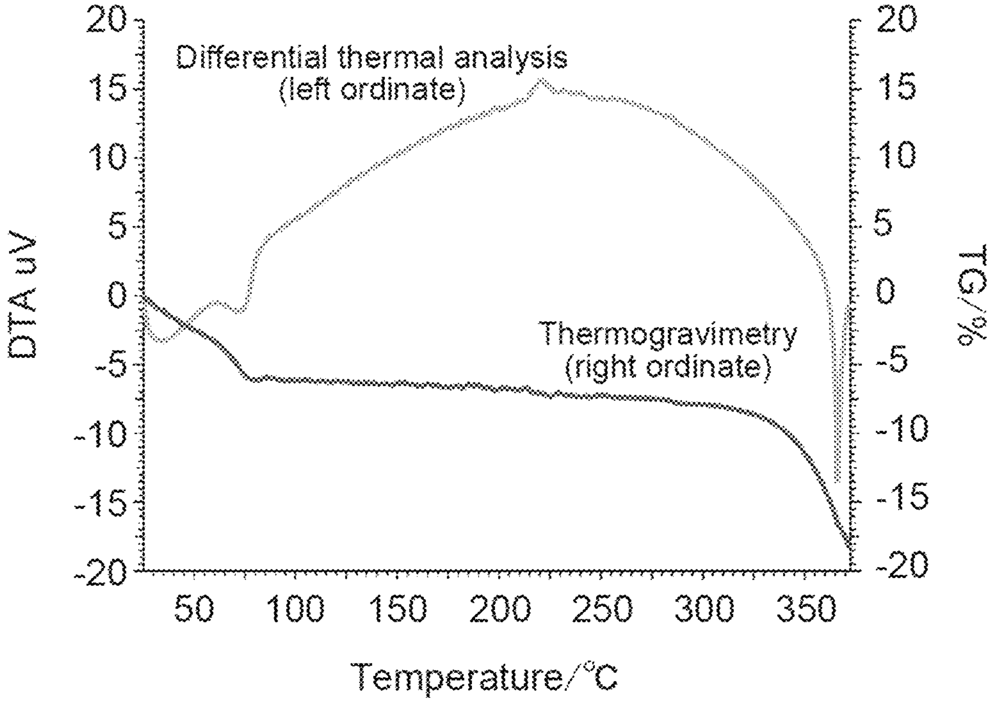
FIG. 18 shows results of simultaneous measurement of thermogravimetry and differential thermal analysis of sample D. The abscissa depicts a temperature (° C.). The right ordinate depicts change (%) in weight of the sample in thermogravimetric analysis. The left ordinate depicts heat flow (u V) observed in differential thermal analysis.

To 3-amino-6-cyclopropyl-4-(7-fluoro-1H-indazol-4-yl)-1H-1,7-phenanthrolin-2-one (compound C84, approximately 6.7 g) in a reaction container, DMSO (50 mL) was added, and the compound was dissolved therein at room temperature. To this solution, water (50 mL) was added twice, and the mixture was filtered and washed with water. The resultant was dried under reduced pressure to obtain a solvate of compound C84 (sample D). FIG. 18 shows results of simultaneous measurement of thermogravimetry and differential thermal analysis of the obtained solid. The obtained solid was confirmed to be a solvate of compound C84.

2-Propanol Solvate of Compound B49

3-Amino-6-cyclopropyl-4-(1H-indazol-4-yl)-1H-benzo[h]quinolin-2-one·2-propanol solvate

[Formula 904]

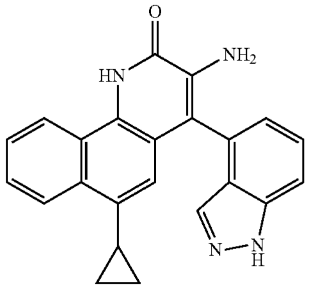

To 3-amino-6-cyclopropyl-4-(1H-indazol-4-yl)-1H-benzo[h]quinolin-2-one (compound B49, 31.2 mg), DMSO (0.312 mL) was added, and the mixture was stirred at room temperature. The obtained suspension (0.03 mL) was freeze-dried at −20° C. for 3 days. To the obtained freeze-dried product, 2-propanol (0.015 mL) was added, and the mixture was stirred by shaking at room temperature for 14 days to obtain crystals of a 2-propanol solvate of compound B49 (sample E).

Figure 19:
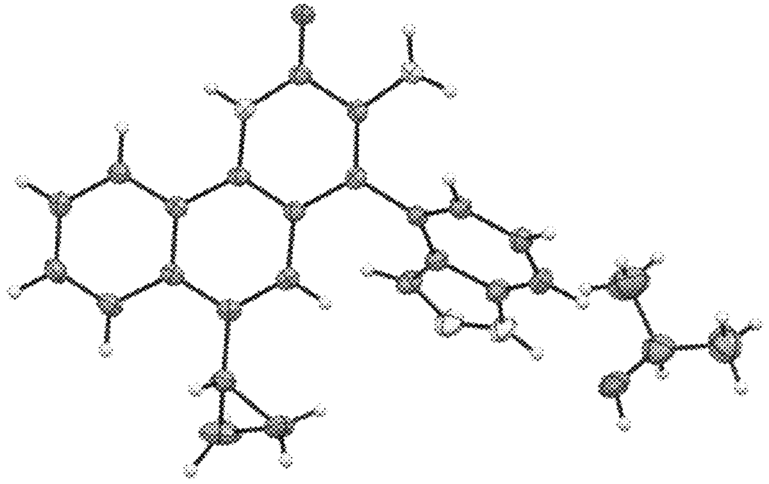
FIG. 19 shows an asymmetric unit of a crystal structure of sample E. The drawing is based on an ellipsoid model (probability level: 50%).

The sample E was confirmed to be a 2-propanol solvate by single-crystal X-ray crystallography. The crystal structure is shown in FIG. 19.

The samples obtained as described above were each analyzed under the following conditions.

The simultaneous measurement of thermogravimetry and differential thermal analysis (TG-DTA) of the sample A-2 and the sample B-2 was carried out under the following conditions.

Measurement apparatus: STA7200RV+AS-3T (manufactured by Hitachi High-Tech Corp.)
Measurement range: 30 to 350° C.
Heating rate: 10° C./min
Atmosphere: Nitrogen
Measurement: The sample was weighed into an open aluminum pan and covered with a mesh, followed by measurement.

The simultaneous measurement of thermogravimetry and differential thermal analysis (TG-DTA) of the sample D was carried out under the following conditions.

Measurement apparatus: STA7200RV+AS-3T (manufactured by Hitachi High-Tech Corp.)
Measurement range: 30 to 380° C.
Heating rate: 10° C./min
Atmosphere: Nitrogen
Measurement: The sample was weighed into an open aluminum pan and covered with a mesh, followed by measurement.

The simultaneous measurement of thermogravimetry, differential scanning calorimetry and mass spectrometry (TG-DSC-MS) of the sample A, the sample B, and the sample C was carried out under the following conditions.

Measurement apparatus: STA449F1 Jupiter (manufactured by NETZSCH Japan K.K.)+JMS-Q1500GC (manufactured by JEOL Ltd.)
Measurement range: 50 to 350° C.
Heating rate: 10° C./min
Atmosphere: Helium, 50 mL/min
Transfer line temperature: 300° C.
Ion source temperature: 250° C.
Ionization method, voltage, and current: EI, 70 eV, and 20 μA
Relative EM voltage: +700 V
Measurement mode: Scan (m/z 10-400)
Measurement: The sample was precisely weighed into an open aluminum pan, followed by measurement.

The simultaneous measurement of thermogravimetry, differential scanning calorimetry and mass spectrometry (TG-DSC-MS) of the sample A-1, the sample B-3, the sample C-1, and the sample C-2 was carried out under the following conditions.

Measurement apparatus: STA449F1 Jupiter (manufactured by NETZSCH Japan K.K.)+JMS-Q1500GC (manufactured by JEOL Ltd.)
Measurement range: 50 to 350° C.
Heating rate: 10° C./min
Atmosphere: Helium, 50 mL/min
Transfer line temperature: 300° C.
Ion source temperature: 250° C.
Ionization method, voltage, and current: EI, 70 eV, and 20 μA
Relative EM voltage: +700 V
Measurement mode: Scan (m/z 10-400)
Measurement: The sample was filtered through a mesh or a sintered filter, dried in vacuum overnight, and then placed on an open aluminum pan, followed by measurement.

The single-crystal X-ray crystallography of the sample E was carried out under the following conditions.

Measurement apparatus: Rigaku XtaLAB Synergy Custom with a VariMax Cu Diffractometer (manufactured by Rigaku Corp.)
Counter negative electrode: Cu
Tube voltage: 40 kV
Tube current: 30 mA
Temperature: −180° C.
Measurement: Measurement was performed using a strategy and an exposure time considered to produce diffraction spots sufficient for structure analysis.
Structure analysis: Olex2 program was used. Initial structure determination was performed by the intrinsic phasing method (SHELXT-2018/2), and structure refinement was performed by the full-matrix least-squares method (SHELXL-2018/3).

The C1 quantitative analysis of the sample A by ultra-high performance liquid chromatography was carried out under the following conditions.

HPLC Analysis Condition 1

Measurement apparatus: Shimadzu Nexera X3 UHPLC (manufactured by Shimadzu Corp.), Corona Veo RS Charged Aerosol Detector (manufactured by Thermo Fisher Scientific Inc.)
Column: Acclaim Trinity P1 3 μm, 2.1×100 mm (manufactured by Thermo Fisher Scientific Inc.)
Detector: Corona Veo RS Charged Aerosol Detector
Mobile phase: 20 mM ammonium acetate solution (pH=6.6)/acetonitrile=55/45 (isocratic condition)

Inverse gradient phase: Acetonitrile
Flow rate: 0.3 mL/min
Injection volume: 5 μL
Analysis time: 7 min
Column temperature: 40° C.
CAD temperature: 35° C.
Sample treatment: 1 mg of the sample was precisely weighed, 1 mL of a 0.1 mg/mL hippuric acid methanol solution and 1 mL of methanol were added thereto, and the mixture was stirred by vortex to obtain a sample solution (sample concentration: 0.5 mg/mL).

The C1 quantitative analysis of the sample B and the sample C by ultra-high performance liquid chromatography was carried out under the following conditions.

HPLC Analysis Condition 2
Measurement apparatus: Waters ACQUITY UPLC H-Class Plus (manufactured by Waters Corp.), Corona Veo RS Charged Aerosol Detector (manufactured by Thermo Fisher Scientific Inc.)
Column: Acclaim Trinity P1 3 μm, 2.1×100 mm (manufactured by Thermo Fisher Scientific Inc.)
Detector: Corona Veo RS Charged Aerosol Detector
Mobile phase: 20 mM ammonium acetate solution (pH=6.6)/acetonitrile=55/45 (isocratic condition)
Inverse gradient phase: Acetonitrile
Flow rate: 0.3 mL/min
Injection volume: 5 μL
Analysis time: 7 min
Column temperature: 40° C.
CAD temperature: 35° C.
Sample treatment: 1 mg of the sample was precisely weighed, 1 mL of a 0.1 mg/mL hippuric acid methanol solution and 1 mL of methanol were added thereto, and the mixture was stirred by vortex to obtain a sample solution (sample concentration: 0.5 mg/mL).

Pharmacological Test

Test Example 1: Test for Binding of Each Example Compound to ATP Binding Site of MYT1 and MYT1 Kinase Activity Inhibition Test

1. Experimental Material and Method (1) Test for Binding to ATP Binding Site of MYT1

The binding capacity of each compound to the ATP binding site of MYT1 Kinase protein was evaluated. 5× Kinase Buffer A (manufactured by Thermo Fisher Scientific Inc., PV3189) was diluted to 5 times with Milli-Q water, thereby preparing 1× Kinase Buffer. Using 1× Kinase Buffer, MYT1 protein (manufactured by Carna Biosciences, Inc.) was diluted to a concentration of 0.005 μM and Eu-Anti-GST Antibody was diluted to a concentration of 1 μM. In addition, Kinase Tracer 178 (manufactured by Thermo Fisher Scientific Inc., PV5593) was diluted to a concentration of 0.1 μM using 1× Kinase Buffer. To a 96 well-plate, 2.5 μL of a compound diluted with DMSO was added. Thereafter, 5 μL of a solution in which MYT1 protein and Eu-GST-Antibody diluted above were mixed in a ratio of 1:1 was added, and 2.5 μL of Kinase Tracer 178 diluted above was further added thereto. The mixture was well mixed and then allowed to stand at room temperature for 30 minutes. Thereafter, fluorescence wavelengths of 665 nm and 615 nm generated by irradiation with excitation light of 340 nm were detected using Envision (manufactured by PerkinElmer). The proportion of Tracer bound to MYT1 protein was calculated for every condition by dividing the intensity at the fluorescence wavelength of 665 nm by the intensity at the fluorescence wavelength of 615 nm. The inhibition rate of each compound added at each concentration was calculated by setting the signal when the compound was not added as 100% and the signal when MYT1 protein was not added as 0%, and the calculation results of $IC_{50}$ were shown in Tables 3-1 to 3-5. When the compound exhibits $IC_{50}$ of 10 μM or less, the compound can be determined to have binding activity to the ATP binding site of MYT1 protein.

(2) MYT1 Kinase Activity Inhibition Test

The MYT1 kinase activity inhibitory capacity of each compound was evaluated by evaluating the phosphorylation level of Y15 of CDK1 protein caused by MYT1 protein, by ELISA. The kit of CycLex Weel Kinase Assay/Inhibitor Screening Kit Ver. 3 (manufactured by MBL, CY-1172V3) was used. Using Kinase Buffer, 10 μL of 5 nM MYT1 protein (manufactured by Carna Biosciences, Inc.) was prepared. In addition, 30 μL of 83.3 μM of ATP was prepared using Kinase Buffer. In addition, 10 μL of each compound was diluted to each concentration using Kinase Buffer. 30 μL of ATP was added to the plate of the kit, and thereafter, 10 μL of each compound was added thereto. Further, 10 μL of the diluted MYT1 protein solution was added thereto, and then the mixture was mixed, which was allowed to stand at room temperature for 60 minutes. The reaction solution was removed from each well, and each well was washed using Wash Buffer. After Wash Buffer was removed, 100 μL of HRP conjugated Anti-phospho-tyrosine antibody was added to each well, which was allowed to stand at room temperature for 60 minutes. Thereafter, the reaction solution was removed from each well, and each well was washed using Wash Buffer. After Wash Buffer was removed, 100 μL of Substrate Reagent was added to each well, which was allowed to stand at room temperature for 8 minutes. Thereafter, 100 μL of Stop Solution (1 N sulfuric acid) was added to each well according to the manual. Absorbances at 450 nm and 590 nm were measured using Envision (manufactured by PerkinElmer). The phosphorylation level of CDK1 protein was evaluated for each well by subtracting the absorbance at 590 nm from the absorbance at 450 nm. The inhibition rate of each compound added at each concentration was calculated by setting the signal when the compound was not added as 100% and the signal when MYT1 protein was not added as 0%, and the calculation results of $IC_{50}$ were shown in Table 4. When the compound exhibits $IC_{50}$ of 10 μM or less, the compound can be determined to exhibit inhibition of kinase activity of MYT1 protein.

TABLE 3-1

| Compound number | Binding $IC_{50}$ (μM) |
|---|---|
| A1 | 0.029 |
| A2 | 0.0093 |
| A3 | 0.0085 |
| A4 | 0.0038 |
| A5 | 0.0018 |
| A6 | 0.0030 |
| A7 | 0.0044 |
| A8 | 0.023 |
| A9 | 0.0039 |
| A10 | 0.0043 |
| A11 | 0.0039 |
| A12 | 0.0026 |
| A13 | 0.018 |
| A14 | 0.0021 |
| A15 | 0.013 |
| A16 | 0.0050 |
| A17 | 0.027 |

TABLE 3-1-continued

| Compound number | Binding $IC_{50}$ (μM) |
|---|---|
| A18 | 0.087 |
| A19 | 0.60 |
| A20 | 0.012 |
| A21 | 0.020 |
| A22 | 0.27 |
| A23 | 0.034 |
| A24 | 0.11 |
| A25 | 0.045 |
| A26 | 0.011 |
| A27 | 0.040 |
| A28 | 0.047 |
| A29 | 0.029 |
| A30 | 0.043 |
| A31 | 0.0076 |
| A32 | 0.016 |
| A33 | 0.013 |
| A34 | 0.026 |
| A35 | 0.019 |
| A36 | 0.018 |
| A37 | 0.0056 |
| A38 | 0.020 |
| A39 | 0.023 |
| A40 | 0.0086 |
| A41 | 0.14 |
| A42 | 0.45 |
| A43 | 0.048 |
| A44 | 5.0 |
| A45 | 5.0 |
| A46 | 5.9 |
| A47 | 3.3 |
| A48 | 5.3 |
| A49 | 0.79 |
| A50 | 5.8 |
| A51 | 2.7 |
| A52 | 4.4 |
| A53 | 0.98 |
| A55 | 0.48 |
| A56 | 0.058 |
| A57 | 0.013 |
| A58 | 0.36 |
| A59 | 0.0058 |
| A60 | 0.0070 |
| A61 | 0.14 |
| A62 | 3.9 |
| A63 | 0.71 |
| A65 | 0.19 |
| A66 | 0.38 |
| A67 | 0.13 |
| A68 | 8.0 |
| A69 | 2.5 |
| A70 | 6.2 |
| A71 | 1.4 |
| A72 | 0.096 |
| B1 | 5.6 |
| B2 | 0.022 |
| B3 | 0.0073 |
| B4 | 0.027 |
| B5 | 0.42 |
| B6 | 0.0070 |
| B7 | 0.0060 |
| B8 | 0.012 |
| B9 | 0.12 |
| B10 | 0.036 |
| B11 | 0.030 |
| B12 | 0.020 |
| B13 | 0.085 |
| B14 | 0.018 |
| B15 | 0.0086 |
| B16 | 0.046 |
| B17 | 0.015 |
| B18 | 0.023 |
| B19 | 0.022 |
| B20 | 0.042 |
| B21 | 0.020 |
| B22 | 0.011 |
| B23 | 0.0083 |
| B24 | 0.016 |

TABLE 3-1-continued

| Compound number | Binding $IC_{50}$ (μM) |
|---|---|
| B25 | 0.024 |
| B26 | 0.010 |
| B27 | 0.0073 |
| B28 | 0.022 |
| B29 | 0.0092 |
| B30 | 0.015 |
| B31 | 0.019 |
| B32 | 0.0030 |
| B33 | 2.6 |
| B34 | 0.033 |
| B35 | 0.0037 |
| B36 | 0.014 |
| B37 | 0.0060 |
| B38 | 0.0046 |
| B39 | 0.010 |
| B40 | 0.013 |
| B41 | 0.014 |
| B42 | 0.25 |
| B43 | 0.015 |
| B44 | 0.014 |
| B45 | 0.033 |
| B46 | 0.0063 |
| B47 | 0.010 |
| B48 | 0.018 |
| B49 | 0.0062 |
| B50 | 0.75 |

TABLE 3-2

| Compound number | Binding $IC_{50}$ (μM) |
|---|---|
| C1 | 0.0020 |
| C2 | 1.1 |
| C3 | 0.0036 |
| C4 | 0.0013 |
| C5 | 0.0014 |
| C6 | 0.0010 |
| C7 | 0.0012 |
| C8 | 0.0016 |
| C9 | 0.0032 |
| C10 | 0.0023 |
| C11 | 0.0014 |
| C12 | 0.0022 |
| C13 | 0.0014 |
| C14 | 0.0025 |
| C15 | 0.0026 |
| C16 | 0.0011 |
| C17 | 0.0045 |
| C18 | 0.0020 |
| C19 | 0.0022 |
| C20 | 0.0036 |
| C21 | 0.0028 |
| C22 | 0.0079 |
| C23 | 0.0050 |
| C24 | 0.0065 |
| C25 | 0.0028 |
| C26 | 0.0023 |
| C27 | 0.0044 |
| C28 | 0.0018 |
| C29 | 0.0033 |
| C30 | 0.0058 |
| C31 | 0.0043 |
| C32 | 0.0035 |
| C33 | 0.0035 |
| C34 | 0.0037 |
| C35 | 0.0044 |
| C36 | 0.0042 |
| C37 | 0.0039 |
| C38 | 0.0057 |
| C39 | 0.0065 |
| C40 | 0.0040 |
| C41 | 0.0061 |
| C42 | 0.0027 |

TABLE 3-2-continued

| Compound number | Binding $IC_{50}$ (μM) |
|---|---|
| C43 | 0.019 |
| C44 | 0.0051 |
| C45 | 0.0036 |
| C46 | 0.0029 |
| C47 | 0.0040 |
| C48 | 0.010 |
| C49 | 0.0017 |
| C50 | 0.0040 |
| C51 | 0.0017 |
| C52 | 0.0026 |
| C53 | 0.0042 |
| C54 | 0.0014 |
| C55 | 0.00092 |
| C56 | 0.0017 |
| C57 | 0.0025 |
| C58 | 0.0015 |
| C59 | 0.0053 |
| C60 | 0.00085 |
| C61 | 0.0017 |
| C62 | 0.0016 |
| C63 | 0.0011 |
| C64 | 0.0074 |
| C65 | 0.0032 |
| C66 | 0.0049 |
| C67 | 0.0024 |
| C68 | 0.0014 |
| C69 | 0.0020 |
| C70 | 0.0011 |
| C71 | 0.0017 |
| C72 | 0.0062 |
| C73 | <0.014 |
| C74 | 0.00083 |
| C75 | 0.0019 |
| C76 | 0.0015 |
| C77 | 0.0085 |
| C78 | 0.0031 |
| C79 | 0.011 |
| C80 | 0.10 |
| C81 | 0.049 |
| C82 | 0.011 |
| C83 | 0.0024 |
| C84 | 0.0023 |
| C85 | 0.0025 |
| C86 | 0.0046 |
| C87 | 0.018 |
| C88 | 0.0044 |
| C89 | 0.0039 |
| C90 | 0.014 |
| C91 | 0.010 |
| C92 | 0.019 |
| C93 | 0.032 |
| C94 | 0.0084 |
| C95 | 0.0087 |
| C96 | 0.0053 |
| C97 | 0.022 |
| C98 | 0.0028 |
| C99 | 0.021 |
| C100 | 0.0015 |
| C101 | 0.0061 |
| C102 | 0.0038 |
| C103 | 0.0043 |
| C104 | 0.0034 |
| C105 | 0.0050 |
| C106 | 0.0027 |
| C107 | 0.0081 |
| C108 | 0.037 |
| C109 | 0.0046 |
| C110 | 0.014 |
| C111 | 0.0049 |
| C112 | 0.078 |
| C113 | 0.0046 |
| C114 | 0.0020 |
| C115 | 0.0037 |
| C116 | 0.0027 |
| C117 | 0.0035 |
| C118 | 0.0023 |
| C119 | 0.0022 |

TABLE 3-2-continued

| Compound number | Binding $IC_{50}$ (μM) |
|---|---|
| C120 | 0.0029 |

TABLE 3-3

| Compound number | Binding $IC_{50}$ (μM) |
|---|---|
| C121 | 0.0030 |
| C122 | 0.0045 |
| C123 | 0.0034 |
| C124 | 0.0034 |
| C125 | 0.0059 |
| C126 | 0.0047 |
| C127 | 0.0015 |
| C128 | 0.0058 |
| C129 | 0.0033 |
| C130 | 0.0037 |
| C131 | 0.033 |
| C132 | 0.011 |
| C133 | 0.0017 |
| C134 | 0.0036 |
| C135 | 0.0023 |
| C136 | 0.0034 |
| C137 | 0.0047 |
| C138 | 0.0020 |
| C139 | 0.0033 |
| C140 | 0.0017 |
| C141 | 0.0049 |
| C142 | 0.018 |
| C143 | 0.0027 |
| C144 | 0.0070 |
| C145 | 0.0031 |
| C146 | 0.0034 |
| C147 | 0.0052 |
| C148 | 0.0041 |
| C149 | 0.38 |
| C150 | 0.0019 |
| C151 | 0.010 |
| C152 | 0.0040 |
| C153 | 0.0044 |
| C154 | 0.0033 |
| C155 | 0.0023 |
| C156 | 0.0021 |
| C157 | 0.31 |
| C158 | 0.0019 |
| C159 | 0.0023 |
| C160 | 0.0025 |
| C161 | 0.0086 |
| C162 | 0.012 |
| C163 | 0.024 |
| C164 | 0.0086 |
| C165 | 0.0071 |
| C166 | 0.0029 |
| C167 | 0.046 |
| C168 | 0.054 |
| C169 | 0.086 |
| C170 | 0.0033 |
| C171 | 0.0022 |
| C173 | 0.095 |
| C174 | 0.14 |
| C175 | 0.016 |
| C176 | 0.0021 |
| C177 | 0.0021 |
| C178 | 0.0023 |
| C179 | 0.00084 |
| C180 | 0.041 |
| C181 | 0.023 |
| C182 | 0.0055 |
| C183 | 0.11 |
| C184 | 0.010 |
| C185 | 0.0028 |
| C186 | 0.0068 |
| C187 | 0.020 |
| C188 | 0.0041 |

TABLE 3-3-continued

| Compound number | Binding $IC_{50}$ (μM) |
|---|---|
| C189 | 0.018 |
| C190 | 0.0025 |
| C191 | 0.0060 |
| C192 | 0.0037 |
| C193 | 0.0017 |
| C194 | 0.0016 |
| C195 | 0.0023 |
| C196 | 0.0036 |
| C197 | 0.020 |
| C198 | 0.0031 |
| C199 | 0.0038 |
| C200 | 0.0024 |
| C201 | 0.0057 |
| C202 | 0.0077 |
| C203 | 0.017 |
| C204 | 0.010 |
| C205 | 0.0034 |
| C206 | 0.0041 |
| C207 | 0.0010 |
| C208 | 0.0021 |
| C209 | 0.0015 |
| C210 | 0.0013 |
| C211 | 0.00087 |
| C212 | 0.0012 |
| C213 | 0.00083 |
| C214 | 0.0017 |
| C215 | 0.0024 |
| D1 | 0.0090 |
| D2 | 0.0040 |
| D3 | 0.0046 |
| D4 | 0.015 |
| D5 | 0.0064 |
| D6 | 0.0021 |
| D7 | 0.015 |
| D8 | 0.010 |
| D9 | 0.022 |
| D10 | 0.0039 |
| D11 | 0.020 |
| D12 | 0.049 |
| D13 | 0.025 |
| D14 | 0.033 |
| D15 | 0.069 |
| D16 | 0.0027 |
| D17 | 0.0031 |
| D18 | 0.00025 |
| D19 | 0.022 |
| D20 | 0.0070 |
| D21 | 0.0038 |
| D22 | 0.0029 |
| D23 | 0.0064 |
| D24 | 0.0069 |
| D25 | 0.0078 |
| D26 | 0.0033 |

TABLE 3-4

| Compound number | Binding $IC_{50}$ (μM) |
|---|---|
| D27 | 0.00053 |
| D28 | 0.0017 |
| D29 | 0.0057 |
| D30 | 0.0029 |
| E1 | 1.1 |
| E2 | 0.84 |
| F1 | 0.012 |
| F2 | 0.0016 |
| F3 | 0.0040 |
| F4 | 0.022 |
| F5 | 0.0033 |
| F6 | 0.0093 |
| G1 | 0.016 |
| G2 | 0.27 |
| G3 | 0.0079 |

TABLE 3-4-continued

| Compound number | Binding $IC_{50}$ (μM) |
|---|---|
| G4 | 0.0032 |
| G5 | 0.0093 |
| G6 | 0.0074 |
| G7 | 0.0025 |
| G8 | 0.0014 |
| G9 | 0.0044 |
| G10 | 0.0022 |
| G11 | 0.0025 |
| G12 | 0.00095 |
| G13 | 0.00049 |
| G14 | 0.00069 |
| G15 | 0.0016 |
| G16 | 0.00091 |
| G17 | 0.00085 |
| G18 | 0.00079 |
| H1 | 0.0062 |
| H2 | 0.0018 |
| H3 | 0.0027 |
| I1 | 0.033 |
| I2 | 0.016 |
| I3 | 0.0080 |
| J1 | 0.0073 |
| J2 | 0.0031 |
| J3 | 0.0035 |
| K1 | 0.0017 |
| K2 | 0.0012 |
| K3 | 0.050 |
| K4 | 0.0027 |
| L1 | 0.0030 |
| L2 | 0.0018 |
| L3 | 0.0023 |
| M1 | 0.010 |
| M2 | 0.014 |
| M3 | 0.099 |
| M4 | 0.019 |
| N1 | 0.0053 |
| N2 | 0.0033 |
| O1 | 0.0011 |
| P1 | 0.0018 |
| P2 | 0.013 |
| P3 | 0.012 |
| P4 | 0.0061 |
| P5 | 0.0039 |
| Q1 | 0.0093 |
| R1 | 0.0034 |
| S1 | 0.37 |
| T1 | 0.0049 |
| T2 | 0.0076 |
| T3 | 0.0061 |
| T4 | 0.0032 |
| T5 | 0.0035 |
| T6 | 0.0022 |

TABLE 3-5

| Compound number | Binding $IC_{50}$ (μM) |
|---|---|
| C216 | 0.0034 |
| C217 | 0.0018 |
| C218 | 0.00043 |
| C219 | 0.0021 |
| C220 | 0.0041 |
| C221 | 0.00072 |
| C222 | 0.0014 |
| C223 | 0.75 |
| C224 | 3.0 |
| C225 | 1.0 |

TABLE 4

| Compound number | ELISA $IC_{50}$ (μM) |
|---|---|
| A27 | 0.00052 |
| A30 | 0.00071 |
| A56 | 0.0011 |
| A57 | 0.00061 |
| A59 | 0.00060 |
| A60 | 0.00055 |
| A61 | 0.0050 |
| B2 | 0.0040 |
| B3 | 0.00052 |
| B7 | 0.0057 |
| B22 | 0.00025 |
| B23 | 0.00026 |
| B24 | 0.00062 |
| B26 | 0.00037 |
| B27 | 0.00021 |
| B31 | 0.00032 |
| B32 | 0.00026 |
| B34 | 0.00086 |
| B35 | 0.00044 |
| B37 | 0.00075 |
| B46 | 0.0064 |
| B47 | 0.0011 |
| B48 | 0.0025 |
| B49 | 0.0064 |
| B50 | 0.21 |
| C1 | <0.00017 |
| C4 | 0.00015 |
| C8 | 0.00030 |
| C13 | 0.00015 |
| C64 | 0.00020 |
| C65 | 0.000083 |
| C67 | 0.00010 |
| C69 | 0.00010 |
| C76 | 0.000092 |
| C78 | <0.00017 |
| C79 | 0.00030 |
| C83 | 0.00020 |
| C84 | 0.00025 |
| C85 | 0.00019 |
| C86 | <0.00017 |
| C88 | <0.00017 |
| C90 | 0.00042 |
| C91 | 0.0011 |
| C92 | 0.0017 |
| C98 | <0.0046 |
| C100 | 0.0055 |
| C101 | 0.0071 |
| C102 | <0.0046 |
| C134 | 0.0076 |
| C135 | <0.0046 |
| C136 | 0.0083 |
| C137 | 0.0077 |
| C138 | <0.0046 |
| C139 | 0.019 |
| C140 | <0.0046 |
| C141 | 0.011 |
| C143 | 0.00020 |
| C144 | 0.00032 |
| C146 | 0.016 |
| C155 | <0.0046 |
| C156 | 0.0062 |
| C184 | <0.0046 |
| C185 | 0.00031 |
| C186 | 0.0039 |
| C190 | 0.00034 |
| C195 | 0.00024 |
| C200 | 0.0070 |
| D1 | 0.017 |
| D2 | 0.015 |
| G16 | 0.000086 |
| P1 | 0.00022 |
| P4 | 0.0059 |
| Q1 | 0.00083 |

2. Results

Tables 3-1 to 3-5 suggested that each compound evaluated by the test for binding to the ATP binding site of MYT1 exhibited $IC_{50}$ of 10 μM or less and had the binding capacity to the ATP binding site of MYT1. In addition, Table 4 suggested that all the compounds evaluated in the MYT1 kinase activity inhibition test exhibited $IC_{50}$ of 10 μM or less and were compounds having MYT1 kinase activity inhibitory capacity, that is, MYT1 inhibitors.

Test Example 2: Cytotoxic Activity Test for Combination of Pemetrexed and Each Example compound 1. Experimental Material and Method (1) Cell Line LU65 (received from human tissue bank (JCRB Cell Bank)) was used in the evaluation of the present invention. LU65 is a lung cancer cell line having a truncated deletion mutation of S82* in RB1 gene (see Nature. 2019 May; 569(7757): 503-508. (Non Patent Literature 22)), in which the function of RB1 is decreased. The cell culture was carried out using RPMI-1640 (manufactured by SIGMA) containing 10% FBS (manufactured by SIGMA).

(2) Cytotoxicity Test with Pemetrexed Upon Addition of Each Example Compound

Each pemetrexed (manufactured by Tokyo Kasei Kogyo Co., Ltd.) and each example compound of each concentration were diluted using a DMSO solution, and 0.04 μL of each of series of dilution and DMSO was added to each well of cell culture plate using Echo 555 Liquid Handler (manufactured by Beckman Coulter Inc.). 1000 LU65 cells (40 L) were added to each well, which was cultured at 37° C. in a 5% $CO_2$ incubator for 7 days. Intracellular ATP level which is a cell survival marker was measured and used in the monitoring of cell number. After culturing, 20 μL of Cell-Titer-Glo (registered trademark) 2.0 (manufactured by Promega) was added to each well, and the emission intensity was measured using Multimode Plate Reader En Vision (registered trademark) Xcite (manufactured by PerkinElmer). The cell survival rate under each condition was calculated by setting the value obtained by subtracting the luminescence of the cell unseeded well from the luminescence of the DMSO-added well as 100%, and calculating the proportion of a value obtained by subtracting the luminescence of the cell unseeded well from the luminescence detected at each well.

In addition, the cytotoxic activity under each condition was calculated by subtracting the survival rate in a combination of pemetrexed of each treatment concentration and each example compound of each treatment concentration, from 100%. Moreover, Bliss score based on Bliss independence (see PLOS Comput Biol. 2019 May 20; 15(5): e1006752. (Non Patent Literature 23)), which was an index of the combination effect in each combination of pemetrexed of each concentration and each example compound of each concentration, was calculated based on the cytotoxic activity of each example compound-free well of each pemetrexed concentration and the cytotoxic activity of each pemetrexed-free well of each example compound concentration, and the maximum value of Bliss score and the concentrations of pemetrexed and each example compound exhibiting the maximum value were set forth in Tables 5-1 to 5-2. In addition, HSA score (see PLOS Comput Biol. 2019 May 20; 15(5): e1006752. (Non Patent Literature 23)), which was an index of the combination effect different from the Bliss independence, was also calculated, and the maximum value of HSA score and the concentrations of pemetrexed and each example compound exhibiting the maximum value were set forth in Tables 5-1 to 5-2. When both the maximum value of Bliss score and the maximum value of HSA score exhibit 10% or more, the compound can be determined to have the combination effect.

TABLE 5-1

| Compound number | MYT1 inhibitor concentration (μM) | Pemetrexed concentration (μM) | Bliss Score (Max) | HSA Score (MAX) |
|---|---|---|---|---|
| A12 | 0.63 | 0.039 | | 70% |
| A12 | 0.63 | 0.020 | 61% | |
| A59 | 2.50 | 0.039 | | 58% |
| A59 | 2.50 | 0.020 | 55% | |
| B3 | 2.50 | 0.039 | 78% | 77% |
| B22 | 0.16 | 0.039 | 56% | 64% |
| B23 | 0.63 | 0.039 | 58% | 63% |
| B24 | 0.16 | 0.078 | 52% | 60% |
| B32 | 0.63 | 0.039 | 52% | 63% |
| B35 | 2.50 | 0.039 | 61% | 70% |
| B37 | 0.16 | 0.039 | 31% | 34% |
| B46 | 2.50 | 0.039 | 52% | 65% |
| B47 | 0.63 | 0.039 | 54% | 62% |
| B48 | 0.63 | 0.039 | 66% | 70% |
| B49 | 0.63 | 0.020 | 86% | 84% |
| C1 | 0.63 | 0.039 | 59% | 71% |
| C4 | 0.16 | 0.020 | 61% | 62% |
| C8 | 0.16 | 0.039 | 68% | 78% |
| C13 | 0.16 | 0.039 | 62% | 66% |
| C64 | 0.63 | 0.039 | 45% | 54% |
| C65 | 0.16 | 0.039 | 53% | 58% |
| C67 | 0.16 | 0.039 | 77% | 79% |
| C69 | 0.16 | 0.078 | 66% | 69% |
| C76 | 0.16 | 0.078 | 68% | 67% |
| C78 | 0.63 | 0.039 | 53% | 66% |
| C83 | 0.63 | 0.039 | 54% | 66% |
| C84 | 0.16 | 0.039 | | 70% |
| C84 | 0.16 | 0.020 | 68% | |
| C85 | 0.16 | 0.039 | 59% | 58% |
| C86 | 0.16 | 0.039 | 67% | 71% |
| C88 | 0.16 | 0.039 | 53% | 61% |
| C90 | 0.63 | 0.039 | 50% | 60% |
| C91 | 0.16 | 0.039 | | 61% |
| C91 | 0.16 | 0.020 | 59% | |
| C92 | 0.16 | 0.078 | 56% | 68% |
| C98 | 0.16 | 0.078 | 46% | 53% |
| C100 | 0.039 | 0.039 | | 50% |
| C100 | 0.039 | 0.020 | 46% | |
| C101 | 0.63 | 0.039 | 46% | 64% |

TABLE 5-2

| Compound number | MYT1 inhibitor concentration (μM) | Pemetrexed concentration (μM) | Bliss Score (Max) | HSA Score (MAX) |
|---|---|---|---|---|
| C102 | 0.16 | 0.039 | 36% | 49% |
| C134 | 0.039 | 0.039 | 49% | 60% |
| C135 | 0.16 | 0.039 | | 58% |
| C135 | 0.16 | 0.020 | 48% | |
| C136 | 0.16 | 0.020 | 45% | 57% |
| C137 | 0.039 | 0.020 | 45% | 56% |
| C138 | 0.039 | 0.039 | 73% | 73% |
| C139 | 0.16 | 0.039 | | 54% |
| C139 | 0.039 | 0.039 | 46% | |
| C140 | 0.16 | 0.039 | 73% | 76% |
| C141 | 0.63 | 0.039 | 78% | 72% |
| C143 | 0.16 | 0.039 | 50% | 67% |
| C144 | 0.63 | 0.039 | 39% | 47% |
| C146 | 0.63 | 0.039 | 44% | 44% |
| C155 | 0.63 | 0.039 | | 61% |
| C155 | 0.16 | 0.039 | 47% | |
| C156 | 0.16 | 0.039 | 51% | 59% |
| C185 | 0.63 | 0.020 | 55% | 68% |
| C190 | 0.63 | 0.039 | 48% | 66% |
| C195 | 0.16 | 0.039 | 52% | 65% |
| C200 | 0.16 | 0.020 | 44% | 56% |
| D2 | 0.63 | 0.039 | 42% | 51% |

TABLE 5-2-continued

| Compound number | MYT1 inhibitor concentration (μM) | Pemetrexed concentration (μM) | Bliss Score (Max) | HSA Score (MAX) |
|---|---|---|---|---|
| F2 | 0.63 | 0.020 | 86% | 83% |
| G16 | 0.16 | 0.078 | 50% | 58% |
| H3 | 0.16 | 0.039 | | 61% |
| H3 | 0.16 | 0.020 | 61% | |
| K4 | 0.16 | 0.039 | | 66% |
| K4 | 0.039 | 0.039 | 56% | |
| L3 | 0.16 | 0.039 | | 61% |
| L3 | 0.16 | 0.020 | 51% | |
| M4 | 2.50 | 0.039 | | 60% |
| M4 | 0.63 | 0.039 | 51% | |
| N2 | 0.63 | 0.039 | | 57% |
| N2 | 0.63 | 0.020 | 50% | |
| O1 | 0.63 | 0.039 | | 44% |
| O1 | 0.63 | 0.020 | 37% | |
| P1 | 0.16 | 0.020 | 49% | 55% |
| P4 | 0.16 | 0.039 | 56% | 67% |
| Q1 | 0.63 | 0.020 | 52% | 58% |

2. Results

FIGS. 1 to 8 and Tables 5-1 to 5-2 suggested that both the maximum value of Bliss score and the maximum value of HSA score of all the example compounds evaluated in the pemetrexed cytotoxicity test upon addition of each example compound exhibited 10% or more, and these example compounds inhibited the function of MYT1 in cells and exhibited the combination effect with pemetrexed.

INDUSTRIAL APPLICABILITY

The present invention provides a compound having new MYT1 inhibitory activity or a salt thereof, or a solvate thereof. In addition, the present invention provides a medicament useful for treatment and prevention of cancer.

The invention claimed is:

1. A compound selected from the following compounds, or a salt thereof:

3-Amino-4-(6,7-difluoro-1H-indazol-4-yl)-6-methyl-1H-1,7-phenanthrolin-2-one,

3-Amino-4-(7-fluoro-1H-indazol-4-yl)-6-methoxy-1H-1,7-phenanthrolin-2-one, and

3-Amino-4-(7-fluoro-1H-indazol-4-yl)-6-methyl-1H-1,7-phenanthrolin-2-one.

2. A compound, or a salt thereof, wherein the compound is 3-Amino-4-(6,7-difluoro-1H-indazol-4-yl)-6-methyl-1H-1,7-phenanthrolin-2-one.

3. A hydrate of the compound or the salt according to claim 2, which is 3-Amino-4-(6,7-difluoro-1H-indazol-4-yl)-6-methyl-1H-1,7-phenanthrolin-2-one hydrochloride monohydrate.

4. A pharmaceutical composition comprising the compound according to claim 2, or the salt thereof.

5. A pharmaceutical composition comprising the hydrate according to claim 3.

6. A method for treating cancer comprising administering an effective amount of the compound according to claim 2, or the solvate thereof, to a subject.

7. A method for treating cancer comprising administering an effective amount of the hydrate according to claim 3 to a subject.

8. A compound, or a salt thereof, wherein the compound is 3-Amino-4-(7-fluoro-1H-indazol-4-yl)-6-methoxy-1H-1,7-phenanthrolin-2-one.

9. The salt according to claim 8, which is 3-Amino-4-(7-fluoro-1H-indazol-4-yl)-6-methoxy-1H-1,7-phenanthrolin-2-one hydrochloride.

10. A pharmaceutical composition comprising the compound according to claim 8, or the salt thereof.

11. A pharmaceutical composition comprising the salt according to claim 9.

12. A method for treating cancer comprising administering an effective amount of the compound according to claim 8, to a subject.

13. A method for treating cancer comprising administering an effective amount of the salt according to claim 9 to a subject.

14. A compound, wherein the compound is 3-Amino-4-(7-fluoro-1H-indazol-4-yl)-6-methyl-1H-1,7-phenanthrolin-2-one.

15. A hydrate of the compound or the salt according to claim 14, which is 3-Amino-4-(7-fluoro-1H-indazol-4-yl)-6-methyl-1H-1,7-phenanthrolin-2-one hydrochloride monohydrate.

16. A pharmaceutical composition comprising the compound according to claim 14, or the salt thereof.

17. A pharmaceutical composition comprising the hydrate according to claim 15.

18. A method for treating cancer comprising administering an effective amount of the compound according to claim 14, or the salt thereof, to a subject.

19. A method for treating cancer comprising administering an effective amount of the hydrate according to claim 15 to a subject.

20. The salt according to claim 2, which is a hydrochloride salt.

21. A pharmaceutical composition comprising the salt of claim 20.

22. A method for treating cancer comprising administering an effective amount of the salt according to claim 20 to a subject.

23. The salt according to claim 14, which is a hydrochloride salt.

24. A pharmaceutical composition comprising the salt of claim 23.

25. A method for treating cancer comprising administering an effective amount of the salt according to claim 23 to a subject.

* * * * *